United States Patent
Wang et al.

(10) Patent No.: US 10,358,453 B2
(45) Date of Patent: *Jul. 23, 2019

(54) ANTIVIRAL COMPOUNDS

(71) Applicant: Alios BioPharma, Inc., South San Francisco, CA (US)

(72) Inventors: Guangyi Wang, Carlsbad, CA (US); Leonid Beigelman, San Mateo, CA (US); Anh Truong, Burlingame, CA (US); Karin Ann Stein, Mountain View, CA (US)

(73) Assignee: Alios BioPharma, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/052,631

(22) Filed: Feb. 24, 2016

(65) Prior Publication Data

US 2016/0244460 A1 Aug. 25, 2016

Related U.S. Application Data

(60) Provisional application No. 62/126,671, filed on Feb. 25, 2015, provisional application No. 62/200,483, filed on Aug. 3, 2015.

(51) Int. Cl.

| | |
|---|---|
| *A61K 31/4355* | (2006.01) |
| *C07D 491/048* | (2006.01) |
| *C07D 401/04* | (2006.01) |
| *A61K 31/536* | (2006.01) |
| *C07D 221/04* | (2006.01) |
| *A61K 31/437* | (2006.01) |
| *C07D 491/20* | (2006.01) |
| *C07D 471/04* | (2006.01) |
| *C07D 213/40* | (2006.01) |
| *A61K 31/4709* | (2006.01) |
| *A61K 45/06* | (2006.01) |
| *A61K 31/444* | (2006.01) |
| *A61K 31/538* | (2006.01) |
| *C07D 519/00* | (2006.01) |
| *A61K 31/4545* | (2006.01) |
| *C07D 413/04* | (2006.01) |
| *A61K 31/436* | (2006.01) |
| *A61K 31/435* | (2006.01) |
| *A61K 31/4375* | (2006.01) |
| *A61K 31/5355* | (2006.01) |
| *A61K 31/44* | (2006.01) |

(52) U.S. Cl.
CPC ........ *C07D 491/048* (2013.01); *A61K 31/435* (2013.01); *A61K 31/436* (2013.01); *A61K 31/437* (2013.01); *A61K 31/4355* (2013.01); *A61K 31/4375* (2013.01); *A61K 31/44* (2013.01); *A61K 31/444* (2013.01); *A61K 31/4545* (2013.01); *A61K 31/4709* (2013.01); *A61K 31/536* (2013.01); *A61K 31/538* (2013.01); *A61K 31/5355* (2013.01); *A61K 45/06* (2013.01); *C07D 213/40* (2013.01); *C07D 221/04* (2013.01); *C07D 401/04* (2013.01); *C07D 413/04* (2013.01); *C07D 471/04* (2013.01); *C07D 491/20* (2013.01); *C07D 519/00* (2013.01)

(58) Field of Classification Search
CPC ........................... C07D 491/048; A61K 31/44
See application file for complete search history.

(56) References Cited

U.S. PATENT DOCUMENTS

| | | | |
|---|---|---|---|
| 6,623,741 B1 | 9/2003 | Artczak et al. | |
| 7,423,368 B2 | 9/2008 | Miyamae et al. | |
| 9,724,351 B2 | 8/2017 | Wang et al. | |
| 2003/0176506 A1 | 9/2003 | Dawson et al. | |
| 2007/0037752 A1 | 2/2007 | Ansorge et al. | |
| 2007/0155744 A1 | 7/2007 | Jones et al. | |
| 2007/0287730 A1 | 12/2007 | Wang et al. | |
| 2009/0238772 A1 | 9/2009 | Vaishnaw et al. | |
| 2010/0045558 A1 | 2/2010 | Rossetto | |
| 2010/0048558 A1 | 2/2010 | Eggenweiler | |
| 2012/0128669 A1 | 5/2012 | Depla et al. | |
| 2012/0225867 A1* | 9/2012 | Wohlfahrt | C07D 231/14 514/230.5 |
| 2013/0090328 A1 | 4/2013 | Liang et al. | |
| 2013/0164280 A1 | 6/2013 | Boojamra et al. | |

(Continued)

FOREIGN PATENT DOCUMENTS

| | | |
|---|---|---|
| CN | 1261276 A | 7/2000 |
| EP | 2786986 | 10/2014 |

(Continued)

OTHER PUBLICATIONS

Barry et al., "Stereoselective Synthesis of the Tetrahydropyran Core of Polycarvernoside A" Organic Letters (2005) 7(13):2683-2686.

(Continued)

*Primary Examiner* — Dennis Heyer
*Assistant Examiner* — Daniel M Podgorski
(74) *Attorney, Agent, or Firm* — Morrison & Foerster LLP

(57) ABSTRACT

Disclosed herein are new antiviral compounds, together with pharmaceutical compositions that include one or more antiviral compounds, and methods of synthesizing the same. Also disclosed herein are methods of ameliorating and/or treating a paramyxovirus viral infection with one or more small molecule compounds. Examples of paramyxovirus infection include an infection caused by human respiratory syncytial virus (RSV).

63 Claims, 11 Drawing Sheets

Specification includes a Sequence Listing.

(56) References Cited

U.S. PATENT DOCUMENTS

| | | |
|---|---|---|
| 2013/0273037 A1 | 10/2013 | Siegel et al. |
| 2014/0072554 A1 | 3/2014 | Babaoglu et al. |
| 2015/0065504 A1 | 3/2015 | Wang et al. |
| 2015/0111885 A1 | 4/2015 | Bennett et al. |
| 2018/0065932 A1 | 3/2018 | Wang et al. |

FOREIGN PATENT DOCUMENTS

| | | |
|---|---|---|
| WO | WO 98/48799 | 11/1998 |
| WO | WO 99/61437 | 12/1999 |
| WO | WO 1999/066925 | 12/1999 |
| WO | WO 03/024955 | 3/2003 |
| WO | WO 03/029245 | 4/2003 |
| WO | WO-2004/026843 A1 | 4/2004 |
| WO | WO-2005/031784 A1 | 4/2005 |
| WO | WO 2005/042530 | 5/2005 |
| WO | WO 2005/058869 | 6/2005 |
| WO | WO-2005/089770 A1 | 9/2005 |
| WO | WO 2006/136561 | 12/2006 |
| WO | WO 2009/087379 | 7/2009 |
| WO | WO 2009/114552 | 9/2009 |
| WO | WO 2010/056722 | 5/2010 |
| WO | WO 2010/071813 | 6/2010 |
| WO | WO 2010/103306 | 9/2010 |
| WO | WO 2010/132615 | 11/2010 |
| WO | WO 2010/132992 | 11/2010 |
| WO | WO 2010/150281 | 12/2010 |
| WO | WO 2011/005842 | 1/2011 |
| WO | WO 2011/097607 | 8/2011 |
| WO | WO 2012/068622 | 5/2012 |
| WO | WO 2012/080446 | 6/2012 |
| WO | WO 2012/080447 | 6/2012 |
| WO | WO 2012/080449 | 6/2012 |
| WO | WO 2012/080450 | 6/2012 |
| WO | WO 2012/080451 | 6/2012 |
| WO | WO 2013/010380 | 1/2013 |
| WO | WO 2013/041457 | 3/2013 |
| WO | WO 2013/059119 | 4/2013 |
| WO | WO 2013/064518 | 5/2013 |
| WO | WO 2013/186332 | 12/2013 |
| WO | WO 2013/186333 | 12/2013 |
| WO | WO 2013/186334 | 12/2013 |
| WO | WO 2013/186335 | 12/2013 |
| WO | WO 2014/009302 | 1/2014 |
| WO | WO 2014/031784 | 2/2014 |
| WO | WO 2015/026792 | 2/2015 |

OTHER PUBLICATIONS

Chiummiento et al., "Concise Total Synthesis of Permethylated Anigopreissin A, a New Benzofuryl Resveratrol Dimer" European Journal of Organic Chemistry (2012) 2012(1):188-192 with Supporting Information.

Demont et al., "Fragment-Based Discovery of Low-Micromolar ATAD2 Bromodomain Inhibitors" Journal of Medicinal Chemistry (2015) 58(14):5649-5673 with Supporting Information.

Desroses et al., "Synthesis of Unsymmetrical Dialkoxy Quinazolines" Organic Preparations and Procedures International (2004) 36(5):445-452.

Ezquerra et al., "Efficient Reagents for the Synthesis of 5-, 7-, and 5,7-Substituted Indoles Starting from Aromatic Amines: Scope and Limitations" Journal of Organic Chemistry (1996) 61(17):5804-5812 with Supporting Information.

Greene, et al., Protective Groups in Organic Synthesis, 3. Ed., John Wiley & Sons, (1999) Cover & Contents pages.

Hénichart, J. et al., "Synthesis of 6-phenyl and 6-styrylthiazolo[3,2-b][1,2,4]triazoles" Journal of Heterocyclic Chemistry (1986) 23(5):1531-1533.

Hotard, A.L., "A stabilized respiratory syncytial virus reverse genetics system amendable to recombination-mediated mutagenesis" Virology (2012) 434(1):129-136.

"IUPAC-IUB Commission on Biochemical Nomenclature Abbreviated Nomenclature of Synthetic Polypeptides (Polymerized Amino Acids)* Revised Recommendations (1971)" Biochemistry. (1972) 11(5):942-944.

Maeno et al., "Novel Catalysis in the Internal Nanocavity of Polyamine Dendrimer for Intramolecular Michael Reaction" Chemistry Letters (2012) 41(8):801-803.

Mcomie, J. F. W., Protective Groups in Organic Chemistry, Plenum Press, 1973. Cover & Contents pages only.

Panda et al., "An Approach to Highly Functionalized Quinolines and Isoquinolines via a Gold-Catalyzed Benzannulation" Synlett (2011) 11(5):689-693.

Patt et al., "The Total Synthesis of the Natural Product Endothelin Converting Enzyme (ECE) Inhibitor, WS75624 B" Tetrahedron Letters (1997) 38(8):1297-1300.

Ramesh et al., "A simple and facile route for the synthesis of 2H-1,4-benzoxazin-3-(4H)-ones via reductive cyclization of 2-(2-nitrophenoxy)acetonitrile adducts in the presence of Fe/acetic acid" Tetrahedron (2011) 67(6):1187-1192.

Rousseau et al., "Halogenation of Pyridinols using Bis(sym-collidine)iodine(I) and Bis(sym-collidine)bromine(I) hexaflurophosphate" Tetrahedron Letters (1997) 38(14):2467-2470.

Sakairi et al., "Synthesis and Biological Evaluation of a 6-Aminofuro[3,2-c]pyridin-3(2H)-one Series of GPR 119 Agonists" Journal of Arzneimittel-Forschung/Drug Research (2012) 62(11):537-544.

Sosič et al., "Development of New Cathepsin B Inhibitors: Combining Bioisosteric Replacements and Structure-Based Design to Explore the Structure-Activity Relationships of Nitroxoline Derivatives" Journal of Medicinal Chemistry (2013) 56(2):521-533 with Supporting Information.

Urban et al., "Aminométhoxypyridines et sulfanilamides correspondants" Journal of Helvetica Chimica Acta (1964) 47:363-379.

Uto et al., "Novel and potent inhibitors of stearoyl-CoA desaturase-1. Part I: Discovery of 3-(2-hydroxyethoxy)-4-methoxy-N-[5-(3-trifluoromethylbenzyl)thiazol-2-yl]benzamide" Bioorganic and Medicinal Chemistry Letters (2009) 19(15):4151-4158.

International Search Report and Written Opinion dated Apr. 27, 2016 for PCT Application No. PCT/US2016/019393, filed Feb. 24, 2016.

Written Opinion dated Jan. 12, 2017 for PCT Application No. PCT/US2016/019393, filed Feb. 24, 2016.

Al-Afaleq et al., "L-Amino Acid Esters Studies: Part II: Synthesis of N-(Dimethoxy/3,5-Diacetoxybenzoyl)-L-Amino Acid Hydrazides and their Reactions with Aldehydes and Ketones" Syn. Comm: An International Journal for Rapid Communication of Synthetic Organic Chemistry (1999) 29(8):1317-1331.

Bhattacharjee et al., "Discovery of non-oxime reactivators using an in silico pharmacophore model of oxime reactivators of OP-inhibited acetylcholinesterase" Eur. J. Med. Chem. (2012) 49:229-238.

CAS Registry No. 1386825-26-8, Entry Date of Aug. 6, 2012, Retrieved Oct. 21, 2013.

CAS Registry No. 1371789-14-8, Entry Date of May 1, 2012, Retrieved Oct. 21, 2013.

CAS Registry No. 1321793-72-9, Entry Date of Aug. 23, 2011, Retrieved Oct. 21, 2013.

CAS Registry No. 1321772-62-6, Entry Date of Aug. 23, 2011, Retrieved Oct. 21, 2013.

CAS Registry No. 1299457-43-4, Entry Date of May 24, 2011, Retrieved Oct. 21, 2013.

CAS Registry No. 1294568-99-2, Entry Date of May 15, 2011, Retrieved Oct. 21, 2013.

CAS Registry No. 1235686-10-8, Entry Date of Aug. 10, 2010, Retrieved Oct. 21, 2013.

CAS Registry No. 1025828-66-3, Entry Date of Jun. 5, 2008, Retrieved Oct. 21, 2013.

CAS Registry No. 847596-86-5, Entry Date of Mar. 30, 2005, Retrieved Oct. 21, 2013.

CAS Registry No. 383168-68-1, Entry Date of Jan. 15, 2002, Retrieved Oct. 21, 2013.

CAS Registry No. 382157-09-7, Entry Date of Jan. 11, 2002, Retrieved Oct. 21, 2013.

(56) References Cited

OTHER PUBLICATIONS

CAS Registry No. 327988-51-2, Entry Date of Mar. 19, 2001, Retrieved Oct. 21, 2013.
CAS Registry No. 1276363-72-4, Entered Apr. 7, 2011.
CAS Registry No. 1235682-49-1, Entered Aug. 10, 2010.
CAS Registry No. 817189-89-2, Entered Jan. 20, 2005.
CAS Registry No. 817189-87-0, Entered Jan. 20, 2005.
CAS Registry No. 476430-91-8, Entered Dec. 17, 2002.
CAS Registry No. 476430-75-8, Entered Dec. 17, 2002.
CAS Registry No. 391891-52-4, Entered Feb. 13, 2002.
CAS Registry No. 391891-51-3, Entered Feb. 13, 2002.
CAS Registry No. 374606-62-9, Entered Dec. 10, 2001.
CAS Registry No. 373613-54-8, Entered Dec. 5, 2001.
CAS Registry No. 373373-41-2, Entered Dec. 4, 2001.
CAS Registry No. 349568-79-2, Entered Jul. 31, 2001.
CAS Registry No. 339005-10-6, Entered May 30, 2001.
CAS Registry No. 328126-15-4, Entered Mar. 20, 2001.

Kametani et al., "Syntheses of Imidazoquinoline Derivatives. II. Synthesis of 9,10-Dimethoxy-3-veratryl-5,6-dihydrobenzoglyoxacoline" *Yakugaku Zasshi* (1950) 70:263-265.
Perni, R.T., et al., "Inhibitors of hepatitis C virus NS3-4A protease 2. Warhead SAR and optimization" Bioorg. & Med. Chem. Letters (2004) 14:1441-1446.
Shao et al., "Synthesis and evaluation of tacrine-E2020 hybrids as acetylcholinesterase inhibitors for the treatment of Alzheimer's disease" *Bio. Med. Chem. Lett.* (2004) 14:4639-4642.
International Report on Patentability dated Jun. 20, 2017 for PCT Application No. PCT/US2016/019393, filed Feb. 24, 2016.
Eurasian Office Action dated Sep. 11, 2018 for EA Application No. 201791886, filed Feb. 24, 2016.
European Extended Search Report dated Jun. 19, 2018 for EP Application No. 16756295.8, filed Feb. 24, 2016.
European Office Action dated May 8, 2019 for EP Application No. 16756295.8, filed Feb. 24, 2016.

\* cited by examiner

Figure 1

| Name or CAS No. | IUPAC Name | Structure |
|---|---|---|
| BMS-433771 | 1-cyclopropyl-3-[[1-(4-hydroxybutyl)benzimidazol-2-yl]methyl]imidazo[4,5-c]pyridin-2-one | 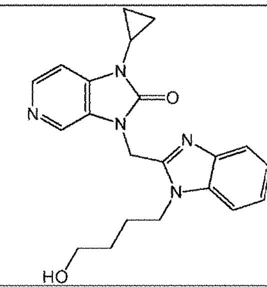 |
| VP-14637 (MDT-637) | 5,5'-bis[1-(((5-amino-1H-tetrazolyl)imino)methyl)]2,2',4''-methylidynetrisphenol | 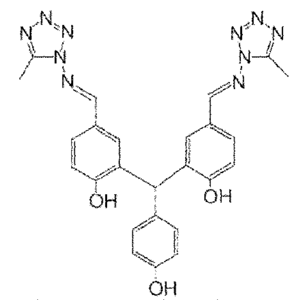 |
| JNJ-2408068 | 2-[[2-[[1-(2-aminoethyl)-4-piperidinyl]amino]-4-methyl-1H-benzimidazol-1-yl]-6-methyl-3-pyridinol | 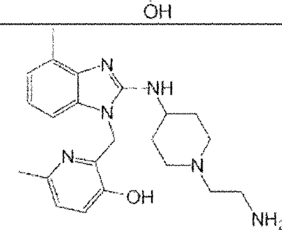 |

Figure 1 (cont.)

| Name or CAS No. | IUPAC Name | Structure |
|---|---|---|
| TMC-353121 | 2-[[6-[[[2-(3-Hydroxypropyl)-5-methylphenyl]amino]methyl]-2-[[3-(morpholin-4-yl)propyl]amino]benzimidazol-1-yl]methyl]-6-methylpyridin-3-ol | 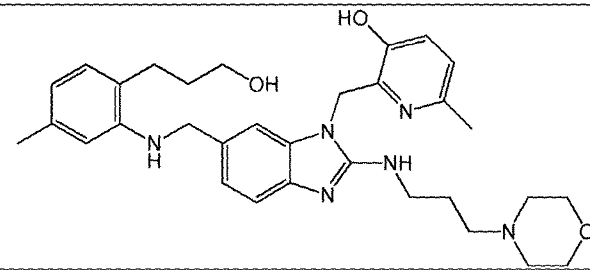 |
| P13 | N-(2-hydroxyethyl)-4-methoxy-N-methyl-3-(6-methyl-[1,2,4]triazolo[3,4-a]phthalazin-3-yl)benzenesulfonamide | 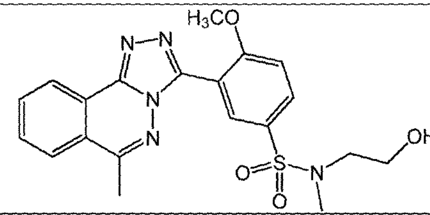 |
| C15 | 1,4-bis(3-methylpyridin-4-yl)-1,4-diazepane | 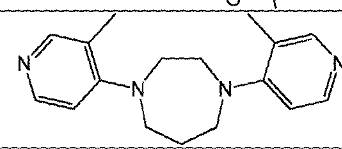 |

Figure 1 (cont.)

| Name or CAS No. | IUPAC Name | Structure |
|---|---|---|
| R170591 | 2-((2-((1-(2-aminoethyl)piperidin-4-yl)amino)-4-methyl-1H-benzo[d]imidazol-1-yl)methyl)-6-methylpyridin-3-ol | 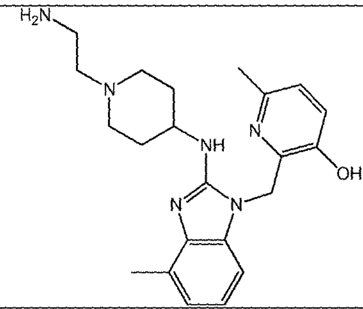 |
| BTA9981 | (R)-9b-(4-chlorophenyl)-1-(4-fluorobenzoyl)-2,3-dihydro-1H-imidazo[1',2':1,2]pyrrolo[3,4-c]pyridin-5(9bH)-one (BTA9981) | 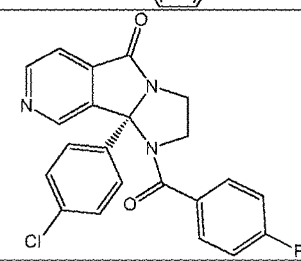 |
| RSV-604 | (S)-1-(2-fluorophenyl)-3-(2-oxo-5-phenyl-2,3-dihydro-1H-benzo[e][1,4]diazepin-3-yl)urea | 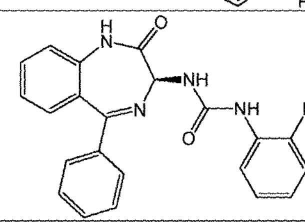 |

Figure 1 (cont.)

| Name or CAS No. | IUPAC Name | Structure |
|---|---|---|
| YM-53403 | 6-{4-[(biphenyl-2-ylcarbonyl) amino]benzoyl}-N-cyclopropyl-5,6-dihydro-4H-thieno[3,2-d][1]benzazepine-2-carboxamide | 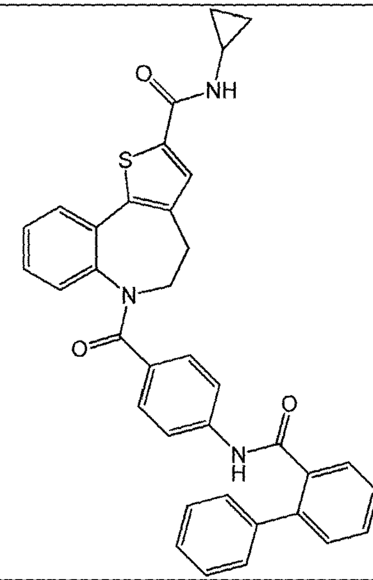 |

Figure 1 (cont.)

| Name or CAS No. | IUPAC Name | Structure |
|---|---|---|
| RFI-641 | 4,4''-bis-{4,6-bis-[3-(bis-carbamoylmethyl-sulfamoyl)-phenylamino]-(1,3,5)triazin-2-ylamino}-biphenyl-2,2''-disulfonic-acid | (structure shown); R = N(CH$_2$CONH$_2$)$_2$ |
| EICAR | 5-ethynyl-1-beta-D-ribofuranosylimidazole-4-carboxamide | (structure shown) |
| leflumomide | 5-methyl-N-[4-(trifluoromethyl) phenyl]-isoxazole-4-carboxamide | (structure shown) |

Figure 1 (cont.)

| Name or CAS No. | IUPAC Name | Structure |
|---|---|---|
| JMN3-003 | N-(2-chloro-4-methylphenyl)-2-((1-(4-methoxyphenyl)-1H-benzo[d]imidazol-2-yl)thio)propanamide | 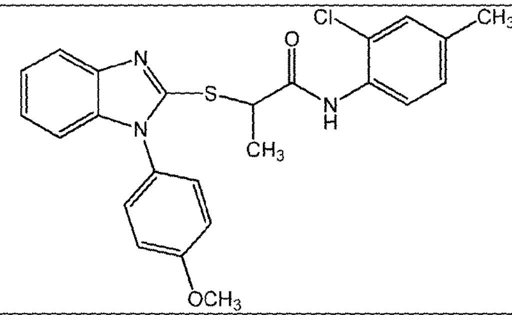 |
| MBX300 | [2,2-bis(docosyloxy-oxymethyl)propyl-5-acetaoamido-3,5-dideoxy-4,7,8,9-tetra-O-(sodium-oxysulfonyl)-D-glycero-D-galacto-2-nonulopyranosid]onate | 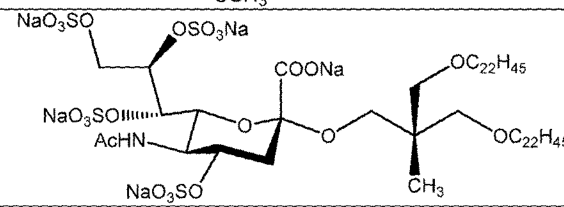 |
| GS-5806 | N-(2-((S)-2-(5-((S)-3-aminopyrrolidin-1-yl)-6-methylpyrazolo[1,5-a]pyrimidin-2-yl)piperidine-1-carbonyl)-4-chlorophenyl)methanesulfonamide | 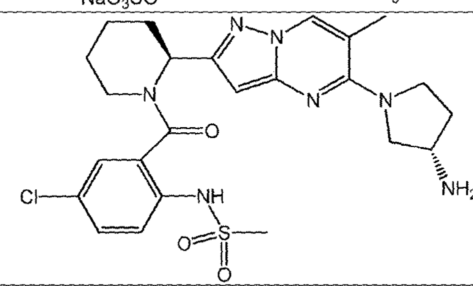 |

Figure 1 (cont.)

| Name or CAS No. | IUPAC Name | Structure |
|---|---|---|
| | N-cyclopropyl-5-(4-(2-(pyrrolidin-1-yl)benzamido)benzoyl)-5,6,7,10-tetrahydrobenzo[b]cyclopenta[d]azepine-9-carboxamide | |
| 851658-10-1 | 4-amino-8-(3-{[2-(3,4-dimethoxyphenyl)ethyl]amino}propyl)-6,6-dimethyl-2-(4-methyl-3-nitrophenyl)-1H-imidazo[4,5-h]-isoquinoline-7,9(6H,8H)-dione | 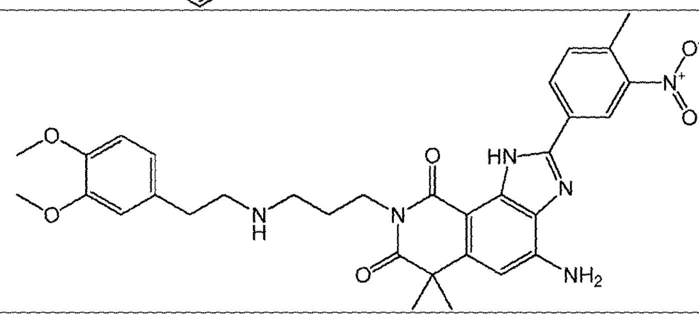 |

Figure 1 (cont.)

| Name or CAS No. | IUPAC Name | Structure |
|---|---|---|
| AZ27 | 6-(4-(2-(2-oxa-7-azaspiro[3.5]nonan-7-yl)nicotinamido)benzoyl)-N-cyclopropyl-5,6-dihydro-4H-benzo[b]thieno[2,3-d]azepine-2-carboxamide | 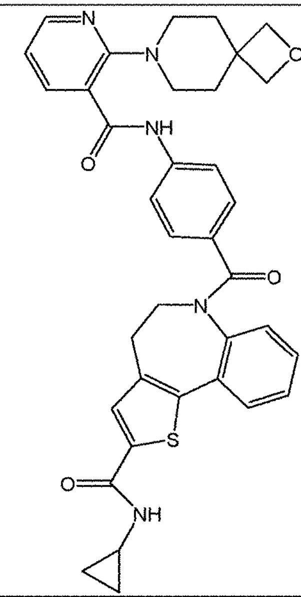 |
| pyrazofurin | 4-hydroxy-3-beta-D-ribofuranosylpyrazole-5-carboxamide | 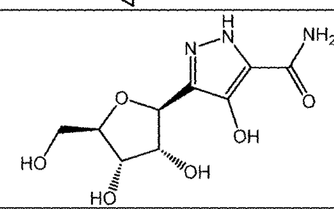 |

Figure 1 (cont.)

| Name or CAS No. | IUPAC Name | Structure |
|---|---|---|
| Taribavirin (viramidine) | 1-((2R,3R,4S,5R)-3,4-dihydroxy-5-(hydroxymethyl)tetrahydrofuran-2-yl)-1H-1,2,4-triazole-3-carboximidamide | 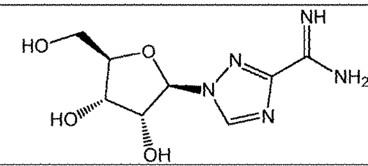 |
| ribavirin | 1-[(2R,3R,4S,5R)-3,4-dihydroxy-5-(hydroxymethyl)oxolan-2-yl]-1H-1,2,4-triazole-3-carboxamide | 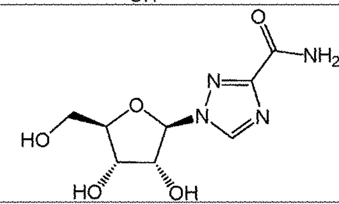 |
| LY253963 | 1,3,4-thiadiazol-2-ylcyanamide | 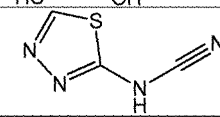 |
| VX-497 | tetrahydrofuran-3-yl 3-(3-(3-methoxy-4-(oxazol-5-yl)phenyl)ureido)benzylcarbamate | 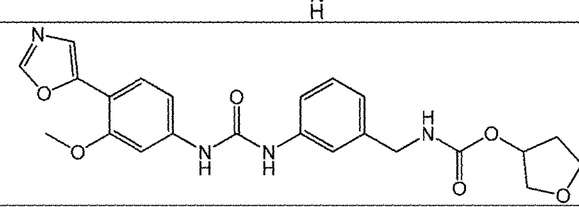 |
| Mycophenolic acid | (4E)-6-(4-Hydroxy-6-methoxy-7-methyl-3-oxo-1,3-dihydro-2-benzofuran-5-yl)-4-methylhex-4-enoic acid | 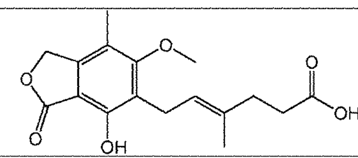 |

Figure 1 (cont.)

| Name or CAS No. | IUPAC Name | Structure |
|---|---|---|
| Mycophenolate Mofetil | 2-morpholin-4-ylethyl (E)-6-(4-hydroxy-6-methoxy-7-methyl-3-oxo-1H-2-benzofuran-5-yl)-4-methylhex-4-enoate | 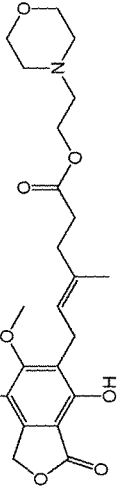 |
| | (2R,3R,4R,5R)-5-(4-amino-2-oxopyrimidin-1(2H)-yl)-2-(chloromethyl)-4-fluoro-2-((isobutyryloxy)methyl)tetrahydrofuran-3-yl isobutyrate | 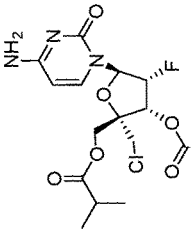 |
| | (2R,3R,4R,5R)-5-(4-amino-2-oxopyrimidin-1(2H)-yl)-2-(chloromethyl)-4-fluoro-2-(hydroxymethyl)tetrahydrofuran-3-yl isobutyrate | 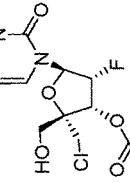 |
| | 4-amino-1-((2R,3R,4R,5R)-5-(chloromethyl)-3-fluoro-4-hydroxy-5-(hydroxymethyl)tetrahydrofuran-2-yl)pyrimidin-2(1H)-one |  |

Figure 1 (cont.)

| Name or CAS No. | IUPAC Name | Structure |
|---|---|---|
| | ((2R,3R,4R,5R)-5-(4-amino-2-oxopyrimidin-1(2H)-yl)-2-(chloromethyl)-4-fluoro-3-hydroxytetrahydrofuran-2-yl)methyl triphosphate | |

ANTIVIRAL COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

REFERENCE TO SEQUENCE LISTING

The present application is filed with a Sequence Listing in Electronic format. The Sequence Listing is provided as a file entitled ALIOS093.txt, created Feb. 24, 2016, which is approximately 4 kb in size. The information in the electronic format of the sequence listing is incorporated herein by reference in its entirety.

BACKGROUND

Field

The present application relates to the fields of chemistry, biochemistry and medicine. More particularly, disclosed herein are new antiviral compounds, together with pharmaceutical compositions, and methods of synthesizing the same. Also disclosed herein are methods of ameliorating and/or treating a paramyxovirus viral infection with one or more small molecule compounds.

Description

Respiratory viral infections, including upper and lower respiratory tract viral infections, are a leading cause of death of millions of people each year. Upper respiratory tract viral infections involve the nose, sinuses, pharynx and/or larynx. Lower respiratory tract viral infections involve the respiratory system below the vocal cords, including the trachea, primary bronchi and lungs. Human respiratory syncytial virus (RSV) is a common cause of respiratory tract infections. Up to 60% of human infants are infected with RSV within their first year of life. Children and adults are also infected with RSV, where it is often manifesting as a lower respiratory tract infection with possible complications of bronchiolitis. RSV infections can be particularly severe in infants and elderly patients. RSV is a negative-sense, single-stranded RNA virus classified within the Paramyxoviridae family, which also includes viruses that cause Newcastle disease, parainfluenza, mumps, measles, and canine distemper.

SUMMARY

Some embodiments disclosed herein relate to a compound of Formula (I), or a pharmaceutically acceptable salt thereof.

Some embodiments disclosed herein relate to a method of ameliorating and/or treating a paramyxovirus viral infection that can include administering to a subject suffering from the paramyxovirus viral infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a paramyxovirus viral infection. Still other embodiments described herein relate to compounds of Formula (I), or a pharmaceutically acceptable salt thereof, that can be used for ameliorating and/or treating a paramyxovirus viral infection. Yet still other embodiments disclosed herein relate to a method of ameliorating and/or treating a paramyxovirus viral infection that can include contacting a cell infected with the paramyxovirus with an effective amount of one or more compounds of Formula (I), or a pharmaceutically acceptable salt thereof, or a pharmaceutical composition that includes one or more compounds of Formula (I), or a pharmaceutically acceptable salt thereof. Some embodiments disclosed herein relate to a method of inhibiting the replication of a paramyxovirus that can include contacting a cell infected with the paramyxovirus with an effective amount of one or more compounds of Formula (I), or a pharmaceutically acceptable salt thereof, or a pharmaceutical composition that includes one or more compounds of Formula (I), or a pharmaceutically acceptable salt thereof. For example, the paramyxovirus viral infection can be caused by a henipavirus, a morbillivirus, a respirovirus, a rubulavirus, a pneumovirus (including a respiratory syncytial viral infection), a metapneumovirus, hendravirus, nipahvirus, measles, sendai virus, mumps, a human parainfluenza virus (HPIV-1, HPIV-2, HPIV-3 and HPIV-4) and/or a metapneumovirus.

Some embodiments disclosed herein relate to a method of ameliorating and/or treating a paramyxovirus viral infection that can include administering to a subject suffering from the viral infection an effective amount of a compound described herein or a pharmaceutically acceptable salt thereof (for example, one or more compounds of Formula (I), or a pharmaceutically acceptable salt thereof), or a pharmaceutical composition that includes one or more compounds described herein, in combination with one or more agents described herein. Some embodiments disclosed herein relate to a method of ameliorating and/or treating a paramyxovirus viral infection that can include contacting a cell infected with the paramyxovirus with an effective amount of a compound described herein or a pharmaceutically acceptable salt thereof (for example, one or more compounds of Formula (I), or a pharmaceutically acceptable salt thereof), or a pharmaceutical composition that includes one or more compounds described herein, in combination with one or more agents described herein.

BRIEF DESCRIPTION OF THE DRAWINGS

FIG. 1 illustrates examples of compounds of Formula (I), or pharmaceutically acceptable salt of any of the foregoing compounds.

DETAILED DESCRIPTION

Paramyxoviridae family is a family of single stranded RNA viruses. Several genera of the paramyxoviridae family include henipavirus, morbillivirus, respirovirus, rubulavirus, pneumovirus and metapneumovirus. These viruses can be transmitted person to person via direct or close contact with contaminated respiratory droplets or fomites. Species of henipavirus include hendravirus and nipahvirus. A species of morbillivirus is measles. Species of respirovirus include sendai virus and human parainfluenza viruses 1 and 3; and species of rubulavirus include mumps virus and human parainfluenza viruses 2 and 4. A species of metapneumovirus is human metapneumovirus.

Human Respiratory Syncytial Virus (RSV), a species of pneumovirus, can cause respiratory infections, and can be associated with bronchiolitis and pneumonia. Symptoms of an RSV infection include coughing, sneezing, runny nose, fever, decrease in appetite, and wheezing. RSV is the most common cause of bronchiolitis and pneumonia in children under one year of age in the world, and can be the cause of tracheobronchitis in older children and adults. In the United States, between 75,000 and 125,000 infants are hospitalized each year with RSV. Among adults older than 65 years of age, an estimated 14,000 deaths and 177,000 hospitalizations have been attributed to RSV.

Treatment options for people infected with RSV are currently limited. Antibiotics, usually prescribed to treat bacterial infections, and over-the-counter medication are not effective in treating RSV. In severe cases, a nebulized bronchodilator, such as albuterol, may be prescribed to relieve some of the symptoms, such as wheezing. Respi-Gram® (RSV-IGIV, MedImmune, approved for high risk children younger than 24 months of age), Synagis® (palivizumab, MedImmune, approved for high risk children younger than 24 months of age), and Virzole® (ribavirin by aerosol, ICN pharmaceuticals) have been approved for treatment of RSV.

Symptoms of the measles include fever, cough, runny nose, red eyes and a generalized rash. Some individuals with measles can develop pneumonia, ear infections and bronchitis. Mumps leads to swelling of the salivary glands. Symptoms of mumps include fever, loss of appetite and fatigue. Individuals are often immunized against measles and mumps via a three-part MMR vaccine (measles, mumps, and rubella). Human parainfluenza virus includes four serotypes types, and can cause upper and lower respiratory tract infections. Human parainfluenza virus 1 (HPIV-1) can be associated with croup; human parainfluenza virus 3 (HPIV-3) can be associated with bronchiolitis and pneumonia. According to the Centers of Disease Control and Prevention (CDC), there are no vaccines against human parainfluenza virus.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, and $R^A$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

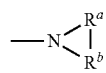

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, acylalkyl, hydroxy, alkoxy, alkoxyalkyl, aminoalkyl, amino acid, aryl, heteroaryl, heterocyclyl, aryl(alkyl), heteroaryl(alkyl), heterocyclyl(alkyl), hydroxyalkyl, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heteroalicyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s) or 3 to 8 atoms in the ring(s). When composed of two or more rings, the rings may be connected together in a fused fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one, two, three or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, those described herein and the following: furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl or heteroalicyclic groups may be unsubstituted or substituted. Examples of such "heterocyclyl" or "heteroalicyclyl" groups include, but are not limited to, those described herein and the following: 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 1,3-thiazinane, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl), and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—), and butylene (—CH$_2$CH$_2$CH$_2$CH$_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) connected, as substituents, via a carbonyl group. Examples include formyl, acetyl, propanoyl, benzoyl and acryl. An acyl may be substituted or unsubstituted.

As used herein, "acylalkyl" refers to an acyl connected, as a substituent, via a lower alkylene group. Examples include aryl-C(=O)—(CH$_2$)$_n$— and heteroaryl-C(=O)—(CH$_2$)$_n$—, where n is an integer in the range of 1 to 6.

As used herein, "alkoxyalkyl" refers to an alkoxy group connected, as a substituent, via a lower alkylene group. Examples include C$_{1-4}$ alkyl-O—(CH$_2$)$_n$—, wherein n is an integer in the range of 1 to 6.

As used herein, "aminoalkyl" refers to an optionally substituted amino group connected, as a substituent, via a lower alkylene group. Examples include H$_2$N(CH$_2$)$_n$—, wherein n is an integer in the range of 1 to 6.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, chloro-fluoroalkyl, chloro-difluoroalkyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, chloro-fluoroalkyl, chloro-difluoroalkoxy and 2-fluoroisobutoxy. A haloalkoxy may be substituted or unsubstituted.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "carbonyl" group refers to a C=O group.

An "S-sulfonamido" group refers to a "—SO$_2$N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

A "urea" group refers to "N(R)—C(=O)—NR$_A$R$_B$ group in which R can be hydrogen or an alkyl, and R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A urea may be substituted or unsubstituted.

The term "halogen atom" or "halogen" as used herein, means any one of the radio-stable atoms of column 7 of the Periodic Table of the Elements, such as, fluorine, chlorine, bromine and iodine.

As used herein, " ------- " indicates a single or double bond, unless stated otherwise.

The term "interferon" is used herein as is commonly understood by one of ordinary skill in the art. Several types of interferons are known to those skilled in the art, such as Type I interferons, Type 2 interferons and Type 3 interferons. A non-limiting list of examples include: alpha-interferons, beta-interferons, delta-interferons, gamma interferons, lambda interferons, omega-interferons, tau-interferons, x-interferons, consensus interferons and asialo-interferons. Interferons can be pegylated. Examples of type 1 interferons include interferon alpha 1A, interferon alpha 1B, interferon alpha 2A, interferon alpha 2B, pegylated-interferon alpha 2a (PEGASYS, Roche), recombinant interferon alpha 2a (RO-FERON, Roche), inhaled interferon alpha 2b (AERX, Aradigm), pegylated-interferon alpha 2b (ALBUFERON, Human Genome Sciences/Novartis, PEGINTRON, Schering), recombinant interferon alpha 2b (INTRON A, Schering), pegylated interferon alpha 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical). Examples of type 2 interferons include interferon gamma 1, interferon gamma 2 and pegylated interferon gamma; and examples of type 3 interferons include interferon lambda 1, interferon lambda 2 and interferon lambda 3.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. As used herein, "amino acid" also includes amino acids wherein the main-chain carboxylic acid group has been converted to an ester group.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z, or a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Formula (I)

Some embodiments disclosed herein relate to a compound of Formula (I), or a pharmaceutically acceptable salt thereof, having the structure:

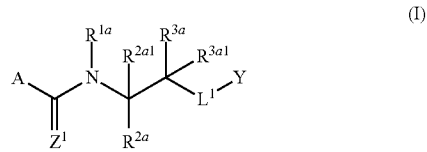

wherein: $L^1$ can be

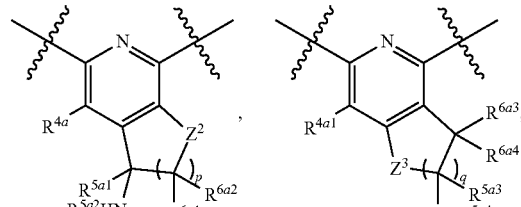

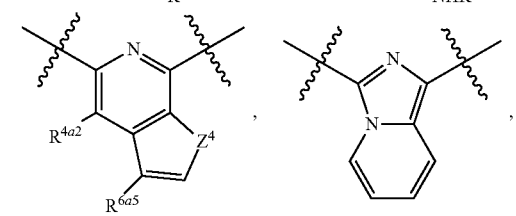

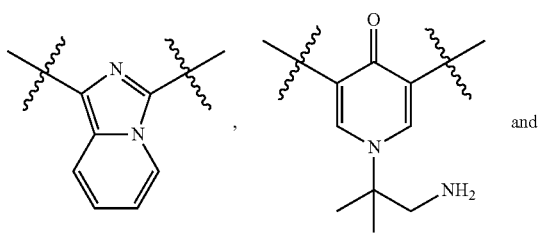

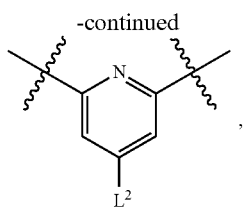

L² can be selected from

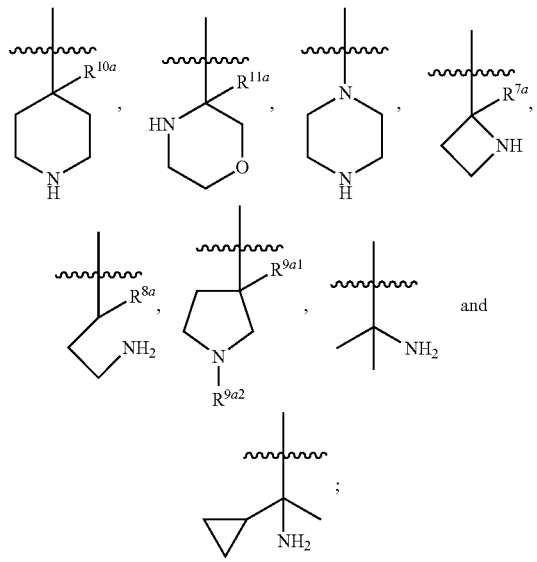

A can be selected from an optionally substituted cycloalkyl, an optionally substituted cycloalkenyl, an optionally substituted aryl, an optionally substituted heteroaryl and an optionally substituted heterocyclyl; Y can be selected from an optionally substituted aryl, an optionally substituted heteroaryl and an optionally substituted heterocyclyl; $R^{1a}$ can be hydrogen or an unsubstituted $C_{1-4}$ alkyl; $R^{2a}$ and $R^{2a1}$ can be each independently hydrogen or an unsubstituted $C_{1-4}$ alkyl; $R^{3a}$ and $R^{3a1}$ can be each independently hydroxy, $CHF_2$, $CF_3$ or $NH_2$; $R^{4a}$, $R^{4a1}$ and $R^{4a2}$ can be independently selected from hydrogen, halogen, hydroxy, an optionally substituted $C_{1-8}$ alkyl, an optionally substituted $C_{1-8}$ alkoxy and haloalkyl; $R^{5a1}$ and $R^{5a3}$ can be independently an unsubstituted $C_{1-6}$ alkyl, an unsubstituted $C_{3-6}$ cycloalkyl or —$(CH_2)_{1-4}OH$; $R^{5a2}$ and $R^{5a4}$ can be independently hydrogen, hydroxy, an unsubstituted $C_{1-6}$ alkyl, an optionally substituted monocyclic heterocyclyl, —C(=O)$R^{5a5}$, an unsubstituted —C-amido, —C(=NH)-an unsubstituted $C_{1-6}$ alkyl; or $R^{5a1}$ and $R^{5a2}$ can be taken together with the atoms they are attached to form an optionally substituted 4 to 6 membered ring; $R^{5a3}$ and $R^{5a4}$ can be taken together with the atoms they are attached to form an optionally substituted 4 to 6 membered ring; $R^{5a5}$ can be an unsubstituted $C_{1-4}$ alkyl; each $R^{6a1}$, each $R^{6a2}$, each $R^{6a3}$ and each $R^{6a4}$ can be independently selected from hydrogen, halogen, an unsubstituted $C_{1-6}$ alkyl and hydroxy; $R^{6a5}$ can be selected from halogen, an unsubstituted $C_{1-6}$ alkyl and hydroxy; $R^{7a}$ and $R^{8a}$ can be each independently an unsubstituted $C_{1-6}$ alkyl; $R^{9a1}$, $R^{9a2}$, $R^{10a}$ and $R^{11a}$ can be independently hydrogen or an unsubstituted $C_{1-6}$ alkyl; $Z^1$ can be O (oxygen) or S (sulfur); $Z^2$ can be O (oxygen), $NR^Z$ or $CR^{Z1}R^{Z2}$; $Z^3$ can be O (oxygen), $NR^{Z3}$ or $CR^{Z4}R^{Z5}$; $Z^4$ can be O (oxygen), $NR^{Z6}$ or $CR^{Z7}R^{Z8}$; $R^Z$, $R^{Z1}$, $R^{Z2}$, $R^{Z3}$, $R^{Z4}$, $R^{Z5}$, $R^{Z6}$, $R^{Z7}$ and $R^{Z8}$ can be independently hydrogen or an unsubstituted $C_{1-4}$ alkyl; and p and q can be independently 1 or 2.

Some embodiments disclosed herein relate to a compound of Formula (I), or a pharmaceutically acceptable salt thereof, having the structure:

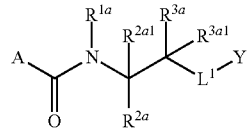

wherein: L¹ can be

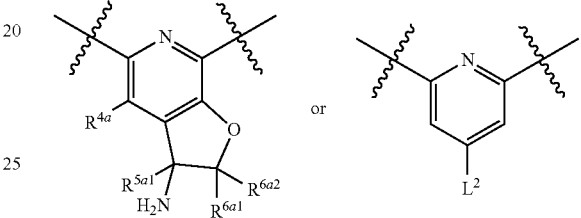

L² can be selected

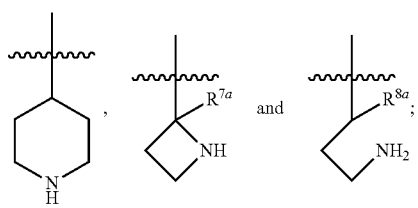

A can be selected from an optionally substituted cycloalkyl, an optionally substituted cycloalkenyl, an optionally substituted aryl, an optionally substituted heteroaryl and an optionally substituted heterocyclyl; Y can be selected from an optionally substituted aryl, an optionally substituted heteroaryl and an optionally substituted heterocyclyl; $R^{1a}$ can be hydrogen or an unsubstituted $C_{1-4}$ alkyl; $R^{2a}$ and $R^{2a1}$ can be each independently hydrogen or an unsubstituted $C_{1-4}$ alkyl; $R^{3a}$ and $R^{3a1}$ can be each independently hydroxy, $CHF_2$ or $CF_3$; $R^{4a}$ can be selected from hydrogen, halogen, hydroxy, an optionally substituted $C_{1-8}$ alkyl, an optionally substituted $C_{1-8}$ alkoxy and haloalkyl; $R^{5a1}$ can be an unsubstituted $C_{1-6}$ alkyl or —$(CH_2)_{1-4}OH$; $R^{6a1}$ and $R^{6a2}$ can be each independently selected from hydrogen, halogen, an unsubstituted $C_{1-6}$ alkyl and hydroxy; and $R^{7a}$ and $R^{8a}$ can be each independently an unsubstituted $C_{1-6}$ alkyl.

In some embodiments, $R^{1a}$ can be hydrogen. In other embodiments, $R^{1a}$ can be an unsubstituted $C_{1-4}$ alkyl. For example, $R^{1a}$ can be methyl, ethyl, n-propyl, iso-propyl, n-butyl, iso-butyl or tert-butyl.

In some embodiments, both $R^{2a}$ and $R^{2a1}$ can be hydrogen. In other embodiments, $R^{2a}$ can be hydrogen and $R^{2a1}$ can be an unsubstituted $C_{1-4}$ alkyl. In still other embodiments, $R^{2a}$ and $R^{2a1}$ each can be an unsubstituted $C_{1-4}$ alkyl.

In some embodiments, $R^{3a}$ can be hydroxy, and $R^{3a1}$ can be $CF_3$. In other embodiments, $R^{3a}$ can be hydroxy, and $R^{3a1}$ can be $CHF_2$. In still other embodiments, $R^{3a}$ can be hydroxy, and $R^{3a1}$ can be $NH_2$. In some embodiments, the carbon to which $R^{3a}$ and $R^{3a1}$ are attached can be a chiral center. When the carbon to which $R^{3a}$ and $R^{3a1}$ are attached a chiral center, in some embodiments, the carbon can have a (R)-configuration. In other embodiments, the carbon to which $R^{3a}$ and $R^{3a1}$ are attached can have a (S)-configuration.

In some embodiments, $L^1$ can be

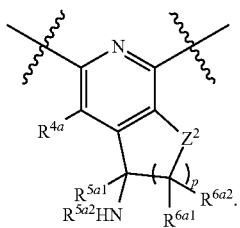

Various substituents can be present at the position indicted with $R^{4a}$. In some embodiments, $R^{4a}$ can be hydrogen. In other embodiments, $R^{4a}$ can be halogen (such as fluoro, chloro, bromo or iodo). In still other embodiments, $R^{4a}$ can be hydroxy. In yet still other embodiments, $R^{4a}$ can be an optionally substituted $C_{1-8}$ alkyl. In some embodiments, $R^{4a}$ can be an unsubstituted $C_{1-8}$ alkyl or an unsubstituted $C_{1-4}$ alkyl. In other embodiments, $R^{4a}$ can be a substituted $C_{1-8}$ alkyl or a substituted $C_{1-4}$ alkyl. In some embodiments, $R^{4a}$ can be an optionally substituted $C_{1-8}$ alkoxy. In some embodiments, $R^{4a}$ can be an unsubstituted $C_{1-8}$ alkoxy. In other embodiments, $R^{4a}$ can be a substituted $C_{1-8}$ alkoxy. Examples of suitable alkoxy groups include, but are not limited to, methoxy, ethoxy, n-propoxy, iso-propoxy, n-butoxy, iso-butoxy, tert-butoxy, pentoxy (branched or straight-chained) and hexoxy (branched or straight-chained). In other embodiments, $R^{4a}$ can be a haloalkyl, for example, $CF_3$, $CHF_2$, $-(CH_2)_{1-4}CF_3$ and $-(CH_2)_{1-4}CHF_2$.

A variety of substituents can also be present on lower ring of the bicyclic ring of Formula (I). In some embodiments, $R^{5a1}$ can be an unsubstituted $C_{1-6}$ alkyl. Examples include methyl, ethyl, n-propyl, iso-propyl, n-butyl, iso-butyl, tert-butyl, pentyl (branched or straight-chained) and hexyl (branched or straight-chained). In some embodiments, $R^{5a1}$ can be methyl. In other embodiments, $R^{5a1}$ can be an unsubstituted $C_{3-6}$ cycloalkyl. For example, $R^{5a1}$ can be one of the following unsubstituted cycloalkyls: cyclopropyl, cyclobutyl, cyclopentyl and cyclohexyl. In still other embodiments, $R^{5a1}$ can be $-(CH_2)_{1-4}OH$. For example, $R^{5a1}$ can be $-CH_2OH$, $-CH_2CH_2OH$, $-CH_2CH_2CH_2OH$ or $-CH_2CH_2CH_2CH_2OH$.

In some embodiments, $R^{5a2}$ can be hydrogen. In other embodiments, $R^{5a2}$ can be hydroxy. In still other embodiments, $R^{5a2}$ can be an unsubstituted $C_{1-6}$ alkyl. In yet still other embodiments, $R^{5a2}$ can be an optionally substituted monocyclic heterocyclyl. For example, $R^{5a2}$ can be an optionally substituted 3-6 membered monocyclic heterocyclyl. In some embodiments, $R^{5a2}$ can be an unsubstituted 3-6 membered monocyclic heterocyclyl. In some embodiments, $R^{5a2}$ can be $-C(=O)R^{5a5}$, wherein $R^{5a5}$ can be an unsubstituted $C_{1-4}$ alkyl (such as methyl, ethyl, n-propyl, iso-propyl, n-butyl, iso-butyl and tert-butyl). In other embodiments, $R^{5a2}$ can be an unsubstituted $-C$-amido. An example of a suitable an unsubstituted $-C$-amido is $-C(=O)NH_2$. In other embodiments, $R^{5a2}$ can be $-C(=NH)$-an unsubstituted $C_{1-6}$ alkyl. Suitable $C_{1-6}$ alkyls are described herein. In some embodiments, $R^{5a2}$ can be $-C(=NH)CH_3$.

In some embodiments, $R^{5a1}$ and $R^{5a2}$ can each be hydrogen. In other embodiments, $R^{5a1}$ can be an unsubstituted $C_{1-6}$ alkyl, and $R^{5a2}$ can be hydrogen. In still other embodiments, $R^{5a1}$ can be an unsubstituted $C_{3-6}$ cycloalkyl, and $R^{5a2}$ can be hydrogen. In yet still other embodiments, $R^{5a1}$ can be an unsubstituted $C_{1-6}$ alkyl, and $R^{5a2}$ can be hydroxy. In some embodiments, $R^{5a1}$ can be an unsubstituted $C_{1-6}$ alkyl, and $R^{5a2}$ can be $-C(=O)R^{5a5}$. In other embodiments, $R^{5a1}$ and $R^{5a2}$ can each be an unsubstituted $C_{1-6}$ alkyl. In still other embodiments, $R^{5a1}$ can be an unsubstituted $C_{1-6}$ alkyl, and $R^{5a2}$ can be an optionally substituted 3-6 membered monocyclic heterocyclyl. In yet still other embodiments, $R^{5a1}$ can be an unsubstituted $C_{1-6}$ alkyl, and $R^{5a2}$ can be an unsubstituted $-C$-amido. In some embodiments, $R^{5a1}$ can be an unsubstituted $C_{1-6}$ alkyl, and $R^{5a2}$ can be $-C(=NH)$-an unsubstituted $C_{1-6}$ alkyl.

In some embodiments, p can be 1, and the lower ring can be a five-membered ring. In other embodiments, p can be 2, and the lower ring can be a six-membered ring. In some embodiments, $R^{6a1}$ and $R^{6a2}$ can be the same. In other embodiments, $R^{6a1}$ and $R^{6a2}$ can be different. In some embodiments, one of $R^{6a1}$ and $R^{6a2}$ can be hydrogen and the other of $R^{6a1}$ and $R^{6a2}$ can be halogen, an unsubstituted $C_{1-6}$ alkyl or hydroxy. In some embodiments, one of $R^{6a1}$ and $R^{6a2}$ can be hydrogen and the other of one of $R^{6a1}$ and $R^{6a2}$ can be halogen. In other embodiments, one of $R^{6a1}$ and $R^{6a2}$ can be hydrogen and the other of one of $R^{6a1}$ and $R^{6a2}$ can be an unsubstituted $C_{1-6}$ alkyl, such as those described herein. In still other embodiments, one of $R^{6a1}$ and $R^{6a2}$ can be hydrogen and the other of one of $R^{6a1}$ and $R^{6a2}$ can be hydroxy. In some embodiments, $R^{6a1}$ and $R^{6a2}$ can be each hydrogen.

In some embodiments, $Z^2$ can be O (oxygen). In other embodiments, $Z^2$ can be $NR^Z$. When $Z^2$ is $NR^Z$, $Z^2$ can be NH. Alternatively, $NR^Z$ can be N (an unsubstituted $C_{1-4}$ alkyl). Examples of unsubstituted $C_{1-4}$ alkyl groups are described herein. In some embodiments, $NR^Z$ can be $N(CH_3)$. In other embodiments, $Z^2$ can be $CR^{Z1}R^{Z2}$, wherein $R^{Z1}$ and $R^{Z2}$ can be independently hydrogen or an unsubstituted $C_{1-4}$ alkyl. In some embodiments, $R^{Z1}$ and $R^{Z2}$ can each be hydrogen. In other embodiments, $R^{Z1}$ and $R^{Z2}$ can each be an unsubstituted $C_{1-4}$ alkyl. In still other embodiments, $R^{Z1}$ can be hydrogen, and $R^{Z2}$ can be an unsubstituted $C_{1-4}$ alkyl.

In other embodiments, $L^1$ can be

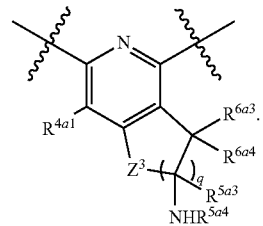

In some embodiments, $R^{5a3}$ can be an unsubstituted $C_{1-6}$ alkyl. Examples include methyl, ethyl, n-propyl, iso-propyl, n-butyl, iso-butyl, tert-butyl, pentyl (branched or straight-chained) and hexyl (branched or straight-chained). In some embodiments, $R^{5a3}$ can be methyl. In other embodiments, $R^{5a3}$ can be an unsubstituted $C_{3-6}$ cycloalkyl. For example, $R^{5a3}$ can be one of the following unsubstituted cycloalkyls: cyclopropyl, cyclobutyl, cyclopentyl and cyclohexyl. In still other embodiments, $R^{5a3}$ can be $-(CH_2)_{1-4}OH$. For example, $R^{5a3}$ can be —CH$_2$OH, —CH$_2$CH$_2$OH, —CH$_2$CH$_2$CH$_2$OH or —CH$_2$CH$_2$CH$_2$CH$_2$OH.

In some embodiments, $R^{5a4}$ can be hydrogen. In other embodiments, $R^{5a4}$ can be hydroxy. In still other embodiments, $R^{5a4}$ can be an unsubstituted C$_{1-6}$ alkyl. In yet still other embodiments, $R^{5a4}$ can be an optionally substituted monocyclic heterocyclyl. For example, $R^{5a4}$ can be an optionally substituted 3-6 membered monocyclic heterocyclyl. In some embodiments, $R^{5a4}$ can be an unsubstituted 3-6 membered monocyclic heterocyclyl. In some embodiments, $R^{5a4}$ can be —C(=O)R$^{5a5}$, wherein $R^{5a5}$ can be an unsubstituted C$_{1-4}$ alkyl (such as methyl, ethyl, n-propyl, iso-propyl, n-butyl, iso-butyl and tert-butyl). In other embodiments, $R^{5a4}$ can be an unsubstituted —C-amido. An example of a suitable an unsubstituted —C-amido is —C(=O)NH$_2$. In other embodiments, $R^{5a4}$ can be —C(=NH)-an unsubstituted C$_{1-6}$ alkyl. Suitable C$_{1-6}$ alkyls are described herein. In some embodiments, $R^{5a4}$ can be —C(=NH)CH$_3$.

In some embodiments, $R^{5a3}$ and $R^{5a4}$ can each be hydrogen. In other embodiments, $R^{5a3}$ can be an unsubstituted C$_{1-6}$ alkyl, and $R^{5a4}$ can be hydrogen. In still other embodiments, $R^{5a3}$ can be an unsubstituted C$_{3-6}$ cycloalkyl, and $R^{5a4}$ can be hydrogen. In yet still other embodiments, $R^{5a3}$ can be an unsubstituted C$_{1-6}$ alkyl, and $R^{5a4}$ can be hydroxy. In some embodiments, $R^{5a3}$ can be an unsubstituted C$_{1-6}$ alkyl, and $R^{5a4}$ can be —C(=O)R$^{5a5}$. In other embodiments, $R^{5a3}$ and $R^{5a4}$ can each be an unsubstituted C$_{1-6}$ alkyl. In still other embodiments, $R^{5a3}$ can be an unsubstituted C$_{1-6}$ alkyl, and $R^{5a4}$ can be an optionally substituted 3-6 membered monocyclic heterocyclyl. In yet still other embodiments, $R^{5a3}$ can be an unsubstituted C$_{1-6}$ alkyl, and $R^{5a4}$ can be an unsubstituted —C-amido. In some embodiments, $R^{5a3}$ can be an unsubstituted C$_{1-6}$ alkyl, and $R^{5a4}$ can be —C(=NH)-an unsubstituted C$_{1-6}$ alkyl.

In some embodiments, q can be 1, and the lower ring can be a five-membered ring. In other embodiments, q can be 2, and the lower ring can be a six-membered ring. In some embodiments, $R^{6a3}$ and $R^{6a4}$ can be the same. In other embodiments, $R^{6a3}$ and $R^{6a4}$ can be different. In some embodiments, one of $R^{6a3}$ and $R^{6a4}$ can be hydrogen and the other of $R^{6a3}$ and $R^{6a4}$ can be halogen, an unsubstituted C$_{1-6}$ alkyl or hydroxy. In some embodiments, one of $R^{6a3}$ and $R^{6a4}$ can be hydrogen and the other of one of $R^{6a3}$ and $R^{6a4}$ can be halogen. In other embodiments, one of $R^{6a3}$ and $R^{6a4}$ can be hydrogen and the other of one of $R^{6a3}$ and $R^{6a4}$ can be an unsubstituted C$_{1-6}$ alkyl, such as those described herein. In still other embodiments, one of $R^{6a3}$ and $R^{6a4}$ can be hydrogen and the other of one of $R^{6a3}$ and $R^{6a4}$ can be hydroxy. In some embodiments, $R^{6a3}$ and $R^{6a4}$ can be each hydrogen.

In some embodiments, $Z^3$ can be O (oxygen). In other embodiments, $Z^3$ can be NR$^{Z3}$. When $Z^3$ is NR$^{Z3}$, $Z^3$ can be NH. Alternatively, NR$^{Z3}$ can be N (an unsubstituted C$_{1-4}$ alkyl). Examples of unsubstituted C$_{1-4}$ alkyl groups are described herein. In some embodiments, NR$^{Z3}$ can be N(CH$_3$). In other embodiments, $Z^3$ can be CR$^{Z4}$R$^{Z5}$, wherein $R^{Z4}$ and $R^{Z5}$ can be independently hydrogen or an unsubstituted C$_{1-4}$ alkyl. In some embodiments, $R^{Z4}$ and $R^{Z5}$ can each be hydrogen. In other embodiments, $R^{Z4}$ and $R^{Z5}$ can each be an unsubstituted C$_{1-4}$ alkyl. In still other embodiments, $R^{Z4}$ can be hydrogen, and $R^{Z5}$ can be an unsubstituted C$_{1-4}$ alkyl.

In still other embodiments, $L^1$ can be

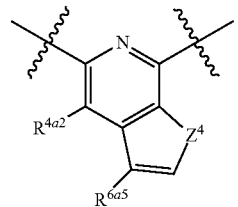

In some embodiments, $R^{4a2}$ can be hydrogen. In other embodiments, $R^{4a2}$ can be halogen. In still other embodiments, $R^{4a2}$ can be hydroxy. In yet still other embodiments, $R^{4a2}$ can be an optionally substituted C$_{1-8}$ alkyl, such as those described herein. In some embodiments, $R^{4a2}$ can be an optionally substituted C$_{1-8}$ alkoxy. In other embodiments, $R^{4a2}$ can be haloalkyl, for example, CF$_3$. In some embodiments, $R^{6a5}$ can be halogen. In other embodiments, $R^{6a5}$ can be an unsubstituted C$_{1-6}$ alkyl. Suitable unsubstituted C$_{1-6}$ alkyls are described herein. In still other embodiments, $R^{6a5}$ can be hydroxy. In some embodiments, $Z^4$ can be O. In some embodiments, $Z^4$ can be NR$^{Z6}$, for example, NH or N (an unsubstituted C$_{1-4}$ alkyl). In still embodiments, $Z^4$ can be CR$^{Z7}$R$^{Z8}$. When $Z^4$ is CR$^{Z7}$R$^{Z8}$, each of $R^{Z7}$ and $R^{Z8}$ can be hydrogen. Alternatively, when $Z^4$ is CR$^{Z7}$R$^{Z8}$, at least one of $R^{Z7}$ and $R^{Z8}$ can be an unsubstituted C$_{1-6}$ alkyl. In some embodiments, one of $R^{Z7}$ and $R^{Z8}$ can be an unsubstituted C$_{1-6}$ alkyl, and the other of $R^{Z7}$ and $R^{Z8}$ can be hydrogen. In other embodiments, $R^{Z7}$ and $R^{Z8}$ can each be hydrogen.

In some embodiments, $L^1$ can be

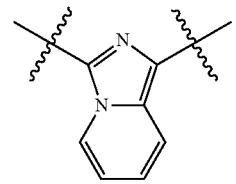

In other embodiments, $L^1$ can be

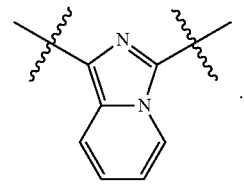 [SMILES: *c1nc(*)n2ccccc12]

In still other embodiments, $L^1$ can be

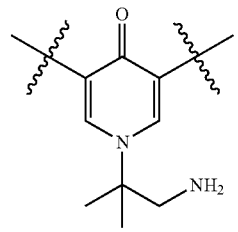

In some embodiments, $L^1$ can be

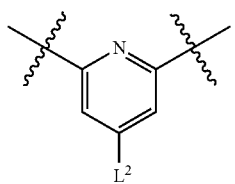

In addition to $L^2$, the pyridinyl ring can be not be further substituted (as shown) or substituted with one or two substituents, such as those substituents listed in the term "substituted." When two or more substituents are present, the substituents can be the same or different. As an example, $L^1$ can be

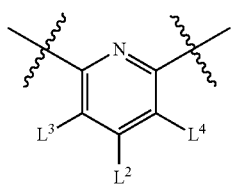, wherein $L^3$ and $L^4$ can be independently selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl, an optionally substituted O-amido and an optionally substituted C-carboxy. In some embodiments, $L^3$ and $L^4$ can be each hydrogen.

When $L^1$ is

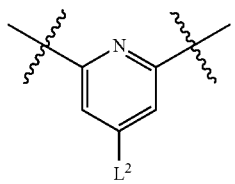, in some embodiments, $L^2$ can be

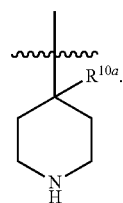

In some embodiments, the piperdinyl can be unsubstituted (wherein $R^{10a}$ is hydrogen). In other embodiments, the piperdinyl ring can be substituted with one or more substituents from those substituents listed in the term "substituted." As an example, in some embodiments, $R^{10a}$ can be an unsubstituted $C_{1-6}$ alkyl (such as methyl, ethyl, n-propyl, iso-propyl, n-butyl, iso-butyl, tert-butyl, pentyl (straight-chained or branched) or hexyl (straight-chained or branched).

In other embodiments, $L^2$ can be

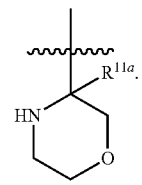

In some embodiments, the morpholinyl ring can be unsubstituted when $R^{11a}$ is hydrogen. In other embodiments, the morpholinyl ring can be substituted, for example, with one or more substituents including those listed in the term "substituted." In some embodiments, $R^{11a}$ can be an unsubstituted $C_{1-6}$ alkyl. Examples of suitable $C_{1-6}$ alkyls are described herein.

In still other embodiments, $L^2$ can be

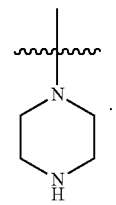

The piperazinyl ring can be unsubstituted or substituted with one or more substituents including those listed in the term "substituted."

In yet still other embodiments, $L^2$ can be

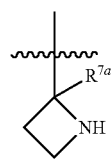

wherein $R^{7a}$ can be an unsubstituted $C_{1-6}$ alkyl. Suitable unsubstituted $C_{1-6}$ alkyls are described herein. In some embodiments, $R^{7a}$ can be an unsubstituted $C_{1-4}$ alkyl. In some embodiments, $R^{7a}$ can be methyl. The four-membered ring of $L^2$ can be unsubstituted (as shown) or substituted. When substituted, one or more substituents can be present, and the possible substituents include those listed in the term "substituted."

In some embodiments, $L^2$ can be

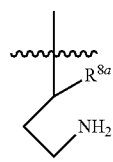, wherein $R^{8a}$ can be an unsubstituted $C_{1-6}$ alkyl. Examples of unsubstituted $C_{1-6}$ alkyls are described herein. In some embodiments, $R^{8a}$ can be an unsubstituted $C_{1-4}$ alkyl. In some embodiments, $R^{8a}$ can be methyl. The alkylene chain between the pyridinyl ring and the NH$_2$ group of $L^2$ can be further substituted or be unsubstituted, as shown. One or more substituents can be present on the alkylene chain when substituted. Examples of suitable substituents that can be present include those listed in the term "substituted."

In other embodiments, $L^2$ can be

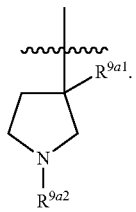

In some embodiments, $R^{9a1}$ and $R^{9a2}$ can each be hydrogen. In other embodiments, $R^{9a1}$ can be hydrogen, and $R^{9a2}$ can be an unsubstituted $C_{1-6}$ alkyl. In still other embodiments, $R^{9a1}$ can be an unsubstituted $C_{1-6}$ alkyl, and $R^{9a2}$ can be hydrogen. In yet still other embodiments, $R^{9a1}$ and $R^{9a2}$ can each be an unsubstituted $C_{1-6}$ alkyl. Examples of suitable an unsubstituted $C_{1-6}$ alkyl groups are described herein.

In still other embodiments, $L^2$ can be

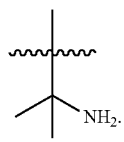

In yet still other embodiments, $L^2$ can be

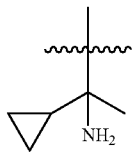

In some embodiments, a compound of Formula (I), or a pharmaceutically acceptable salt thereof, has a structure selected from Formula (Ia), Formula (Ia1), Formula (Ia2), Formula (Ia3), Formula (Ib), Formula (Ib1), Formula (Ib2), Formula (Ic), Formula (Id), Formula (Ie), Formula (If), Formula (Ig), Formula (Ig1), Formula (Ig2), Formula (Ig3), Formula (Ig4), Formula (Ig5), Formula (Ig6), Formula (Ih), Formula (Ij), Formula (Ik), Formula (Il), Formula (Im), Formula (In), Formula (In1), Formula (In2), Formula (In3), Formula (Io), Formula (Io1), Formula (Io2), Formula (Ip), Formula (Iq) and Formula (Ir):

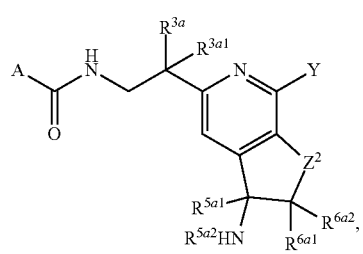
(Ia)

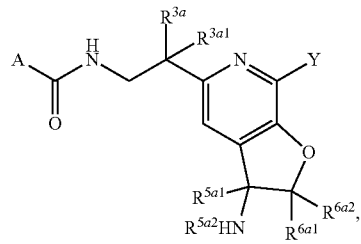
(Ia1)

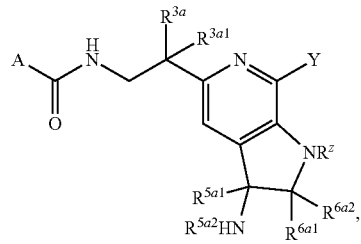
(Ia2)

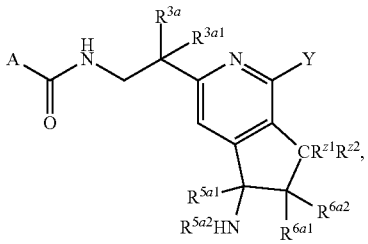
(Ia3)

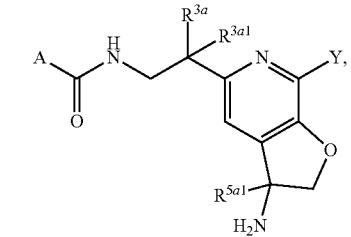
(Ib)

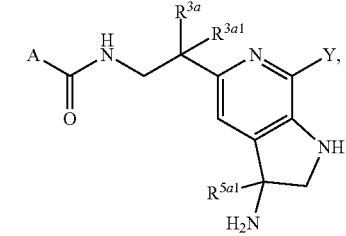
(Ib1)

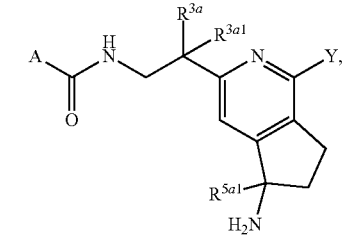
(Ib2)

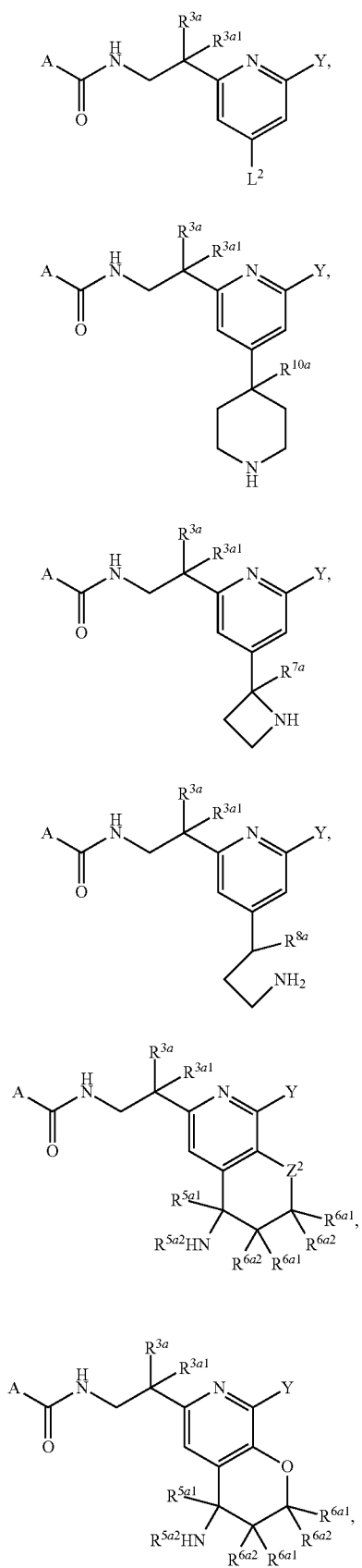
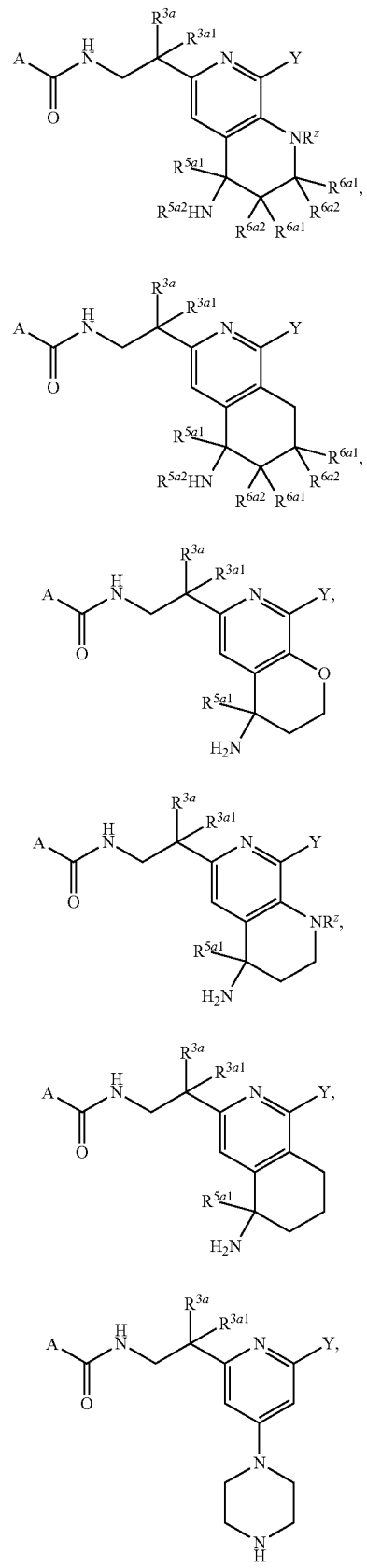

-continued
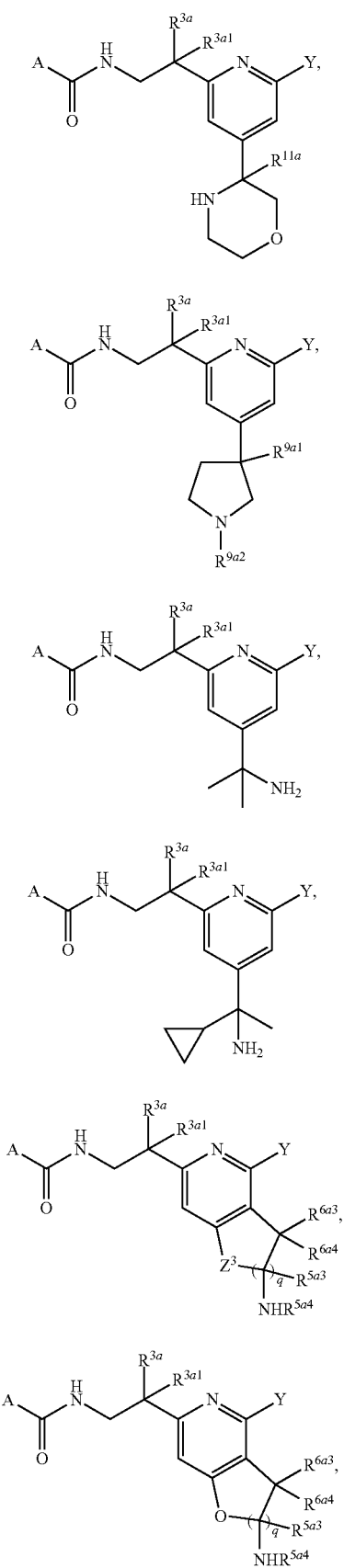
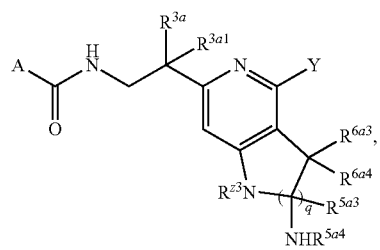
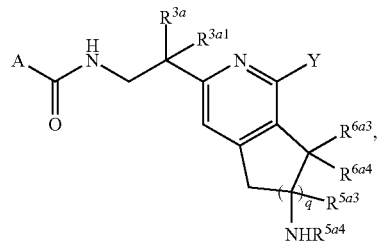
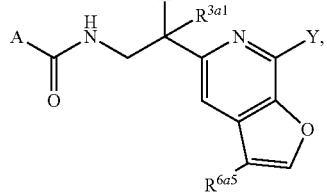
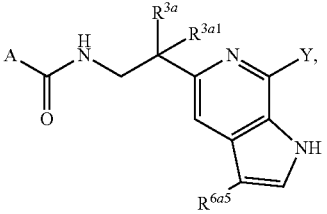
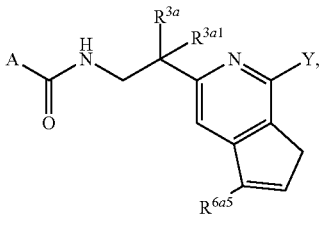
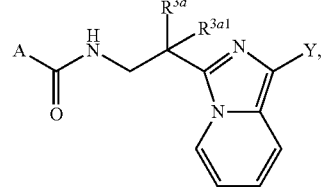
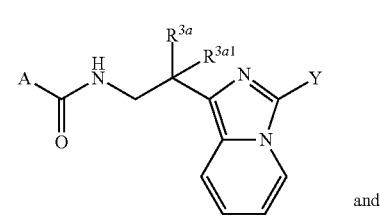
and -continued

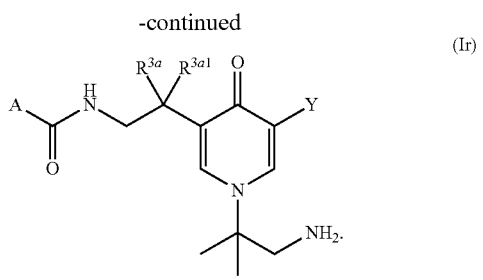

(Ir)

In some embodiments of this paragraph, $R^{3a}$ can be hydroxy, and $R^{3a1}$ can be $CF_3$. In some embodiments of this paragraph, Y can be a substituted phenyl (for example, a para-substituted phenyl). In some embodiments of this paragraph, A can be a substituted phenyl. In some embodiments of this paragraph, A can be a substituted heteroaryl. In some embodiments of this paragraph, A can be a substituted heterocyclyl.

In some embodiments, A can be substituted. In other embodiments, A can be unsubstituted. When A is substituted, possible substituent(s) includes those provided in the list of "substituted" along with those described herein.

In some embodiments, A can be an optionally substituted aryl. For example, A can be an optionally substituted phenyl. In some embodiments, A can be a para-substituted phenyl, a meta-substituted phenyl or an ortho-substituted phenyl. In some embodiments, A can be a di-substituted phenyl. For example, A can be a 3,4-substituted phenyl, such as

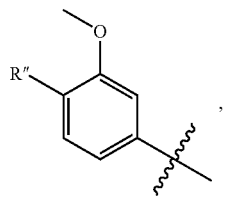

wherein R″ can be a substituent from the list of "substituted" along with those substituents described herein. In some embodiments, A can be a substituted phenyl that is substituted with 3 more substituents. In other embodiments, A can be unsubstituted phenyl. In some embodiments, A can be an optionally substituted naphthyl.

In some embodiments and without limitation, A can be a phenyl substituted with one or more substituents selected from an unsubstituted $C_{1-4}$ alkyl, an optionally substituted $C_{1-4}$ alkyl, cycloalkyl, hydroxy, an optionally substituted $C_{1-4}$ alkoxy, $C_{1-4}$ alkoxy, halogen, haloalkyl, an optionally substituted haloalkoxy, nitro, amino, mono-substituted amino, di-substituted amino, —O-amido, sulfenyl, alkyoxyalkyl, an optionally substituted aryl (for example, an optionally substituted phenyl), an optionally substituted monocyclic heteroaryl, an optionally substituted monocyclic heterocyclyl, an optionally substituted aryl($C_{1-4}$ alkyl), an optionally substituted monocyclic heteroaryl($C_{1-4}$ alkyl), an optionally substituted monocyclic heterocyclyl($C_{1-4}$ alkyl), hydroxyalkyl and aminoalkyl. In some embodiments, the optionally substituted $C_{1-4}$ alkoxy can be further substituted, for example, further substituted with a substituent selected from $C_{1-4}$ alkyl, halo, hydroxy, C-carboxy, C-amido, amino, mono-alkyl amine, di-alkyl amine and an amino acid. In some embodiments, the optionally substituted haloalkoxy can be further substituted, for example, further substituted with an $C_{1-4}$ alkoxy. In some embodiments, the optionally substituted heteroaryl can be further substituted, for example, further substituted with an $C_{1-4}$ alkyl.

Examples of suitable substituents include, but are not limited to, methyl, ethyl, propyl, butyl, hydroxy, methoxy, ethoxy, n-propoxy, iso-propoxy, n-butoxy, iso-butoxy, t-butoxy, phenoxy, bromo, chloro, fluoro, trifluoromethyl, difluoromethoxy, trifluoromethoxy, cyano, N,N-di-methyl-amine, N,N-di-ethyl-amine, N-methyl-N-ethyl-amine, N-methyl-amino, N-ethyl-amino, amino, N-amido, N-sulfonamido, alkylthio, an optionally substituted phenyl, an optionally substituted imidazole, an optionally substituted morpholinyl, an optionally substituted pyrazole, an optionally substituted pyrrolidinyl, an optionally substituted pyridinyl, an optionally substituted piperidinyl, an optionally substituted piperidinone, an optionally substituted pyrrolidinone, an optionally substituted pyrimidine, an optionally substituted pyrazine, an optionally substituted 1,2,4-oxadiazole, —$(CH_2)_{1-4}$—OH, —$(CH_2)_{1-2}$—$NH(CH_3)$, an optionally substituted —$(CH_2)_{1-2}$-imidazole, an optionally substituted —$(CH_2)_{1-2}$-pyrrolidinone, an optionally substituted —$(CH_2)_{1-2}$-imidazolidinone, —$O(CH_2)_2$—$NH_2$, —$O(CH_2)_2$—$NH(CH_3)$, —$O(CH_2)_2$—$N(CH_3)_2$, —$O$—$(CH_2)_{2-4}OH$, —$O(CH_2)_2OCH_3$, an optionally substituted —$O(CH_2)_{0-2}$-cyclopentanone, an optionally substituted —$O(CH_2)_{0-2}$pyrrolidinone, an optionally substituted —$O(CH_2)_{0-2}$-morpholinyl, an optionally substituted —$O(CH_2)_{0-2}$-triazole, an optionally substituted —$O(CH_2)_{0-2}$-imidazole, an optionally substituted —$O(CH_2)_{0-2}$-pyrazole, an optionally substituted —$O(CH_2)_{0-2}$-tetrahydrofuran, an optionally substituted —$O(CH_2)_{0-2}$-pyrrolidinone, an optionally substituted —$O(CH_2)_{0-2}$-tetrazole, an optionally substituted —$O(CH_2)_{0-2}$-tetrazolone, —$NH(CH_2)_{1-2}OH$,

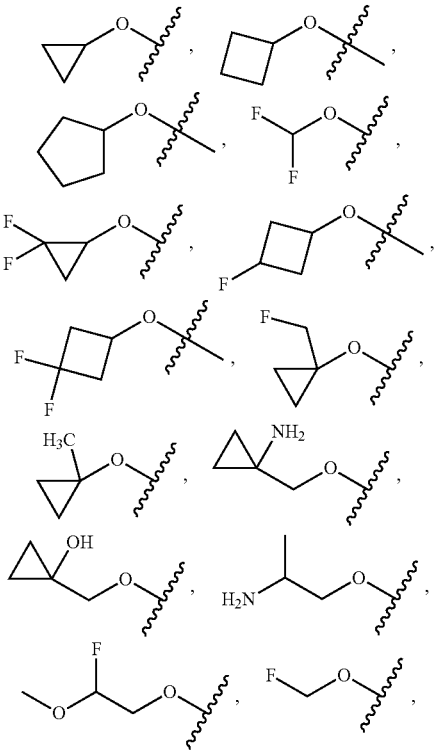

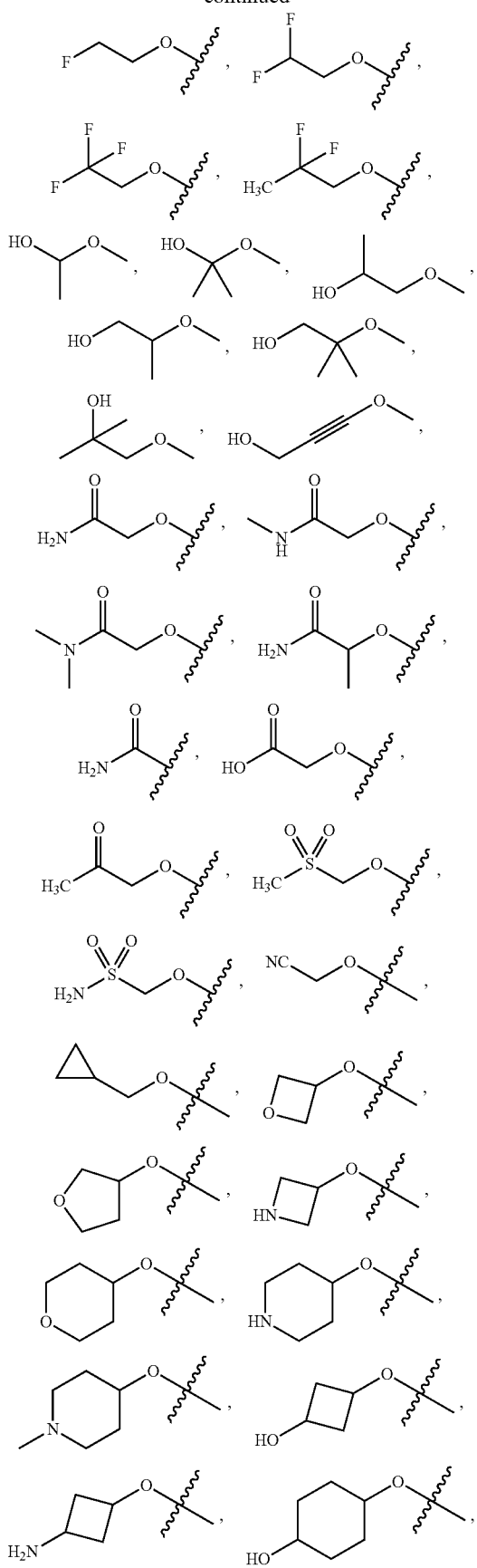

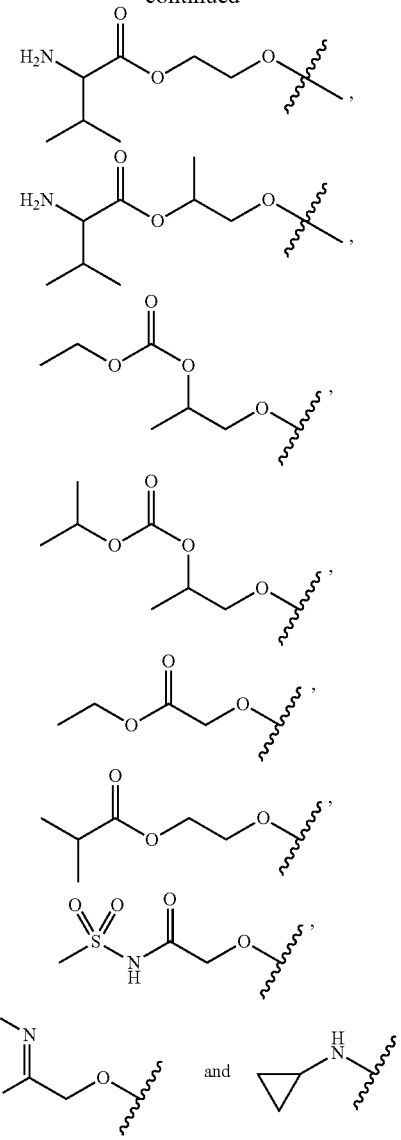

In some embodiments, A can be an optionally substituted cycloalkyl. Suitable examples of optionally substituted cycloalkyls include, but are not limited to, an optionally substituted cyclohexyl and an optionally substituted cycloheptyl. In other embodiments, A can be an optionally substituted cycloalkenyl, for example, an optionally substituted cyclohexenyl. In some embodiments, A can be an optionally substituted bi-cyclic cycloalkenyl, such as

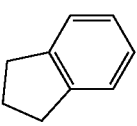

In some embodiments, A can be an optionally substituted mono-cyclic heteroaryl. In some embodiments, A can be an optionally substituted mono-cyclic 5-membered heteroaryl. In other embodiments, A can be an optionally substituted mono-cyclic 6-membered heteroaryl. In some embodiments, A can be an optionally substituted bi-cyclic heteroaryl.

In some embodiments, the optionally substituted heteroaryl can be selected from an optionally substituted imidazole, an optionally substituted indole, an optionally substituted thiazole, an optionally substituted furan, an optionally substituted thiophene, an optionally substituted pyrrole, an optionally substituted pyridine, an optionally substituted pyrimidine, an optionally substituted pyrazine, an optionally substituted pyrazole, an optionally substituted quinolone, an optionally substituted imidazole, an optionally substituted oxazole, an optionally substituted isoxazole, an optionally substituted benzoimidazole, an optionally substituted benzooxazole, an optionally substituted benzothiazole and an optionally substituted imidazo[1,2-a]pyrimidine. In some embodiments, A can be an optionally substituted thiophene. In other embodiments, A can be an optionally substituted thiazole. In still other embodiments, A can be an optionally substituted pyridine. In yet still other embodiments, A can be an optionally substituted pyrimidine. In some embodiments, A can be an optionally substituted pyrazine. In other embodiments, A can be an optionally substituted imidazole. In still other embodiments, A can be an optionally substituted benzoimidazole, an optionally substituted benzooxazole or an optionally substituted benzothiazole. In yet still other embodiments, A can be an optionally substituted indole. In some embodiments, A can be an optionally substituted pyrazole.

In some embodiments, A can be an optionally substituted heterocyclyl, for example, an optionally substituted monocyclic heterocyclyl or an optionally substituted bi-cyclic heterocyclyl. In some embodiments, A can be an optionally substituted

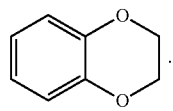

In other embodiments, A can be an optionally substituted

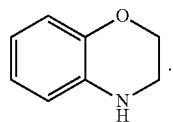

In still other embodiments, A can be an optionally substituted

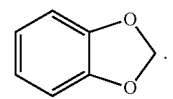

In yet still other embodiments, A can be an optionally substituted

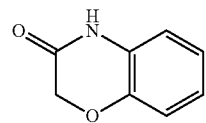

In some embodiments, A can be an optionally substituted

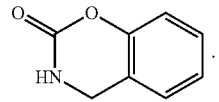

In other embodiments, A can be an optionally substituted

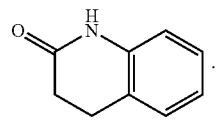 [SMILES: O=C1CCc2ccccc2N1]

In still other embodiments, A can be an optionally substituted

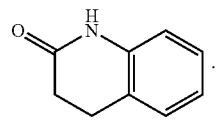 [SMILES: O=C1CCc2ccccc2N1]

In yet still other embodiments, A can be an optionally substituted

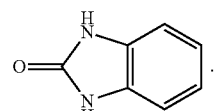

In some embodiments, A can be an optionally substituted

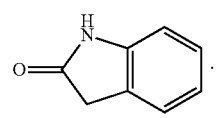

In other embodiments, A can be an optionally substituted

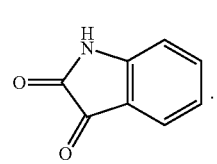 [SMILES: O=C1Nc2ccccc2C1=O]

In still other embodiments, A can be an optionally substituted

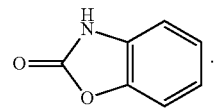

In yet still other embodiments, A can be an optionally substituted

In some embodiments, A can be an optionally substituted

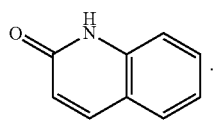

In other embodiments, A can be an optionally substituted

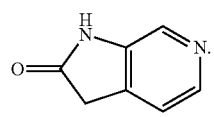

In still other embodiments, A can be an optionally substituted

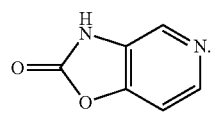

In the moieties shown above for A, the moieties can be attached to the carbon of the C(=Z$^1$) group of Formula (I) at any carbon atom of A. Furthermore, any hydrogens in the moiety A can be substituted with one or more substituents listed in the term "substituted."

In some embodiments, A can be substituted with one or more R$^A$'s. In some embodiments, one R$^A$ can be present. In some embodiments, two R$^A$'s can be present. In some embodiments, three R$^A$'s can be present. In some embodiments, four or more R$^A$'s can be present. When two or more R$^A$'s are present, two or more R$^A$'s can be the same or two or more R$^A$'s can be different. In some embodiments, at least two R$^A$'s can be the same. In some embodiments, at least two R$^A$'s can be different. In some embodiments, all the R$^A$'s can be the same. In other embodiments, all the R$^A$'s can be different. In some embodiments, A can have one of the following structures:

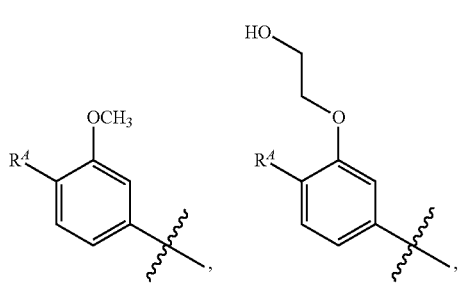

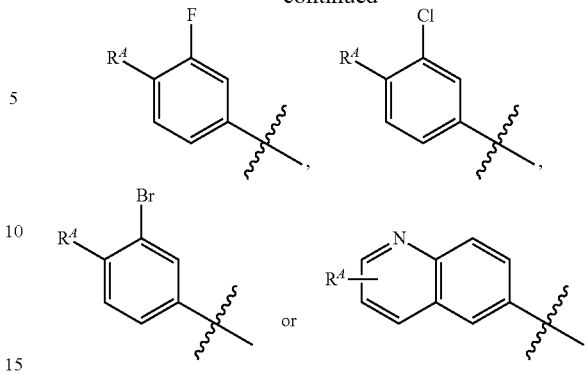

In some embodiments, R$^A$ can be each independently selected from an unsubstituted C$_{1-4}$ alkyl, an optionally substituted C$_{1-4}$ alkyl, cycloalkyl, hydroxy, an optionally substituted C$_{1-4}$ alkoxy, C$_{1-4}$ alkoxy, halogen, haloalkyl, an optionally substituted haloalkoxy, nitro, amino, mono-substituted amine, di-substituted amine, sulfenyl, alkyoxyalkyl, aryl, monocyclic heteroaryl, monocyclic heterocyclyl and aminoalkyl. In some embodiments, the optionally substituted C$_{1-4}$ alkoxy can be further substituted, for example, further substituted with a substituent selected from C$_{1-4}$ alkyl, halo, hydroxy, C-carboxy, C-amido, N-amido, amino, mono-alkyl amine, di-alkyl amine and an amino acid. In some embodiments, the optionally substituted haloalkoxy can be further substituted, for example, further substituted with an C$_{1-4}$ alkoxy. In some embodiments, the optionally substituted heteroaryl can be further substituted, for example, further substituted with an C$_{1-4}$ alkyl.

In some embodiments, each R$^A$ can be an alkyl, such as methyl, ethyl, propyl (n-propyl and iso-propyl) and/or butyl (n-butyl, iso-butyl and t-butyl).

In some embodiments, each R$^A$ can be an optionally substituted alkoxy, for example, methoxy, ethoxy, propoxy (n-propoxy and iso-propoxy), butoxy (n-butoxy, iso-butoxy and t-butoxy), phenoxy, —O(CH$_2$)$_2$—NH$_2$, —O(CH$_2$)$_2$—NH(CH$_3$), —O(CH$_2$)$_2$—N(CH$_3$)$_2$, —O—(CH$_2$)$_{2-4}$OH,

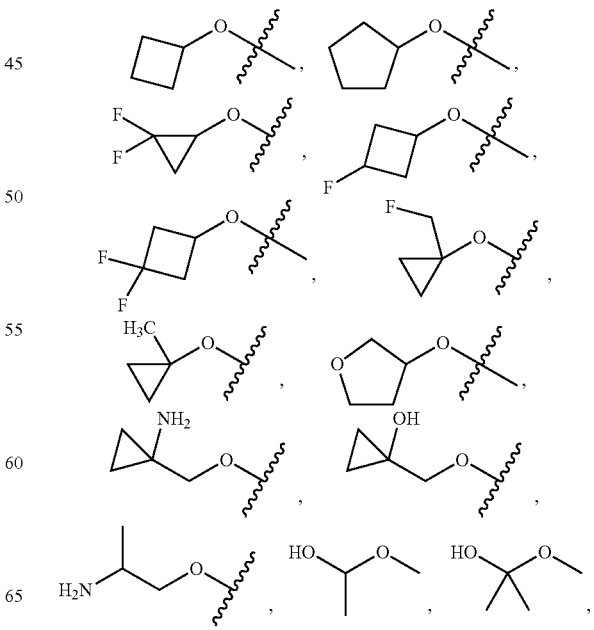

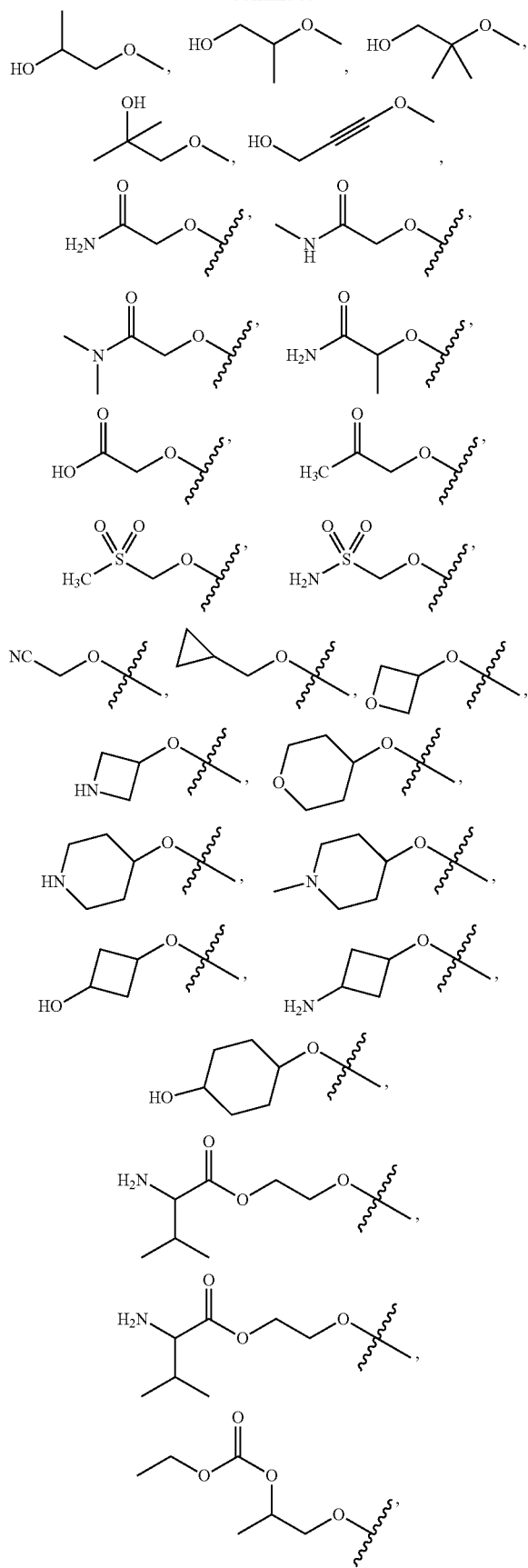

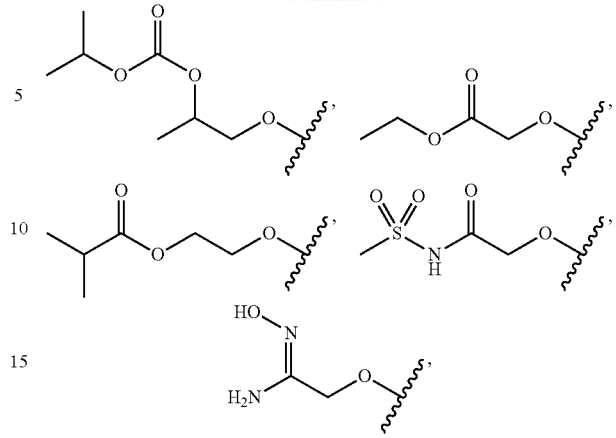

—O(CH$_2$)$_2$OCH$_3$, an optionally substituted —O(CH$_2$)$_{0-2}$-morpholinyl, an optionally substituted —O(CH$_2$)$_{0-2}$-triazole, an optionally substituted —O(CH$_2$)$_{0-2}$-imidazole, an optionally substituted —O(CH$_2$)$_{0-2}$-cyclopentanone, an optionally substituted —O(CH$_2$)$_{0-2}$pyrrolidinone, an optionally substituted —O(CH$_2$)$_{0-2}$-pyrazole, an optionally substituted —O(CH$_2$)$_{0-2}$-tetrahydrofuran, an optionally substituted —O(CH$_2$)$_{0-2}$-pyrrolidinone, an optionally substituted —O(CH$_2$)$_{0-2}$-tetrazole, an optionally substituted —O(CH$_2$)$_{0-2}$-tetrazolone and/or

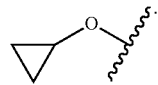

In some embodiments, R$^A$ can be substituted C$_{1-6}$ alkoxy substituted by one or more of the following: halo, hydroxy, C$_{1-4}$ alkyl, cyano, amino, mono-substituted amino, di-substituted amino, sulfonamidocarbonyl, hydroxamidine, C-amido, acyl, C-carboxy, O-carboxy, sulfonyl, S-sulfonamido, O-linked amino acid and carbonate ester.

In some embodiments, each R$^A$ can be haloalkyl, for example, trifluoromethyl.

In some embodiments, each R$^A$ can be an optionally substituted haloalkoxy, for example, difluoromethoxy, trifluoromethoxy,

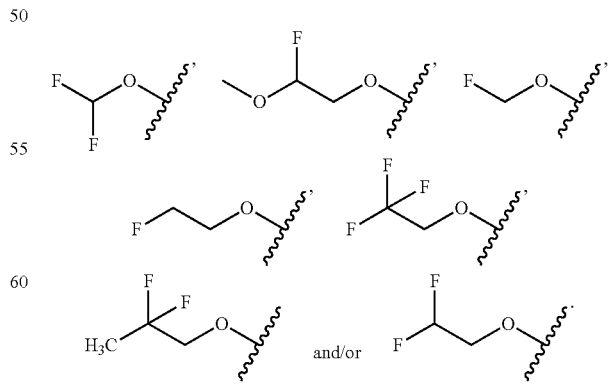

In some embodiments, each R$^A$ can be halogen, for example, chloro, bromo and/or fluoro.

In some embodiments, each $R^A$ can be amino, a mono-substituted amine or a di-substituted amine. For examples, $R^A$ can be N,N-di-methyl-amine, N,N-di-ethyl-amine, N-methyl-N-ethyl-amine, N-methyl-amino, N-ethyl-amino, amino,

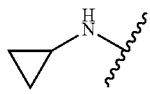

and/or —NH(CH$_2$)$_{1-2}$OH.

In some embodiments, each $R^A$ can be hydroxy.

In some embodiments, each $R^A$ can be alkylthio, for example ethylthio.

In some embodiments, each $R^A$ can be aminoalkyl, such as —(CH$_2$)$_{1-2}$—NH(CH$_3$).

In some embodiments, each $R^A$ can be alkoxyalkyl, for example, —CH$_2$—O—CH$_3$.

In some embodiments, each $R^A$ can be an optionally substituted aryl(C$_{1-4}$ alkyl). In some embodiments, each $R^A$ can be an optionally substituted monocyclic heteroaryl(C$_{1-4}$ alkyl). In some embodiments, each $R^A$ can be an optionally substituted monocyclic heterocyclyl(C$_{1-4}$ alkyl). Non-limiting examples include an optionally substituted —(CH$_2$)$_{1-2}$-imidazole, an optionally substituted —(CH$_2$)$_{1-2}$-pyrrolidinone, an optionally substituted —(CH$_2$)$_{1-2}$-imidazolidinone.

In some embodiments, each $R^A$ can be hydroxyalkyl, for example, —(CH$_2$)$_{1-4}$—OH.

In some embodiments, each $R^A$ can be —O-amido, for example,

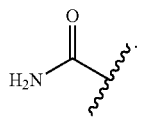

In some embodiments, each $R^A$ can be —N-amido, for example,

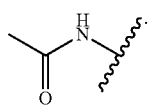 [SMILES: *NC(C)=O]

In some embodiments, each $R^A$ can be —N-sulfonamido, for example,

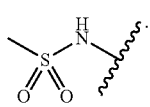

In some embodiments, each $R^A$ can be aminoalkyl, for example, —CH$_2$—NH$_2$ and/or —CH$_2$—N(CH$_3$)H.

In some embodiments, each $R^A$ can be an optionally substituted aryl, for example, an optionally substituted phenyl.

In some embodiments, each $R^A$ can be an optionally substituted mono-cyclic heteroaryl, such as an optionally substituted imidazole, an optionally substituted pyrazole, an optionally substituted pyridinyl, an optionally substituted pyrimidine, an optionally substituted pyrazine and/or an optionally substituted 1,2,4-oxadiazole.

In some embodiments, each $R^A$ can be an optionally substituted mono-cyclic heterocyclyl, for example, an optionally substituted pyrrolidinyl, an optionally substituted piperidinyl, an optionally substituted morpholinyl and/or an optionally substituted pyrrolidinone.

In some embodiments, Y can be an optionally substituted aryl. In some embodiments, Y can be a para-substituted phenyl, a meta-substituted phenyl or an ortho-substituted phenyl. In some embodiments, Y can be a mono-substituted phenyl, such as a mono-halo substituted phenyl. In some embodiments, Y can be a di-substituted phenyl, for example a di-halo substituted phenyl. For example, mono-halo substituted phenyls and di-halo substituted phenyls include, but are not limited to,

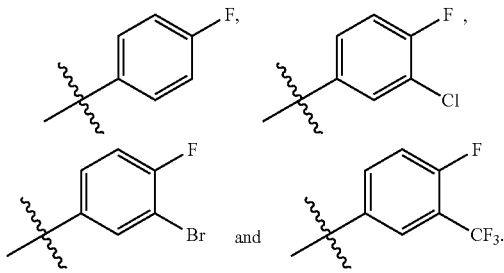

In some embodiments, Y can be di-substituted phenyl of the structure

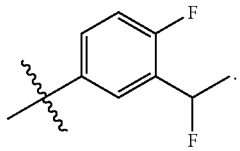 [SMILES: *c1ccc(F)c(C(C)F)c1]

In some embodiments, Y can be a substituted phenyl that is substituted with 3 more substituents. In other embodiments, Y can be unsubstituted phenyl. In some embodiments, Y can be a substituted naphthyl. In other embodiments, Y can be an unsubstituted naphthyl.

In some embodiments, Y can be an optionally substituted mono-cyclic heteroaryl. In some embodiments, Y can be selected from an optionally substituted imidazole, an optionally substituted furan, an optionally substituted thiophene, an optionally substituted pyrrole, an optionally substituted pyrimidine, an optionally substituted pyrazine, an optionally substituted pyridine, an optionally substituted pyrazole, an optionally substituted oxazole and an optionally substituted isoxazole. In some embodiments, Y can be a substituted mono-cyclic heteroaryl, including those described herein. In some embodiments, Y can be an unsubstituted mono-cyclic heteroaryl, including those described herein.

In some embodiments, Y can be an optionally substituted bi-cyclic heteroaryl. In some embodiments, Y can be selected from an optionally substituted benzothiophene, an optionally substituted benzofuran, an optionally substituted indole, an optionally substituted quinoline, an optionally substituted isoquinoline, an optionally substituted benzoxazole, an optionally substituted benzoisoxazole, an optionally substituted benzoisothiazole, an optionally substituted benzothiazole, an optionally substituted benzoimidazole, an optionally substituted benzotriazole, an optionally substituted 1H-indazole and an optionally substituted 2H-indazole. In some embodiments, Y can be selected from an optionally substituted

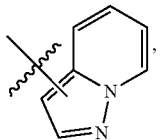

an optionally substituted

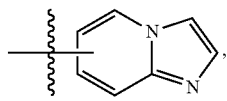

an optionally substituted

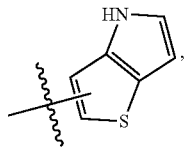

an optionally substituted

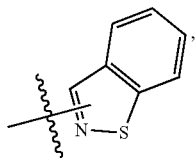

an optionally substituted

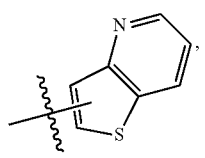

an optionally substituted

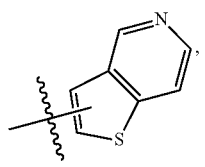

an optionally substituted

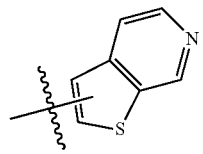

and an optionally substituted

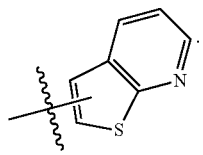

In some embodiments, Y can be a substituted bi-cyclic heteroaryl, including those described herein. In some embodiments, Y can be an unsubstituted bi-cyclic heteroaryl, including those described herein.

In some embodiments, Y can be an optionally substituted heterocyclyl. In some embodiments, Y can be an optionally substituted mono-cyclic heterocyclyl, such as an optionally substituted pyridinone. In other embodiment, Y can be an optionally substituted bi-cyclic heterocyclyl. For example, Y can be an optionally substituted

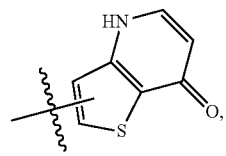

an optionally substituted

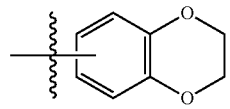

or an optionally substituted

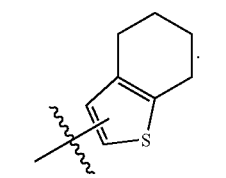

When Y is substituted, Y can be substituted with one or more $R^B$'s. In some embodiments, each $R^B$ can be independently selected from cyano, halogen, an optionally substituted $C_{1-4}$ alkyl, an unsubstituted $C_{2-4}$ alkenyl, an unsubstituted $C_{2-4}$ alkynyl, an optionally substituted aryl, an optionally substituted 5 or 6 membered heteroaryl, an optionally substituted 5 or 6 membered heterocyclyl, hydroxy, $C_{1-4}$ alkoxy, alkoxyalkyl, $C_{1-4}$ haloalkyl, haloalkoxy, an unsubstituted acyl, an optionally substituted —C-carboxy, an optionally substituted —C-amido, sulfonyl, carbonyl, amino, mono-substituted amine, di-substituted amine and

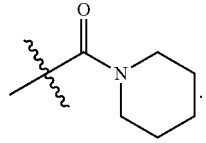 [SMILES: *C(=O)N1CCCCC1]

In some embodiments, when Y is an optionally substituted phenyl, the phenyl can be substituted 1, 2, 3 or more times with cyano, halogen, an optionally substituted $C_{1-4}$ alkyl, an unsubstituted $C_{2-4}$ alkenyl, an unsubstituted $C_{2-4}$ alkynyl, an optionally substituted aryl, an optionally substituted 5 or 6 membered heteroaryl, an optionally substituted 5 or 6 membered heterocyclyl, hydroxy, $C_{1-4}$ alkoxy, $C_{1-4}$ haloalkyl (such as $CF_3$, $CHF_2$), haloalkoxy (such as $OCF_3$), an unsubstituted acyl, an optionally substituted —C-carboxy, an optionally substituted —C-amido, sulfonyl, amino, mono-$C_{1-4}$ alkyl amine, di-$C_{1-4}$ alkyl amine and/or

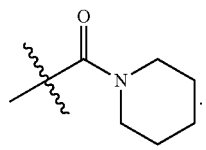 [SMILES: *C(=O)N1CCCCC1]

In other embodiments, when Y is an optionally substituted mono-cyclic heteroaryl, the mono-cyclic heteroaryl can be substituted 1, 2, 3 or more times with halo, an optionally substituted $C_{1-4}$ alkyl, an optionally substituted phenyl and/or an unsubstituted acyl. In still other embodiments, when Y is an optionally substituted bi-cyclic heteroaryl, the bi-cyclic heteroaryl can be substituted 1, 2, 3 or more times with halo, an optionally substituted $C_{1-4}$ alkyl, an optionally substituted phenyl, hydroxy, $C_{1-4}$ alkoxy, an unsubstituted acyl, carbonyl, cyano, amino, mono-$C_{1-4}$ alkyl amine and/or di-$C_{1-4}$ alkyl amine.

In some embodiments, Y can be an optionally substituted benzothiophene. In some embodiments, Y can be a substituted benzothiophene. In other embodiments, Y can be an unsubstituted benzothiophene. In some embodiments, the benzothiophene can be substituted with one or more of the following: halogen (such as fluoro, chloro and/or bromo), carbonyl, $C_{1-4}$ alkyl, hydroxy, $C_{1-4}$ alkoxy, $NH_2$ and/or mono-substituted amine. For example, the benzothiophene can be an optionally substituted

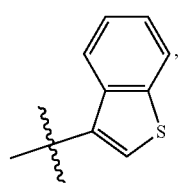 [SMILES: *c1csc2ccccc12]

such as an optionally substituted

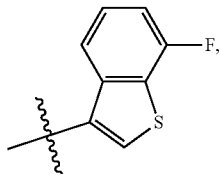 [SMILES: *c1csc2c(F)cccc12]

an optionally substituted

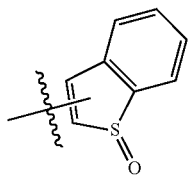

and an optionally substituted

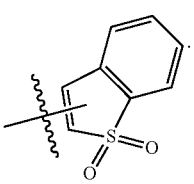

In some embodiments, Y can be an optionally substituted benzofuran.

In some embodiments, Y can be an optionally substituted indole. In some embodiments, Y can be a substituted indole. In some embodiments, the indole can be substituted 1, 2, 3 or more time with phenyl (substituted or unsubstituted), $C_{1-4}$ alkyl and/or halo. In other embodiments, Y can be an unsubstituted indole.

In some embodiments, Y can be substituted with one or more halogen. In some embodiments, Y can be substituted with one or more unsubstituted $C_{1-4}$ alkyl. In some embodiments, Y can be substituted with more or more hydroxy. In some embodiments, Y can be substituted with one or more optionally substituted phenyl. In some embodiments, Y can be substituted with one or more alkoxy. In some embodiments, Y can be substituted with one or more acyl. In some embodiments, Y can be substituted with one or more amino, mono-substituted amino, or di-substituted amino. In some embodiments, Y can be substituted with one or more haloalkyl. In some embodiments, Y can be substituted with one or more haloalkoxy. In some embodiments, Y can be substituted with one or more C-carboxy. In some embodiments, Y can be substituted with one or more C-amido. In some embodiments, Y can be substituted with one or more hydroxyalkyl.

In some embodiments, a compound of Formula (I) can be selected from the following compounds:

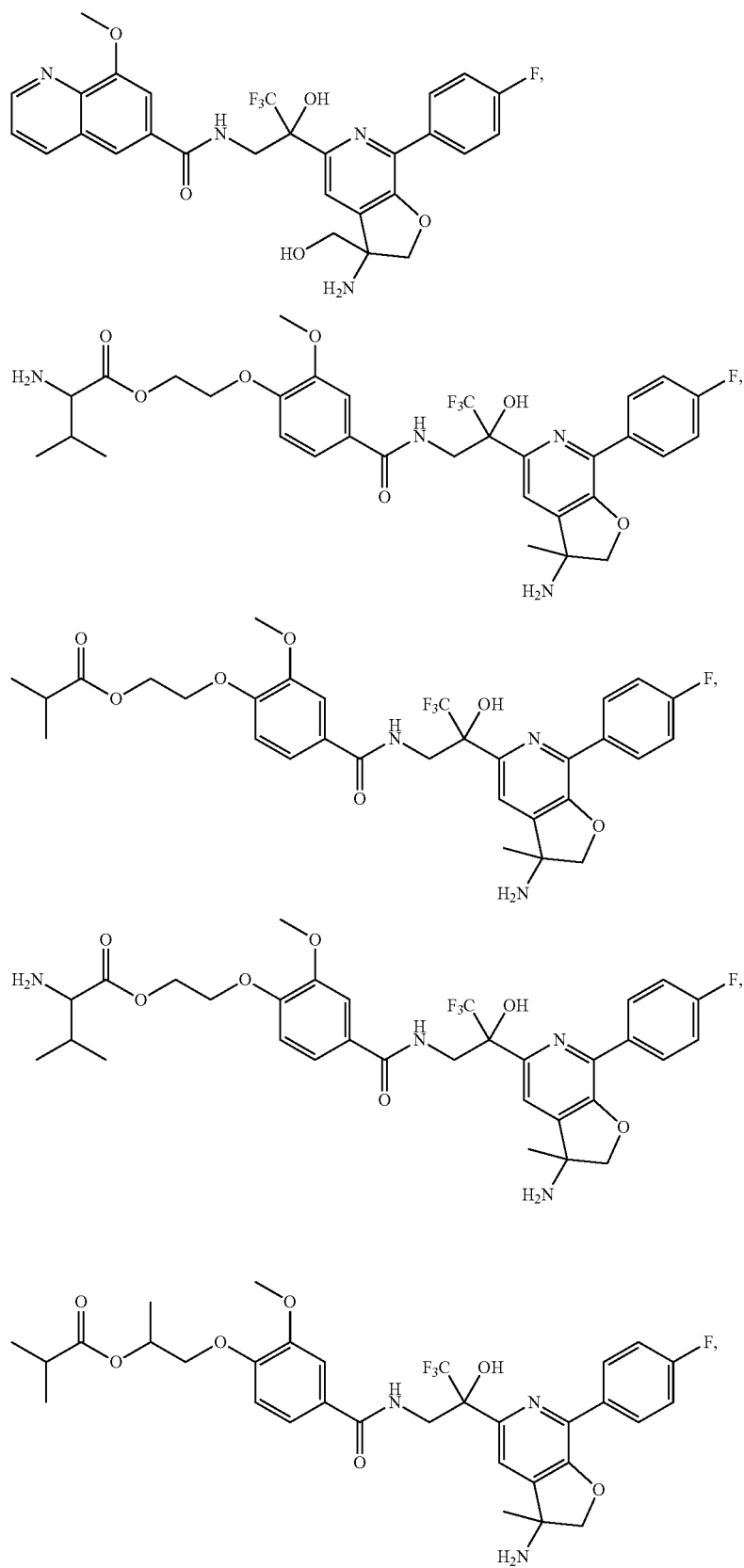

-continued
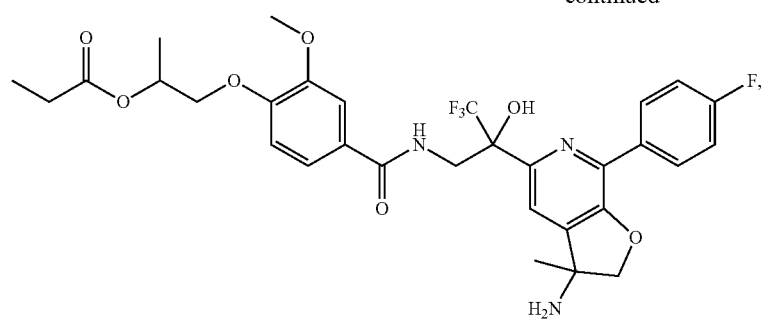
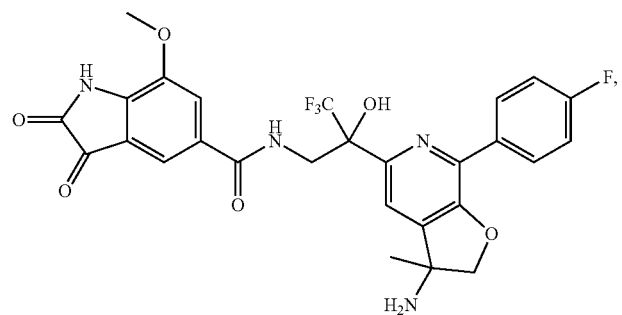
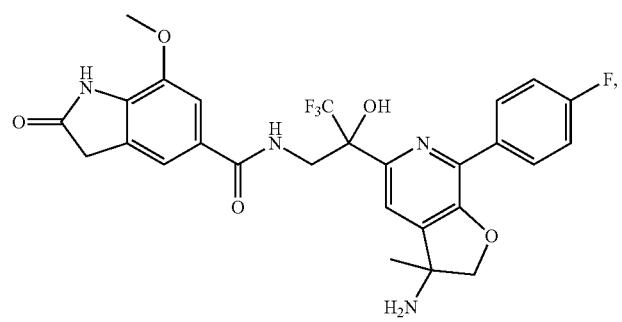
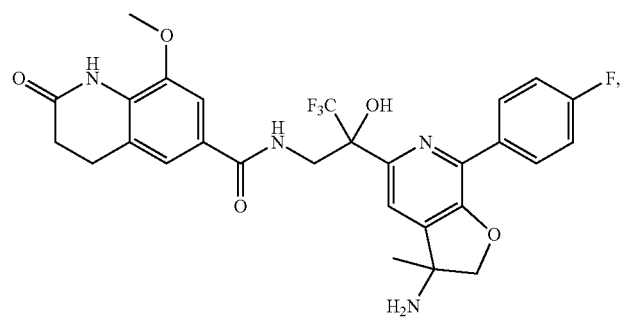
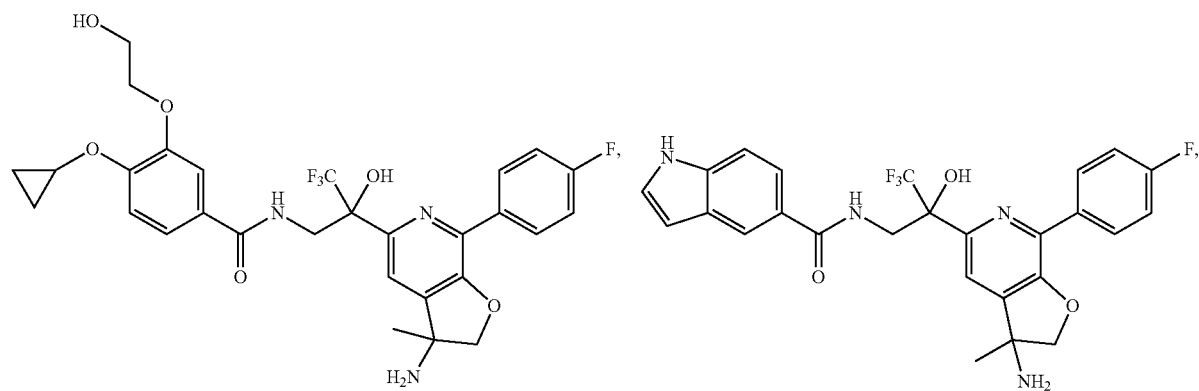

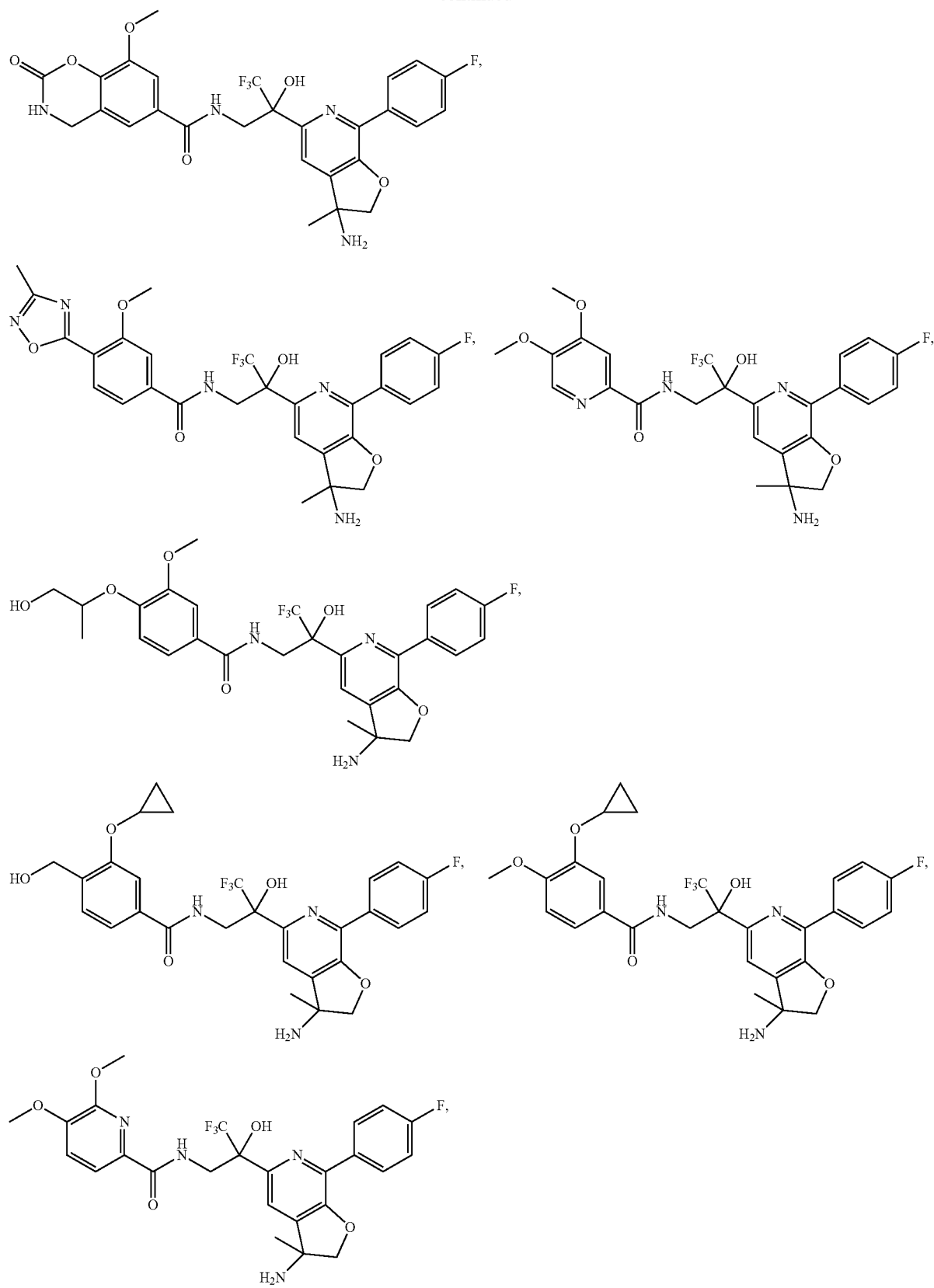

-continued
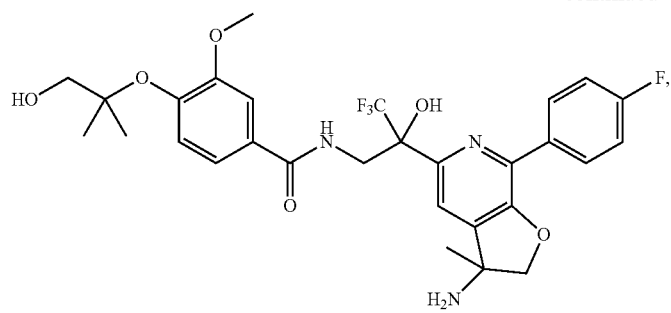
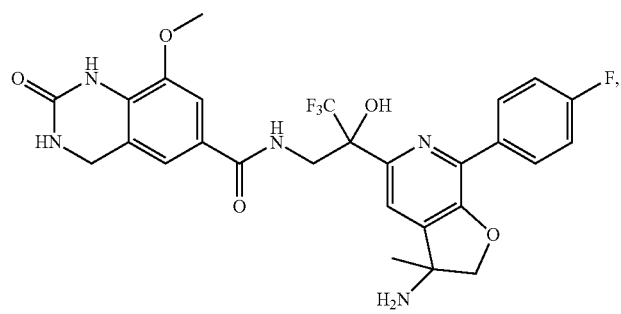
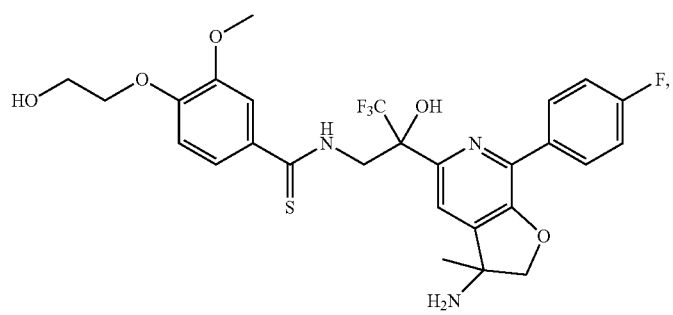
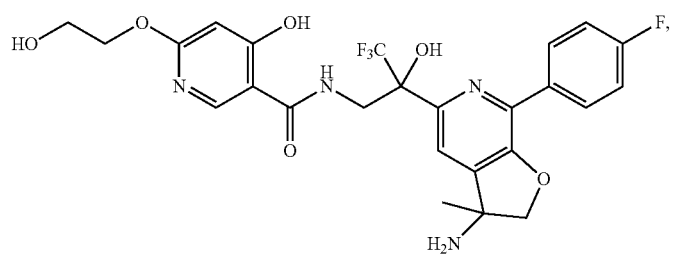
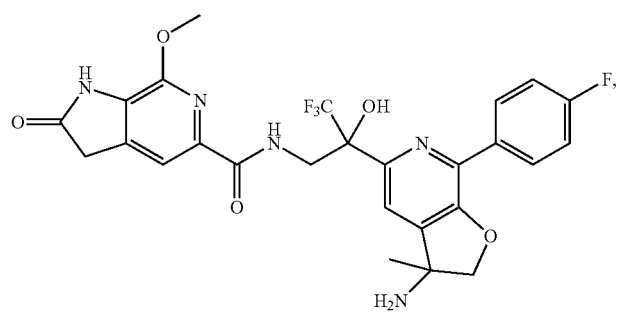

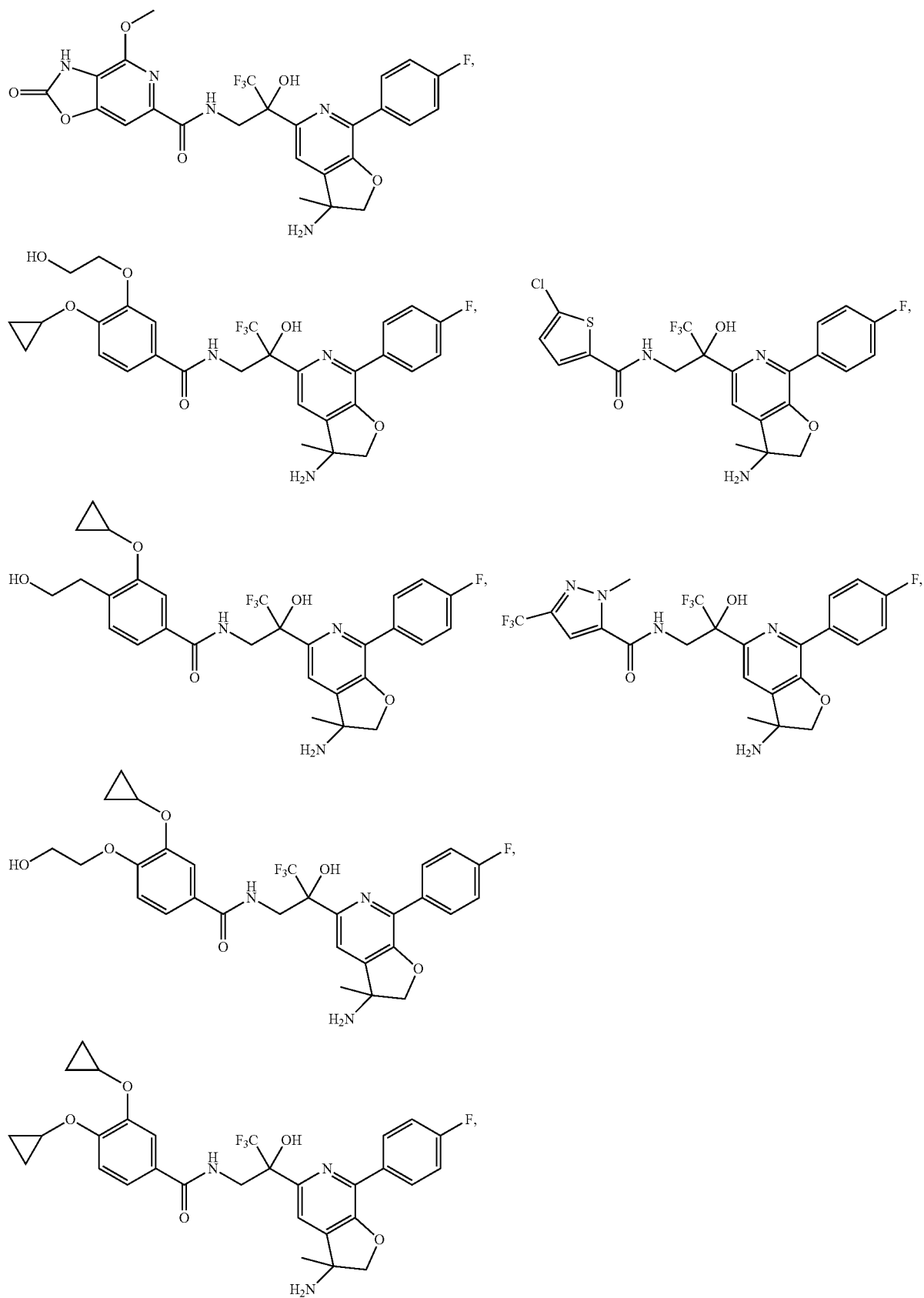

-continued
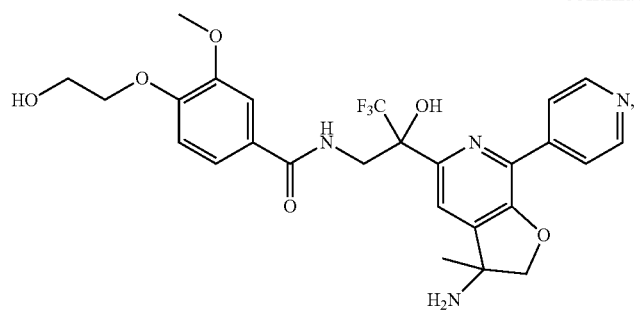
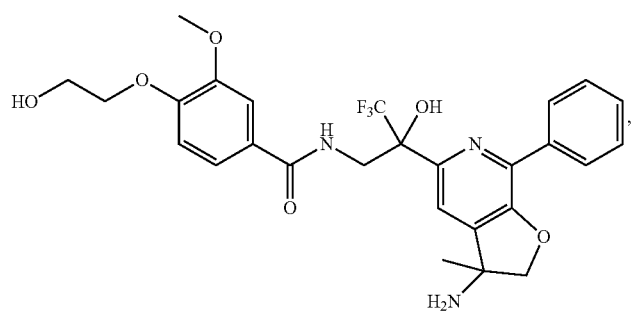
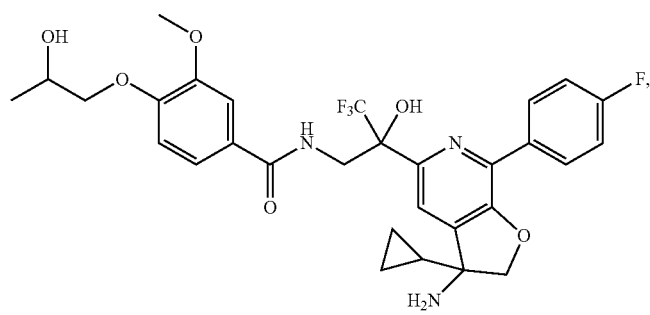
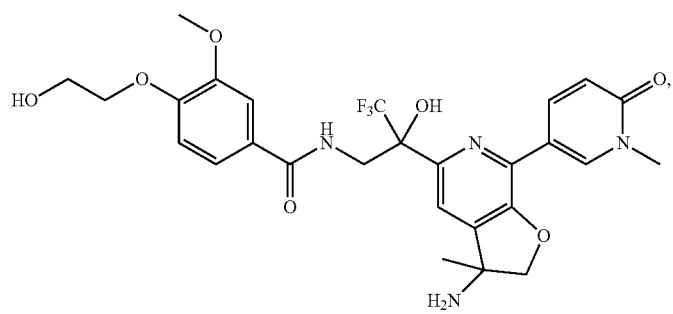

-continued
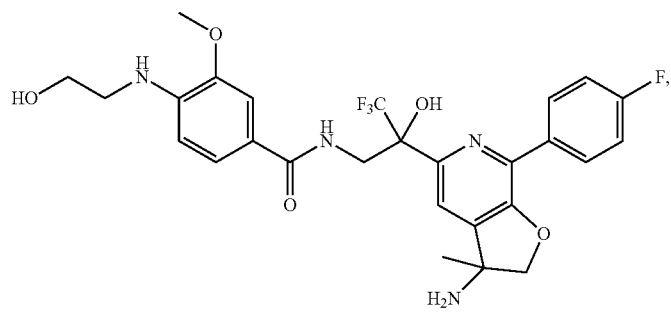
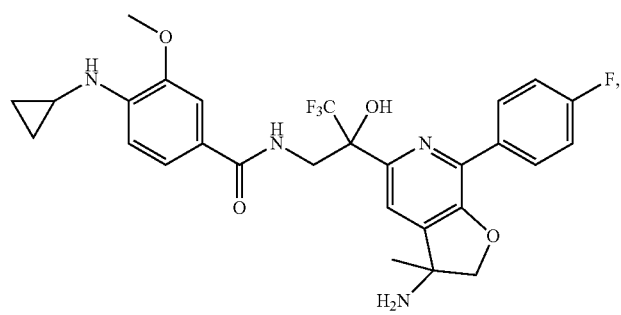
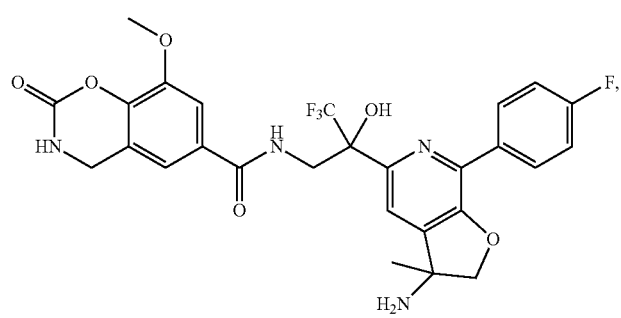
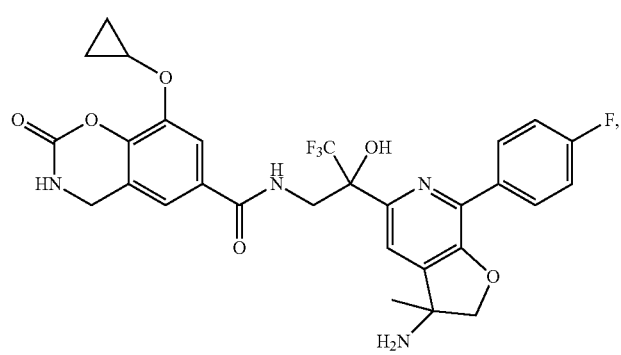 [SMILES: CC1(N)COc2c1cc(C(O)(CNC(=O)c1cc3c(c(OC4CC4)c1)OC(=O)NC3)C(F)(F)F)nc2-c1ccc(F)cc1]
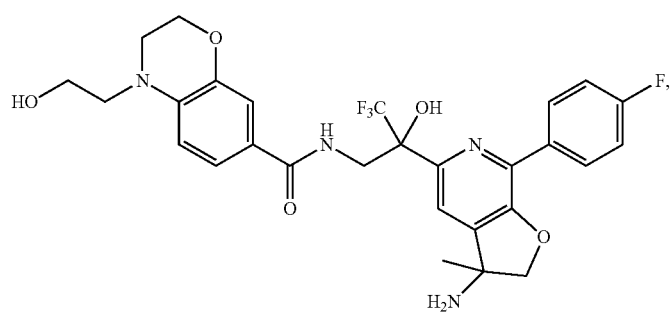

-continued
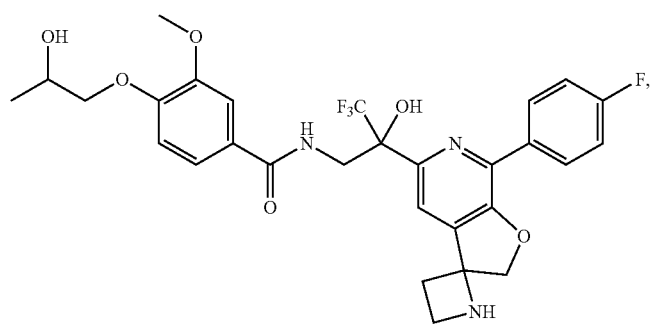
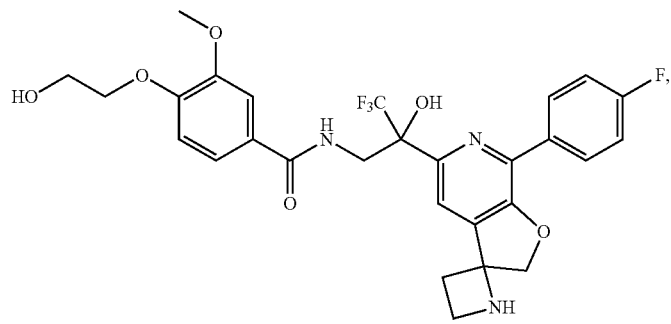
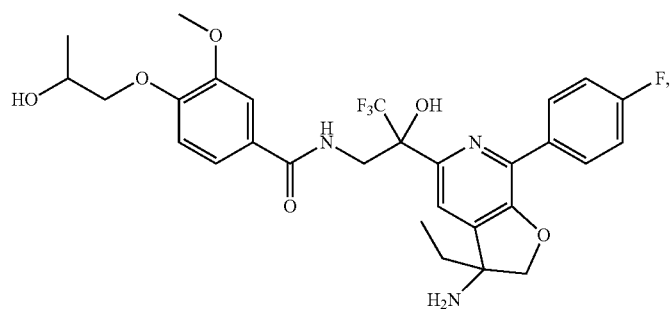
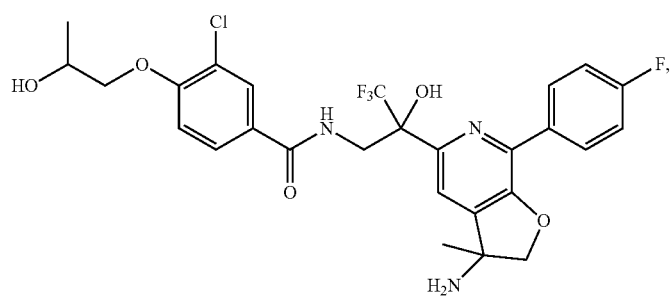
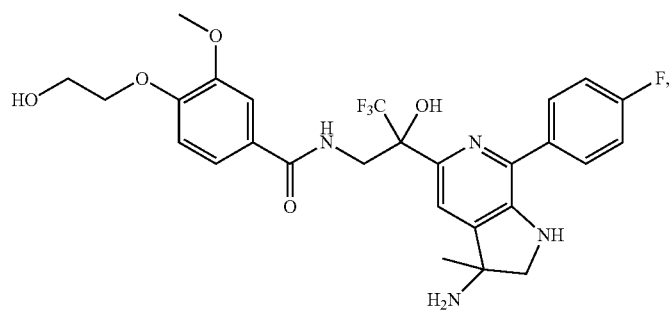

-continued
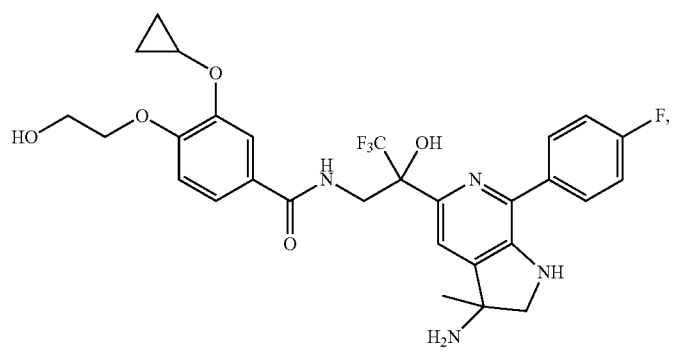
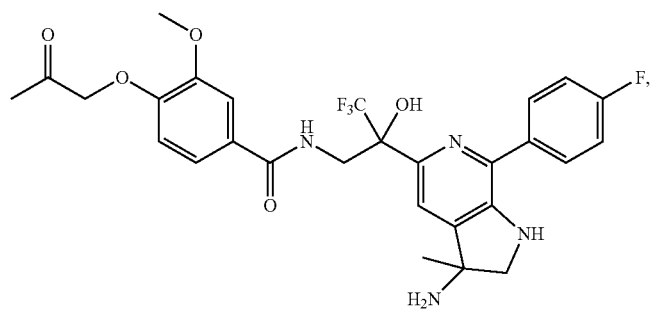
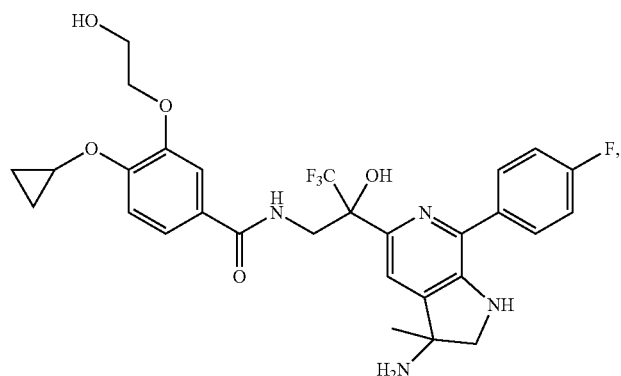
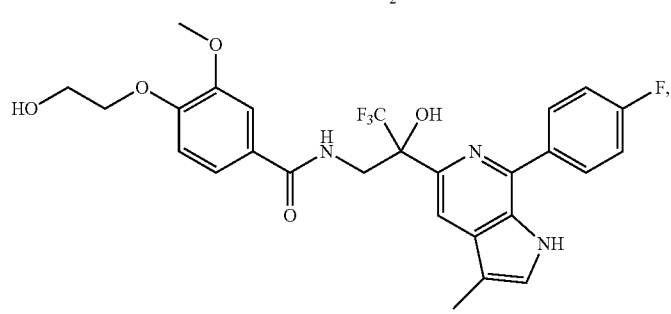
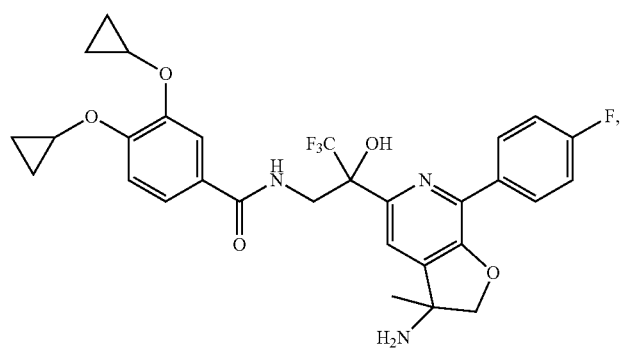

-continued
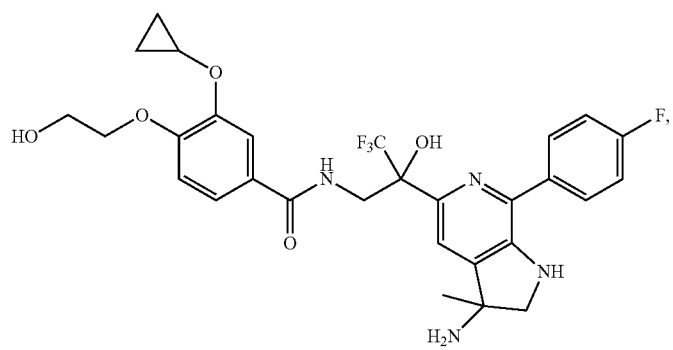
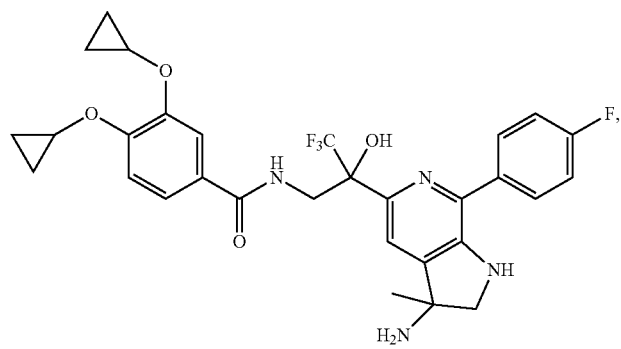
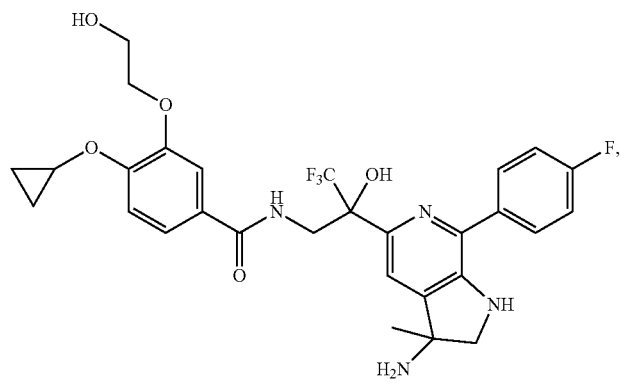
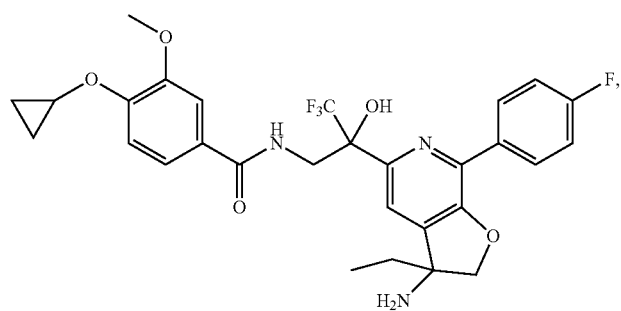
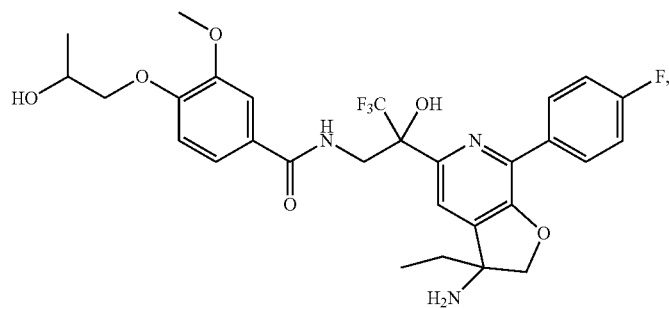

-continued
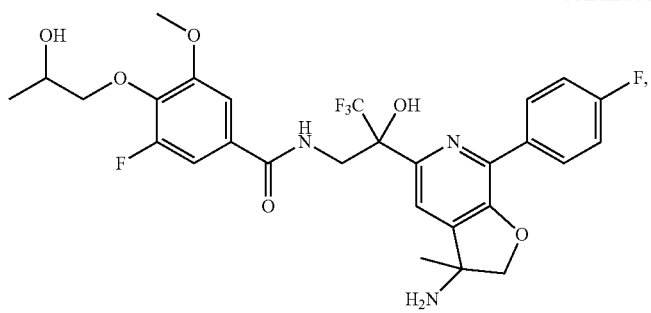
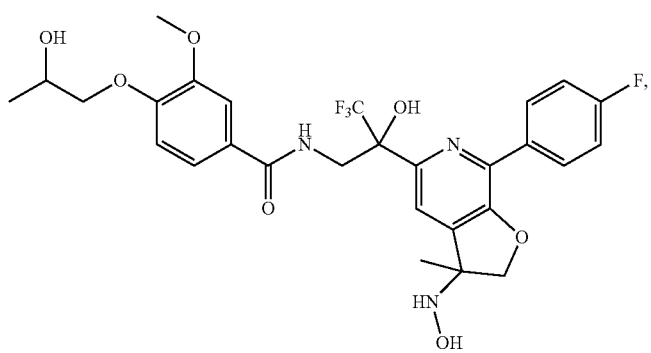
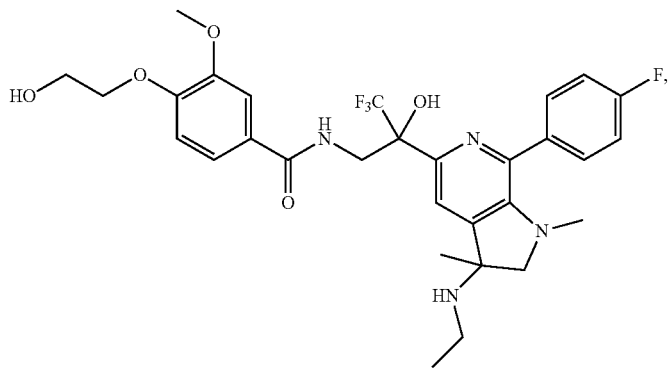
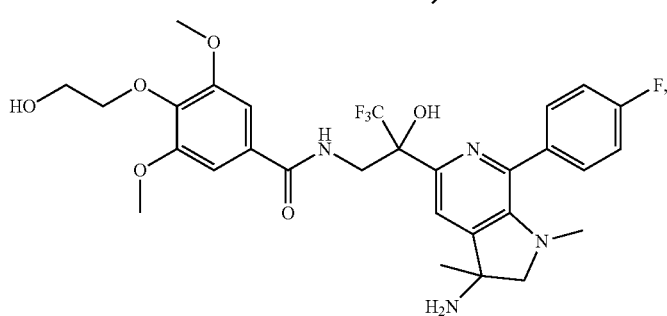
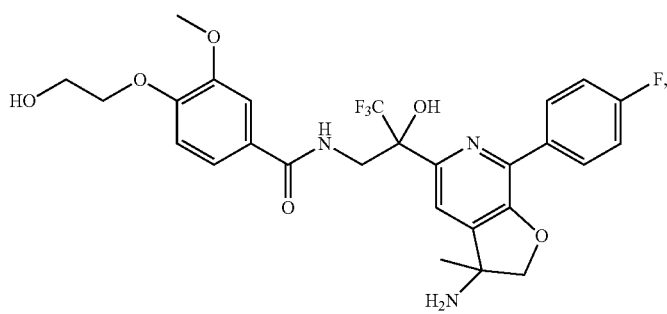

-continued
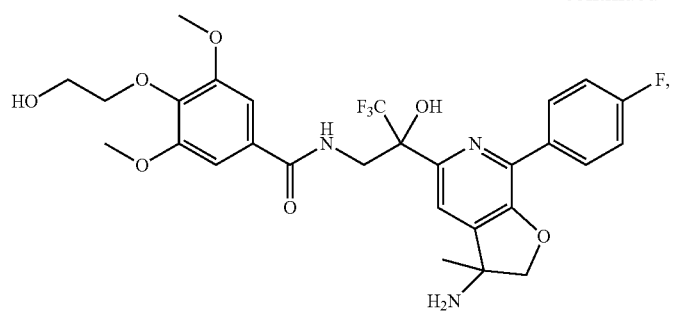
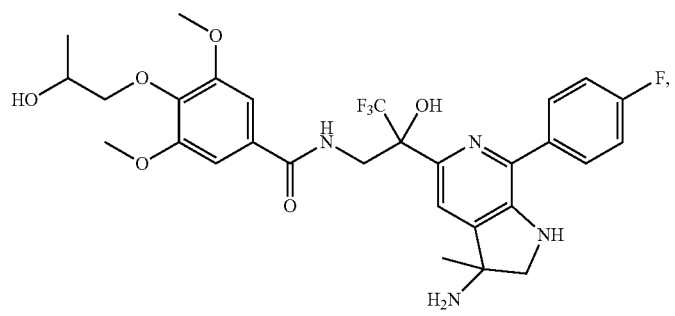
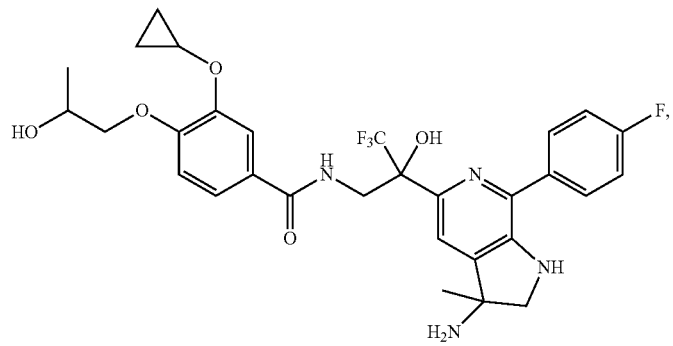
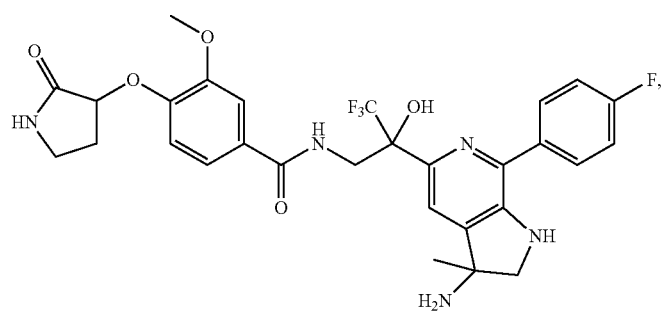
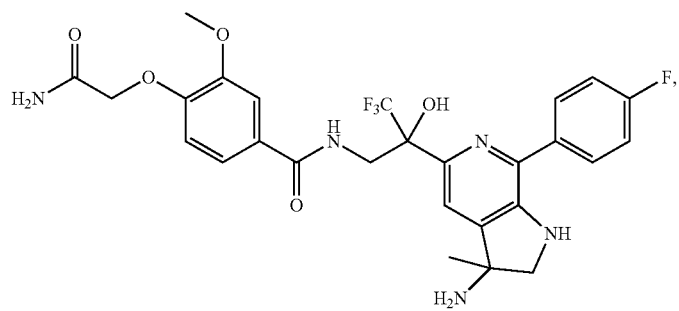

-continued
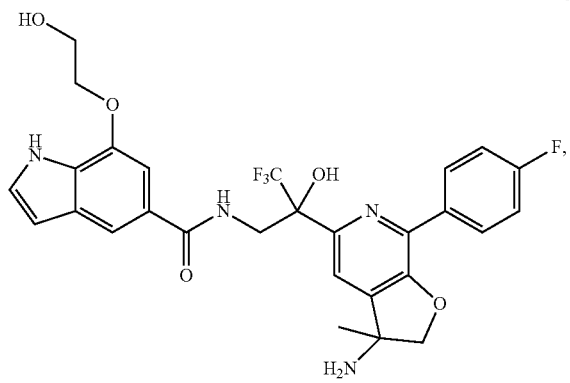
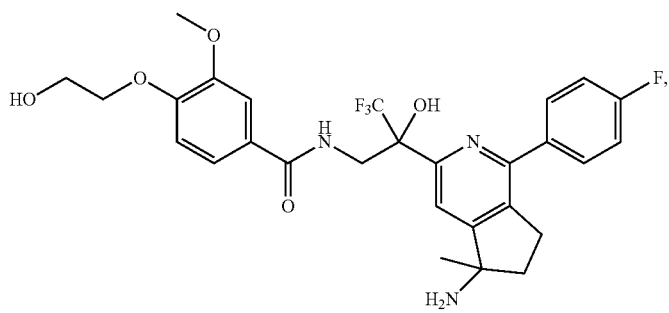
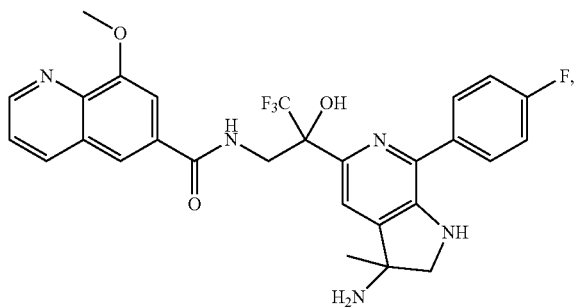
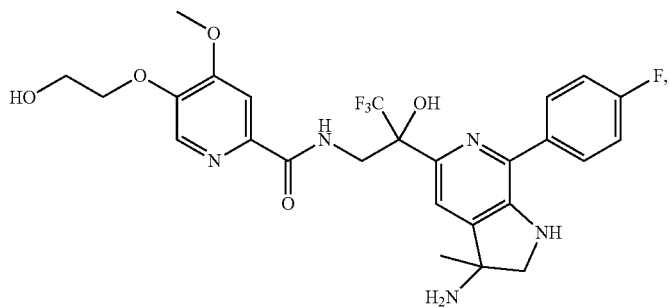
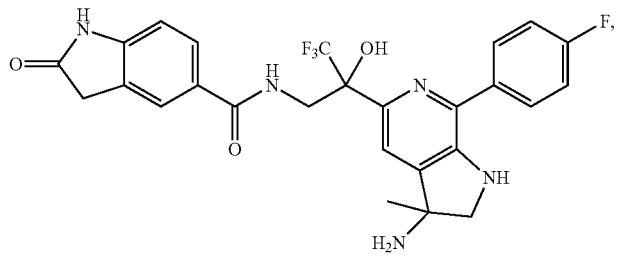

-continued
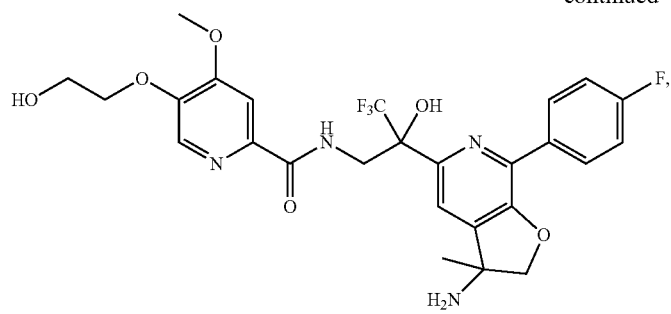
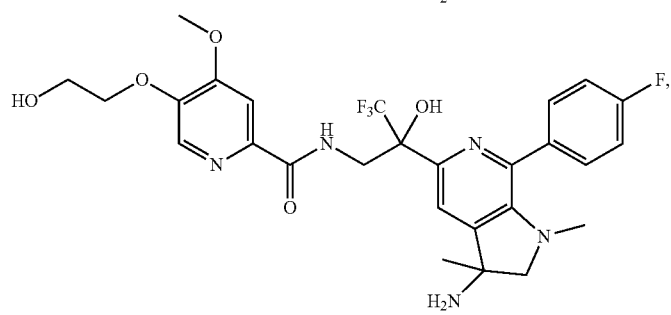
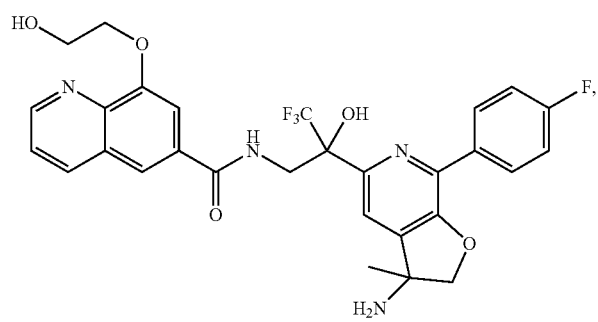
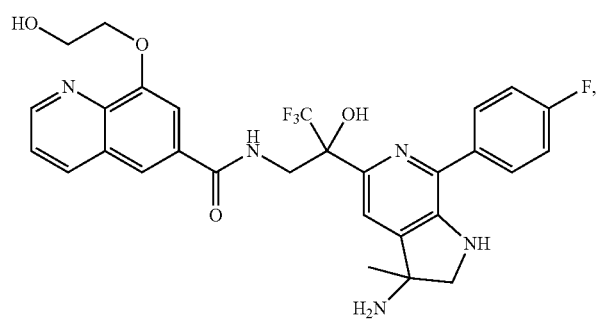
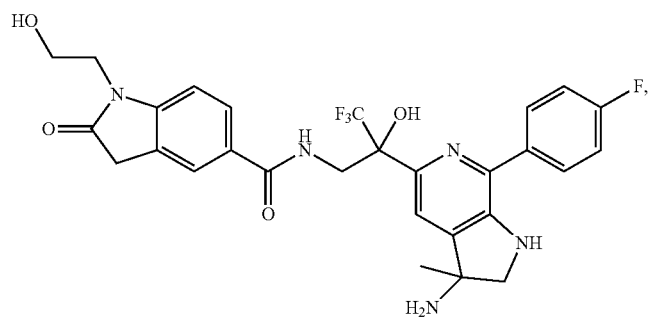

-continued
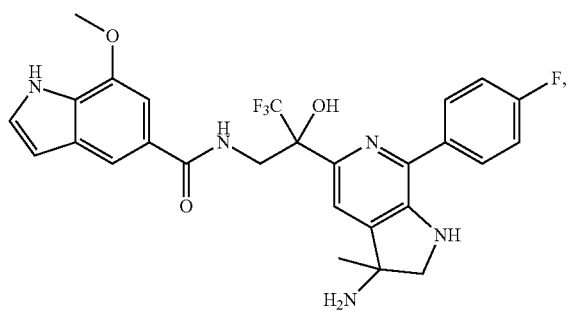
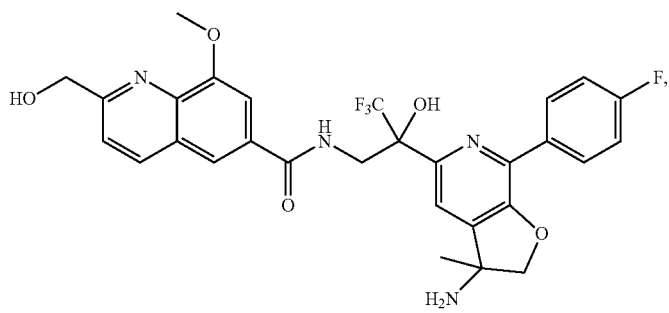
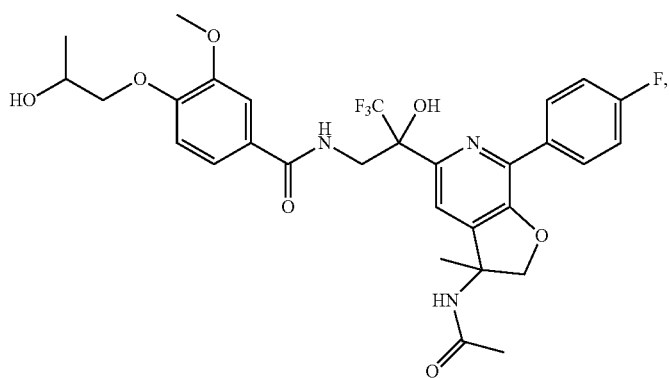
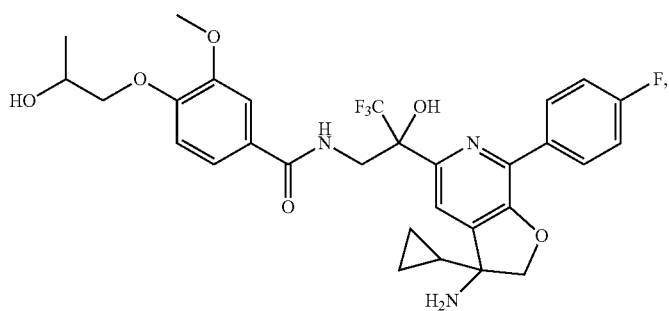
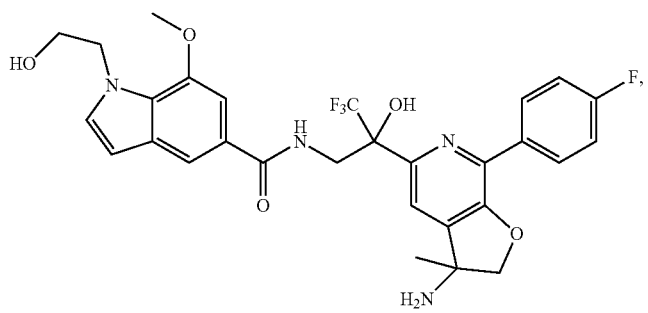

-continued
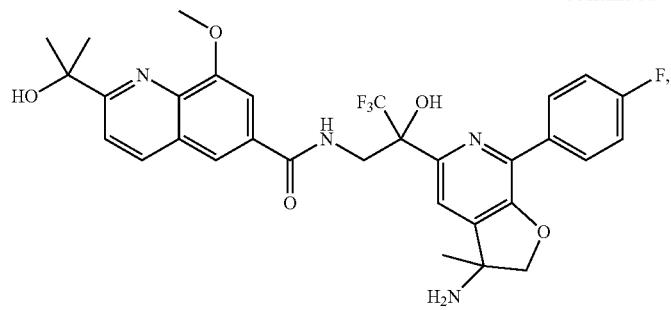
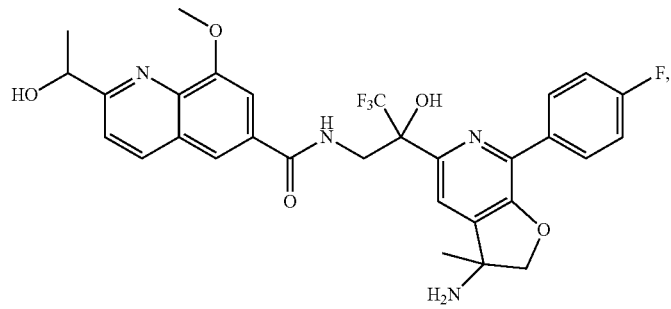
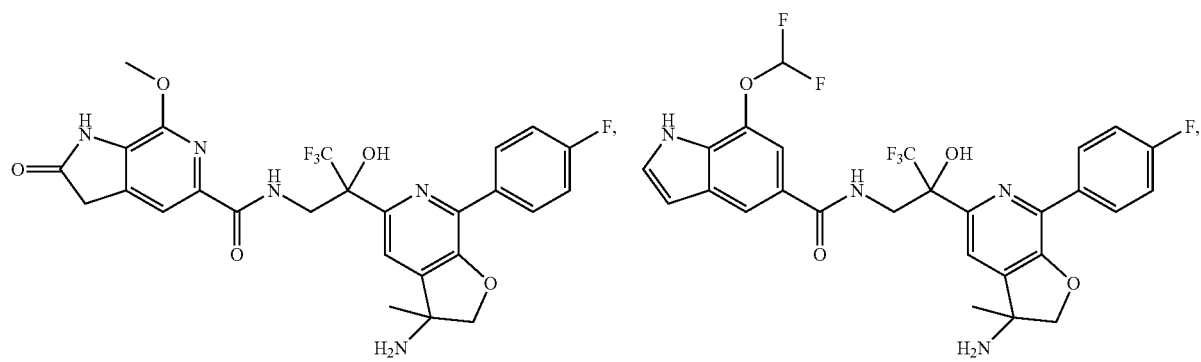
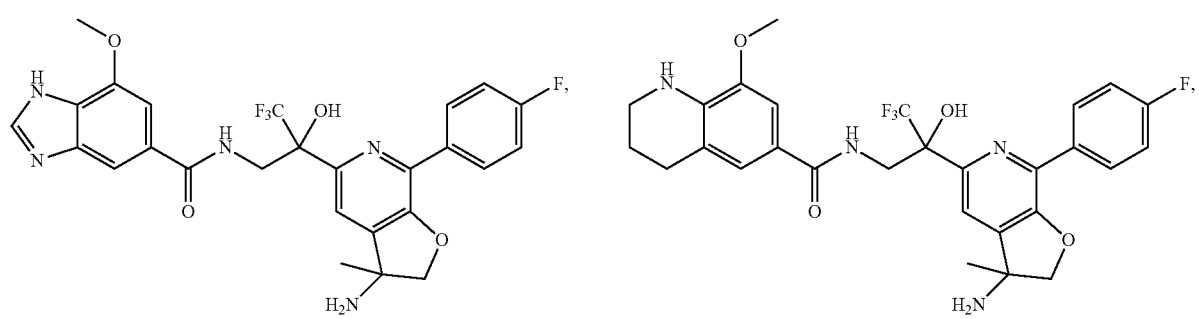
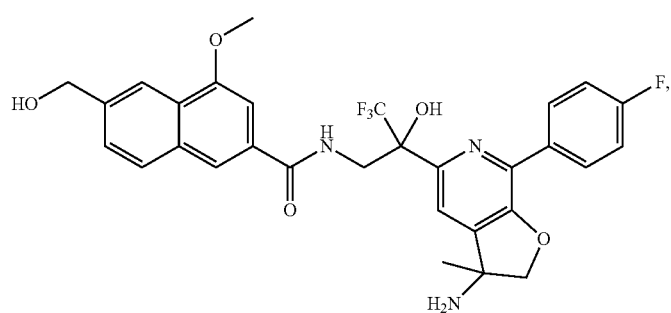

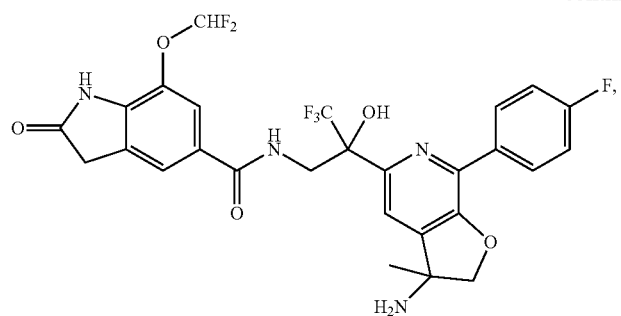
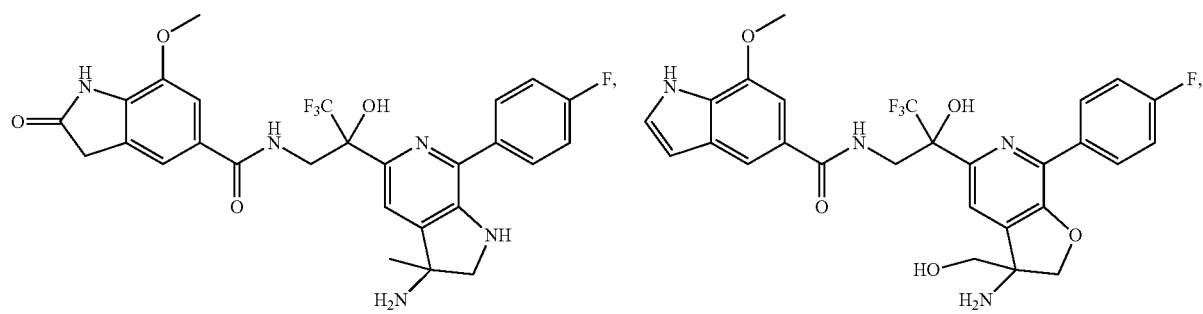
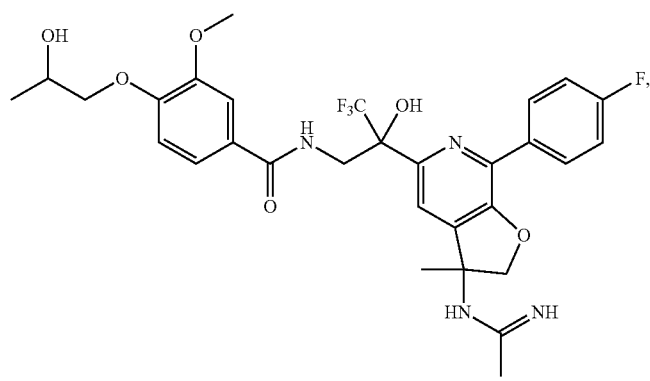
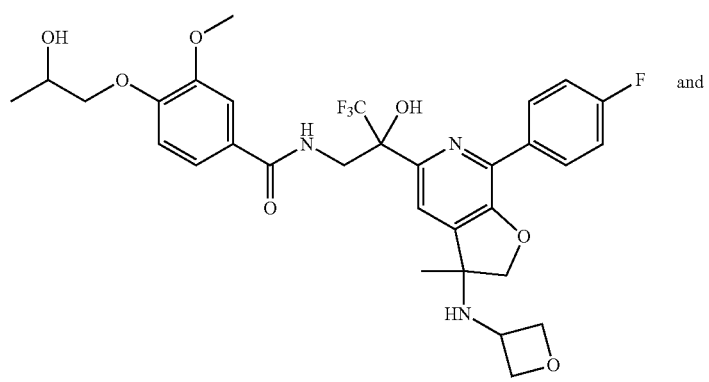

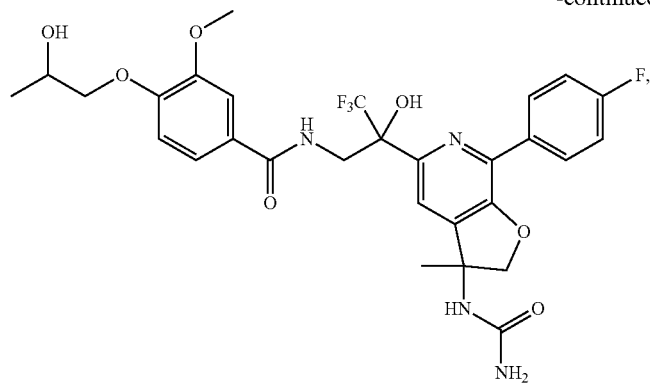
or a pharmaceutically acceptable salt of the foregoing.
In some embodiments, a compound of Formula (I) can be selected from the following compounds:
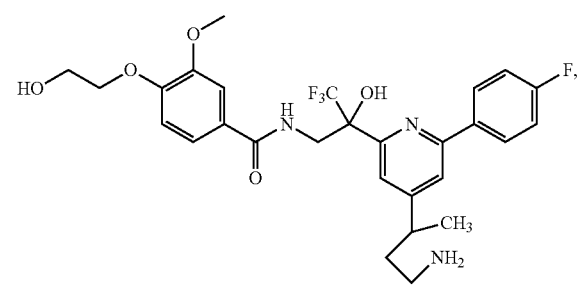
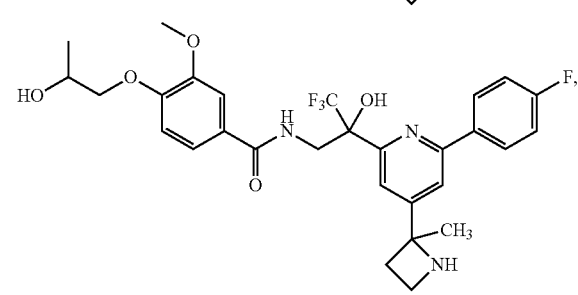
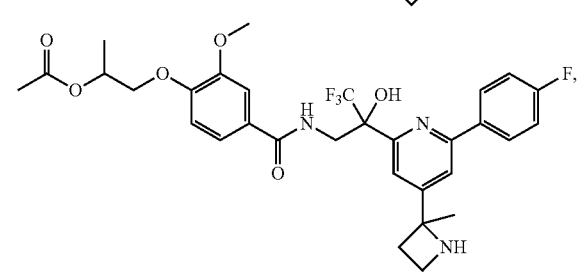
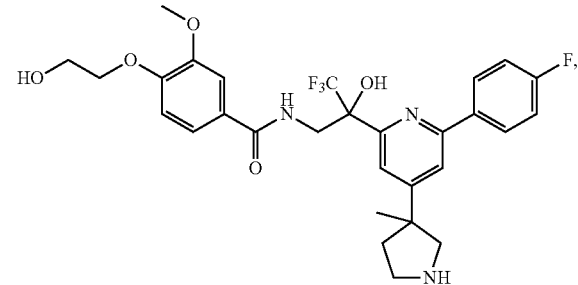
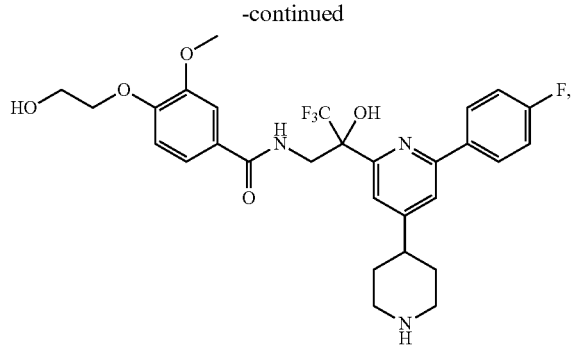
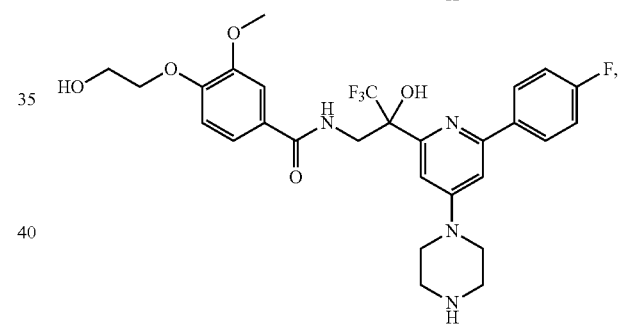
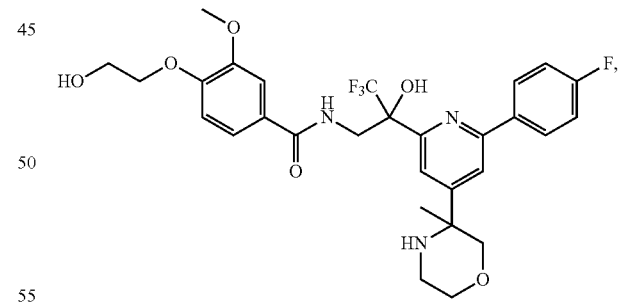
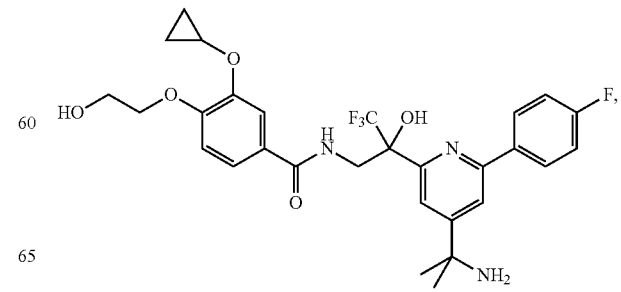

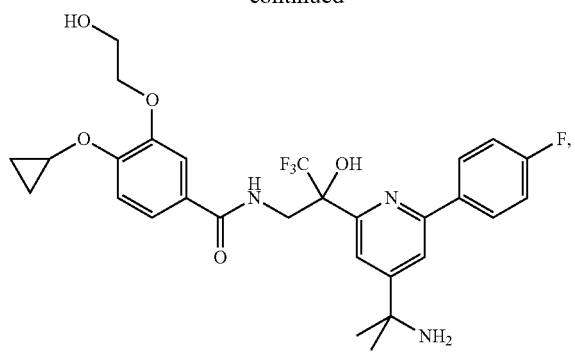
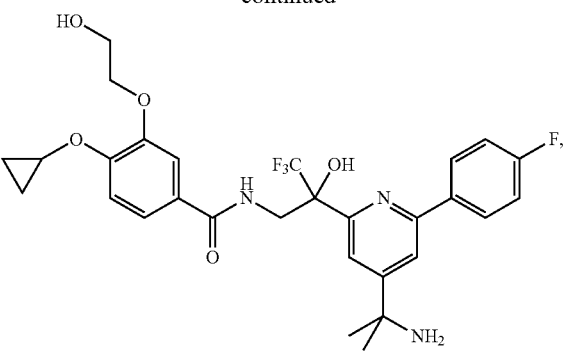
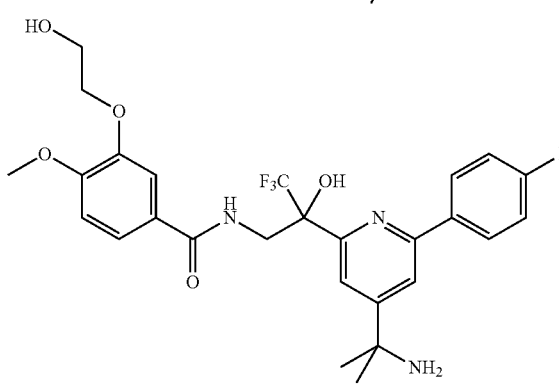
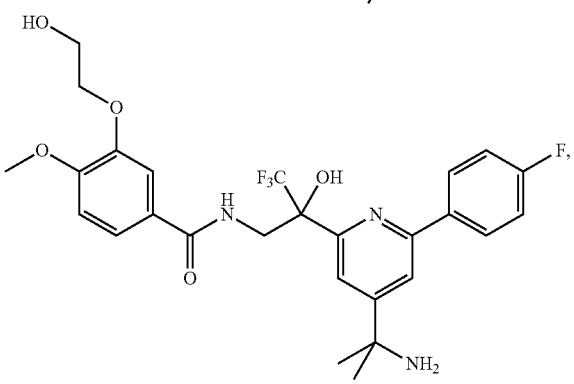
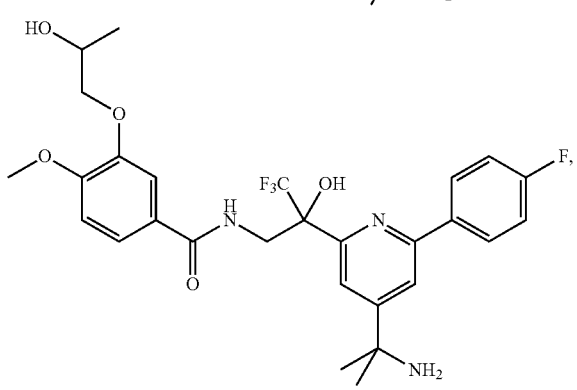
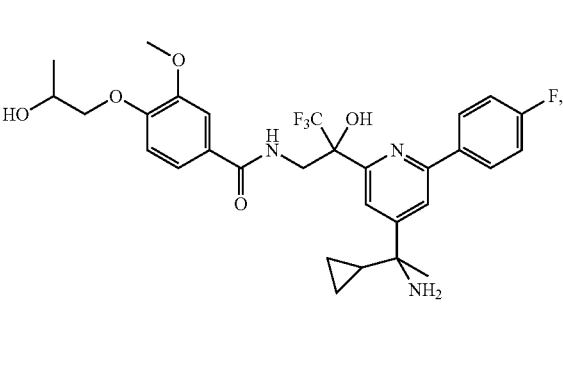
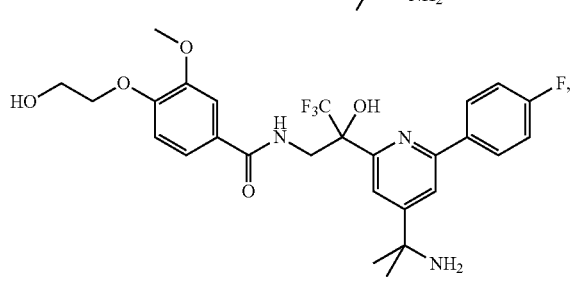

-continued

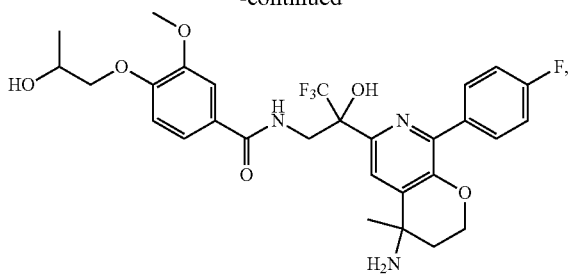
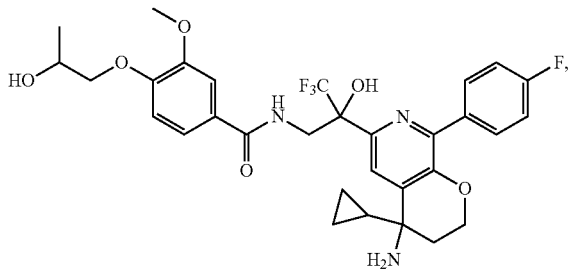
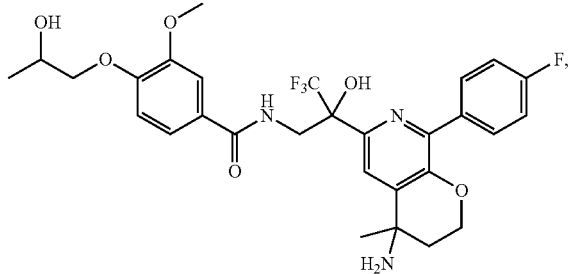
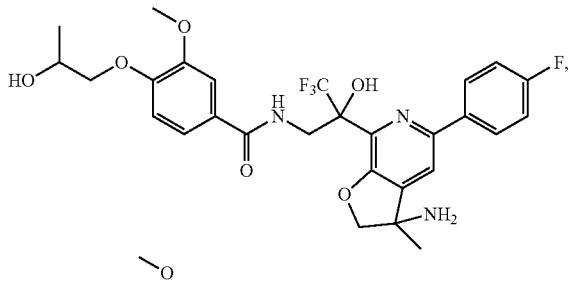
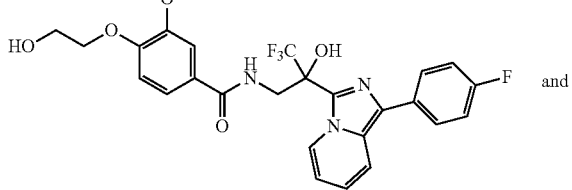

and

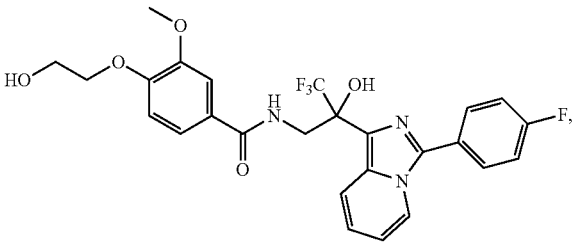

or a pharmaceutically acceptable salt of the foregoing.

In some embodiments, a compound of Formula (I), or a pharmaceutically acceptable salt thereof, cannot be a compound provided in PCT Publication WO 2014/031784, published Feb. 27, 2014. In some embodiments, a compound of Formula (I), or a pharmaceutically acceptable salt thereof, cannot be a compound provided in U.S. Publication No. 2015/0065504, published Mar. 5, 2015. In some embodiments, a compound of Formula (I), or a pharmaceutically acceptable salt thereof, cannot be selected from:

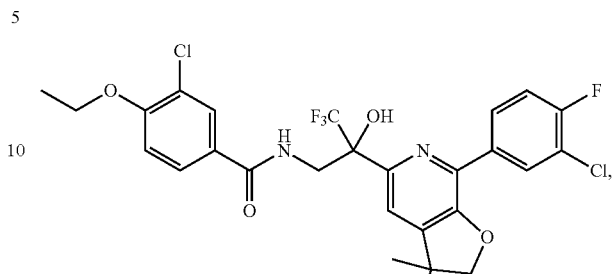
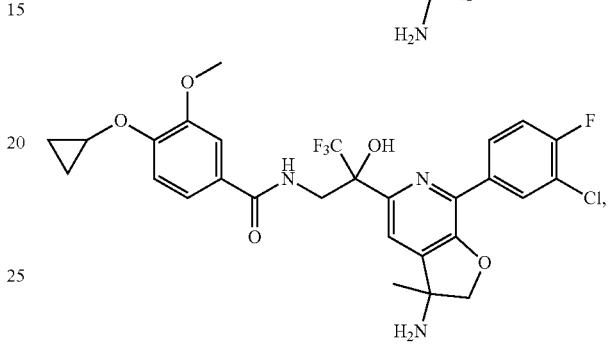
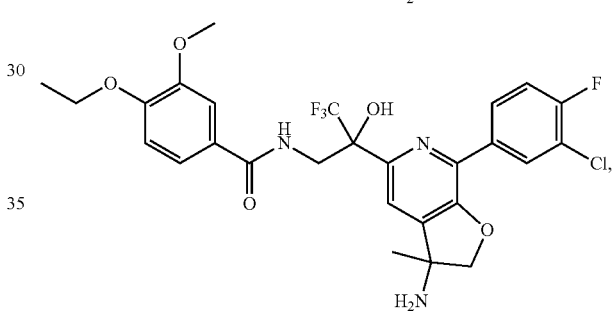
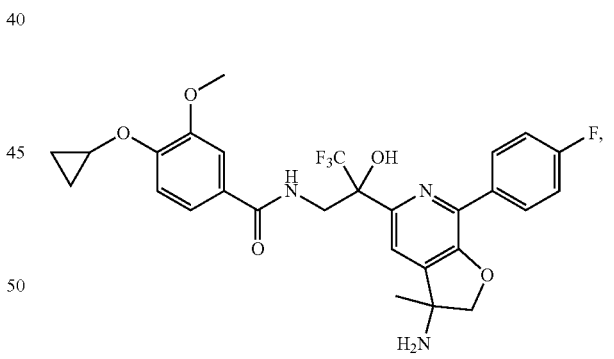
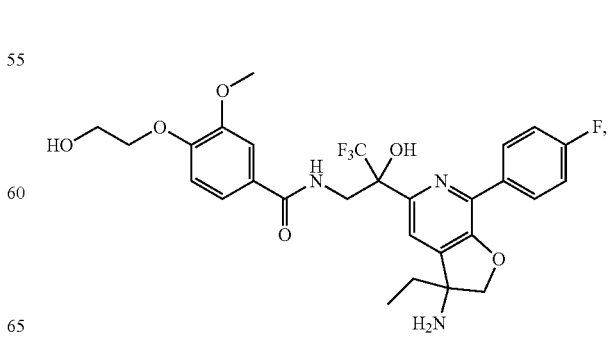

83
-continued
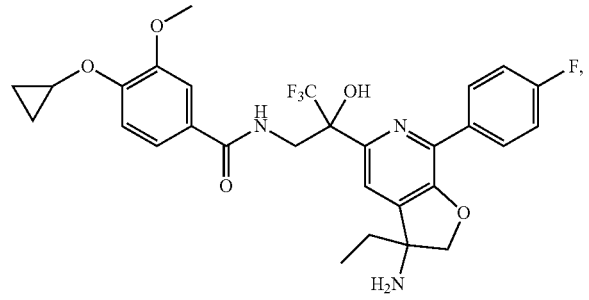
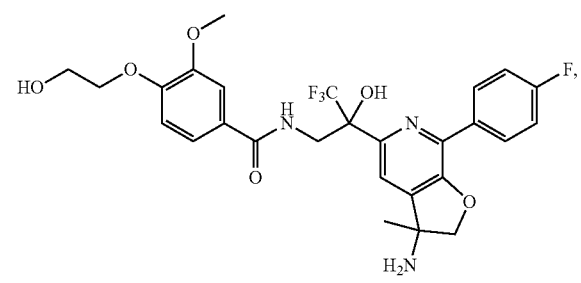
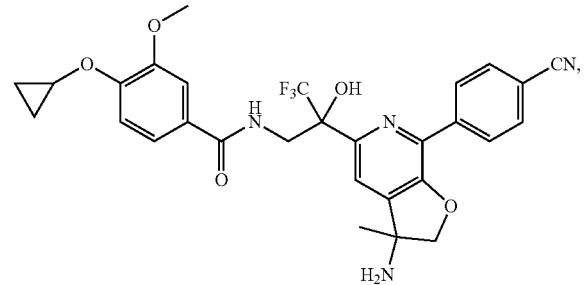
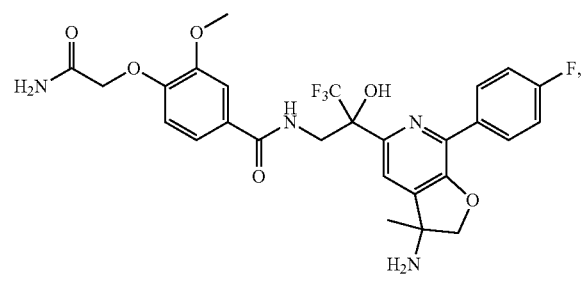
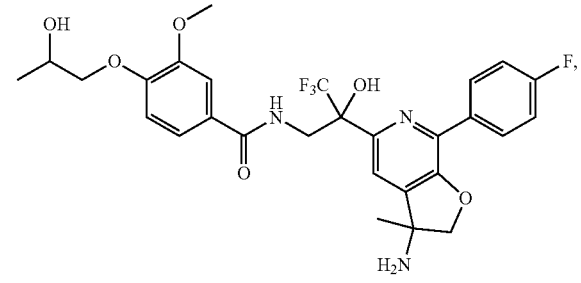
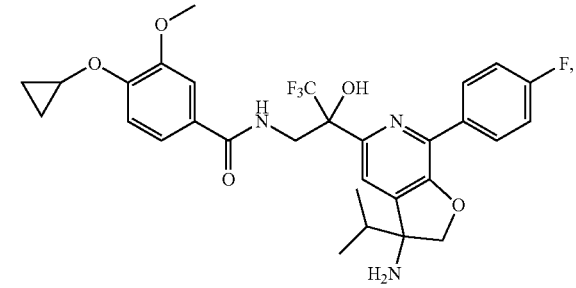
84
-continued
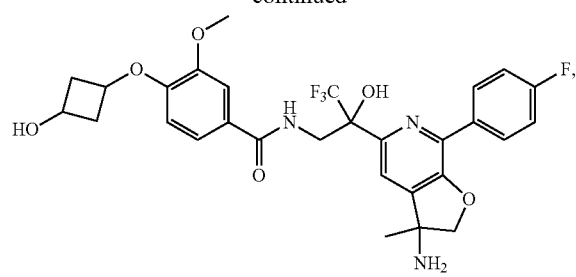
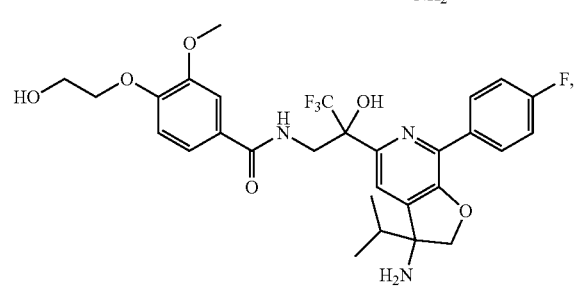
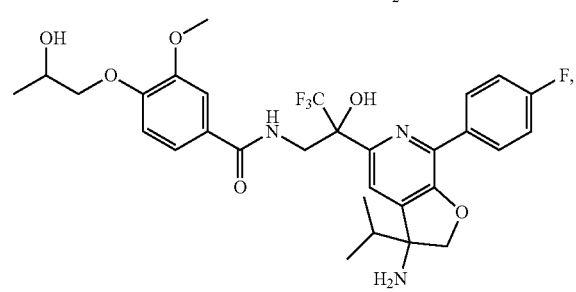
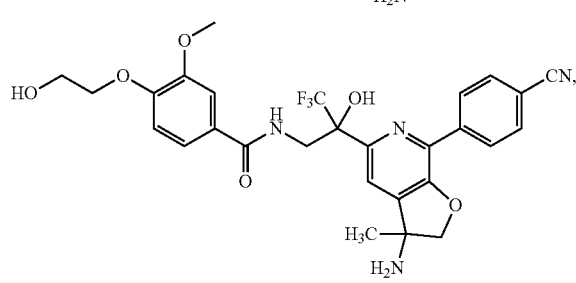
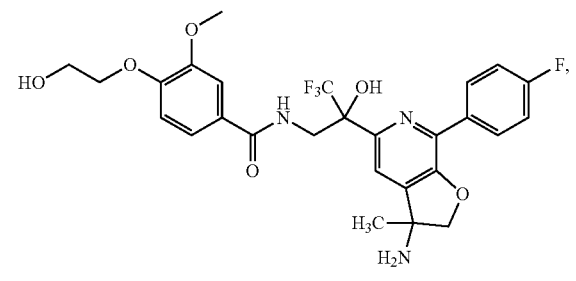
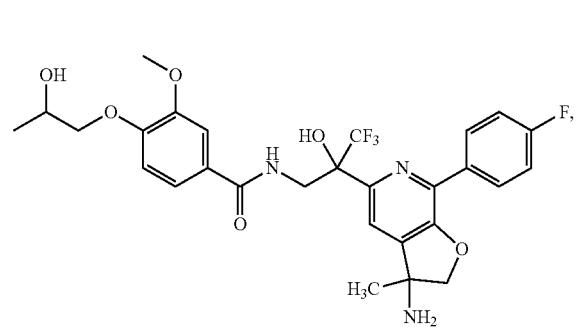

85
-continued
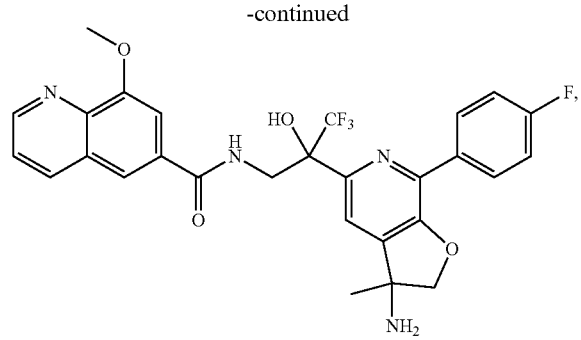
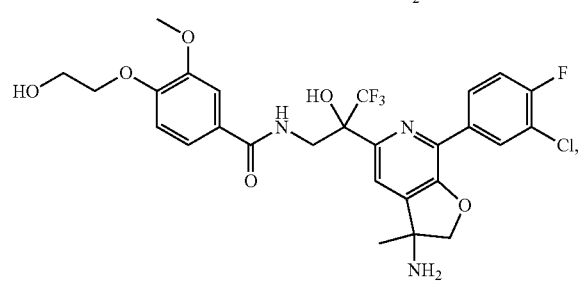
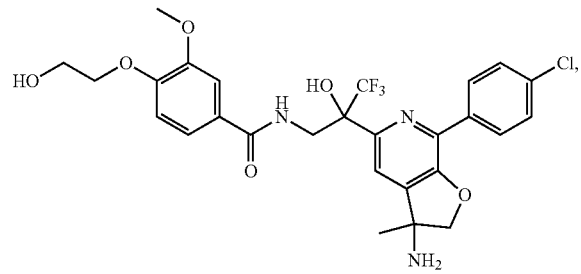
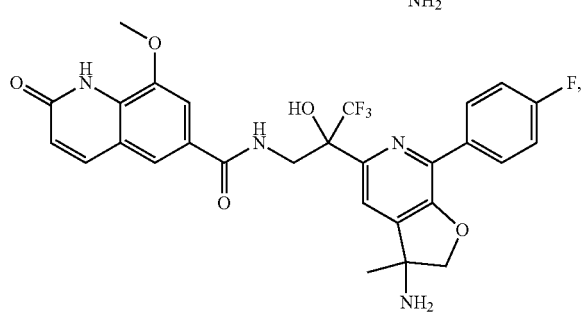
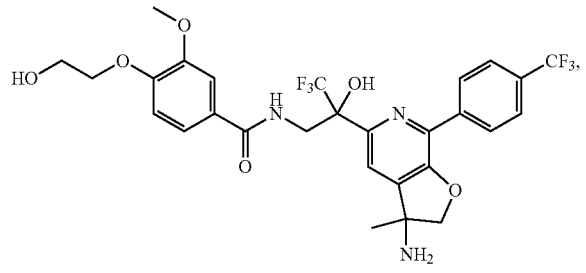
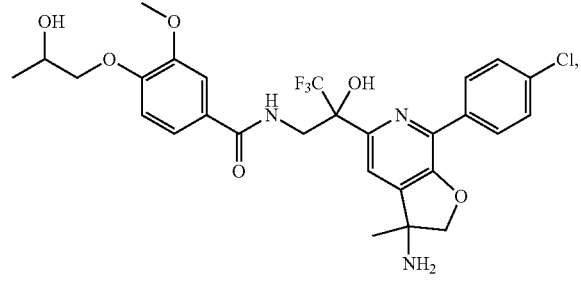
86
-continued
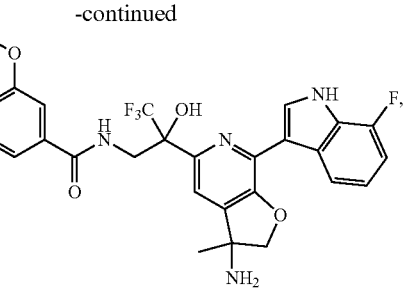
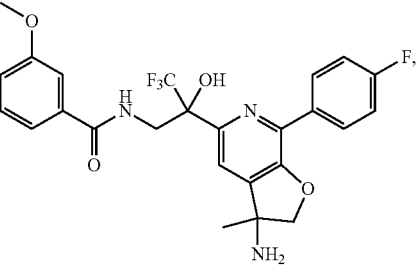
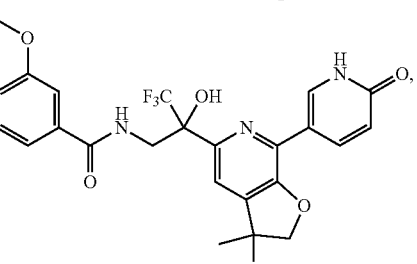
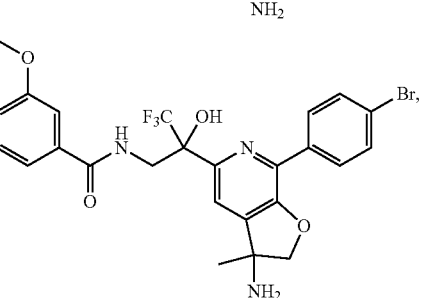
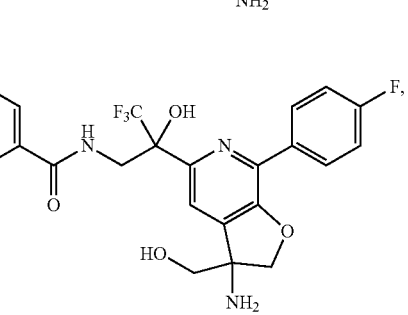
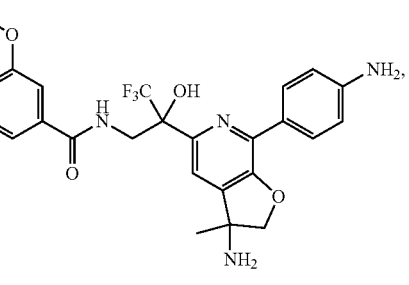

87
-continued
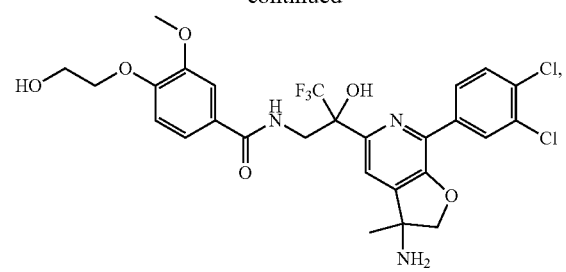
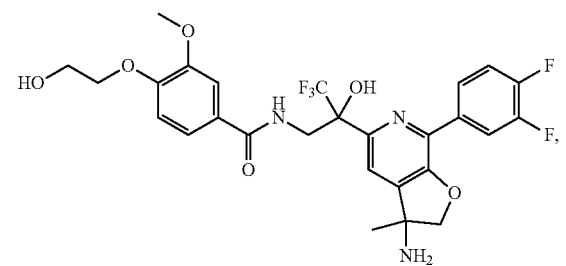
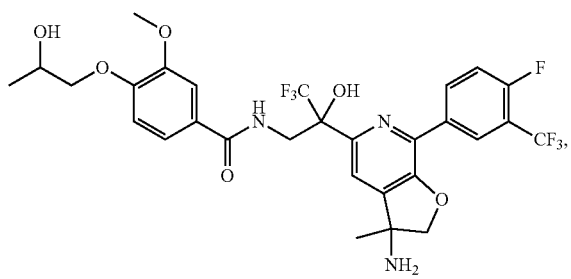
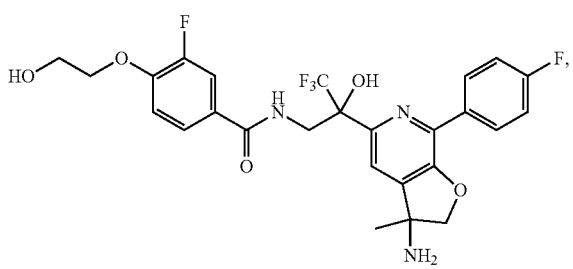
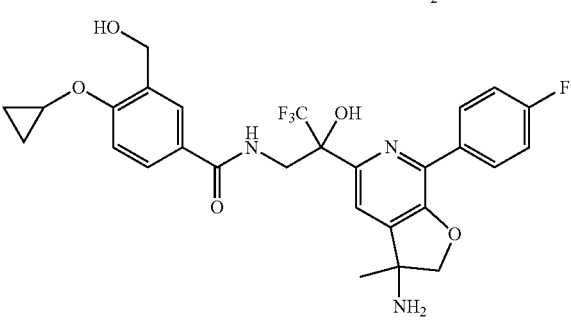
88
-continued
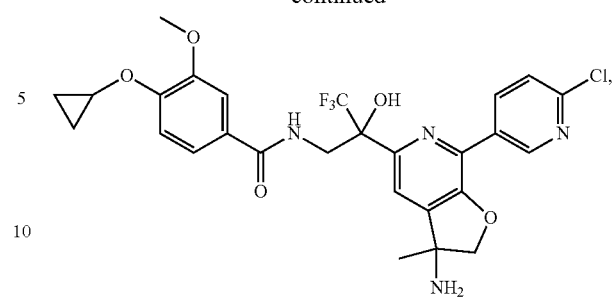
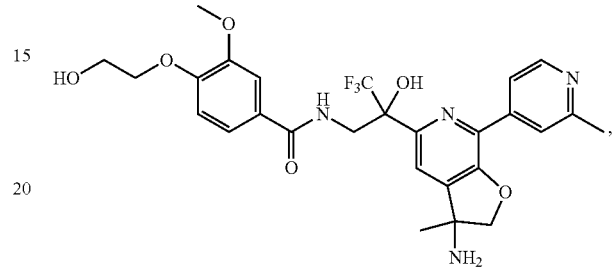
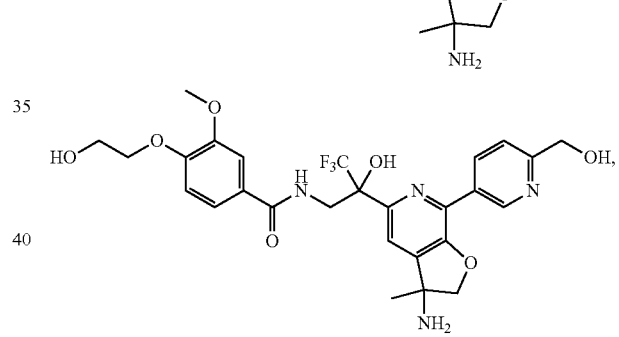
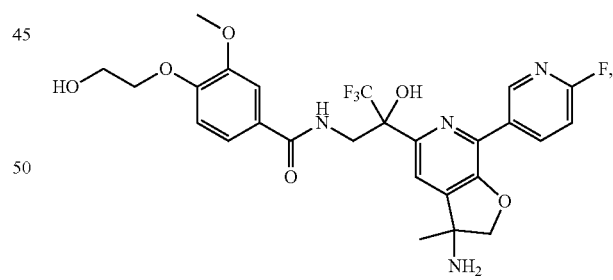
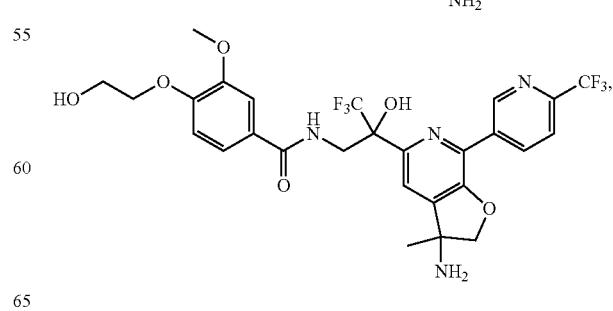

-continued
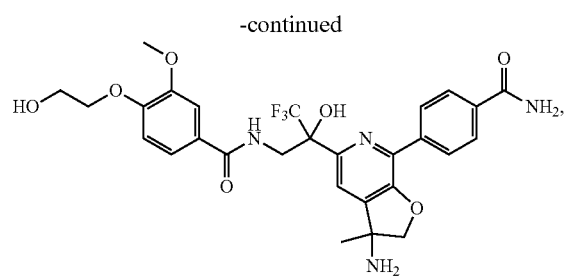
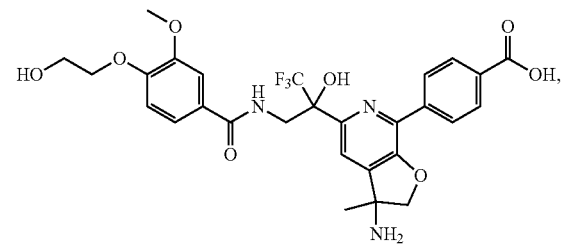
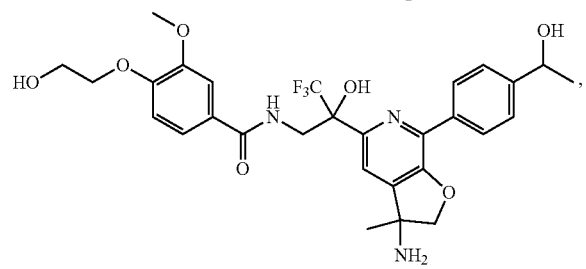
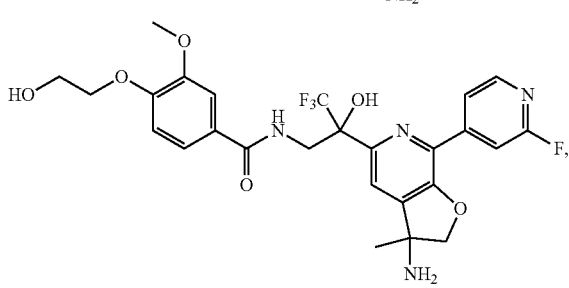
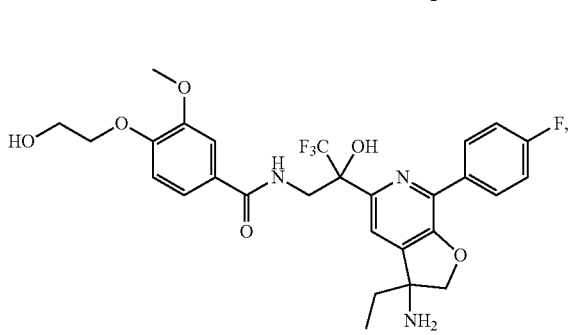
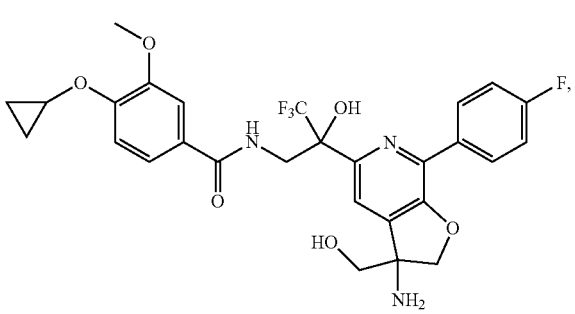
-continued
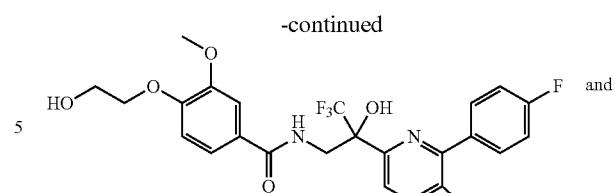
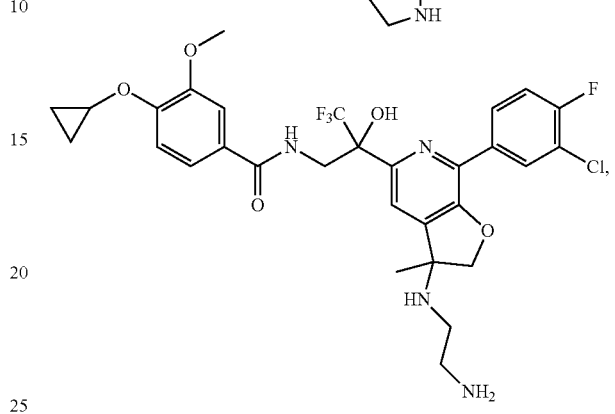
or a pharmaceutically acceptable salt of the foregoing.
In some embodiments, a compound of Formula (I), or a pharmaceutically acceptable salt thereof, cannot be selected from:
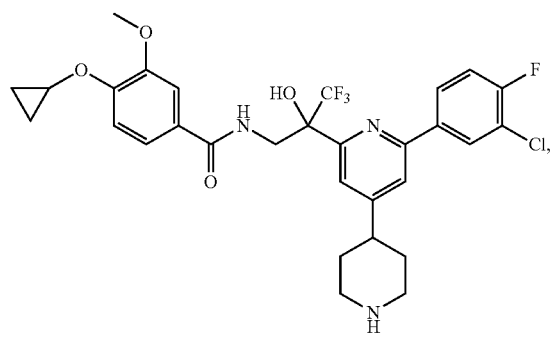
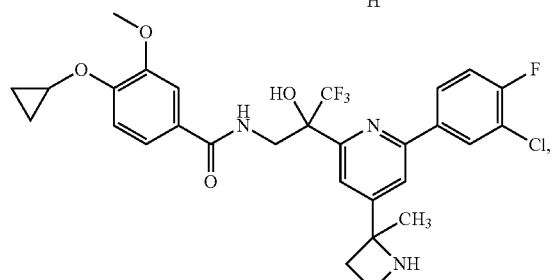
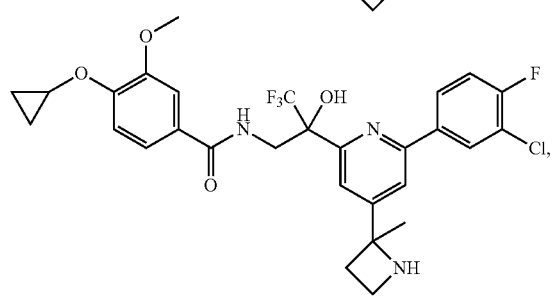

-continued

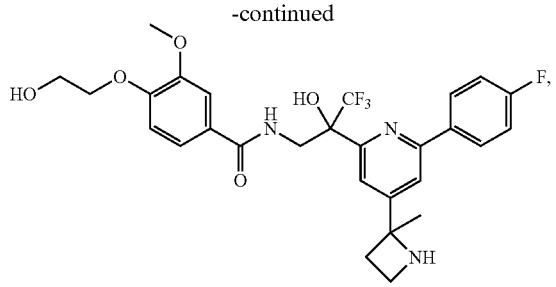

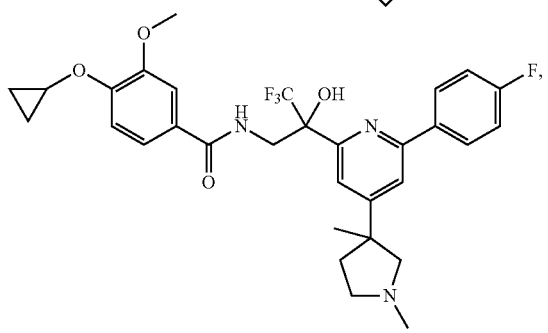

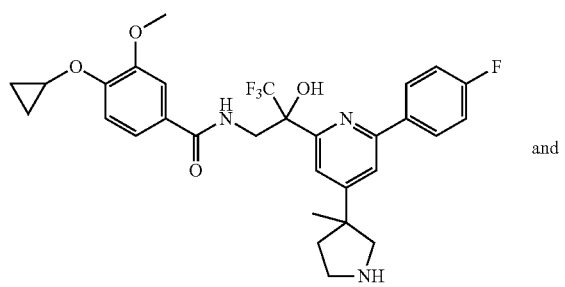

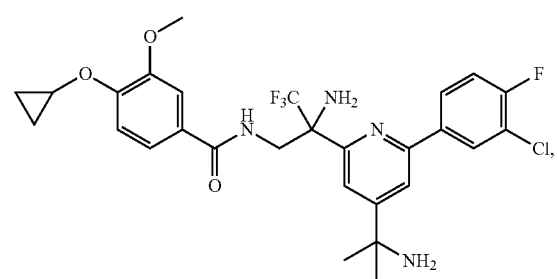

or a pharmaceutically acceptable salt of the foregoing.

In some embodiments, A cannot be a mono-substituted phenyl. For example, A cannot be a mono-chloro-substituted phenyl, a mono-fluoro-substituted phenyl or a mono-hydroxyalkyl-substituted phenyl. In some embodiments, A cannot be

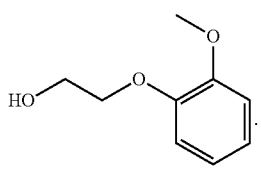

In some embodiments, A cannot be

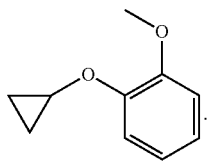

In some embodiments, In some embodiments, Y cannot be a mono-chloro-substituted phenyl or a mono-bromo-substituted phenyl. In some embodiments, Y cannot be an alkyl substituted phenyl (for example, $C_{1-4}$ alkyl substituted phenyl), a haloalkyl substituted phenyl (for example, $CF_3$ substituted phenyl), an amino substituted phenyl, a C-amido-substituted phenyl (such as a —C(=O)NH$_2$ substituted phenyl), a C-carboxy phenyl (for example, —C(=O)OH substituted phenyl) or a hydroalkyl-substituted phenyl (such as —CH(OH)CH$_3$ substituted phenyl). In some embodiments, Y cannot be a di-substituted phenyl. For example, Y cannot be a di-halogen-substituted phenyl. In some embodiments, Y cannot be an optionally substituted heteroaryl (for example, an optionally substituted indole or an optionally substituted pyridine). In some embodiments, Y cannot be a mono-substituted heteroaryl (for example, a mono-substituted heteroaryl, wherein the substituent is a $C_{1-4}$ alkyl, amino, haloalkyl (such as $CF_3$), C-amido (such as —C(=O)NH$_2$), C-carboxy (such as —C(=O)OH) or halogen). In other embodiments, Y cannot be an optionally substituted heterocyclyl (such as an optionally substituted pyridin-2-one). In some embodiments, Y cannot be a mono-substituted heterocyclyl. For example, Y cannot be a mono-substituted heteroaryl, wherein the substituent is a $C_{1-4}$ alkyl, amino, haloalkyl (such as $CF_3$), C-amido (such as —C(=O)NH$_2$), C-carboxy (such as —C(=O)OH) or halogen. In some embodiments, $Z^2$ cannot be O. In some embodiments, $L^1$ cannot be

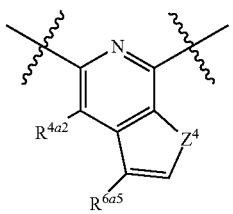

In some embodiments, $L^1$ cannot be

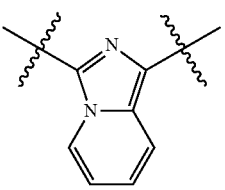

In some embodiments, L¹ cannot be

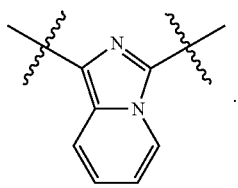 [SMILES: *c1nc(*)n2ccccc12]

In some embodiments, L¹ cannot be

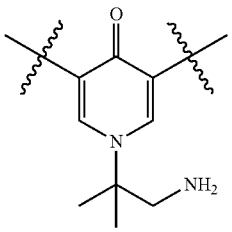

In some embodiments, L¹ cannot be

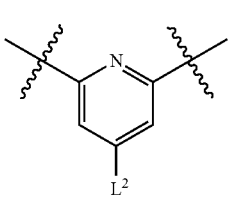

In some embodiments, L² cannot be

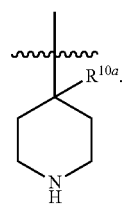

In some embodiments, L² cannot be

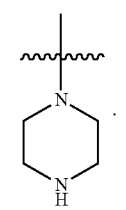

In some embodiments, L² cannot be

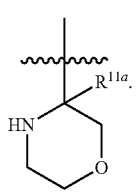

In some embodiments, L² cannot be

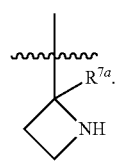

In some embodiments, L² cannot be

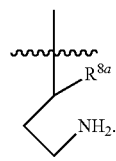

In some embodiments, L² cannot be

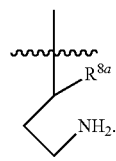

In some embodiments, L² cannot be

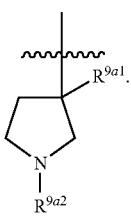

In some embodiments, L² cannot be

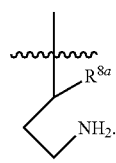

In some embodiments, L² cannot be

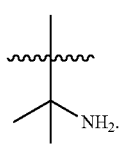 [SMILES: *C(C)(C)N]

In some embodiments, L² cannot be

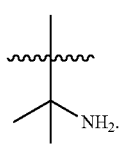 [SMILES: *C(C)(C)N]

In some embodiments, L² cannot be

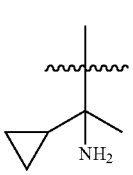

In some embodiments, when $L^1$ is

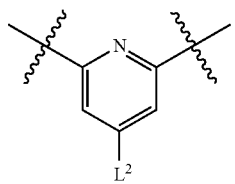

and $L^2$ is

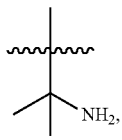

then one of $R^{3a}$ and $R^{3a1}$ is $NH_2$, and the other of $R^{3a}$ and $R^{3a1}$ is OH. In some embodiments, when $L^1$ is

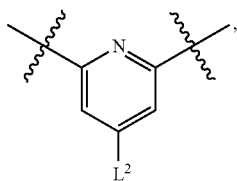

$L^2$ is

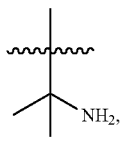

one of $R^{3a}$ and $R^{3a1}$ is $CF_3$, and the other of $R^{3a}$ and $R^{3a1}$ is OH, then Y is

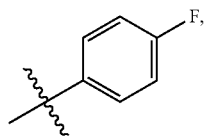 [SMILES: *c1ccc(F)cc1]

and A is a disubstituted phenyl wherein one substituent is

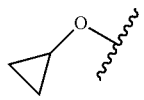

and the other substituent is $-O-(CH_2)_{2-4}OH$ or

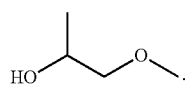

In some embodiments, when $L^1$ is

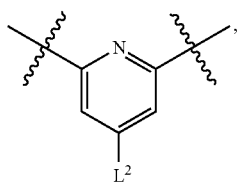

$L^2$ is

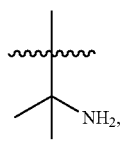 [SMILES: *C(C)(C)N]

then one of $R^{3a}$ and $R^{3a1}$ cannot be $CF_3$, and the other of $R^{3a}$ and $R^{3a1}$ cannot be OH. In some embodiments, $R^{9a1}$ cannot be hydrogen. In some embodiments, $R^{9a2}$ cannot be hydrogen. In some embodiments, $R^{10a}$ cannot be hydrogen. In some embodiments, $R^{11a}$ cannot be hydrogen.

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, pulmonary, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory infection may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments described herein relate to a method for ameliorating, treating and/or preventing a paramyxovirus viral infection, which can comprise administering an effective amount of one or more compounds described herein, or a pharmaceutical composition that includes one or more compounds described herein (e.g., a compound of Formula (I), or a pharmaceutically acceptable salt thereof).

Some embodiments described herein relate to a method for inhibiting viral replication of a paramyxovirus, which can comprise contacting a cell infected with the virus with an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof).

Some embodiments described herein relate to a method for contacting a cell infected with a paramyxovirus, which can comprise contacting a cell infected with the virus with an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof).

In some embodiments, the paramyxovirus infection is a human respiratory syncytial virus infection.

In some embodiments, an effective amount of one or more compounds of Formula (I), or a pharmaceutically acceptable salt thereof, one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a respiratory syncytial viral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a respiratory syncytial viral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication a respiratory syncytial virus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the RSV polymerase complex. In some embodiments, the RSV can be RSV A. In some embodiments, the RSV can be RSV B.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a hendraviral infection and/or nipahviral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a hendraviral infection and/or nipahviral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication a hendravirus and/or nipahvirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the hendravirus polymerase complex and/or nipahvirus polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a measles. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a measles. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication a measles virus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the measles polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate mumps. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent mumps. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication a mumps virus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the mumps polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a sendai viral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a sendai viral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication a sendai virus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the sendai virus polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a HPIV-1 infection and/or HPIV-3 infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a HPIV-1 infection and/or HPIV-3 infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication of a HPIV-1 and/or HPIV-3. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the HPIV-1 polymerase complex and/or HPIV-3 polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a HPIV-2 infection and/or HPIV-4 infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a HPIV-2 infection and/or HPIV-4 infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication of a HPIV-2 and/or HPIV-4. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the HPIV-2 polymerase complex and/or HPIV-4 polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a human metapneumoviral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a human metapneumoviral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication of a human metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the human metapneumovirus polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate an upper respiratory viral infection caused by a virus selected from a henipavirus, a morbillivirus, a respirovirus, a rubulavirus, a pneumovirus, and a metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate a lower respiratory viral infection caused by a virus selected from a henipavirus, a morbillivirus, a respirovirus, a rubulavirus, a pneumovirus, and a metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate one or more symptoms of an infection caused by a virus selected from a henipavirus, a morbillivirus, a respirovirus, a rubulavirus, a pneumovirus, and a metapneumovirus (such as those described herein).

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate an upper respiratory viral infection caused by RSV infection, measles, mumps, parainfluenza infection, and/or metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate a lower respiratory viral infection caused by RSV infection, measles, mumps, parainfluenza infection, and/or metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate one or more symptoms of an infection caused by RSV infection, measles, mumps, parainfluenza infection, and/or metapneumovirus (such as those described herein).

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate bronchiolitis and/or tracheobronchitis due to a RSV infection and/or human parainfluenza virus 3 (HPIV-3) infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate pneumonia due to a RSV infection and/or human parainfluenza virus 3 (HPIV-3) infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate croup due to a RSV infection and/or human parainfluenza virus 1 (HPIV-1) infection.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate due to fever, cough, runny nose, red eyes, a generalized rash, pneumonia, an ear infection and/or bronchitis due to measles. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate due to swelling of the salivary glands, fever, loss of appetite and/or fatigue due to mumps.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a human parainfluenza viral infection. In some embodiments, the human parainfluenza viral infection can be a human parainfluenza virus 1 (HPIV-1). In other embodiments, the human parainfluenza viral infection can be a human parainfluenza virus 2 (HPIV-2). In other embodiments, the human parainfluenza viral infection can be a human parainfluenza virus 3 (HPIV-3). In other embodiments, the human parainfluenza viral infection can be a human parainfluenza virus 4 (HPIV-4). In some embodiments, one or more compounds of Formula (I), or a pharmaceutically acceptable salt thereof, can be used to treat and/or ameliorate one or more subtypes of human parainfluenza virus. For example, one or more compounds of Formula (I), or a pharmaceutically acceptable salt thereof, can be used to treat HPIV-1 and/or HPIV-3.

The one or more compounds of Formula (I) or a pharmaceutically acceptable salt thereof, that can be used to treat, ameliorate and/or prevent a paramyxovirus viral infection can be a compound of Formula (I), or pharmaceutically acceptable salt thereof, provided in any of the embodiments described in the paragraphs following the header "Compounds".

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "prevent" and "preventing," mean lowering the efficiency of viral replication and/or inhibiting viral replication to a greater degree in a subject who receives the compound compared to a subject who does not receive the compound. Examples of forms of prevention include prophylactic administration to a subject who has been or may be exposed to an infectious agent, such as a paramyxovirus (e.g., RSV).

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance, and may positively affect one or more symptoms or aspects of the disease while having effects on other aspects of the disease or on unrelated systems that may be considered undesirable.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, treat, alleviate or ameliorate one or more symptoms or conditions of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Various indicators for determining the effectiveness of a method for treating a viral infection, such as a paramyxovirus, are known to those skilled in the art. Example of suitable indicators include, but are not limited to, a reduction in viral load, a reduction in viral replication, a reduction in viral RNA, a reduction in time to seroconversion (virus undetectable in patient serum), a reduction of morbidity or mortality in clinical outcomes, and/or other indicator of disease response.

In some embodiments, an effective amount of a compound of Formula (I), or a pharmaceutically acceptable salt thereof, is an amount that is effective to reduce viral titers to essentially undetectable or very low levels, for example, to less than 1.7 $\log_{10}$ plaque forming units equivalents (PFUe)/mL, or less than 0.3 $\log_{10}$ plaque forming units equivalents (PFUe)/mL. In some embodiments, a compound of Formula (I), or a pharmaceutically acceptable salt thereof, can reduce the viral load compared to the viral load before administration of the combination (for example, 60 hours after receiving the initial dosage of the combination). In some embodiments, a compound of Formula (I), or a pharmaceutically acceptable salt thereof, described herein can reduce the viral load to lower than 1.7 $\log_{10}$ (PFUe)/mL, or lower than 0.3 $\log_{10}$ (PFUe)/mL. In some embodiments, a combination of compounds described herein can achieve a reduction in viral titer in the serum of the subject in the range of about 1.5-log to about a 2.5-log reduction, about a 3-log to about a 4-log reduction, or a greater than about 5-log reduction compared to the viral load before administration of the combination. For example, the viral load is measure before administration of the combination, and several hours after receiving the initial dosage of the combination (for example, 60 hours after receiving the initial dosage of the combination).

In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of a paramyxovirus relative to pre-treatment levels in a subject, as determined several hours after receiving the initial dosage of the combination (for example, 60 hours after receiving the initial dosage of the combination). In some embodiments, a compound of Formula (I), or a pharmaceutically acceptable salt thereof, described herein can result in a reduction of the replication of a paramyxovirus relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of a paramyxovirus replication in the range of 1 to 1.5 log, 1.5 log to 2 log, 2 log to 2.5 log, 2.5 to 3 log, 3 log to 3.5 log or 3.5 to 4 log more reduction of a paramyxovirus replication compared to the reduction of a paramyxovirus reduction achieved by ribavirin (Virazole®), or may achieve the same reduction as that of ribavirin (Virazole®) therapy in a shorter period of time, for example, in one day, two days, three days, four days, or five days, as compared to the reduction achieved after 5 days of ribavirin (Virazole®) therapy.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be administered to a subject infected with RSV that is resistant to one or more different anti-RSV agents (for example, ribavirin). In some embodiments, development of resistant RSV strains is delayed when subjects are treated with a compound of Formula (I), or a pharmaceutically acceptable salt thereof, compared to the development of RSV strains resistant to other RSV drugs.

In some embodiments, a compound of Formula (I), or a pharmaceutically acceptable salt thereof, can decrease the percentage of subjects that experience complications from a RSV viral infection compared to the percentage of subjects that experience complication being treated with ribavirin. For example, the percentage of subjects being treated with a compound of Formula (I), or a pharmaceutically acceptable salt thereof, that experience complications can be 10%, 25%, 40%, 50%, 60%, 70%, 80% and 90% less compared to subjects being treated with ribavirin.

In some embodiments, a compound of Formula (I), or a pharmaceutically acceptable salt thereof, or a pharmaceutical composition that includes a compound described herein, can be used in combination with one or more additional agent(s). In some embodiments, a compound of Formula (I), or a pharmaceutically acceptable salt thereof, can be used in combination with one or more agents currently used in a conventional standard of care for treating RSV. For example, the additional agent can be ribavirin, palivizumab, and RSV-IGIV. For the treatment of RSV, additional anti-RSV agents include but are not limited to an anti-RSV antibody, a fusion protein inhibitor, an N-protein inhibitor, a RSV polymerase inhibitor, an IMPDH inhibitor, an interferon and an other compound that inhibits the RSV virus, or a pharmaceutically acceptable salt of any of the foregoing. A non-limiting list of examples of additional agents is provided herein.

```
anti-RSV      RSV-IGIV (RespiGam ®)
antibodies    palivizumab (Synagis ®, a chimeric humanized IgG monoclonal
              antibody)
              motavizumab (MEDI-524, humanized monoclonal antibody)

fusion        1-cyclopropyl-3-[[1-(4-hydroxybutyl)benzimidazol-2-
protein       yl]methyl]imidazo[4,5-c]pyridin-2-one (BMS-433771)
inhibitors    4,4"-bis-{4,6-bis-[3-(bis-carbamoylmethyl-sulfamoyl)-phenylamino]-
              (1,3,5)triazin-2-ylamino}-biphenyl-2,2"-disulfonic-acid (RFI-641)
              4,4'-Bis[4,6-di[3-aminophenyl-N,N-bis(2-carbamoylethyl)-
              sulfonilimino]-1,3,5-triazine-2-ylamino]-biphenyl-2,2'-disulfonic
              acid, disodium salt (CL387626)
              2-[[2-[[1-(2-aminoethyl)-4-piperidinyl]amino]-4-methyl-1H-
              benzimidazol-1-yl]-6-methyl-3-pyridinol (JNJ-2408068)
              2-[[6-[[[2-(3-Hydroxypropyl)-5-methylphenyl]amino]methyl]-2-[[3-
              (morpholin-4-yl)propyl]amino]benzimidazol-1-yl]methyl]-6-
              methylpyridin-3-ol (TMC-353121)
              5,5'-bis[1-(((5-amino-1H-tetrazolyl)imino)methyl)]2,2',4"-
              methylidynetrisphenol (VP-14637, MDT-637)
              N-(2-hydroxyethyl)-4-methoxy-N-methyl-3-(6-methyl-
              [1,2,4]triazolo[3,4-a]phtalazin-3-yl)bensenesulfonamide(P13)
              2-((2-((1-(2-aminoethyl)piperidin-4-yl)amino)-4-methyl-1H-
              benzo[d]imidazol-1-yl)methyl)-6-methylpyridin-3-ol (R170591)
              1,4-bis(3-methylpyridin-4-yl)-1,4-diazepane (C15)
              (R)-9b-(4-chlorophenyl)-1-(4-fluorobenzoyl)-2,3-dihydro-1H-
              imidazo[1',2':1,2]pyrrolo[3,4-c]pyridin-5(9bH)-one (BTA9981)
              [2,2-bis(docosyloxy-oxymethyl)propyl-5-acetaoamido-3,5-dideoxy-
              4,7,8,9-tetra-O-(sodium-oxysulfonyl)-D-glycero-D-galacto-2-
              nonulopyranosid]onate (MBX-300)
              BTA-C286
              N-(2-((S)-2-(5-((S)-3-aminopyrrolidin-1-yl)-6-methylpyrazolo
              [1,5-a]pyrimidin-2-yl)piperidine-1-carbonyl)-4-
              chlorophenyl)methanesulfonamide (GS-5806)
              an anti-RSV nanobody (e.g., ALX-0171 (a trivalent nanobody,
              Ablynx)
              a peptide fusion inhibitor (such as a peptide having the sequence
              DEFDASISQVNEKINQSLAFIRKSDELL (T-67)
              a peptide having the sequence
              FDASISQVNEKINQSLAFIRKSDELLHNVNAGKST (T-118)

N-protein     (S)-1-(2-fluorophenyl)-3-(2-oxo-5-phenyl-2,3-dihydro-1H-
inhibitors    benzo[e][1,4]diazepin-3-yl)urea(RSV-604)
              STP-92 (siRNA delivered through nanoparticle based delivery
              systems, Sirnaomics)
              iKT-041 (Inhibikase)

RSV           6-{4-[(biphenyl-2-ylcarbonyl)amino]benzoyl}-N-cyclopropyl-5,6-
polymerase    dihydro-4H-thieno[3,2-d][1]benzazepine-2-carboxamide (YM-53403)
inhibitors    N-cyclopropyl-5-(4-(2-(pyrrolidin-1-yl)benzamido)benzoyl)-5,6,7,
              10-
              tetrahydrobenzo[b]cyclopentaazepine-9-carboxamide
              6-(4-(2-(2-oxa-7-azaspiro[3.5]nonan-7-yl)nicotinamido)benzoyl)-N-
              cyclopropyl-5,6-dihydro-4H-benzo[b]thieno[2,3-d]azepine-2-
              carboxamide
              4-amino-8-(3-{[2-(3,4-dimethoxyphenyl)ethyl]amino}propyl)-6,6-
              dimethyl-2-(4-methyl-3-nitrophenyl)-1H-imidazo[4,5-h]-isoquinoline-
              7,9(6H,8H)-dione (CAS Reg. No. 851658-10-1)
              6-(4-(2-(2-oxa-7-azaspiro[3.5]nonan-7-yl)nicotinamido)benzoyl)-N-
              cyclopropyl-5,6-dihydro-4H-benzo[b]thieno[2,3-d]azepine-2-
              carboxamide (AZ27)
```

|  |  |
|---|---|
|  | (2R,3R,4R,5R)-5-(4-amino-2-oxopyrimidin-1(2H)-yl)-2-(chloromethyl)-4-fluoro-2-((isobutyryloxy)methyl)tetrahydrofuran-3-yl isobutyrate<br>(2R,3R,4R,5R)-5-(4-amino-2-oxopyrimidin-1(2H)-yl)-2-(chloromethyl)-4-fluoro-2-(hydroxymethyl)tetrahydrofuran-3-yl isobutyrate<br>4-amino-1-((2R,3R,4R,5R)-5-(chloromethyl)-3-fluoro-4-hydroxy-5-(hydroxymethyl)tetrahydrofuran-2-yl)pyrimidin-2(1H)-one<br>((2R,3R,4R,5R)-5-(4-amino-2-oxopyrimidin-1(2H)-yl)-2-(chloromethyl)-4-fluoro-3-hydroxytetrahydrofuran-2-yl)methyl triphosphate |
| IMPDH inhibitors | ribavirin<br>5-ethynyl-1-beta-D-ribofuranosylimidazole-4-carboxamide (EICAR)<br>4-hydroxy-3-beta-D-ribofuranosylpyrazole-5-carboxamide (pyrazofurin)<br>1-((2R,3R,4S,5R)-3,4-dihydroxy-5-(hydroxymethyl)tetrahydrofuran-2-yl)-1H-1,2,4-triazole-3-carboximidamide (Taribavirin, viramidine)<br>1,3,4-thiadiazol-2-ylcyanamide (LY253963)<br>tetrahydrofuran-3-yl-3-(3-(3-methoxy-4-(oxazol-5-yl)phenyl)ureido)benzylcarbamate (VX-497)<br>(4E)-6-(4-Hydroxy-6-methoxy-7-methyl-3-oxo-1,3-dihydro-2-benzofuran-5-yl)-4-methylhex-4-enoic acid (Mycophenolic acid)<br>2-morpholin-4-ylethyl-(E)-6-(4-hydroxy-6-methoxy-7-methyl-3-oxo-1H-2-benzofuran-5-yl)-4-methylhex-4-enoate (Mycophenolate Mofetil) |
| Interferons | Type 1 interferon<br>Type 2 interferon<br>Type 3 interferon<br>an alpha-interferon (IFN-α)<br>Pegylated interferon-alpha-2a (PEGASYS ®)<br>Pegylated interferon-alpha-2b (PEG-INTRON ®)<br>interferon alfacon-1 (INFERGEN ®)<br>beta-interferon (IFN-β)<br>lambda-interferon (IFN-λ) |
| other compounds | a double stranded RNA oligonucleotide<br>5-methyl-N-[4-(trifluoromethyl) phenyl]-isoxazole-4-carboxamide (leflumomide)<br>N-(2-chloro-4-methylphenyl)-2-((1-(4-methoxyphenyl)-1H-benzo[d]imidazol-2-yl)thio)propanamide (JMN3-003)<br>an intratracheal formulation of recombinant human CC10 (CG-100)<br>high titer, human immunoglobulin (RI-001, ADMA Biologics Inc.)<br>a non-neutralizing mAb against the G protein (mAb 131-2G)<br>ALN-RSV01 (an siRNA agent with the sense strand sequence (5' to 3')<br>GGCUCUUAGCAAAGUCAAGdTdT (SEQ ID NO. 3) and the antisense strand sequence (5' to 3')<br>CUUGACUUUGCUAAGAGCCdTdT (SEQ ID NO. 4)<br>ALN-RSV02<br>Medi-559<br>Medi-534<br>Medi-557 |

ALN-RSV01 and/or ALN-RSV02 can be found in U.S. Publication No. 2009/0238772, filed Dec. 15, 2008 (Alnylam Pharmaceuticals).
ALX-0171 described in U.S. Publication No. 2012/0128669, filed June 7, 2010.
T-67, SEQ ID NO: 1, U.S. Pat. No. 6,623,741, filed Feb. 29, 2000.
T-118, SEQ ID NO: 2, U.S. Pat. No. 6,623,741, filed Feb. 29, 2000.

Other examples of compounds that can be used in combination with a compound of Formula (I), or a pharmaceutically acceptable salt, include those provided in WO 2013/186333, published Dec. 19, 2013; WO 2013/186332, published Dec. 19, 2013; WO 2013/186335, published Dec. 19, 2013; WO 2013/186334, published Dec. 19, 2013; WO 2012/080447, published Jun. 21, 2012; WO 2012/080449, published Jun. 21, 2012; WO 2012/080450, published Jun. 21, 2012; WO 2012/080451, published Jun. 21, 2012; WO 2012/080446, published Jun. 21, 2012; WO 2010/103306, published Sep. 16, 2010; WO 2012/068622, published May 31, 2012; WO 2005/042530, published May 12, 2005; WO 2006/136561, published Dec. 28, 2006; WO 2005/058869, published Jun. 30, 2005; U.S. 2013/0090328, published Apr. 11, 2013; WO 2014/009302, published Jan. 16, 2014; WO 2011/005842, published Jan. 13, 2011; U.S. 2013/0273037, published Oct. 17, 2013; U.S. 2013/0164280, published Jun. 27, 2013; U.S. 2014/0072554, published Mar. 13, 2014; WO 2014/031784, published Feb. 27, 2014 and WO 2015/026792, published Feb. 26, 2015, all of which are hereby incorporated by reference.

In combination therapy, the additional agents can be administered in amounts that have been shown to be effective for those additional agents. Such amounts are known in the art; alternatively, they can be derived from viral load or replication studies using the parameters for "effective amount" set forth above. Alternatively, the amount used can be less than the effective monotherapy amount for such additional agents. For example, the amount used could be between 90% and 5% of such amount, e.g., 90%, 80%, 70%, 60%, 50%, 40%, 30%, 20%, 10%, or 5%, or intermediate values between those points.

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

A potential advantage of utilizing a compound of Formula (I), or a pharmaceutically acceptable salt thereof, in combination with one or more additional agent(s) described in the paragraph under the heading "Methods of Use," containing the table listing anti-RSV antibodies, fusion protein inhibitors, N-protein inhibitors, RSV polymerase inhibitors, IMPDH inhibitors, interferons, and other compounds, as well as the following paragraph, including pharmaceutically acceptable salts and prodrugs thereof, may be a reduction in the required amount(s) of one or more compounds of the paragraph under the heading"Methods of Use," containing the table listing anti-RSV antibodies, fusion protein inhibitors, N-protein inhibitors, RSV polymerase inhibitors, IMPDH inhibitors, interferons, and other compounds, as well as the following paragraph (including pharmaceutically acceptable salts and prodrugs thereof) that is effective in treating a disease condition disclosed herein (for example, RSV), as compared to the amount required to achieve same therapeutic result when one or more compounds described in the paragraph under the heading "Methods of Use," containing the table listing anti-RSV antibodies, fusion protein inhibitors, N-protein inhibitors, RSV polymerase inhibitors, IMPDH inhibitors, and other compounds, as well as the following paragraph (including the table), including pharmaceutically acceptable salts thereof, are administered without a compound of Formula (I), or a pharmaceutically acceptable salt thereof. For example, the amount of a compound described in the paragraph under the heading "Methods of Use," containing the table listing anti-RSV antibodies, fusion protein inhibitors, N-protein inhibitors, RSV polymerase inhibitors, IMPDH inhibitors, interferons, and other compounds, as well as the following paragraph, including a pharmaceutically acceptable salt and prodrug thereof, can be less compared to the amount of the compound described in the paragraph under the heading "Methods of Use," containing the table listing anti-RSV antibodies, fusion protein inhibitors, N-protein inhibitors, RSV polymerase inhibitors, IMPDH inhibitors, interferons, and other compounds, as well as the following paragraph, including a pharmaceutically acceptable salt and prodrug thereof, needed to achieve the same viral load reduction when administered as a monotherapy. Another potential advantage of utilizing a compound of Formula (I), or a pharmaceutically acceptable salt thereof, in combination with one or more additional agent(s) described in the paragraph under the heading "Methods of Use," containing the table listing anti-RSV antibodies, fusion protein inhibitors, N-protein inhibitors, RSV polymerase inhibitors, IMPDH inhibitors, interferons, and other compounds, as well as the following paragraph, including pharmaceutically acceptable salts and prodrugs thereof, is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) described in the paragraph under the heading "Methods of Use," containing the table listing anti-RSV antibodies, fusion protein inhibitors, N-protein inhibitors, RSV polymerase inhibitors, IMPDH inhibitors, interferons, and other compounds, as well as the following paragraph, including pharmaceutically acceptable salts and prodrugs thereof, may include little to no cross resistance between a compound of Formula (I), or a pharmaceutically acceptable salt thereof, and one or more additional agent(s) described in the paragraph under the heading "Methods of Use," containing the table listing anti-RSV antibodies, fusion protein inhibitors, N-protein inhibitors, RSV polymerase inhibitors, IMPDH inhibitors, interferons, and other compounds, as well as the following paragraph(including pharmaceutically acceptable salts and prodrugs thereof); different routes for elimination of a compound of Formula (I), or a pharmaceutically acceptable salt thereof, and one or more additional agent(s) described in the paragraph under the heading "Methods of Use," containing the table listing anti-RSV antibodies, fusion protein inhibitors, N-protein inhibitors, RSV polymerase inhibitors, IMPDH inhibitors, interferons, and other compounds, as well as the following paragraph (including pharmaceutically acceptable salts and prodrugs thereof); little to no overlapping toxicities between a compound of Formula (I), or a pharmaceutically acceptable salt thereof, and one or more additional agent(s) described in the paragraph under the heading "Methods of Use," containing the table listing anti-RSV antibodies, fusion protein inhibitors, N-protein inhibitors, RSV polymerase inhibitors, IMPDH inhibitors, interferons, and other compounds, as well as the following paragraph (including pharmaceutically acceptable salts and prodrugs thereof); little to no significant effects on cytochrome P450; and/or little to no pharmacokinetic interactions between a compound of Formula (I), or a pharmaceutically acceptable salt thereof, and one or more additional agent(s) described in the paragraph under the heading "Methods of Use," containing the table listing anti-RSV antibodies, fusion protein inhibitors, N-protein inhibitors, RSV polymerase inhibitors, IMPDH inhibitors, interferons, and other compounds, as well as the following paragraph, including pharmaceutically acceptable salts and prodrugs thereof).

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Synthesis

Compounds of Formula (I), and those described herein may be prepared in various ways. Some compounds of Formula (I) can be obtained commercially and/or prepared utilizing known synthetic procedures. General synthetic routes to the compounds of Formula (I), and some examples of starting materials used to synthesize the compounds of Formula (I) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

EXAMPLES

Additional embodiments are disclosed in further detail in the following examples, which are not in any way intended to limit the scope of the claims.

Example 1

Preparation of Compound 8

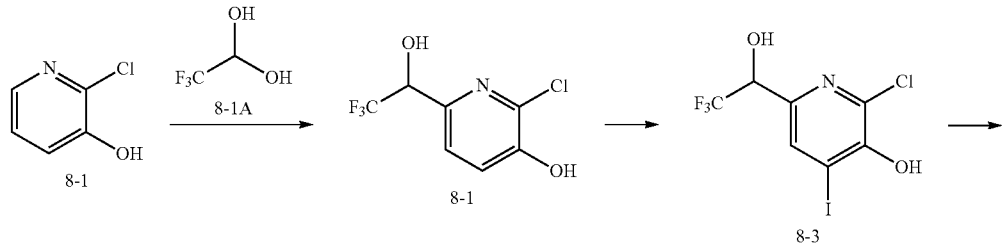

-continued
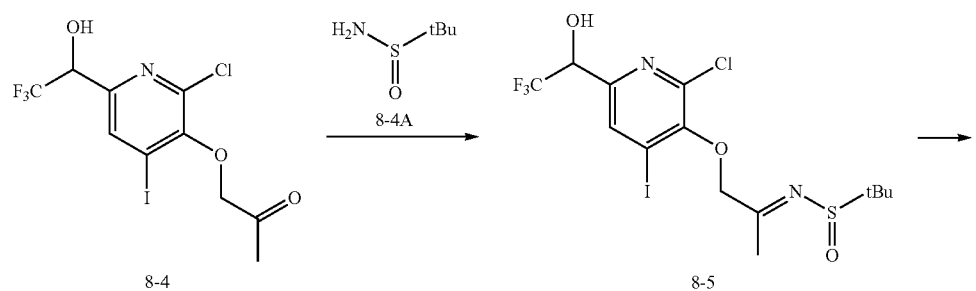
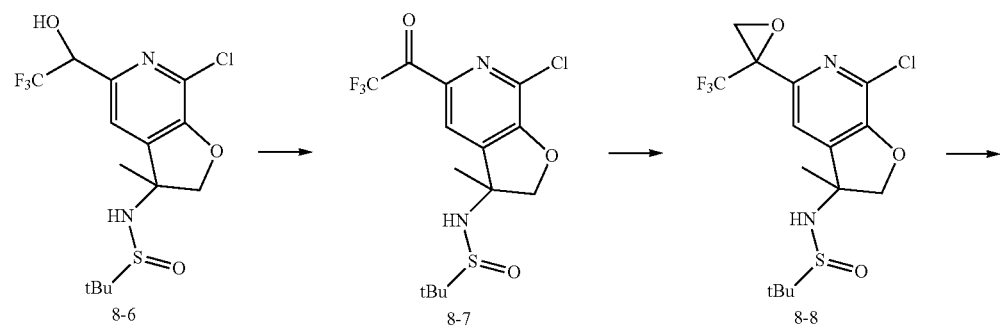
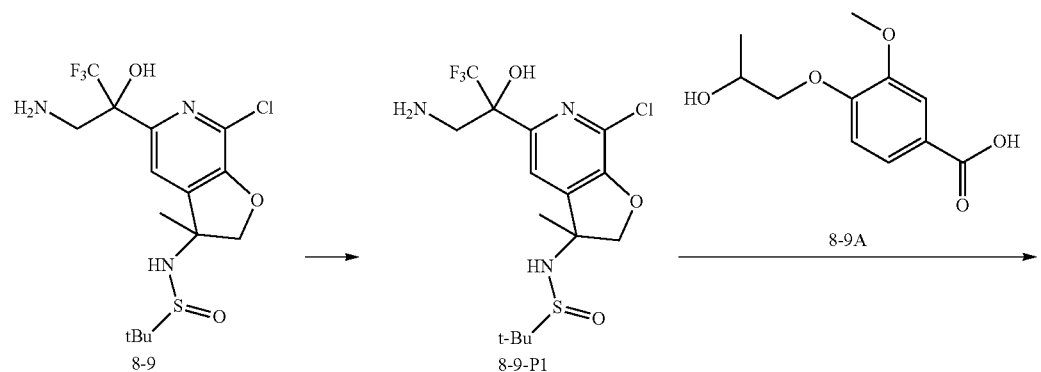
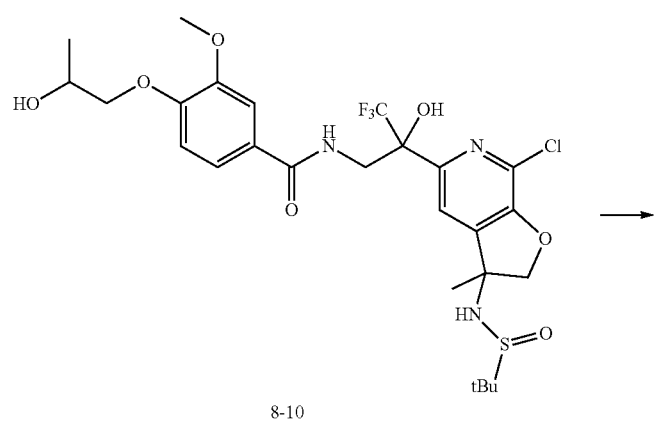

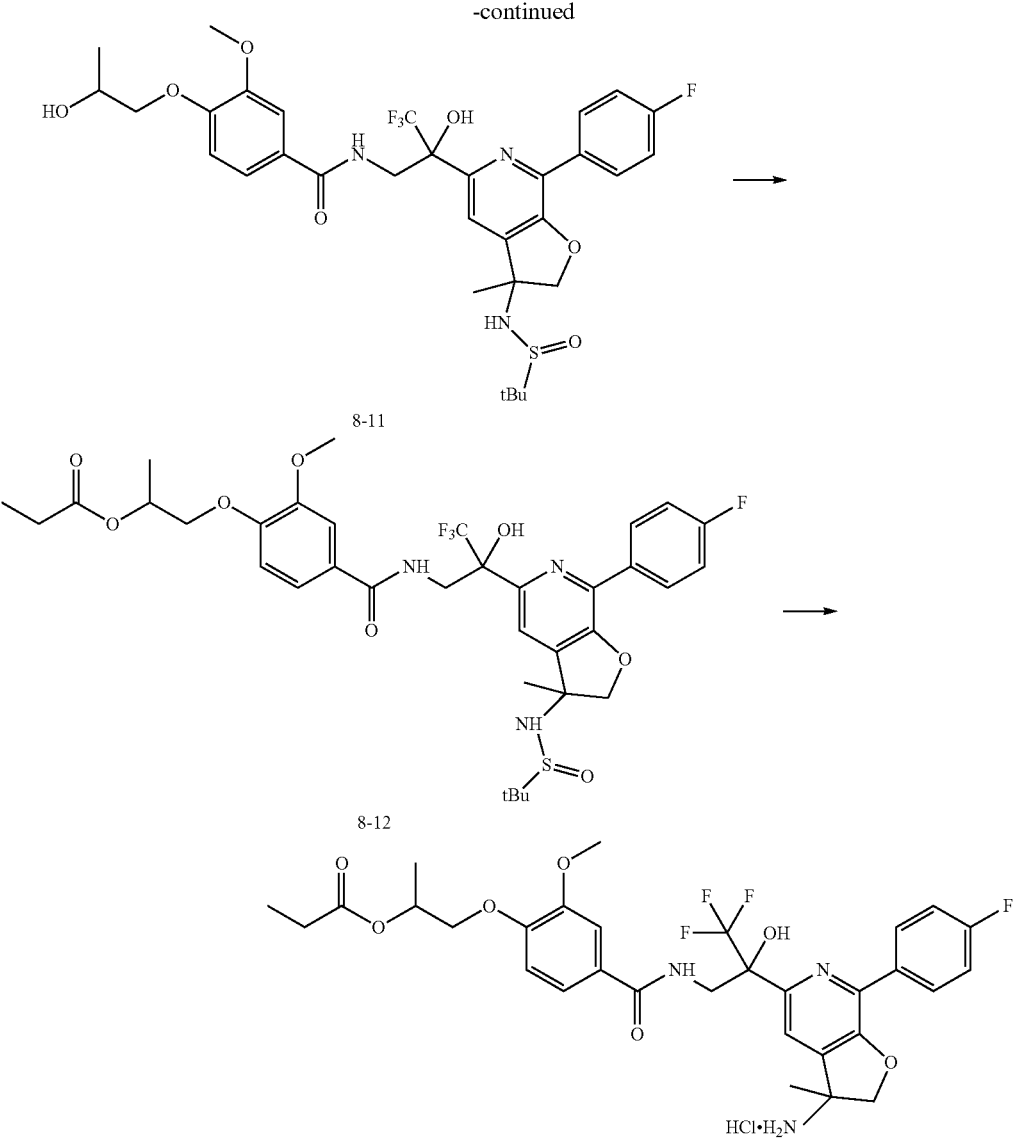

An internal metal surface autoclave (2 L) was charged with 8-1 (200 g, 1.54 mol), 8-1A (538 g, 4.63 mol) and K₂CO₃ (427 g, 3.09 mol) in H₂O (0.8 L). The vessel was sealed and heated to 120° C. for 20H. The mixture was cooled to room temperature (RT), diluted with water (500 mL) and acidified to pH=3~4 using a 6.0 M HCl solution. A white precipitate formed and was collected by filtration. The solid was dried under vacuum to give 8-2 as a white solid (312 g, 89%).

To a stirring solution of 8-2 (300 g, 1.32 mol) and Na₂CO₃ (280 g, 2.64 mol) in H₂O (2 L) was added I₂ (436 g, 1.72 mol) in portions. The mixture was stirred at 25° C. for 48 h. The reaction was monitored by LCMS. After 8-2 was consumed, a sat. sodium sulfite solution (2 L) was used to quench the reaction. The mixture was acidified with 3.0 M HCl solution and diluted with EA (1 L). The organic phase was separated, and the aqueous phase was extracted with EA (3×500 mL). The combined organic phase was dried over anhydrous Na₂SO₄, filtered and concentrated under reduced pressure. The residue was solidified to give 8-3 (416 g, 89.3%) as a yellow solid.

To a solution of 8-3 (397 g, 1.12 mol) and 1-chloropropan-2-one (258 g, 2.8 mol) in DMF (1.5 L) was added NaHCO₃ (282 g, 3.36 mmol) in portions at RT under N₂. The mixture was stirred at 25° C. for 25 h. After 8-3 was consumed, the solid was removed by filtration. The filtrate was concentrated to dryness under reduced pressure, and the residue was washed by DCM (1 L). The white solid was collected with filtration and dried under vacuum to give 8-4 (402 g, 87%).

A mixture of 8-4 (41 g, 100 mmol), 8-4A (S-configuration, 12.74 g, 105 mmol) and titanium(IV) ethoxide (48 g, 210 mmol) in anhydrous THF (160 mL) was heated to 80° C. under N₂ and stirred for 1 h. The reaction was monitored by TLC (DCM:EA=8:1). After 8-4 was consumed, the mixture was concentrated to dryness. The residue was dissolved in EA (400 mL). The solution was poured into sat. aq. NaHCO₃ (500 mL), and the mixture was stirred for 2 mins. The mixture was filtered through a pad of celite, and the cake was washed with EA (2×400 mL). The combined organic phase was removed under reduced pressure, and the residue was purified by column chromatography using 10% EA in DCM as the eluent to give 8-5 (~39 g, 76%) as a yellow oil. 8-5 was used for next step immediately.

To a solution of EtMgBr (25.4 mL, 76.2 mmol, 3 M in ether) in dry THF (400 mL) was added n-BuLi (61 mL, 152.5 mmol, 2.5 M in hexane), and the mixture was stirred at 0° C. After stirring for 10 mins, the mixture was cooled to −78° C. A solution of 8-5 (39 g, 76 mmol) in dry THF (100 mL) was added dropwise, and the mixture was stirred at −78° C. for 30 mins. The reaction was quenched with $H_2O$ (100 mL) and extracted with EA (2×400 mL). The combined organic phase was washed with brine, dried over anhydrous $Na_2SO_4$, filtered and concentrated under reduced pressure. The residue was purified by column chromatography (eluent: 0~10% EA in DCM) to afford 8-6 (17 g, 58%).

To a stirring solution of 8-6 (6.8 g, 17.6 mmol) in DCM (50 mL) was added Dess-Martin reagent (8.95 g, 21.1 mmol), and the mixture stirred at RT under $N_2$ atmosphere for 1 h. The reaction was quenched with a sat. aq. $Na_2SO_3$ solution and a sat. aq. $NaHCO_3$ solution. After 30 mins of vigorous stirring, the organic layers were separated. The aqueous layer was extracted with EA (2×100 mL). The combined organic phase was washed with brine, dried over anhydrous $Na_2SO_4$, filtered and concentrated under reduced pressure. The residue was purified by column chromatography (eluent: 0~10% EA in DCM) to afford 8-7 (5.1 g, 75.4%).

To a solution of t-BuOK (1.64 g, 14.58 mmol) in $CH_3CN$ (150 mL) was added $Me_3SOI$ (3.21 g, 14.58 mmol). The mixture was degassed and stirred at RT for 30 mins. The solution containing the ylide was filtered, and the filtrate was treated with a solution of 8-7 (5.1 g, 13.25 mmol, previously degassed) in $CH_3CN$ (150 mL). The mixture was stirred at RT for 1 h. The volatiles were removed under reduced pressure, and the residue was purified by column chromatography using DCM:EA=9:1 as the eluent to give 8-8 (3.2 g, 60.5%).

8-8 (3.2 g, 8.02 mmol) was dissolved in $NH_3$-MeOH (7.0 M, 80 mL). The solution was stirred at 25° C. for 18 h. The volatiles were removed under reduced pressure to afford the crude 8-9 (3.1 g, 93%). 8-9 (~100 g) was submitted for prep-HPLC (TFA condition). The separated solution was neutralized by $NaHCO_3$, and extracted with EA. The organic phase was concentrated to give 8-9-P1 (~17 g, 17%).

To a solution of 8-9A (0.8 g, 3.5 mmol) in DMF (10.0 mL) was added HATU (1.35 g, 3.5 mmol) and DIEA (0.92 g, 7.1 mmol). The mixture was stirred at 25° C. for 10 mins, and 8-9-P1 (1.47 g, 3.5 mmol) was added. The mixture was stirred for 1 h. LCMS trace showed that 8-9-P1 was consumed. The mixture was partitioned between water (10 mL) and EA (30 mL). The organic phase was separated, washed with brine (2×10 mL), dried over $Na_2SO_4$, filtered and concentrated under reduced pressure to dryness. The residue was purified by column chromatography using 10% EA in DCM as the eluent to give 8-10 (2.10 g, 95.1%) as a colorless oil. +ESI-MS: m/z 624.0 $[M+H]^+$.

A 100 mL round bottom flask was charged with a mixture of 8-10 (2.1 g, 3.36 mmol), 4-fluorophenyl-boronic acid (0.94 g, 6.72 mmol), $Na_2CO_3$ (1.07 g, 10.1 mmol) and $Pd(PPh_3)_4$ (0.25 g, 0.35 mol, 0.10 eq.) in dioxane (13.0 mL) and $H_2O$ (3 mL). The mixture was degassed *3×) and refilled with $N_2$. The mixture was heated to 90° C. overnight. The mixture was partitioned between water (20 mL) and EA (35 mL). The organic phase was separated, washed with brine (2×10 mL), dried over anhydrous $Na_2SO_4$, filtered and concentrated under reduced pressure to dryness. The residue was purified by column chromatography using 10% EA in DCM as THE eluent to give 8-11 (1.95 g, 85%) as a pale yellow oil. +ESI-MS: m/z 684.2 $[M+H]^+$.

To a mixture of 8-11 (500 mg, 731.0 µmol) and propionic acid (163 mg, 2.2 mmol) in THF (20.0 mL) was added DCC (453 mg, 2.2 mmol) and DMAP (4.5 mg, 36.6 µmol) in one portion at 25° C. The mixture was stirred at 25° C. for 4 h. LCMS trace showed that the reaction was completed. The mixture was filtered, and the filtrate was concentrated to dryness. The residue was purified by column chromatography using 5~50% EA in PE as the eluent to give 8-12 (450 mg, 83%) as a light yellow solid. +ESI-MS: m/z 740.1 $[M+H]^+$.

To a solution of 8-12 (450 mg, 608 µmol) in dioxane (5.0 mL) was added HCl/dioxane (4 M, 1 mL) dropwise at 25° C. The mixture was stirred at 25° C. for 30 mins. LCMS trace showed that the reaction was completed. The mixture was concentrated under reduced pressure to dryness. The residue was purified by prep-HPLC (HCOOH) and lyophilized to give a white solid. The white solid was dissolved in $CH_3CN$ (5.0 mL) and $H_2O$ (20.0 mL). HCl (1 M, 0.6 mL) was added dropwise with stirring. The mixture was lyophilized to give 8 (220 mg, 52%) as a white solid. +ESI-MS: m/z 636.1$[M+H]^+$; 658.1 $[M+Na]^+$.

Example 2

Preparation of Compound 4

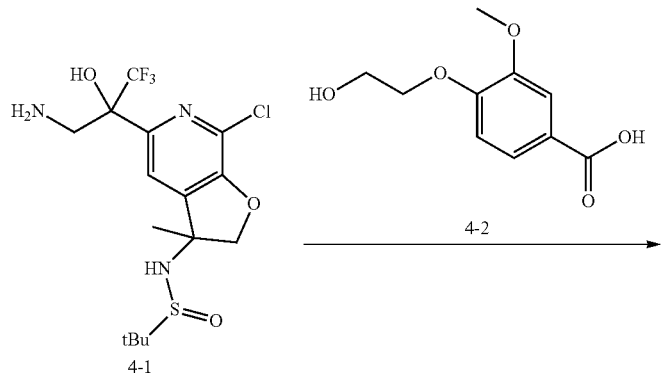

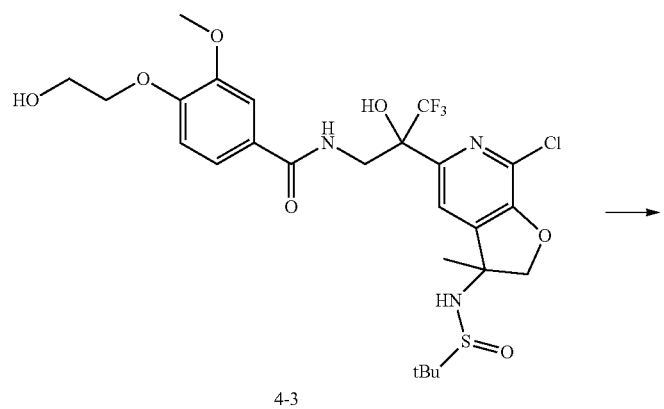
4-3
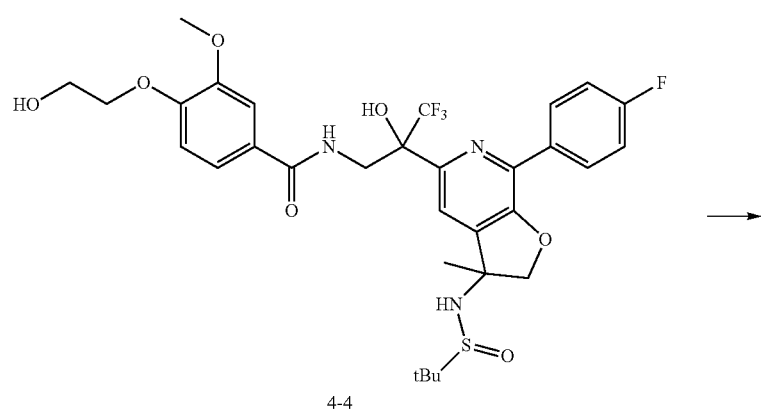
4-4
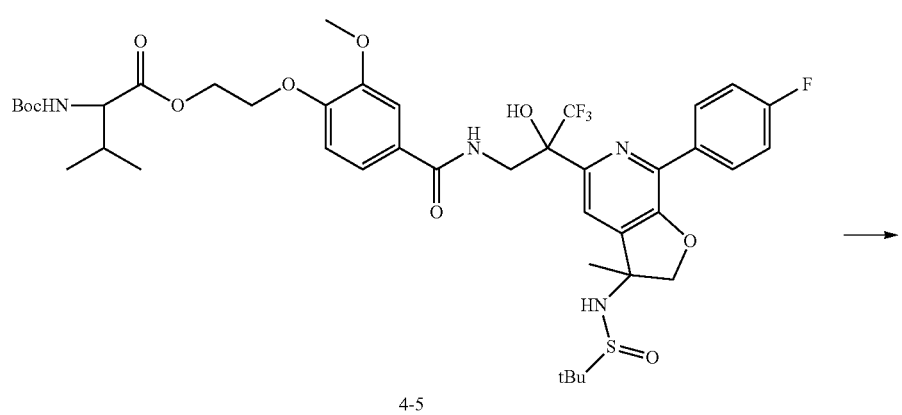
4-5
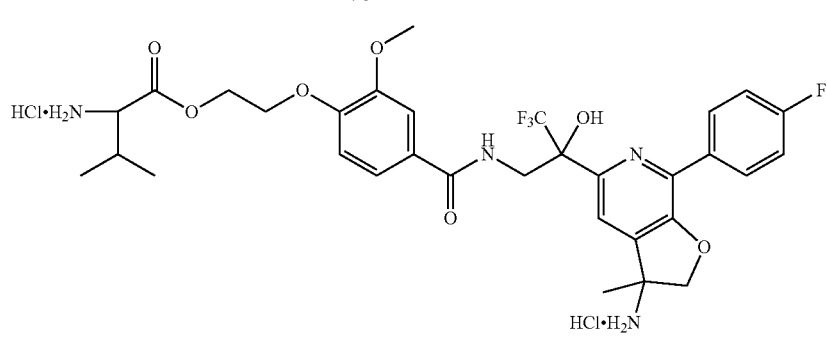
4

Compound 4 (432 mg, white solid) was using procedures similar to those used for preparing 8 using 4-1 and 4-2. +ESI-MS: m/z 665.1[M+H]$^+$; 687.2 [M+Na]$^+$.
Example 3
Preparation of Compound 5
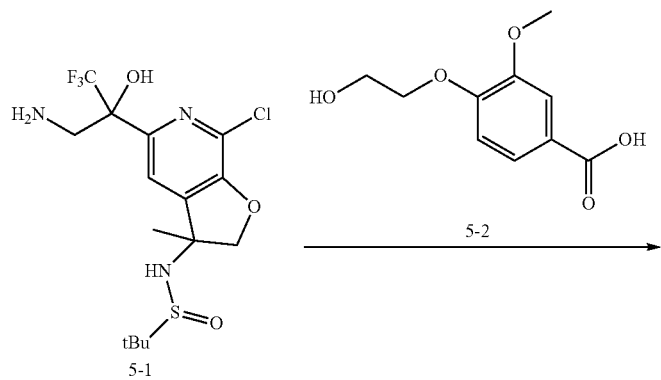
5-1
5-2
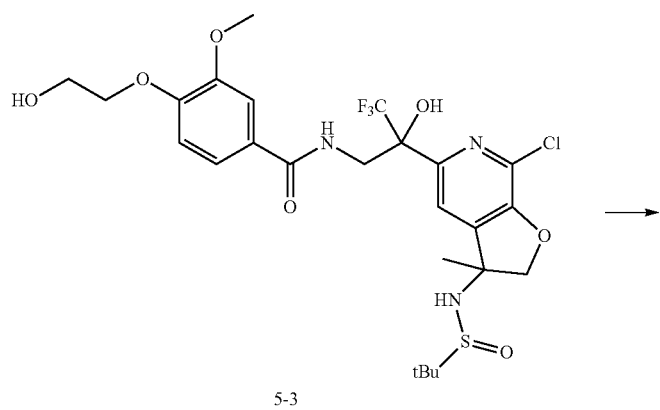
5-3
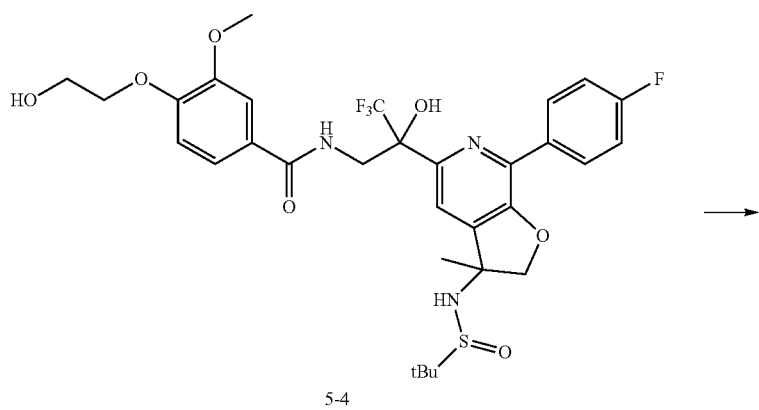
5-4

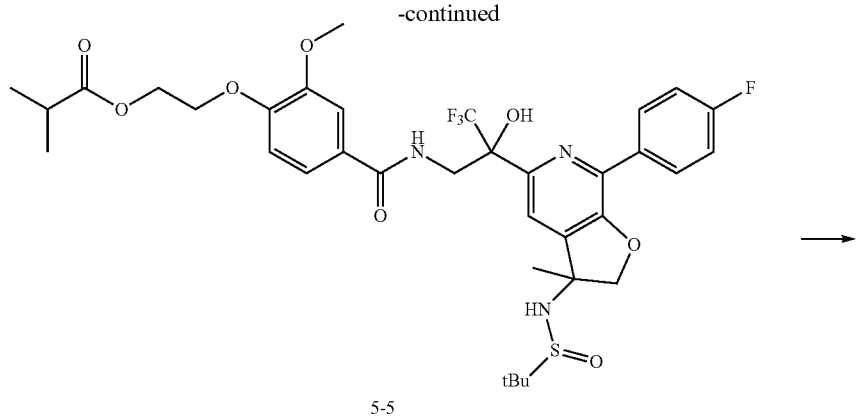
5-5
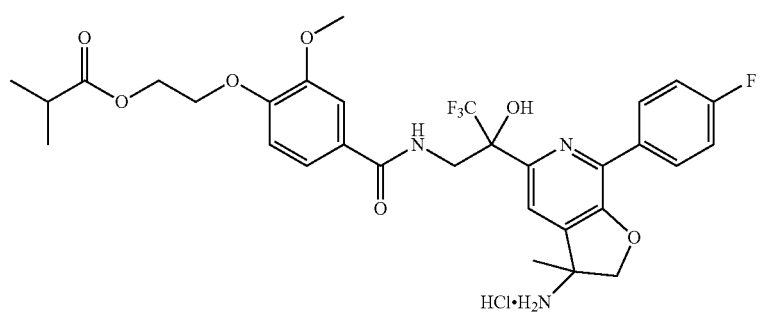
5
Compound 5 (350 mg, white solid) was using procedures similar to those used for preparing 8 using 5-2 and 5-1. +ESI-MS: m/z 636.1[M+H]$^+$; 658.2 [M+Na]$^+$.
Example 4
Preparation of Compound 6
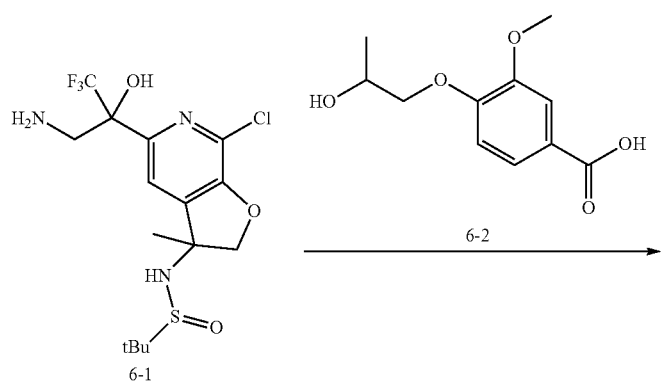

-continued
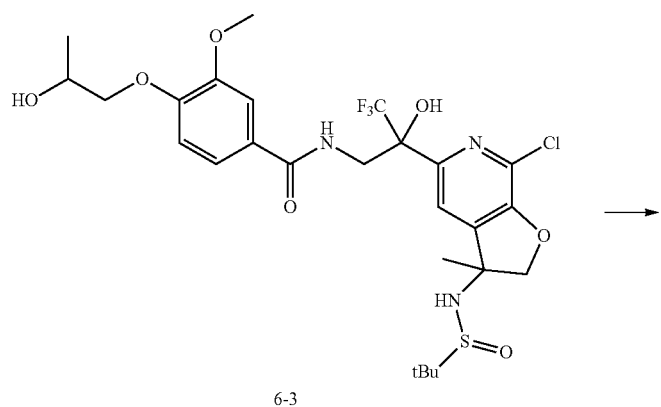
6-3
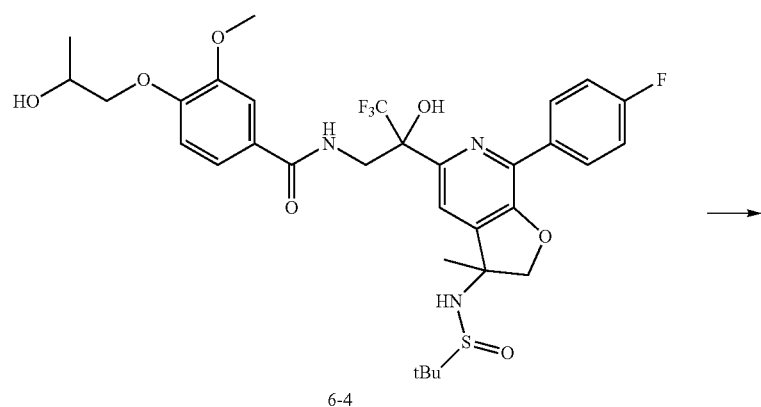
6-4
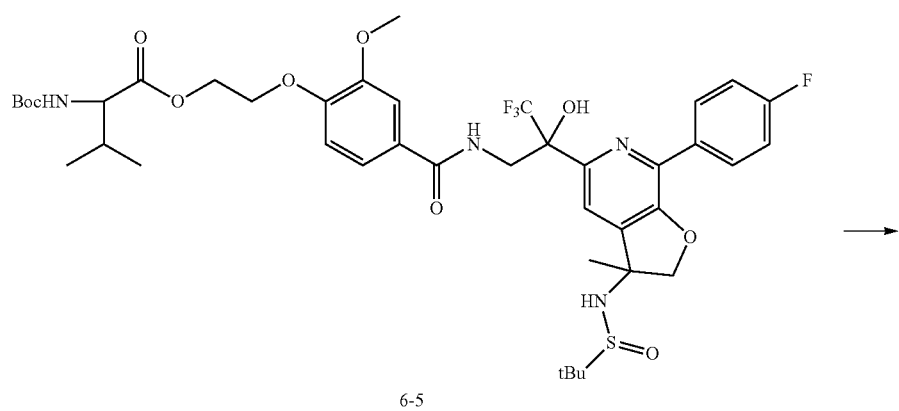
6-5
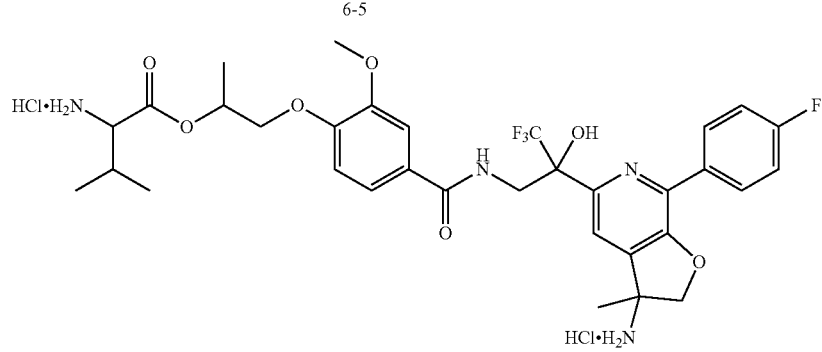
6

Compound 6 (210 mg, white solid) was using procedures similar to those used for preparing 8 using 6-2 and 6-1. +ESI-MS: m/z 679.2[M+H]$^+$.
Example 5
Preparation of Compound 7
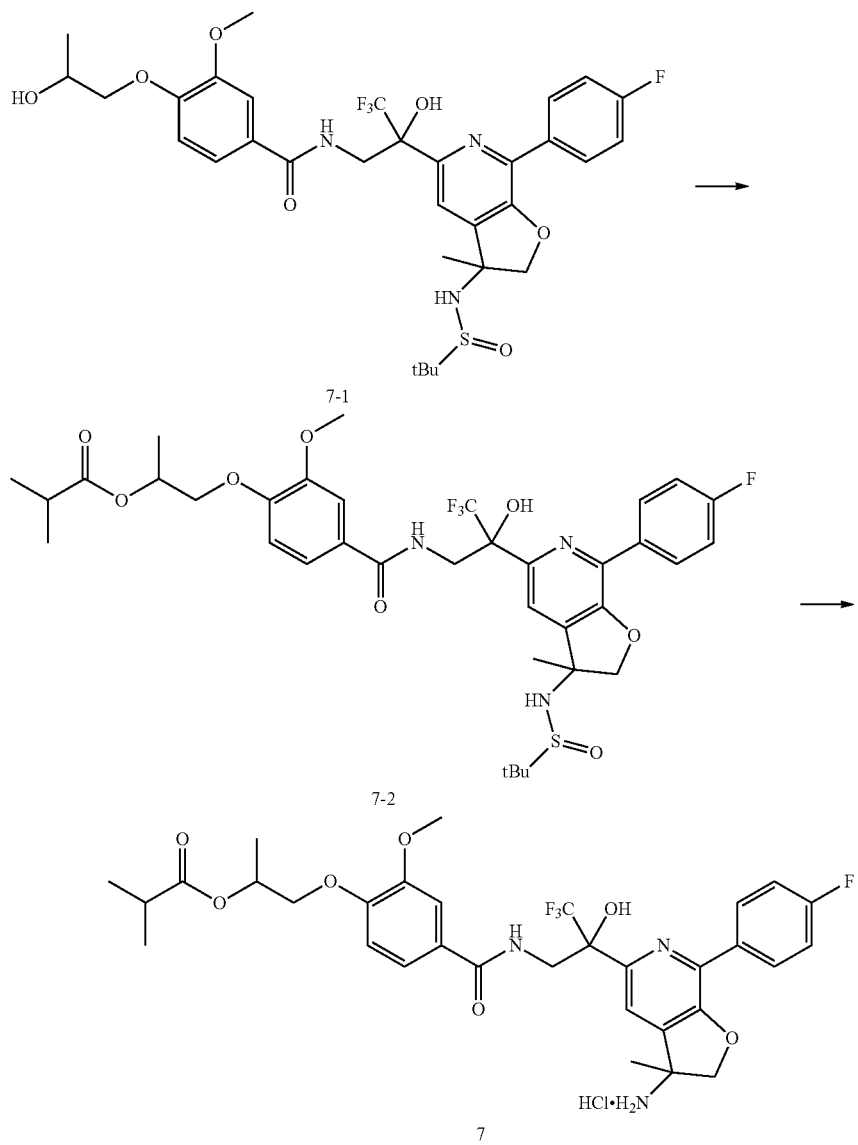
Compound 7 (306 mg, white solid) was using procedures similar to those used for preparing 8 using 7-1 and isobutyl acid. +ESI-MS: m/z 650.1[M+H]$^+$, 672.2 [M+Na]$^+$.
Example 6
Preparation of Compound 1
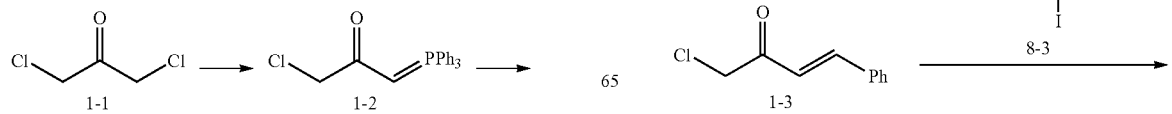
-continued

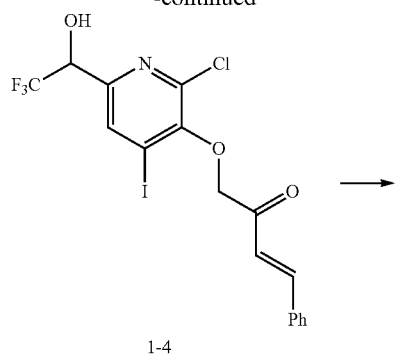
1-4
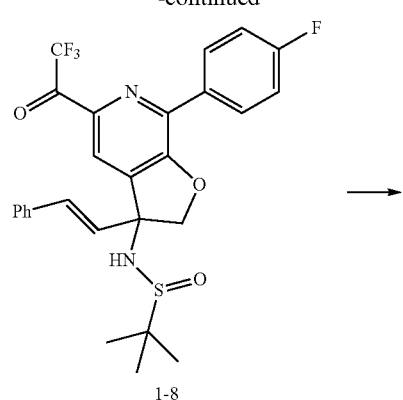
1-8
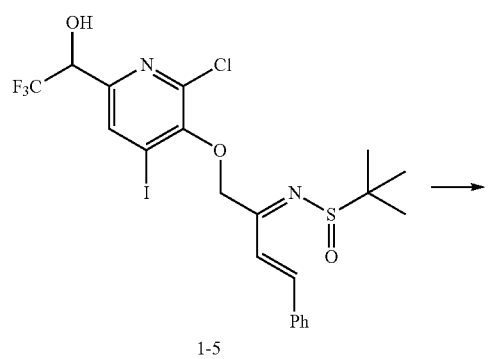
1-5
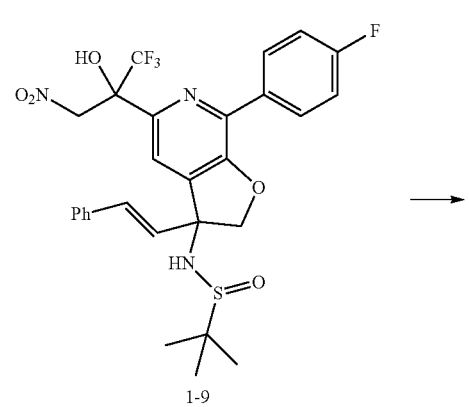
1-9
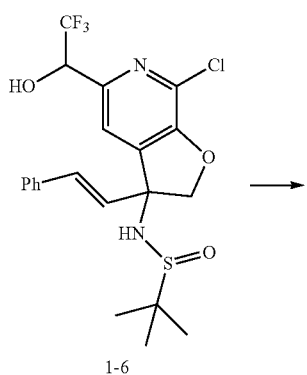
1-6
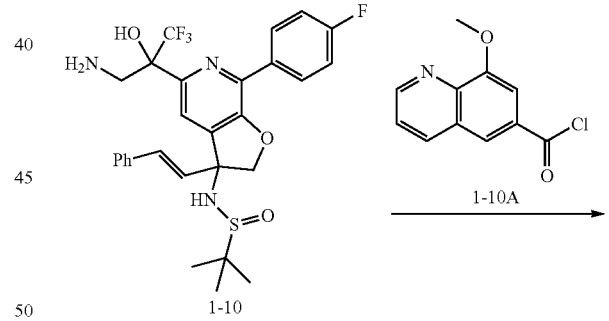
1-10    1-10A
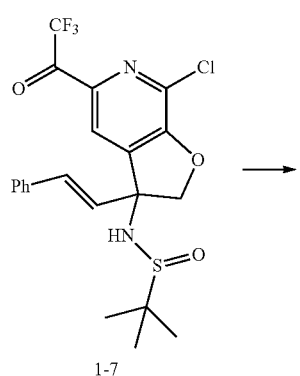
1-7
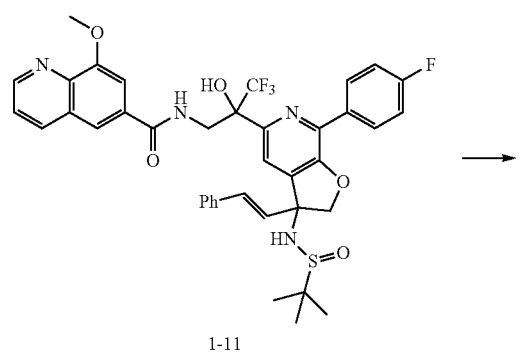
1-11

-continued

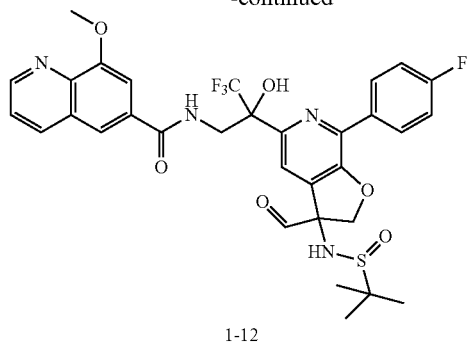

1-12

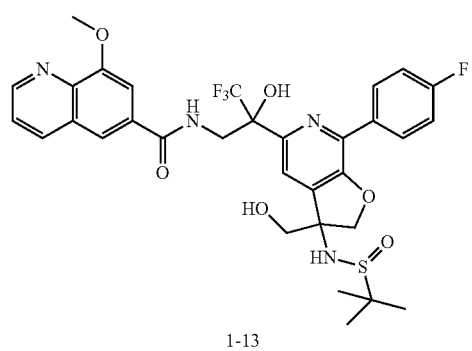

1-13

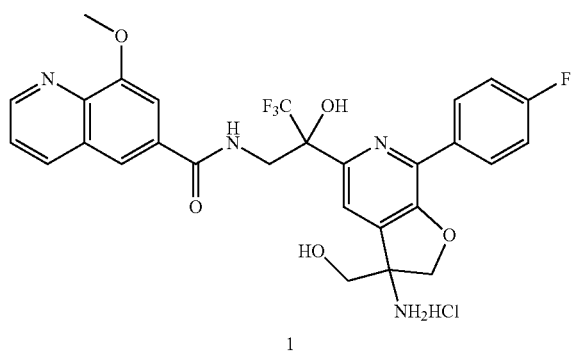

1

1-3 was prepared according to procedures provided in Hénichart, J. et al., Journal of Heterocyclic Chemistry (1986) 23(5):1531-3.

To a solution of 8-3 (16 g, 45.3 mmol) in CH$_3$CN (150 mL) was added K$_2$CO$_3$ (12.5 g, 90.5 mmol) in one portion. After stirring at RT for 5 mins, a solution of 1-3 (9.8 g, 54.3 mmol) in CH$_3$CN (10 mL) was added slowly under N$_2$. The mixture was stirred at 90° C. for 1 h in a pre-heated oil bath. TLC showed that the reaction was completed. After cooling to RT, the mixture was poured into water (150 mL) and stirred for 5 mins. The mixture was extracted with EA (2×150 mL). The combined organic phase was washed with brine, dried with anhydrous Na$_2$SO$_4$, filtered and concentrated in vacuum. The residue was purified by column chromatography using 2~5% EA in PE as the eluent to afford 1-4 (10.9 g, 49%) as a yellow solid.

1-8 was prepared from 1-4 using procedures similar to those used for preparing 8. To a solution of 1-8 (5.1 g, 9.6 mmol) in CH$_3$NO$_2$ (15 mL) was added TEA (2.0 mL) in one portion at RT. The mixture was stirred for 2 h and concentrated under reduced pressure. The residue was purified by column chromatography using 10~20% EA in PE as the eluent to afford 1-9 (2 g, 35%) as a yellow solid. +ESI-MS: m/z 593.9 [M+H]$^+$.

To a solution of 1-9 (2.0 g, 3.4 mmol) in EtOH (20 mL) and H$_2$O (10 mL) was added Fe (753 mg, 13.5 mmol) and NH$_4$Cl (721 mg, 13.5 mmol) in one portion. The mixture was stirred at 80° C. for 2 h. After cooling to RT, the mixture was poured into water (20 mL) and extracted with EA (3×20 mL). The combined organic phase was washed with brine, dried with anhydrous Na$_2$SO$_4$, filtered and concentrated in vacuum. The residue was purified by column chromatography using EA as the eluent to afford the 1-10 (950 mg, 50%) as a yellow solid. +ESI-MS: m/z 564.1 [M+H]$^+$.

To a solution of 1-10A (349 mg, 1.7 mmol) in THF (10 mL) was added DMF (0.5 mL) and SOCl$_2$ (2.1 g, 17.2 mmol), and the mixture was stirred at 80° C. for 1 h. The mixture was concentrated in vacuum to give crude 8-methoxyquinoline-6-carbonyl chloride. Crude 8-methoxyquinoline-6-carbonyl chloride was dissolved in DCM (12 mL), and 1-10 (950 mg, 1.7 mmol) and TEA (2.1 g, 20.6 mmol) was added at 30° C. The mixture was stirred at 30° C. for 1 h. The mixture was washed with NaHCO$_3$ solution (40 mL) and extracted with EA (3×60 mL). The combined organic phase was washed with sat. brine (2×20 mL), dried with anhydrous Na$_2$SO$_4$, filtered and concentrated in vacuum. The residue was purified by column chromatography using 50~100% EA in PE as the eluent to give 1-11 (560 mg, 34%) as a yellow solid. +ESI-MS: m/z 749.3 [M+H]$^+$.

To a solution of 1-11 (500 mg, 0.67 mmol) in acetone (20.0 mL) and H$_2$O (4.0 mL) was added NMO (94 mg, 0.8 mmol) in one portion at 30° C. OsO$_4$ (5.1 mg, 0.02 mmol) was added. The mixture was stirred at 30° C. for 20 mins, and concentrated under reduced pressure. The residue was dissolved in THF (15 mL), and the solution was treated with NaIO$_4$ (286 mg, 1.3 mmol) in one portion. The mixture was stirred at 30° C. for 12 h. The mixture was washed with Na$_2$SO$_3$ solution (50 mL) and extracted with EA (3×50 mL). The combined organic phase was washed with sat. brine (2×50 mL), dried with anhydrous Na$_2$SO$_4$, filtered and concentrated in vacuum to dryness. The residue was purified by column chromatography using EA as the eluent to give 1-12 (381 mg, 77.8%) as a yellow oil. +ESI-MS: m/z 674.1 [M+H]$^+$.

To a solution of 1-12 (381 mg, 0.56 mmol) in MeOH (10 mL) was added NaBH$_4$ (107 mg, 2.8 mmol) in one portion at 25° C. The mixture was stirred at 25° C. for 30 mins. The reaction was quenched with water (10 mL). The aqueous phase was extracted with EA (3×30 mL). The combined organic phase was washed with sat. brine (2×20 mL), dried with anhydrous Na$_2$SO$_4$, filtered and concentrated in vacuum to dryness. The residue was purified by column chromatography using EA as the eluent to give 1-13 (347 mg, 84%) as a yellow solid. +ESI-MS: m/z 677.0 [M+H]$^+$.

To a solution of 1-13 (347 mg, 0.51 mmol) in dioxane (15 mL) was added HCl/dioxane (4 M, 1 mL) in one portion at 30° C. The mixture was stirred at 30° C. for 0.5 h. The mixture was concentrated to dryness. The residue was purified by prep-HPLC (neutral condition) to afford a yellow solid. The yellow solid was dissolved in CH$_3$CN (8 mL) and H$_2$O (10 mL). HCl (3 M, 0.4 mL) was added in one portion at 0° C. with stirring. The mixture was lyophilized to give 1 (135 mg) as a yellow solid. +ESI-MS: m/z 573.1 [M+H]$^+$.

2
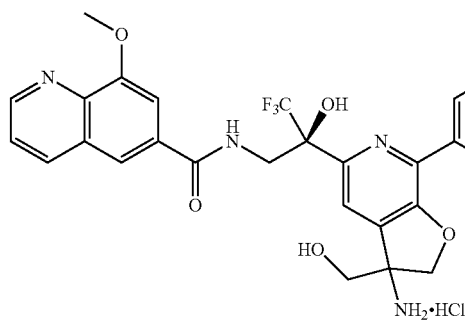
3
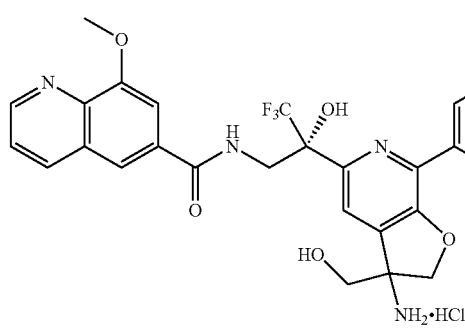
Compound 1 (126 mg) was separated by SFC to give two isomers. The two isomers were dissolved in CH₃CN (5 mL), and then 3 M HCl was added. The solution was lyophilized to give 2 (40 mg, white solid) and 3 (62 mg, white solid). 2: +ESI-MS: m/z 573.1 [M+H]⁺; 3: +ESI-MS: m/z 573.1 [M+H]⁺. Compounds 2 and 3 are shown above with relative stereochemistry arbitrarily assigned.
Example 7
Preparation of Compounds 9 and 10
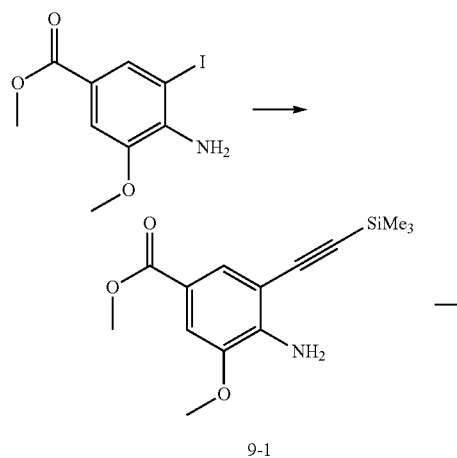
9-1
-continued
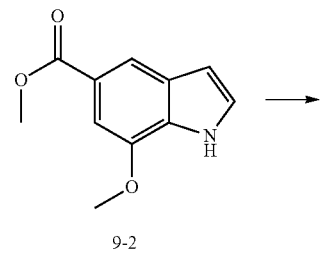
9-2
9-3
9-4
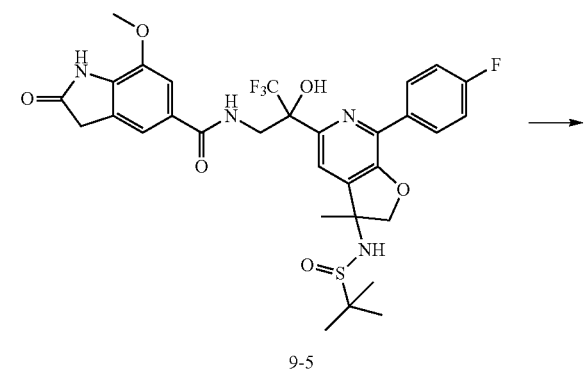
9-5
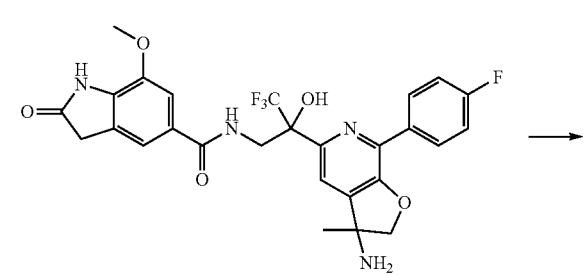
9

-continued

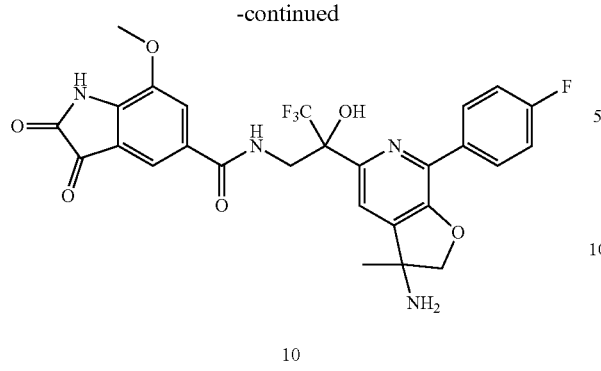

10

Methyl 3-iodo-4-amino-5-methoxybenzoate (1.0 g, 3.25 mmol) was dissolved in triethylamine (6 mL). 1,1'-Bis(diphenylphosphino)ferrocene]dichloropalladium(II) (0.11 g, 0.16 mmol) and cuprous chloride (16 mg, 0.16 mmol) were added, and the mixture was cooled to 0° C. Trimethylsilylacetylene (0.55 mL, 3.9 mmol) was added dropwise. The mixture was warmed to RT and stirred for 1.5 h. The mixture was concentrated, then re-dissolved in EA, washed with brine, dried and concentrated. The crude material was purified by chromatography on silica gel (hexane:EA) to give 9-1 (0.27 g, 30%).

John-Phos AuMeCNBF$_4$ (120 mg, 0.15 mmol) was added to 9-1 (0.21 g, 0.76 mmol) in toluene (2 mL). The mixture was heated at 60° C. for 2 h. The mixture was purified by silica gel chromatography (hexane:EA) to give 9-2 (57 mg, 27%). LC/MS: 206.05 [M+H]$^+$.

A solution of lithium bromide (33 mg, 0.39 mmol) and bromine (19 µL, 0.38 mmol) in acetic acid (0.4 mL) was added dropwise to a solution of 9-2 (24 mg, 0.12 mmol) in EtOH (0.5 mL) and acetic acid (0.5 mL) at 0° C. The mixture was slowly warmed to RT and stirred for 2 h total. Zinc (76 mg, 1.2 mmol) and acetic acid (0.5 mL) were added, and the mixture was stirred for 2 h. The mixture was concentrated, then re-dissolved in EA. The organic layer was washed with sodium bicarbonate and brine, dried and concentrated. The crude material was purified by chromatography (hexane:EA) to give 9-3 (6 mg, 25%). LC/MS: 222.05 [M+H]$^+$.

9-3 (30 mg, 0.13 mmol) was dissolved in conc. HCl (0.5 mL) and 4N HCl in dioxane (0.5 mL). The mixture was heated at 95° C. for 1 h. The mixture was concentrated and the resulting 9-4 was used without further purification. LC/MS: 206.15 [M−H].

DIEA (20 µL, 0.11 mmol) was added to a solution of N-(5-(3-amino-1,1,1,-trifluoro-2-hydroxypropan-2-yl)-7-(4-fluorophenyl-3-methyl-2,3-dihydrofuro[2,3-c]pyridine-3-yl)-2-methylpropane-2-sulfinamide (13 mg, 0.027 mmol), 9-4 (0.13 mmol) and HATU (23 mg, 0.06 mmol). The mixture was stirred at RT for 2 h. The mixture was purified by reverse-phase HPLC to provide 9-5 (12 mg, 70%). LCMS: 665.20 [M+H]$^+$.

HCl (4N in dioxane, 0.2 mL) was added to a solution of 9-5 (32 mg, 0.049 mmol) in CH$_2$Cl$_2$ (1 mL). The mixture was stirred at RT for 5 h. The mixture was concentrated, and the crude product purified by HPLC to give 9. LC/MS: 561.15 [M+H]$^+$. 9 air oxidizes to 10. LC/MS: 576.05 [M+H]$^+$.

Example 8

Preparation of Compound 11

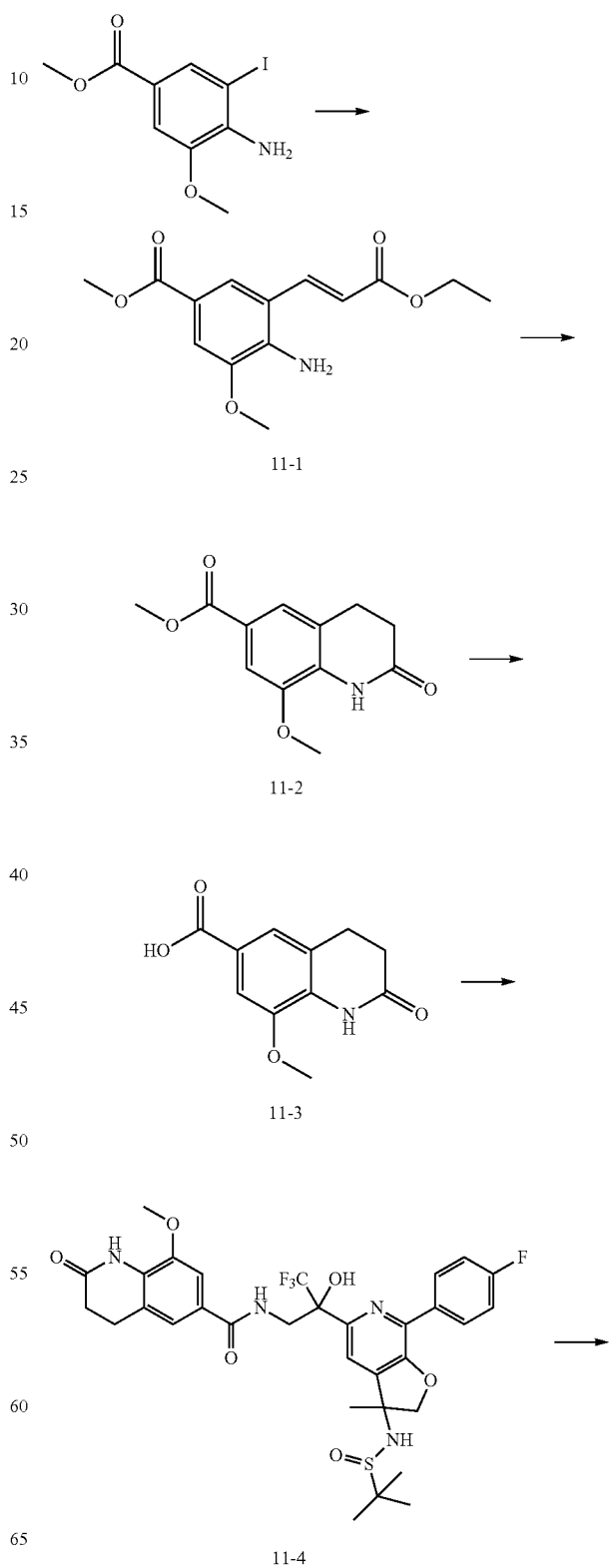

-continued

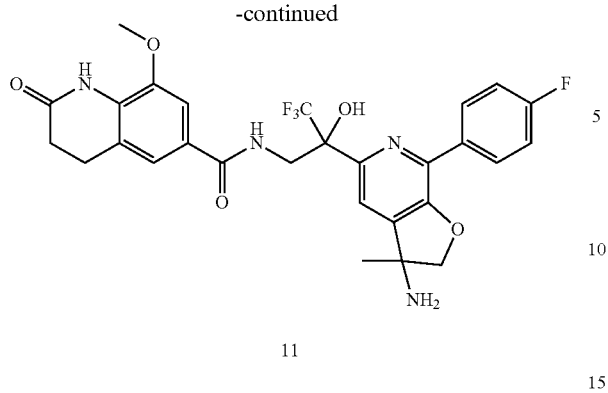

11

Palladium acetate (73 mg, 0.22 mmol) was added to a solution of 3-iodo-4-amino-5-methoxybenzoate (1.0 g, 3.25 mmol), methyl acrylate (0.32 mL, 3.6 mmol), triphenylphosphine (0.17 g, 0.65 mmol), and triethylamine (0.9 mL, 6.5 mmol) in CH$_3$CN (10 mL). The mixture was flushed with Ar and heated at 80° C. in a sealed tube for 90 mins. The mixture was diluted with EA, and washed with 1N HCl and brine. The organic layers were dried and concentrated. Crude 11-1 was chromatographed (hexane:EA) to give 11-1 (0.52 g, 57%). LC/MS: 280.05 [M+H]$^+$.

11-1 (0.52 g, 1.9 mmol) was hydrogenated over 10% Pd/C (250 mg) in acetic acid (5 m:) at 60 psi for 2 h. The catalyst was removed by filtration, and the solvent was evaporated to provide crude 11-2, which was purified by chromatography (hexane:EA) to give 11-2 (0.40 g, 89%). LC/MS: 236.05 [M+H]$^+$.

2N NaOH (4 mL, 8.0 mmol) was added to a solution of 11-2 (0.40 g, 1.7 mmol) in MeOH (20 mL), and the mixture was stirred at RT for 1 h. The mixture was acidified with 1N HCl, and 11-3 was extracted with EA. The organic extracts were washed with brine, dried, concentrated and the obtained 11-3 was used without further purification.

11-4 was prepared using similar procedures as 9-5. LC/MS: 665.20 [M+H]$^+$. Compound 11 using similar procedures as 9. LC/MS: 575.15 [M+H]$^+$.

Example 9

Preparation of Compound 12

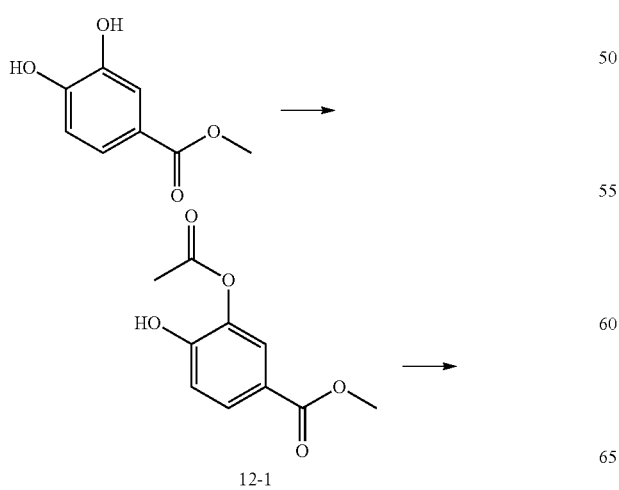

12-1

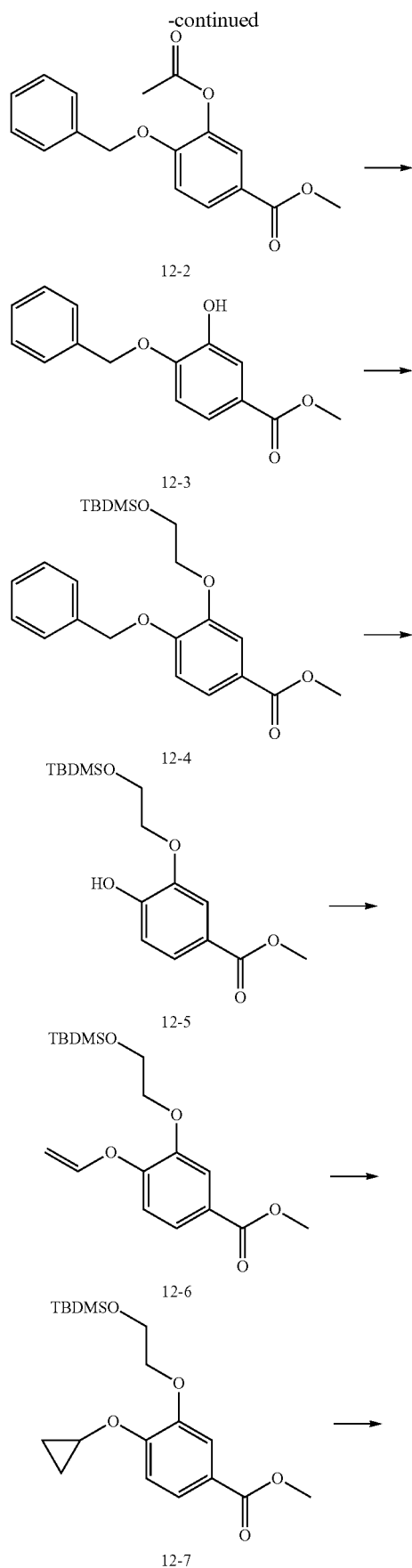

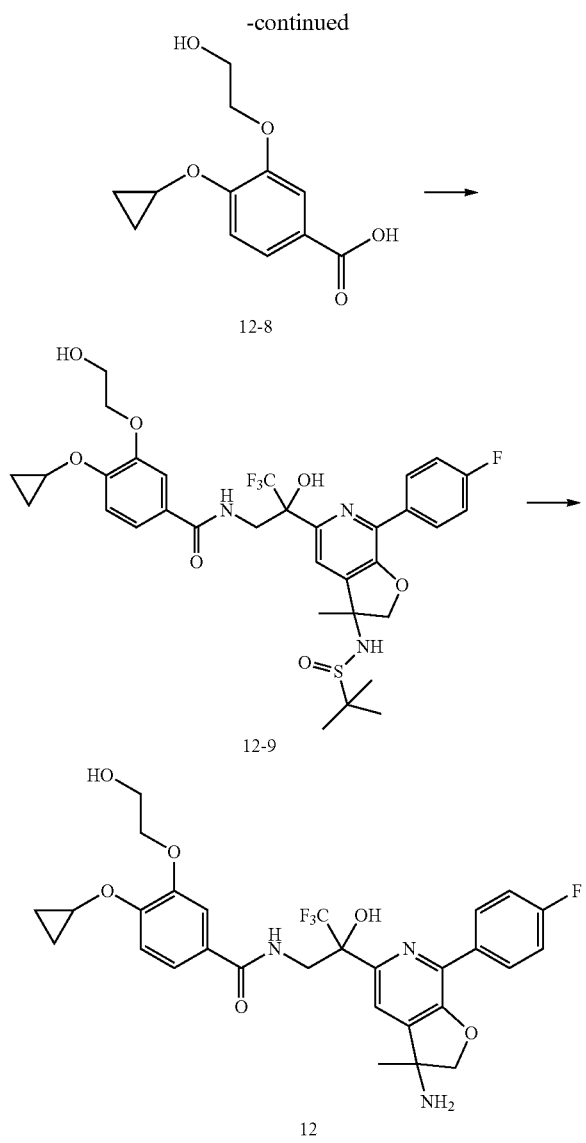

diluted with EA, and washed with water and brine. The product was purified by chromatography (hexane:EA) to give 12-1 (0.56 g, 78%).

Benzyl bromide (0.62 mL, 5.2 mmol) was added to a solution of 12-1 (91.1 g, 5.2 mmol) and potassium carbonate (1.1 g, 7.9 mmol) in DMF (5 mL), and the mixture was stirred at RT overnight. The mixture reaction was diluted with EA, and washed with water and brine. The product was purified by chromatography (hexane:EA) to give 12-2 (1.26 g, 81%).

Potassium carbonate (16 mg, 0.12 mmol) was added to a solution of 12-2 (1.26 g, 4.2 mmol) in MeOH (100 mL). The mixture was heated at reflux for 30 mins and then stirred at RT overnight. The mixture was concentrated, and the product purified by chromatography (hexane:EA) to give 12-3 (0.91 g, 88%).

Potassium carbonate (0.78 g, 5.7 mmol) was added to a solution of 12-3 (0.91 g, 3.7 mmol) and (2-bromoethoxy)(tert-butyl)dimethylsilane (0.87 mL, 4.0 mmol) in DMF (5 mL). The mixture was heated at 60° C. for 1 h. The mixture was diluted with EA, and washed with water and brine. The product was chromatographed (hexane:EA) to give 12-4 (0.91 g, 57%).

12-4 (0.91 g, 2.2 mmol) was hydrogenated over 10% Pd/C (93 mg) in EtOH (10 mL). The catalyst was removed by filtration, and the crude product was chromatographed (hexane:EA) to give 12-5 (0.50 g, 55%).

1,5-Cyclooctadiene-irdinium (I) chloride dimer (12 mg, 0.018 mmol) and sodium carbonate (69 mg, 0.65 mmol) were pre-mixed in toluene (1.2 mL). 12-5 (0.60 g, 1.8 mmol) and vinyl acetate (0.33 mL, 3.6 mmol) were added. The mixture was flushed with Ar and then stirred at 100° C. 2 h. The crude material was purified by chromatography (hexane:EA) to give 12-6 (0.23 g, 35%).

Diethylzinc (5.1 mL, 1M in hexane) was added dropwise to a solution of 12-6 (0.23 g, 0.64 mmol) and diiodoethane (0.41 mL, 5.1 mmol) in dichloroethane (2 mL) at 0° C. The mixture was stirred at RT overnight. The reaction was quenched with 1N HCl, and extracted with dichloromethane. The product was purified by chromatography (hexane:EA) to give 12-7 (80 mg, 32%).

Compound 12-8 was prepared using similar procedures as 11-3. Compound 12-9 was prepared using similar procedures as 9-5. LC/MS: 696.25 [M+H]⁺. Compound 12 was prepared using similar procedures as 10. LC/MS: 592.70 [M+H]⁺.

Potassium t-butoxide (210 mg, 1.9 mmol) was added to 3,4-dihydroxybenzoic acid methyl ester (0.55 g, 3.3 mmol) in DMF (5 mL) at 0° C. The mixture was stirred for 15 minutes. Acetic anhydride (0.31 mL, 3.3 mmol) was added, and the mixture was stirred for 20 mins. The reaction was Example 10

The following compounds were prepared following one or more of the methods provided herein.

| No. | Structure | MS [M + 1]⁺ |
|---|---|---|
| 15 | 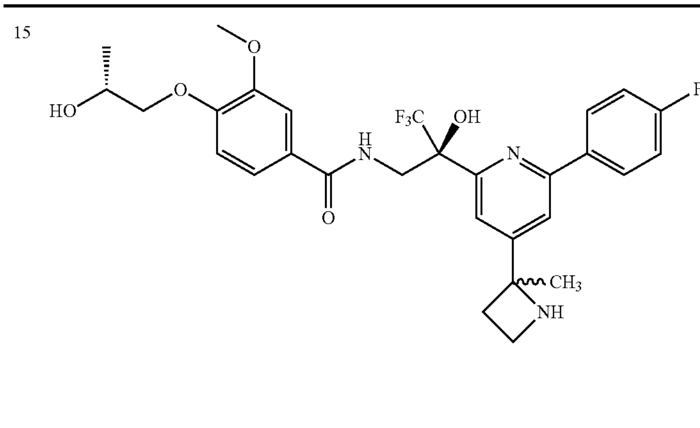 | 578.1 |

| No. | Structure | MS [M + 1]+ |
|---|---|---|
| 22 | 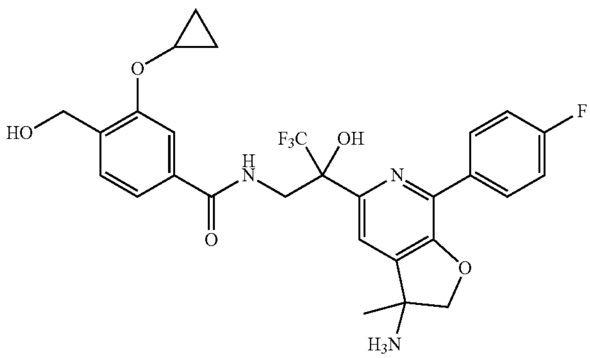 [SMILES: CC1(N)COc2c1cc(C(O)(CNC(=O)c1ccc(CO)c(OC3CC3)c1)C(F)(F)F)nc2-c1ccc(F)cc1] | 562.0 |
| 23 | 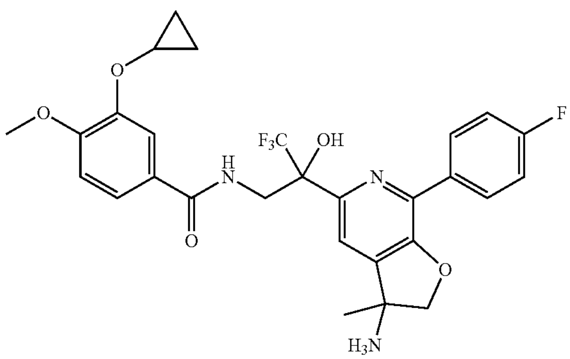 [SMILES: COc1ccc(C(=O)NCC(O)(c2cc3c(c(-c4ccc(F)cc4)n2)OCC3(C)N)C(F)(F)F)cc1OC1CC1] | 583.9 [M + 1 + Na]+ |
*Compound 15 is individual isomer with relative stereochemistry arbitrarily assigned
Example 11
Preparation of Compound 21
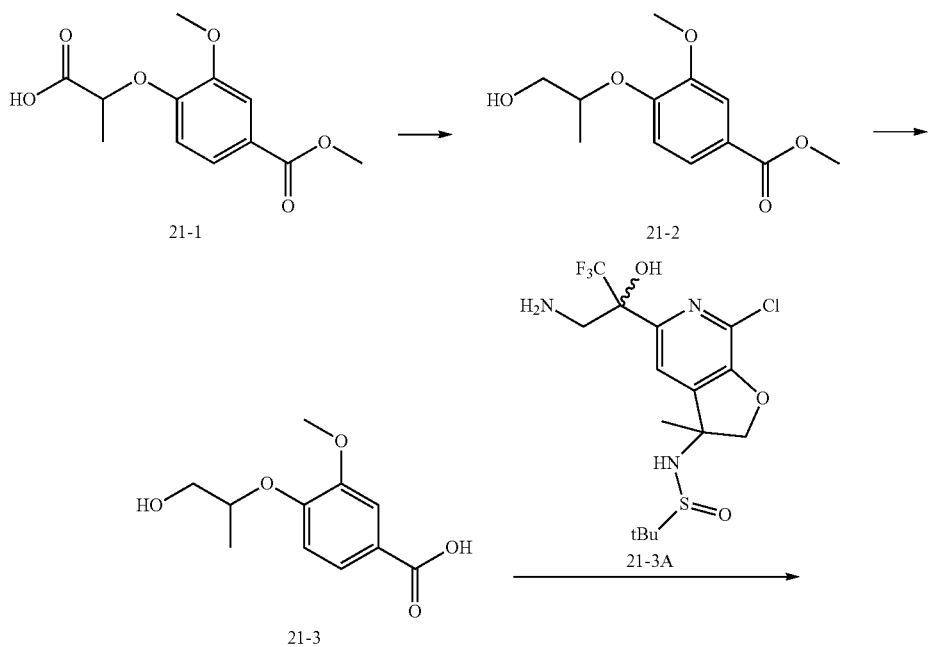

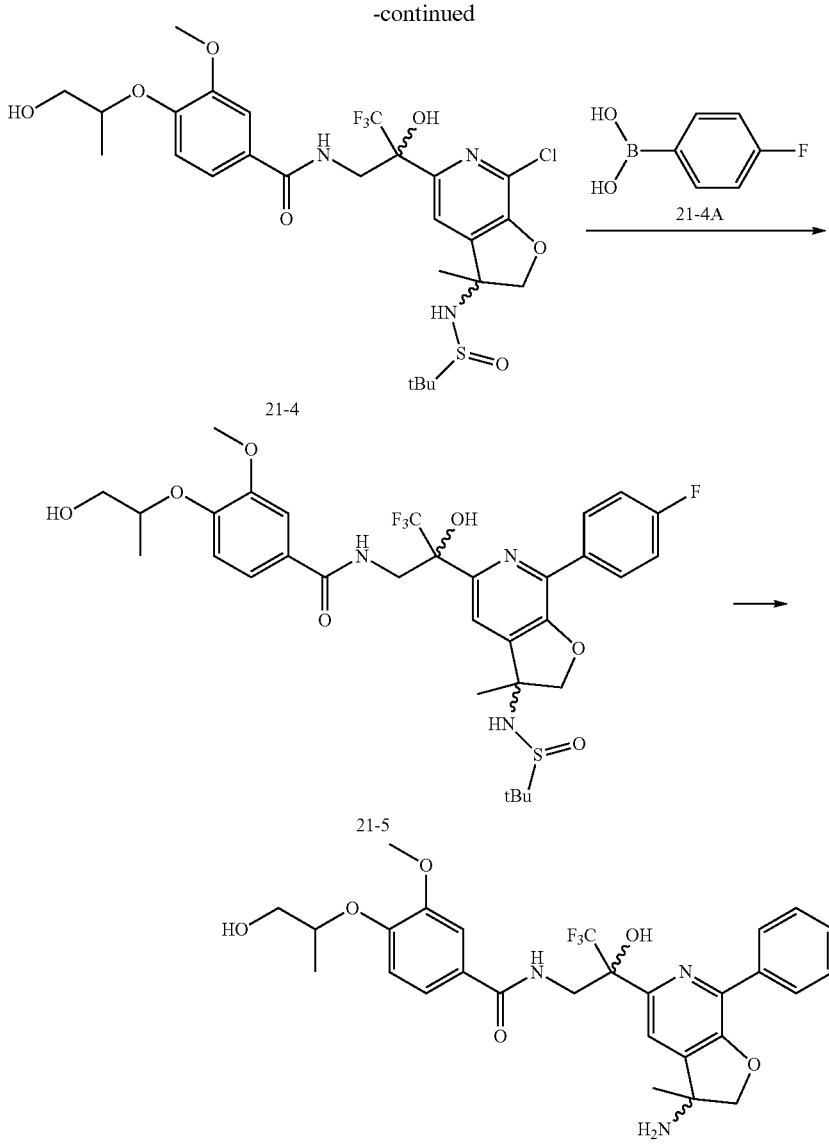

Compound 21-1 was prepared according to the procedures provided US 2007/287730 A1, and compound 21-3A can be prepared according to procedures provided in WO 2016/26792 A1.

To a solution of 21-1 (673 mg, 2.65 mmol) in anhydrous THF (15 mL) was added $BH_3$-$Me_2S$ (10 M, 0.8 mL) dropwise at 0° C. with stirring. The mixture was stirring at 50° C. for 1 h. The reaction was quenched with MeOH (2 mL), acidified with HCl (2M, 1 mL) and extracted with EA (3×20 mL). The combined organic phases were dried over $Na_2SO_4$ and concentrated. The residue was purified by column chromatography using 5~10% EA in PE to give 21-2 (351 mg, 55.1%). MS: m/z 240.8 [M+H]+.

To a solution of 21-2 (351 mg, 1.46 mmol) in MeOH (4 mL) was added aqueous NaOH (4 M, 2 mL). The mixture was stirred at 70° C. for 1 h. The MeOH was evaporated. The aqueous solution was acidified with 1 M HCl to pH 3~4 and extracted with EA (3×10 mL). The combined organic phases were washed with brine (10 mL), dried over anhydrous $Na_2SO_4$ and concentrated to give 21-3 (280 mg, 84.8%). MS: m/z 226.9 [M+H]+.

To a solution of 21-3 (145 mg, 0.64 mmol) in DMF (10 mL) was added HATU (244 mg, 0.64 mmol) and DIEA (204 mg, 1.58 mmol) with stirring at 25° C. After 10 mins, 21-3A (240 mg, 0.58 mmol) was added. The mixture was stirred for 1 h. The reaction was partitioned between water (10 mL) and EA (30 mL). The organic phase was separated, washed with brine (2×10 mL), dried over $Na_2SO_4$, filtered and concentrated. The residue was purified by column chromatography using 25~50% EA in PE as eluent to give 21-4 (332 mg, 92%) as yellow oil. MS: m/z 623.9 [M+H]+.

To a mixture of 21-4 (280 mg, 0.45 mmol), 21-4A (250 mg, 1.79 mmol) in dioxane:$H_2O$ (8 mL:2 mL) was added $K_2CO_3$ (124 mg, 0.9 mmol) and Pd(dppf)$Cl_2$ (33 mg, 0.045 mmol) under $N_2$. The mixture was stirring at 130° C. under microwave for 50 mins. The reaction was diluted with EA (20 mL) and water (10 mL). The organic phase was washed with brine (10 mL), dried over $Na_2SO_4$ and concentrated. The residue was purified by column chromatography using 3~8% MeOH in DCM as eluent to give 21-5 (51 mg, 16.7%). MS: m/z 684.1 [M+H]+.

To a solution of 21-5 (51 mg, 73 μmol) in THF (1 mL) was added HCl/dioxane (4 M, 0.5 mL). The mixture was stirred at 25° C. for 10 mins, concentrated and purified by prep-HPLC (HCl condition) to give 21 (11 mg, 25.8%) as a white solid. MS: m/z 580.1 [M+H]⁺.

Example 12

Preparation of Compound 24

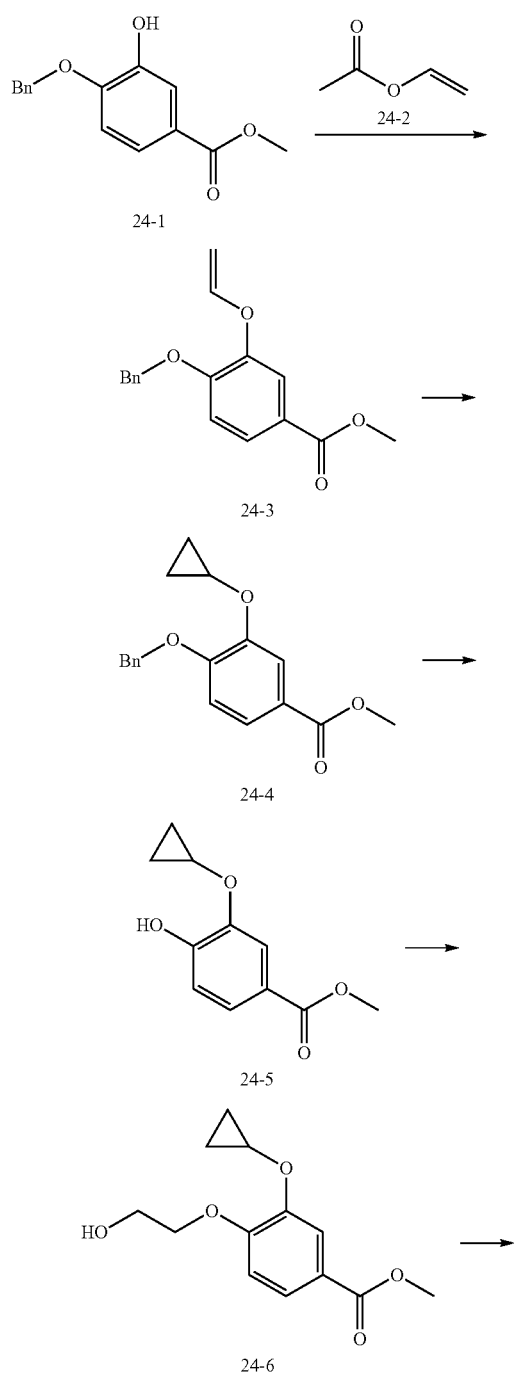

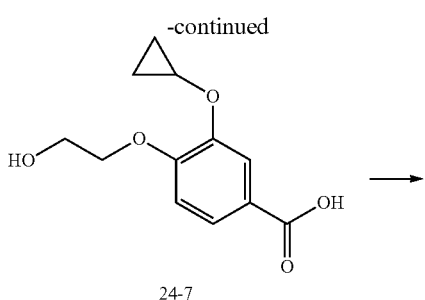

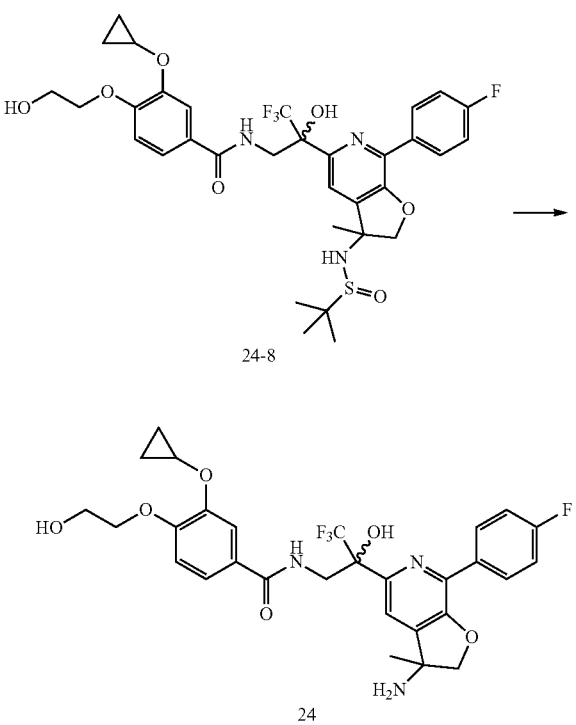

Compound 24-1 was prepared according to the procedures provided in Desroses et al., Organic Preparations and Procedures International (2004) 36(5):445-452. Compound 24-4 was prepared according to a similar procedure for preparing 23 starting with 24-1 and 24-2.

To a solution of 24-4 (236 mg, 0.79 mol) in DCM (5 mL) was added BBr₃ (238 mg, 0.95 mmol) at −20° C., and the mixture was stirred for 10 mins. The solution was poured into ice and extracted with EA (2×10 mL). The organic phase was concentrated and purified by column chromatography using 15~25% DCM in PE to give 24-5 (122 mg, 74.1%) as a yellow solid. MS: m/z 209.1 [M+H]⁺.

To a solution of 24-5 (122 mg, 0.59 mmol) in DMF (2 mL) was added NaH (24 mg, 0.59 mol) at 0° C. After stirring for 0.5 h, 2-bromoethanol (146 mg, 1.18 mmol) was added, and the mixture was stirred at RT overnight. The mixture was poured into water (10 mL) and extracted with EA (2×20 mL). The organic phase was dried over Na₂SO₄ and concentrated to give 24-6 (150 mg, crude) as a yellow solid. MS: m/z 253.1 [M+H]⁺.

Compound 24 (49 mg, white solid) was obtained from 24-6 using a similar procedure for preparing 21. MS: m/z 614.0 [M+Na]⁺.

Example 13
Preparation of Compound 25
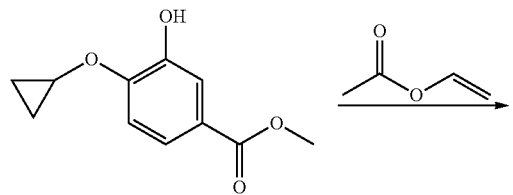
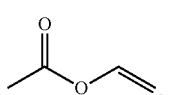
25-1
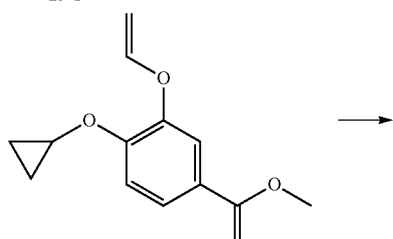
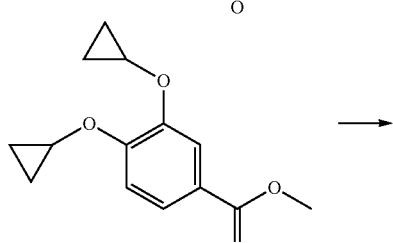
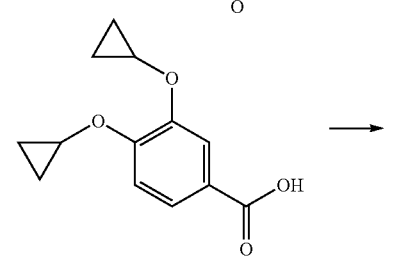
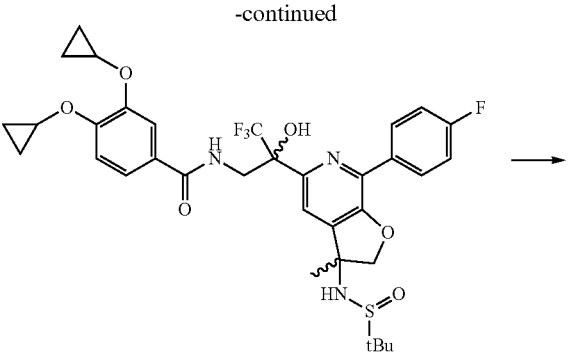
25
Compound 25 (5 mg, white solid) was obtained from 25-1 using a similar procedure for preparing 23. MS: m/z 588.1 [M+H]$^+$.
Example 14
Preparation of Compound 26
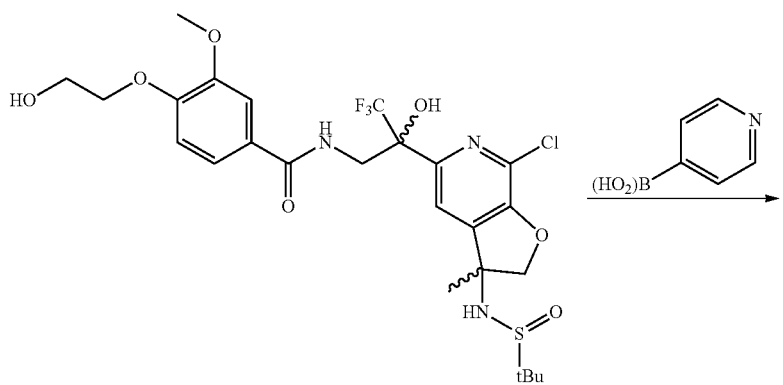
26-1

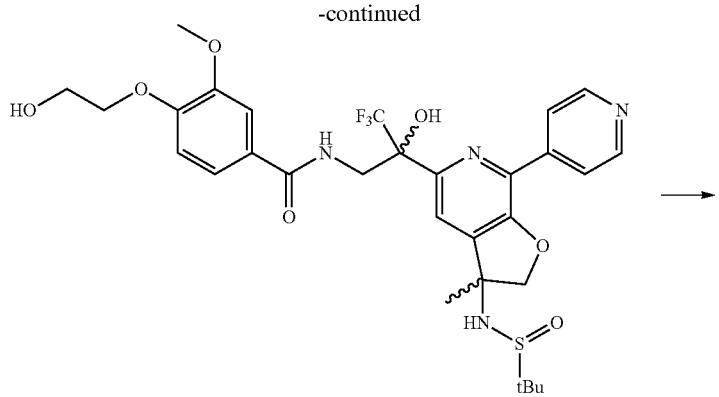

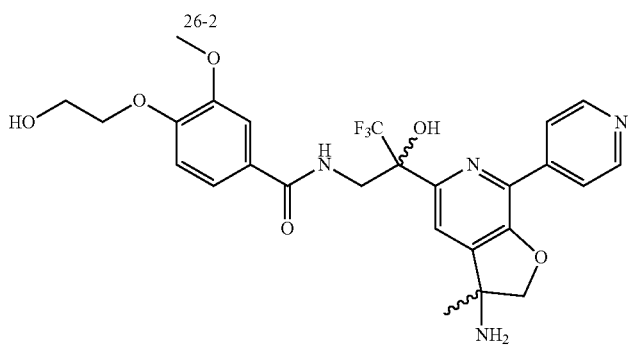

26

Compound 26-1 was prepared according to a similar procedure as provided in PCT Publication No. WO 2015/26792 A1.

A mixture of 26-1 (267 mg, 0.44 mmol), 4-pyridylboronic acid (108 mg, 0.88 mmol), Pd(dppf)Cl$_2$ (32 mg, 0.044 mmol) and K$_2$CO$_3$ (242 mg, 1.75 mmol) in dioxane (3.00 mL) and H$_2$O (1.00 mL) was heated at 130° C. for 1 h under microwave. The mixture was diluted with water (10 mL), and extracted with EA (2×10 mL). The organic phase was washed with brine, dried over Na$_2$SO$_4$, and concentrated to give 26-2 (250 mg, crude) as a yellow liquid.

To a solution of 26-2 (250 mg, crude) in MeOH (5 mL) was added HCl/MeOH (4 M, 0.3 mL). The mixture was stirred at 25° C. for 10 mins and concentrated. The residue was purified by purified by prep-HPLC (HCl condition) to give 26 (98.7 mg, 46%) as a white solid. MS: m/z 549.0 [M+H]$^+$.

Example 15

Preparation of Compound 27

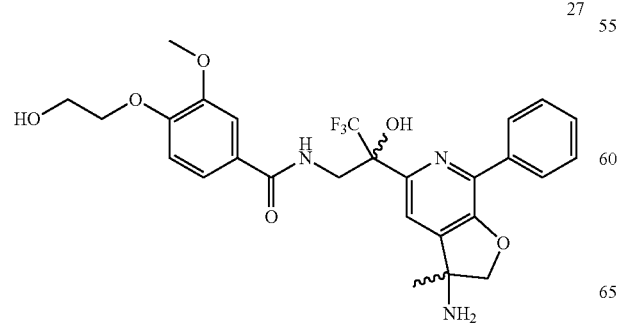

27

Compound 27 (23 mg, pale yellow solid) was obtained from 26-2 using a similar procedure for preparing 26. MS: m/z 548.0 [M+H]$^+$.

Example 16

Preparation of Compound 28

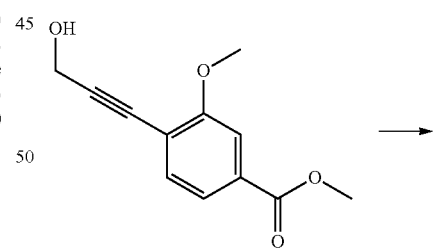

28-1

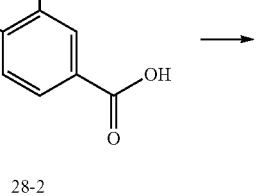

28-2

151
-continued
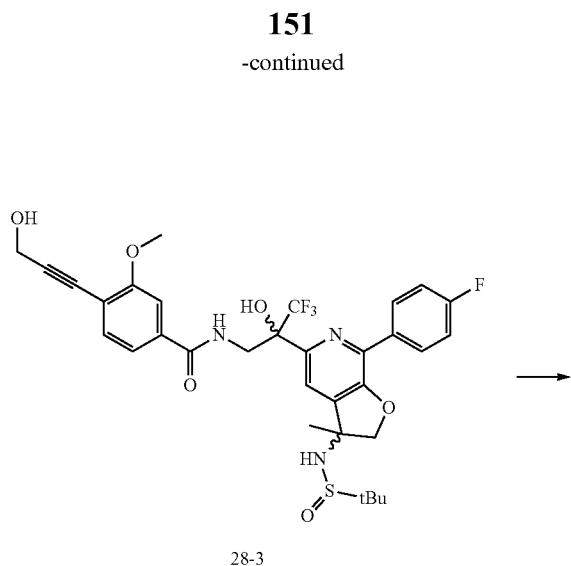
28-3
152
-continued
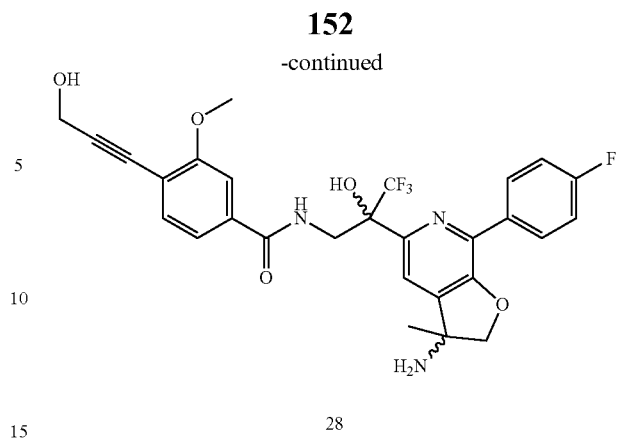
28
Compound 28-1 was prepared according to a similar procedure as provided in PCT Publication No. WO 2015/26792 A1. Compound 28 (68 mg, white solid) was obtained from 28-1 using a similar procedure for preparing 21. m/z 560.1 [M+H]$^+$.
Example 17
Preparation of Compound 29
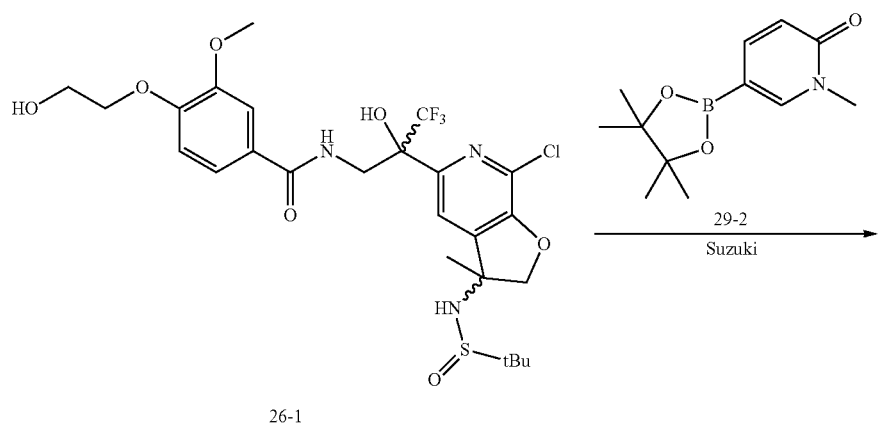
26-1
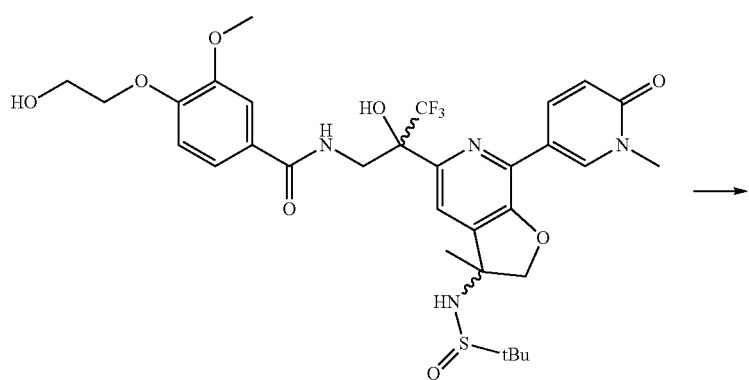
29-3

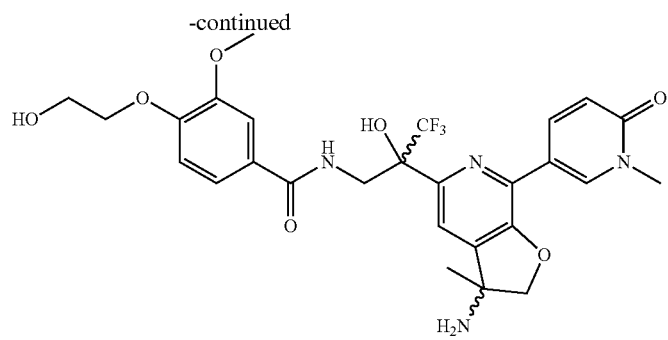
29
Compound 29-2 was prepared according to similar procedure as provided in U.S. Publication No. 2015/111885 A1. Compound 29 (108 mg, white solid) was obtained from 26-1 and 29-2 using a similar procedure for preparing 26. MS: m/z 579.0 [M+H]+.
Example 18
Preparation of Compound 30
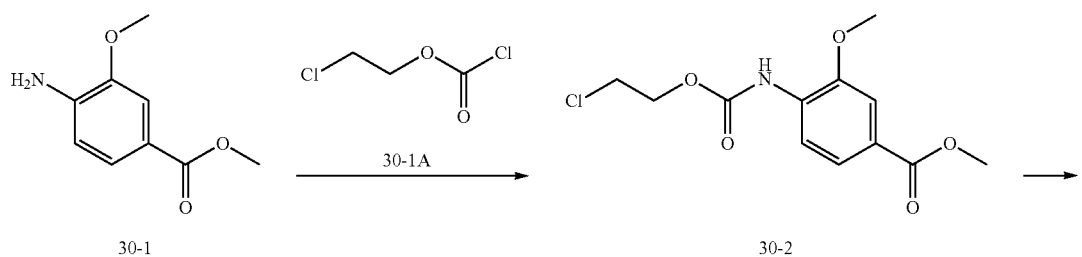
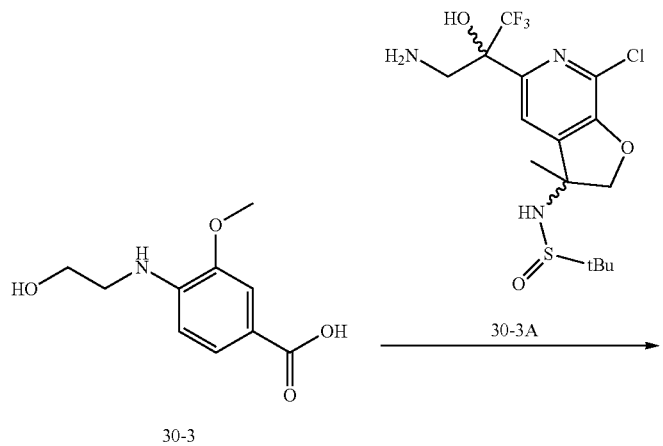

-continued

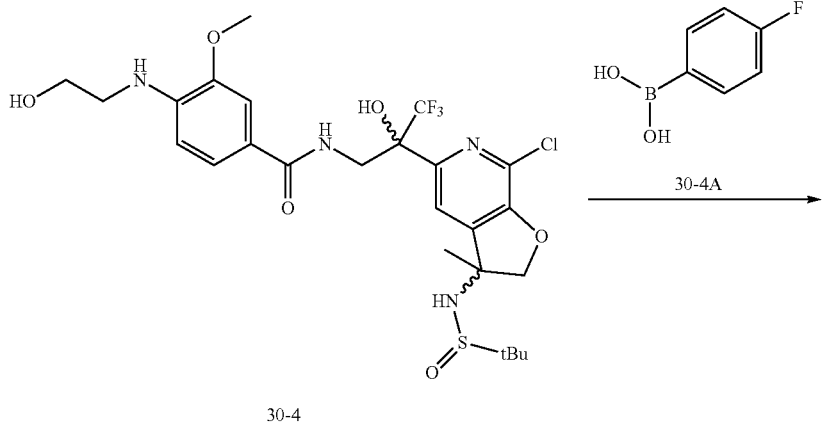

30-4

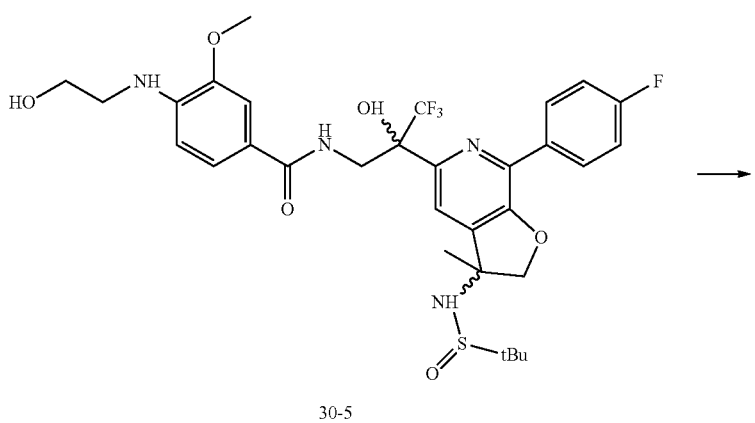

30-5

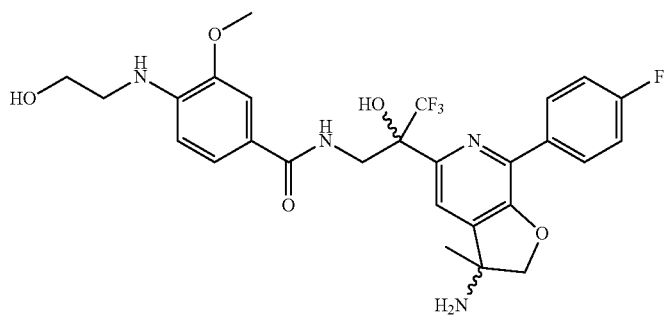

30

Compound 30-3A was prepared according to a similar procedure as provided in PCT Publication No. WO 2015/26792 A1. To a mixture of 30-1 (350 mg, 1.93 mmol) and pyridine (458 mg, 5.79 mmol) in DCM (5 mL) was added 30-1A (276 mg, 1.93 mmol) dropwise at 0° C. The mixture was stirred for 2 h. The mixture was diluted with water (10 mL) and EA (10 mL). The organic phase was isolated and washed with brine (10 mL), dried over Na$_2$SO$_4$, and concentrated to give 30-2 (521 mg, crude) as a colorless oil. MS: m/z 288.0 [M+H]$^+$.

To a solution of 30-2 (520 mg crude) in EtOH (10 mL) was added KOH (304 mg, 5.42 mmol). The mixture was heated to 80° C. and stirred for 0.5 h. The reaction was cooled to RT, acidified to pH 3~4 by 3 M HCl, and concentrated to give 30-3 (192 mg, crude) as a brown solid. MS: m/z 212.0 [M+H]$^+$.

Compound 30 (62 mg, yellow solid) was obtained from 30-3 and 30-3A using a similar procedure for preparing 21. MS: m/z 565.1 [M+H]$^+$.

Example 19
Preparation of Compound 31
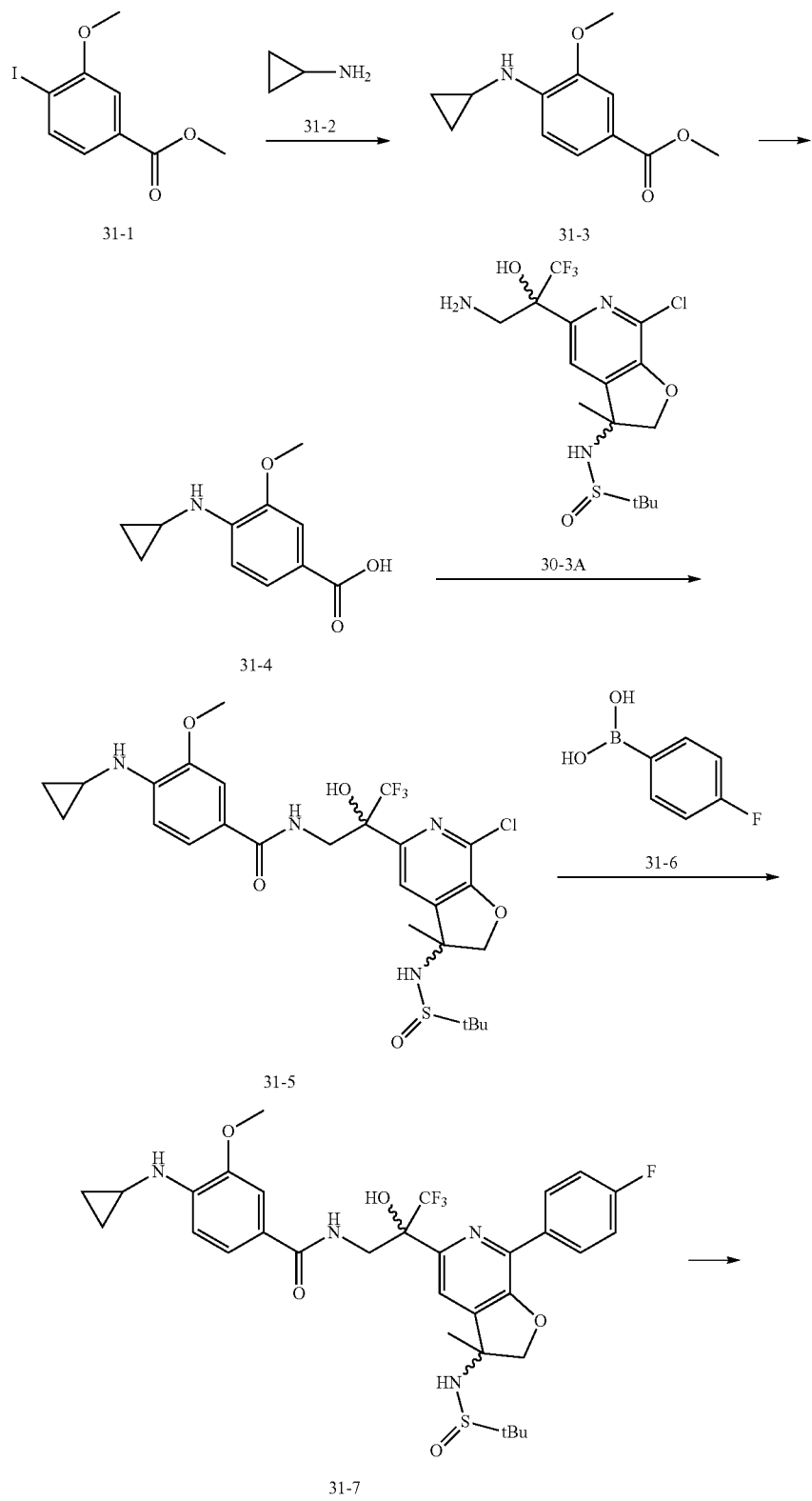

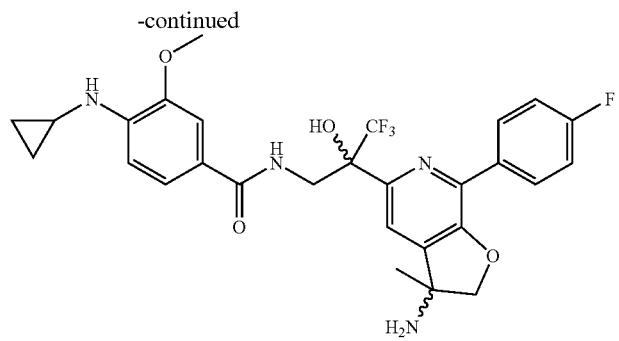

31

Compound 31-1 was prepared according to a similar procedure as provided in PCT Publication No. WO 2010/56722 A1. A mixture of 31-1 (1.0 g, 3.42 mmol), 31-2 (293 mg, 5.13 mmol), Cs$_2$CO$_3$ (4.46 g, 13.68 mmol), Pd$_2$(dba)$_3$ (326 mg, 0.68 mmol), and X-phos (313 mg, 0.34 mmol) in DMF (15 mL) was stirred at 100° C. for 12 h under N$_2$. The mixture was cooled to RT, diluted with H$_2$O (20 mL) and extracted with EA (2×20 mL). The organic phase was washed with brine, dried over Na$_2$SO$_4$, concentrated and purified by column chromatography using 10% EA in PE to give 31-4 (251 mg, 33%) as a light yellow oil. MS: m/z 221.9 [M+H]$^+$.

Compound 31 (18 mg, yellow solid) was obtained from 31-3 and 30-3A using a similar procedure for preparing 21. MS: m/z 561.2 [M+H]$^+$.

Example 20

Preparation of Compound 32

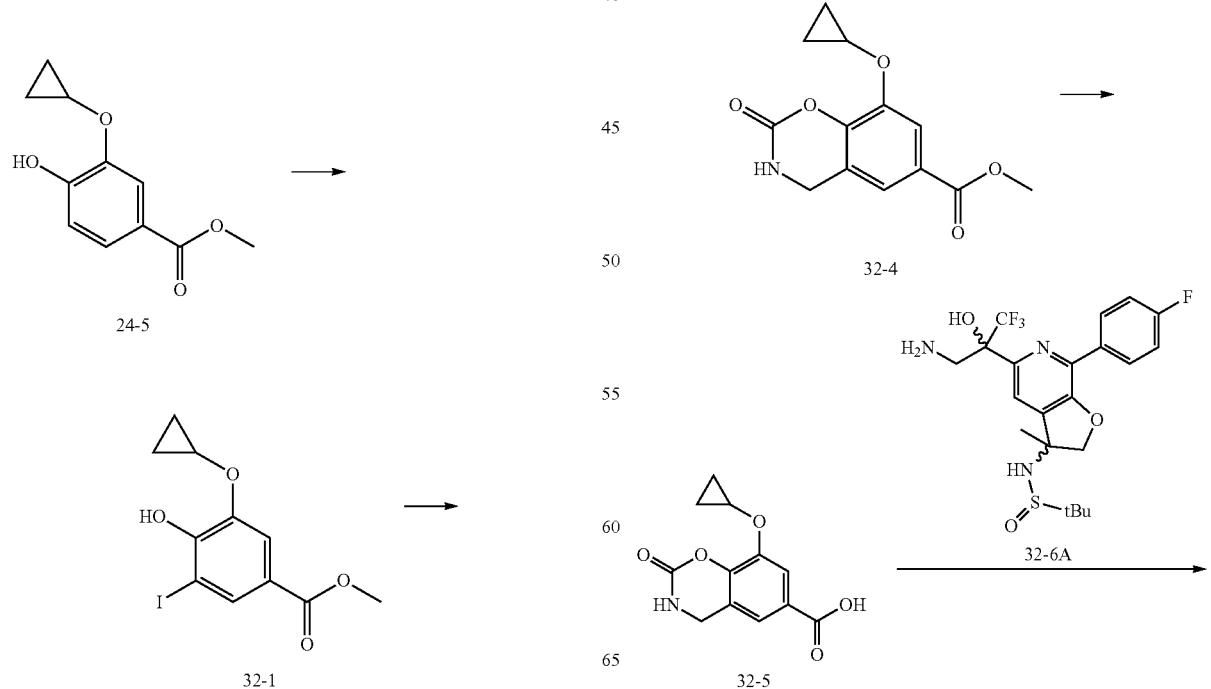

-continued

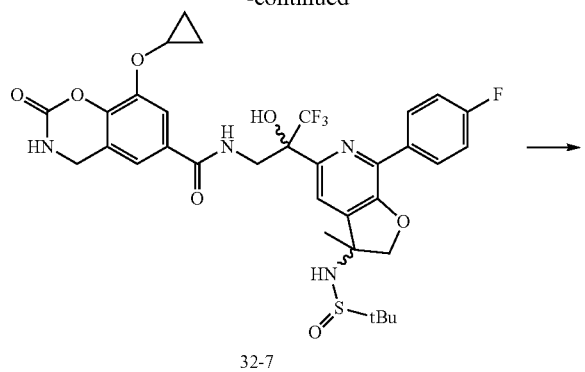

32-7

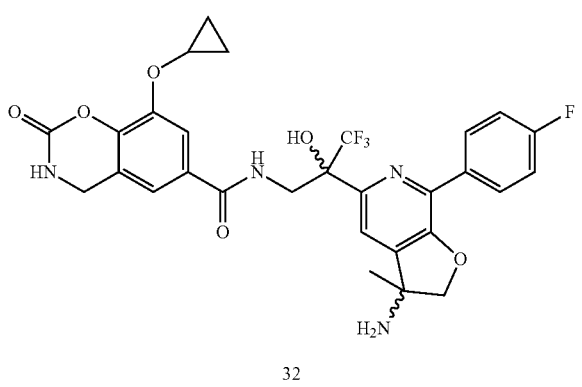

32

Compound 32-6A was prepared according to a similar procedure as provided in PCT Publication No. WO 2015/26792 A1.

To a mixture of 24-5 (1.0 g, 4.8 mmol) and Na$_2$CO$_3$ (1.02 g, 9.6 mmol) in DCM (20 mL) and H$_2$O (1 mL) was added I$_2$ (2.44 g, 9.6 mmol). The mixture was stirred at RT for 1 h. The reaction was quenched with aq. Na$_2$SO$_3$ (50 mL), extracted with EA (50 mL). The organic phase was washed with brine, dried over Na$_2$SO$_4$ and concentrated. The residue was purified by flash column using 0~25% EA in PE to give 32-1 (920 mg, 57.4%) as a white solid. MS: m/z 334.9 [M+H]$^+$.

A mixture of 32-1 (920 mg, 2.75 mmol) and CuCN (985 mg, 11.00 mmol) in NMP (8 mL) was heated to 140° C. and stirred for 1 h under microwave. The mixture was cooled to RT, poured into water (30 mL) and extracted with EA (2×60 mL). The organic phase was concentrated and purified by column chromatography using 10~100% EA in PE to give the 32-3 (618 mg, 96.7%) as a yellow oil. MS: m/z 233.9 [M+H]$^+$.

To a solution of 32-2 (618 mg, 2.66 mmol) in THF (5 mL) was added BH$_3$.THF (1 M, 5.0 mL). The solution was heated to 70° C. and stirred for 0.5 h. The reaction was quenched by water (30 mL) and extracted with EA (3×30 mL). The organic phase was concentrated to give 32-3 (432 mg, crude) as a yellow oil. MS: m/z 237.9 [M+H]$^+$.

To a solution of 32-3 (430 mg, crude) in THF (10 mL) was added CDI (587 mg, 3.62 mmol). The solution was stirred at RT for 15 h. The mixture was then diluted with EA (20 mL) and water (10 mL). The organic phase was isolated and washed with brine, dried over Na$_2$SO$_4$, concentrated purified by prep-TLC (EA) to give 32-4 (212 mg, 44.1%). MS: m/z 264.1 [M+H]$^+$.

A solution of 32-4 (50 mg, 0.19 mmol) in HCl/dioxane (4M, 1.0 mL) and conc. HCl (12 M, 1.0 mL) was heated to 100° C. and stirred for 0.5 h. The solution was cooled to RT, poured into water (10 mL) and extracted with EA (2×20 mL). The organic phase was concentrated and purified by prep-HPLC (FA condition) to give 32-5 (31 mg) as a white solid. MS: m/z 250.1 [M+H]$^+$.

Compound 32 (6.4 mg, a yellow solid) was prepared using methods similar to those for preparing 21 from 32-5 and 32-6A. MS: m/z 603.2 [M+H]$^+$.

Example 21

Preparation of Compound 33

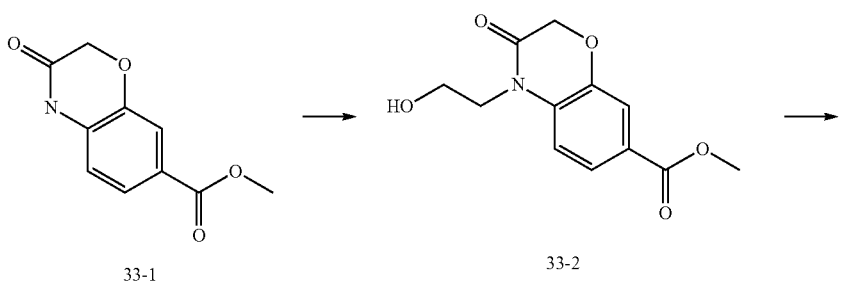

-continued
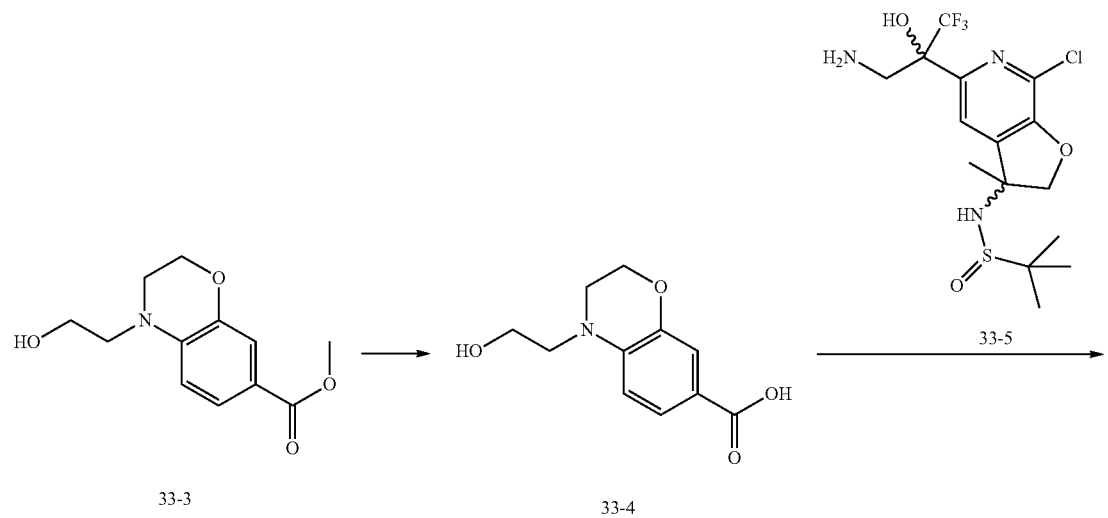
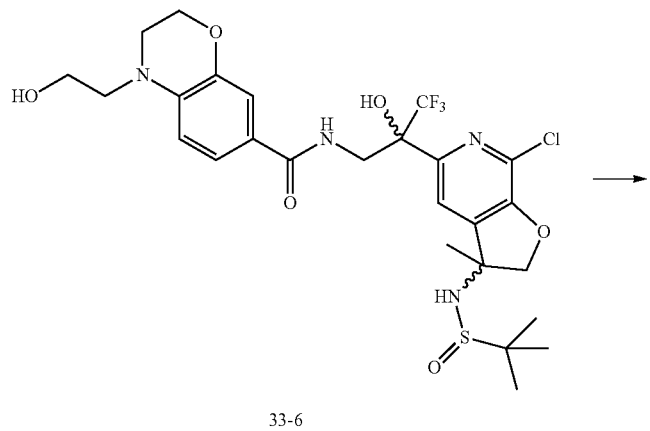
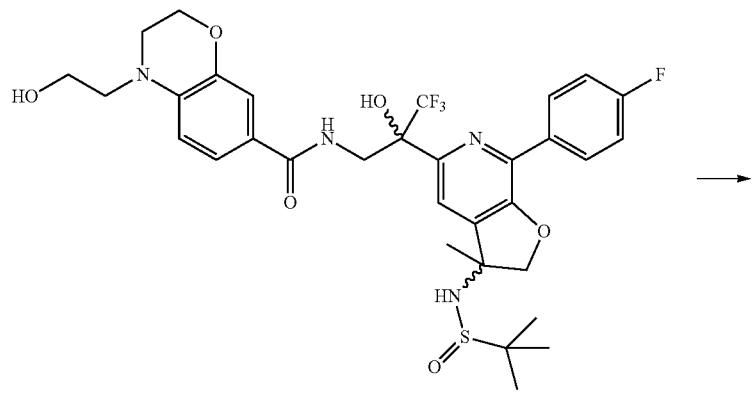

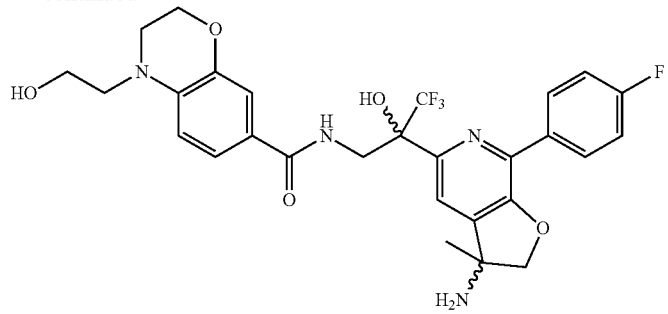

33

Compound 33-1 was prepared according to a similar procedure as provided in Ramesh et al., Tetrahedron (2011) 67(6):1187-1192. Compound 33-5 was prepared according to a similar procedure as provided in WO 2015/26792 A1.

To a solution of 33-1 (810 mg, 3.9 mmol) in DMF (10 mL) was added NaH (313 mg, 7.8 mmol) at RT. After stirring for 5 mins, 2-bromoethanol (489 mg, 3.9 mmol) was added, heated to 80° C. and stirred for 0.5 h. The reaction was cooled to RT, poured into water (50 mL) and extracted with EA (2×50 mL). The organic phase was washed with brine, dried over $Na_2SO_4$ and concentrated to give 33-2 (520 mg, crude) as a brown solid. MS: m/z 251.8 $[M+H]^+$.

To a solution of 33-2 (200 mg, crude) in THF (1.0 mL) was added $BH_3$-THF (1 M, 2.0 mL) at RT. The solution was heated to 70° C. and stirred for 1 h. The reaction was quenched with water (2 mL), and extracted with EA (2×5 mL). The organic phase was concentrated to give 33-3 (182 mg, crude) as a yellow oil. MS: m/z 237.9 $[M+H]^+$.

Compound 33 (14 mg, a white solid) was prepared using methods similar to those for preparing 21 from 33-5 and 33-5. MS: m/z 577.0 $[M+H]^+$.

Example 22

Preparation of Compound 34

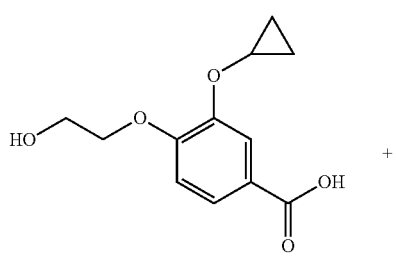

24-5

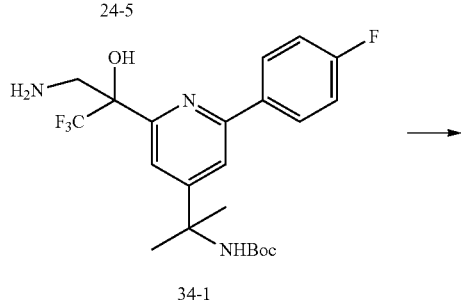

34-1

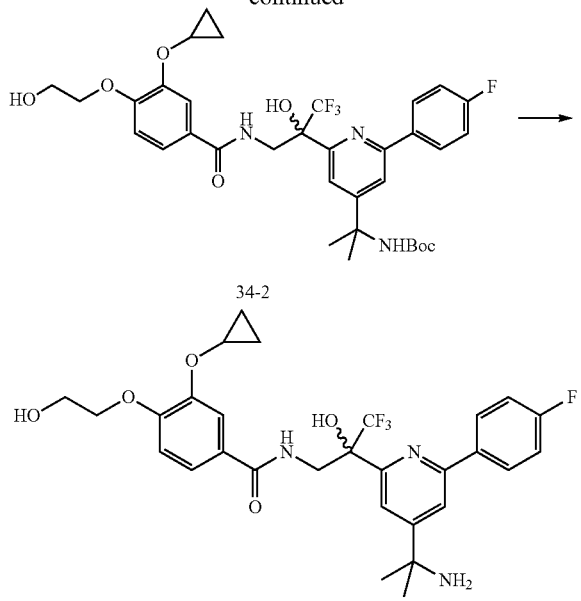

34

Compound 34-1 was prepared according to a similar procedure as provided in WO 2015/26792 A1. Compound 34 (46 mg, a yellow solid) was prepared using methods similar to those for preparing 21 from 24-5 and 34-1. MS: m/z 578.0 $[M+H]^+$.

Example 23

Preparation of Compound 35

35-1

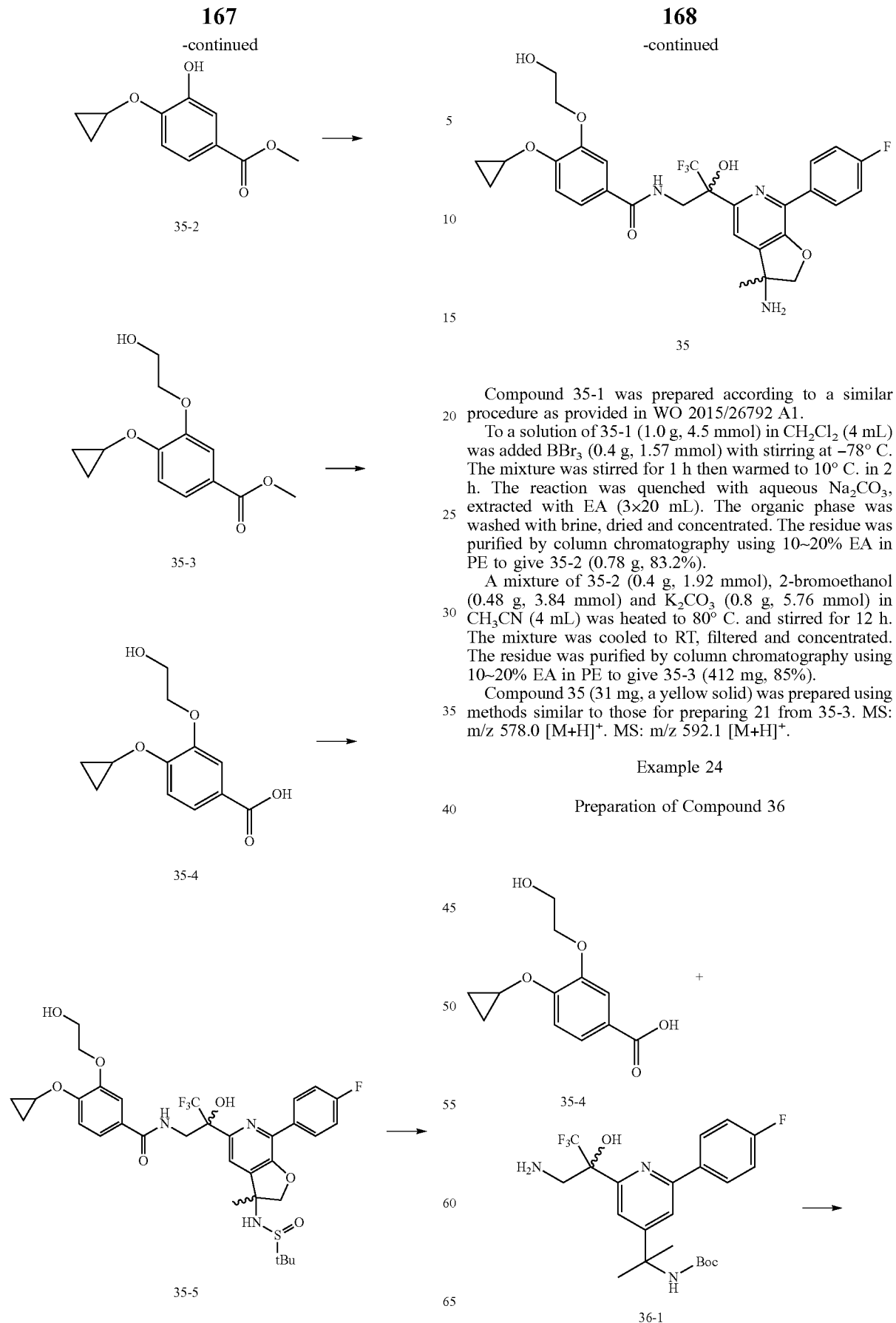

Compound 35-1 was prepared according to a similar procedure as provided in WO 2015/26792 A1.

To a solution of 35-1 (1.0 g, 4.5 mmol) in $CH_2Cl_2$ (4 mL) was added $BBr_3$ (0.4 g, 1.57 mmol) with stirring at −78° C. The mixture was stirred for 1 h then warmed to 10° C. in 2 h. The reaction was quenched with aqueous $Na_2CO_3$, extracted with EA (3×20 mL). The organic phase was washed with brine, dried and concentrated. The residue was purified by column chromatography using 10~20% EA in PE to give 35-2 (0.78 g, 83.2%).

A mixture of 35-2 (0.4 g, 1.92 mmol), 2-bromoethanol (0.48 g, 3.84 mmol) and $K_2CO_3$ (0.8 g, 5.76 mmol) in $CH_3CN$ (4 mL) was heated to 80° C. and stirred for 12 h. The mixture was cooled to RT, filtered and concentrated. The residue was purified by column chromatography using 10~20% EA in PE to give 35-3 (412 mg, 85%).

Compound 35 (31 mg, a yellow solid) was prepared using methods similar to those for preparing 21 from 35-3. MS: m/z 578.0 [M+H]+. MS: m/z 592.1 [M+H]+.

Example 24

Preparation of Compound 36

169

-continued

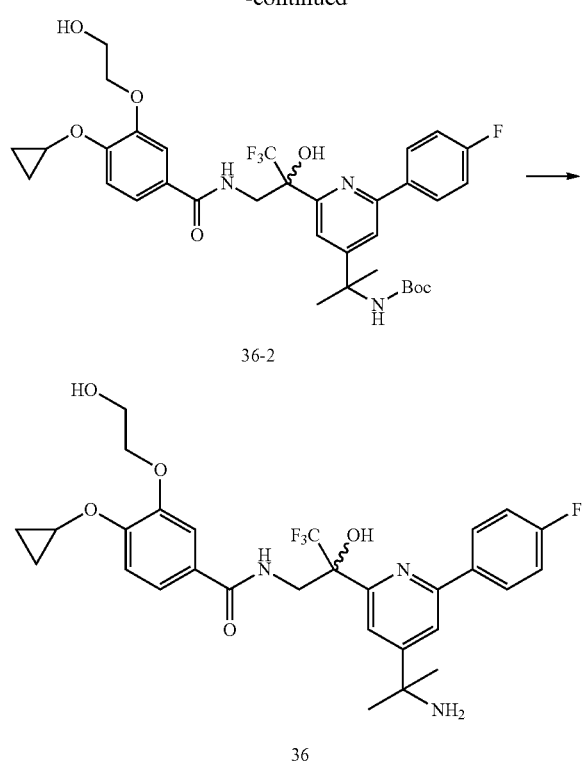

Compound 36-1 was prepared according to a similar procedure as provided in WO 2015/26792 A1. Compound 36 (77 mg, a white solid) was prepared using methods similar to those for preparing 21 from 35-4 and 36-1. MS: m/z 578.1 [M+H]⁺.

Example 25

Preparation of Compound 37

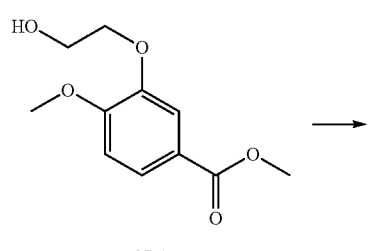

170

-continued

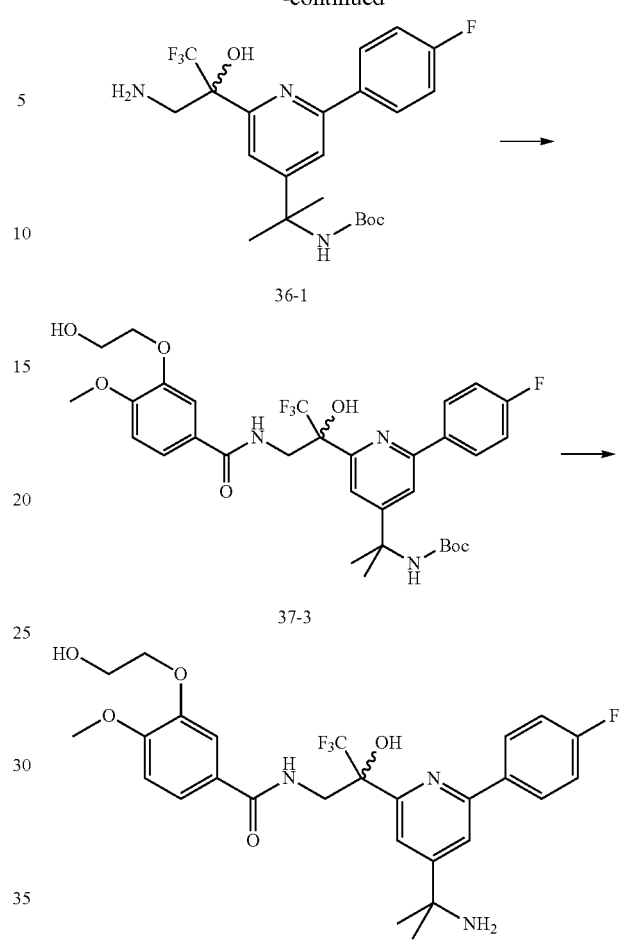

Compound 37-1 was prepared according to a similar procedure as provided in Uto et al., Bioorganic and Medicinal Chemistry Letters (2009) 19(15):4151-4158. Compound 37 (42 mg, a white solid) was prepared using methods similar to those for preparing 21 from 36-1 and 37-1. MS: m/z 552.2 [M+H]⁺.

Example 26

Preparation of Compound 38

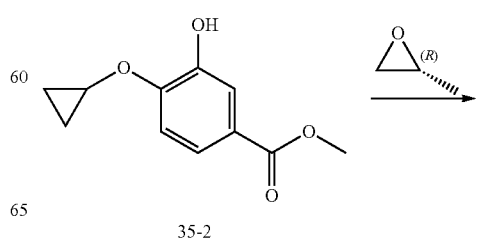

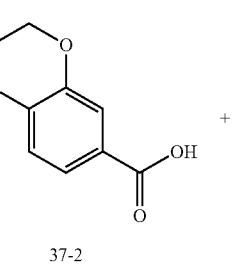

171

-continued

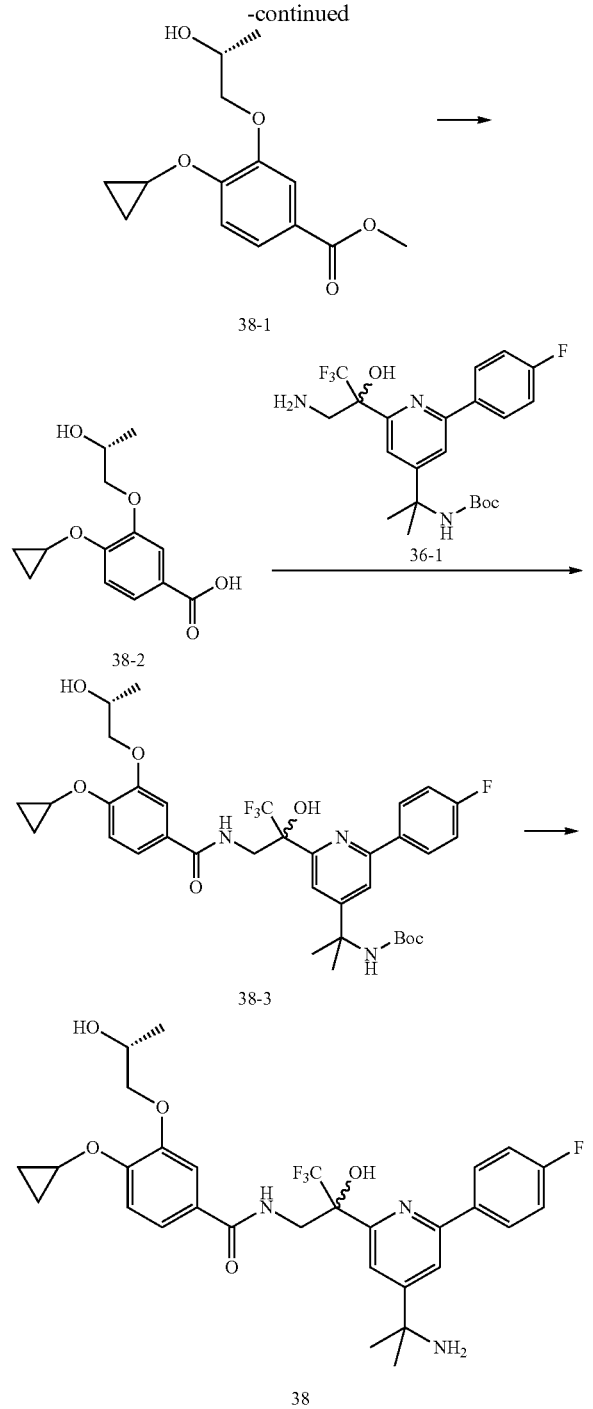

A mixture of 35-2 (700 mg, 3.36 mmol), (2R)-2-methyloxirane (1.95 g, 33.6 mmol) and $K_2CO_3$ (550 mg, 4.0 mmol) in acetone (10 mL) was heated to 80° C. in a sealed tube and stirred for 18 h. The mixture was cooled to RT and filtered. The filtrate was concentrated, and the residue was purified by column chromatography using 5~10% EA in PE to give 38-1 (813 mg, 90.7%) as a colorless oil. MS: m/z 226.9 $[M+H]^+$.

Compound 38 (39 mg, a white solid) was prepared using methods similar to those for preparing 21 from 38-1. MS: m/z 592.1 $[M+H]^+$.

172

Example 27

Preparation of Compound 39

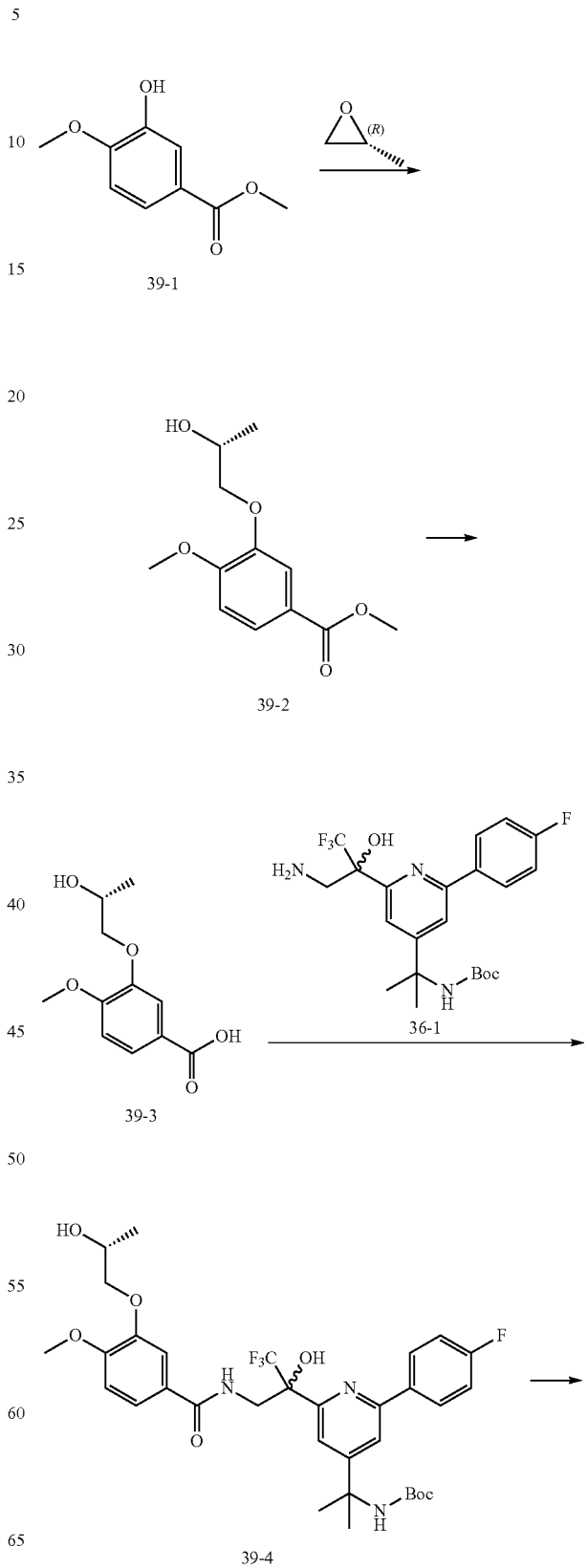

-continued
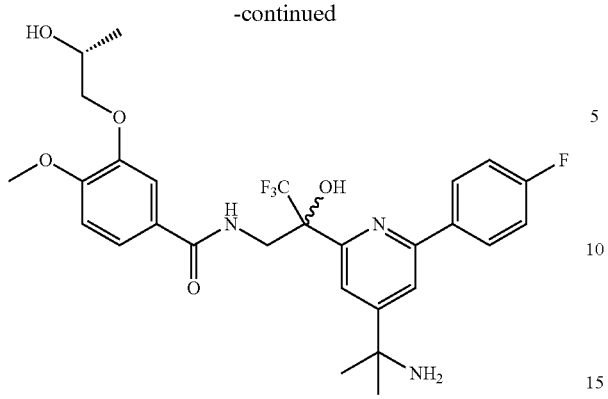
39
Compound 39-1 was prepared according to a similar procedure as provided in WO 2015/26792 A1. Compound 39 (68 mg, a white solid) was prepared using methods similar to those for preparing 21 from 39-1. MS: m/z 566.1 $[M+H]^+$.
Example 28
Preparation of Compound 40
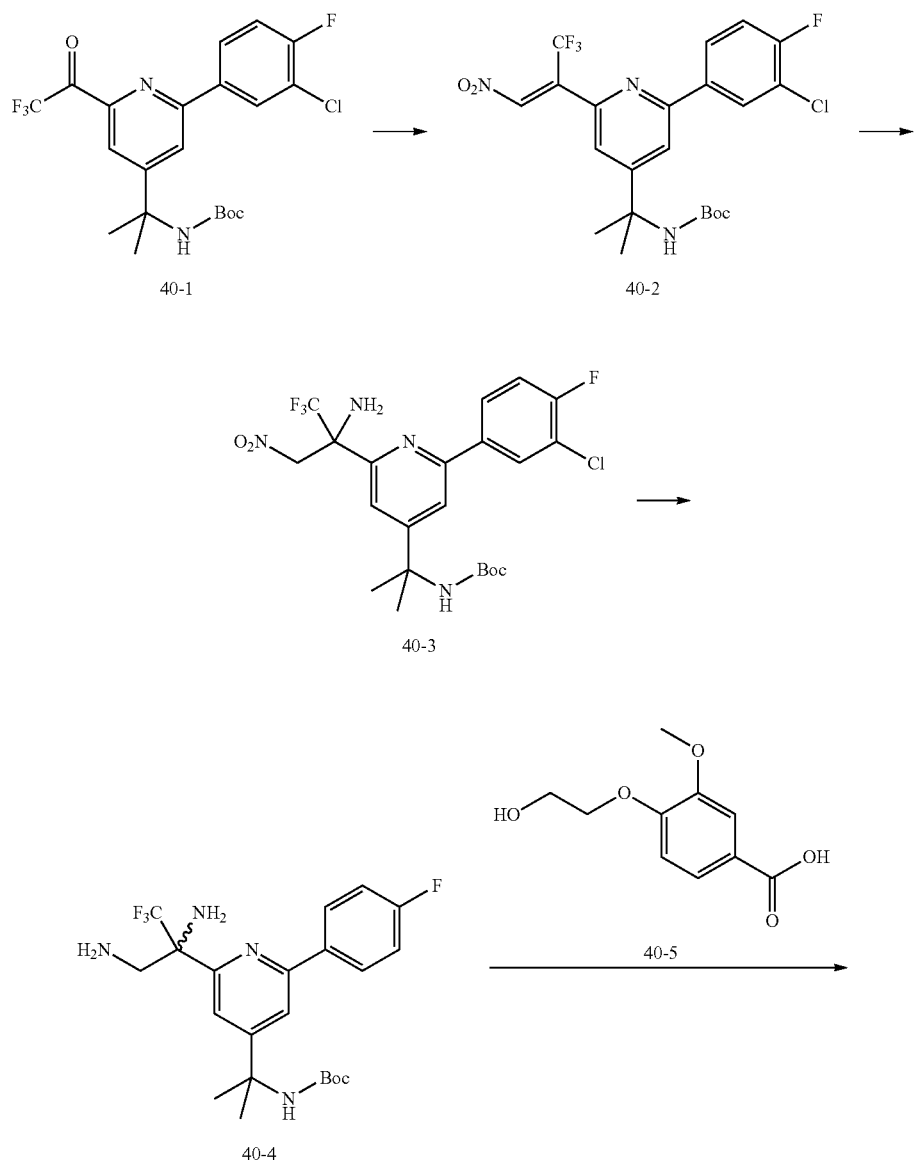

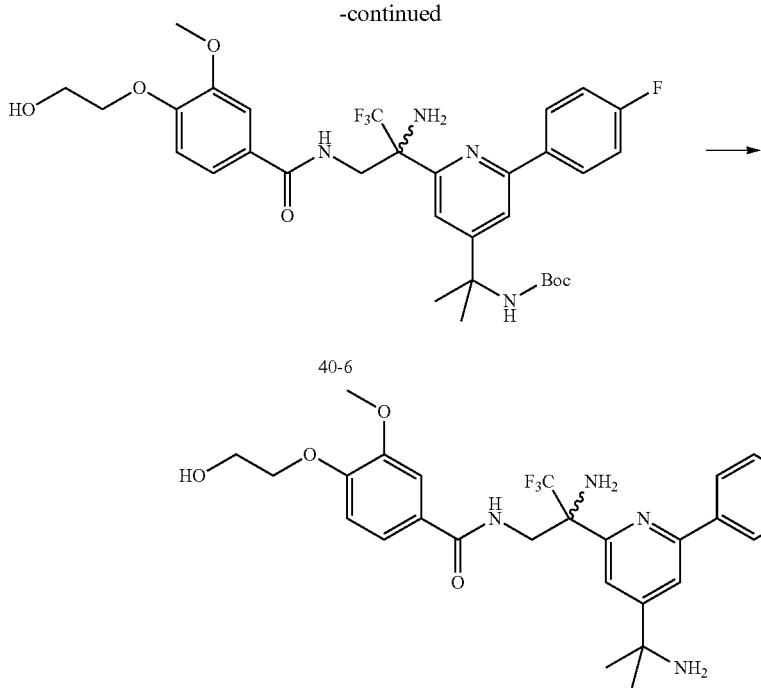

40-6

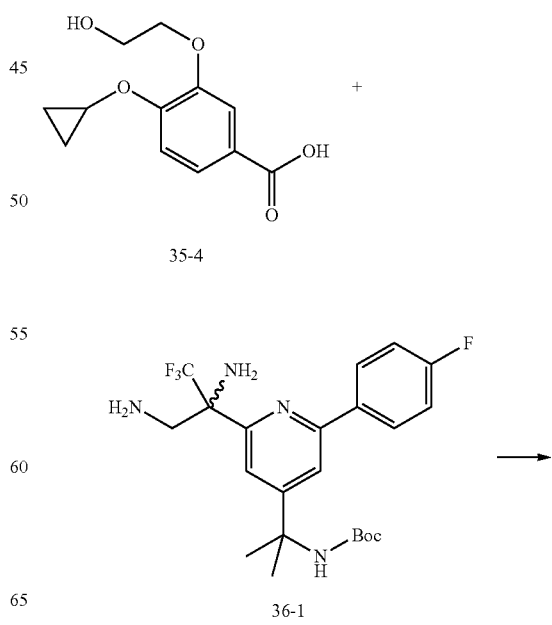

40

Compound 40-1 was prepared according to a similar procedure as provided in WO 2015/26792 A1, and compound 40-5 was prepared according to a similar procedure as provided in WO 2013/31784 A1.

A mixture of 40-1 (821 mg, 1.78 mmol) and $K_2CO_3$ (542 mg, 3.92 mmol) in $CH_3NO_2$ (10 mL) was stirred at RT for 3 h, diluted with $H_2O$ (20 mL) and extracted with EA (2×10 mL). The organic layers were washed with brine, dried over $Na_2SO_4$ and concentrated. The residue (815 mg, crude) and pyridine (370 mg, 4.68 mmol) were dissolved in toluene (10 mL) and stirred at 0° C. for 10 mins. $SOCl_2$ (0.28 mL 3.90 mmol) was added slowly at 0° C. The mixture was stirred at 0° C. for 30 mins, quenched by water (20 mL), extracted with EA (2×20 mL). The organic layers were washed with brine, dried over $Na_2SO_4$, filtered and concentrated. The residue was purified by column chromatography using ~20% EA in PE to give 40-2 (721 mg, 73.1%) as a white solid. MS: m/z 503.9 [M+H]$^+$.

A mixture of 40-2 (721 mg, 1.43 mmol) and ammonia water (1 mL, 14 M) in DMSO (6 mL) was stirred at 0° C. for 1 h. The mixture was diluted with $H_2O$ (50 mL), and extracted with EA (3×30 mL). The organic layers were washed with brine, dried over $Na_2SO_4$, filtered and concentrated. The residue was purified by column chromatography using 20% EA in PE to give 40-3 (651 mg, 87.4%) as a yellow oil. MS: m/z 521.1 [M+H]$^+$.

A mixture of 40-3 (650 mg, 1.25 mmol) and Raney-Ni (0.2 g) in MeOH (20 mL) was stirred under hydrogen (45 Psi) at RT for 16 h. The mixture was filtered through a pad of celite and Pd/C (65 mg, 10%) was added. The mixture was stirred under hydrogen (45 Psi) at RT for 16 h. The mixture was filtered through a pad of Celite, and the filtrate was concentrated to give 40-4 (382 mg 38.8%). MS: m/z 457.1 [M+H]$^+$.

Compound 40 (29 mg, a white solid) was prepared using methods similar to those for preparing 21 from 40-4 and 40-5. MS: m/z 551.1 [M+H]$^+$.

Example 29

Preparation of Compound 41

177
-continued
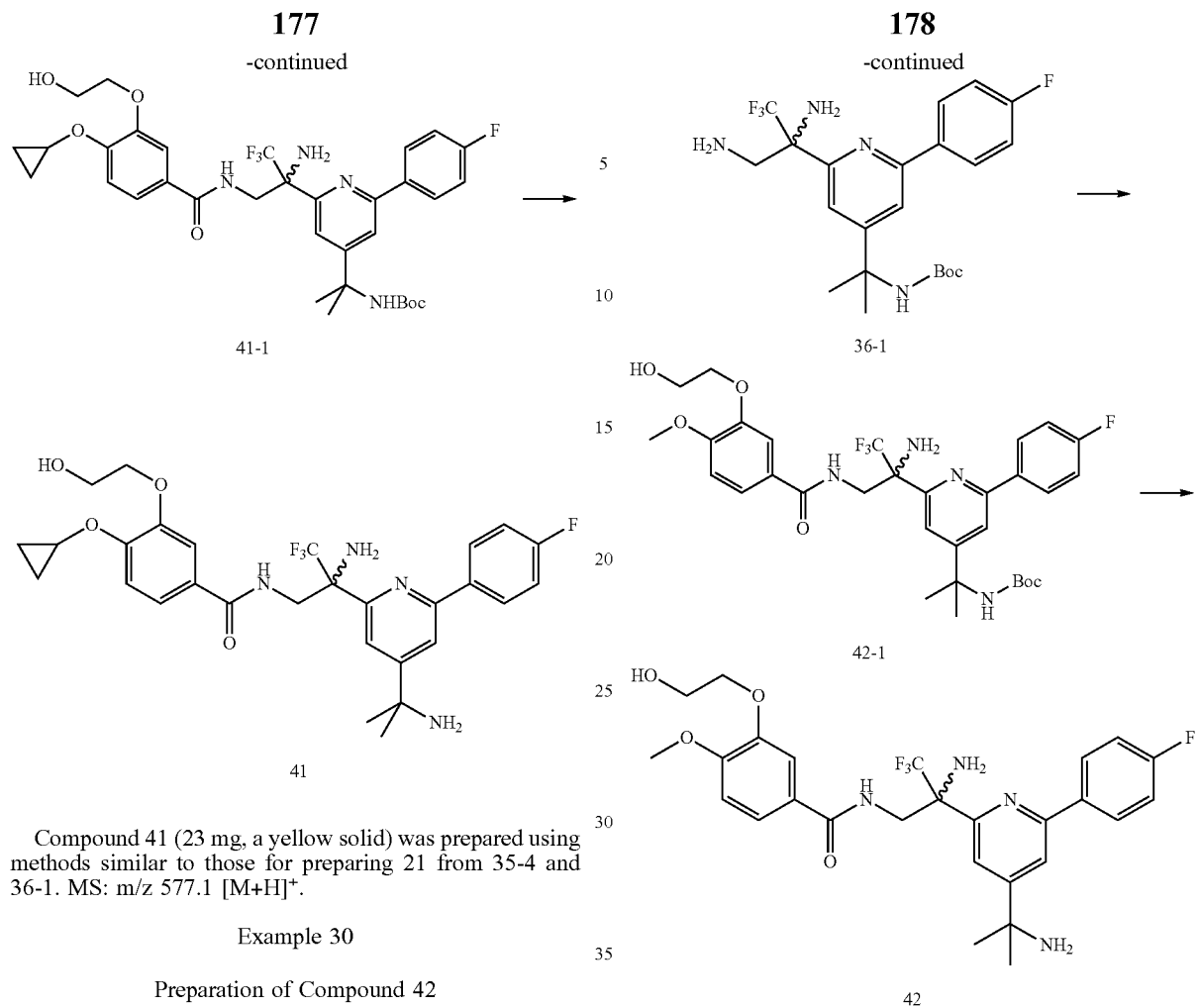
Compound 41 (23 mg, a yellow solid) was prepared using methods similar to those for preparing 21 from 35-4 and 36-1. MS: m/z 577.1 [M+H]$^+$.
Example 30
Preparation of Compound 42
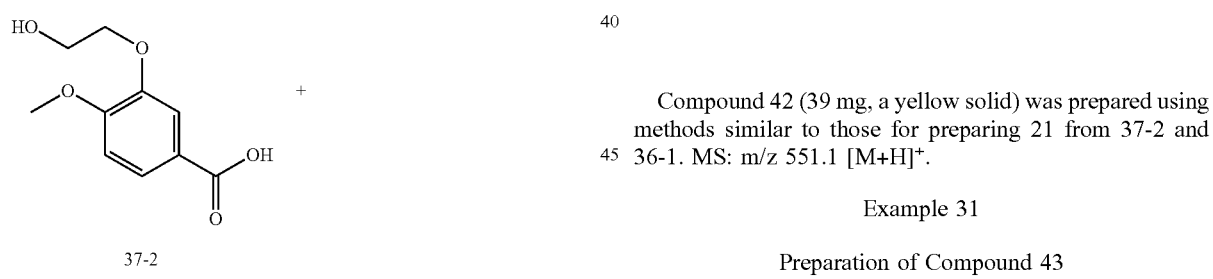
178
-continued
Compound 42 (39 mg, a yellow solid) was prepared using methods similar to those for preparing 21 from 37-2 and 36-1. MS: m/z 551.1 [M+H]$^+$.
Example 31
Preparation of Compound 43
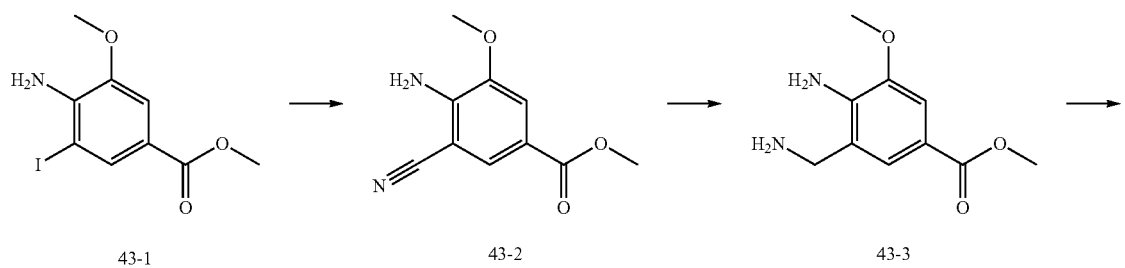

-continued
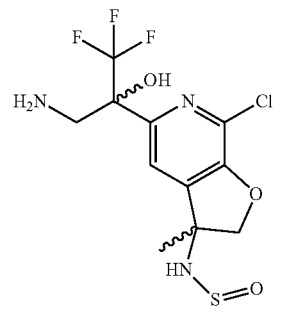
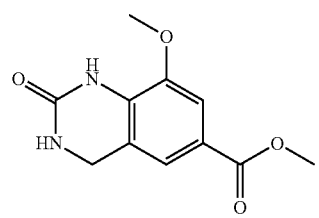 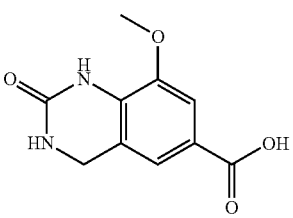
43-4    43-5
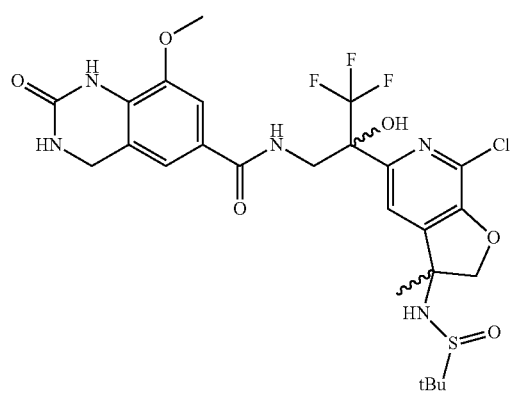 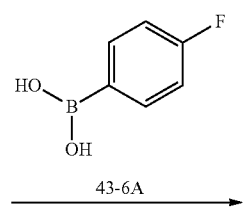
43-6A
43-6
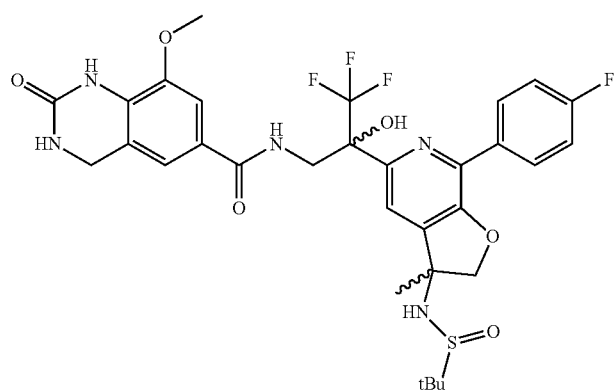

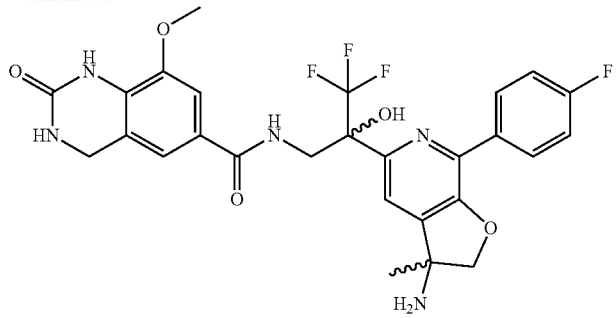

43

Compound 43-1 was prepared according to a similar procedure as provided in Ezquerra et al., Journal of Organic Chemistry (1996) 61(17):5804-5812, and compound 43-5A was prepared according to a similar procedure as provided in WO 2015/26792 A1.

A mixture of 43-1 (2.5 g, 4.1 mmol), CuCN (1.46 g, 8.2 mmol) in DMF (15 mL*2) was heated to 120° C. and stirred for 1 h under microwave irradiation. The mixture was poured into water (50 mL) and extracted with EA (2×50 mL). The organic phase was concentrated, and the residue was purified by column chromatography using 5~20% EA in PE to give 43-2 (1.6 g, 95.3%) as a yellow solid. MS: m/z 206.9 [M+H]⁺.

A mixture 43-2 (1.1 g, 5.3 mmol) in BH₃-THF (1 M, 20 mL) was heated to 70° C. and stirred for 2 h. The solution was quenched with water, basified by aqueous K₂CO₃ to pH 11~12, and extracted with EA (2×30 mL). The organic phase was washed with brine, dried over Na₂SO₄ and concentrated to give 43-3 (1.02 g, crude) as a brown oil. MS: m/z 193.9 [M-NH₂]⁺.

To a solution of 43-3 (1.0 g, 4.7 mmol) in THF (20 mL) was added CDI (1.6 g, 9.5 mmol) at 20° C. The mixture was stirred overnight. The mixture was then poured into water (50 mL) and extracted with EA (2×40 mL). The organic phase was washed with brine, dried over Na₂SO₄ and concentrated to give 43-4 (1.10 g, crude) as a yellow solid. MS: m/z 236.9 [M+H]⁺.

Compound 43 (46 mg, a yellow solid) was prepared using methods similar to those for preparing 21 from 43-4. MS: m/z 575.3 [M+H]⁺, 598.1 [M+Na]⁺.

Example 32

Preparation of Compound 44

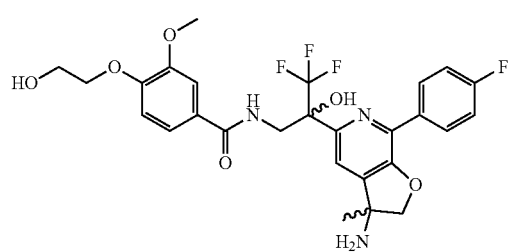

44-1

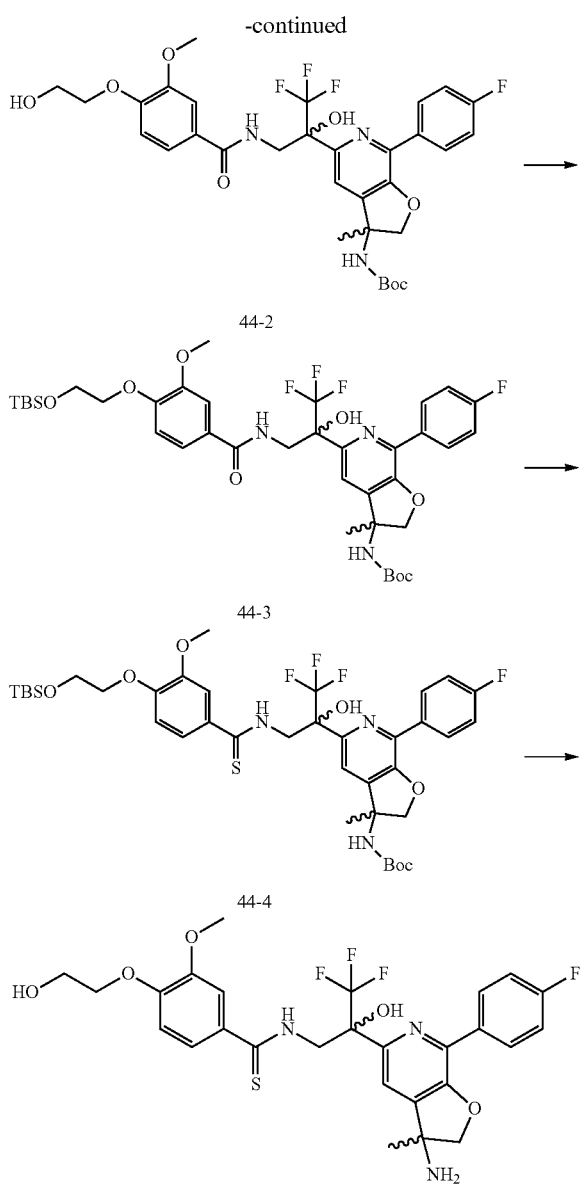

44

A solution of 44-1 (800 mg, 1.41 mmol), TEA (281 mg, 2.77 mmol) and Boc₂O (309 mg, 1.41 mmol) in toluene (2 mL) stirred at 110° C. for 2 h. The solution was concentrated, and the residue was purified by column chromatography using 25% EA in PE to give 44-2 (582 mg, 62%) as a white solid. MS: m/z 665.9 [M+H]⁺.

To a solution of 44-2 (580 mg, 0.87 mmol) and imidazole (118 mg, 1.74 mmol) in DCM (20 mL) was added TBSCl (159 mg, 1.05 mmol, 1.21 eq.). The mixture was stirred at 20° C. for 1 h, washed with water (20 mL) and concentrated. The residue was purified by column chromatography using 10% of EA in PE to give 44-3 (562 mg, 82.7%) as a colorless oil. MS: m/z 780.1 [M+H]⁺.

A mixture of 44-3 (560 mg, 0.72 mmol) and Lawesson reagent (290 mg, 0.72 mmol) in toluene (3 mL) was heated to 110° C. and stirred for 1 h. The solution was quenched with H₂O (5 mL) and extracted with EA (2×10 mL). The organic phase was concentrated and purified by column chromatography using 15% EA in PE to give 44-4 (121 mg, 21.1%) as a yellow solid. MS: m/z 796.2 [M+H]⁺.

A mixture of 44-4 (110 mg, 138 μmol) in HCl/MeOH (4 M, 5 mL) was stirred at 20° C. for 20 mins, concentrated and purified by prep-HPLC (HCl) to give 44 (16 mg, 19.9%) as a yellow solid. MS: m/z 582.0 [M+H]⁺, 604.0 [M+Na]⁺.

Example 33

Preparation of Compound 45

Compound 45-1 (226 mg) was purified by SFC (Column: Chiralpak AD-3 150×4.6 mm I.D., 3 um Mobile phase: A: CO₂ B:iso-propanol (0.05% DEA) Gradient: from 5% to 40% of B in 5.5 min and hold 40% for 2 min, then 5% of B for 2.5 min Flow rate: 2.5 mL/min Column temp.: 35° C. Wavelength: 220 nm" "Column: Chiralcel OJ-3 150×4.6 mm I.D., 3 um Mobile phase: A: CO2 B: methanol (0.05% DEA) Gradient: from 5% to 40% of B in 5.5 min and hold 40% for 2 min, then 5% of B for 2.5 min Flow rate: 2.5 mL/min Column temp.: 35° C. Wavelength: 220 nm) to get 45 (180 mg, 79.6%) as a white solid. MS: m/z 634.1 [M+H]⁺.

Example 34

Preparation of Compound 46

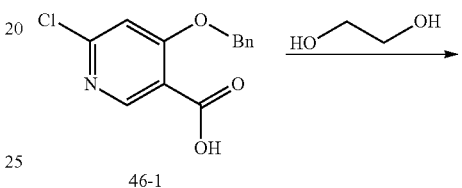

46-1

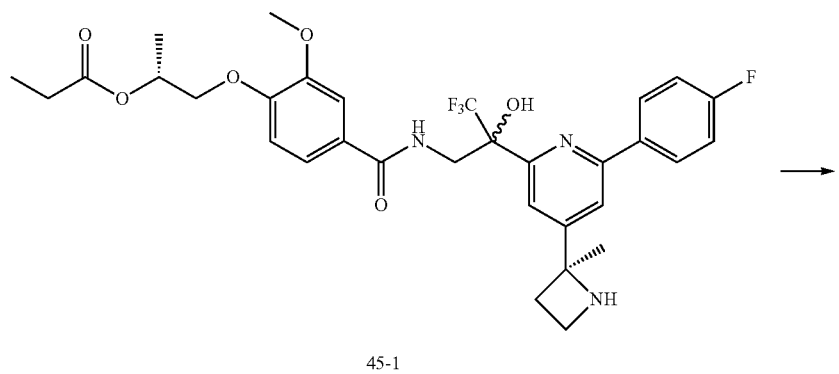

45-1

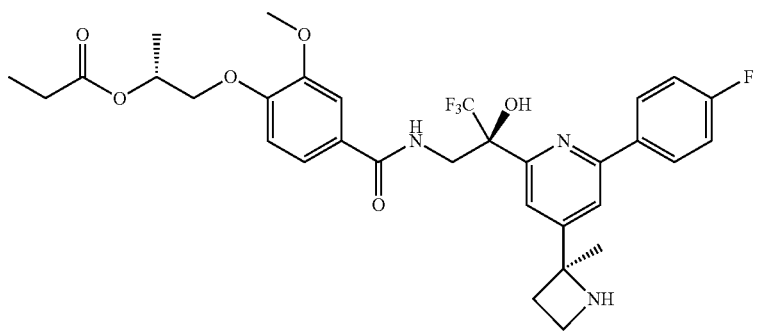

45

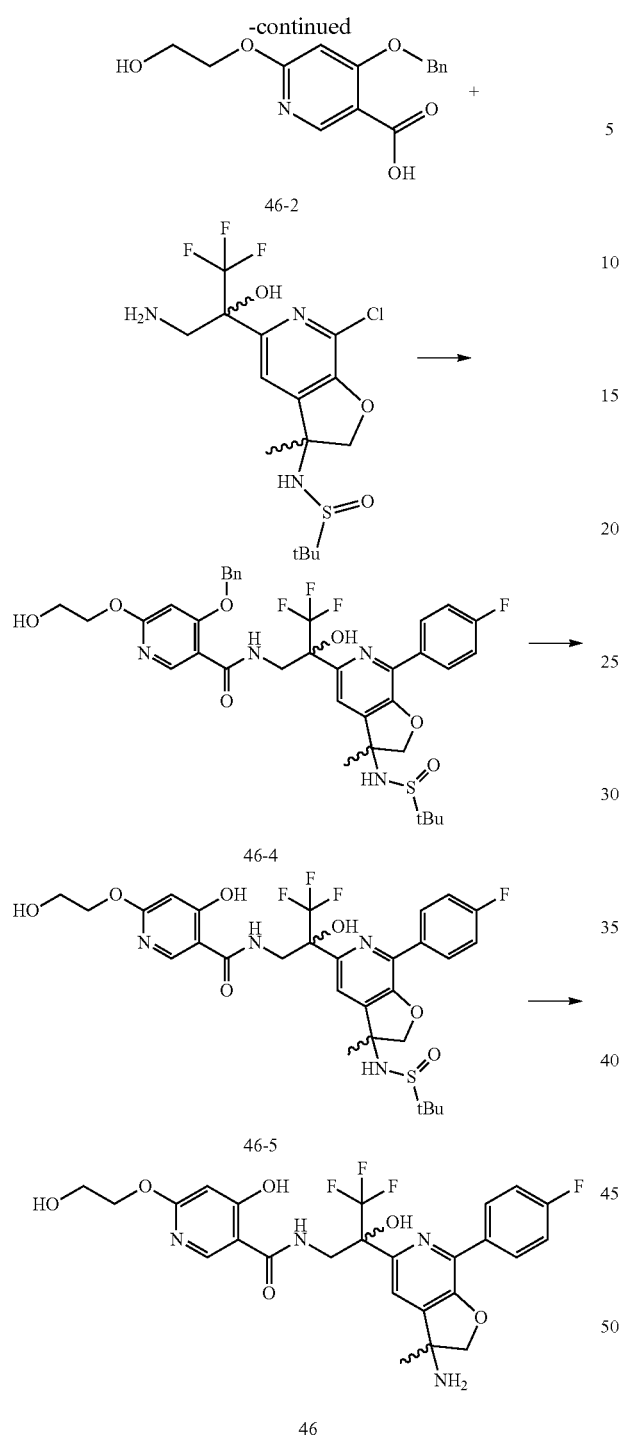

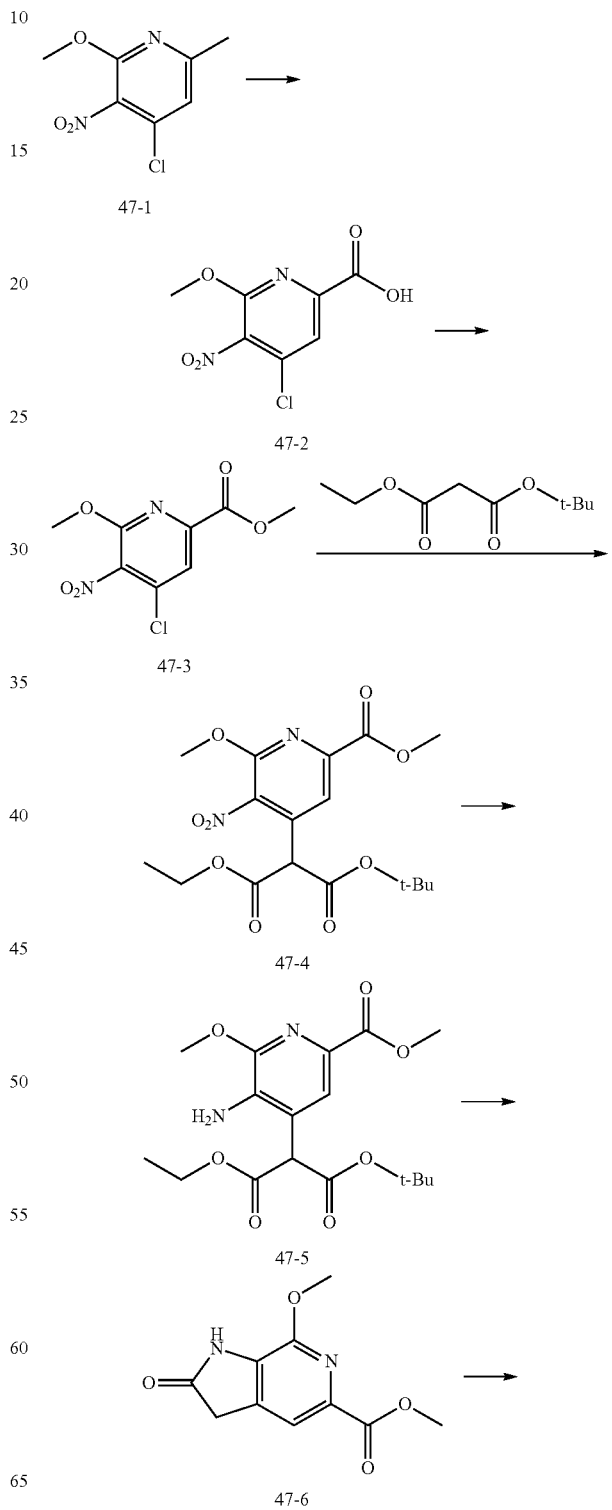

Compound 46 (7.1 mg, a yellow solid) was prepared using methods similar to those for preparing 21 from 46-2 and 46-3. MS: m/z 575.1 [M+Na]⁺.

Example 35

Preparation of Compound 47

Compound 46-1 was prepared according to a similar procedure as provided in Sakairi et al., Journal of Arzneimittel-Forschung/Drug Research (2012) 62(11):537-544, and compound 46-3 was prepared according to procedures as provided in WO 2015/26792 A1.

To a solution of 46-1 (1.0 g, 3.8 mmol) in ethylene glycol (20 mL) was added t-BuOK (1.3 g, 11.4 mmol). The mixture was stirred at 130° C. for 1 h under microwave irradiation. The mixture was poured into water (50 mL) and extracted with EA (3×20 mL). The organic phase was dried over Na₂SO₄ and concentrated to give 46-2 (820 mg, crude) as a white solid. MS: m/z 290.1 [M+H]⁺.

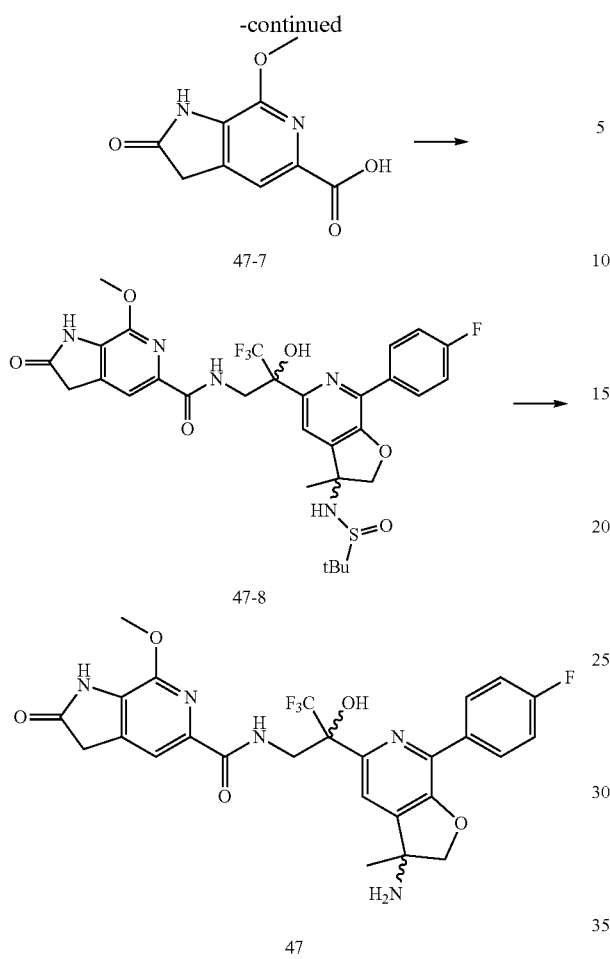

C. for 17 h. The mixture was filtered, and the filtrate was concentrated to give 47-5 (0.87 g, crude) as a white solid. MS: m/z 369.0 [M+H]+.

To a solution of 47-5 (0.8 g, 2.2 mmol) in MeOH (2 mL) was added conc. HCl (12 M, 0.78 mL). The mixture was stirred at 70° C. for 1 h. The reaction was concentrated, and the residue was purified by column chromatography using 30~100% EA in PE to give 47-6 (172 mg, 33.8%) as a light yellow solid. MS: m/z 222.9 [M+H]+.

Compound 47 (7.1 mg, a yellow solid) was prepared using methods similar to those for preparing 21 from 47-6. MS: m/z 561.9 [M+H]+.

Example 36

Preparation of Compound 48

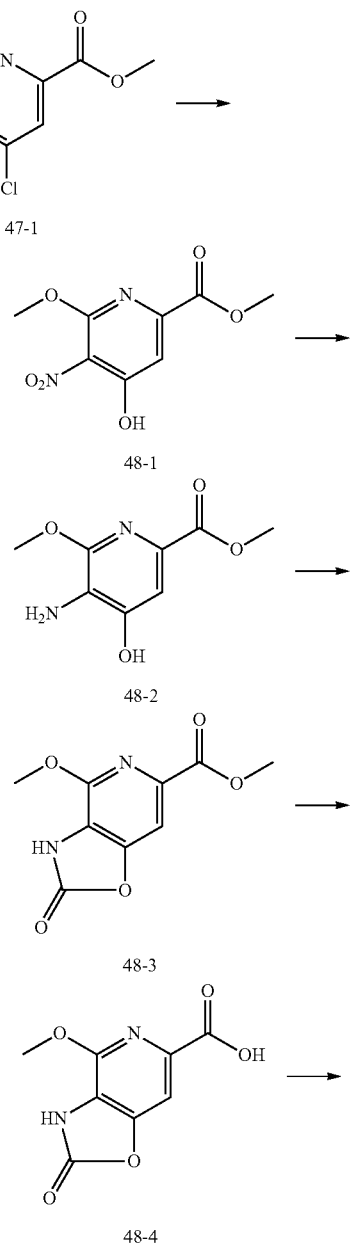

Compound 47-1 was prepared according to a similar procedure as provided in Urban et al., Journal of Helvetica Chimica Acta (1964) 47:363-379.

To a solution of 47-1 (10.0 g, 49.4 mmol) in $H_2SO_4$ (80 mL) was added $CrO_3$ (14.8 g, 148.1 mmol) in small portions and kept at an internal temperature below 70° C. After addition, the mixture was stirred at 60° C. for 2 h. The reaction was poured into ice/water (200 mL). The slurry was filtered, washed with water (3×20 mL), and dried over $Na_2SO_4$ to give 47-2 (8.20 g, crude) as a white solid. MS: m/z 233.1 [M+H]+.

To a solution of 47-2 (8.1 g, 34.8 mmol) in MeOH (90 mL) was added $SOCl_2$ (16.6 g, 139.3 mmol) slowly. The mixture was stirred at 50° C. for 2 h. The mixture was then diluted with water (100 mL), neutralized to pH 7~8 using aq. $NaHCO_3$ and extracted with EA (2×50 mL). The organic layers were washed with brine (2×10 mL), dried over $Na_2SO_4$, filtered and concentrated to give 47-3 (6.80 g, crude) as a yellow solid. MS: m/z 247.1 [M+H]+.

A mixture of 47-3 (1.0 g, 4.1 mmol), $Cs_2CO_3$ (4.0 g, 12.2 mmol) and maleic acid ester (2.29 g, 12.2 mmol) in 2-methyltetrahydrofuran (10 mL) was stirred at 80° C. for 2 h. The mixture was diluted with EA (20 mL) and water (30 mL). The organic phase was washed with brine (10 mL), dried over $Na_2SO_4$, filtered and concentrated. The residue was purified by column chromatography using 3~15% EA in PE to give 47-4 (1.2 g, 74.2%) as a white solid. MS: m/z 399.1 [M+H]+.

A mixture of 47-4 (0.95 mg, 2.4 mmol) and Pd/C (20.0 mg) in MeOH (10 mL) was stirred under $H_2$ (15 PSI) at 20°

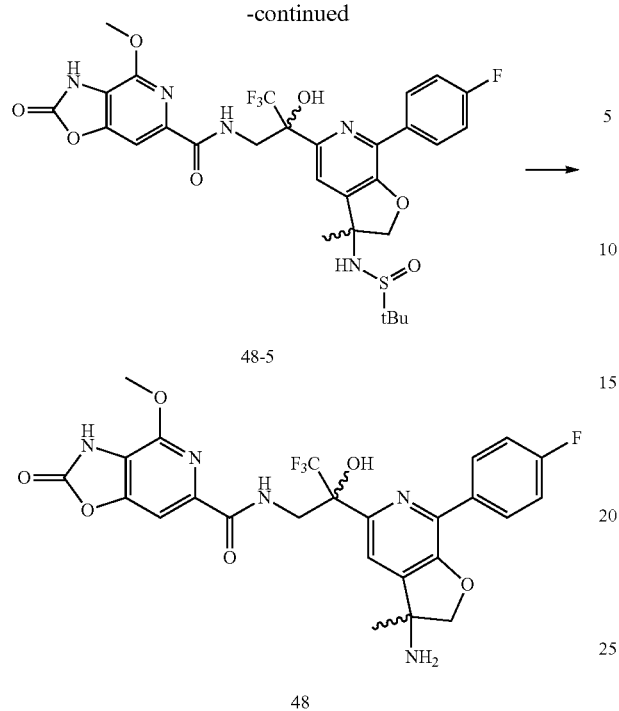

A mixture of 47-1 (1.05 g, 4.26 mmol), CH₃COOK (2.09 g, 21.29 mmol) and H₂O (154 mg, 8.52 mmol) in DMSO (10 mL) was heated to 90° C. and stirred for 1 h. TLC (PE:EA=5:1) showed the reaction was complete. The reaction was diluted with water (30 mL), and extracted with EA (2×30 mL). The organic phase was concentrated, and the residue was purified by column chromatography on silica gel using 6~20% EA in PE to give 48-1 (0.91 g, 93.6%) as a light yellow solid. MS: m/z 229.0 [M+H]⁺.

A mixture of 48-1 (0.91 g, 4.0 mmol) and Pd/C (300 mg) in CH₃OH (40 mL) was stirred at 25° C. for 12 h under H₂ (50 Psi). The mixture was filtered, and the filtrate was concentrated. The residue was purified by column chromatography using 10~30% EA in PE to give 48-2 (0.52 g, 65.7%) as a light yellow solid. MS: m/z 198.9 [M+H]⁺.

A solution of 48-2 (0.5 g, 2.52 mmol) and CDI (0.49 g, 3.02 mmol) in THF (15 mL) was stirred at 25° C. for 2 h. TLC (DCM:MeOH=20:1) showed the reaction was completed. The mixture was concentrated to give crude 48-3 (720 mg) as a light yellow solid. MS: m/z 224.8 [M+H]⁺.

Compound 48 (35 mg, a yellow solid) was prepared using methods similar to those for preparing 21 from 48-3. MS: m/z 564.0 [M+H]⁺.

Example 37

Preparation of Compound 49

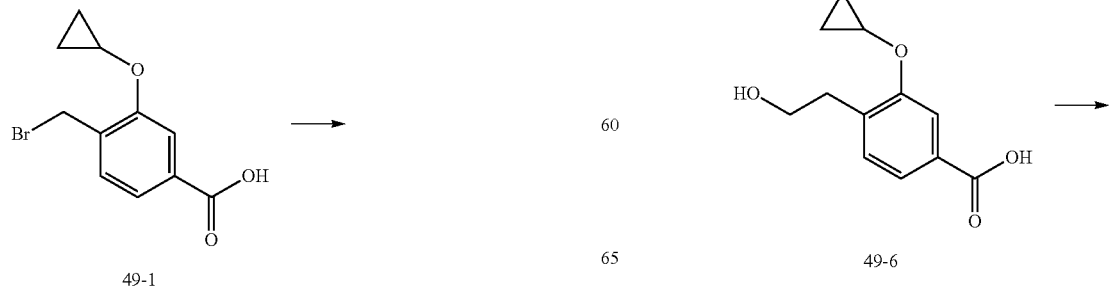

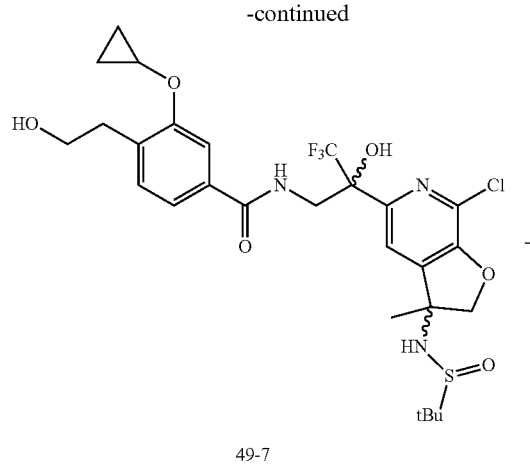

49-7

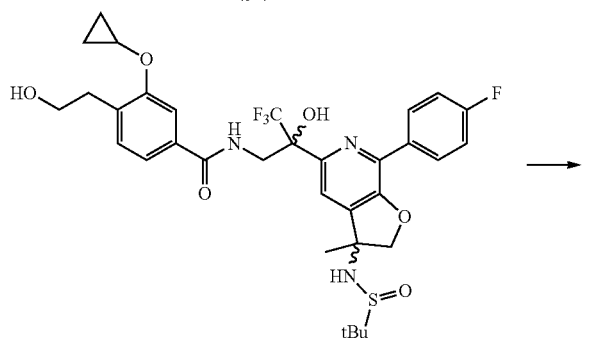

49-8

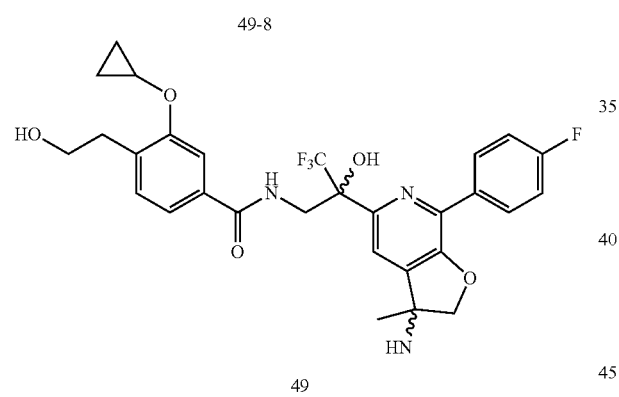

49

A mixture of 49-1 (1.0 g, 3.5 mmol), CaCO$_3$ (1.05 g, 10.5 mmol) in dioxane (10 mL) and H$_2$O (10 mL) was heated at 140° C. under microwave for 30 mins. The mixture was cooled to RT, and extracted with EA (2×20 mL). The organic phase was washed with brine, dried over Na$_2$SO$_4$, concentrated and purified by column chromatography using 10% EA in PE to give 49-2 (0.65 g, 83.5%).

To a solution of 49-2 (650 mg, 2.9 mmol) in DCM (10 mL) was added Dess-Martin (1.36 g, 3.2 mmol). The mixture was stirred at 20° C. for 1 h, and the reaction was quenched with aq. Na$_2$S$_2$O$_3$, and extracted with EA (2×20 mL). The organic phase was washed with brine, dried over Na$_2$SO$_4$, concentrated and purified by column chromatography using 3~10% EA in PE to give 49-3 (612 mg, 98.3%) as a white solid. MS: m/z 221.0 [M+H]$^+$.

To a solution of 49-3 (330 mg, 1.50 mmol) in THF (15 mL) was added MeMgBr (3 M, 0.55 mL) dropwise at −78° C. The mixture was stirred at −78° C. for 20 mins. The reaction was quenched with sat. NH$_4$Cl and extracted with EA (2×20 mL). The organic phase was washed with brine, dried over Na$_2$SO$_4$ and concentrated. The residue and 4-methylbenzenesulfonic acid (109 mg, 0.63 mmol) were dissolved in toluene (20 mL) and heated to 110° C. for 1 h with stirring. The mixture was concentrated and purified by column chromatography using 2~10% EA in PE to give 49-4 (231 mg, 83%) as a colorless oil. MS: m/z 219.1 [M+H]$^+$.

To a solution of 49-4 (150 mg, 0.69 mmol) in THF (5 mL) was added BH$_3$-THF (1 M, 6.9 mL). The mixture was stirred at 0° C. for 3 h, followed by addition of NaOH (1 M, 6.89 mL) and H$_2$O$_2$ (0.67 mL). The mixture was stirred for 1 h and then diluted with EA (20 mL) and water (10 mL). The organic phase was washed with brine, dried over Na$_2$SO$_4$, concentrated and purified by column chromatography using 10~20% EA in PE to give 49-5 (52 mg, 31%) as a white solid. MS: m/z 237.1 [M+H]$^+$.

Compound 49 (65 mg, a yellow solid) was prepared using methods similar to those for preparing 21 from 49-5. MS: m/z 575.9 [M+H]$^+$.

Example 38

Preparation of Compounds 50 and 51

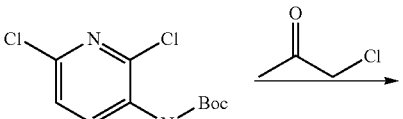

50-1

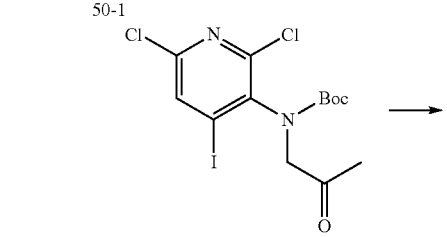

50-2

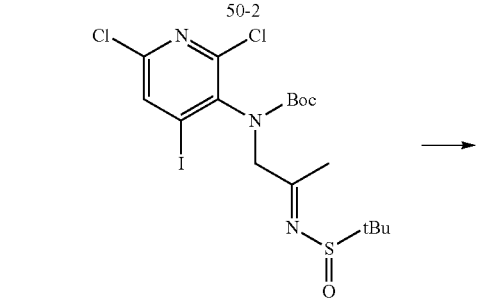

50-3

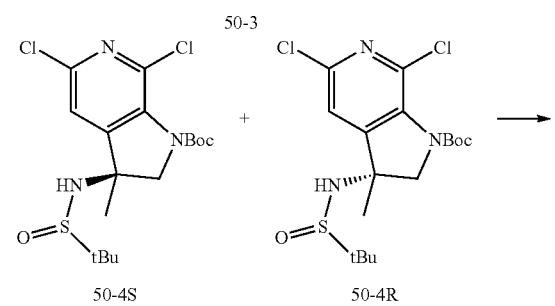

50-4S                50-4R

-continued
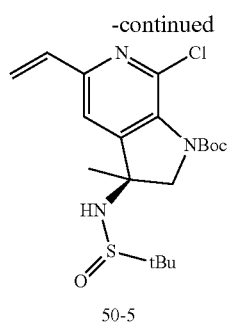
50-5
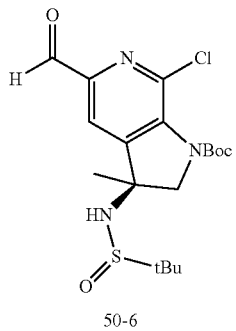
50-6
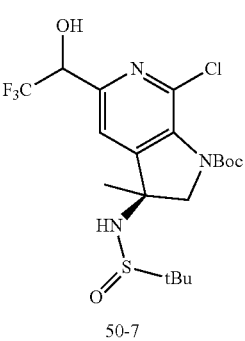
50-7
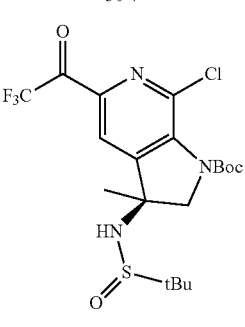
50-8
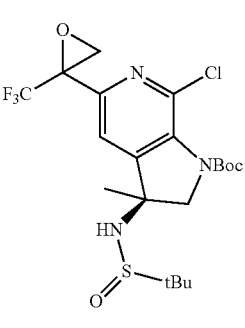
50-9
-continued
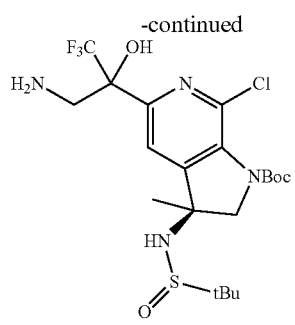
50-10
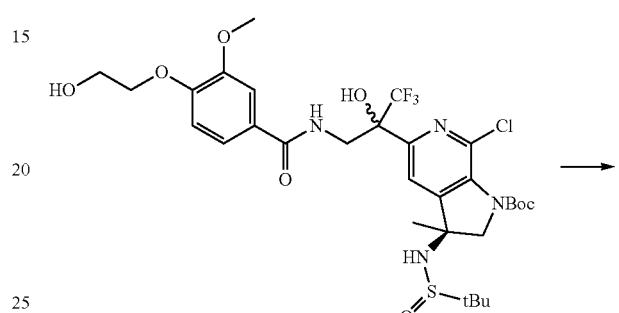
50-11
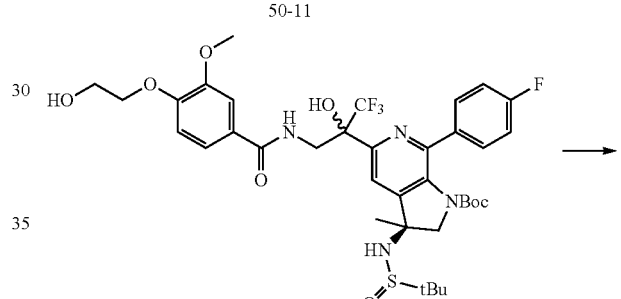
50-12
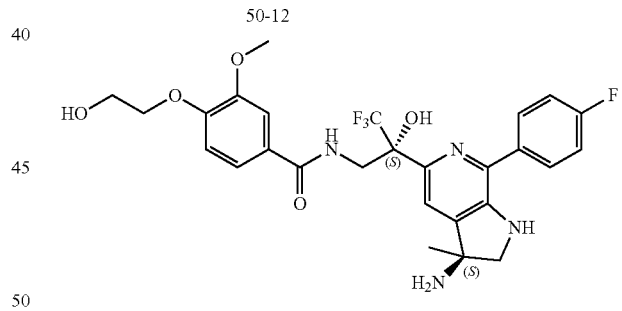
50
+
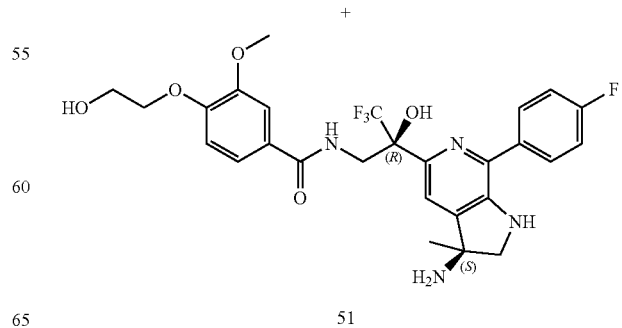
51

Compound 50-1 was prepared according to a similar procedure as provided in WO 2015/26792 A1.

To a solution of 50-1 (7.50 g, 19.28 mmol) in DMF (100 mL) was added NaH (848, mg, 21.21 mmol, 60% purity) and 1-chloropropan-2-one (1.96 g, 21.2 mmol) at RT with stirring. The mixture was stirred at 30° C. for 1 h and diluted with water (500 mL). A white precipitate was formed, filtered and washed with water (200 mL) and PE (100 mL). The solid was dried under vacuum to give 50-2 (7.5 g, 87.4%). MS: m/z 445.1 [M+H]+.

A mixture of 50-2 (7.50 g, 16.85 mmol), R-2-methylpropane-2-sulfinamide (3.27 g, 26.96 mmol) and Ti(OEt)$_4$ (11.53 g, 50.55 mmol) in THF (60 mL) was stirred at 70° C. for 1 h under N$_2$. The mixture was concentrated, and the residue was dissolved in EA (100 mL). The solution was poured into sat. aq. NaHCO$_3$ (50 mL) and stirred for 2 mins. The mixture was filtered through a celite pad, and the cake was washed with EA (2×50 mL). The combined organic phase was concentrated and purified by column chromatography using PE:EA=10:1~1:1 to give 50-3 (7.3 g, 79%) as a brown oil. MS: m/z 548.0 [M+H]+.

To a solution of EtMgBr (3 M, 4.6 mL) in dry THF (50 mL) was added n-BuLi (2.5 M, 11 mL) at −78° C. with stirring. After 10 mins, a solution of 50-3 (7.5 g, 13.68 mmol) in dry THF (20 mL) was added dropwise, and the reaction was stirred at −78° C. for 30 mins. The reaction was quenched by the addition of H$_2$O (10 mL) at −78° C. The mixture was warmed to RT and extracted with EA (2×40 mL). The organic phase was washed with brine, dried over anhydrous Na$_2$SO$_4$, filtered and concentrated. The residue was purified by column chromatography using 5~10% EA in PE to give 50-4R (1.6 g, 27.7%) and 50-4S (1.4 g, 24.4%) as pale yellow solids. MS: m/z 422.1 [M+H]+.

A mixture of 50-4S (1.4 g, 3.3 mmol), potassium trifluoro(vinyl)boranuide (581 mg, 4.34 mmol), Na$_2$CO$_3$ (923 mg, 8.71 mmol) and Pd(PPh$_3$)$_4$ (116 mg, 0.1 mmol) in EtOH (100 mL) was stirred at 80° C. for 1 h under N$_2$. The mixture was concentrated, and the residue was purified by column chromatography using 10~20% EA in PE to give 50-5 (1.3 g, 82.8%) as a white solid. MS: m/z 414.0 [M+H]+.

To a solution of 50-5 (1.2 g, 2.9 mmol) in DCM (80 mL) was bubbled ozone at −78° C. for 30 mins. After the excess ozone was purged by N$_2$, Me$_2$S (720 mg, 11.6 mmol) was added. The mixture was stirred at −78° C. for 30 mins. The mixture was concentrated and purified by column chromatography using 10~20% EA in PE to give 50-6 (1.01 g, 87.3%) as a yellow solid. MS: m/z 416.1 [M+H]+.

To a mixture of 50-6 (1.0 g, 2.4 mmol) and TMSCF$_3$ (1.02 g, 7.2 mmol) in DMF (10 mL) was added TBAF (1 M, 2.4 mL) dropwise at −10° C. The mixture was stirred for 1 h, partitioned between EA (60 mL) and water (60 mL). The aqueous was extracted with EA (2×10 mL). The combined organic layers were washed with brine, dried over Na$_2$SO$_4$, filtered and concentrated. The residue was purified by column chromatography using 2% MeOH in DMC to give 50-7 (790 mg, 67.7%) as a white solid. MS: m/z 486.1 [M+H]+.

To a solution of 50-7 (790 mg, 1.63 mmol) in DCM (6 mL) was added DMP (793 mg, 1.87 mmol). The mixture was stirred at RT for 1 h. The reaction quenched with sat. aq. Na$_2$SO$_3$, and extracted with EA (2×30 mL). The organic phase was washed with brine, dried over Na$_2$SO$_4$, filtered and concentrated. The residue was purified by column chromatography using 5~20% EA in PE to give 50-8 (750 mg, 95.3%) as a white solid. MS: m/z 502.1 [M+H$_3$O]+.

To a solution of t-BuOK (217 mg, 1.94 mmol) in CH$_3$CN (30 mL) was added Me$_3$SOI (375 mg, 1.71 mmol) in one portion. After stirring at RT for 5 mins, the mixture was left standing for a while. The clean liquid containing the ylide was poured into a solution of 50-8 (750 mg, 1.55 mmol) in CH$_3$CN (10 mL) which had been previously degassed. The mixture was stirred at RT for 10 mins, and then concentrated to give a residue. The residue was further purified by column chromatography using 0~20% EA in DCM to give 50-9 (310 mg, 40.2%) as a pale yellow oil. MS: m/z 498.1 [M+H]+.

A mixture of 50-9 (310 mg, 0.62 mmol) in NH$_3$/MeOH (7 M, 30 mL) was stirred at 25° C. for 1 h. The reaction was concentrated to give crude 50-10 (322 mg, crude) as a yellow solid. MS: m/z 515.1 [M+H]+.

Compounds 50 (55 mg, a white solid) and 51 (60 mg, a yellow solid) were prepared using methods similar to those for preparing 21 from 50-10, and by prep-HPLC (basic condition) for separation. Compounds 50 and 51 are shown above with relative stereochemistry arbitrarily assigned. 50: MS: m/z 565.1 [M+H]+; 51: MS: m/z 565.1 [M+H]+.

Example 39

Preparation of Compounds 52 and 53

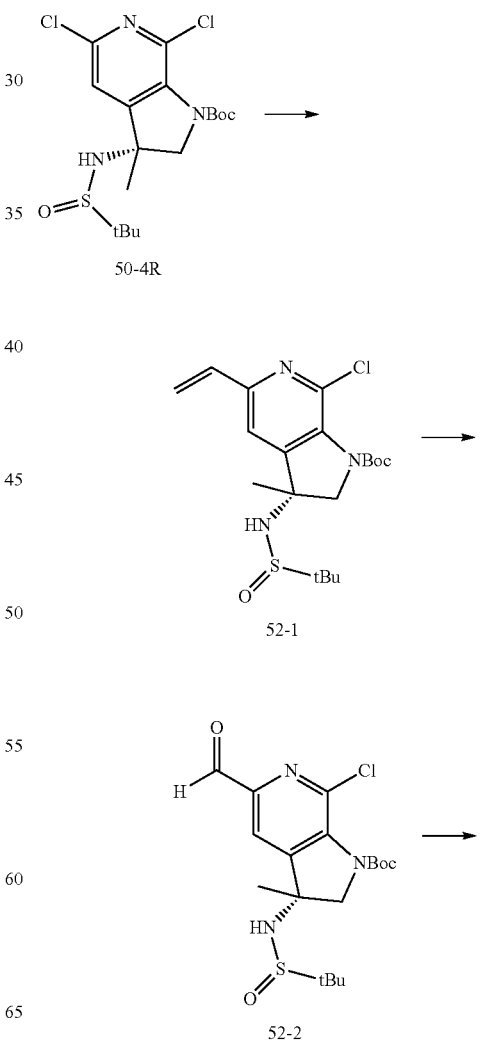

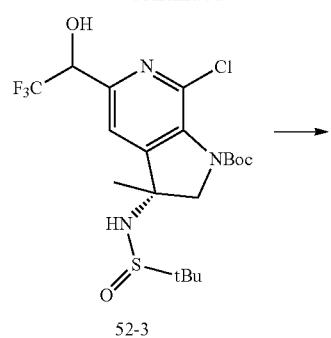
52-3
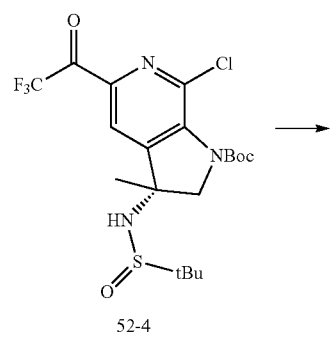
52-4
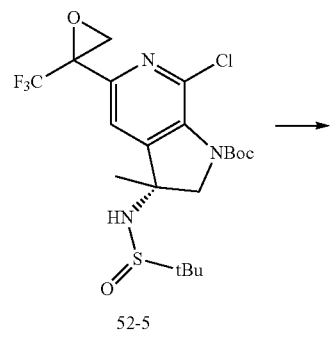
52-5
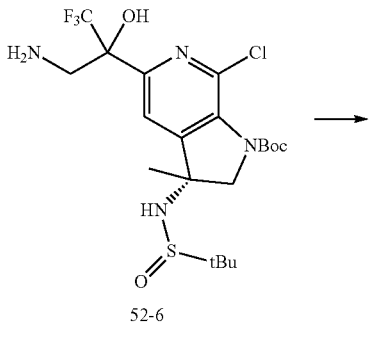
52-6
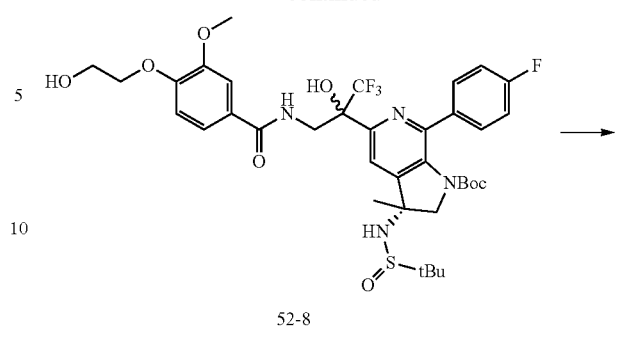
52-8
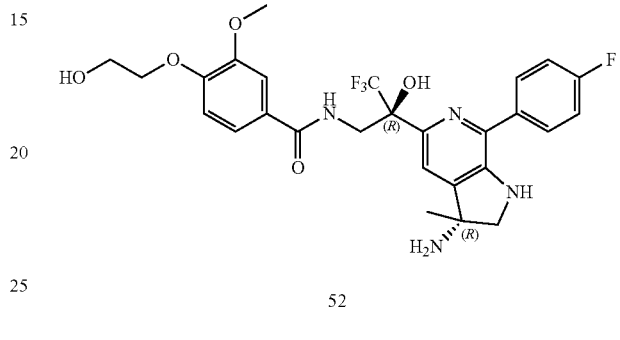
52
+
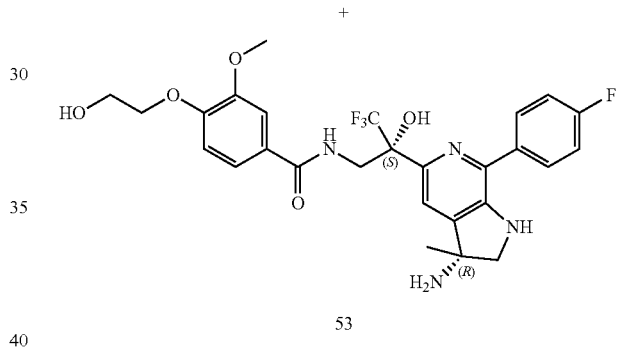
53
Compounds 52 (31 mg, a white solid) and 53 (33 mg, a yellow solid) were prepared using methods similar to those for preparing 50 from 50-4R, and by prep-HPLC (basic condition) for separation. Compounds 52 and 53 are shown above with relative stereochemistry arbitrarily assigned. 52: MS: m/z 565.1 [M+H]⁺; 53: MS: m/z 565.1 [M+H]⁺.
Example 40
Preparation of Compound 54
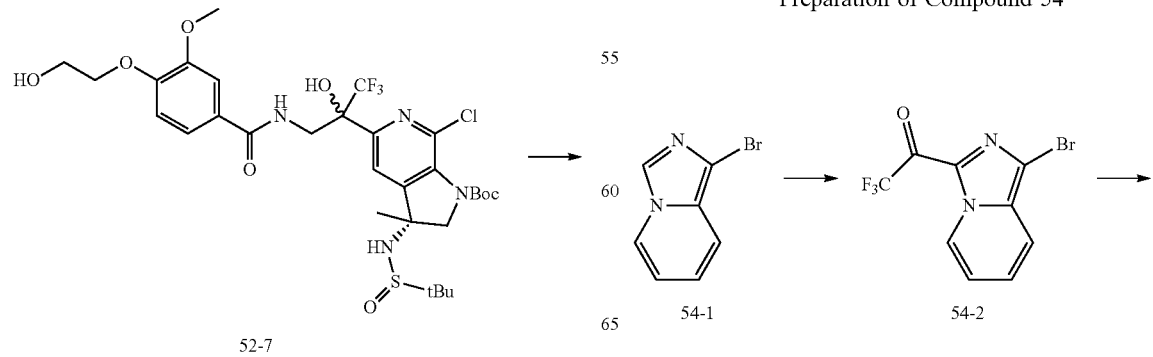
52-7
54-1      54-2

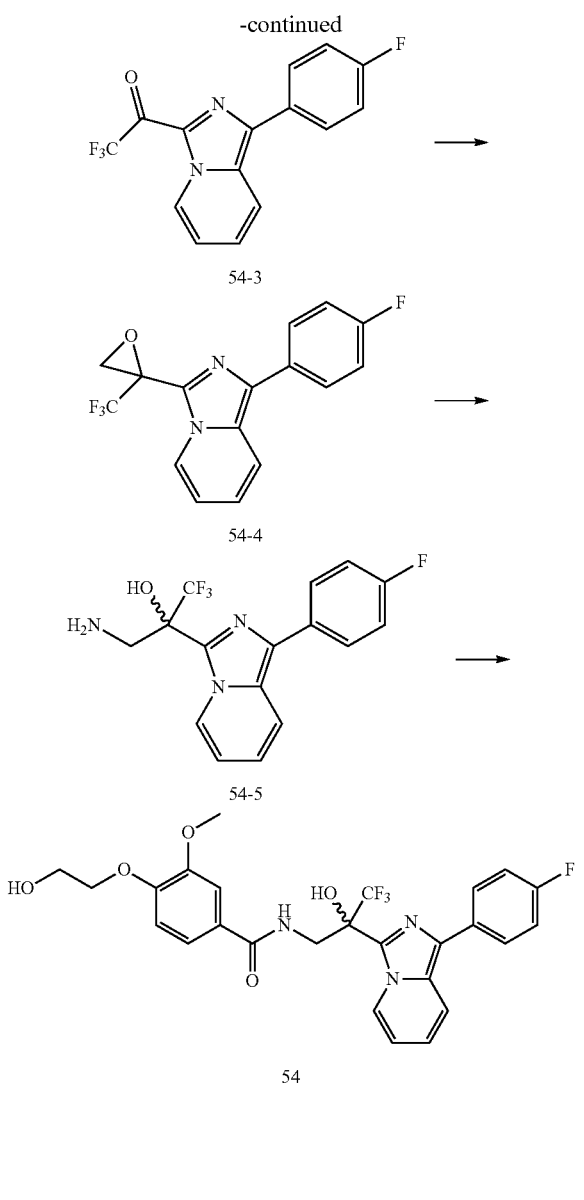

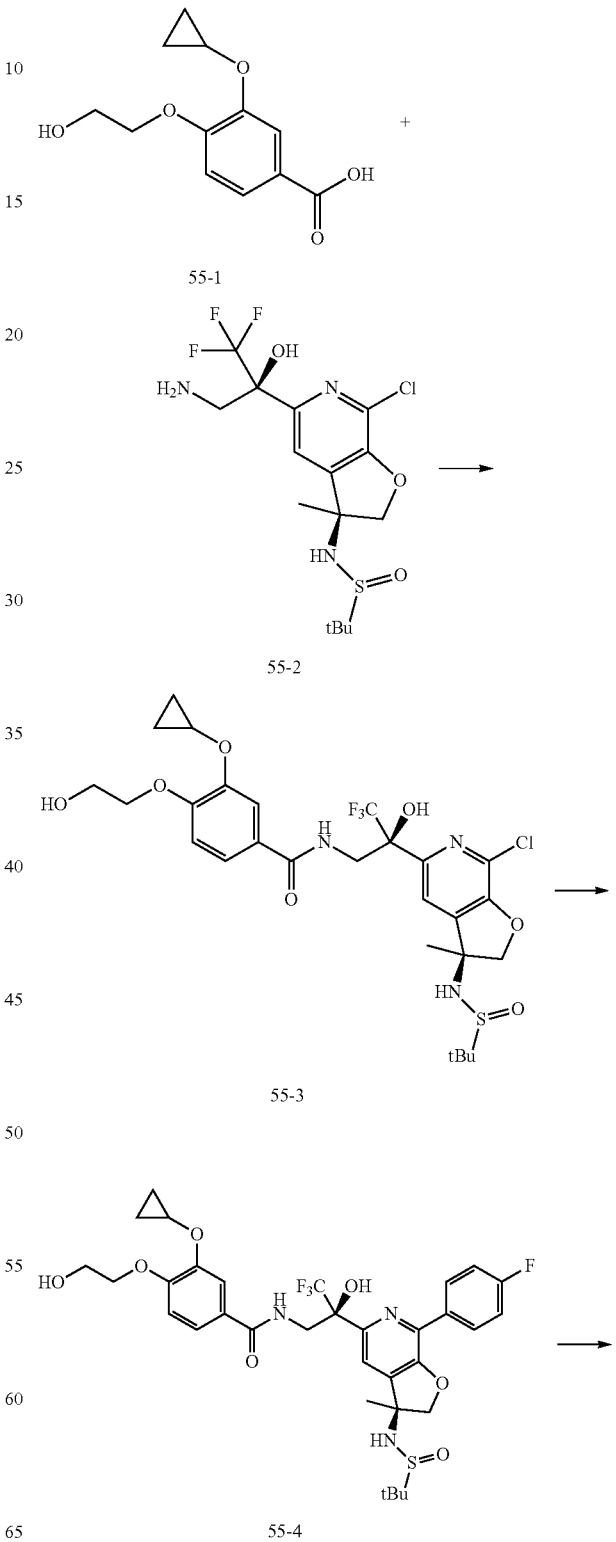

Example 41

Preparation of Compound 55

Compound 54-1 was prepared according to a similar procedure as provided in WO 2015/26792 A1.

To a solution of 54-1 (900 mg, 4.6 mmol) in DMF (8 mL) was added TFAA (1.06 g, 5.0 mmol) at 0° C. The solution was slowly warmed to 25° C. and stirred for 2 h. The mixture was poured into water (30 mL), and the precipitate was collected. The precipitate was dried to afford 54-2 (1.1 g, 82.1%) as a yellow solid. MS: m/z 293,295 [M+H]+.

A mixture of 54-2 (1.0 g, 3.4 mmol), 4-F-Phenylboronic acid (954 mg, 6.8 mmol), Cs$_2$CO$_3$ (1.67 g, 5.1 mmol) and Pd(dppf)Cl$_2$ (250 mg, 0.34 mmol) in dioxane (10 mL) and H$_2$O (2 mL) was heated to 130° C. under microwave with stirring for 0.5 h. The mixture was cooled to RT, diluted with water (50 mL) and EA (50 mL). The organic phase was washed with brine, concentrated and purified by column chromatography using 10% EA in PE to give 54-3 (721 mg, 68.6%) as a yellow solid. MS: m/z 308.8 [M+H]+.

Compound 54 (66 mg, a pale yellow solid) was prepared using methods similar to those for preparing 50 from 54-3. MS: m/z 533.9 [M+H]+.

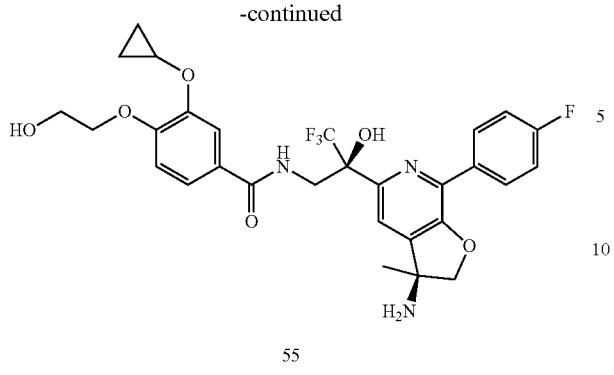

55

Compound 55-1 was prepared according to a similar procedure as provided in WO 2015/26792 A1. Compound 55 (46 mg, a pale yellow solid) was prepared using methods similar to those for preparing 21 from 55-1 and 55-2. MS: m/z 592.0 [M+H]$^+$.

Example 42

Preparation of Compounds 56 and 57

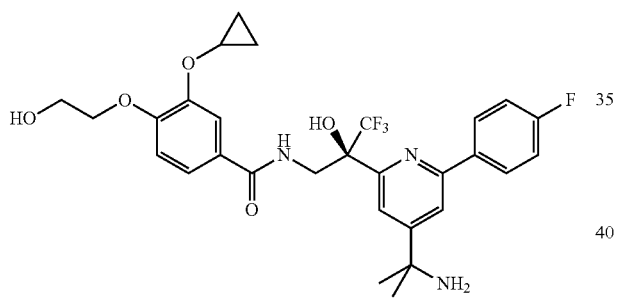

56

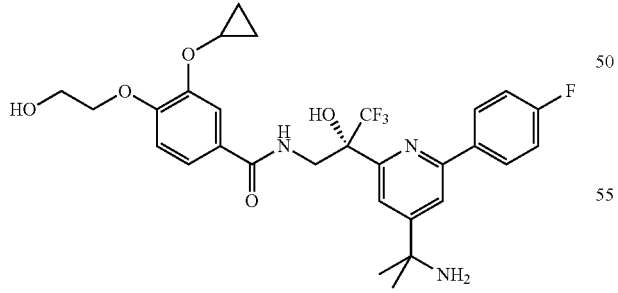

57

Compound 34 (37 mg) was separated by SFC (Column: Lux Cellulose-2 150×4.6 mm I.D., 3 μm; Mobile phase: A: CO$_2$ B: ethanol (0.05% DEA); Gradient: from 5% to 40% of B in 5.5 min and hold 40% for 3 mins, then 5% of B for 1.5 min; Flow rate: 2.5 mL/min Column temperature: 40° C.) and HPLC to give 56 (13.1 mg) and 57 (13.2 mg). 56: MS: m/z 578.0 [M+H]$^+$; 57: MS: m/z 578.0 [M+H]$^+$.

Example 43

Preparation of Compounds 58 and 59

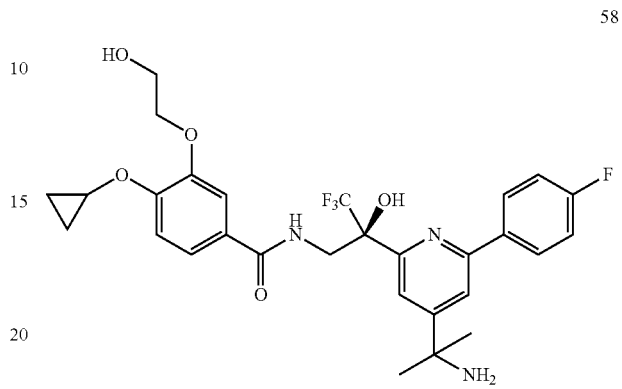

58

59

Compound 36 (73 mg) was separated by SFC (Column: Lux Cellulose-2 150×4.6 mm I.D., 3 μm; Mobile phase: A: CO$_2$ B: ethanol (0.05% DEA); Gradient: from 5% to 40% of B in 5.5 min and hold 40% for 3 mins, then 5% of B for 1.5 mins; Flow rate: 2.5 mL/min Column temperature: 40° C.) and HPLC to give 58 (17.1 mg) and 59 (17.3 mg). 58: MS: m/z 578.1 [M+H]$^+$; 59: m/z 578.1 [M+H]$^+$.

Example 44

Preparation of Compound 60

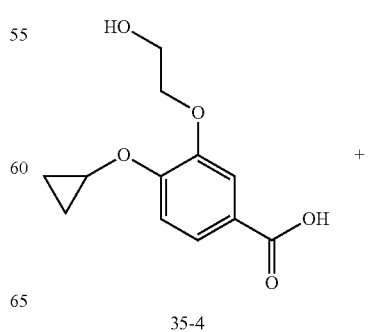

35-4

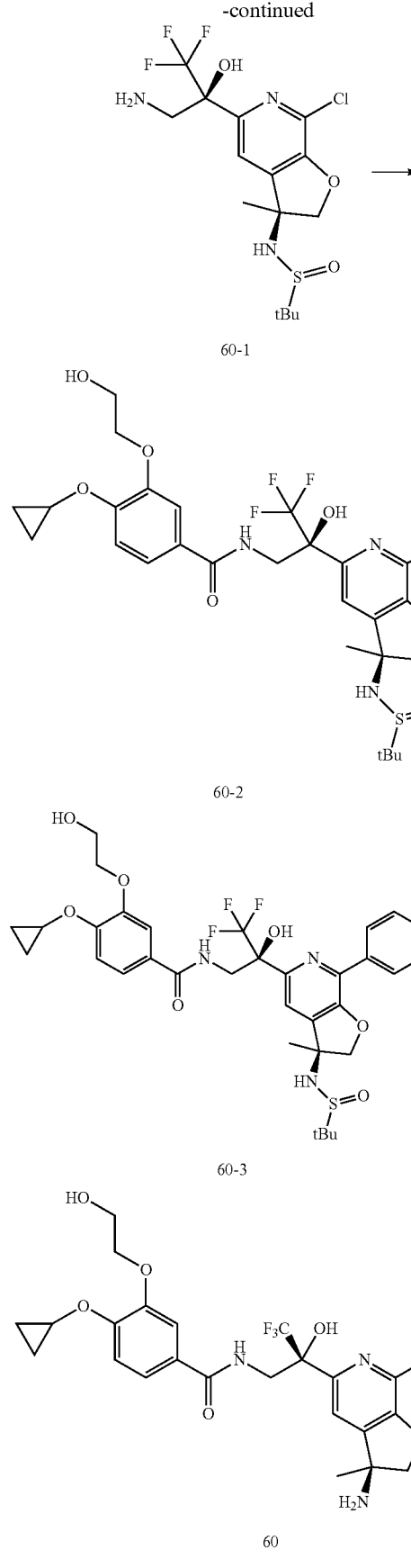
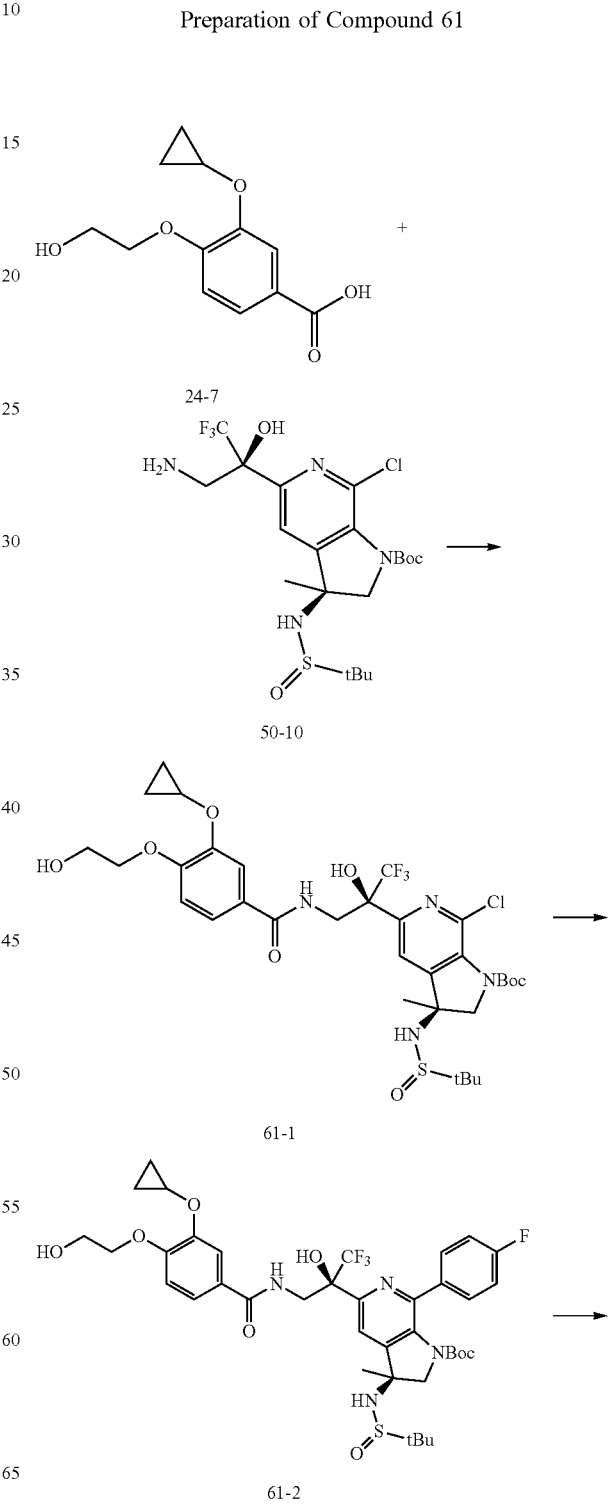
Compound 60-1 was prepared according to a similar procedure as provided in WO 2015/26792 A1. Compound 60 (35.2 mg, a pale yellow solid) was prepared using methods similar to those for preparing 21 from 35-4 and 60-1. MS: m/z 592.1 [M+H]$^+$.
Example 45
Preparation of Compound 61

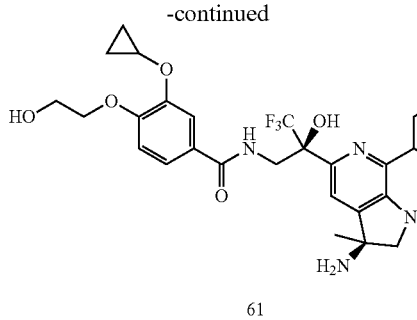
Compound 61 (35.2 mg, a pale yellow solid) was prepared using methods similar to those for preparing 21 from 27-47 and 50-10. MS: m/z 591.1 [M+H]$^+$.
Example 46
Preparation of Compound 62
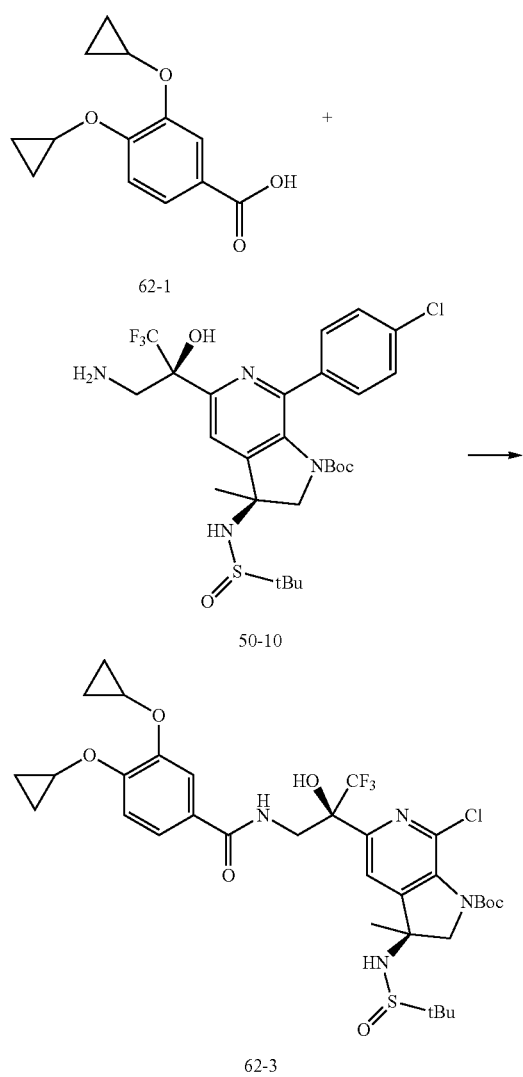
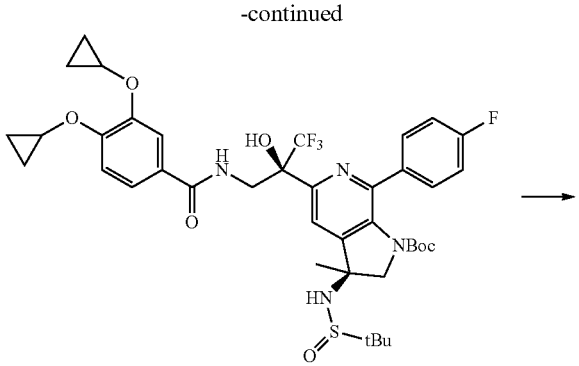
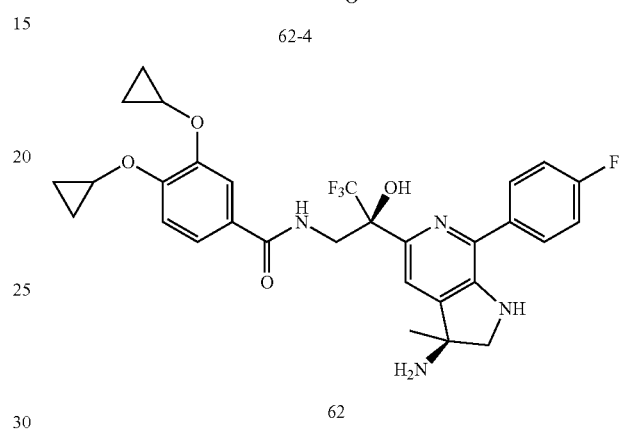
Compound 62 (11 mg, a pale yellow solid) was prepared using methods similar to those for preparing 21 from 62-1 and 50-10. MS: m/z 609.1 [M+Na]$^+$.
Example 47
Preparation of Compound 63
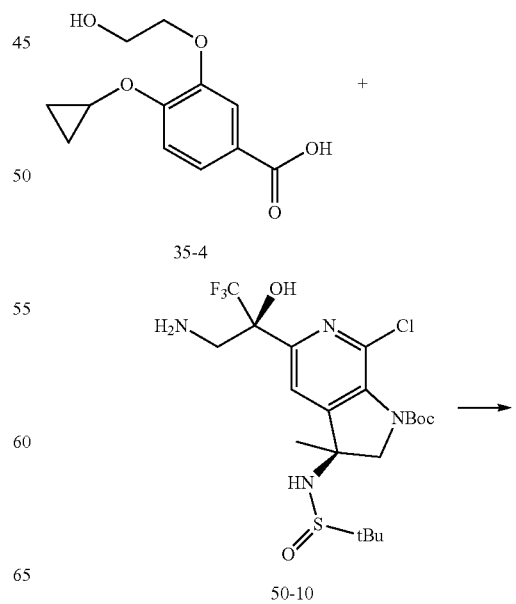

-continued
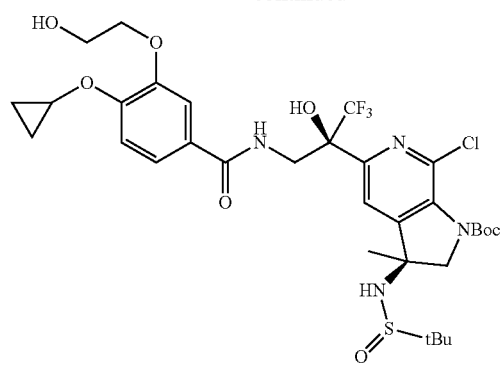
63-1
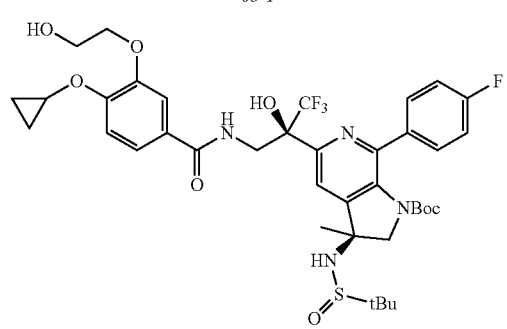
63-2
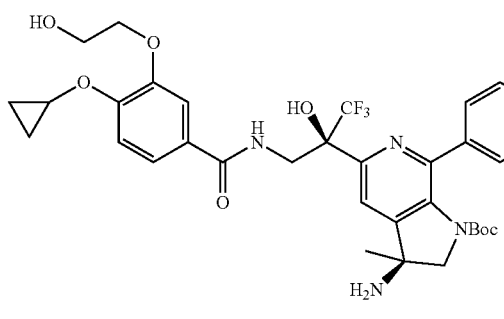
63
Compound 63 (15 mg, a pale yellow solid) was prepared using methods similar to those for preparing 21 from 35-4 and 50-10. MS: m/z 613.2 [M+Na]$^+$.
Example 48
Preparation of Compound 64
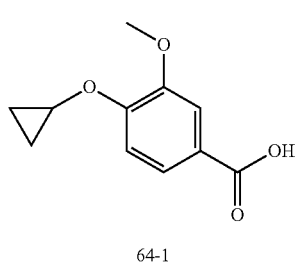
64-1
-continued
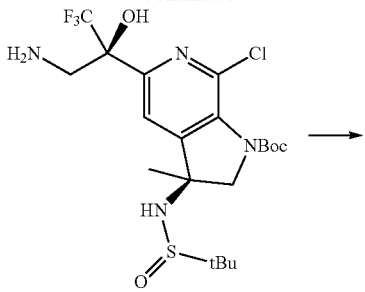
50-10
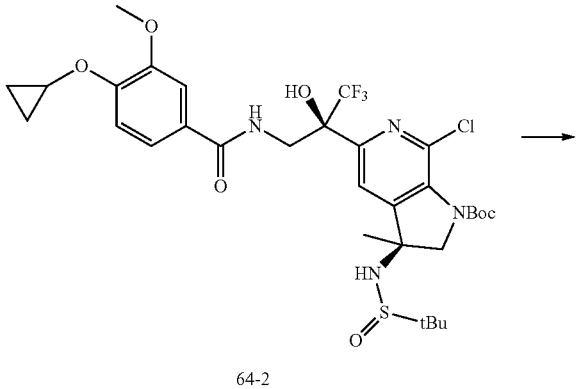
64-2
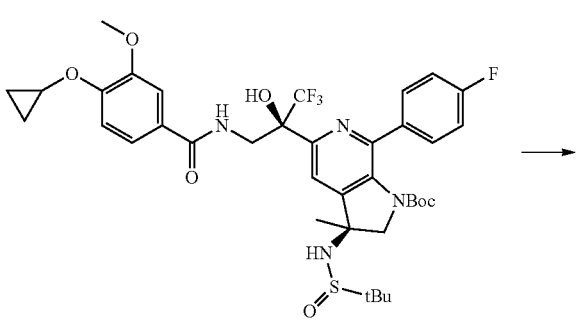
64-3
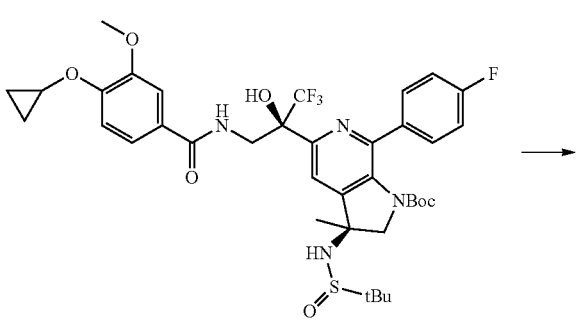
64
Compound 64-1 was prepared according to a similar procedure as provided in WO 2015/26792 A1. Compound 63 (46 mg, a yellow solid) was prepared using methods similar to those for preparing 21 from 64-1 and 50-10. MS: m/z 561.1 [M+H]$^+$.

Example 49

Preparation of Compound 65

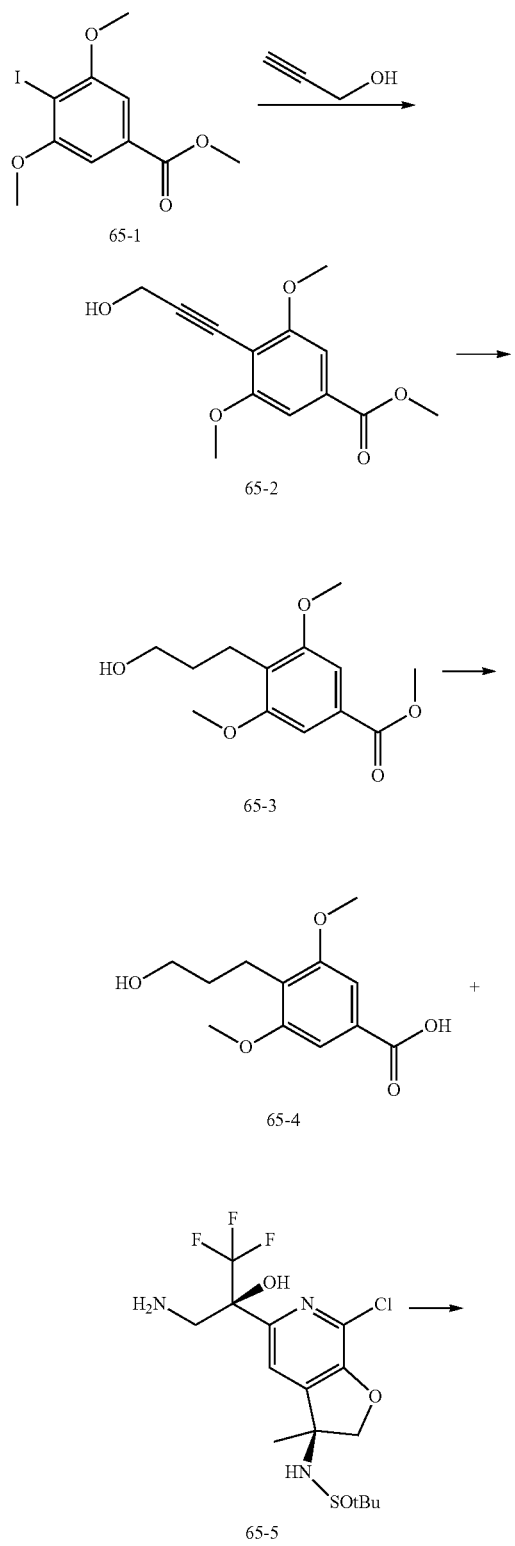

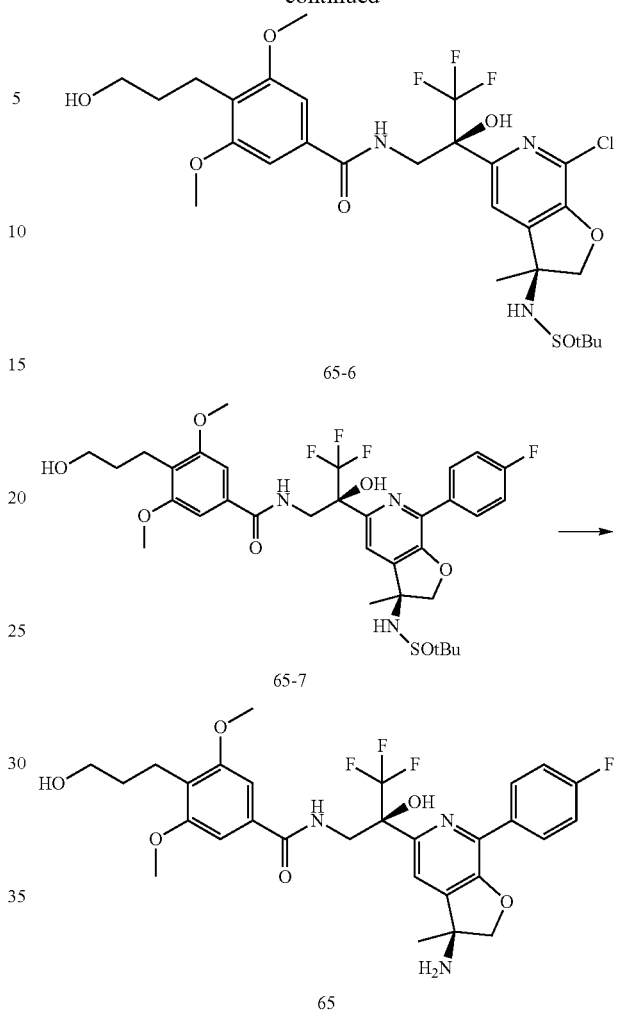

Compound 65-1 was prepared according to a similar procedure as provided in Chiummiento et al., European Journal of Organic Chemistry (2012) 2012(1):188-192, and compound 65-5 was prepared according to a similar procedure as provided in WO 2015/26792 A1.

A mixture of 65-1 (3.22 g, 10 mmol), prop-2-yn-1-ol (1.12 g, 20 mmol), Pd(PPh$_3$)$_2$Cl$_2$ (351 mg, 0.5 mmol), CuI (190 mg, 1 mmol), PPh$_3$ (262 mg, 1 mmol) and TEA (50 mL) in DMF (100 mL) was heated to 60° C. for 12 h under N$_2$ with stirring. The reaction was cooled to RT, poured into water (200 mL), and extracted with EA (2×50 mL). The organic phase was washed with brine, dried over Na$_2$SO$_4$ and concentrated. The residue was purified by column chromatography using 20~50% EA in PE to give 2 (1.9 g, 76%) as a pale yellow solid. MS: m/z 250.9 [M+H]$^+$.

A mixture of 65-2 (1.9 g, 7.6 mmol) and Pd/C (10%, 200 mg) in MeOH (100 mL) was stirred at RT under hydrogen (45 PSI) for 12 h. The mixture was filtered, and the filtrate was concentrated. The residue was purified by column chromatography using 20% EA in PE to give 65-3 (1.3 g, 67.4%) as a white solid. MS: m/z 254.9 [M+H]$^+$.

Compound 65 (52.6 mg, a white solid) was prepared using methods similar to those for preparing 21 from 65-3 and 65-5. MS: m/z 616.1 [M+Na]$^+$.

Example 50

Preparation of Compound 66

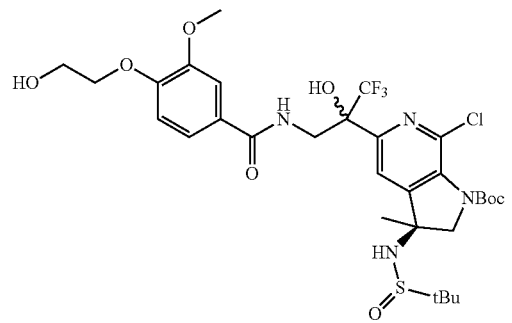
66-1

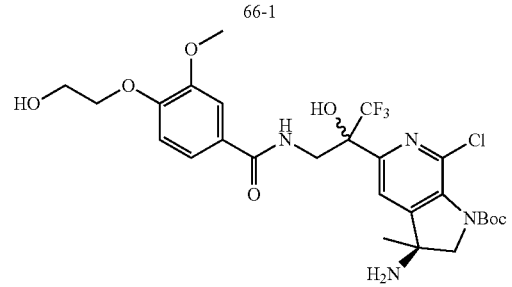
66-2

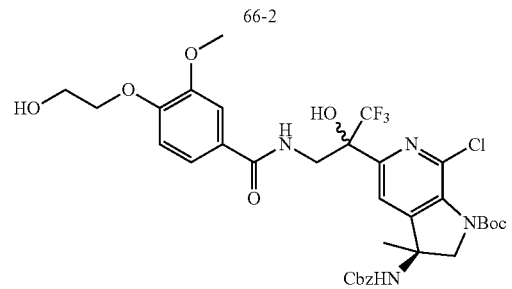
66-3

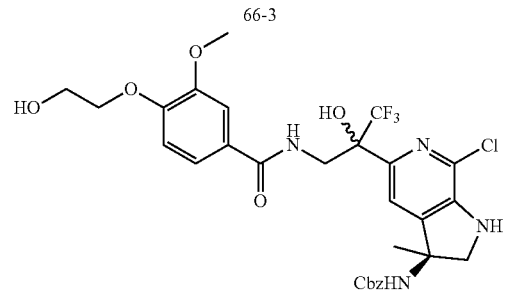
66-4

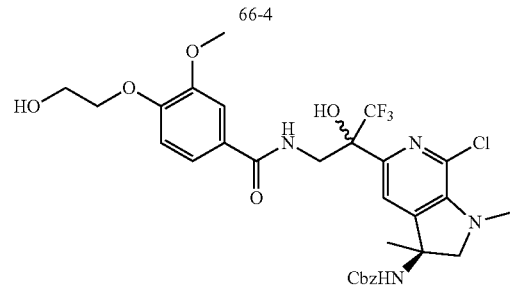
66-5

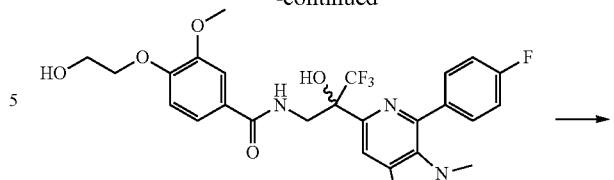
66-6

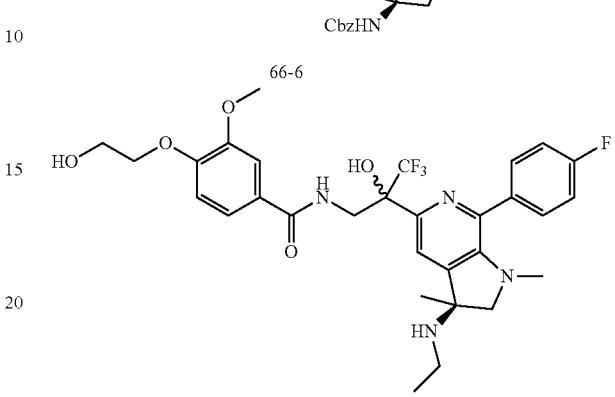
66

To a solution of 66-1 (150 mg, 0.21 mmol) in MeOH (3 mL) was added HCl/MeOH (4 M, 105 μL) at 25° C. The mixture was stirred at 25° C. for 1 h. The reaction was quenched by the addition of a sat. NaHCO$_3$ solution and extracted with EA (2×10 mL). The organic phase was washed with brine, dried over Na$_2$SO$_4$, filtered and concentrated to give 66-2 (130 mg, crude) as a white solid. MS: m/z 627.2 [M+Na]$^+$.

A mixture of 66-2 (130 mg, crude), CbzCl (73 mg, 0.43 mmol), NaHCO$_3$ (72 mg, 0.86 mmol) in DCM (10 mL) and H$_2$O (5 mL) was stirred at 25° C. for 1 h. The mixture was diluted with EA (30 mL) and water (30 mL). The organic phase was separated, washed with brine, dried over Na$_2$SO$_4$, filtered and concentrated to give 66-3 (160 mg, crude) as a colorless oil. MS: m/z 739.1 [M+H]$^+$.

A mixture of 66-3 (160 mg, crude) in HCl/MeOH (4 M, 5 mL) was stirred at 25° C. for 1 h. The mixture was concentrated to give 66-4 (120 mg, crude) as a yellow oil. MS: m/z 639.1 [M+H]$^+$.

To a stirring solution of 66-4 (100 mg, crude), aq. HCHO (0.11 mL, 38%) and AcOH (0.1 mL) in MeOH (10 mL) was added NaBH$_3$CN (30 mg, 0.47 mmol) at RT. The mixture was stirred for 16 h, diluted with water (30 mL) and extracted with EA (2×20 mL). The organic layers were washed with brine, dried over Na$_2$SO$_4$, filtered and concentrated. The residue was purified by column chromatography using 50~100% EA in PE to give 66-5 (81 mg) as a colorless oil. MS: m/z 653.1 [M+H]$^+$.

A mixture of 66-5 (81 mg, 0.12 mmol), 4-F-phenyl boronic acid (34 mg, 0.24 mmol), Pd(PPh$_3$)$_4$ (7.1 mg, 0.006 mmol) and K$_2$CO$_3$ (17 mg, 0.12 mmol) in dioxane (3 mL) and H$_2$O (0.5 mL) was heated to 110° C. by microwave and stirred for 30 mins. The reaction was cooled to RT, diluted with EA (10 mL) and water (10 mL). The organic phase was washed with brine, dried over Na$_2$SO$_4$, filtered and concentrated to give 66-6 (71 mg, crude) as a yellow solid MS: m/z 713.1 [M+H]$^+$.

A mixture of 66-6 (71 mg, crude) and Pd/C (10%, 20 mg) in EtOH (10 mL) was stirred under H$_2$ (15 Psi) at RT for 16 h. The mixture was concentrated, and the residue was

Example 51

Preparation of Compound 67

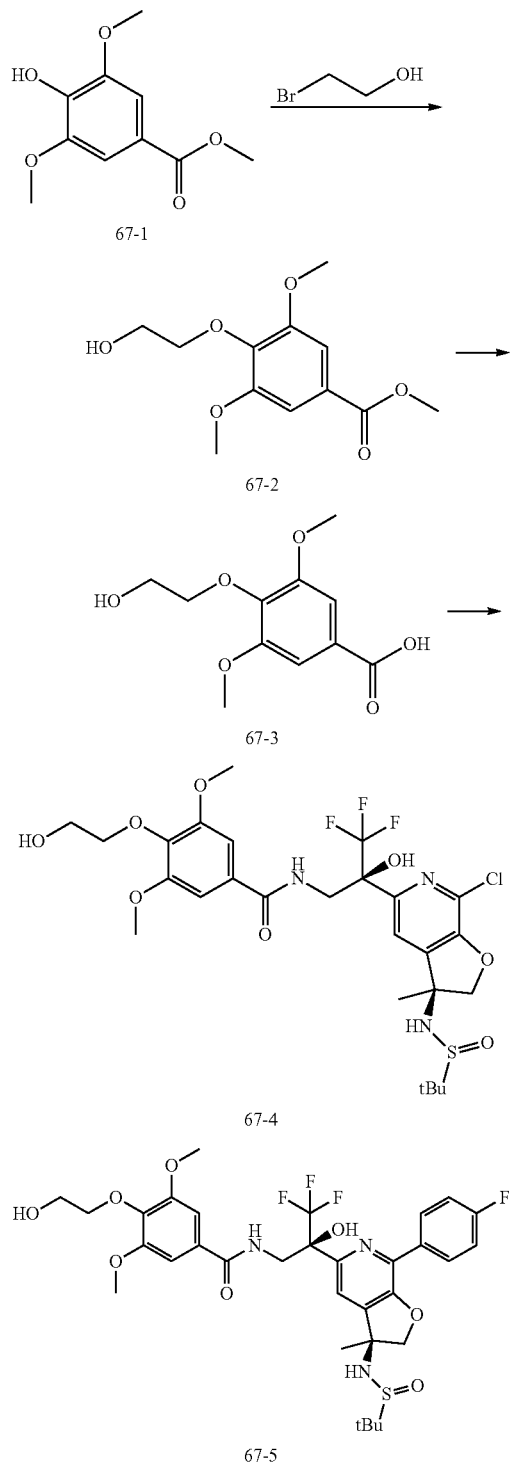

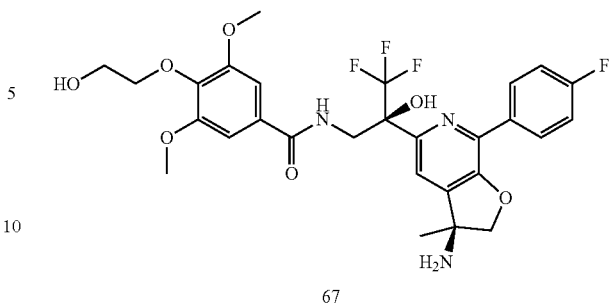

Compound 67-1 was prepared according to a similar procedure as provided in EP2786986 A2.

To a solution of 67-1 (2.1 g, 10 mmol) in DMF (20 mL) was added NaH (60%, 400 mg, 10 mmol) at 0° C. The mixture was stirred for 30 mins, followed by addition of bromoethanol (3.12 g, 25 mmol). The reaction was stirred at 80° C. for 2 h, and cooled to RT. The reaction was quenched with $H_2O$, and extracted with EA. The organic phase was washed with brine, dried over $Na_2SO_4$, filtered and concentrate. The residue was purified by column chromatography using 10~20% EA in PE to give 67-2 (1.9 g, 74%) as a white solid. MS: m/z 256.9 $[M+H]^+$.

Compound 67 (57 mg, a white solid) was prepared using methods similar to those for preparing 21 from 67-1 and phenyl boronic acid. MS: m/z 596.1 $[M+H]^+$.

Example 52

Preparation of Compound 68

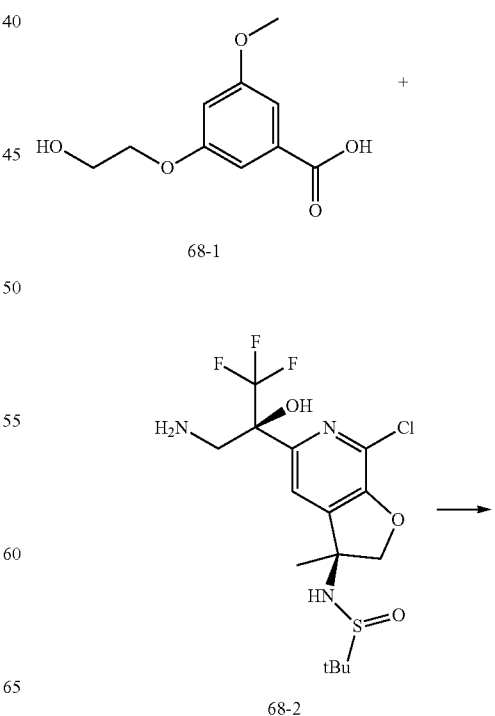

purified by prep-HPLC (basic condition) to give 66 (11 mg) as a white solid. MS: m/z 629.1 $[M+Na]^+$.

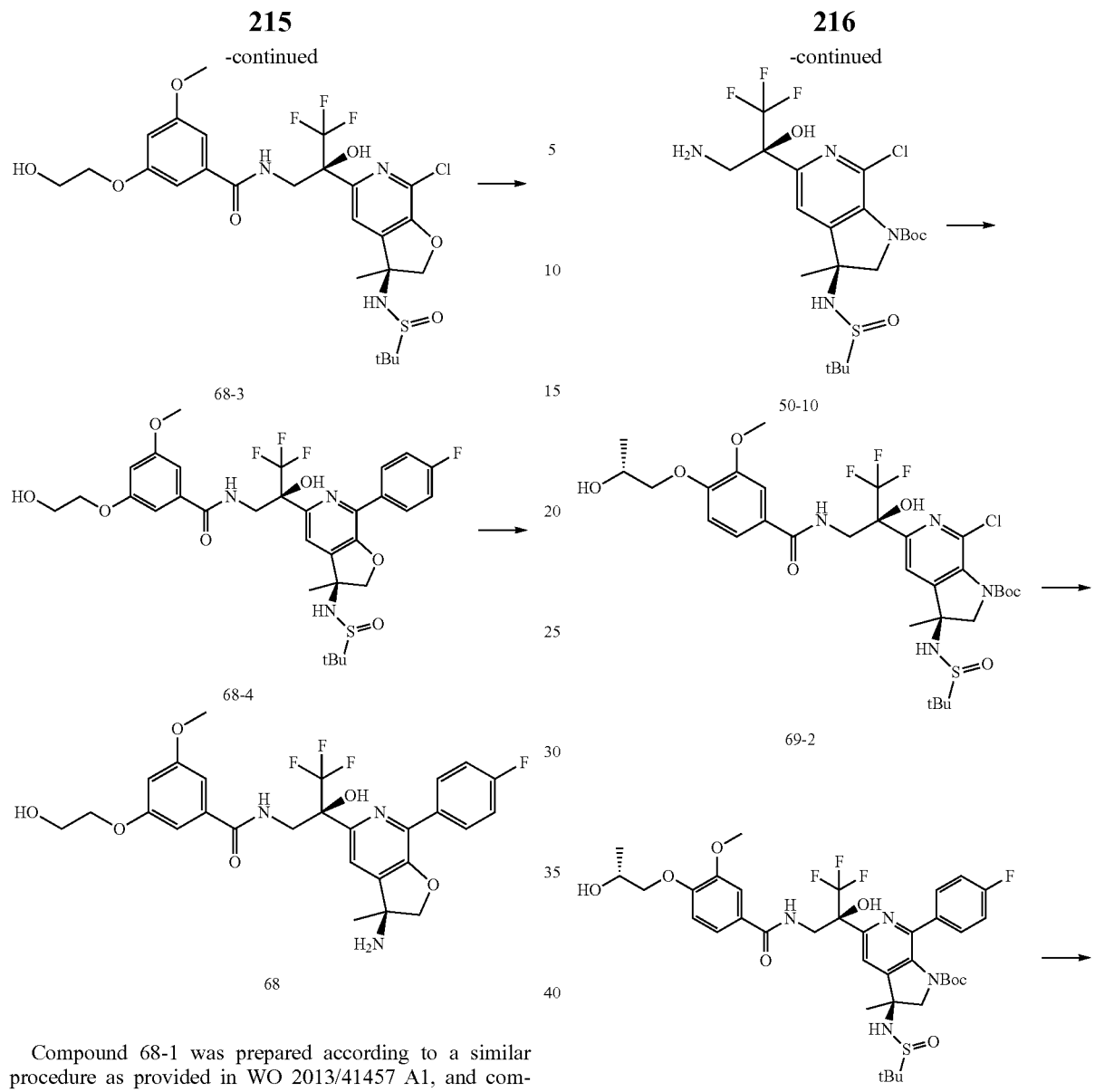

Compound 68-1 was prepared according to a similar procedure as provided in WO 2013/41457 A1, and compound 68-2 was prepared according to a similar procedure as provided in WO 2015/26792 A1. Compound 68 (22 mg, a pale yellow solid) was prepared using methods similar to those for preparing 21 from 68-1 and 68-2. MS: m/z 566.1 [M+H]$^+$.

Example 53

Preparation of Compound 69

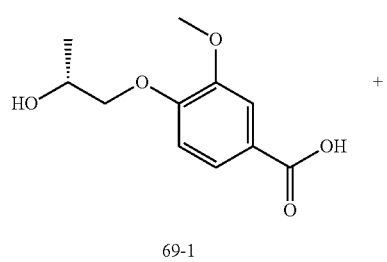

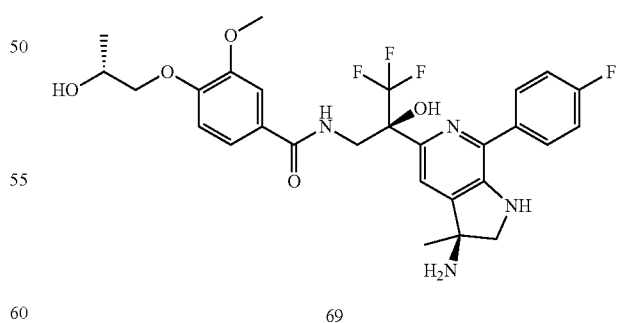

Compound 69-1 was prepared according to a similar procedure as provided in WO 2015/26792 A1. Compound 69 (17 mg, a white solid) was prepared using methods similar to those for preparing 21 from 69-1 and 50-10. MS: m/z 579.1 [M+H]$^+$.

Example 54
Preparation of Compound 70
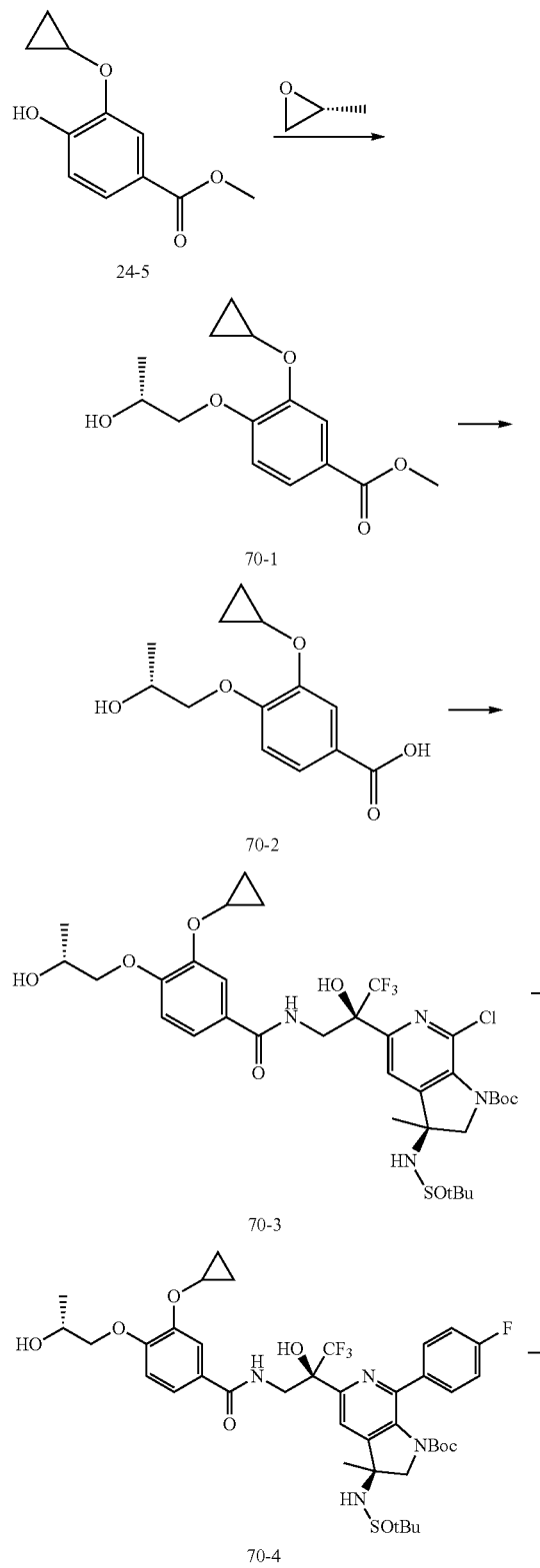
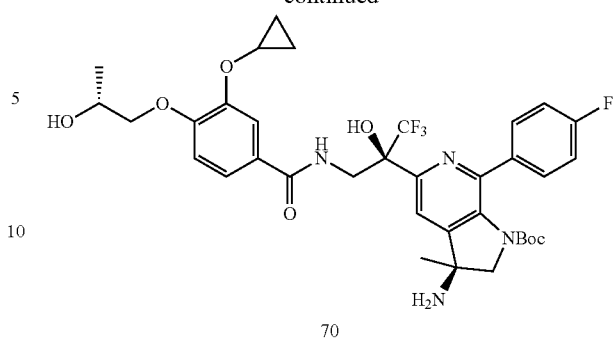
Compound 70 (21 mg, a white solid) was prepared using methods similar to those for preparing 21 and 38 from 24-5. MS: m/z 605.1 [M+H]$^+$.
Example 55
Preparation of Compound 71
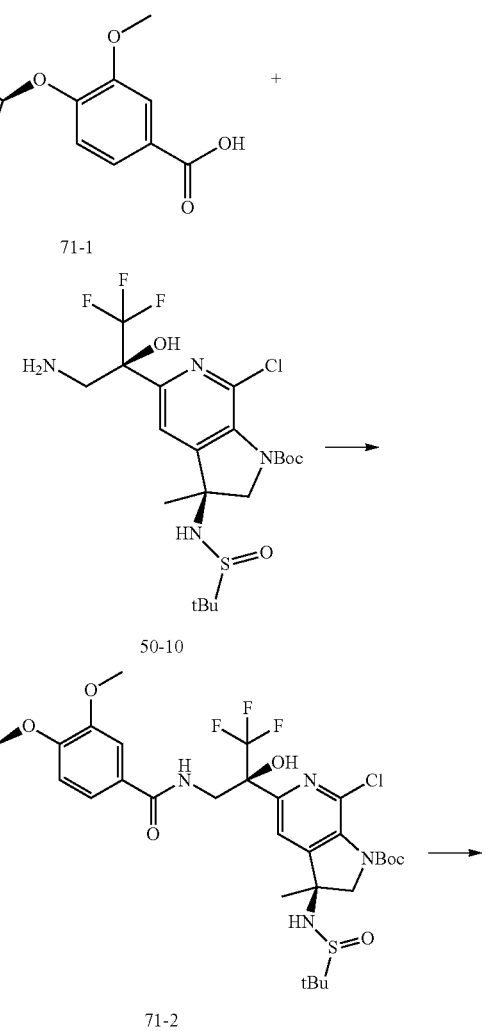

219

-continued

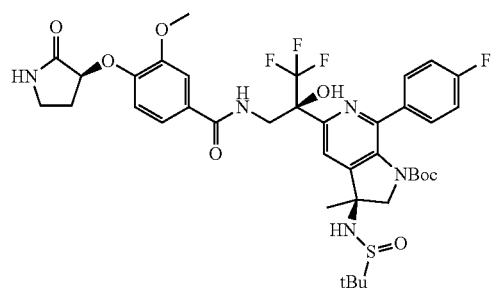

71-3

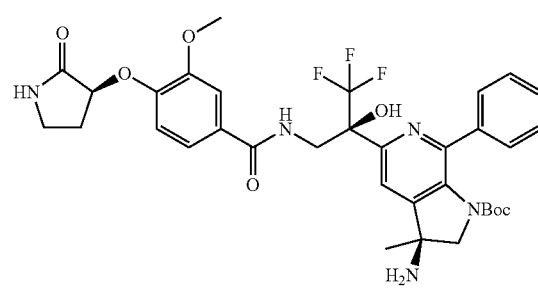

71

Compound 71-1 was prepared according to a similar procedure as provided in WO 2015/26792 A1. Compound 71 (2.1 mg, a white solid) was prepared using methods similar to those for preparing 50 from 71-1 and 50-10. MS: m/z 626.3 [M+Na]⁺.

Example 56

Preparation of Compound 72

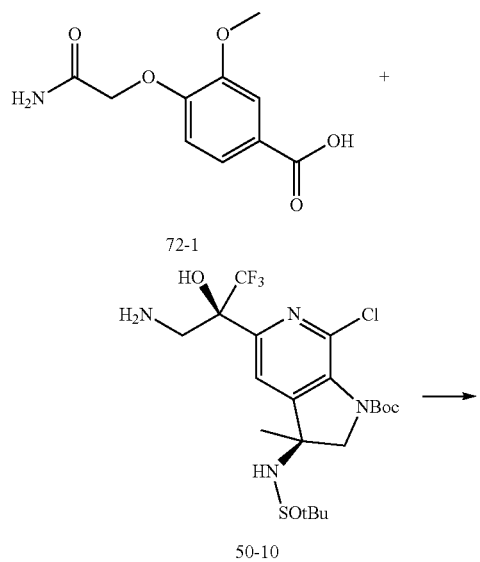

220

-continued

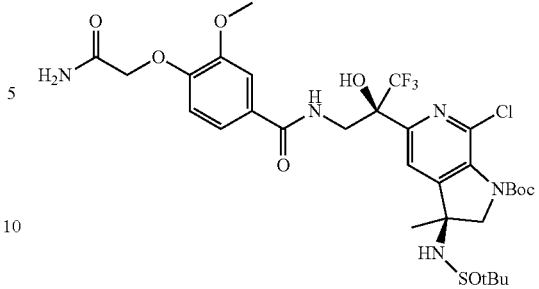

72-2

72-3

72

Compound 72-1 was prepared according to a similar procedure as provided in WO 2015/26792 A1. Compound 72 (20 mg, a white solid) was prepared using methods similar to those for preparing 50 from 72-1 and 50-10. MS: m/z 578.2 [M+H]⁺.

Example 57

Preparation of Compound 73

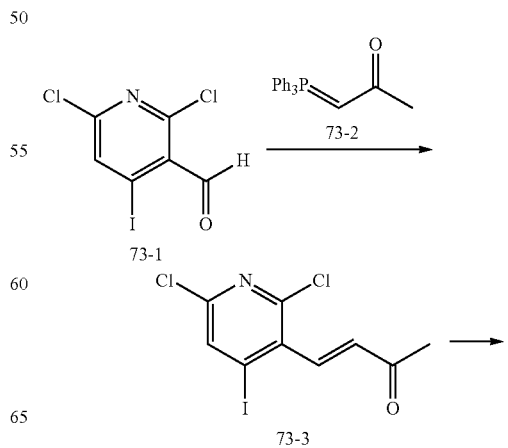

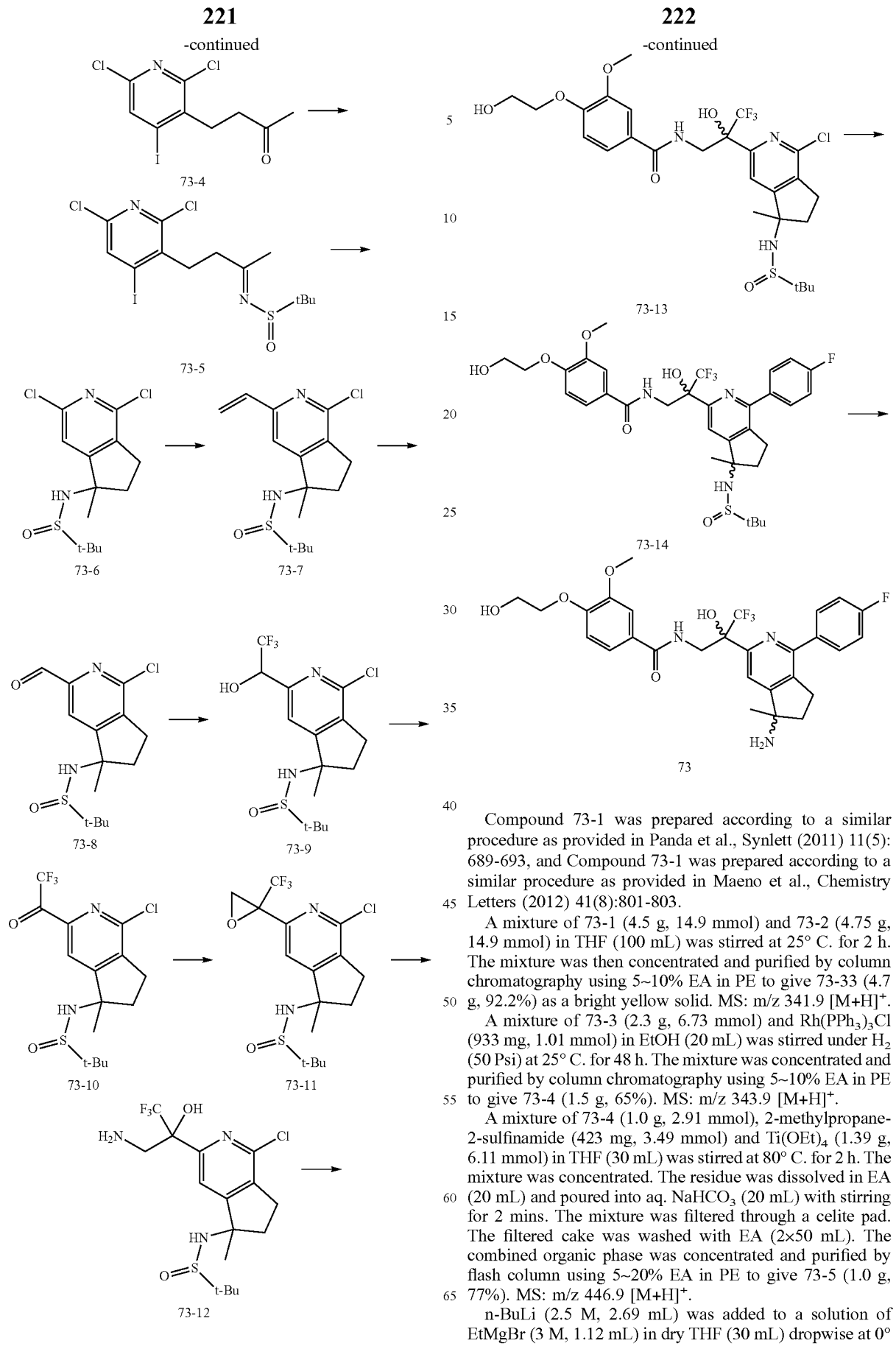

Compound 73-1 was prepared according to a similar procedure as provided in Panda et al., Synlett (2011) 11(5): 689-693, and Compound 73-1 was prepared according to a similar procedure as provided in Maeno et al., Chemistry Letters (2012) 41(8):801-803.

A mixture of 73-1 (4.5 g, 14.9 mmol) and 73-2 (4.75 g, 14.9 mmol) in THF (100 mL) was stirred at 25° C. for 2 h. The mixture was then concentrated and purified by column chromatography using 5~10% EA in PE to give 73-33 (4.7 g, 92.2%) as a bright yellow solid. MS: m/z 341.9 [M+H]$^+$.

A mixture of 73-3 (2.3 g, 6.73 mmol) and Rh(PPh$_3$)$_3$Cl (933 mg, 1.01 mmol) in EtOH (20 mL) was stirred under H$_2$ (50 Psi) at 25° C. for 48 h. The mixture was concentrated and purified by column chromatography using 5~10% EA in PE to give 73-4 (1.5 g, 65%). MS: m/z 343.9 [M+H]$^+$.

A mixture of 73-4 (1.0 g, 2.91 mmol), 2-methylpropane-2-sulfinamide (423 mg, 3.49 mmol) and Ti(OEt)$_4$ (1.39 g, 6.11 mmol) in THF (30 mL) was stirred at 80° C. for 2 h. The mixture was concentrated. The residue was dissolved in EA (20 mL) and poured into aq. NaHCO$_3$ (20 mL) with stirring for 2 mins. The mixture was filtered through a celite pad. The filtered cake was washed with EA (2×50 mL). The combined organic phase was concentrated and purified by flash column using 5~20% EA in PE to give 73-5 (1.0 g, 77%). MS: m/z 446.9 [M+H]$^+$.

n-BuLi (2.5 M, 2.69 mL) was added to a solution of EtMgBr (3 M, 1.12 mL) in dry THF (30 mL) dropwise at 0°

C. After stirring for 10 mins, the mixture was cooled to −78° C. A solution of 73-5 (1.0 g, 2.24 mmol) in dry THF (5 mL) was added to the above solution dropwise. After addition, the reaction was stirred at −78° C. for 30 mins, quenched with water (10 mL) and extracted with EA (2×50 mL). The organic phase was washed with brine, dried over $Na_2SO_4$, filtered and concentrated. The residue was purified by column chromatography using 5~10% EA in PE to give 73-6 (450 mg, 62.5%) as a yellow oil. MS: m/z 321.0 $[M+H]^+$.

Compound 73 (3.2 mg, a yellow solid) was prepared using methods similar to those for preparing 50 from 73-6. MS: m/z 564.1 $[M+H]^+$.

Example 58

Preparation of Compound 74

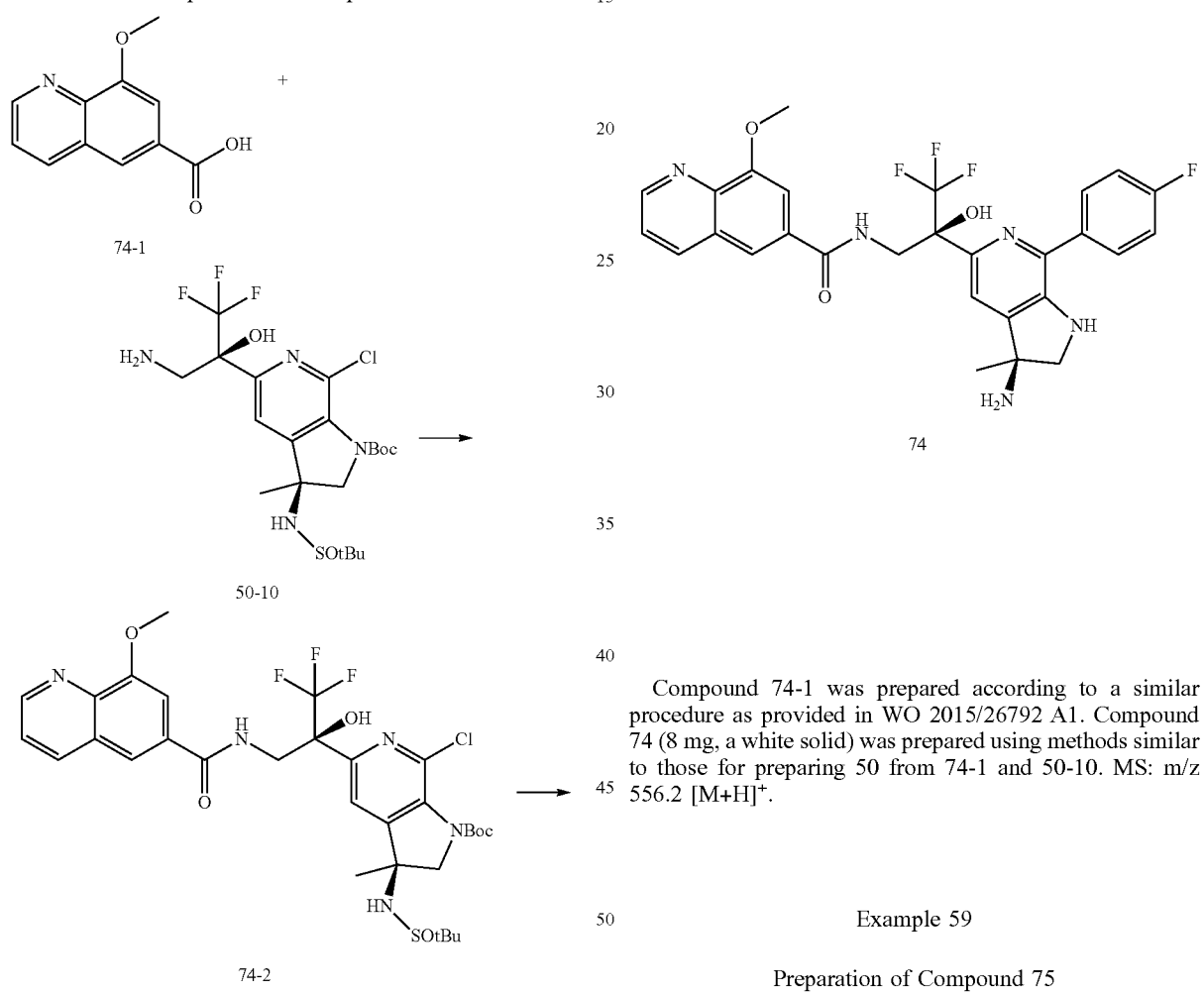

Compound 74-1 was prepared according to a similar procedure as provided in WO 2015/26792 A1. Compound 74 (8 mg, a white solid) was prepared using methods similar to those for preparing 50 from 74-1 and 50-10. MS: m/z 556.2 $[M+H]^+$.

Example 59

Preparation of Compound 75

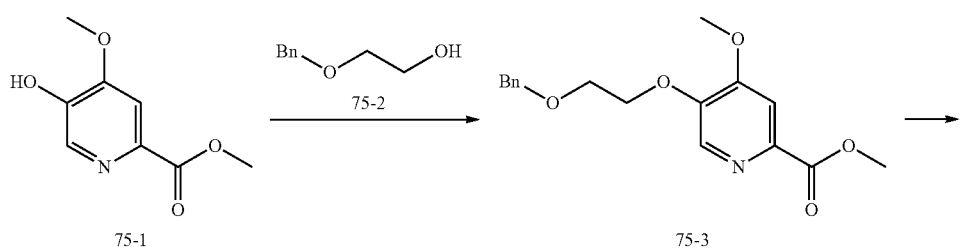

-continued
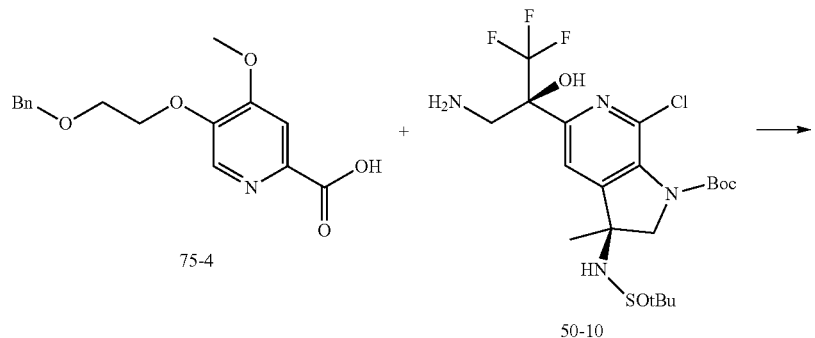
75-4
50-10
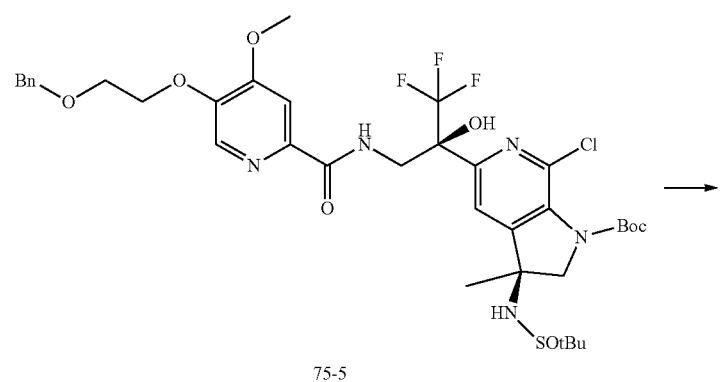
75-5
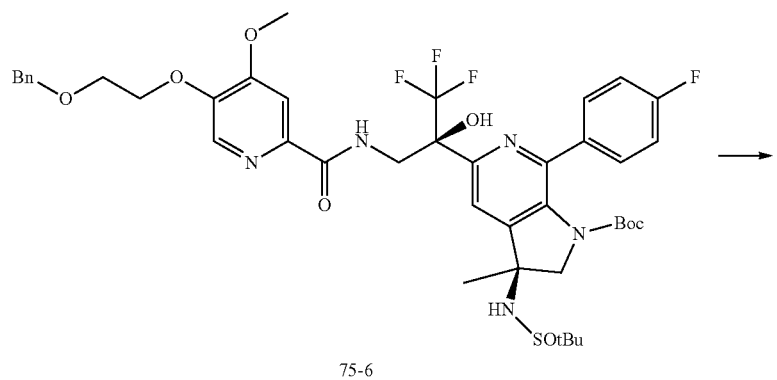
75-6
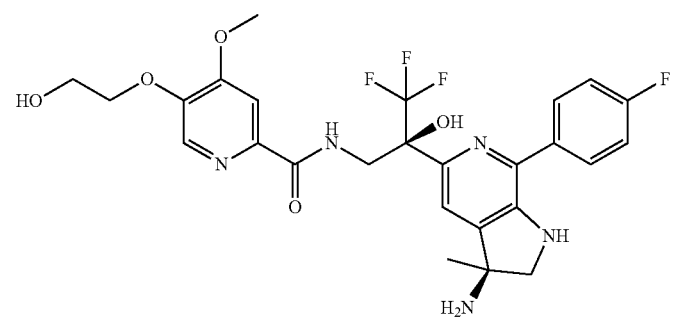
75

Compound 75-1 was prepared according to a similar procedure as provided in Patt et al., Tetrahedron Letters (1997) 38(8):1297-1300. Compound 75 (12 mg, a yellow solid) was prepared using methods similar to those for preparing 21 from 75-1 and 50-10. MS: m/z 566.1 [M+H]⁺.

Example 60

Preparation of Compound 76

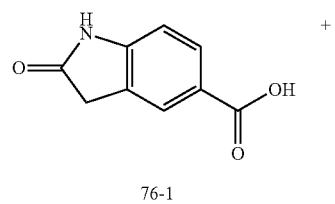

76-1

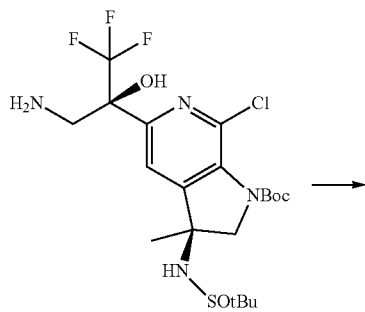

50-10

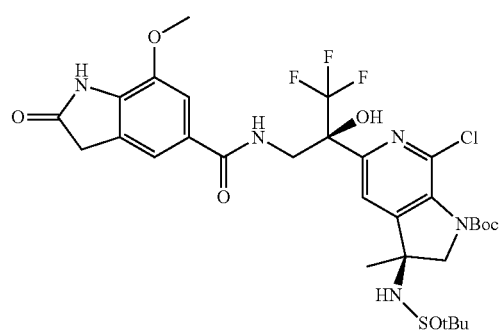

76-2

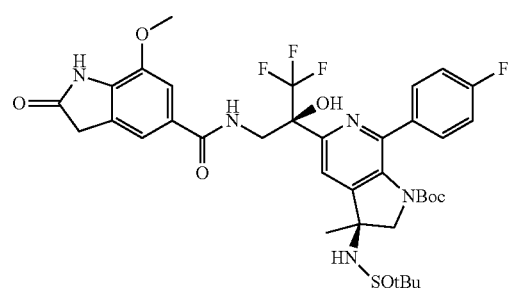

76-3

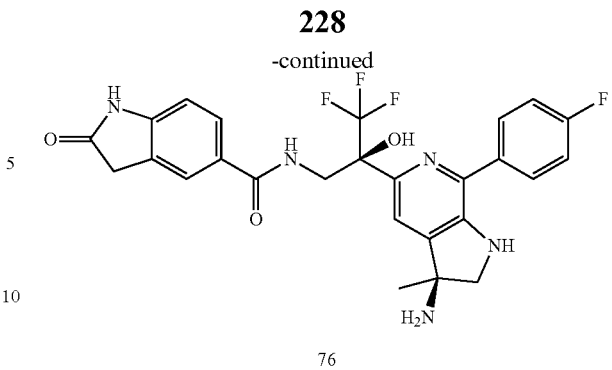

76

Compound 76 (8 mg, a white solid) was prepared using methods similar to those for preparing 21 from 76-1 and 50-10. MS: m/z 531.2 [M+H]⁺.

Example 61

Preparation of Compound 77

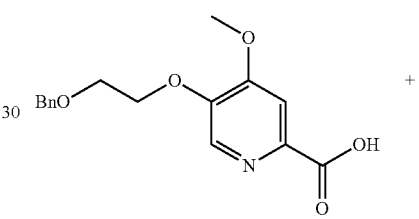

77-1

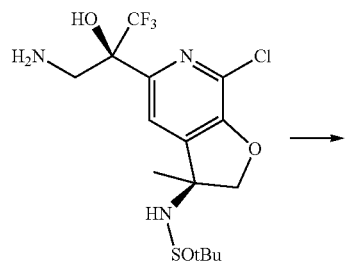

68-2

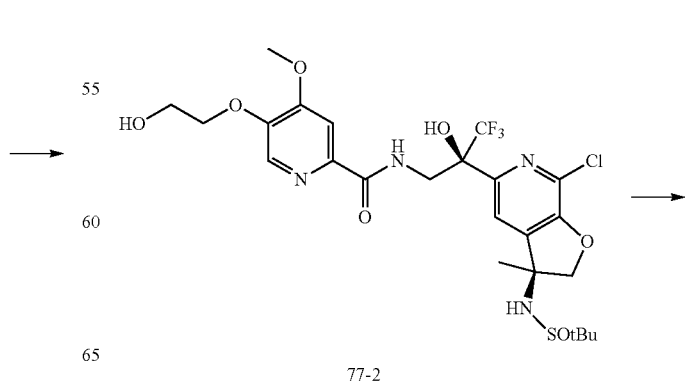

77-2

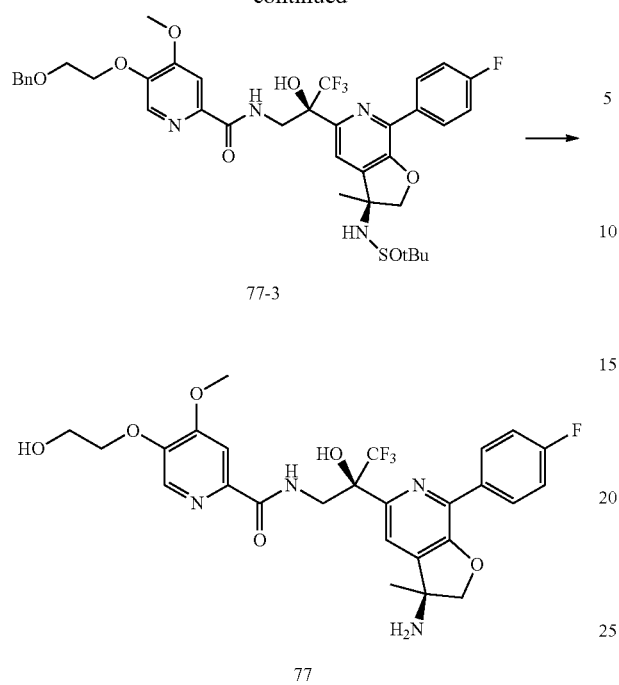
Compound 77 (9.7 mg, a white solid) was prepared using methods similar to those for preparing 21 from 77-1 and 68-2. MS: m/z 567.1 [M+H]$^+$.
Example 62
Preparation of Compound 78
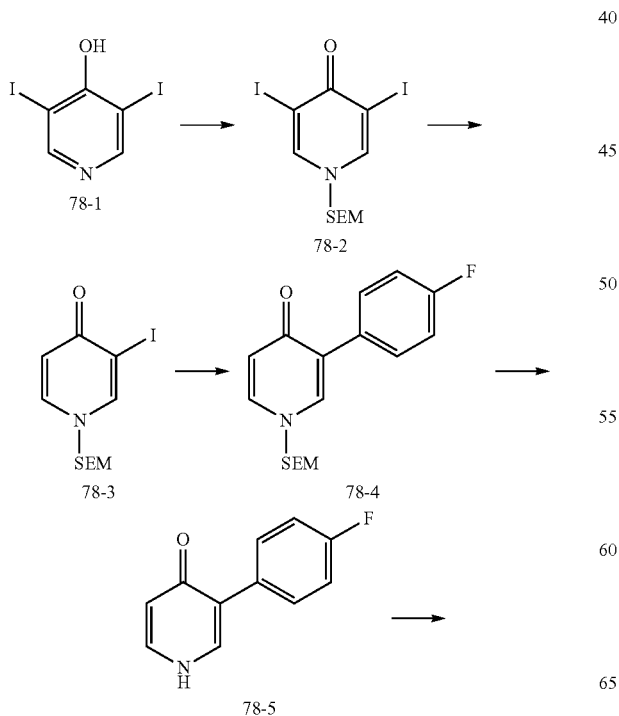
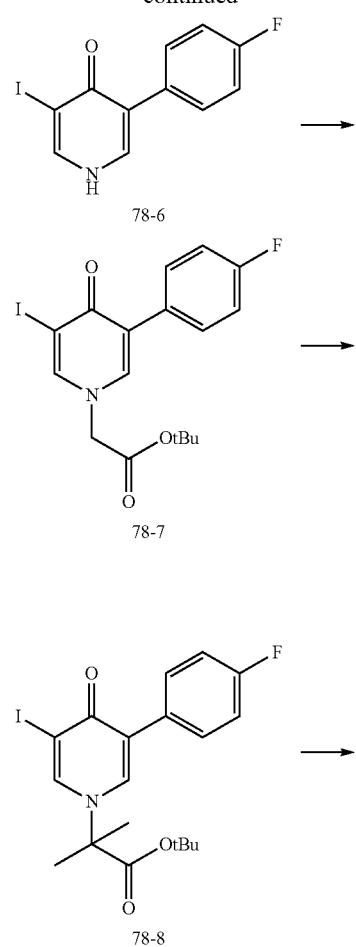

-continued

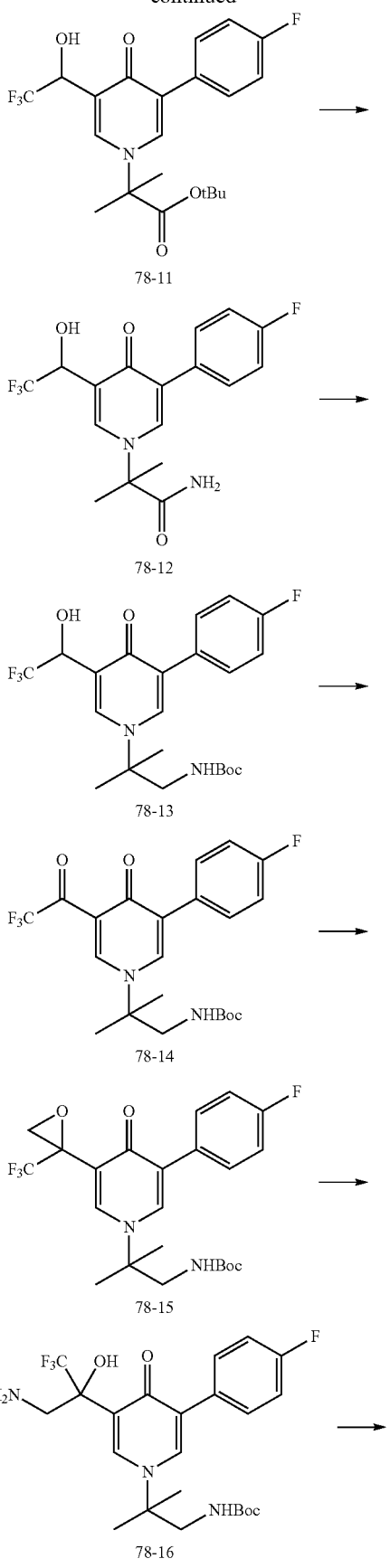

-continued

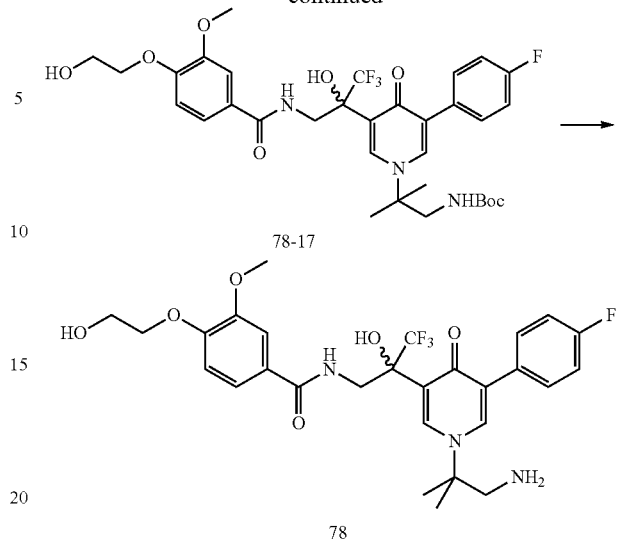

Compound 78-1 was prepared according to a similar procedure as provided in Rousseau et al., Tetrahedron Letters (1997) 38(14):2467-2470.

To a stirring solution of 78-1 (67 g, 193 mmol) in DMF (50 mL) was added NaH (60%, 11.6 g, 290 mmol) in portion at 0° C. After 30 mins, SEM-Cl (38.6 g, 231.77 mmol) was added dropwise and stirred for 1 h at 25° C. The reaction was quenched with aq. NH$_4$Cl, and extracted with EA (3×200 mL). The combined organic layers were washed with brine, dried over Na$_2$SO$_4$, filtered and concentrated. The residue was purified by column chromatography using 10% EA in DCM to give 78-2 (84 g, 91.2%) as a white solid. MS: m/z 477.9 [M+H]$^+$.

To a stirring solution of 78-2 (84 g, 176 mmol) in THF (500 mL) was added i-PrMgCl (2 M, 132 mL) dropwise at −78° C. for 1 h. The reaction was quenched aq. NH$_4$Cl, and extracted with EA (3×300 mL). The combined organic layers were washed with brine, dried over Na$_2$SO$_4$, filtered and concentrated to give crude 78-3 (51 g, crude) as a red oil. MS: m/z 351.9 [M+H]$^+$.

A mixture of 78-3 (50 g, crude), 4-F-phenyl boronic acid (23.9 g, 170.8 mmol), Pd(dppf)Cl$_2$ (5.2 g, 7.1 mmol) and Cs$_2$CO$_3$ (92.8 g, 285 mmol) in dioxane (500 mL) and H$_2$O (50 mL) was stirred at 80° C. for 12 h under N$_2$. The reaction was cooled to RT, and extracted with EA (3×500 mL). The combined organic layers were washed with brine, dried over Na$_2$SO$_4$, filtered and concentrated. The residue was purified by column chromatography using 50% EA in DCM to give 78-4 (40.7 g, 90.4%) as a yellow oil. MS: m/z 319.9 [M+H]$^+$.

To a solution of 78-4 (40.7 g, 125 mmol) in THF (300 mL) was slowly added HCl (12 M, 120 mL). The mixture was stirred at 25° C. for 1 h, neutralized by NaHCO$_3$, and extracted with EA (3×200 mL). The combined organic layers were washed with brine, dried over Na$_2$SO$_4$, filtered and concentrated to give 78-5 (28.3 g, crude) as a red oil. MS: m/z 190.0 [M+H]$^+$.

A mixture of 78-5 (28 g, crude) and NIS (40 g, 177.6 mmol) in CH$_3$CN (400 mL) was stirred at 80° C. for 12 h. The mixture was cooled to RT, and the reaction was quenched with aqueous Na$_2$SO$_3$. A brown precipitate was formed and collected by filtration. The precipitate was dried to give 78-6 (35 g, 75.1%) as a brown solid. MS: m/z 315.9 [M+H]$^+$.

To a solution of 78-6 (32 g, 101.6 mmol) in THF (400 mL) was added NaH (60%, 6.5 g, 163 mmol) in portions at 0° C. The mixture was stirred at 0° C. for 30 mins, followed by addition of tert-butyl 2-bromoacetate (25.8 g, 132 mmol) dropwise. The reaction was stirred at 25° C. for 1.5 h, quenched with aq. NH$_4$Cl, and extracted with EA (3×300 mL). The Combined organic layers were washed with brine, dried over Na$_2$SO$_4$, filtered and concentrated. The residue was purified by column chromatography using 10% EA in DCM to give 78-7 (35 g, 80.3%) as a yellow solid. MS: m/z 429.9 [M+H]$^+$.

To a solution of 78-7 (35 g, 81.5 mmol) in THF (400 mL) was added NaHMDS (1 M, 489 mL) at −78° C. After 30 mins, MeI (116 g, 815 mmol) was added, and the mixture was stirred at −78° C. for 2 h. The reaction was quenched by aq. NH$_4$Cl, and extracted with EA (3×200 mL). The combined organic layers were washed with brine, dried over Na$_2$SO$_4$, filtered and concentrated. The residue was purified by column chromatography using 10% EA in DCM to give 78-8 (28 g, 75.1%) as a red oil. MS: m/z 458.1 [M+H]$^+$.

Compound 78-11 was prepared using methods similar to those for preparing 51 from 78-8.

A solution of 78-11 (8.1 g, 18.9 mmol) in HCl/MeOH (4 M, 41 mL) was stirred at 70° C. for 2 h and concentrated. The residue was neutralized by aq. NaHCO$_3$, and extracted with EA (2×50 mL). The organic phase was washed with brine, dried over Na$_2$SO$_4$, filtered and concentrated. The residue was purified by column chromatography using 20% EA in DCM to give the methyl ester (6.0 g, 81.8%) as a yellow oil. A mixture of the methyl ester (6.0 g, 15.5 mmol) in NH$_3$/MeOH (7 M, 50 mL) was stirred at 60° C. in a sealed vial for 18 h. The reaction was concentrated, and the residue was purified by column chromatography using 25% EA in DCM to give 78-12 (4.5 g, 78%) as a yellow oil. MS: m/z 372.9 [M+H]$^+$.

A mixture of 78-12 (1.5 g, 4 mmol) in BH$_3$-THF (1 M, 20 mL) was stirred at 80° C. for 1 h. The reaction was quenched by MeOH (50 mL), and the mixture was concentrated. The residue was purified by prep-HPLC to give the amine (50 mg) as a yellow solid. To a solution of the amine in DCM (5 mL) were added TEA (0.1 mL) and (Boc)$_2$O (46 mg, 0.21 mmol). The mixture was stirred at 25° C. for 3 h and then concentrated. The residue was purified by prep-TLC (EA: PE=1:1) to give 78-13 (61 mg) as a yellow solid. MS: m/z 458.9 [M+H]$^+$.

Compound 78 (3.5 mg, a white solid) was prepared using methods similar to those for preparing 51 from 78-13. MS: m/z 582.2 [M+H]$^+$.

Example 63

Preparation of Compound 79

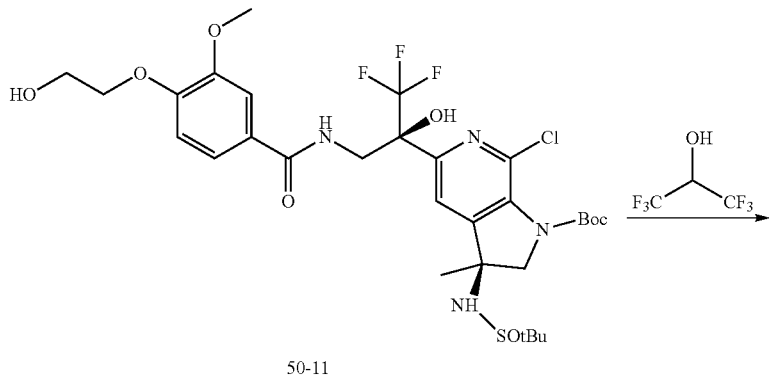

50-11

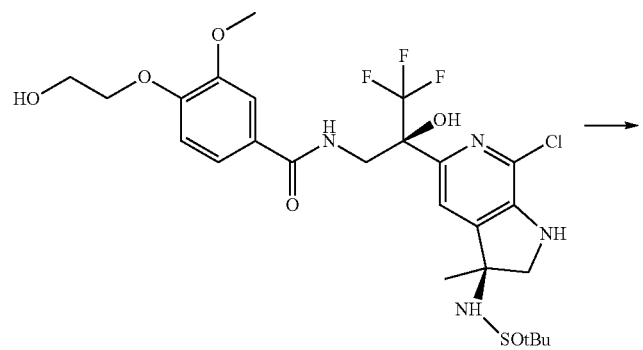

79-1

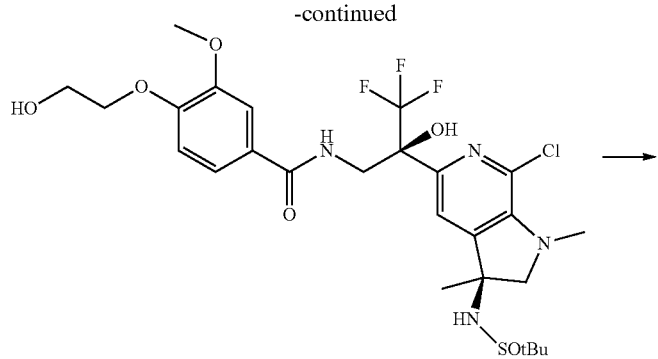

79-2

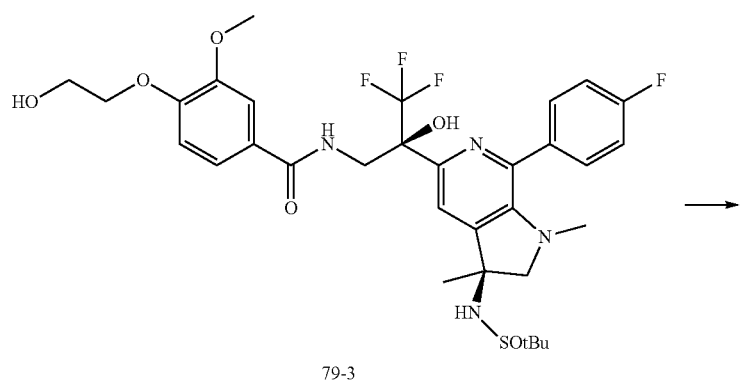

79-3

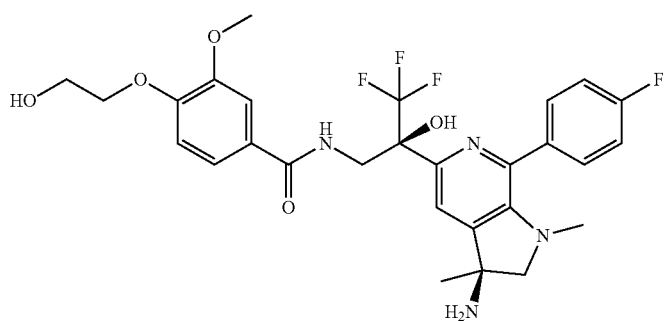

79

A mixture of 50-11 (100 mg, 0.14 mmol) in HFIP (1,1,1,3,3,3-Hexafluoro-2-propanol, 1.00 mL) was heated at 90° C. for 20 mins under microwave. The mixture was concentrated and purified by prep-TLC (EA) to give 79-1 (21 mg, 24.5%) as a colorless oil. MS: m/z 609.1 [M+H]$^+$.

A mixture of 79-1 (21 mg, 0.033 mmol), aq. HCHO (0.8 mL, 35%) and NaBH$_3$CN (90 mg, 1.43 mmol) in MeOH (5 mL) was stirred at 25° C. for 24 h. The mixture was concentrated and purified by prep-TLC (DCM: MeOH=20: 1) to give 79-2 (18 mg, 88%) as a white solid. MS: m/z 623.1 [M+H]$^+$.

Compound 79 (8.5 mg, a white solid) was prepared using methods similar to those for preparing 51 from 79-2. MS: m/z 579.1 [M+H]$^+$.

Example 64

Preparation of Compound 80

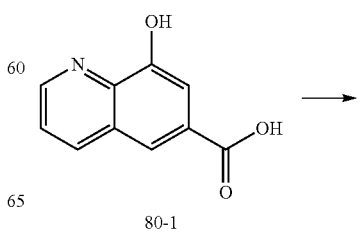

80-1

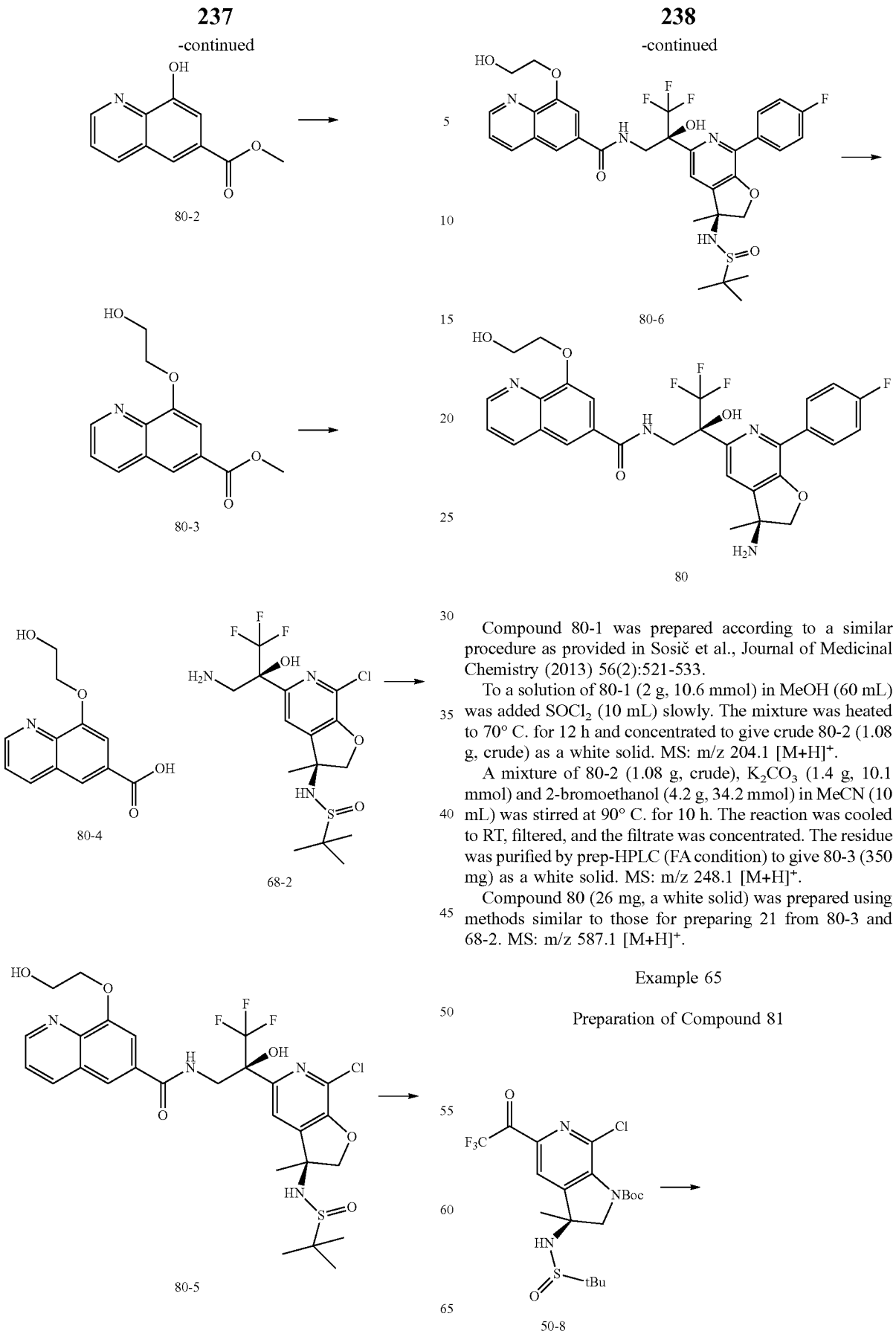

Compound 80-1 was prepared according to a similar procedure as provided in Sosič et al., Journal of Medicinal Chemistry (2013) 56(2):521-533.

To a solution of 80-1 (2 g, 10.6 mmol) in MeOH (60 mL) was added SOCl₂ (10 mL) slowly. The mixture was heated to 70° C. for 12 h and concentrated to give crude 80-2 (1.08 g, crude) as a white solid. MS: m/z 204.1 [M+H]⁺.

A mixture of 80-2 (1.08 g, crude), K₂CO₃ (1.4 g, 10.1 mmol) and 2-bromoethanol (4.2 g, 34.2 mmol) in MeCN (10 mL) was stirred at 90° C. for 10 h. The reaction was cooled to RT, filtered, and the filtrate was concentrated. The residue was purified by prep-HPLC (FA condition) to give 80-3 (350 mg) as a white solid. MS: m/z 248.1 [M+H]⁺.

Compound 80 (26 mg, a white solid) was prepared using methods similar to those for preparing 21 from 80-3 and 68-2. MS: m/z 587.1 [M+H]⁺.

Example 65

Preparation of Compound 81

-continued
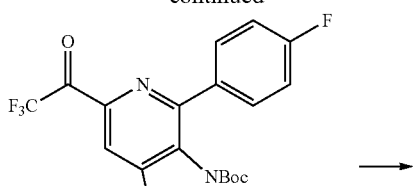
81-1
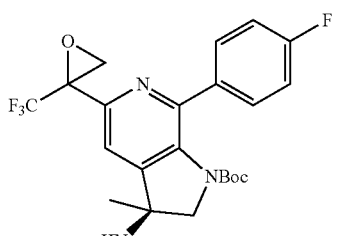
81-2
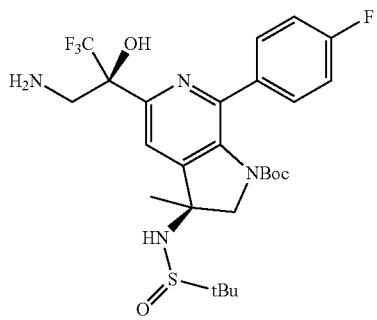
81-3
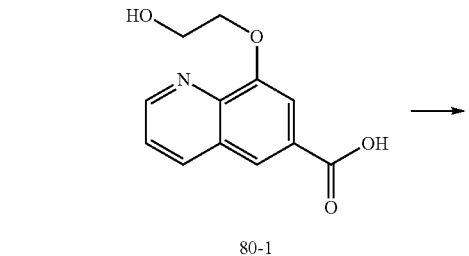
80-1
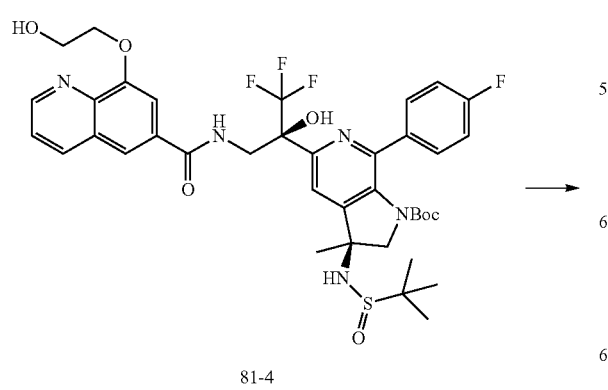
81-4
-continued
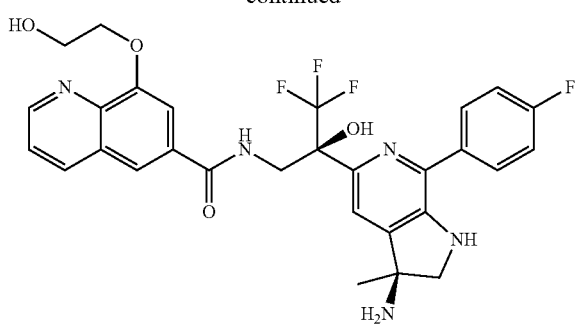
81
Compound 81-3 was prepared using methods similar to those for preparing 51, and 81-3 was separated by prep-HPLC from the racemic material. Compound 81 (22.5 mg, a yellow solid) was prepared using methods similar to those for preparing 21 from 81-3 and 68-2. MS: m/z 608.1 [M+Na]$^+$.
Example 66
Preparation of Compound 82
82-1
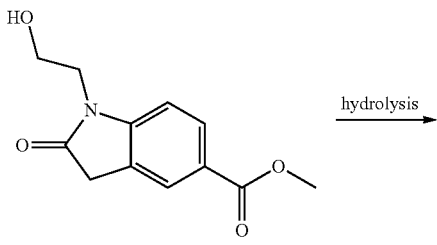
82-2
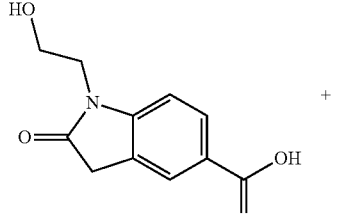
82-3

Example 67

Preparation of Compound 83

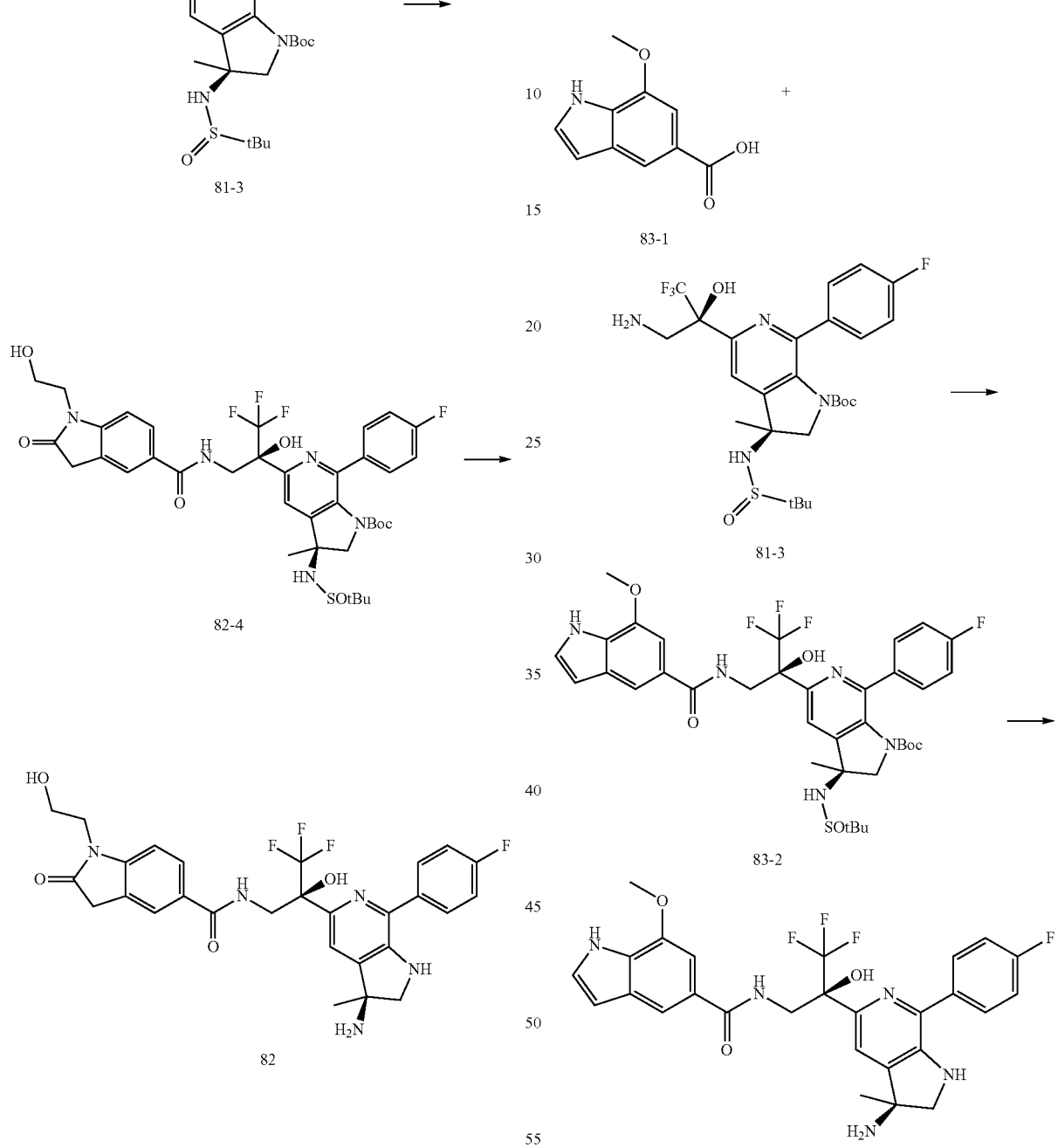

A mixture of 82-1 (200 mg, 1.05 mmol), K$_2$CO$_3$ (435 mg, 3.15 mmol) and bromo-ethanol (260 mg, 2.1 mmol) in DMF (2 mL) was stirred at 80° C. for 4 h. The mixture was cooled to RT, and then diluted with EA (20 mL) and water (30 mL). The organic phase was washed with brine and dried over Na$_2$SO$_4$. The solution was concentrated, and the residue was purified by prep-TLC (EA:PE=1:1) to give 82-2 (93 mg, 37.6%) as a white solid. MS: m/z 236.1 [M+Na]$^+$.

Compound 82 (14 mg, a yellow solid) was prepared using methods similar to those for preparing 21 from 82-2 and 81-3. MS: m/z 574.1 [M+H]$^+$.

Compound 83-1 was prepared according to a similar procedure as provided in Ezquerra et al., Journal of Organic Chemistry (1996) 61(17):5804-5812. Compound 83 (32 mg, a yellow solid) was prepared using methods similar to those for preparing 21 from 83-1 and 81-3. MS: m/z 566.1 [M+Na]$^+$.

Example 68
Preparation of Compound 84
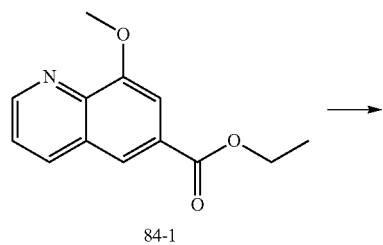
84-1
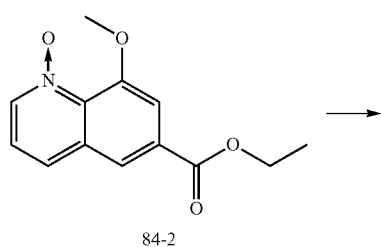
84-2
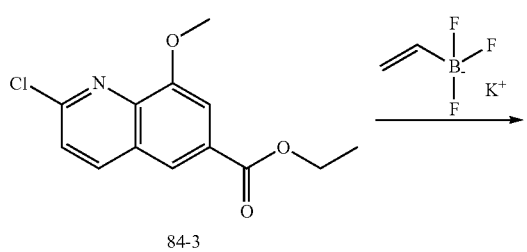
84-3
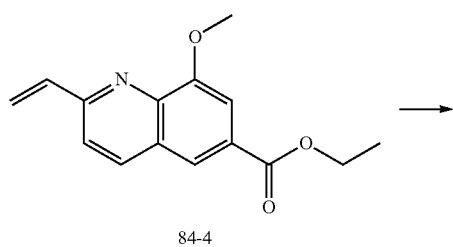
84-4
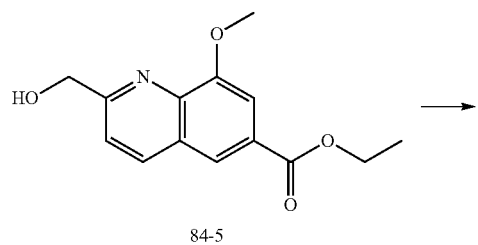
84-5
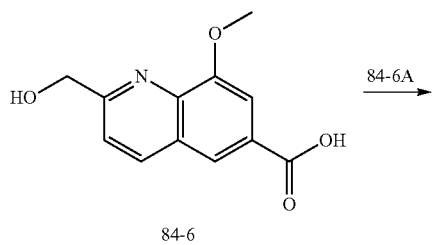
84-6
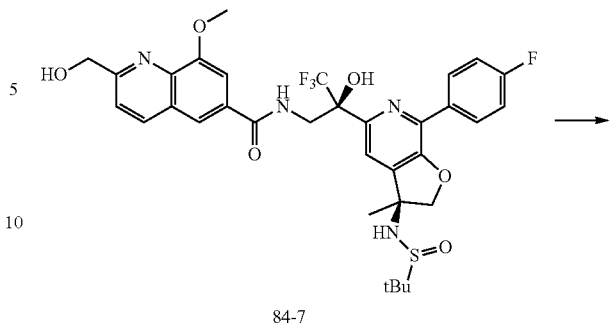
84-7
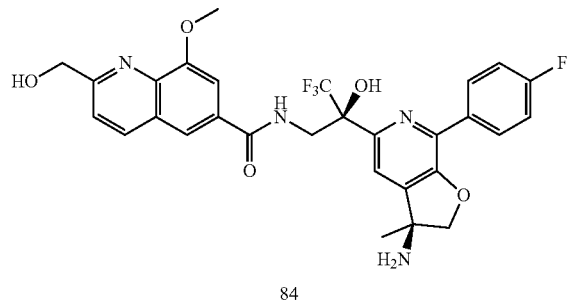
84
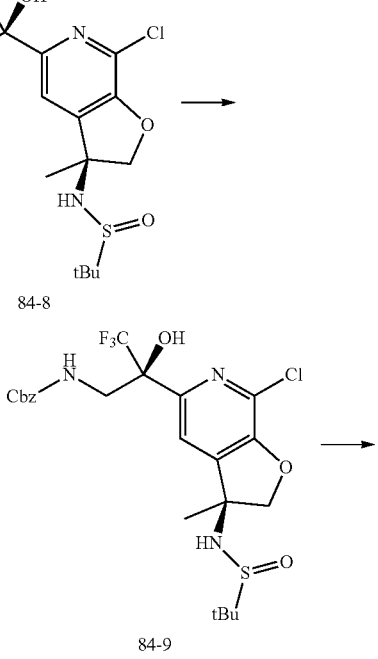
84-8
84-9
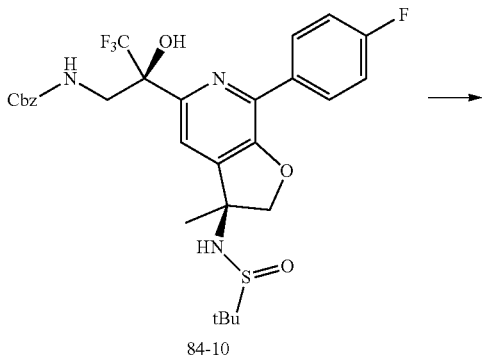
84-10

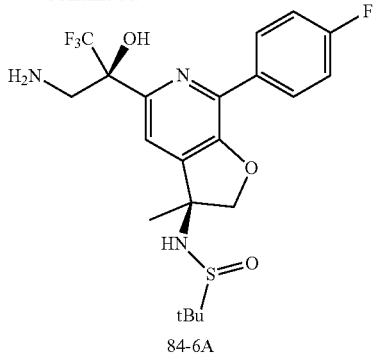 [SMILES: CC(C)(C)S(=O)N[C@]1(C)COc2c1cc([C@](O)(CN)C(F)(F)F)nc2-c1ccc(F)cc1]

84-6A

Compound 84-1 was prepared according to a similar procedure as provided in WO 2010/132615 A1, and compound 84-8 was prepared according to a similar procedure as provided in WO 2015/26792 A1.

To a mixture of 84-1 (2.0 g, 8.65 mmol) in CHCl₃ (10 mL) was added m-CPBA (4.97 g, 21.62 mmol, 75% purity). The mixture was stirred at 60° C. for 3 h and concentrated to give crude 84-2 (1.81 g, crude) as a yellow solid, which was used for next step without purification. MS: m/z 247.9 [M+H]⁺.

A mixture of 84-2 (1.8 g, crude) in POCl₃ (17.8 mL) was stirred at 90° C. for 3 h. The reaction was quenched with H₂O (350 mL). The mixture was neutralized slowly with aq. NaOH to pH 7~8 and extracted with EA (550 mL). The organic layer was washed with brine, dried over Na₂SO₄ and concentrated. The residue was purified by column chromatography using 0~20% EA in PE as eluent to give 84-3 (805 mg, crude) as a white solid, which was used for next step without purification. MS: m/z 266.1 [M+H]⁺.

To a mixture of 84-3 (805 mg, crude) and 84-3A (812 mg, 6.06 mmol) in EtOH (40 mL) was added Pd(dppf)Cl₂ (222 mg, 0.303 μmol) and Na₂CO₃ (642 mg, 6.06 mmol). The mixture was stirred at 70° C. for 3 h. The mixture was concentrated, and the residue was purified by column chromatography using 5~20% EA in PE as eluent to give 84-4 (692 mg, 88.7%) as a white solid. MS: m/z 258.1 [M+H]⁺.

To a mixture of 84-4 (500 mg, 1.94 mmol) in dioxane (6 mL), H₂O (6 mL) and t-BuOH (3 mL) were added OsO₄ (147 mg, 0.58 mmol) and NMO (273 mg, 2.33 mmol). The mixture was stirred at 25° C. for 20 mins. NaIO₄ (2.07 g, 9.70 mmol) was added with stirring at 25° C. for 10 mins. The mixture was quenched with H₂O (20 mL) and extracted with EA (100 mL). The organic layer was dried over Na₂SO₄ and concentrated. The residue was dissolved in MeOH (8 mL) and NaBH₄ (145 mg, 3.88 mmol) was added. The mixture was stirred at 25° C. for 20 mins. The reaction was quenched with H₂O (100 mL) and extracted with EA (100 mL). The organic layer was dried over Na₂SO₄ and concentrated. The residue was purified by column chromatography using 20~100% EA in PE as eluent to give 84-5 (346 mg, 68.3%) as a white solid. MS: m/z 261.9 [M+H]⁺.

To a mixture of 84-5 (300 mg, 1.15 mmol) in EtOH (5 mL) was added a solution of NaOH (138 mg, 3.45 mmol) in H₂O (5 mL). The mixture was stirred at 70° C. for 1 h with monitoring by LCMS. The mixture was cooled to RT, acidified with 1N HCl to pH=3 and concentrated. The residue was triturated into MeOH (30 mL). The solid was removed, and the filtrate was concentrated to give 84-6 (254 mg, crude) as a brown solid. MS: m/z 234.2 [M+H]⁺.

To a mixture of 84-8 (2.5 g, 6.01 mmol) in DCM (10 mL) were added TEA (1.8 g, 18.03 mmol) and CbzCl (2.1 g, 12.02 mmol). The mixture was stirred at 25° C. for 12 h. The mixture was concentrated, and the residue was purified by column chromatography using 10~100% EA in PE as eluent to give 84-9 (2.9 g, 66.8%) as a colorless oil. MS: m/z 550.1 [M+H]⁺.

A mixture of 84-9 (1.5 g, 2.73 mmol), (4-fluorophenyl)boronic acid (1.2 g, 8.19 mmol), K₂CO₃ (754 mg, 5.46 mmol) and Pd(PPh₃)₄ (315 mg, 273 umol) in dioxane (20 mL) and H₂O (4 mL) was heated to 100° C. for 12 h under N₂. The mixture was concentrated, and the residue was purified by column chromatography using 10~80% EA in PE as eluent to give 84-10 (1.15 g, 69.1%) as a white solid. MS: m/z 610.1 [M+H]⁺.

A mixture of 84-10 (1.0 g, 1.64 mmol) and Pd/C (10% purity, 500 mg) in MeOH (15 mL) was stirred under H₂ (45 psi) at 25° C. for 12 h. The mixture was filtered, and the filtrate was concentrated to give crude 84-6A (732 mg, crude) as a colorless oil. MS: m/z 476.1 [M+H]⁺.

A mixture of 84-6 (98 mg, 420 umol), HATU (40 mg, 105 μmol) and DIPEA (41 mg, 315 umol) in DMF (2.00 mL) was stirred at 25° C. for 30 mins. Compound 84-6A (50 mg, 105 umol) was added, and the reaction was stirred at 25° C. for 30 mins with monitored by LCMS. The reaction was quenched with H₂O (100 mL) and extracted with EA (100 mL). The organic layer was dried over Na₂SO₄ and concentrated. The residue was purified by prep-TLC using DCM:MeOH=10:1 as eluent to give 84-7 (41 mg, 38.6%) as a colorless oil. MS: m/z 691.3 [M+H]⁺.

To a mixture of 84-7 (41 mg, 58 umol) in MeOH (3 mL) was added HCl/MeOH (4.0 M, 3 mL). The mixture was stirred at 25° C. for 15 mins with monitored by LCMS. The mixture was concentrated, and the residue was purified by prep-HPLC (HCl condition) to give 84 (15 mg, 45%) as a yellow solid. MS: m/z 587.3 [M+H]⁺.

Example 69

Preparation of Compound 85

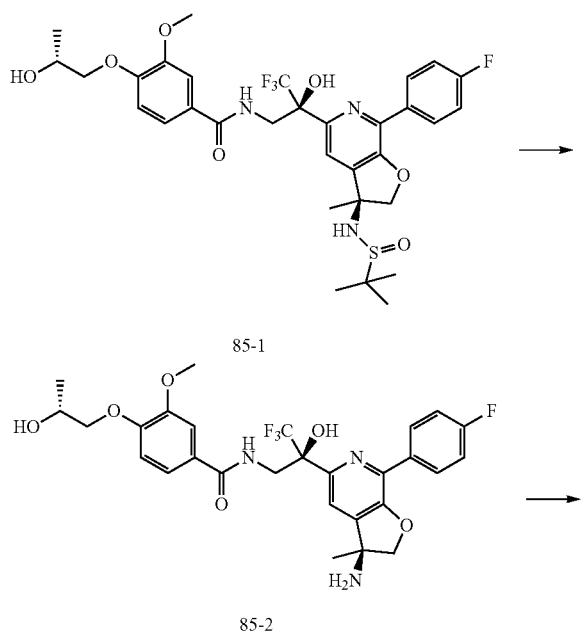

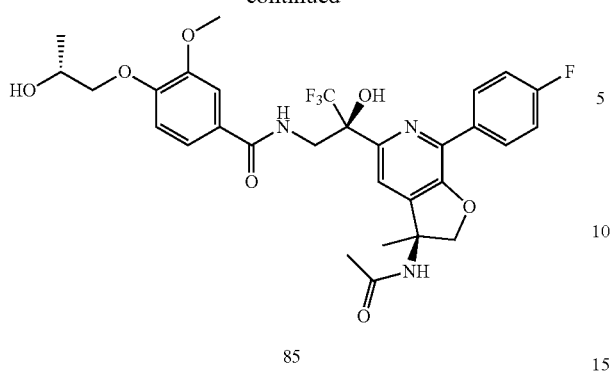

Compounds 85-1 and 85-2 were prepared according to a similar procedure as provided in WO 2015/26792 A1.

To a mixture of 85-2 (100 mg, 173 μmol) in EtOH (4 mL) was added ethyl ethanimidate hydrochloride (43 mg, 345 μmol). The mixture was stirred at 70° C. for 12 h with monitored by LCMS. The mixture was concentrated, and the residue was purified by prep-HPLC (HCl condition) to give 85 (75 mg, 70.1%) as a white solid. MS: m/z 622.3 [M+H]$^+$.

Example 70

Preparation of Compounds 86 and 87

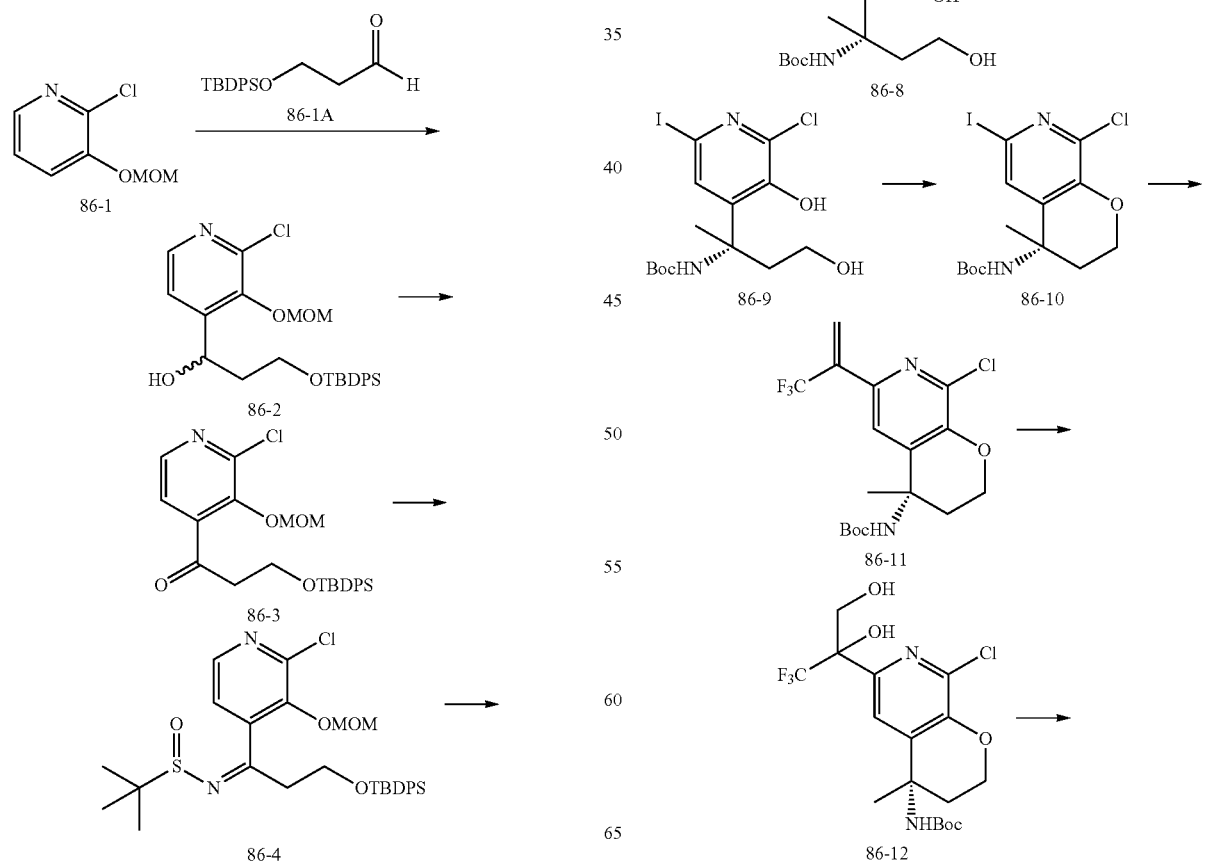

-continued

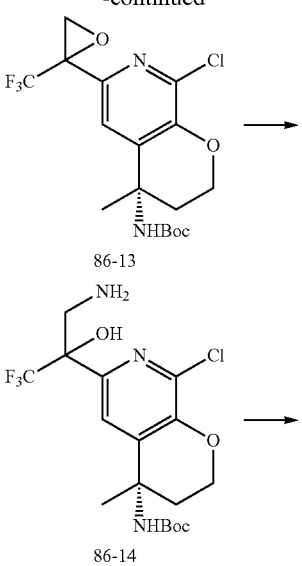

86-13

86-14

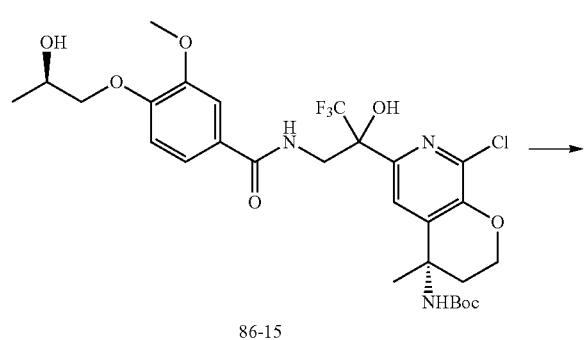

86-15

86-16

86-17

-continued

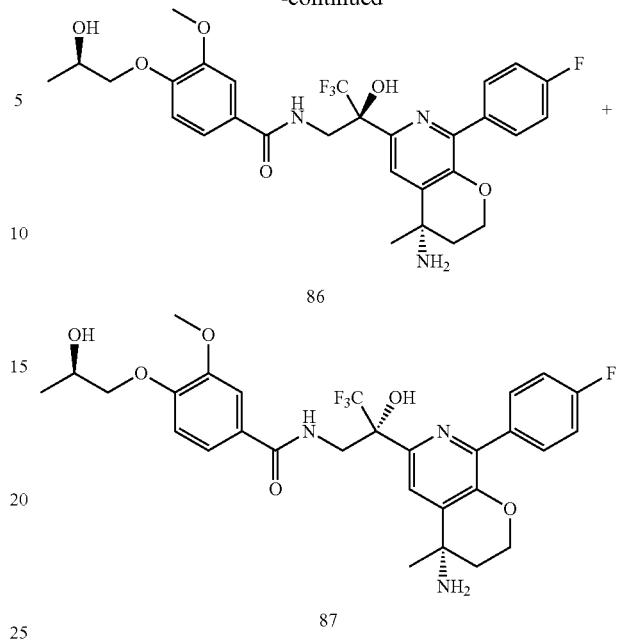

86

87

Compound 86-1 was prepared according to a similar procedure as provided in US 2007/155744 A1, and compound 86-1A was prepared according to a similar procedure as provided in Barry et al., Organic Letters (2005) 7(13): 2683-2686.

n-BuLi (2.5 M, 110.6 mL) was added to the solution of 86-1 (32.0 g, 184.33 mmol) in THF (100 mL) at −78° C. with stirring for 20 mins. Compound 86-1A (90.3 g, 276.50 mmol) was added and stirred at −78° C. for 1 h with monitored by LCMS. The reaction was quenched with aq. NH₄Cl (100 mL) and extracted with EA (2×500 mL). The combined organic layers were washed with brine (50 mL), dried over Na₂SO₄ and concentrated. The residue was purified by column chromatography using 10~20% EA in PE as eluent to give 86-2 (52.1 g, 58.1%) a yellow oil. MS: m/z 486.0 [M+H]⁺.

To a solution of 86-2 (52.0 g, 106.98 mmol) in DCM (200 mL) was added DMP (113.4 g, 267.45 mmol). The mixture was stirred at 25° C. for 1 h with monitoring by TLC. The reaction was quenched with aq. Na₂SO₃ (100 mL), aq. NaHCO₃ (300 mL) and extracted with EA (2×300 mL). The combined organic layers were dried over Na₂SO₄ and concentrated. The residue was purified by column chromatography using 5~15% EA in PE as eluent to give 86-3 (42.1 g, 81.3%) as a yellow oil.

A mixture of 86-3 (42.0 g, 86.77 mmol), 2-methylpropane-2-sulfinamide (15.8 g, 130.16 mmol) and Ti(OEt)4 (49.5 g, 216.93 mmol) in toluene (200 mL) was stirred at 90° C. for 2 h. The solution was concentrated, and the residue was dissolved in EA (200 mL). The solution was poured into aq. NaHCO₃ (200 mL) and stirred for 2 mins. The mixture was filtered through a celite pad, and the filter cake was washed with EA (200 mL). The combined organic phases were dried over Na₂SO₄ and concentrated. The residue was purified by column chromatography using 5~20% EA in PE as eluent to give 86-4 (28.3 g, 55.6%) as a yellow oil.

To a solution of 86-4 (28.3 g, 47.8 mmol) in DCM (200 mL) was added MeMgBr (3 M, 95.7 mL) at −45° C. with stirring. The mixture was stirred at −45° C. for 2 h and at 25° C. for 0.5 h. The reaction was quenched with aq. NH₄Cl


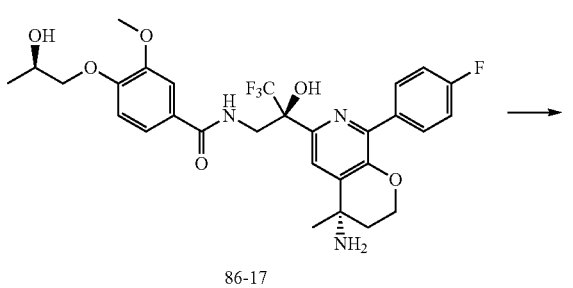

(200 mL) and extracted with EA (2×500 mL). The combined organic layers were washed with brine, dried over $Na_2SO_4$ and concentrated. The residue was purified by column chromatography using 10~25% EA in PE as eluent to give 86-5 (26.4 g, 99.0%) as a yellow solid.

To a solution of 86-5 (26.4 g, 47.21 mmol) in MeOH (100 mL) was added HCl/MeOH (0.2 M, 236 mL). The mixture was stirred at 25° C. for 5 mins with monitoring by LCMS. The reaction was quenched with aq. $NaHCO_3$ (100 mL) and extracted with EA (500 mL). The organic layer was washed with brine, dried over $Na_2SO_4$ and concentrated. The residue was purified by column chromatography using 10~50% EA in PE as eluent to give 86-6 (9.2 g, 42.8%) as a yellow oil. MS: m/z 455.1 $[M+H]^+$.

A solution of 86-6 (9.2 g, 20.2 mmol) and Boc2O (17.6 g, 80.9 mmol) in toluene (30 mL) was stirred at 110° C. for 4 h with monitoring by TLC. The mixture was concentrated and purified by column chromatography using 5~30% EA in PE as eluent to give 86-7 (8.8 g, 78.2%) as a yellow oil.

To a solution of 86-7 (8.7 g, 15.7 mmol) in THF (150 mL) was added 3HF.TEA (20.2 g, 125.4 mmol). The mixture was stirred at 25° C. for 3 h with monitoring by TLC. The reaction was quenched with $H_2O$ (100 mL) and extracted with EA (300 mL). The organic layer was washed with brine, dried over $Na_2SO_4$ and concentrated. The residue was purified by column chromatography using 20~60% EA in PE as eluent to give 86-8 (4.5 g, 89.6%) as a yellow solid. MS: m/z 361.9 $[M+H]^+$.

A mixture of solution of 86-8 (4.5 g, 14 mmol) in DMF (40 mL) was added NIS (4.74 g, 21 mmol). The mixture was stirred at 25° C. for 0.5 h with monitoring by TLC. The reaction was quenched with aq. $Na_2SO_3$ (200 mL) and extracted with EA (300 mL). The organic layer was washed with brine, dried over $Na_2SO_4$ and concentrated. The residue was purified by column chromatography using 5~40% EA in PE as eluent to give 86-9 (5.3 g, 85.2%) as a yellow solid. MS: m/z 443.0 $[M+H]^+$.

To a solution of 86-9 (5.0 g, 11.3 mmol) and $PPh_3$ (3.6 g, 13.55 mmol) in THF (60 mL) was added DIAD (2.74 g, 13.55 mmol) dropwise at 20° C. The mixture was stirred at 20° C. for 1 h, concentrated. The residue was purified by column chromatography using 1~10% EA in PE as eluent to give 86-10 (2.7 g, 81.3%) as a white solid. MS: m/z 424.9 $[M+H]^+$.

A mixture of 86-10 (500 mg, 1.18 mmol), 86-10A (339 mg, 1.53 mmol), Pd(dppf)Cl$_2$ (86 mg, 118 umol) and $Cs_2CO_3$ (767 mg, 2.35 mmol) in DME (8 mL) and $H_2O$ (2 mL) was heated at 95° C. for 40 mins under microwave. The mixture was concentrated, and the residue was purified by column chromatography using 5~30% EA in PE as eluent to give 86-11 (1.3 g, 70.1%, 4 batches) as a white solid. MS: m/z 392.9 $[M+H]^+$.

A mixture of 86-11 (1.3 g, 3.31 mmol), (DHQD)$_2$PHAL (516 mg, 662 μmol), $K_2OsO_4.2H_2O$ (244 mg, 662 μmol) and NMO (582 mg, 4.97 mmol) in t-BuOH (20 mL) and $H_2O$ (6 mL) was stirred at 20° C. for 16 h under $N_2$. The reaction was quenched with aq. $Na_2S_2O_3$ (20 mL) and extracted with EA (200 mL). The organic layer was washed with brine, dried over $Na_2SO_4$, filtered and concentrated. The residue was purified by flash silica gel chromatography using 0~2% MeOH in DCM as eluent to give 86-12 (1.3 g, 92.2%) as a colorless oil. MS: m/z 426.9 $[M+H]^+$.

To a stirring mixture of 86-12 (268 mg, 628 umol) in THF (30 mL) at 0° C. was added NaH (63 mg, 1.57 mmol, 60% purity) with stirring for 30 mins. TsCl (144 mg, 754 umol) was added, and the mixture was stirred at 0° C. for 30 mins with monitoring by LCMS. The reaction was quenched with $H_2O$ (20 mL) and extracted with EA (4×30 mL). The combined organic layers were washed with brine, dried over $Na_2SO_4$, filtered and concentrated to give 86-13 (256 mg, crude) as a white solid, which was used into the next step without further purification. MS: m/z 408.9 $[M+H]^+$.

A mixture of 86-13 (250 mg, crude) in $NH_3$/MeOH (7M, 20 mL) was stirred at 15° C. for 10 h with monitoring by LCMS. The mixture was concentrated to give 86-14 (262 mg, crude) as a white solid. MS: m/z 426.0 $[M+H]^+$.

Compounds 86-14A was prepared according to a similar procedure as provided in WO 2015/26792 A1. Compounds 86 (95 mg, a white solid) and 87 (86 mg, a white solid) were prepared using methods similar to those for preparing 21 from 86-14A and 86-14. 86: MS: m/z 616.1 $[M+Na]^+$; and 87: MS: m/z 616.1 $[M+Na]^+$. Compounds 86 and 87 are shown above with relative stereochemistry arbitrarily assigned.

Example 71

Preparation of Compound 88

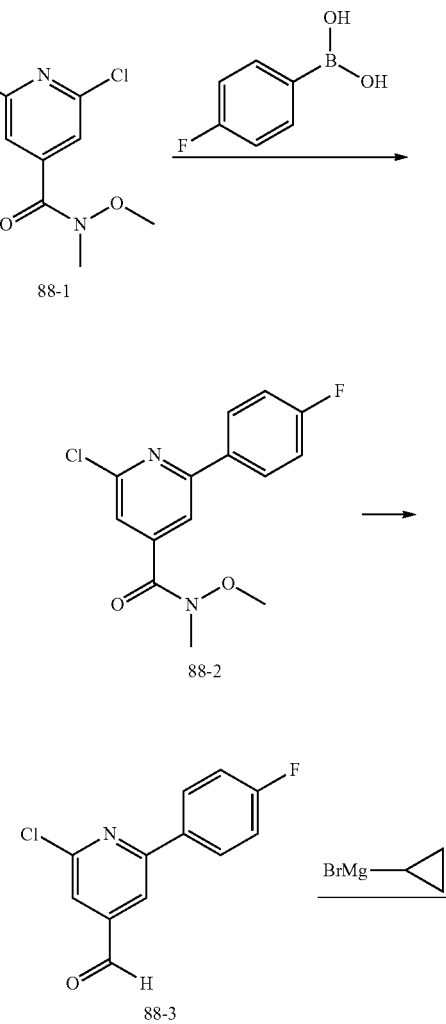

253
-continued
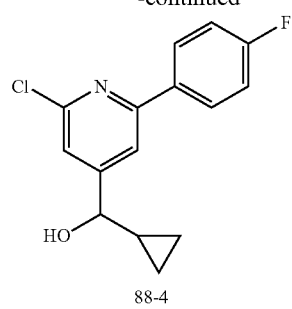
88-4
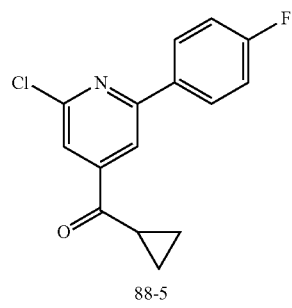
88-5
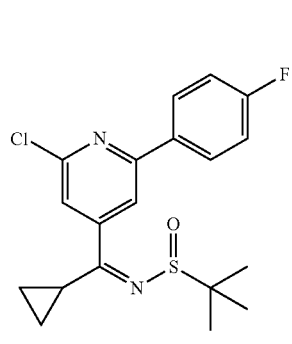
88-6
88-7
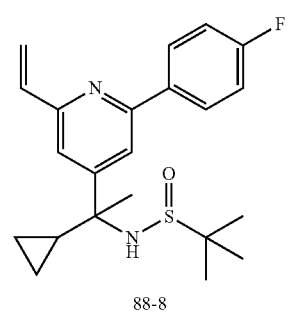
88-8
254
-continued
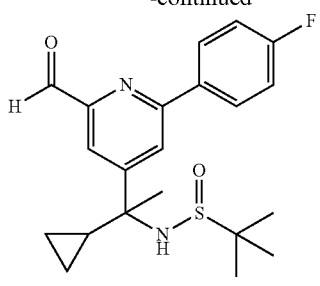
88-9
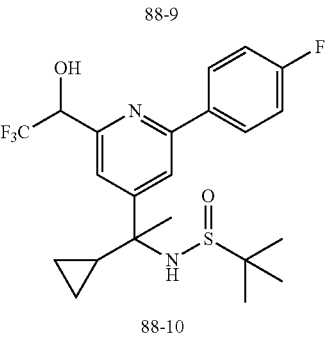
88-10
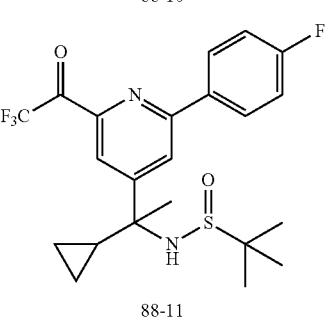
88-11
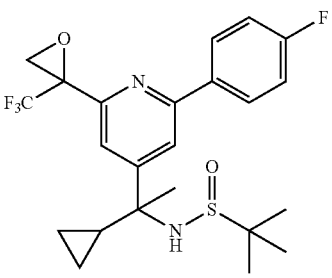
88-12
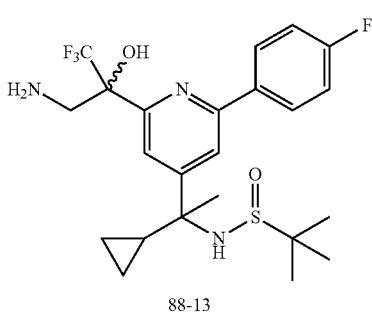
88-13

-continued

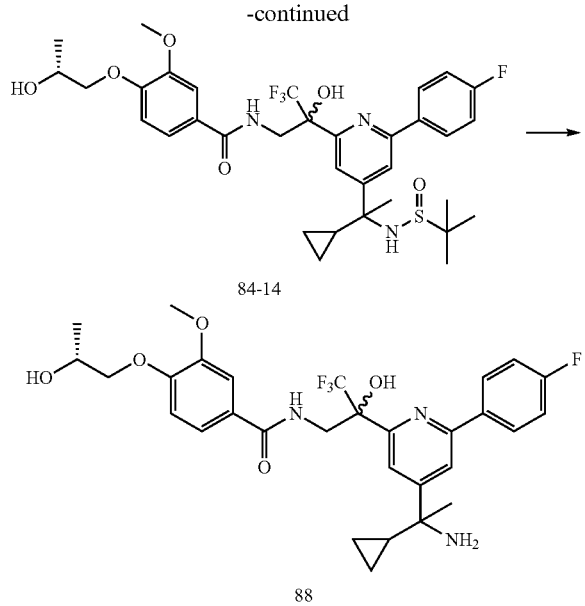

Compound 88-1 was prepared according to a similar procedure as provided in WO 2009/114552 A1.

A mixture of 88-1 (20.0 g, 85.1 mmol), boronic acid (13.1 g, 93.6 mmol), Pd(dppf)Cl$_2$ (3.1 g, 4.25 mmol) and TBAF (1 M, 127.6 mL) in DCM (400 mL) was stirred at 25° C. for 12 h under N$_2$. The solution was concentrated, and the residue was diluted with H$_2$O (1 L) and extracted with EA (800 mL). The organic phase was washed with brine, dried with anhydrous Na$_2$SO$_4$, filtered and concentrated. The residue was purified by column chromatography using 5~20% EA in PE as eluent to give 88-2 (17.2 g, 68.6%) as a yellow oil. MS: m/z 295.7 [M+H]$^+$.

To a solution of 88-2 (8.0 g, 27.2 mmol) in THF (100 mL) was added DIBAL-H (1 M, 54.3 mL) dropwise at −30° C. The mixture was stirred at 25° C. for 1 h with monitoring by TLC. The reaction was quenched with a saturated NH$_4$Cl (50 mL) and extracted with EA (2×250 mL). The organic phase was washed with brine (50 mL), dried over anhydrous Na$_2$SO$_4$, filtered and concentrated. The residue was purified by column chromatography using 1~20% EA in PE as eluent to give 88-3 (4.1 g, 63.3%) as a white solid. MS: m/z 237.7 [M+H]$^+$.

To a solution of 88-3 (9.0 g, 38.2 mmol) in THF (100 mL) was added Grignard reagent (0.5 M, 305 mL) at 25° C. under N$_2$. After addition, the mixture was stirred at 25° C. for 1 h. The solution was poured into aq. NH$_4$Cl (200 mL) and stirred and extracted with EA (2×250 mL). The combined organic phase was washed with brine (50 mL), dried over anhydrous Na$_2$SO$_4$, filtered and concentrated. The residue was purified by column chromatography using 1~20% EA in PE as eluent to give 88-4 (6.30 g, 59.4%) as a yellow oil. MS: m/z 277.9 [M+H]$^+$.

To a solution of 88-4 (6.3 g, 22.7 mmol) in DCM (150 mL) was added DMP (19.2 g, 45.4 mmol) at 25° C. The mixture stirred at 25° C. for 2 h. The reaction was quenched by saturated Na$_2$SO$_3$ (300 mL) and extracted with DCM (2×250 mL). The organic phase was washed with aq. NaHCO$_3$ (200 mL) and brine (100 mL), dried over anhydrous Na$_2$SO$_4$, filtered and concentrated. The residue was purified by column chromatography using 1~20% EA in PE as eluent to give 88-5 (4.4 g, 70.4%) as a white solid. MS: m/z 276.8 [M+H]$^+$.

A mixture of 88-5 (3.6 g, 13.06 mmol), NH$_2$SOtBu (4.7 g, 39.18 mmol) and Ti(OEt)$_4$ (8.9 g, 39.18 mmol) in THF (100 mL) was stirred at 70° C. for 2 h. The reaction was quenched by aq. NaHCO$_3$ (10 mL) with stirring until white titanium salts precipitate was formed. The solid was filtered throng a celite pad. The filtrate was dried over anhydrous Na$_2$SO$_4$ and concentrated. The residue was purified by column chromatography using 5~30% EA in PE as eluent to give 88-6 (4.2 g, 85.1%) as a yellow oil. MS: m/z 379.8 [M+H]$^+$.

To a solution of 88-6 (4.0 g, 10.6 mmol) in THF (50 mL) was added MeMgBr (3 M, 10.5 mL) dropwise at 25° C. under N$_2$. The mixture was stirred at 25° C. for 1 h. The reaction was quenched with aq. NH$_4$Cl (100 mL) and extracted with EA (250 mL). The organic phase was washed with brine, dried over anhydrous Na$_2$SO$_4$, filtered and concentrated. The residue was purified by column chromatography using 5~50% EA in PE as eluent to give 88-7 (4.1 g, 96.5%) as a yellow oil. MS: m/z 394.9 [M+H]$^+$.

Compound 88-7 was synthesized using method similar to those for preparing 86-5. Compound 88-8 and 88-9 were synthesized using methods similar to those preparing 50-5 and 50-6.

Compound 88 (32 mg, a white solid) was prepared using methods similar to those for preparing 51 from 88-9. MS: m/z 592.1 [M+H]$^+$.

Example 72

Preparation of Compound 89

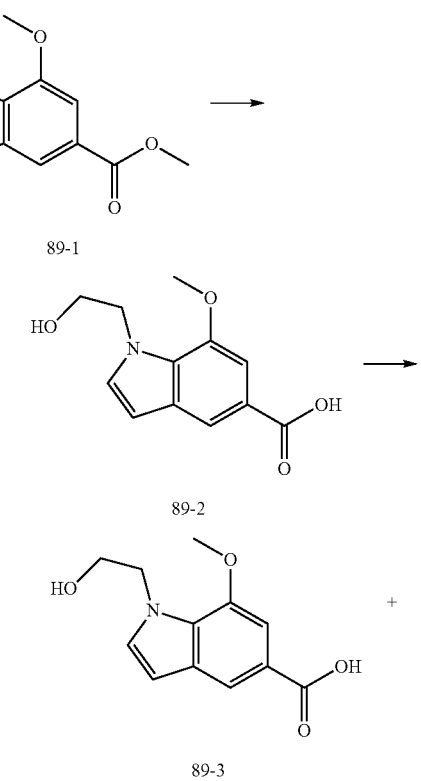

257

-continued

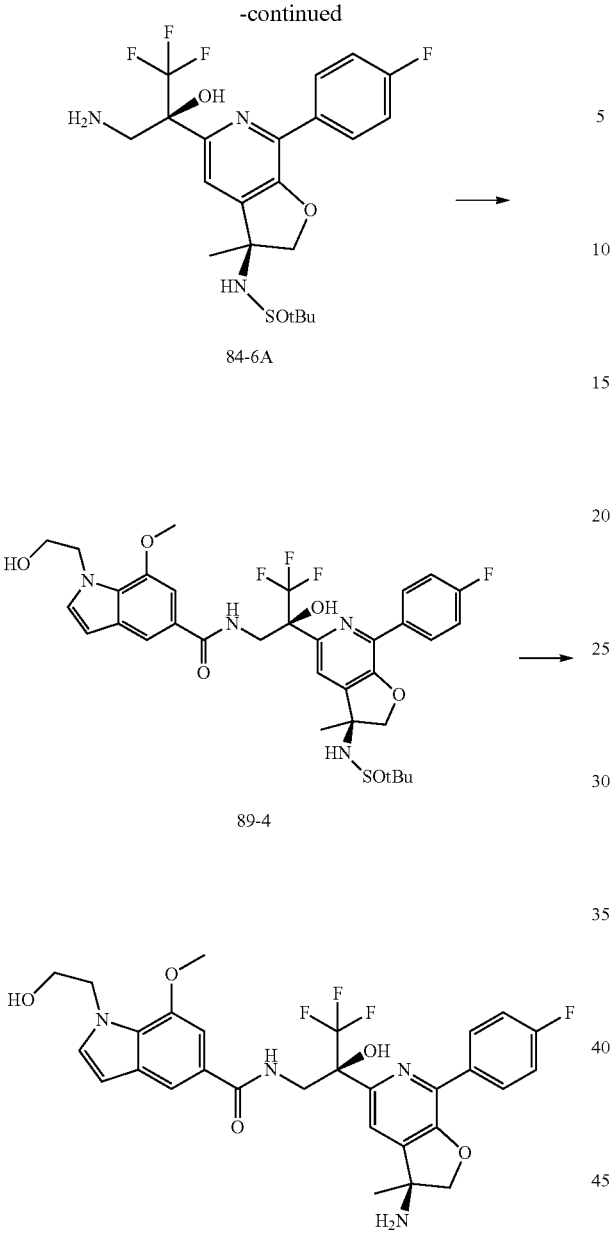

Compound 89-1 was prepared according to a similar procedure as provided in Ezquerra et al., Journal of Organic Chemistry (1996) 61(17):5804-5812.

To a solution of 89-1 (400 mg, 1.95 mmol) in DMF (5 mL) was added NaH (60%, 234 mg, 5.85 mmol) in one portion at 0° C. The mixture was stirred for 30 mins. 2-bromoethanol (730 mg, 5.85 mmol) was added, and the mixture was stirred at 60° C. for 5 h. The reaction was quenched with H$_2$O (100 mL) and extracted with EA (50 mL). The organic layer was washed with brine (15 mL), dried over Na$_2$SO$_4$, filtered and concentrated. The residue was purified by column chromatography using 1~20% EA in PE as eluent to give 89-2 (57 mg, 11.5%) as a colorless oil. MS: m/z 250.1 [M+H]$^+$.

Compound 89 (1.86 mg, a white solid) was prepared using methods similar to those for preparing 21 from 89-2 and 84-6A. MS: m/z 589.0 [M+H]$^+$.

258

Example 73

Preparation of Compound 90

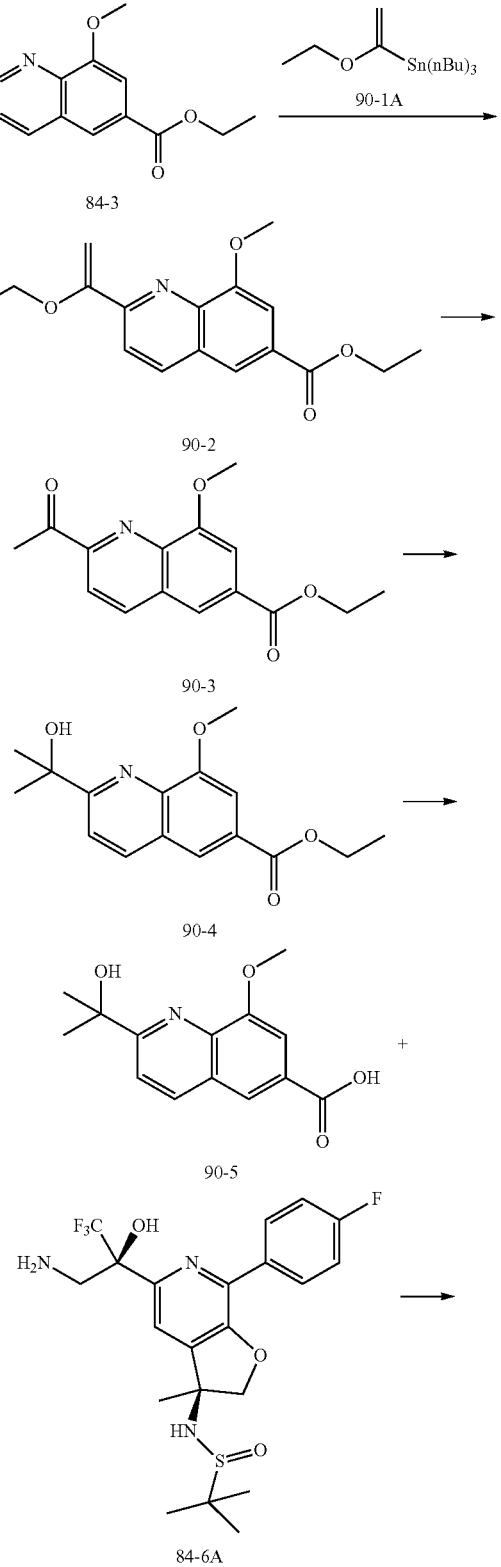

-continued

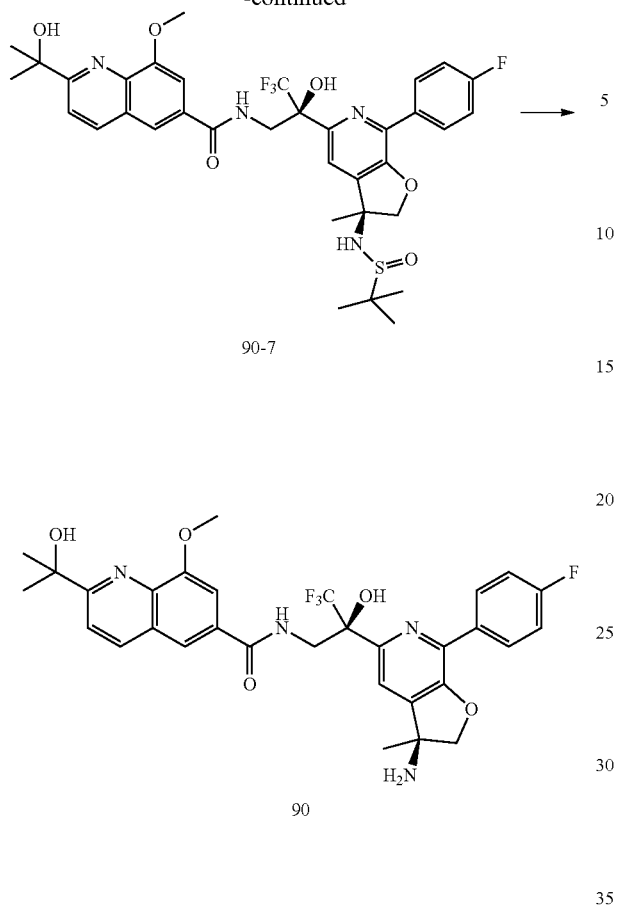

A mixture of 84-3 (1.5 g, 5.65 mmol), K₂CO₃ (1.4 g, 10.17 mmol), 90-1A (4.1 g, 11.30 mmol) and Pd(dppf)Cl₂ (413 mg, 0.56 mmol) in DMF (15 mL) was stirred at 90° C. for 12 h under N₂. The reaction was quenched with H₂O (200 mL) and extracted with EA (300 mL). The organic layer was washed with brine (20 mL), dried over Na₂SO₄, filtered and concentrated to give 90-2 (810 mg, crude) as a brown solid. MS: m/z 301.9 [M+H]⁺.

To a solution of 90-2 (0.8 g, crude) in THF (8 mL) was added HCl (3 M, 2 mL). The mixture was stirred at 25° C. for 10 mins. The reaction was quenched with aq. NaHCO₃ (60 mL) and extracted with EA (2×50 mL). The organic layer was washed with brine (20 mL), dried over Na₂SO₄, filtered and concentrated. The residue was purified by column chromatography using 5~50% EA in PE as eluent to give 90-3 (561 mg, 77.3%) as a yellow oil. MS: m/z 290.1 [M+H]⁺.

To a mixture of 90-3 (400 mg, 1.46 mmol) in THF (5 mL) was added MeMgBr (3.0 M, 0.6 mL) at −40° C. under N₂. The mixture was stirred at −40° C. for 30 mins. The reaction was quenched with aq. NH₄Cl (30 mL) and extracted with EA (2×50 mL). The organic layer was dried over Na₂SO₄ and concentrated. The residue was purified by column chromatography using 10~50% EA in PE as eluent to give 90-4 (232 mg, 54.9%) as a red oil. MS: m/z 273.9 [M+H]⁺.

Compound 90 (23 mg, a white solid) was prepared using methods similar to those for preparing 21 from 89-4 and 84-6A. MS: m/z 615.1 [M+H]⁺.

Example 74

Preparation of Compound 91

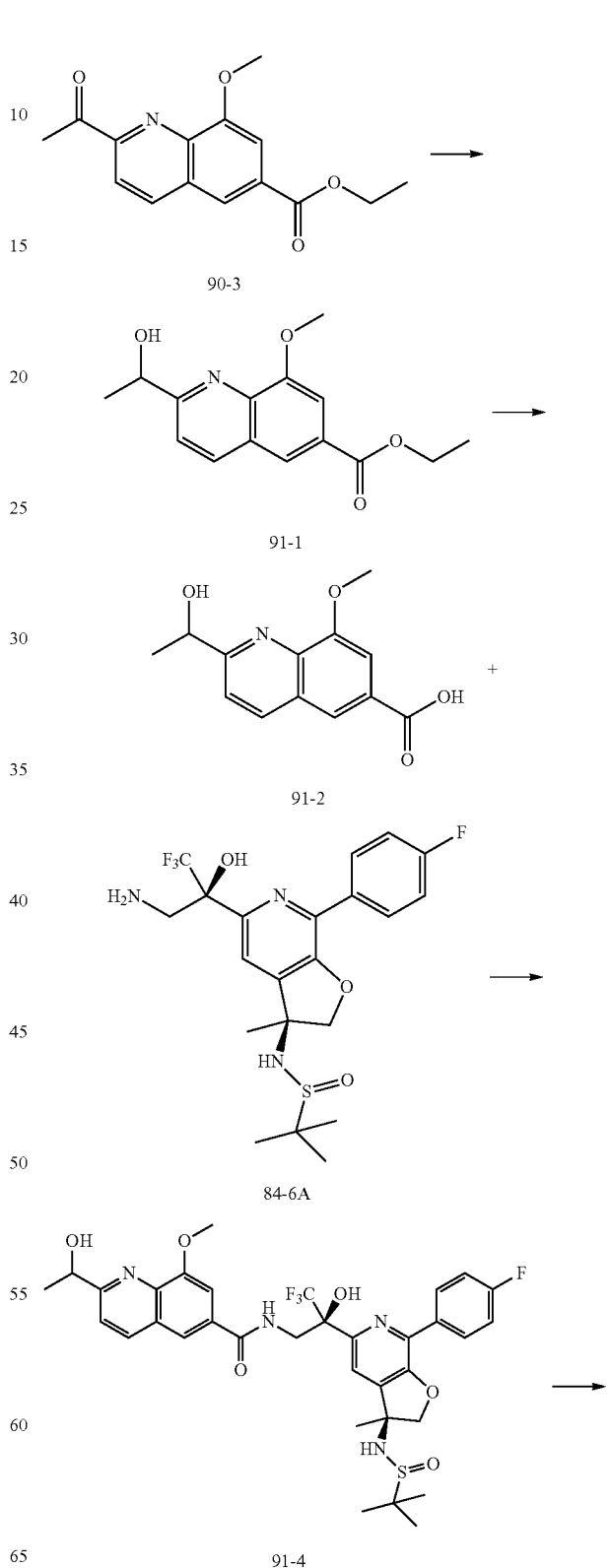

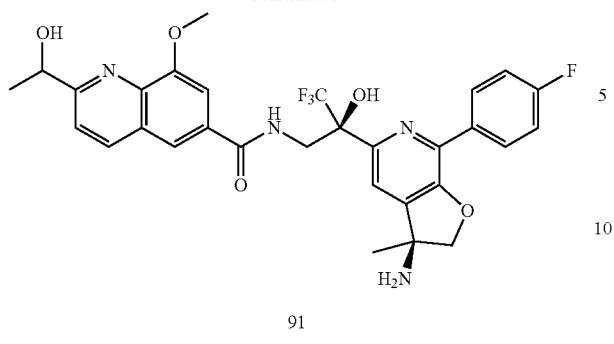

91

To a solution of 90-3 (200 mg, 0.73 mmol) in MeOH (5 mL) was added NaBH$_4$ (56 mg, 1.46 mmol) at 25° C. The mixture was stirred at 25° C. for 10 mins, and the reaction was quenched with H$_2$O (30 mL) and extracted with EA (50 mL). The organic layer was dried over Na$_2$SO$_4$ and concentrated. The residue was purified by column chromatography using 20~60% EA in PE as eluent to give 91-1 (153 mg, 75.9%) as a colorless oil. MS: m/z 276.2 [M+H]$^+$.

Compound 91 (10 mg, a white solid) was prepared using methods similar to those for preparing 21 from 91-1 and 84-6A. MS: m/z 601.1 [M+H]$^+$.

Example 75

Preparation of Compound 92

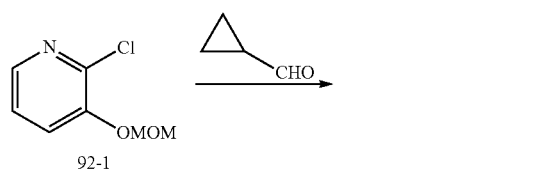
92-1

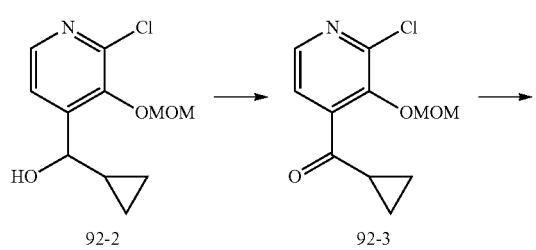
92-2  92-3

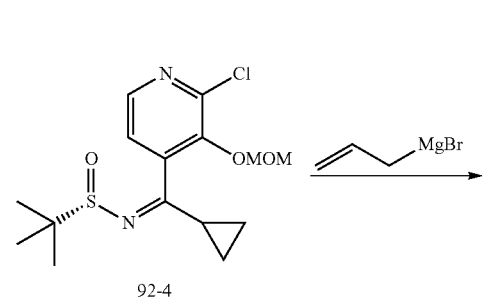
92-4

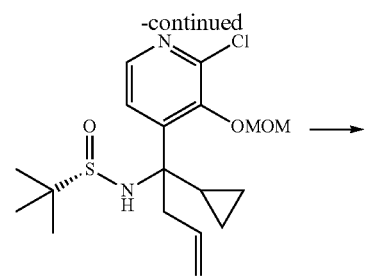
92-5

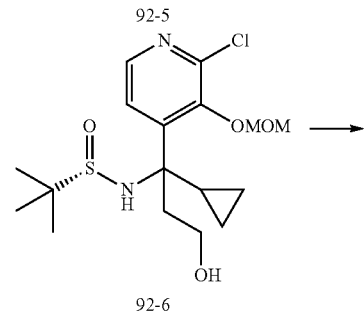
92-6

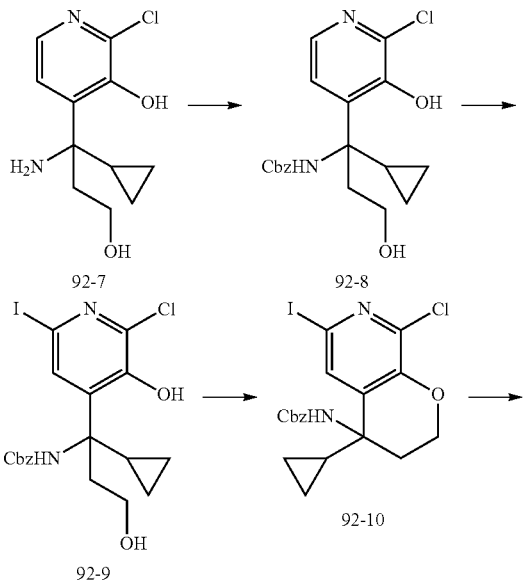
92-7  92-8

92-9  92-10

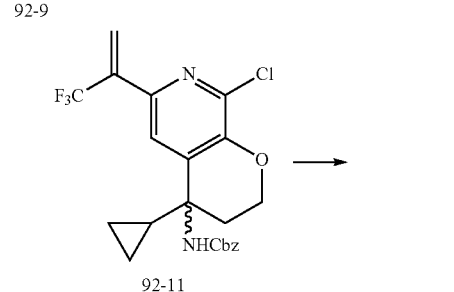
92-11

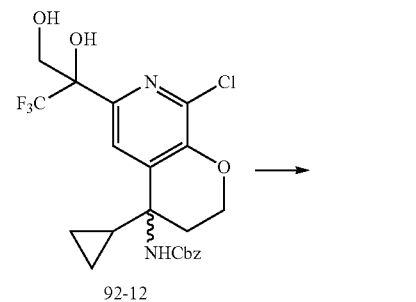
92-12

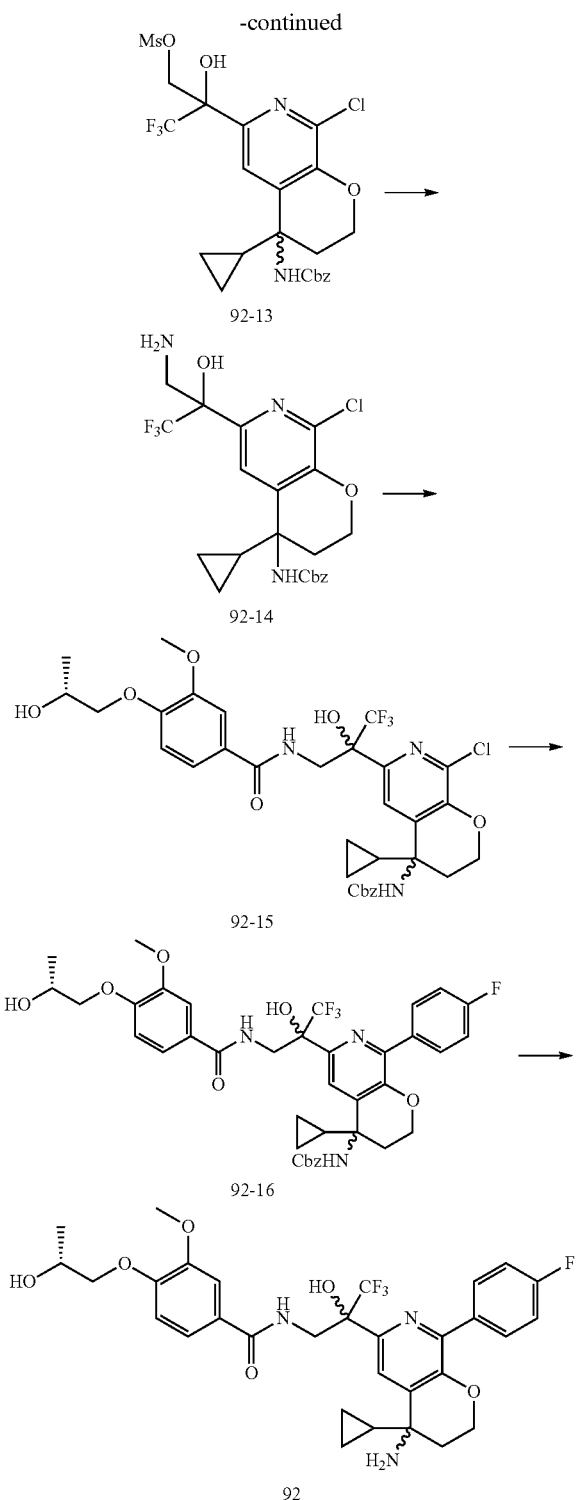

Compound 92-1 was prepared according to a similar procedure as provided in US 2007/155744 A1.

To a solution of 92-1 (22.0 g, 126.7 mmol) in THF (220 mL) was added n-BuLi (2.5 M, 76 mL) in dropwise at −78° C. under N$_2$. After addition, the mixture was stirred at −78° C. for 30 mins and followed by addition of aldehyde (13.3 g, 190.1 mmol). The reaction was stirred for 1.5 h at −78° C. The reaction was quenched with aq. NH$_4$Cl (300 mL) and extracted with EA (2×500 mL). The combined organic phases were washed with brine (300 mL), dried over anhydrous Na$_2$SO$_4$, filtered and concentrated. The residue was purified by column chromatography using 10~20% EA in PE as eluent to give 92-2 (30.2 g, 97.2%) as a yellow oil. MS: m/z 243.8 [M+H]$^+$.

To a solution of 92-2 (28.0 g, 114.9 mmol) in MeCN (250 mL) was added IBX (48.3 g, 172.3 mmol) in portions. The mixture was stirred at 85° C. for 3 h. The mixture was cooled to 20° C., and the solid was removed by filtration. The filtrate was concentrated, and the residue was purified by column chromatography using 10~20% EA in PE as eluent to give 92-3 (24.7 g, 86.5%) as a yellow oil. MS: m/z 241.8 [M+H]$^+$.

A mixture of 92-3 (13.0 g, 53.79 mmol), NH$_2$SOtBu (7.8 g, 64.55 mmol) and Ti(OEt)4 (27.0 g, 118.34 mmol) in toluene (120 mL) was stirred at 90° C. for 5 h. The mixture was cooled to 20° C. and poured into aq. NaHCO$_3$ (150 mL). The solid was filtered through a short pad of celite, and the filtrate was extracted with EA (3×200 mL). The combined organic phase was washed with brine (150 mL), dried with anhydrous Na$_2$SO$_4$, filtered and concentrated. The residue was purified by column chromatography using 10~20% EA in PE as eluent to give 92-4 (5.5 g, 27.8%) as a yellow oil. MS: m/z 344.9 [M+H]$^+$.

To a solution of 92-4 (5.5 g, 15.9 mmol) in THF (55 mL) was added Grignard reagent (1 M, 64 mL) dropwise at −78° C. under N$_2$. The mixture was stirred at −78° C. for 1 h. The reaction was quenched with NH$_4$Cl (100 mL) and extracted with DCM (3×150 mL). The combined organic phase was washed with brine (100 mL), dried over anhydrous Na$_2$SO$_4$, filtered and concentrated. The residue was purified by column chromatography using 10~50% EA in PE as eluent to give 92-5 (2.3 g, 37.3%) as colorless oil. MS: m/z 387.0 [M+H]$^+$.

Ozone was bubbled into a solution of 92-5 (5.0 g, 12.9 mmol) in MeOH (30 mL) and DCM (30 mL) at −78° C. for 30 mins. After excess O$_3$ was purged by nitrogen, NaBH$_4$ (2.4 g, 63.9 mmol) was added to the solution at 0° C. The mixture was stirred for 1 h. The reaction was quenched with H$_2$O (100 mL) and extracted with DCM (3×120 mL). The combined organic phase was washed with brine (100 mL), dried with anhydrous Na$_2$SO$_4$, filtered and concentrated. The residue was purified by column chromatography using 50~80% EA in PE as eluent to give 92-6 (2.8 g, 55.4%) as a colorless oil. MS: m/z 391.8 [M+H]$^+$.

To a solution of 92-6 (2.7 g, 7.03 mmol) in MeOH (25 mL) was added HCl/MeOH (4 M, 25 mL). The solution was stirred at 20° C. for 4 h, neutralized with aq. NaHCO$_3$ and extracted with DCM (3×150 mL×3). The combined organic phase was washed with brine (50 mL), dried with anhydrous Na$_2$SO$_4$, filtered and concentrated. The residue was purified by column chromatography using 5~15% MeOH in DCM as eluent to give 92-7 (1.4 g, 80.3%) as a yellow solid. MS: m/z 242.9 [M+H]$^+$.

To a solution of 92-7 (1.4 g, 5.6 mmol) in pyridine (14 mL) was added TMSCl (3.1 g, 27.9 mmol) under N$_2$. The mixture was stirred at 20° C. for 5 h, followed by the addition of CbzCl (1.9 g, 11.2 mmol). The mixture was stirred for 11 h at 20° C. The solution was concentrated, and the residue was purified by column chromatography using 1~10% MeOH in DCM as eluent to give 92-8 (821 mg, 39.1%) as a white solid. MS: m/z 377.0 [M+H]$^+$.

Compound 92 (10 mg, a white solid) was prepared using methods similar to those for preparing 87 from 92-8. MS: m/z 620.1 [M+H]$^+$.

Example 76
Preparation of Compound 93
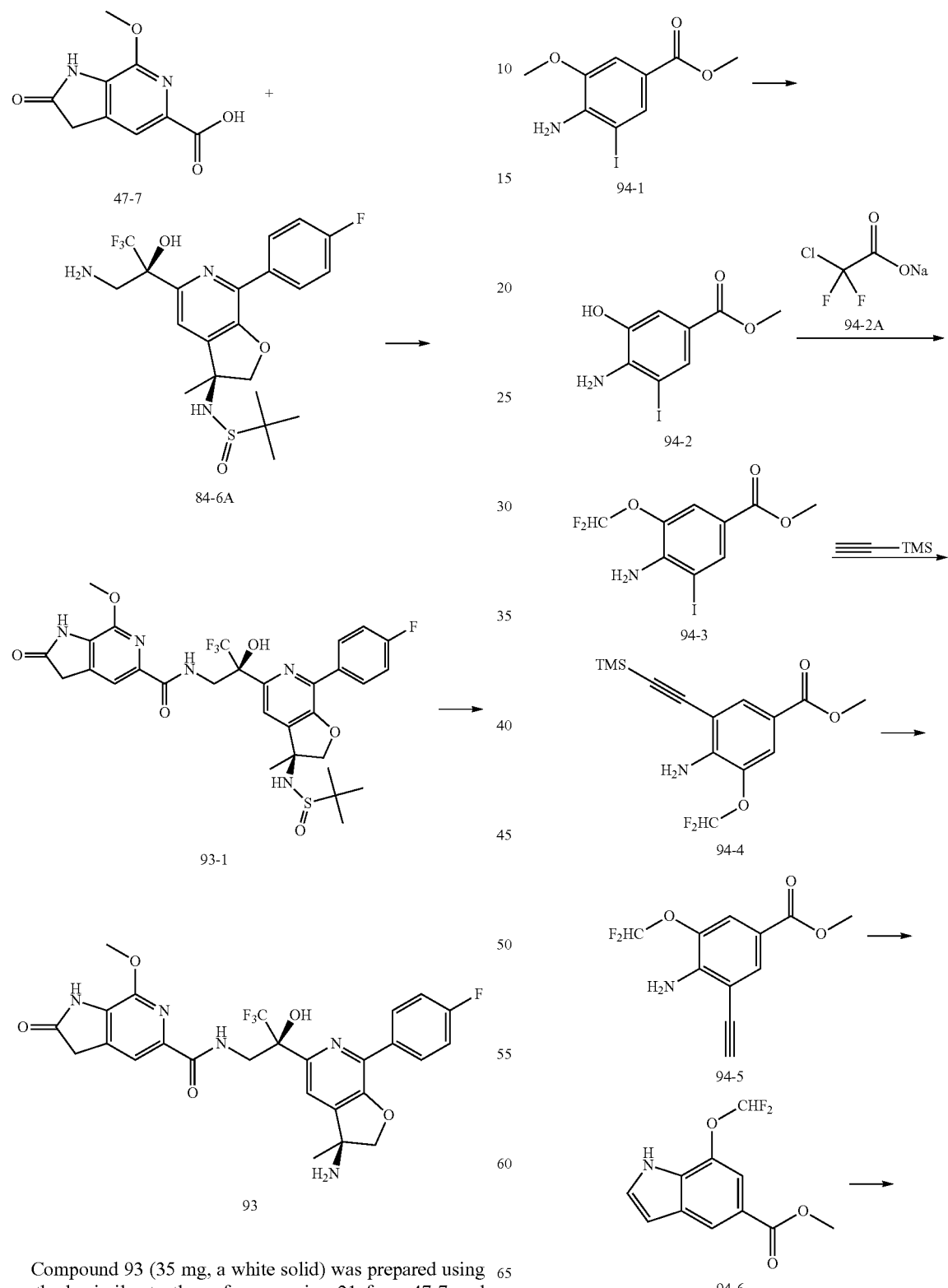
Compound 93 (35 mg, a white solid) was prepared using methods similar to those for preparing 21 from 47-7 and 84-6A. MS: m/z 562.0 [M+H]$^+$.
Example 77
Preparation of Compound 94

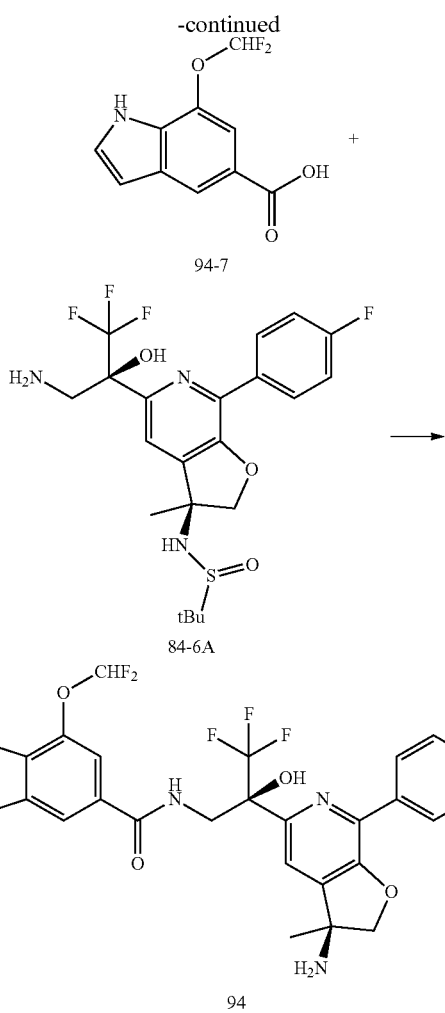

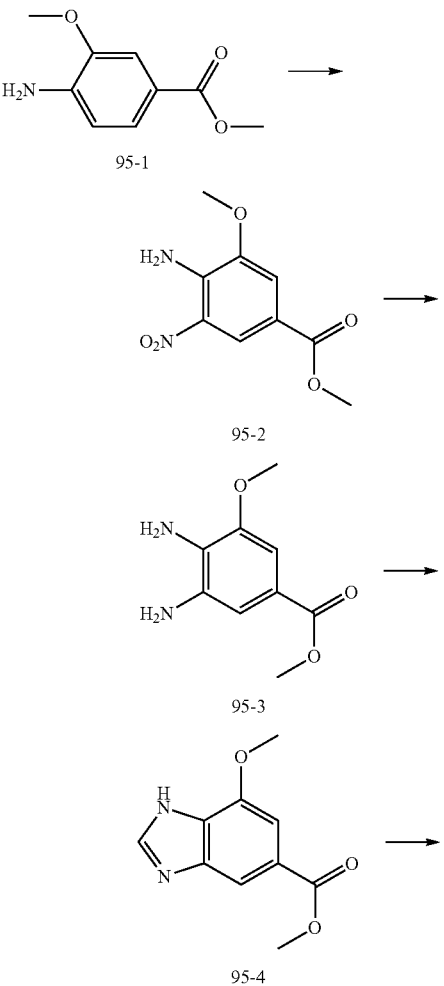

To a solution of 94-4 (1.2 g, 3.8 mmol) in THF (5 mL) was added TBAF (3.0 g, 11.49 mmol). The mixture was stirred at 25° C. for 10 mins, concentrated and purified by column chromatography using 10~40% EA in PE as eluent to give 94-5 (650 mg, 69.2%) as a yellow oil. MS: m/z 241.8 [M+H]$^+$.

A mixture of 94-5 (390 mg, 1.6 mmol) CuI (772 mg, 4.0 mmol) and TBAF (636 mg, 2.4 mmol) in DMF (5 mL) stirred at 120° C. for 30 mins. The reaction was cooled to RT, diluted with H$_2$O (50 mL) and extracted with EA (2×50 mL). The combined organic layers were washed with brine (20 mL), dried over Na$_2$SO$_4$, filtered and concentrated. The residue was purified by column chromatography using 10~50% EA in PE as eluent to give 94-6 (250 mg, 64.2%) as a white solid. MS: m/z 241.8 [M+H]$^+$.

Compound 94 (41 mg, a white solid) was prepared using methods similar to those for preparing 21 from 94-6 and 84-6A. MS: m/z 581.0 [M+H]$^+$.

Example 78

Preparation of Compound 95

To a solution of 94-1 (7.1 g, 23 mmol) in DCM (10 mL) was added BBr$_3$ (3 mL) at 0° C. The mixture was stirred at 0° C. for 30 mins, and the reaction was quenched with aq. NaHCO$_3$ (150 mL) and extracted with EA (300 mL). The organic layer was washed with brine (50 mL), dried over Na$_2$SO$_4$, filtered and concentrated. The residue was purified by column chromatography using 30~80% EA in PE as eluent to give 94-2 (4.8 g, 71.3%) as a yellow oil. MS: m/z 293.8 [M+H]$^+$.

To a solution of 94-2 (4.8 g, 16.4 mmol) in DMF (10 mL) was added Cs$_2$CO$_3$ (16.1 g, 49.1 mmol) and 94-2A (3.8 g, 24.6 mmol). The mixture was stirred at 80° C. for 1 h. The mixture was cooled to RT, diluted with H$_2$O (50 mL) and extracted with EA (2×100 mL). The combined organic layers were washed with brine (50 mL), dried over Na$_2$SO$_4$, filtered and concentrated. The residue was purified by column chromatography using 5~40% EA in PE as eluent to give 94-3 (3.9 g, 69.4%) as a white solid. MS: m/z 343.9 [M+H]$^+$.

A mixture of 94-3 (3.9 g, 11.4 mmol), 94-3A (2.2 g, 22.7 mmol), Et$_3$N (5.8 g, 57 mmol), Pd(PPh$_3$)$_2$Cl$_2$ (399 mg, 0.57 mmol) and CuI (433 mg, 2.27 mmol) in toluene (20 mL) was stirred at 25° C. for 12 h under N$_2$. The mixture was diluted with H$_2$O (50 mL) and extracted with EA (150 mL). The organic layer was dried over Na$_2$SO$_4$, filtered and concentrated. The residue was purified by column chromatography using 10~40% EA in PE as eluent to give 94-4 (2.8 g, 78.6%) as a yellow oil. MS: m/z 313.9 [M+H]$^+$.

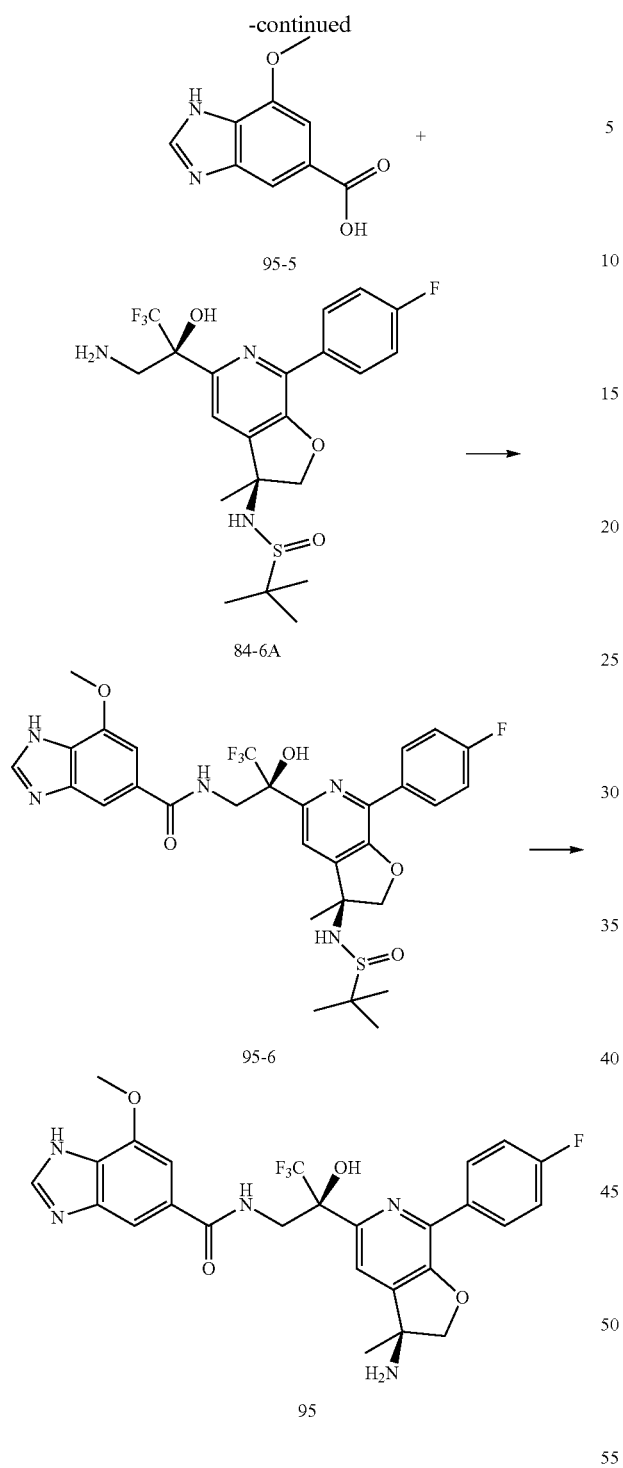

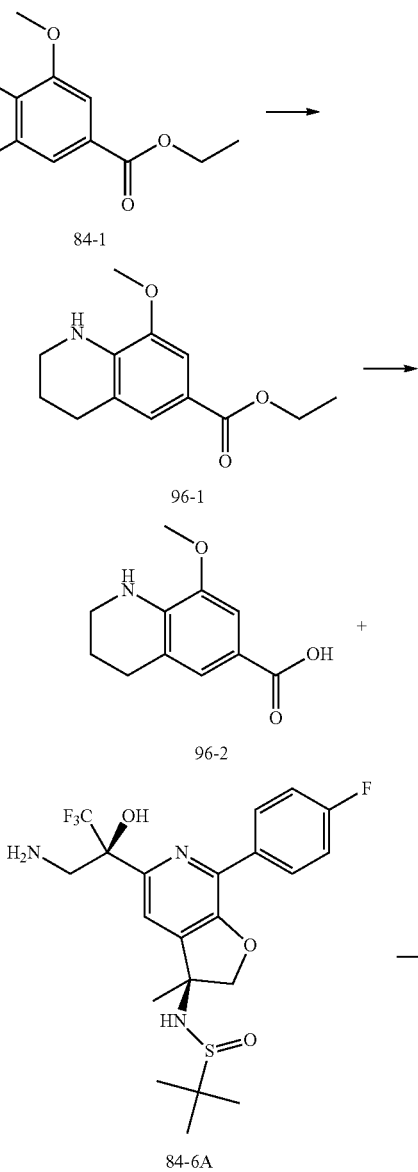

was concentrated. The residue was purified by column chromatography using 50~100% EA in PE as eluent to give 95-3 (900 mg, 69.2%) as a yellow solid. MS: m/z 197.0 [M+H]$^+$.

A mixture of 95-3 (500 mg, 2.55 mmol) in HCOOH (6 mL) was stirred at 100° C. for 12 h. The mixture was concentrated and purified by column chromatography using 2~10% MeOH in DCM as eluent to give 95-4 (120 mg, 22.8%) as a white solid. MS: m/z 207.1 [M+H]$^+$.

Compound 95 (23 mg, a white solid) was prepared using methods similar to those for preparing 21 from 95-4 and 84-6A. MS: m/z 545.9 [M+H]$^+$.

Example 79

Preparation of Compound 96

To a mixture of 95-1 (1.5 g, 8.3 mmol) in TFA (10 mL) was added KNO$_3$ (1.3 g, 12.4 mmol) in portions. The mixture was stirred at 0° C. for 3 h. The reaction was quenched with H$_2$O (80 mL) and extracted with EA (3×50 mL). The organic layer was washed with brine (15 mL), dried over Na$_2$SO$_4$, filtered and concentrated. The residue was purified by column chromatography using 10~60% EA in PE as eluent to give 95-2 (1.5 g, 80.0%) as a yellow solid. MS: m/z 226.9 [M+H]$^+$.

A mixture of 95-2 (1.5 g, 6.6 mmol) and Pd/C (500 mg, 10% purity) in MeOH (15 mL) was stirred under H$_2$ (45 PSI) at 25° C. for 12 h. The mixture was filtered, and the filtrate -continued

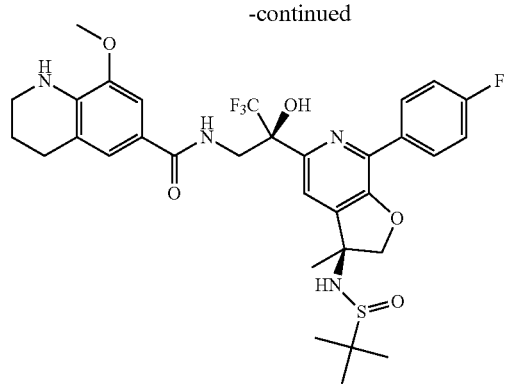

96-3

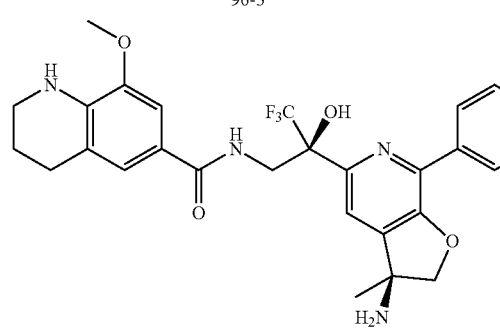

96

A mixture of 84-1 (1.5 g, 5.60 mmol) and Pd/C (500 mg, 10% purity) in MeOH (15 mL) and HCl (1 mL) was stirred under $H_2$ (45 psi) at 25° C. for 12 h. The mixture was filtered, and the filtrate was concentrated. The residue was neutralized by aq. $Na_2CO_3$ and extracted with EA (200 mL). The organic layer was dried over $Na_2SO_4$ and concentrated. The residue was purified by column chromatography using 10~50% EA in PE as eluent to give 96-1 (1.2 g, 91.0%) as a yellow solid. MS: m/z 236.2 [M+H]$^+$.

Compound 95 (38 mg, a light yellow solid) was prepared using methods similar to those for preparing 21 from 96-1 and 84-6A. MS: m/z 561.1 [M+H]$^+$.

Example 80

Preparation of Compound 97

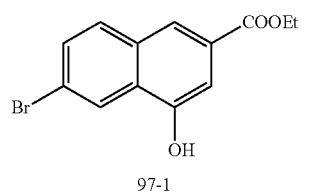

97-1

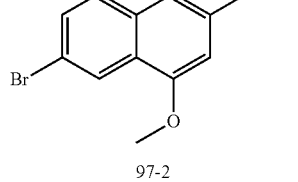

97-2

-continued

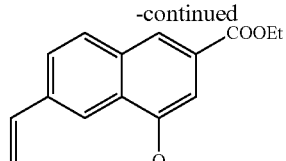

97-3

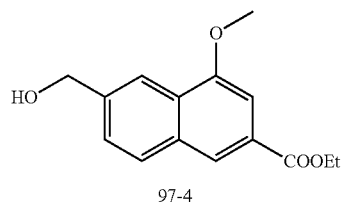

97-4

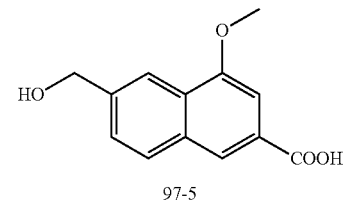

97-5

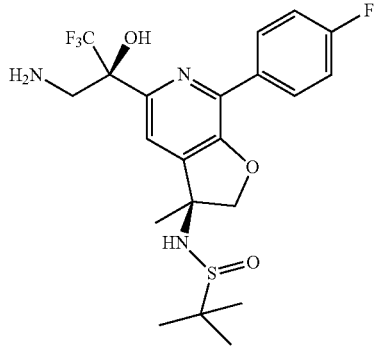

84-6A

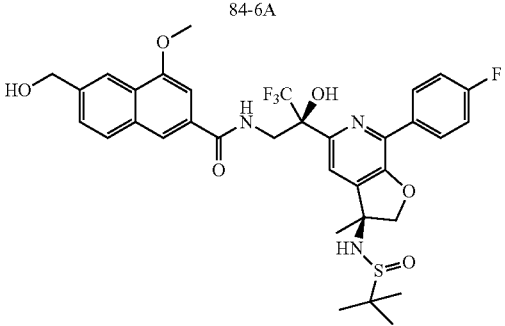

97-6

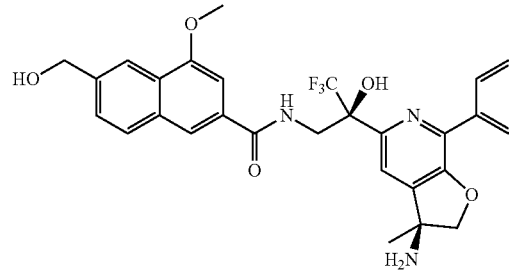

97

Compound 97-1 was prepared using methods similar to those described in US 2003/176506 A1.

To a mixture of 97-1 (2.6 g, 8.8 mmol) in DMF (10 mL) was added NaH (60%, 353 mg, 8.8 mmol) in portions. After stirring for 5 mins, MeI (4.1 g, 28.4 mmol) was added. The mixture was stirred at 50° C. for 1 h and then cooled to RT. The reaction was quenched with H₂O (150 mL) and extracted with EA (150 mL). The organic layer was dried over Na₂SO₄ and concentrated. The residue was purified by column chromatography using 10~15% EA in PE as eluent to give 97-2 (2.2 g, 78.9%) as a white solid.

Compound 97 (39 mg, a light yellow solid) was prepared using methods similar to those for preparing 84 from 97-2 and 84-6A. MS: m/z 601.1 [M+H]⁺.

EA (50 mL). The organic layer was dried over Na₂SO₄, filtered and concentrated to give 98-2 (92 mg, crude) as a white solid. MS: m/z 587.1 [M+H]⁺.

To a solution of 98-2 (91 mg, crude) in AcOH (1 mL) was added zinc powder (70 mg, 1.06 mmol). The mixture was stirred at 70° C. for 1 h. The mixture was cooled to RT, neutralized by aqueous NaHCO₃ and extracted with EA (50 mL). The organic layers was washed with brine (10 mL), dried over Na₂SO₄, filtered and concentrated. The residue was purified by prep-HPLC (HCl condition) to give 98 (21 mg, 31.6%) as a white solid. MS: m/z 597.0 [M+H]⁺.

Example 81

Preparation of Compound 98

Example 82

Preparation of Compound 99

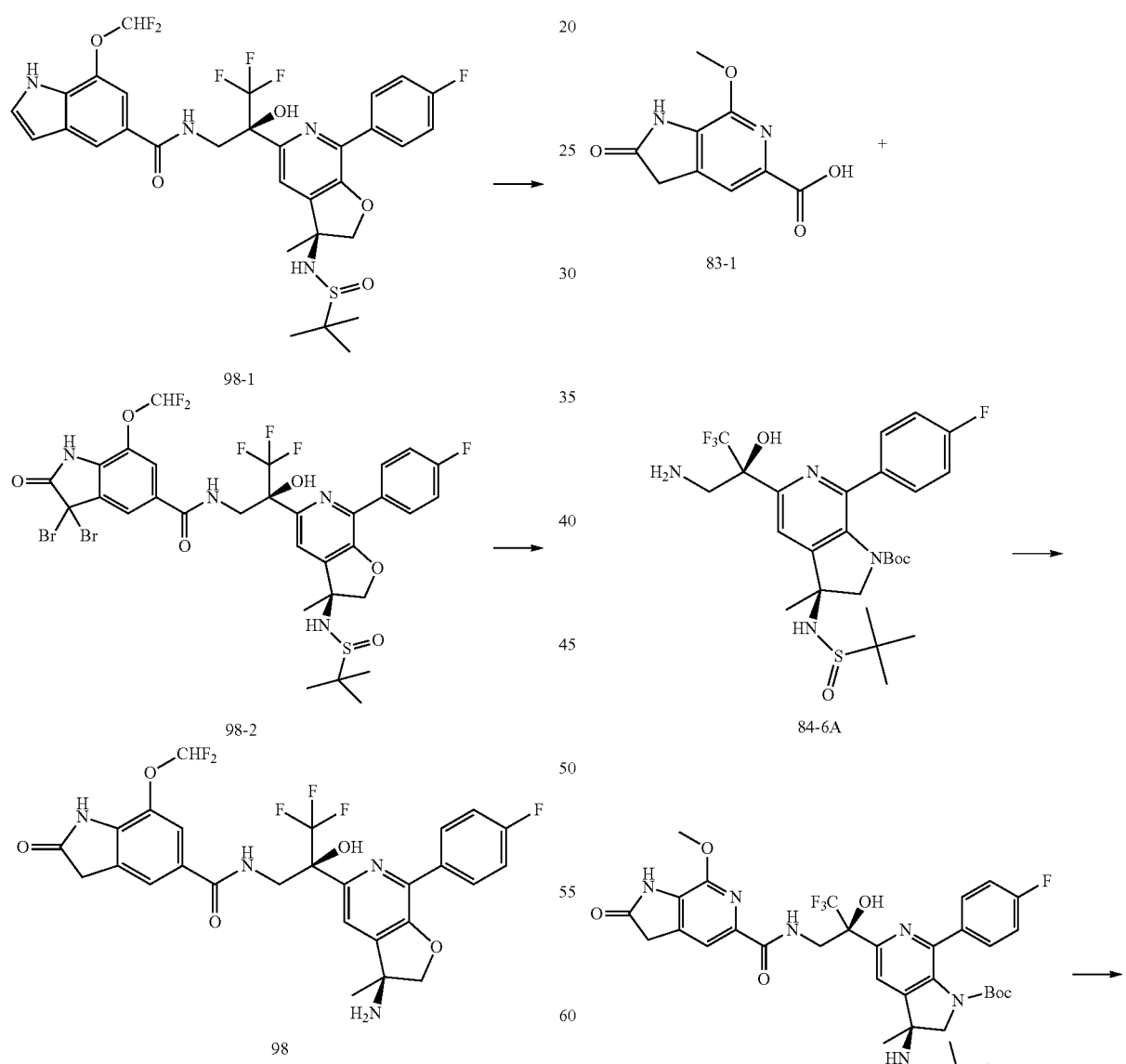

To a mixture of 98-1 (85 mg, 124 umol) in i-PrOH (1 mL) and H₂O (100 μL) was added NBS (110 mg, 620 μmol). The mixture was stirred at 25° C. for 1 h. The reaction was diluted with aqueous NaHCO₃ (30 mL) and extracted with

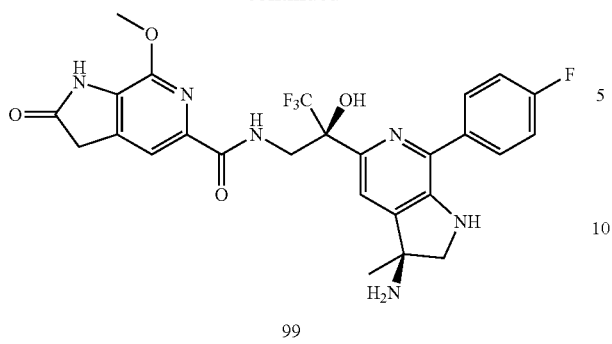
Compound 99 (1.5 mg, a white solid) was prepared using methods similar to those for preparing 21 from 83-1 and 84-6A. MS: m/z 561.0 [M+H]⁺.
Example 83
Preparation of Compounds 100 and 101
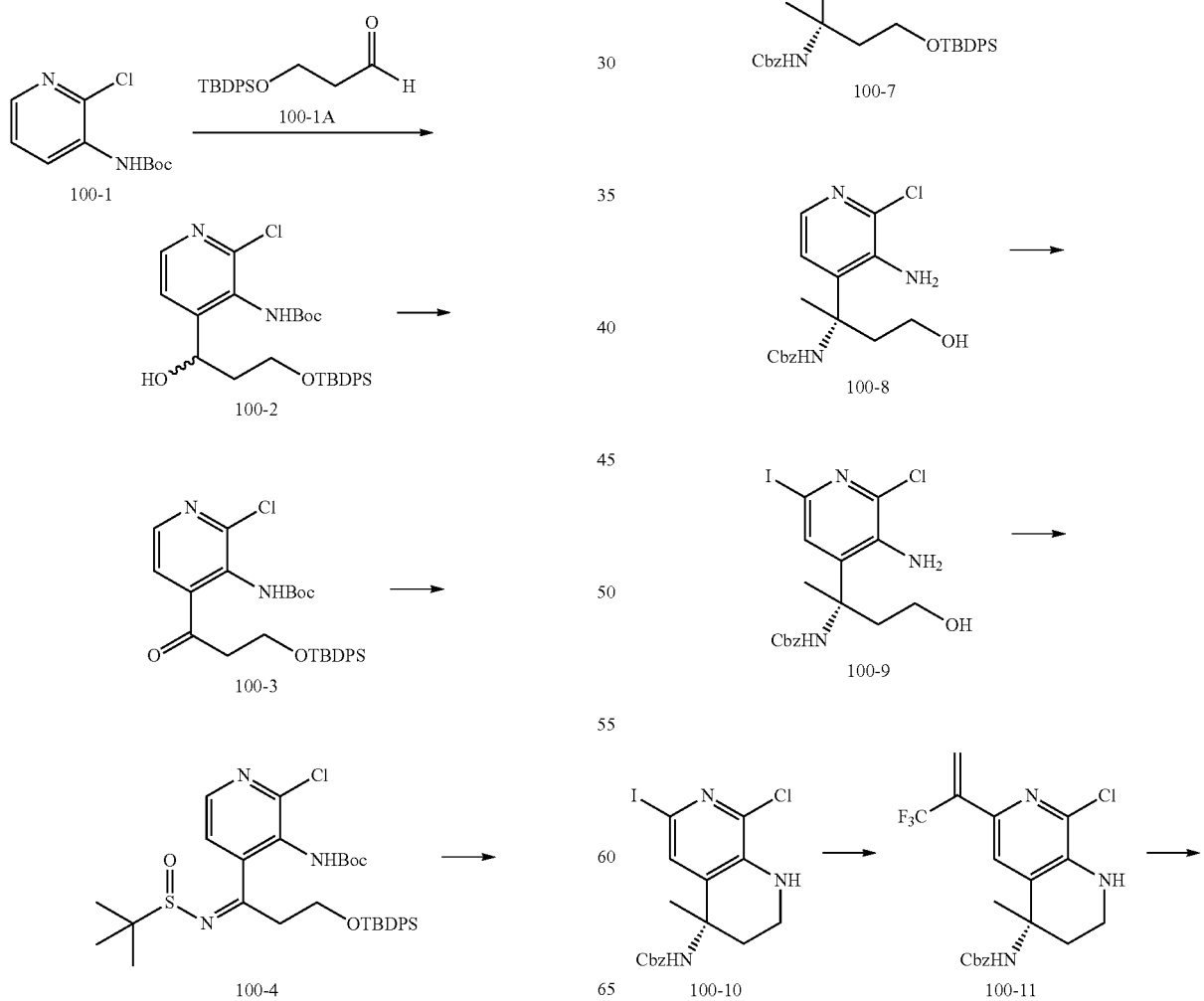

-continued

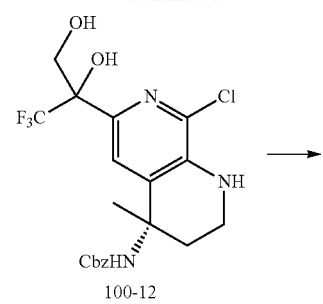

100-12

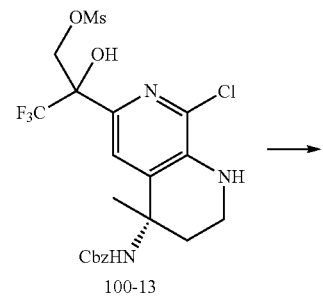

100-13

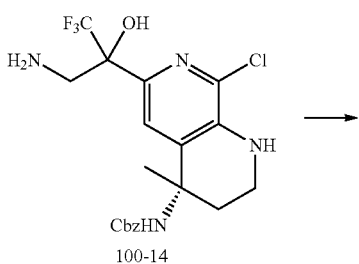

100-14

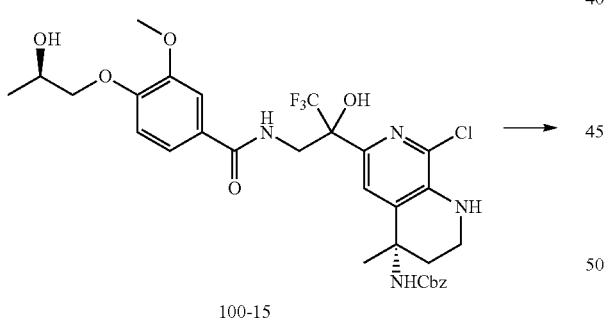

100-15

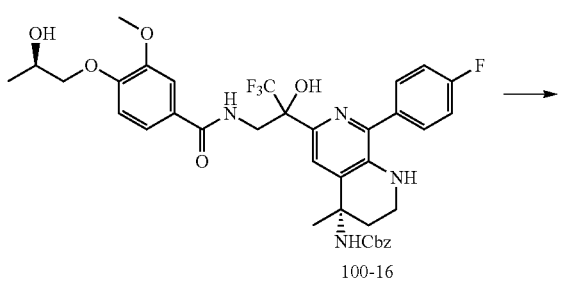

100-16

-continued

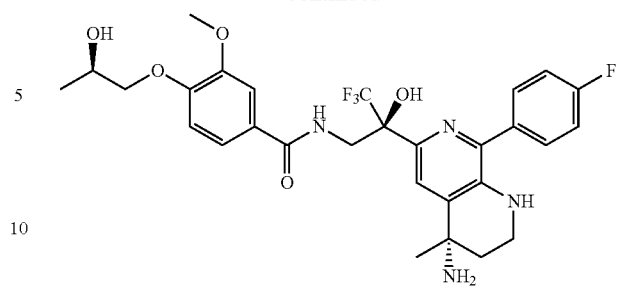

100

+

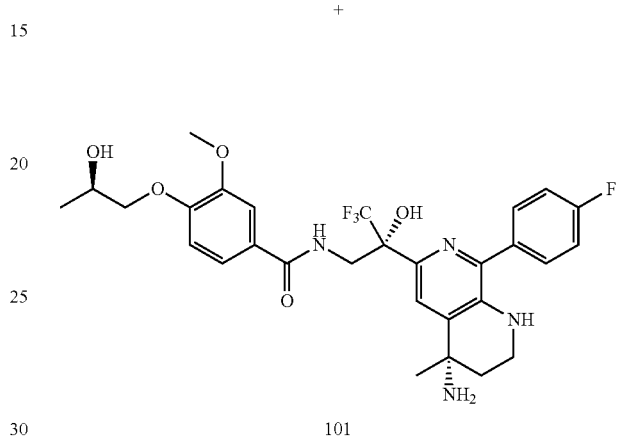

101

Compound 100-1 was prepared using methods similar to those described in Demont et al., Journal of Medicinal Chemistry (2015) 58(14):5649-5673; and compound 100-1A was prepared using methods similar to those described in Barry et al., Organic Letters (2005) 7(13):2683-2686.

Compounds 100 (4.6 mg, a light yellow solid) and 101 (6.5 mg, a light yellow solid) were prepared using methods similar to those for preparing 87 from 100-1 and 100-1A. 100: MS: m/z 593.1 [M+H]$^+$; and 101: MS: m/z 593.1 [M+H]$^+$.

Example 84

Preparation of Compound 102

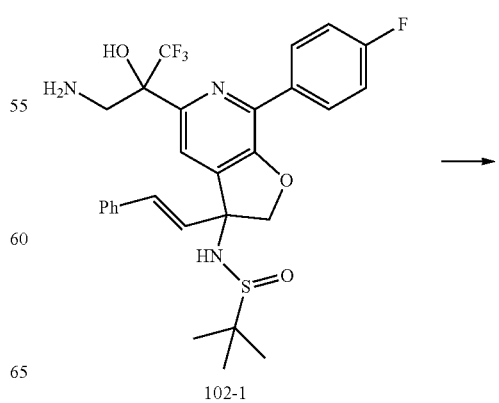

102-1

-continued

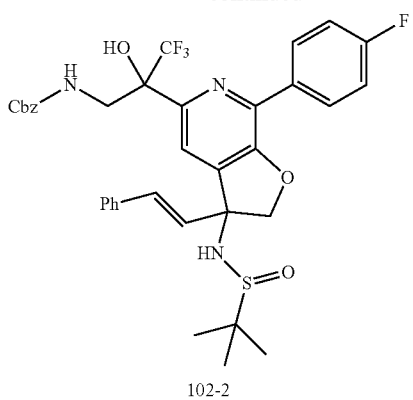

102-2

102-3

102-4

102-5

-continued

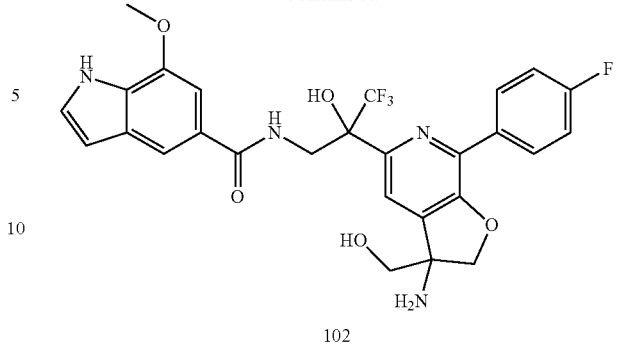

102

Compound 102-1 was prepared using methods similar to those described in WO 2015/26792 A1.

To a mixture of 102-1 (1.8 g, crude) and TEA (646 mg, 6.38 mmol) in DCM (20 mL) was added CbzCl (817 mg, 4.79 mmol) with stirring. The mixture was stirred 25° C. for 1 h. The mixture was then concentrated and purified by column chromatography using 10~100% EA in PE as eluent to give 102-2 (0.95 g) as a white solid. MS: m/z 698.1 [M+H]$^+$.

Ozone was bubbled into a solution of 102-2 (0.95 g) in MeOH (15 mL) at −78° C. for 5 mins. After excess O$_3$ was purged by N$_2$, NaBH$_4$ (163 mg, 4.3 mmol) was added in portions. The mixture was stirred at 25° C. for 10 mins. The reaction was quenched with H$_2$O (100 mL) and extracted with EA (150 mL). The organic layer was washed with brine (10 mL), dried over Na$_2$SO$_4$, filtered and concentrated. The residue was purified by column chromatography using 1~10% MeOH in DCM as eluent to give 102-3 (683 mg, crude) as a colorless oil. MS: m/z 626.0 [M+H]$^+$.

A mixture of 102-3 (680 mg, crude) and Pd/C (300 mg, 10% purity) in MeOH (15 mL) was stirred under H$_2$ (45 PSI) at 50° C. for 12 h. The mixture was filtered, and the filtrate was concentrated to give 102-4 (496 mg, crude) as a colorless oil. MS: m/z 492.0 [M+H]$^+$.

Compound 102 (32 mg, a white solid) was prepared using methods similar to those for preparing 21 from 83-1 and 102-1. MS: m/z 582.9 [M+H]$^+$.

Example 85

Preparation of Compound 103

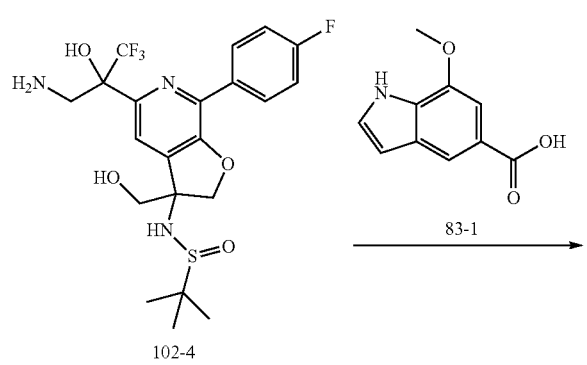

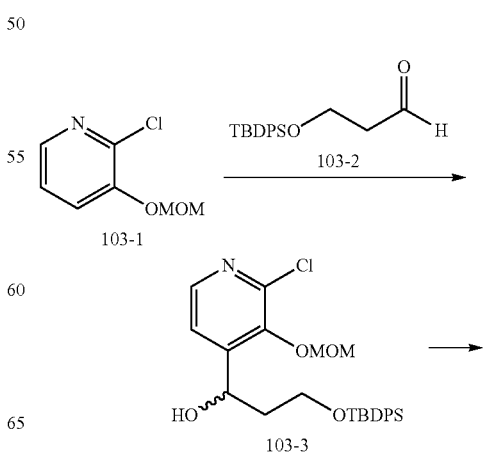

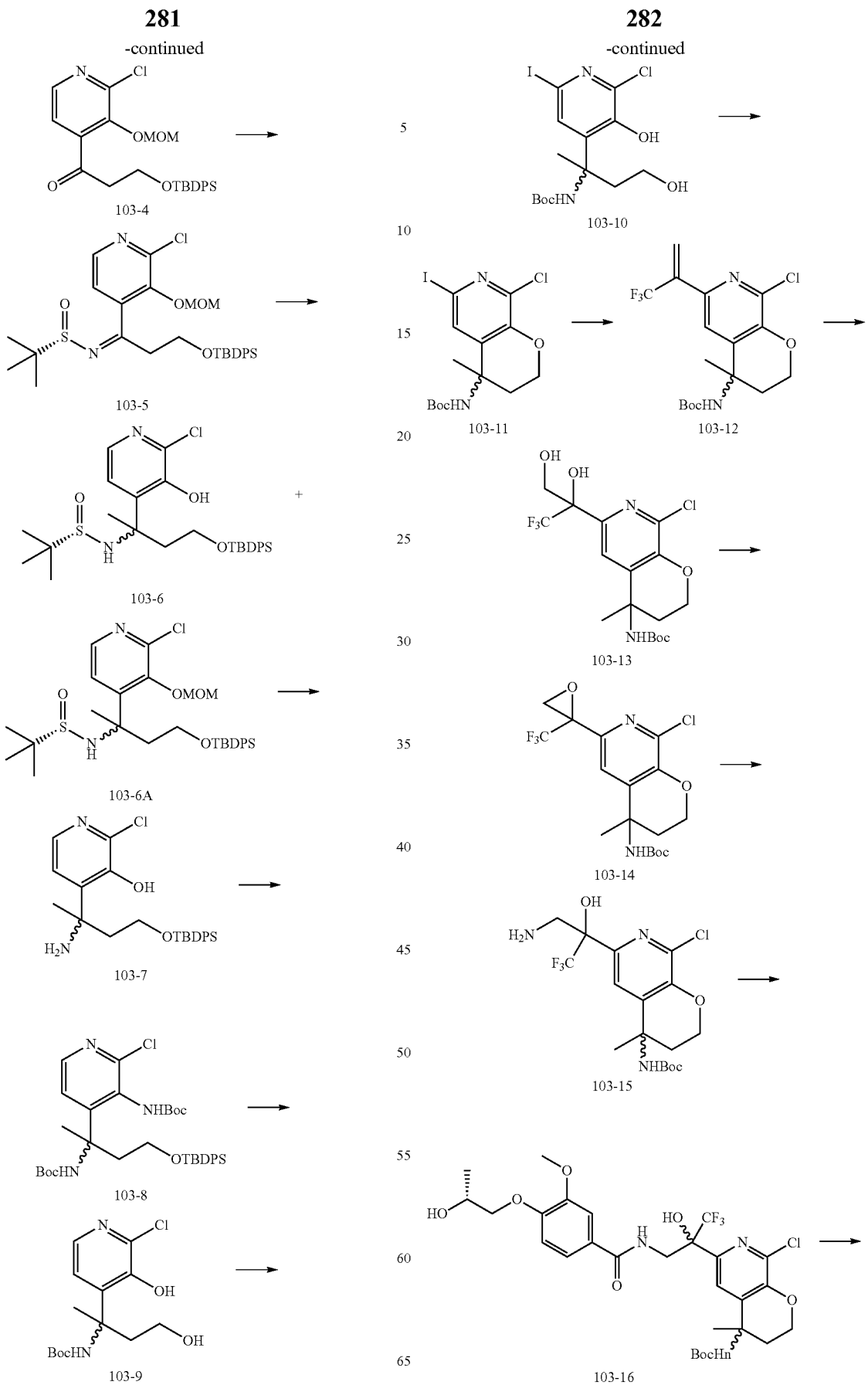

-continued

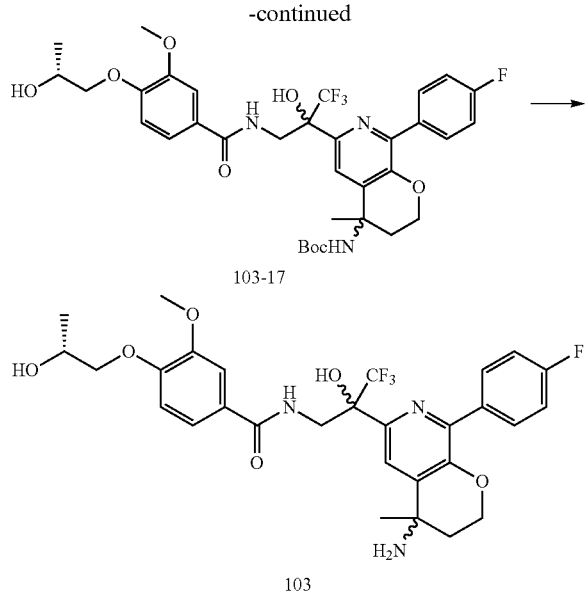

103-17

103

To a stirring mixture of 103-1 (1.7 g, 1.0 eq.) and TMEDA (1.61 mL, 1.05 eq.) in THF (0.5 M) at −78° C. was added dropwise a solution of n-BuLi in hexane (4.3 mL, 1.05 eq., 2.5 M in hexane). The mixture was stirred at −78° C. for 1 h before a solution of aldehyde 103-2 (4.2 g, 1.4 eq.) in THF (1.0 M) was added. The mixture was stirred for 1 h at −78° C. before the reaction was quenched with a sat. NH$_4$Cl solution. The mixture was diluted with EtOAc. A normal work-up with EtOAc was followed. The crude product was purified via a silica gel column to afford the desired product was a colorless oil (4.1 g, 86%). LC/MS 486.15 m/z [M+H]$^+$.

To a stirring mixture of 103-3 (4.1 g, 1.0 eq.) in DCM (28 mL) at RT was added DMP reagent (5.4 g, 1.8 eq.). The mixture was stirred at RT until all of 103-3 was consumed. The reaction was quenched with a sat. NaHCO$_3$ and Na$_2$S$_2$O$_3$ solution. A normal work-up with EtOAc was followed. The crude product was purified via a silica gel column to afford 103-4 (3.34 g). LC/MS 484.2 m/z [M+H]$^+$.

To a stirring mixture of 103-4 (3.34 g, 1.0 eq.) in toluene (0.3 M, deoxygenated prior to use) were added S-sulfinamide (990 mg, 1.2 eq.) and Ti(OEt)$_4$ (3.2 mL, 2.3 eq.). The mixture was stirred at 95° C. for several hours. The mixture was cooled to RT and diluted with toluene. The reaction was quenched with a saturated NaHCO$_3$ solution, and celite was added. The mixture was stirred at RT for 20 mins before it was filtered through a plug of celite. The crude product mixture was purified via a silica gel column to afford 103-5 as a colorless oil. LC/MS 587.2 m/z [M+H]$^+$.

To a stirring mixture of 103-5 (2.6 g, 1.0 eq.) in DCM (17 mL) at −45° C. was added dropwise a solution of MeMgBr in Et$_2$O (7.4 mL, 3.0 M). The mixture was stirred at −45° C. for several hours before the cold bath was removed. The mixture was stirred at RT for 10 mins, and the reaction was slowly quenched with a saturated NH$_4$Cl solution. The mixture was diluted with EtOAc. A normal work-up with EtOAc was followed. The crude product was purified via a silica gel column to afford 103-6 as a reddish oil as the major product, and a small amount of 103-6A. LC/MS 559.2 and 603.2 m/z [M+H]$^+$.

To a stirring mixture of 103-6 and 103-6A (950 mg, 1.0 eq.) in MeOH (10 mL) at RT was added a solution of HCl in dioxane (2 mL, 1.2 eq.). The mixture was stirred for 10 mins before it was concentrated under reduced pressure to afford the crude 103-7. Crude 103-7 was purified via a silica gel column to afford 103-7. LC/MS 455.1 m/z [M+H]$^+$.

To a stirring mixture of 103-7 (470 mg, 1.0 eq.) in DCM (4.1 mL) at 0° C. was added TEA (975 µL) and (Boc)$_2$O (675 mg). The mixture was stirred at 0° C. for 20 mins and warmed to RT. The mixture was stirred at RT for 3 h before it was quenched with a saturated NaHCO$_3$ solution. A normal work-up with EtOAc was followed. The crude product was purified via a silica gel column to afford 103-8 as a colorless oil. LC/MS 555.2 m/z [M+H]$^+$.

To a stirring mixture of 103-8 (280 mg) in THF (2.0 mL) at 0° C. (plastic vial) was added 3HF.TEA (1.3 eq.). The mixture was stirred at RT for 20 mins. The mixture was poured into a cold beaker that contained a saturated NaHCO$_3$ solution. The mixture was diluted with EtOAc and a normal aqueous work with EtOAc was followed. The crude mixture was purified via a silica gel to afford 103-9. LC/MS 317.2 m/z [M+H]$^+$.

To a stirring mixture of 103-9 (88 mg) in DMF (1.0 mL) at RT was added NIS (81 mg). The mixture was stirred at RT for 1 h before it was quenched with a 20% aqueous Na$_2$S$_2$O$_3$ solution. A normal aqueous work up with EtOAc was followed. The crude mixture was purified via a silica gel to afford 103-10. LC/MS 443.0 m/z [M+H]$^+$.

To a stirring mixture of 103-10 (96 mg) in THF (1.0 mL) at RT were added PPh$_3$ (109 mg) and DIAD (110 µL). The mixture was reacted at RT for 1 h before it was concentrated under reduced pressure to afford 103-11. LC/MS 425 m/z [M+H]$^+$.

To a stirring mixture of 103-11 (63 mg) in DME/water (0.15 M, 10:1 deoxygenated prior to use) were added boronic ester (34 mg), Cs$_2$CO$_3$ (110 mg) and PdCl$_2$(dppf) (23 mg). The mixture was carried out under microwave irradiation reaction at 110° C. for 45 mins. The mixture was diluted with water and EtOAc. A normal aqueous work up with EtOAc was followed. The crude mixture was purified via a silica gel to afford 103-12. LC/MS 393.2 m/z [M+H]$^+$.

To a stirring mixture of 103-12 (43 mg) in t-BuOH/water (0.5 mL each) were added NMO (65 mg) and K$_2$OsO$_4$.2H$_2$O (12 mg). The mixture was stirred at RT overnight. The reaction was quenched with a saturated Na$_2$S$_2$O$_3$ solution and diluted with EtOAc. A normal aqueous work up with EtOAc was followed. The crude mixture was purified via a silica gel to afford 103-13. LC/MS 427.1 m/z [M+H]$^+$.

To a stirring mixture of 103-13 (36 mg) in THF (1.0 mL) at 0° C. was added NaH (8.5 mg, 60% by weight). The mixture was stirred at 0° C. for 30 mins before TsCl (19.3 mg) was added. The mixture was stirred for 30 mins and quickly warmed to RT for 5 mins. The reaction was quenched with water and diluted with EtOAc. A normal aqueous work up with EtOAc was followed. The crude mixture was purified via a silica gel to afford 103-14. LC/MS 409.1 m/z [M+H]$^+$.

To a stirring mixture of 103-14 (26 mg) in DMF (0.96 mL) at RT was added NH$_4$OH (20 µL). The mixture was stirred at RT until all the starting material was consumed. The reaction was quenched with water and diluted with EtOAc. A normal aqueous work up with EtOAc was followed. The crude mixture (containing 103-15) was taken directly to the next reaction without further purification. LC/MS 426.1 m/z [M+H]$^+$.

To a stirring mixture of acid (21 mg), HATU (38 mg) in DMF (1.0 mL) at RT was added DIPEA (26 µL). The mixture was stirred for 10 mins before a solution of crude 103-15 in DMF (0.5 mL) was added. The mixture was stirred for 20 mins. The reaction was quenched with a 10% aqueous NaHCO₃ solution and diluted with EtOAc. A normal aqueous work up with EtOAc was followed. The crude mixture was purified via a silica gel and then further purified via HPLC to afford 103-16. LC/MS 634.1 m/z [M+H]⁺.

To a stirring mixture of 103-16 (13 mg) in DME (1.5 mL/0.1 mL, 10:1, deoxygenated prior to use) were added boronic acid (12 mg), Cs₂CO₃ (34 mg), and PdCl₂(dppf) (13.2 mg). The mixture was carried out under microwave irradiation reaction at 110° C. for 2 h. The mixture was diluted with water and EtOAc. A normal aqueous work up with EtOAc was followed. The crude mixture was purified via a silica gel to afford 103-17. LC/MS 694.3 m/z [M+H]⁺.

Compound 103-17 was dissolved in a solution of HCl in dioxane (5 mL). The mixture was stirred at RT for several hours until all the starting material was consumed. The crude product mixture was concentrated under reduced pressure and purified via HPLC to afford 103 as a white solid. LCMS 594.1 m/z [M+H]⁺.

Example 86

Preparation of Compound 104

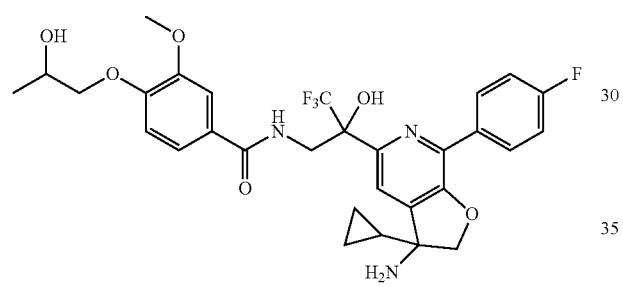

Compound 104 was prepared using methods similar to those for preparing compound 539 of US 2015/0065504. LCMS: 606.2 m/z [M+H]⁺.

Example 87

Preparation of Compound 105

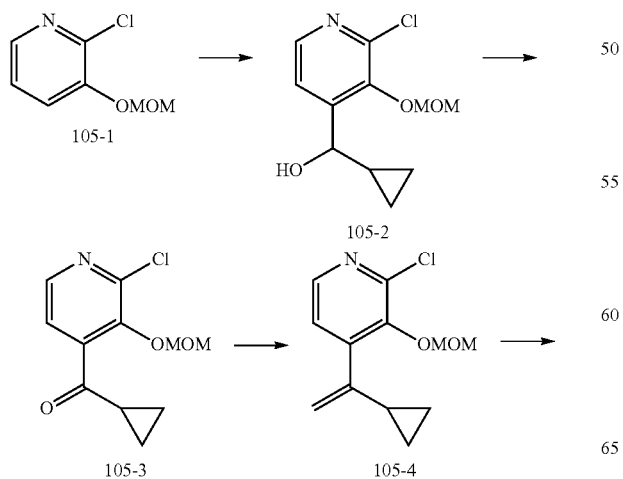

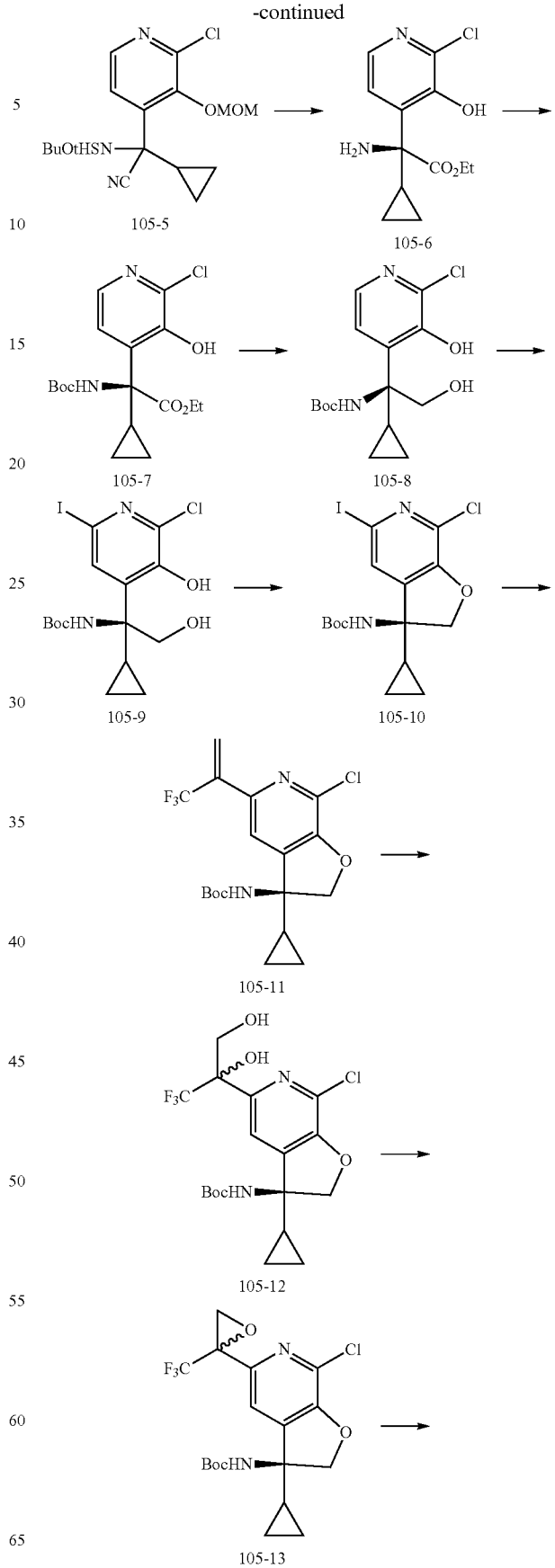

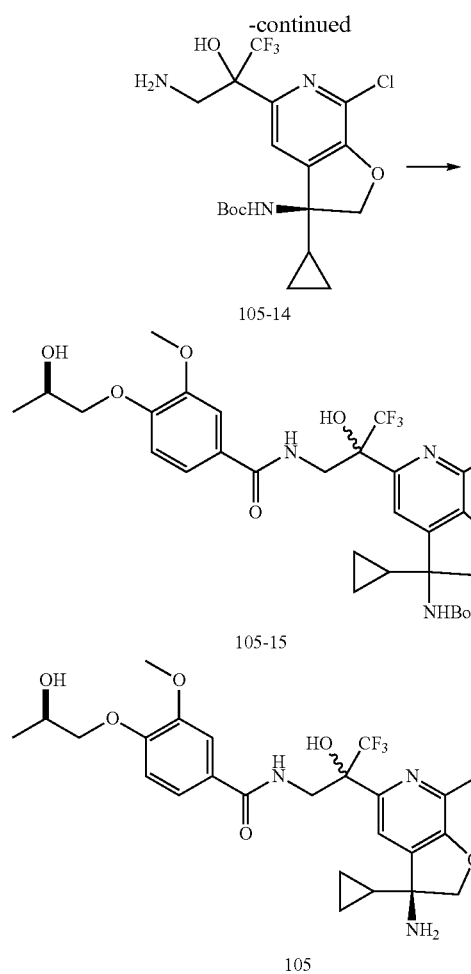

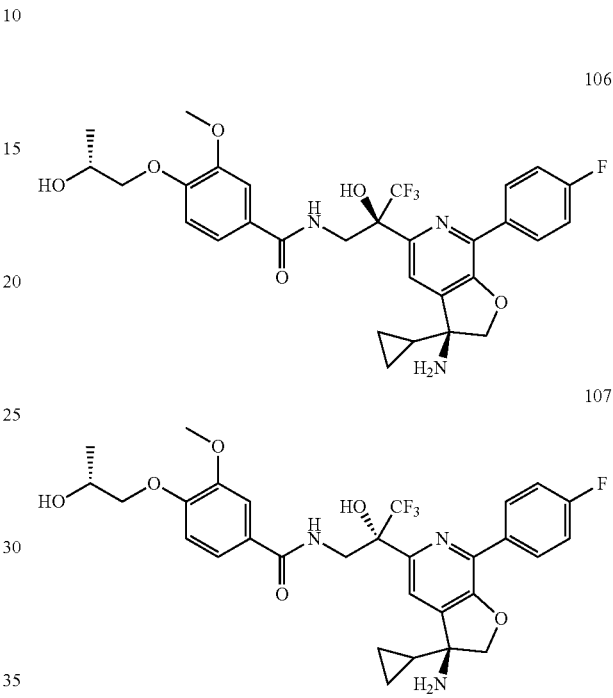

Compound 105-2 was prepared using methods similar to those for preparing 103-3. LCMS: 244.0 m/z [M+H]⁺. Compound 105-3 was prepared using methods similar to those for preparing 103-4. LCMS: 242.1 m/z [M+H]⁺. Compound 105-4 was prepared using methods similar to those for preparing 103-5. LCMS: 345.1 m/z [M+H]⁺.

To a stirring mixture of $Et_2AlCN$ in toluene (12.4 mL, 1.0 M) in DCM (10.5 mL) at 0° C. was added iPrOH (0.95 mL). The mixture was stirred at 0° C. for 10 mins and quickly warmed up to RT. The mixture was stirred for 1 h and then cooled to 0° C. To this mixture was added a solution of 105-4 (1.07 g, 3.11 mmol) in DCM (2 mL). The mixture was stirred at 0° C. for 3 h before it was warmed up to RT overnight. The reaction was quenched slowly with $Na_2SO_4 \cdot 10H_2O$. The mixture was stirred at RT for 20 mins before it was filtered through a plug of celite. The crude product was concentrated under reduced pressure and purified via a silica gel column to afford the desired product as a colorless oil. LC/MS: 371.95 m/z [M+H]⁺.

Compound 105-7 was prepared using methods similar to those for preparing 103-7 and 103-8. LCMS: 371.1 m/z [M+H]⁺.

To a stirring mixture of 105-7 (320 mg, 1 eq.) in THF (3 mL) at RT was added dropwise a solution of $LiBH_4$ (3.4 mL) in THF. The mixture was stirred at RT for several hours before it was quenched with a saturated $NH_4Cl$ solution at RT. The mixture was heated at reflux for 2 mins before it was cooled to RT and diluted with EtOAc. A normal aqueous workup with EtOAc was followed. The crude product was purified via a silica gel column to afford 105-8 as a colorless oil. LC/MS: 327.1 m/z [M+H]⁺.

Compound 105 was prepared using methods similar to those for preparing 103. LCMS 606.1 m/z [M+H]⁺.

Example 88

Preparation of Compounds 106 and 107

The racemic mixture of 105 (115 mg) was separated by SFC using as follows: Column: Chiralpak AD-3 150×4.6 mm I.D., 3 µm Mobile phase: A: $CO_2$ B:iso-propanol (0.05% DEA), Gradient: from 5% to 40% of B in 5.0 mins and hold 40% for 2.5 mins, then 5% of B for 2.5 mins Flow rate: 2.5 mL/mins. After SFC separation, the solution was concentrated and re-purified by prep-HPLC (HCl condition) to give 106 (12 mg, 10.4%) as a white solid and 107 (13 mg, 10.5%) as a white solid. 106: MS: m/z 628.0 [M+Na]⁺. 107: MS: m/z 628.0 [M+Na]⁺. Compounds 106 and 107 are shown above with relative stereochemistry arbitrarily assigned.

Example 89

Preparation of Compound 108

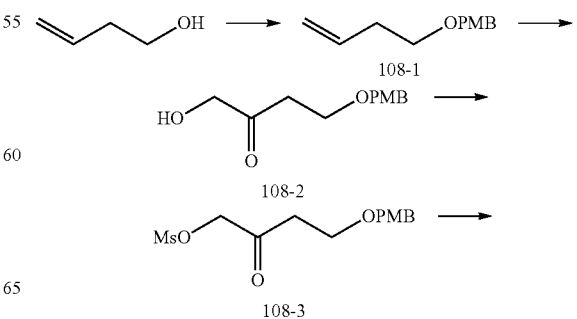

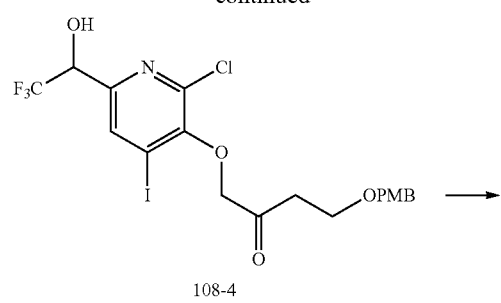
108-4
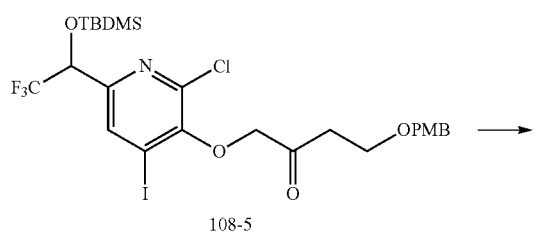
108-5
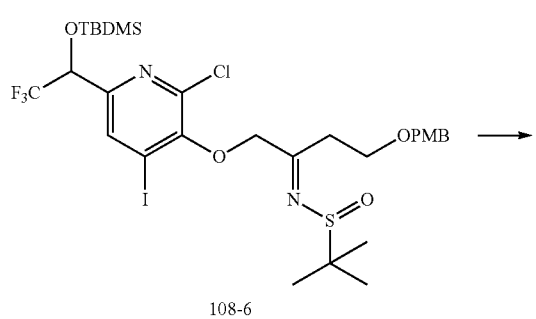
108-6
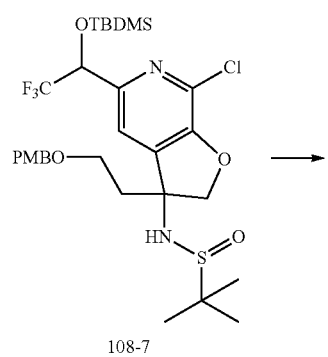
108-7
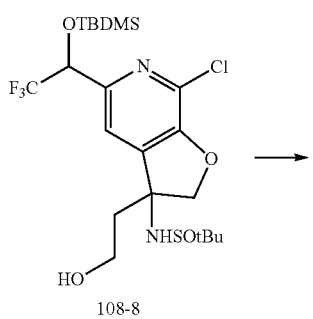
108-8
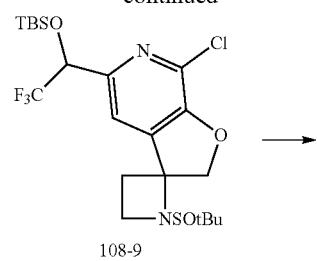
108-9
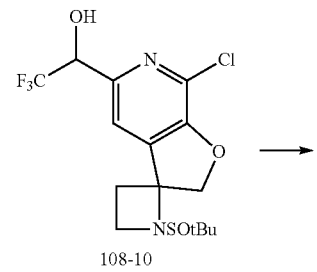
108-10
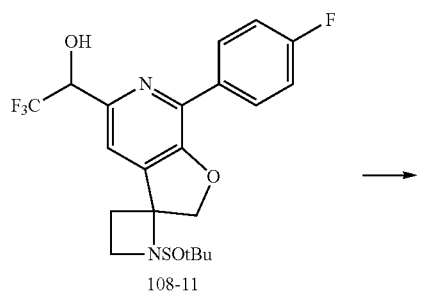
108-11
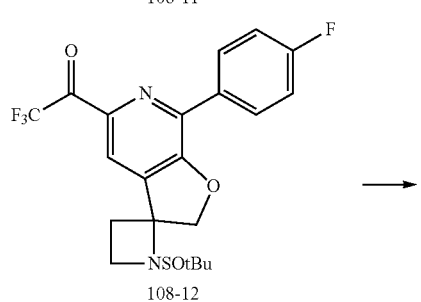
108-12
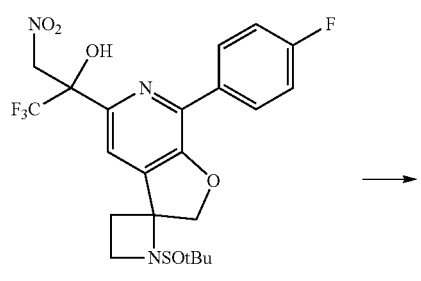
108-13
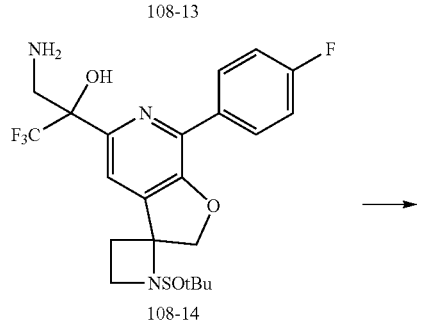
108-14

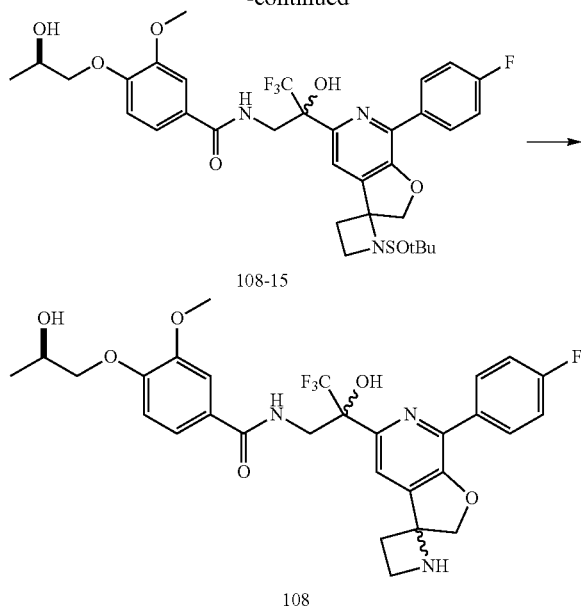

3-Butene-1-ol (2.0 mL, 23 mmol) was added dropwise to a solution of sodium hydride (1.0 g, 26 mmol) in THF at 0° C., and the solution was stirred at RT for 30 mins. Tetrabutylammonium iodide (0.85 g, 2.3 mmol) and para-methoxybenzyl chloride (3.3 mL, 30 mmol) were added, and the reaction was stirred overnight. The reaction was quenched with NH$_4$Cl and extracted with EA. The organic layer was washed with brine, dried and concentrated. 108-1 (1.69 g, 26%) was purified by flash chromatography (hexane:EA). $^1$H NMR (400 MHz, CDCl$_3$): δ 7.24 (d, J=8.8, 2H), 6.56 (d, J=8.8, 2H), 5.78-5.85 (m, 1H), 5.00-5.10 (m, 1H), 4.44 (s, 2H), 3.78 (s, 3H), 3.58 (7, J=6.4 2H), 2.32-2.37 (m, 2H).

Potassium permanganate (1.08 g, 6.8 mmol) in acetone (12.8 mL) and water (4.2 mL) was added dropwise to a solution of 108-1 (0.82 g, 4.3 mmol) in acetone (34 mL), water (7.6 mL) and acetic acid (1.6 mL). The solution was stirred at RT for 3 h. EtOH (1 mL) was added, and the solids were removed by filtration. The reaction was concentrated. The residue was dissolved in EA, washed with sodium bicarbonate and brine, dried and concentrated to afford 108-2 (0.34 g, 35%). $^1$H NMR (400 MHz, CDCl$_3$): δ 7.22 (2, J=8.8, 2H), 6.85 (d, J=8.8, 2H), 4.42 (s, 2H), 4.25 (d, J=4.0, 2H), 3.78 (s, 3H), 3.72 (t, j=6.0, 2H), 2.65 (t, J=6.0, 2H).

Methanesulfonyl chloride (1.8 mL, 23 mmol) was added dropwise to a solution of 108-2 (2.0 g, 19 mmol) and DIEA (5.0 mL, 29 mmol) in dichloromethane (100 mL) at 0° C., and the reaction was stirred at RT for 1 h. The reaction was diluted with EA, washed with 1N HCl and brine, dried and concentrated. 108-3 (1.25 g) was purified by flash chromatography (hexane:EA). $^1$H NMR (400 MHz, CDCl$_3$): δ 7.21 (d, J=8.8, 2H), 6.87 (d, J=8.8, 2H), 4.82 (s, 2H), 4.42 (s, 2H), 3.78 (s, 3H), 3.70 (t, J=6.0 2H), 3.14 (s, 3H), 2.68 (t, J=6.0, 3H).

Compound 108-4 was prepared using similar method for preparing 50-2. LC/MS: m/z 559.95 [M+H]$^+$. Compound 108-5 was prepared using methods similar to those for preparing 34. LC/MS: m/z 674.10 [M+H]$^+$. Compound 108-6 was prepared using similar method for preparing 50-3. LC/MS: m/z 777.10 [M+H]$^+$. Compound 108-7 was prepared using similar method for preparing 50-4. LC/MS: m/z 651.20 [M+H]$^+$.

To a stirring mixture of 108-7 (410 mg, 1.0 eq.) in dichloromethane:water (9 mL:0.4 mL) at RT was added DDQ (286 mg, 2.0 eq.). The mixture was stirred for 1 h. An additional 1 equivalent of DDQ was added. The mixture was stirred for 1 h. The reaction was quenched with a saturated NaHCO$_3$ solution. A normal aqueous work up with DCM was followed. The crude product mixture was purified via a silica gel column to afford 108-8 (220 mg, 66%) as a colorless oil. LC/MS: m/z 531.2 [M+H]$^+$.

To a stirring mixture of 108-8 (210 mg, 1 eq.) in THF (5.6 mL) at RT was added PPh$_3$ (155 mg, 1.5 eq.) followed by DIAD (156 μL, 2 eq.). The mixture was heated at reflux for 1 h. The mixture was concentrated under reduced pressure and purified via a silica gel column to afford 108-9 as a colorless oil. LC/MS: m/z 513.2 [M+H]$^+$.

To a stirring mixture of 108-9 (168 mg, 1 eq.) in THF (3.2 mL) at RT was added a solution of TBAF (632 μL, 2 eq.). The mixture was stirred at RT for 30 mins. The mixture was diluted with EtOAc and quenched a saturated NaHCO$_3$ solution. A normal aqueous workup with EtOAc was followed, and the crude product mixture was purified via a silica gel column to afford 108-10 as a white solid (100 mg, 80%). LC/MS: m/z 399.1 [M+H]$^+$.

To stirring mixture of 108-10 (100 mg, 1 eq.) in DME:water (1.5 mL:0.4 mL, deoxygenated prior to use) were added (4-fluorophenyl)boronic acid (53 mg, 1.5 eq.), PdCl$_2$(dppf) (55 mg, 0.075 eq.), and Cs$_2$CO$_3$ (325 mg, 4 eq.). The mixture was carried under a microwave irradiation condition at 110° C. for 2 h. The mixture was concentrated under reduced pressure and purified via a silica gel column to afford 108-11 as a white foam. LC/MS: m/z 459.1 [M+H]$^+$.

To a stirring mixture of 108-11 (70 mg, 1 eq.) in DCM (1.8 mL) at RT was added DMP (77 mg, 1.2 eq.). The mixture was stirred at RT for 20 mins before it was quenched with a 10% Na$_2$S$_2$O$_3$ solution and a saturated NaHCO$_3$ solution. A normal aqueous work up with DCM was followed. The crude product was purified via a silica gel column to afford 108-12. LC/MS: m/z 475.1 [M+H+H$_2$O]$^+$.

To a stirring mixture of 108-12 (60 mg, 1 eq.) in MeNO$_2$ (0.5 mL) at RT was added Et$_3$N (25 μL). The mixture was stirred at RT for 30 mins before it was directly loaded into a silica gel column to afford 108-13 as a white solid (45 mg, 70%). LCMS: m/z 518.1 [M+H]$^+$.

To a stirring mixture of 108-13 (35 mg, 1 eq.) in MeOH (0.45 mL) at 0° C. were added NaBH$_4$ (31 mg) and NiCl$_2$.6H$_2$O (16.1 mg). The mixture was stirred at 0° C. for 15 mins before it was quenched with a saturated NaHCO$_3$ solution and diluted with EtOAc. A normal aqueous work up with EtOAc was followed, and the crude product was purified via a silica gel column to afford 108-14 as a white solid (28 mg, 85%). LC/MS: m/z 488.0 [M+H]$^+$.

To a stirring mixture of (R)-4-(2-hydroxypropoxy)-3-methoxybenzoic acid (12 mg, 1.0 eq.) in DMF (0.26 mL) at RT were added HATU (20 mg, 1 eq.) and DIPEA (20 μL, 2 eq.). The mixture was stirred at RT for 20 mins before a solution of 108-14 (25 mg, 1 eq.) in DMF (0.25 mL) was added. The mixture was stirred at RT for 15 mins before it was quenched with a 10% aq. NaHCO$_3$ solution and diluted with DCM. A normal aqueous work up with DCM was followed. The crude product was purified via HPLC column to afford 108-15 as a white solid (20 mg, 56%). LC/MS: 696.2 m/z [M+H]$^+$.

To a stirring mixture of 108-15 (20 mg) in MeOH (1.0 mL) was added a solution of HCl in dioxane (0.2 mL). The mixture was stirred at RT for 10 mins before it was con-

Example 90

Preparation of Compound 109

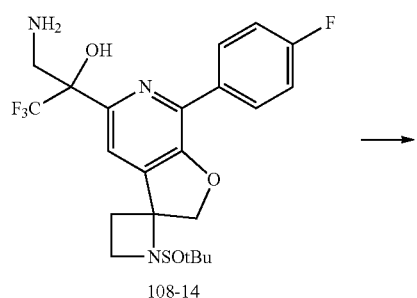

108-14

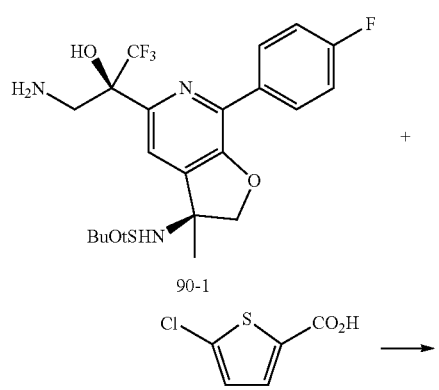

109

Compound 108-14 was coupled with 4-(2-hydroxyethoxy)-3-methoxybenzoic using methods similar to those for preparing 108 to afford 109 as a white solid. LC/MS: m/z 578.1 [M+H]⁺.

Example 91

Preparation of Compound 110

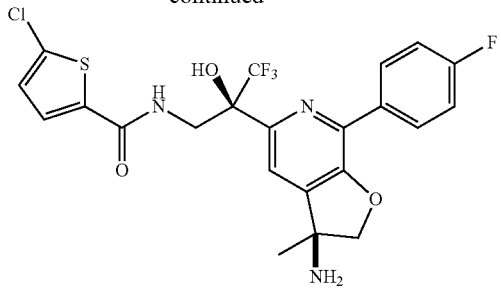

110

Compound 90-1 was coupled with 5-chlorothiophene-2-carboxylic acid using methods similar to those for preparing 108 to afford 110 as a white solid. LC/MS: m/z 516.0 [M+H]⁺.

Example 92

Preparation of Compound 111

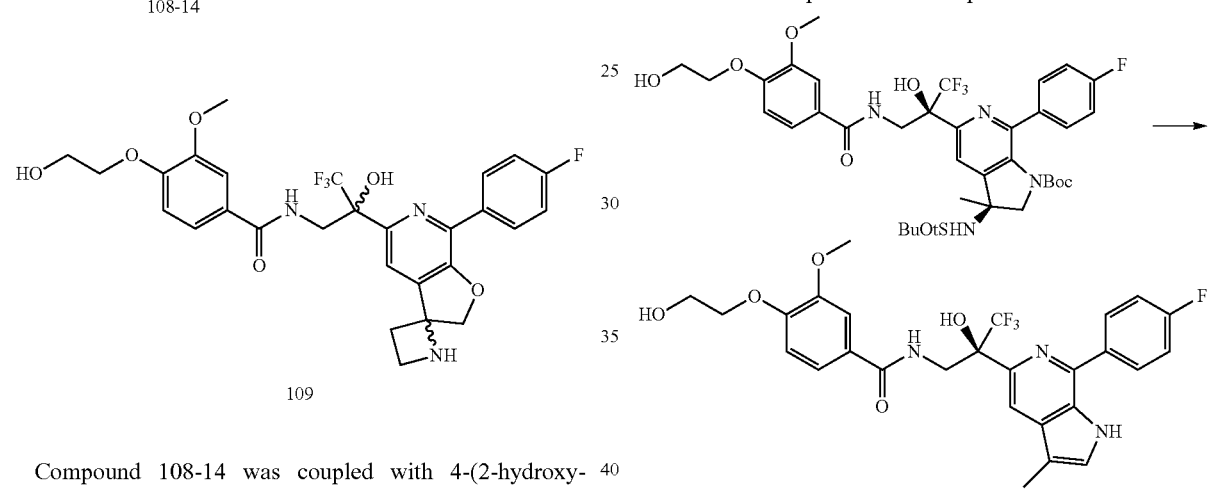

111

Compound 111 was obtained as a byproduct during the deprotection step using HCl in MeOH of 51. LCMS: 548.0 m/z [M+H]⁺.

Example 93

Preparation of Compound 16

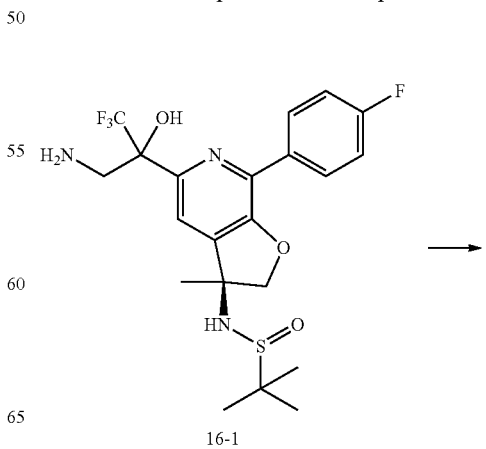

16-1

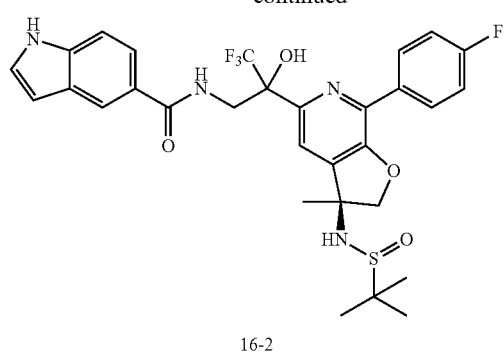

16-2

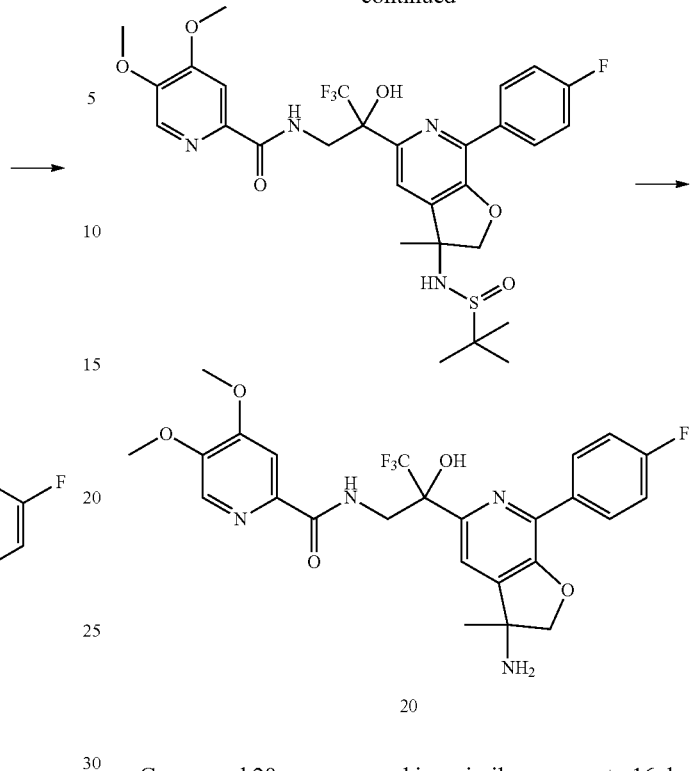

16

Triethylamine (35 μL, 0.25 mmol) was added to a solution of 16-1 (40 mg, 0.084 mmol), indole-5-acetic acid (27 mg, 0.17 mmol) and HATU (67 mg, 0.18 mmol) in DMF (1 mL). The reaction was stirred at RT for 1 h. The crude reaction product was purified by HPLC to afford 16-2 (41 mg, 78%). LC/MS: m/z 619.20 [M+H]$^+$.

HCl in dioxane (4N, 0.2 mL) was added to a solution of 16-2 (41 mg, 0.066 mmol) in methanol (1 mL), and the reaction was stirred at RT for 10 mins. The reaction was concentrated, and the crude product purified by HPLC to afford 16 (35.4 mg, 95%). LC/MS: m/z 515.15 [M+H]$^+$.

Example 94

Preparation of Compound 20

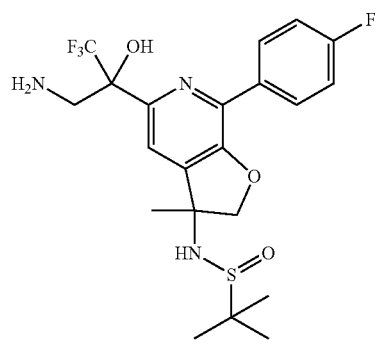

20

Compound 20 was prepared in a similar manner to 16, by substituting 4,5-dimethoxypicolinic acid in the coupling step. LC/MS: m/z 537.15 [M+H]$^+$.

Example 95

Preparation of Compound 112

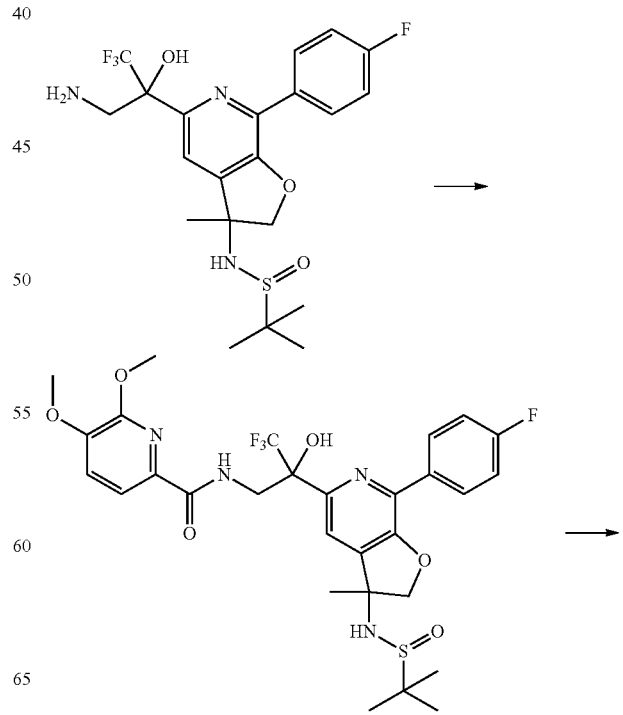

-continued

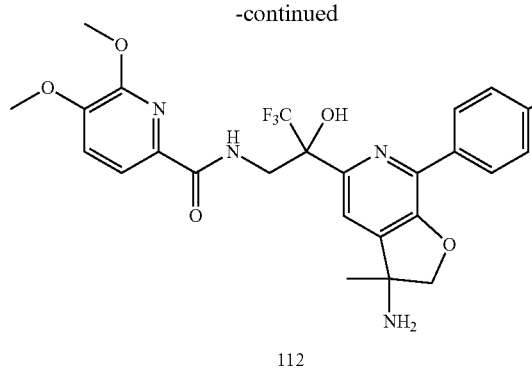

112

Compound 112 was prepared in a similar manner to 16, by substituting 5,6-dimethoxypicolinic acid in the coupling step. LC/MS: 537.15 [M+H]⁺.

Example 96

Preparation of Compound 113

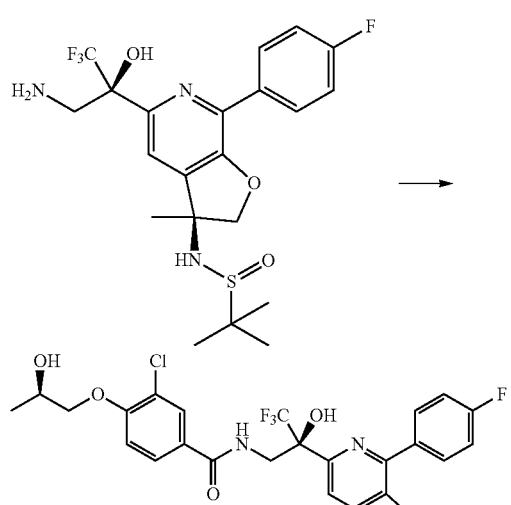

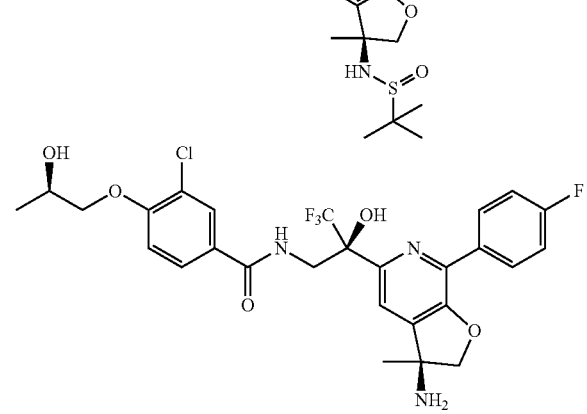

113

Compound 113 was prepared in a similar manner to 16, by substituting (R)-3-chloro-4-(2-hydroxypropoxy)benzoic acid in the coupling step. LC/MS: m/z 583.95 [M+H]⁺.

Example 97

Preparation of Compound 114

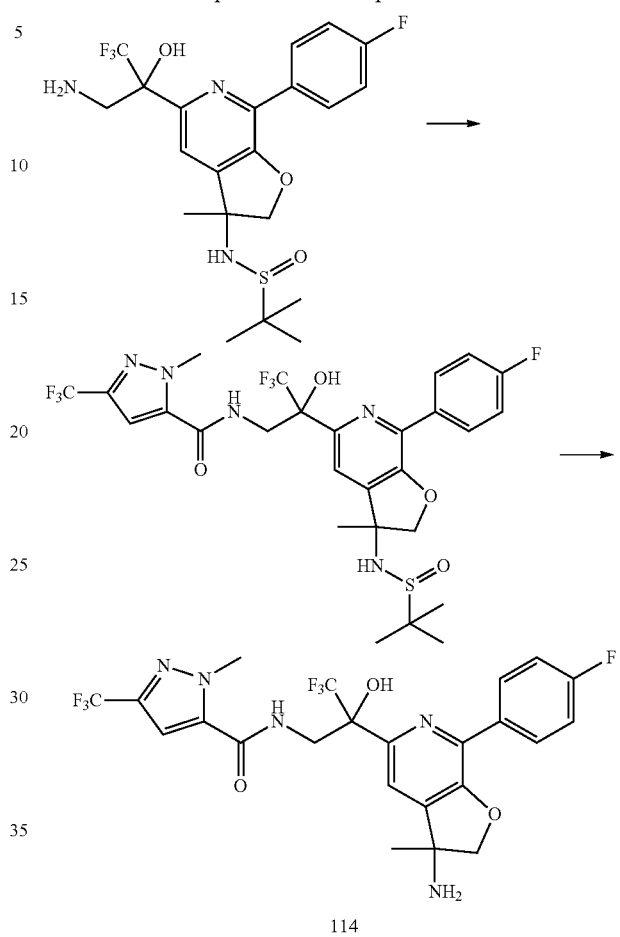

114

Compound 114 was prepared in a similar manner to 16, by substituting 1-methyl-3-(trifluoromethyl)-1H-pyrazole-5-carboxylic acid in the coupling step. LC/MS: m/z 548.15 [M+H]⁺.

Example 98

Preparation of Compound 115

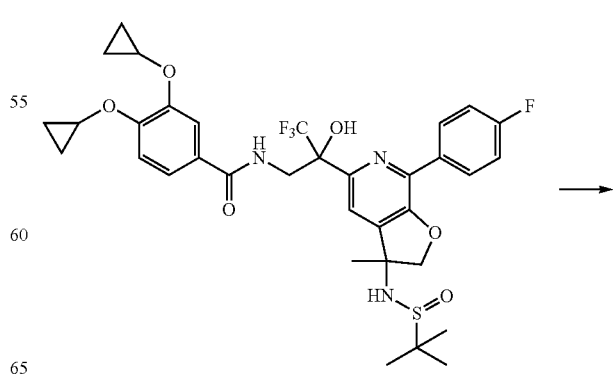

115-1

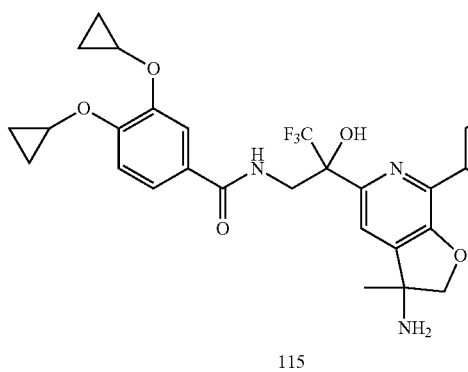

115

Compound 115 was prepared by deprotecting 115-1 (an intermediate in the synthesis of 25) in a similar manner to 16. LC/MS: m/z 558.05 [M+H]⁺.

Example 99

Preparation of Compound 17

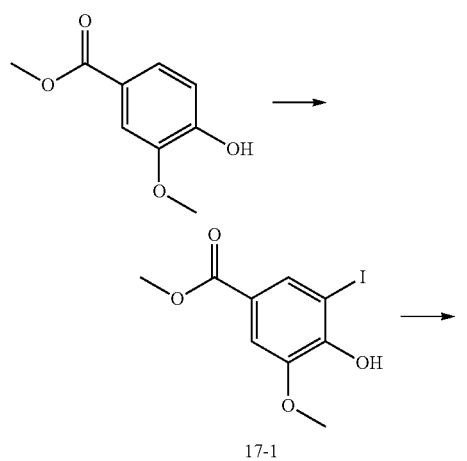

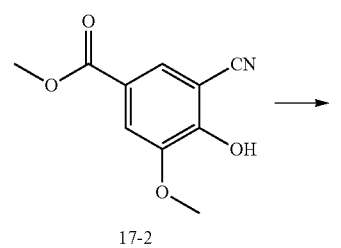

17-2

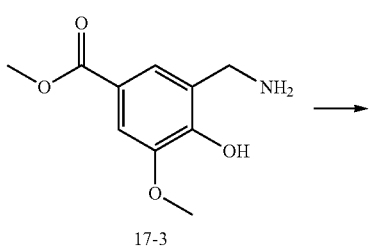

17-3

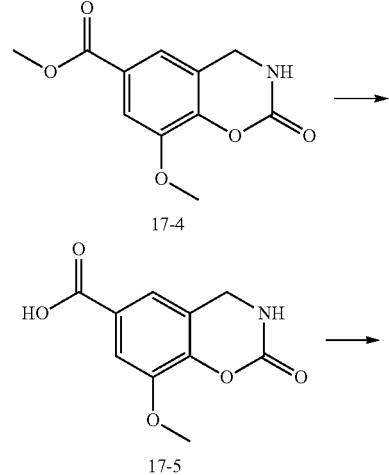

17-4

17-5

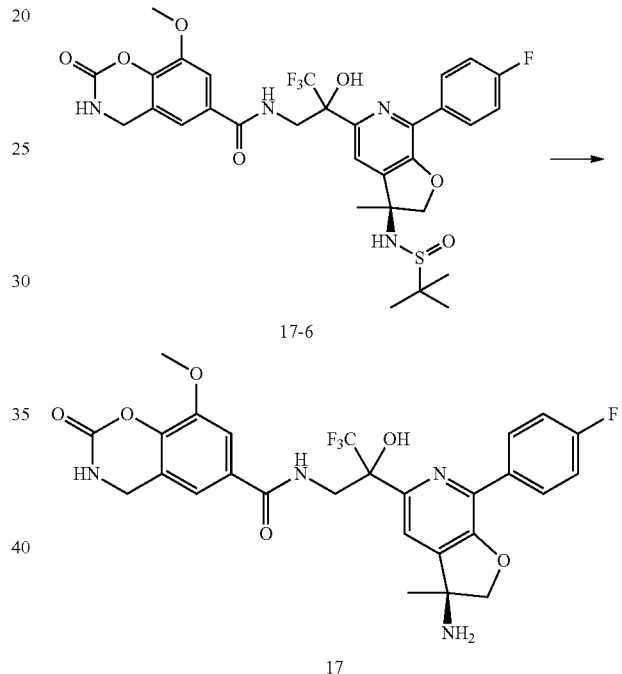

17-6

17

N-Iodosuccinimide (1.2 g, 5.5 mmol) was added portion wise to a solution of methyl vanillate (1.0 g, 5.5 mmol) in trifluoroacetic acid (10 mL). The reaction was monitored by LC/MS and judged complete after 3 h. The reaction was concentrated to remove the TFA then diluted with EA. The organic layer was washed with sodium thiosulfate and brine, dried and concentrated to afford 17-1 (0.50 g, 29%). LC/MS: m/z 308.95 [M+H]⁺.

Copper cyanide (250 mg, 3.0 mmol) and sodium cyanide (50 mg, 1.0 mmol) were added to a solution of 17-1 (0.33 g, 1.0 mmol) in DMF (1 mL). The reaction was flushed with argon and heated at 100° C. for 5 h. The mixture was diluted with EA, washed with water and brine, dried and concentrated. The crude product was purified by chromatography (hexane:EA) to yield 17-2 (46 mg, 22%). LC/MS: m/z 206.10 [M−H]⁻.

Compound 17-2 (46 mg, 0.22 mmol) was reduced over 10% Pd/C (40 mg) for 2 h. The catalyst was removed by filtration, and the product was concentrated. 17-3 was used without further purification. LC/MS: m/z 212.15 [M+H]⁺.

Carbonyldiimidazole (50 mg, 0.33 mmol) was added to a solution of 17-3 (50 mg, 0.298 mmol) and triethylamine (0.11 mL, 0.83 mmol) in DMF. The mixture was stirred at RT for 2 h. The mixture was diluted with EA and washed with 1M HCl and brine, dried and concentrated. The product was purified by flash chromatography (hexane:EA) to afford 17-4 (12 mg, 17%). LC/MS: m/z 238.05 [M+H]$^+$.

Concentrated HCl (0.5 mL) was added to a solution of 17-4 (12 mg, 0.051 mmol) in 4N HCl/dioxane (0.5 mL), and the reaction was heated at 100° C. for 1 h. The mixture was concentrated, and crude 17-5 was used without purification. LC/MS: m/z 221.75 [M−H]$^-$.

Compounds 17-6 and 17 were prepared using a similar methodologies for preparing 16. 17-6: LC/MS: m/z 681.20 [M+H]$^+$. 17: LC/MS: m/z 515.15 [M+H]$^+$.

Example 100

Preparation of Compound 18

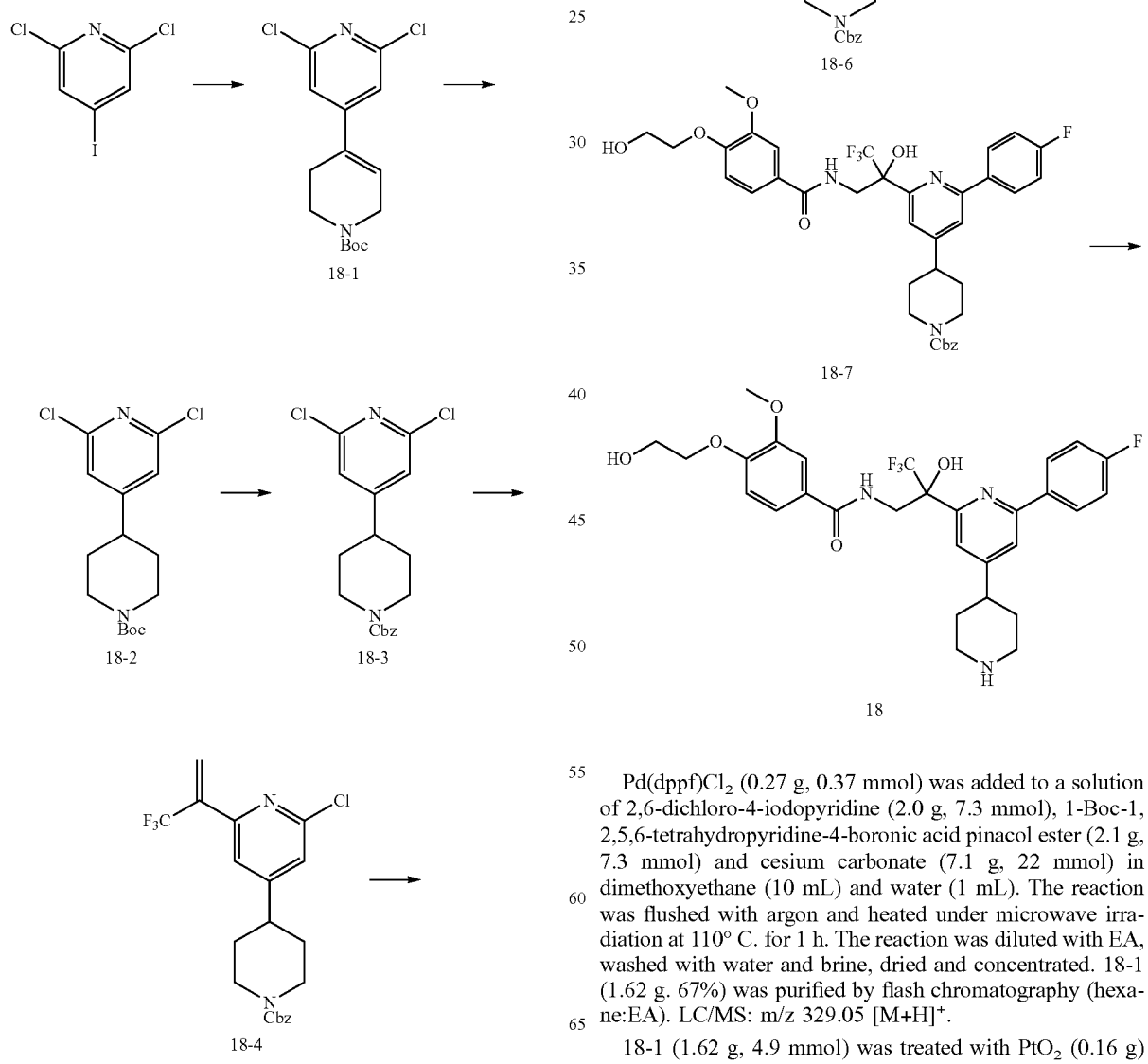

Pd(dppf)Cl$_2$ (0.27 g, 0.37 mmol) was added to a solution of 2,6-dichloro-4-iodopyridine (2.0 g, 7.3 mmol), 1-Boc-1,2,5,6-tetrahydropyridine-4-boronic acid pinacol ester (2.1 g, 7.3 mmol) and cesium carbonate (7.1 g, 22 mmol) in dimethoxyethane (10 mL) and water (1 mL). The reaction was flushed with argon and heated under microwave irradiation at 110° C. for 1 h. The reaction was diluted with EA, washed with water and brine, dried and concentrated. 18-1 (1.62 g, 67%) was purified by flash chromatography (hexane:EA). LC/MS: m/z 329.05 [M+H]$^+$.

18-1 (1.62 g, 4.9 mmol) was treated with PtO$_2$ (0.16 g) under a H$_2$ atmosphere for 1 h. The catalyst was removed by filtration, and 18-2 (1.46 g, 90%) was used without further purification. LC/MS: m/z 331.10 [M+H]⁺.

4N HCl/dioxane (10 mL) was added to 18-2 (1.46 g, 4.4 mmol), and the reaction was stirred for 1 h. The reaction was concentrated and immediately re-suspended in dichloromethane. Benzyl chloroformate (0.75 mL, 5.3 mmol) and triethyl amine (1.5 mL, 11 mmol) were added, and the reaction was stirred at RT for 1 h. The reaction was washed with 1N HCl and brine, dried and concentrated. The product was purified by flash chromatography (hexane:EA) to afford 18-3 (0.84 g, 52%). LC/MS: m/z 365.05 [M+H]⁺.

Pd(dppf)Cl$_2$ (84 mg, 0.11 mmol) was added to a solution of 18-3 (0.84 g, 2.3 mmol), 1-(trifluoromethyl)vinylboronic acid hexylene glycol ester (0.51 g, 2.3 mmol) and cesium carbonate (2.2 g, 6.9 mmol) in dimethoxyethane (6 mL) and water (0.6 mL). The reaction was flushed with argon and heated under microwave irradiation at 110° C. for 30 mins. The reaction was worked up and purified as described above for 18-1 to afford 18-4 (0.266 g, 27%). LC/MS: m/z 425.10 [M+H]⁺.

Pd(dppf)Cl$_2$ (23 mg, 0.031 mmol) was added to a solution of 18-4 (0.266 g, 0.63 mmol), 4-fluorophenyl boronic acid (88 mg, 0.63 mmol) and cesium carbonate (0.61 g, 1.9 mmol) in dimethoxyethane (2 mL) and water (0.2 mL). The reaction was flushed with argon and heated under microwave irradiation at 110° C. for 90 mins. The reaction was worked up and purified as described above for 18-1 to afford 18-5 (0.27 g, 88%). LC/MS: m/z 485.15 [M+H]⁺.

Potassium osmate (41 mg, 0.11 mmol) was added to a solution of 18-5 (0.27 g, 0.56 mmol) and tert-butyl tosyloxycarbamate (0.30 g, 1.1 mmol) in t-butanol (2 mL) and water (0.6 mL). The reaction was stirred at RT overnight. The crude mixture was applied directly to a flash column and 18-6 (45 mg, 13%) was eluted with hexane:EA. LC/MS: m/z 618.30 [M+H]⁺.

Compound 18-7 was prepared in a manner similar to 16-2. LC/MS: m/z 712.25 [M+H]⁺.

Compound 18-7 (17 mg) was hydrogenated over 10% Pd/C (5 mg) in EtOH (5 mL) for 1 h. The catalyst was removed by filtrated, and the product purified by HPLC to afford 18 (5.7 mg). LC/MS: m/z 578.02 [M+H]⁺.

Example 101

Preparation of Compound 19

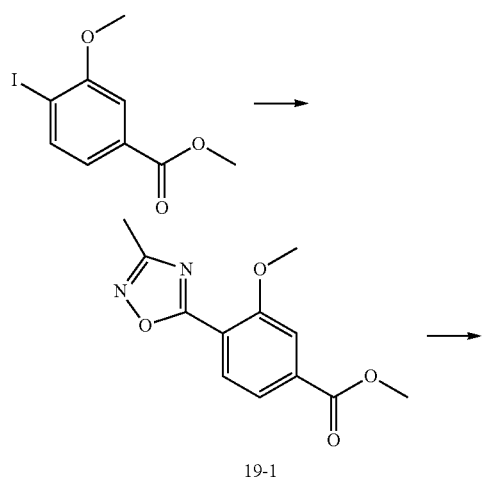

19-1

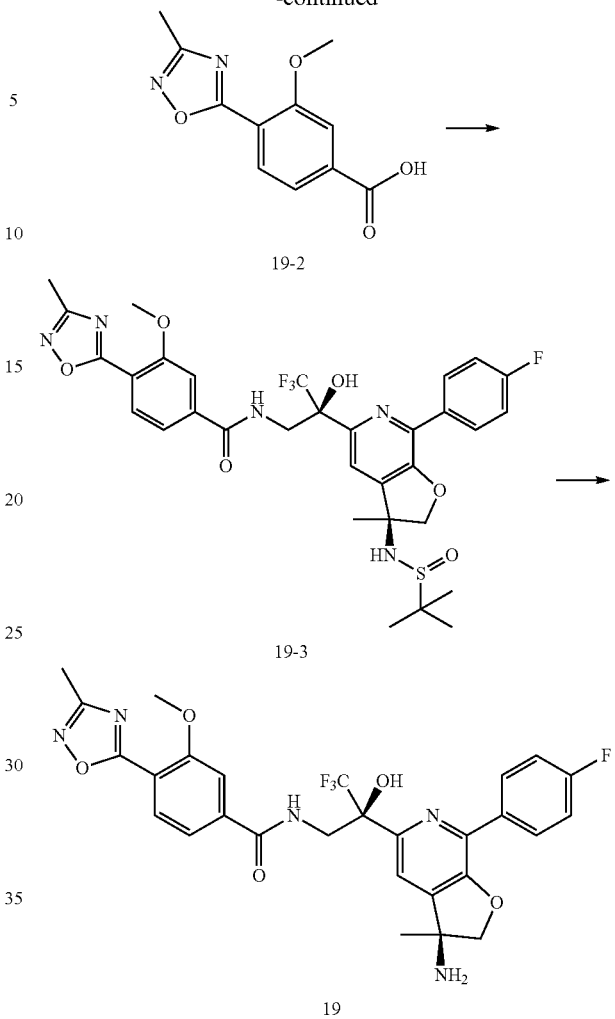

PdCl$_2$(PPh$_3$)$_2$ (0.12 g, 0.17 mmol) was added to a solution of methyl 4-iodo-3-methoxybenzoate (1.0 g, 3.4 mmol), (Z)—N'-hydroxyacetimidamide (0.7 g, 10 mmol), and trimethylamine (0.95 mL, 6.8 mmol) in toluene (20 mL). The reaction was flushed with argon, then carbon monoxide was bubbled through the solution for 5 mins. The reaction was heated at reflux under carbon monoxide atmosphere overnight. The reaction was diluted with EA and washed with brine, dried and concentrated. 19-1 (60 mg 7%) was purified by flash chromatography (hexane:EA). ¹H NMR (400 MHz, CDCl$_3$): δ 8.07 (d, J=8.8, 1H), 7.71-7.73 (m, 2H), 4.03 (s, 3H0, 3.95 (s, 3H), 2.49 (s, 3H).

Sodium hydroxide (2 N, 1 mL) was added to a solution of 19-1 (60 mg, 0.24 mmol) in methanol (4 mL), and the mixture stirred at RT for 2 h. The reaction was acidified with 2N HCl. The product was extracted with EA, washed with brine, dried and concentrated to afford 19-2 (42 mg, 75%). LC/MS: m/z 235.10 [M+H]⁺.

Compound 19-3 was prepared in a manner similar to 16-2. LC/MS: m/z 692.20 [M+H]⁺.

Compound 19 was prepared in a similar manner to 16. LC/MS: m/z 588.15 [M+H]⁺.

Example 102
Preparation of Compound 116
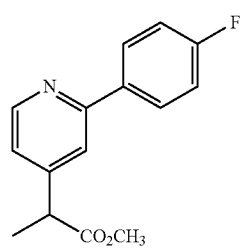
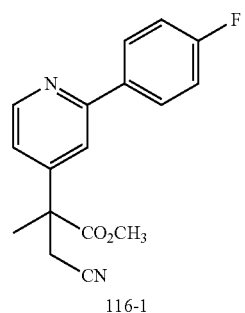
116-1
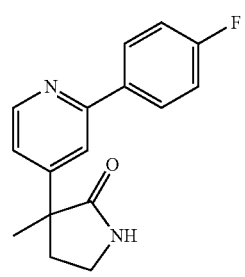
116-2
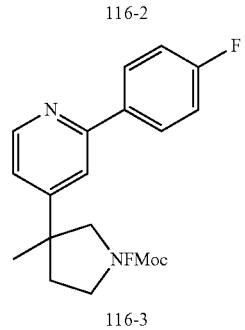
116-3
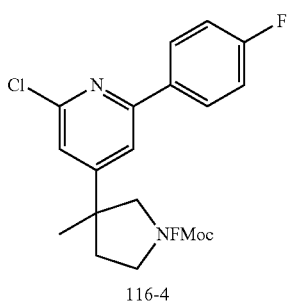
116-4
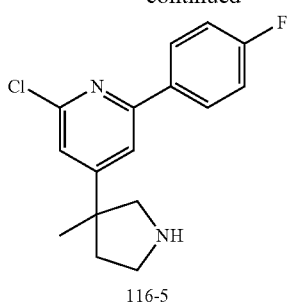
116-5
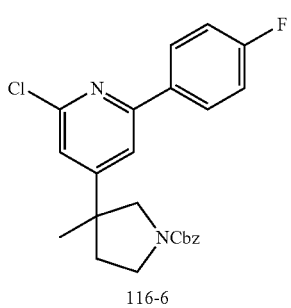
116-6
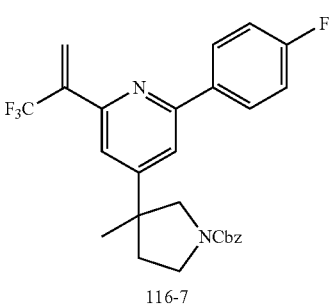
116-7
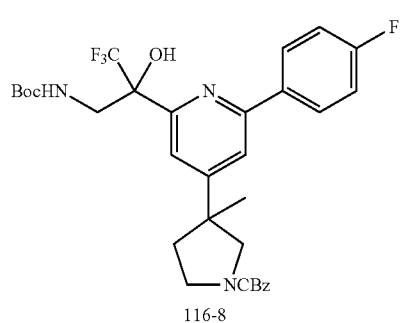
116-8
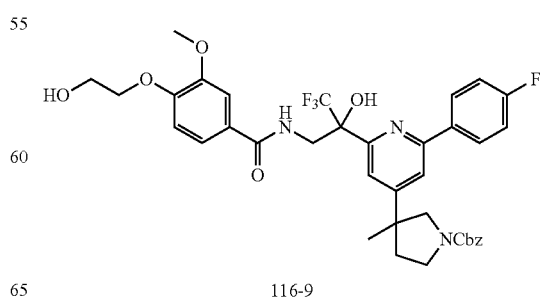
116-9

-continued

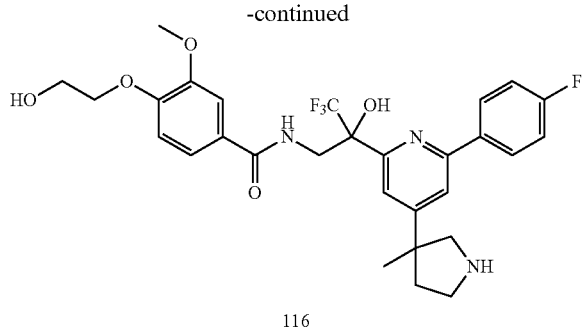

116

To a stirring mixture of methyl 2-(2-(4-fluorophenyl) pyridin-4-yl)propanoate (320 mg, 1.234 mmol) in THF (4.6 mL) at −78° C. were added dropwise a solution of LiHMDS in THF (1.87 mL, 1.85 mmol). The mixture was stirred at −78° C. for 30 mins before a solution of bromoacetonitrile (178 mg, 1.48 mmol) in THF (0.5 mL) was added. The mixture was stirred at −78° C. for 1 h before it was warmed to RT for 1 h. The reaction was quenched with water and diluted with EtOAc. A normal aqueous work up with EtOAc was followed. The crude product was purified via a silica gel column to afford 116-1 as a colorless oil (150 mg); LC/MS: m/z 299.10 [M+H]$^+$.

Compound 116-1 (1.13 g, 3.8 mmol) was hydrogenated at 50 psi over PtO$_2$ (200 mg) in EtOH (20 mL) and 1N HCl (1 mL) for 4 h. The catalyst was removed by filtration, and the reaction was concentrated to 5 mL. Saturated sodium bicarbonate was added until the reaction was basic, and the mixture was heated at reflux for 1 h. The mixture was diluted with EA, washed with water and brine, dried and concentrated. 116-2 (0.30 g, 26%) was purified by flash chromatography (EA).

Lithium aluminum hydride (2 mL, 2.0 mmol) was added to a solution of 116-2 (0.30 g, 0.99 mmol) in THF (3 mL), and the solution was heated at reflux for 1 h. The reaction was cooled to RT and quenched with Na$_2$SO$_4$10H$_2$O. The solids were removed by filtration, and washed with EA. The filtrate was concentrated and used immediately. The crude amine from step 1 was dissolved in dichloromethane. To this stirring mixture was added DIEA (0.52 mL, 3.0 mmol) and 9-fluorenylmethylchloroformate (0.51 g, 1.9 mmol). The solution was stirred at RT for 3 h. The reaction mixture was diluted with EA, washed with 1N HCl and brine, dried and concentrated. 116-3 (0.30 g, 64%) was purified by flash chromatography. LC/MS: m/z 479.20 [M+H]$^+$.

meta-Chloroperbenzoic acid (0.30 g, 1.1 mmol) was added to a solution of 116-3 (0.30 g, 0.63 mmol) in dichloromethane (3 mL), and the reaction was stirred at RT overnight. The reaction was diluted with EA and washed with sodium carbonate and brine, dried and concentrated. The crude N-oxide was immediately dissolved in POCl$_3$ (10 mL) and heated at 60° C. for 4 h. The solvent was removed by evaporation, and the residue was dissolved in EA. The organic layers were washed with NaHCO$_3$ and brine, dried and concentrated. 116-4 (0.16 g, 49%) was purified by flash chromatography (hexaneEA). LC/MS: m/z 513.15 [M+H]$^+$.

Piperidine (0.2 mL) was added to a solution of 116-4 (0.16 g, 0.31 mmol) in DMF (1 mL), and the mixture stirred at RT for 10 mins. 116-5 (0.064 g, 71%) was purified by HPLC. LC/MS: m/z 291.10[M+H]$^+$.

Benzyl chloroformate (0.047 mL, 0.33 mmol) was added to a solution of 116-5 (64 mg, 0.22 mmol) and DIEA (0.11 mL, 0.66 mmol) in CH$_2$Cl$_2$ (1 mL), and the solution was stirred at RT for 1 h. The reaction was diluted with EA, washed with 1N HCl, bicarbonate and brine, dried and concentrated. 116-6 (53 mg, 55%) was purified by flash chromatography (hexane:EA). LC/MS: m/z 425.10 [M+H]$^+$.

Compound 116-7 was prepared in a similar manner to 18-4. LC/MS: m/z 485.15 [M+H]$^+$. Compound 116-8 was prepared in a similar manner to 18-6. LC/MS: m/z 618.25 [M+H]$^+$. Compound 116-9 was prepared in a similar manner to 18-7. LC/MS: m/z 712.25 [M+H]$^+$.

Compound 116 was prepared in a similar manner to 18. LC/MS: m/z 578.25 [M+H]$^+$.

Example 103

Preparation of Compound 117

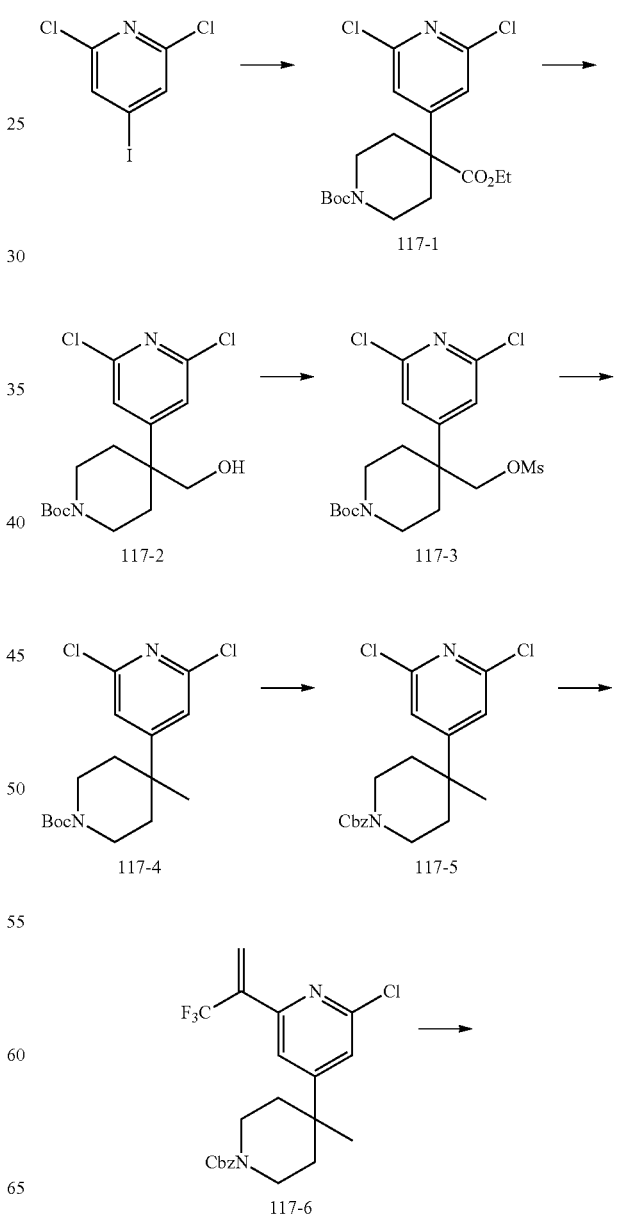

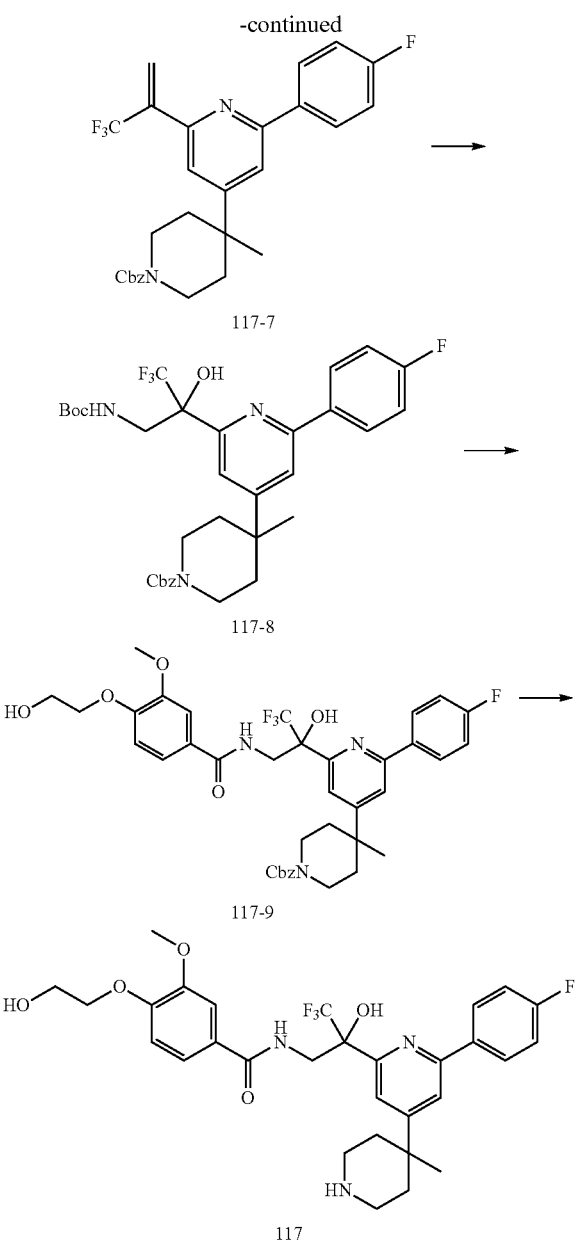

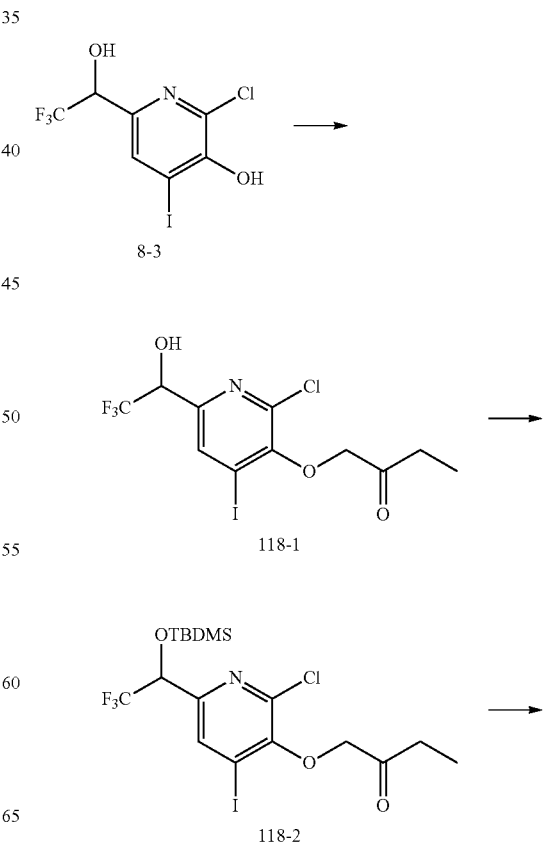

Methanesulfonyl chloride (0.18 mL, 2.3 mmol) was added to a solution of 117-2 (0.59 g, 1.6 mmol) and DIEA (0.56 mL, 3.2 mmol) in CH$_2$Cl$_2$ (10 mL) at 0° C. The mixture was stirred at 0° C. for 45 minx. The mixture was diluted with CH$_2$Cl$_2$ and washed with 1N HCl and brine, dried and concentrated. 117-3 (0.498 g, 58%) was purified by flash chromatography (hexane:EA). LC/MS: m/z 461.10 [M+Na]$^+$.

Zn (0.89 g, 14 mmol) was added to a solution of 117-3 (0.435 g, 0.92 mmol) and sodium iodide (0.69 g, 4.6 mmol) in DMF (2 mL), and the mixture stirred at 110° C. overnight. The mixture was diluted with EA and washed with water and brine, dried and concentrated. 117-4 (0.165 g, 52%) was purified by flash chromatography (hexane:EA). LC/MS: m/z 366.95 [M+Na]$^+$.

Compound 117-5 was prepared in a similar manner to 18-3. LC/MS: m/z 378.95 [M+H]$^+$. Compound 117-6 was prepared in a similar manner to 18-4. LC/MS: m/z 438.95 [M+H]$^+$. Compound 117-7 was prepared in a similar manner to 18-5. LC/MS: m/z 499.00 [M+H]$^+$. Compound 117-8 was prepared in a similar manner to 18-6. LC/MS: m/z 632.10 [M+H]$^+$. Compound 117-9 was prepared in a similar manner to 18-7. LC/MS: m/z 726.15 [M+H]$^+$.

Compound 117 was prepared in a similar manner to 18. LC/MS: m/z 529.15 [M+H]$^+$.

Example 104

Preparation of Compound 118

NaHMDS (10.0 mL, 10 mmol) was added dropwise to a solution of 1-tert-butyl-4-ethyl piperidine-1,4-dicarboxylate (2.0 g, 7.8 mmol) in THF (5 mL) at 0° C. The mixture was allowed to stir at 0° C. for 30 mins. The anion was added to a solution of 2,6-dichloro-4-iodopyridine (2.0 g, 7.8 mmol) in THF (5 mL) at 0° C., and the reaction was stirred for 1.5 h. The reaction was quenched with 1N HCl and extracted with EA. The organic layers were washed with brine, dried and concentrated. 117-1 (1.21 g, 41%) was purified by flash chromatography (hexane:EA). LC/MS: m/z 425.10 [M+Na]$^+$.

Sodium borohydride (0.36 g, 9.4 mmol) was added to a solution of 117-1 (0.76 g, 1.9 mmol) in EtOH (15 mL) at RT, and the mixture was stirred at RT overnight. The mixture was concentrated slightly and diluted with EA. The organic layers were washed with brine, dried and concentrated. 117-2 (0.59 g, 84%) was purified by flash chromatography (hexane:EA). LC/MS: m/z 380.05 [M+Na]$^+$.

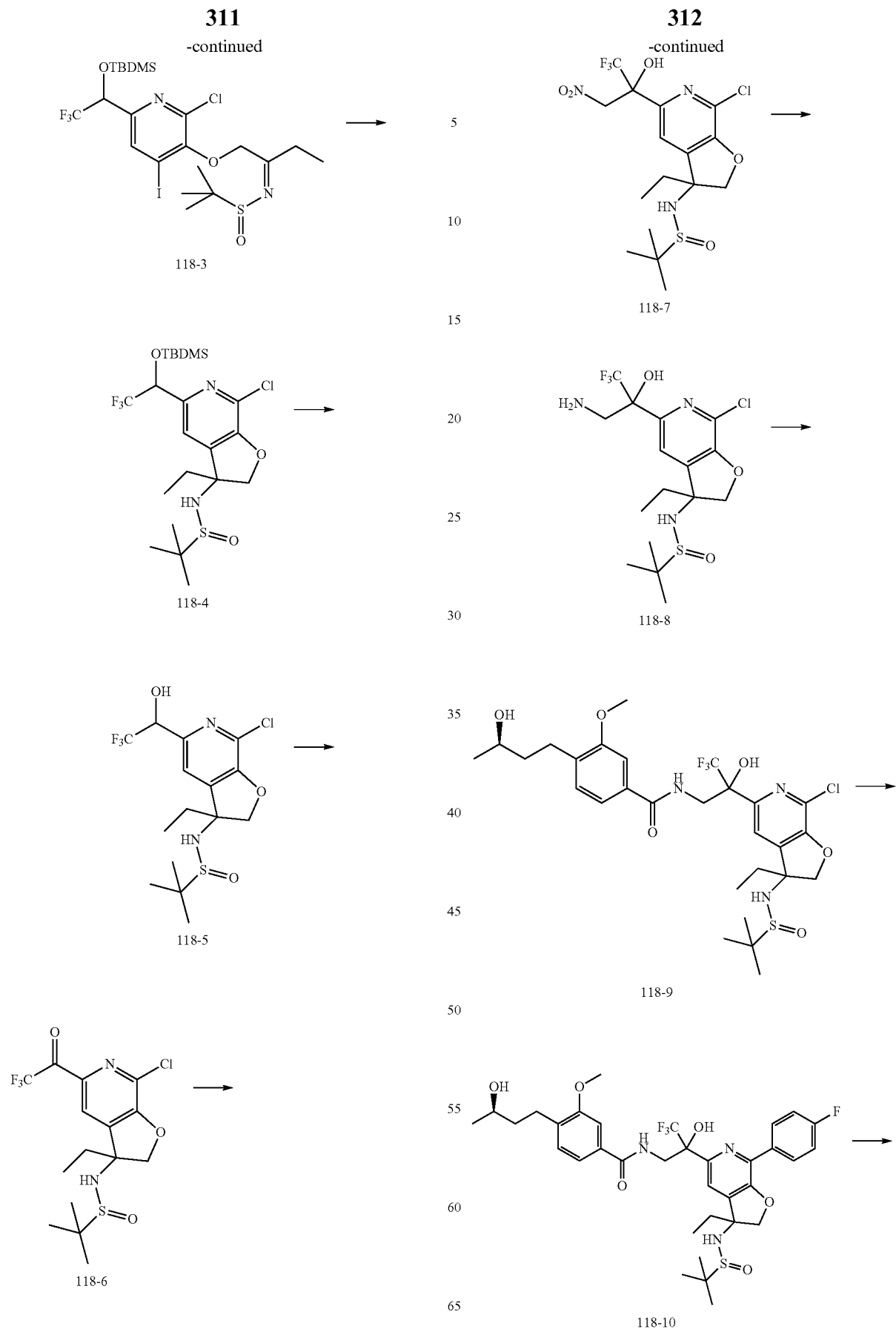

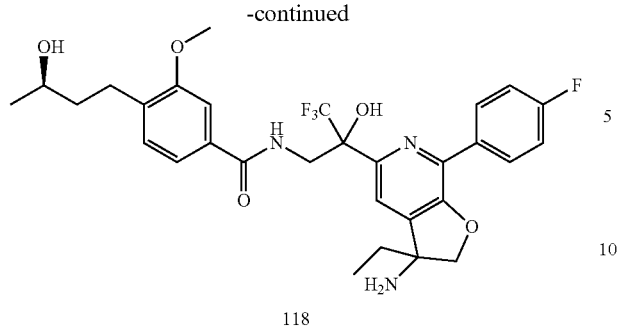

118

Compound 118-1 was prepared from 8-3 in a similar manner to 8-4. LC/MS: m/z 423.75 [M+H]$^+$.

Tert-butyldimethylsilyl chloride (1.2 g, 8.0 mmol) was added to a solution of 118-1 (1.7 g, 4.0 mmol) and imidazole (0.82 g, 8.0 mmol) in DMF (8 mL), and the mixture was stirred at RT for 8 h. The mixture was diluted with EA and washed with water and brine. The solvent was removed by filtration, and 118-2 (1.53 g, 70%) purified by flash chromatography (hexane:EA). LC/MS: m/z 537.90.

Compound 118-3 was prepared in a similar manner to 8-5. LC/MS: m/z 640.90 [M+H]$^+$. Compound 118-4 was prepared in a similar manner to 8-6. LC/MS: m/z 515.00 [M+H]$^+$.

Tetrabutylammonium fluoride (1.6 mL, 1.6 mmol) was added to a solution of 118-4 (0.76 g, 1.48 mmol) in THF (10 mL), and the solution was stirred at RT for 1 h. The mixture was concentrated, and 118-5 (0.52 g, 80%) purified by flash chromatography. LC/MS: m/z 400.95 [M+H]$^+$.

Compound 118-6 was prepared in a similar manner to 8-7. LC/MS: m/z 398.95 [M+H]$^+$.

Triethylamine (0.18 mL, 1.3 mmol) was added dropwise to a solution of 118-6 (90.44 g, 1.1 mmol) in nitromethane (4 mL), and the solution was stirred at RT for 1 h. The crude material was loaded directly onto a flash column and 118-7 (0.47 g, 91%) was eluted (hexane:EA). LC/MS: m/z 459.95 [M+H]$^+$.

Sodium borohydride (0.46 g, 12 mmol) was added to a solution of 118-7 (0.47 g, 1.0 mmol) and NiCl$_2$ (0.24 g, 1.0 mmol) in MeOH (7 mL) at 0° C. The mixture was stirred at 0° C. for 30 mins. The reaction was quenched with sodium bicarbonate and extracted with EA. 118-8 was used without further purification. LC/MS: m/z 429.95 [M+H]$^+$.

Compound 118-9 was prepared in a similar manner to 16-2. LC/MS: m/z 638.00 [M+H]$^+$. Compound 118-10 was prepared in a similar manner to 18-5. LC/MS: m/z 698.10 [M+H]$^+$.

Compound 118 was prepared in a similar manner to 8. LC/MS: m/z 594.10 [M+H]$^+$.

Example 105

Preparation of Compound 119

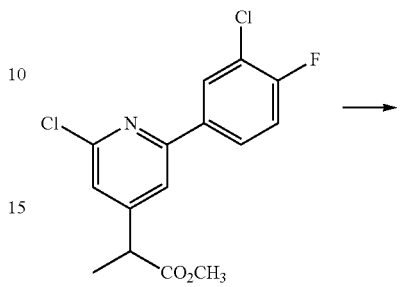

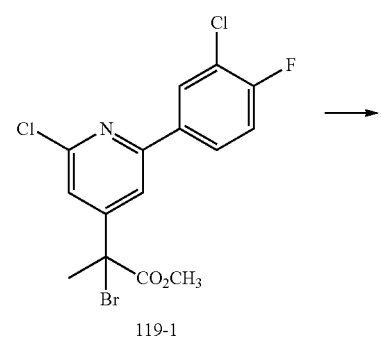

119-1

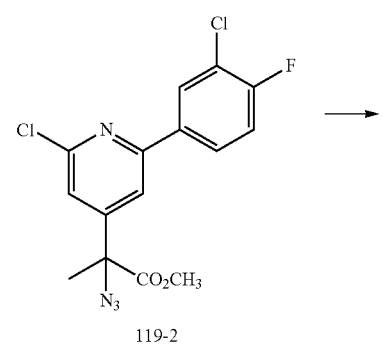

119-2

119-3

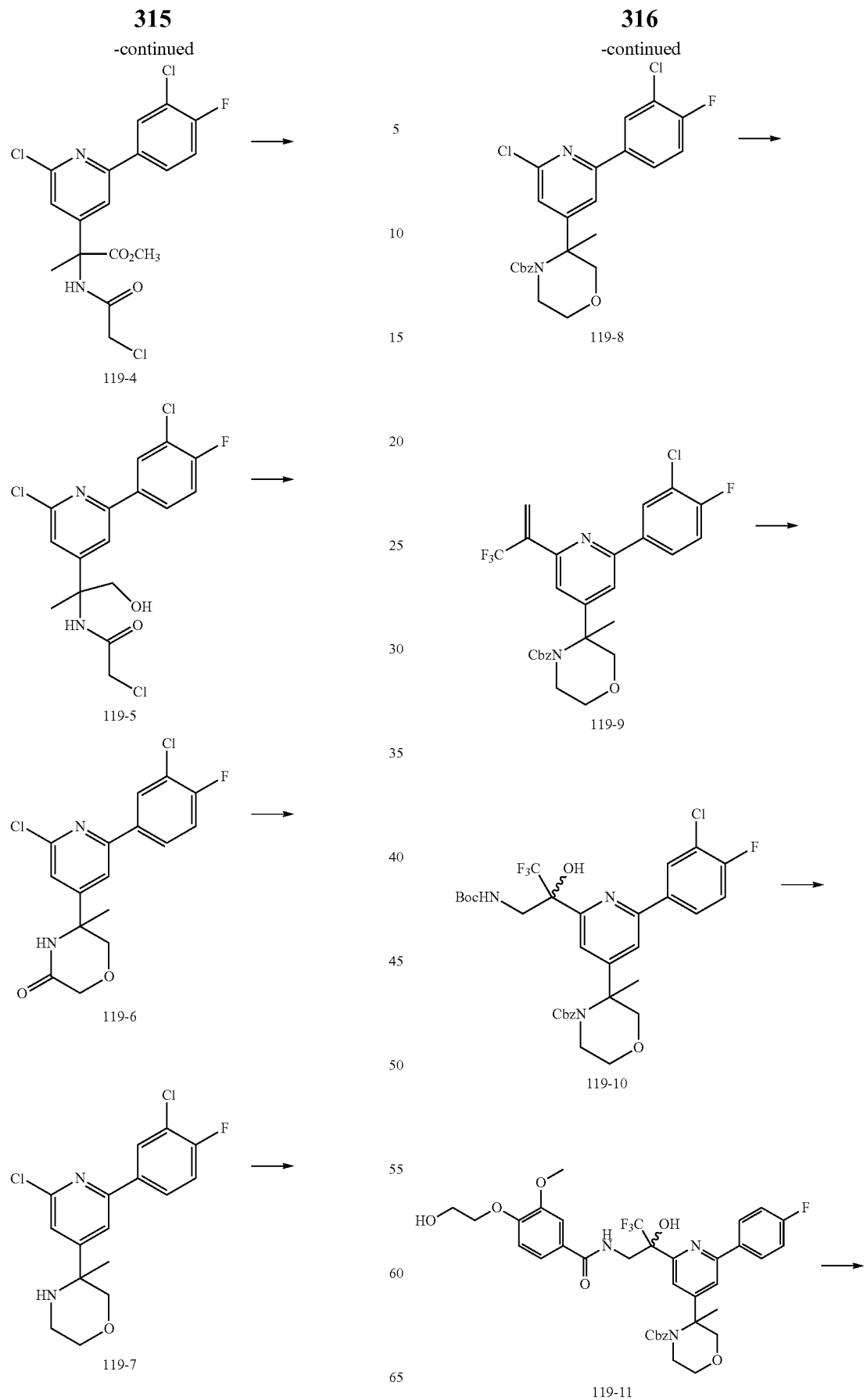

317

-continued

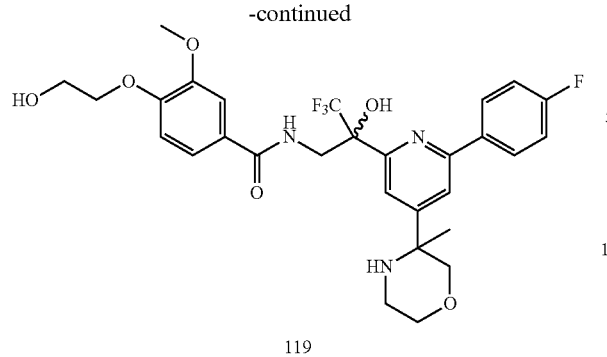

119

Bromine (42 µL, 0.84 mmol) was added to a solution of methyl 2-(2-chloro-6-(3-chloro-4-fluorophenyl)pyridine-4-yl) proprionate (0.213 mg, 0.76 mmol) in acetic acid (1 mL), and the solution was heating at 100° C., for 1 h. The solvent was removed, and the mixture was concentrationed. The mixture was then diluted with EA, washed with $Na_2S_2O_3$, $NaHCO_3$ and brine. 119-1 (0.224 g, 72%) was purified by flash chromatography (EA:hexane). LC/MS: m/z 407.80 $[M+H]^+$.

Sodium azide (5 eq) was added to a solution of 119-1 (0.224 g, 0.69 mmol) in MeOH (3 mL), and the mixture was heated at 60° C. for 5 h. The mixture was diluted with EA, washed with brine, dried and concentrated. Crude 119-2 (0.32 g) was purified by flash chromatography (hexane:EA). LC/MS: m/z 414.80 $[M+H]^+$.

Compound 119-2 (0.32 g, 0.87) was hydrogenated over 10% Pd/C (30 mg) in EtOH for 1 h. The catalyst was removed by filtration, and 119-3 was used without further purification. LC/MS: m/z 342.85 $[M+H]^+$.

Chloroacetylchloride (68 µL, 8.9 mmol) was added to a solution of 119-3 (0.27 g, 0.78 mmol) and DIEA (0.20 mL, 1.2 mmol) in $CH_2Cl_2$ at 0° C. The mixture was stirred at 0° C. for 1 h. The mixture was diluted with EA, washed with 1N HCl and brine, dried and concentrated to afford 119-4. LC/MS: m/z 419.80 $[M+H]^+$.

Compound 119-4 was reduced with sodium borohydride in MeOH at RT for 1 h. The reaction was quenched with 1N HCl and extracted with EA. The crude product was purified by flash chromatography (EA) to provide 119-5. LC/MS: m/z 392.75 $[M+H]^+$.

Potassium t-butoxide (10 mg) was added to a solution of 119-5 in THF (1 mL), and the mixture stirred at RT for 1 h. The reaction was quenched with 1N HCl and extracted with EA. The product was purified by flash chromatography (hexane:EA) to afford 119-6 (30 mg). LC/MS: m/z 354.90 $[M+H]^+$.

Borane-dimethyl sulfide (10 µL, 0.006 mmol) was added to a solution of 119-6 (30 mg, 0.088 mmol) in THF (2 mL), and the mixture was heated at reflux for 30 mins. The reaction was cooled to RT and quenched with MeOH and 3 drops conc. HCl. The mixture was heated at reflux for 1.5 h to break up the borate complex. The reaction was concentrated to remove the solvents, and 119-7 used without further purification. LC/MS: m/z 342.85 $[M+H]^+$.

Compound 119-8 was prepared in a similar manner to 18-3. LC/MS: m/z 474.95 $[M+H]^+$. Compound 119-9 was prepared in a similar manner to 18-4. LC/MS: m/z 535.00 $[M+H]^+$. Compound 119-10 was prepared in a similar manner to 18-6. LC/MS: m/z 668.05 $[M+H]^+$. Compound 119-11 was prepared in a similar manner to 16-2. LC/MS: m/z 762.10 $[M+H]^+$.

318

Compound 119 was prepared in a similar manner to 18. LC/MS: m/z 594.05 $[M+H]^+$.

Example 106

Preparation of Compound 120

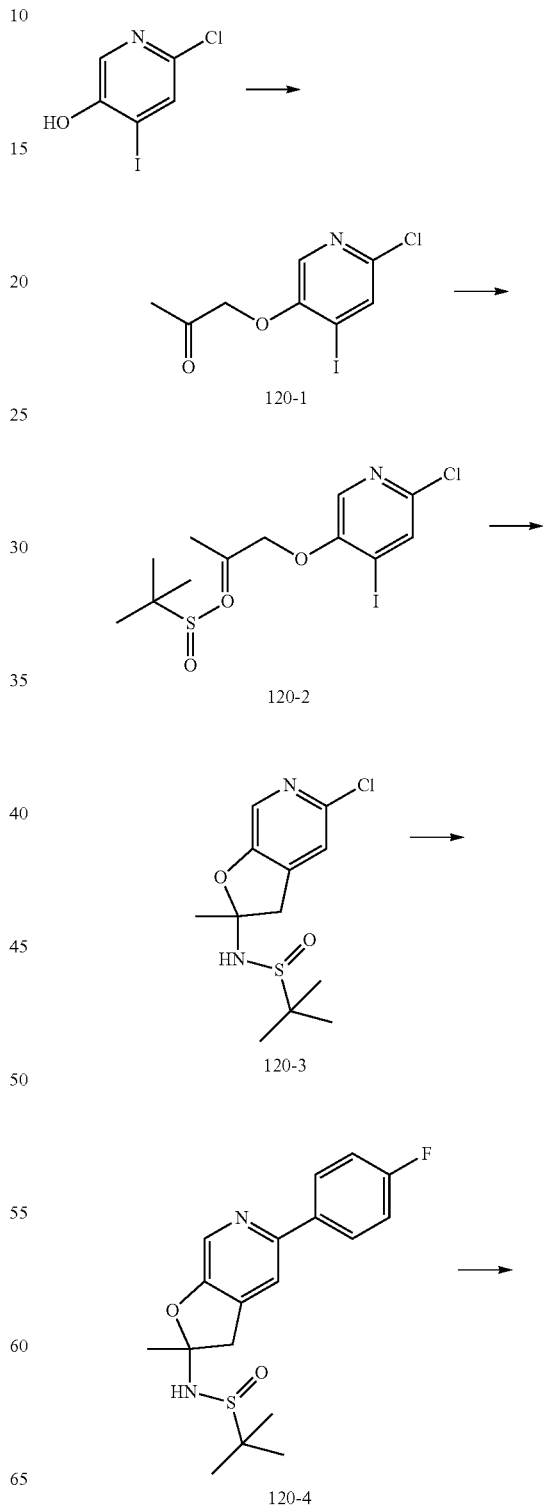

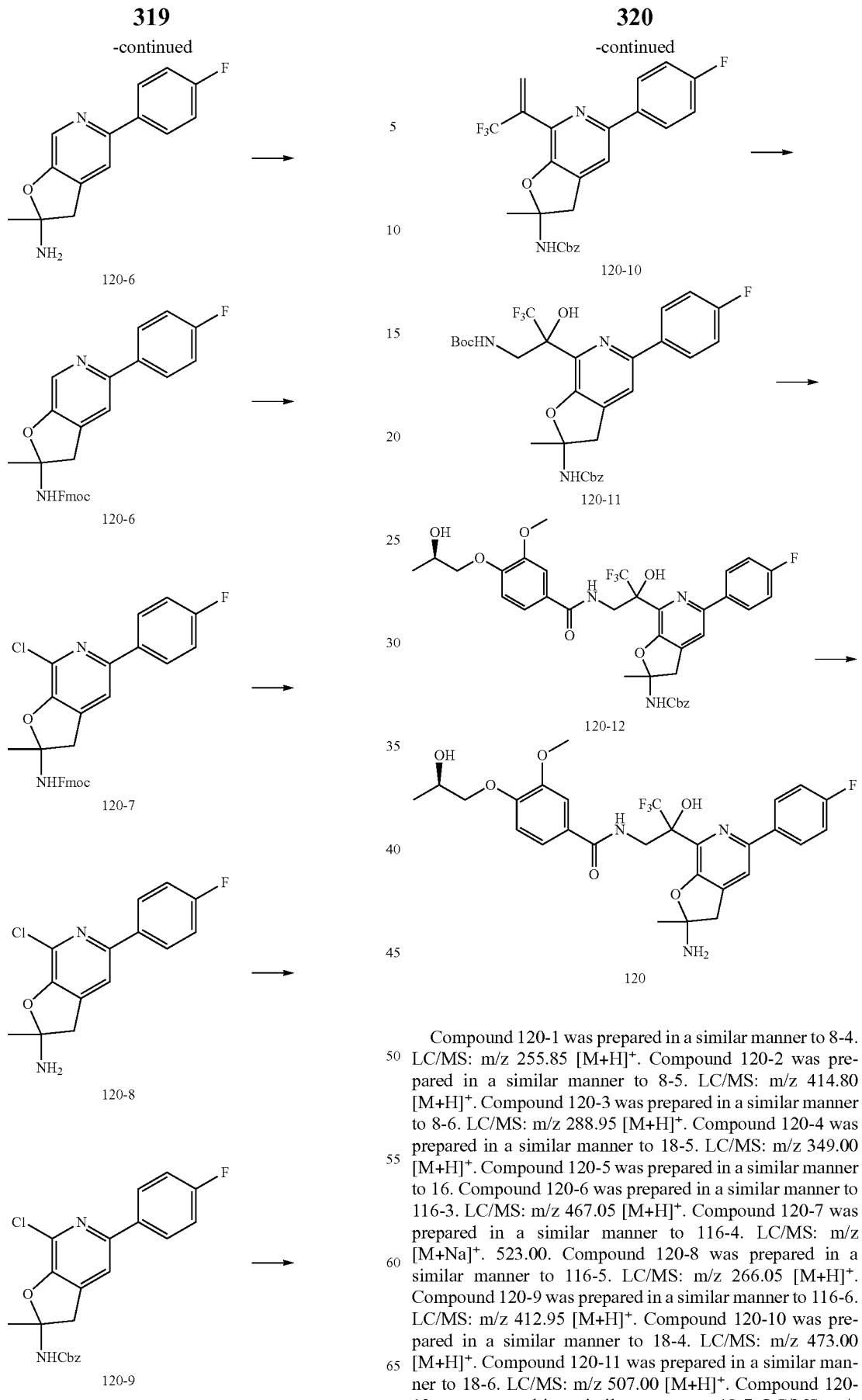

Compound 120-1 was prepared in a similar manner to 8-4. LC/MS: m/z 255.85 [M+H]$^+$. Compound 120-2 was prepared in a similar manner to 8-5. LC/MS: m/z 414.80 [M+H]$^+$. Compound 120-3 was prepared in a similar manner to 8-6. LC/MS: m/z 288.95 [M+H]$^+$. Compound 120-4 was prepared in a similar manner to 18-5. LC/MS: m/z 349.00 [M+H]$^+$. Compound 120-5 was prepared in a similar manner to 16. Compound 120-6 was prepared in a similar manner to 116-3. LC/MS: m/z 467.05 [M+H]$^+$. Compound 120-7 was prepared in a similar manner to 116-4. LC/MS: m/z [M+Na]$^+$. 523.00. Compound 120-8 was prepared in a similar manner to 116-5. LC/MS: m/z 266.05 [M+H]$^+$. Compound 120-9 was prepared in a similar manner to 116-6. LC/MS: m/z 412.95 [M+H]$^+$. Compound 120-10 was prepared in a similar manner to 18-4. LC/MS: m/z 473.00 [M+H]$^+$. Compound 120-11 was prepared in a similar manner to 18-6. LC/MS: m/z 507.00 [M+H]$^+$. Compound 120-12 was prepared in a similar manner to 18-7. LC/MS: m/z 714.10 [M+H]⁺. Compound 120 was prepared in a similar manner to 18. LC/MS: m/z 580.05 [M+H]⁺.

Example 107

Preparation of Compound 121

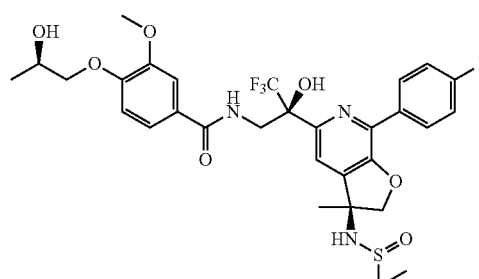

8-11

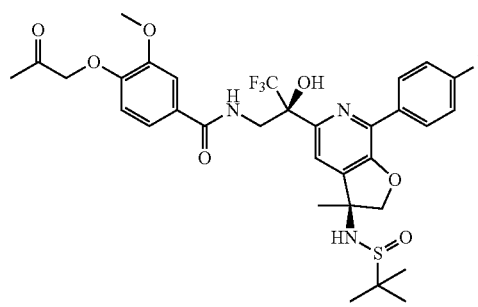

121-1

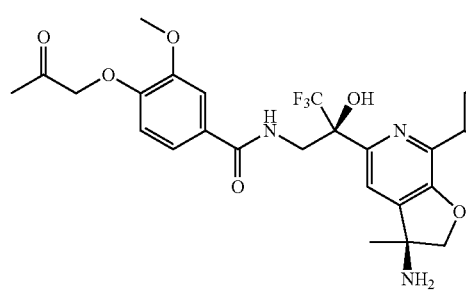

121

Dess-Martin periodinane (25 mg, 0.061 mmol) was added to a solution of 8-11 (32 mg, 0.047 mmol) in dichloromethane (1 mL). The mixture was stirred at RT for 2 h. The reaction was diluted with EA, washed with Na₂CO₃ and brine, dried and concentrated. 121-1 was used crude in the next reaction. LC/MS: m/z 682.25 [M+H]⁺.

Compound 121-1 was deprotected in a similar manner to 16 to provide 121. LC/MS: m/z 578.00 [M+H]⁺.

Example 108

Preparation of Compound 122

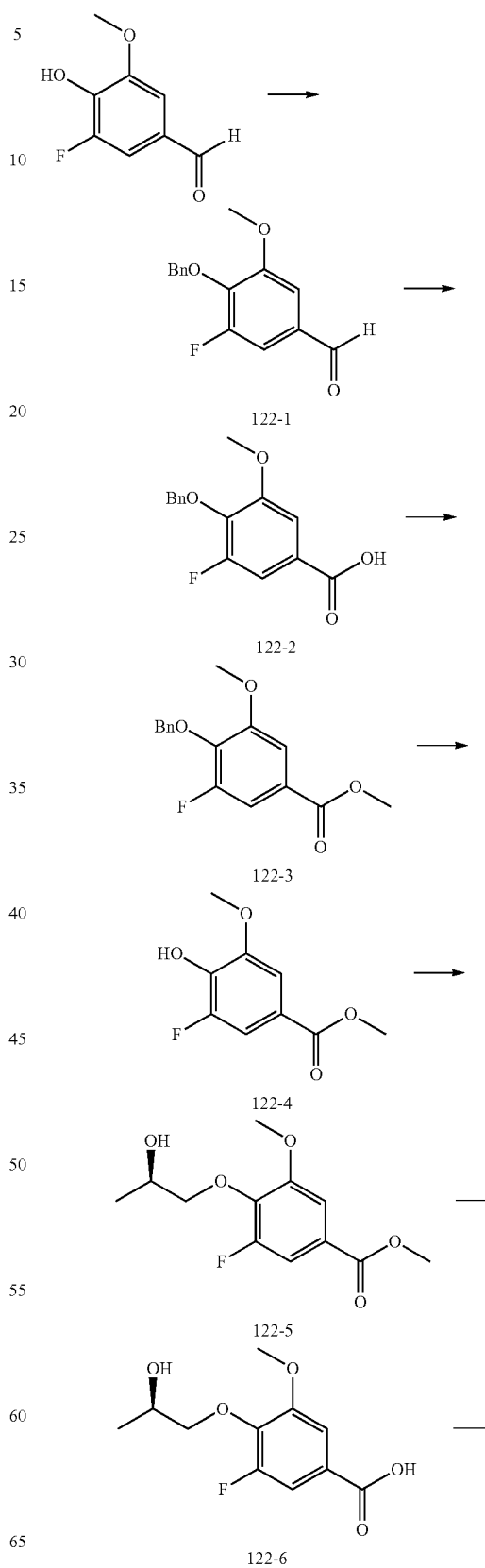

-continued

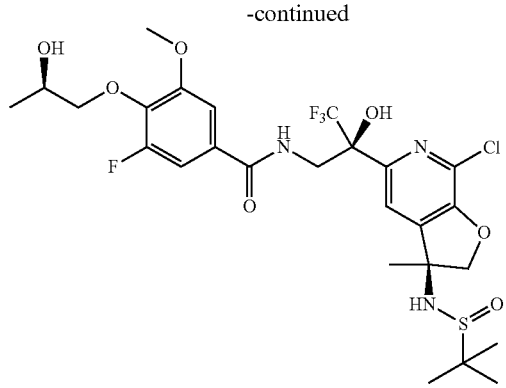

122-7

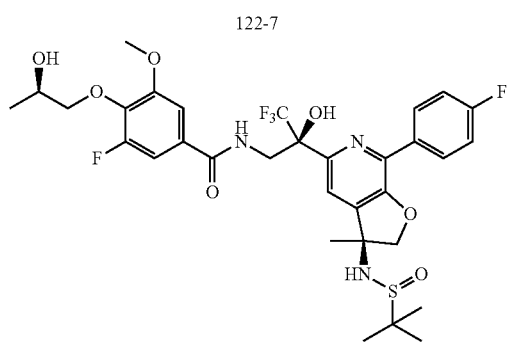

122-8

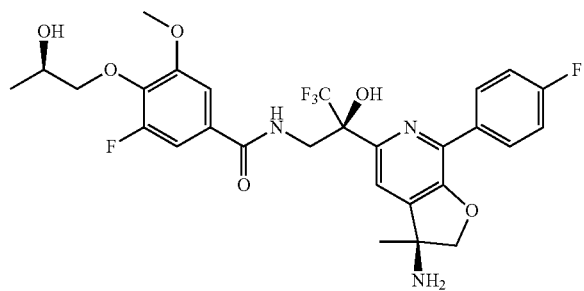

122

Benzyl bromide (0.64 mL, 5.4 mmol) was added to a solution of 3-fluoro-4-hydroxy-5-methoxybenzaldehyde (0.70 g, 4.12 mmol) and potassium carbonate (1.7 g, 12 mmol) in acetonitrile (10 mL). The solution was stirred at RT overnight. The reaction was diluted with EA, washed with water and brine, dried and concentrated. 122-1 (0.37 g, 34%) was purified by flash chromatography (hexane:EA). $^1$H NMR (400 MHz, CDCl$_3$): δ 9.81 (d, J=1.2, 1H0, 7.42-7.44 (m, 2H), 7.31-7.34 (m, 2H), 7.19-7.30 (m, 2H), 7.42 (s, 2H), 3.92 (s, 3H).

Compound 122-1 (0.37 g, 1.4 mmol) in acetone (2 mL) was added dropwise to a solution of potassium permanganate (0.29 g, 2.1 mmol) in water (2 mL). The solution was stirred at RT for 1 h. The reaction was quenched with saturated sodium bisulfite solution and acidified with HCl. 122-2 (0.34 g, 86%) was extracted with EA and used without further purification. $^1$H NMR (400 MHz, CDCl$_3$): δ 7.42-7.45 (m, 4H), 7.24-7.34 (m, 3H), 5.20 (s, 2H), 3.90 (s, 3H).

Acetyl chloride (1.0 mL) was added to MeOH (15 mL) dropwise at 0° C. This solution was added to 122-2 0.34 g, 1.2 mmol), and the mixture was heated at reflux overnight. The solvent was removed by evaporation and 122-3 (0.172 g, 42%) was purified by flash chromatography (hexane:EA). $^1$H NMR (400 MHz, CDCl$_3$): δ 7.30-7.44 (m, 7H), 5.17 (s, 2H), 3.88 (s, 3H), 3.87 (s, 3H).

Compound 122-3 (0.172 g, 0.59 mmol) was hydrogenated over 10% Pd/C (25 mg) in ethanol (20 mL) for 1 h. The catalyst as removed by filtration, and the reaction was concentrated. 122-4 (0.104 g, 88%) was used without further purification. $^1$H NMR (400 MHz, CDCl$_3$): δ 7.45 (dd, J=16.1, 10.8, 1H), 7.36 (m, 1H), 3.94 (s, 3H), 3.87 (s, 3H).

(R)-Propyleneoxide (0.18 mL, 2.6 mmol) was added to a solution of 122-4 (0.104 g, 0.52 mmol) and potassium carbonate (0.14 g, 1.0 mmol) in DMF (2 mL). The reaction was heated at 80° C. overnight. The reaction was diluted with EA, washed with water and brine, dried and concentrated. 122-5 (20 mg, 15%) was purified by flash chromatography (hexane:EA). $^1$H NMR (400 MHz, CDCl$_3$): δ 7.24-7.44 (m, 2H), 4.20-4.21 (ml, 1H), 4.02-4.07 (m, 1H0, 3.90 (s, 3H), 3.88 (s, 3H), 3.7603.86 (m, 1H), 1.17 (d, J=6.0, 3H).

Compound 122-6 was prepared in a similar manner to 19-2. Compound 122-7 was prepared in a similar manner to 18-7. LC/MS: m/z 442.15 [M+H]$^+$. Compound 122-8 was prepared in a similar manner to 18-5. LC/MS: m/z 702.25 [M+H]$^+$.

Compound 122-8 was deprotected in a similar manner to 16-2 to provide 122. LC/MS: m/z 599.05 [M+H]$^+$.

Example 109

Preparation of Compound 123

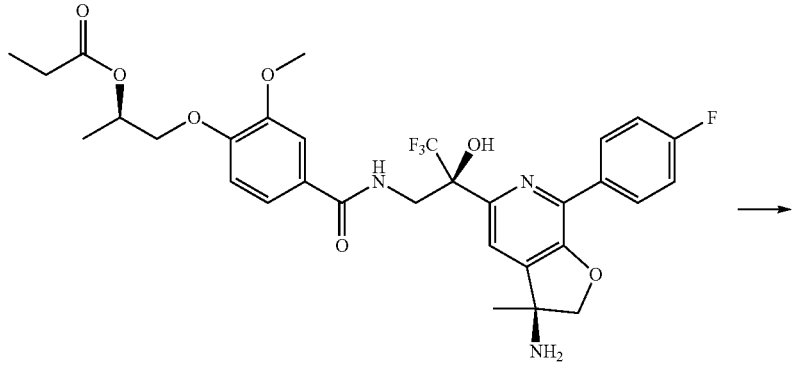

-continued

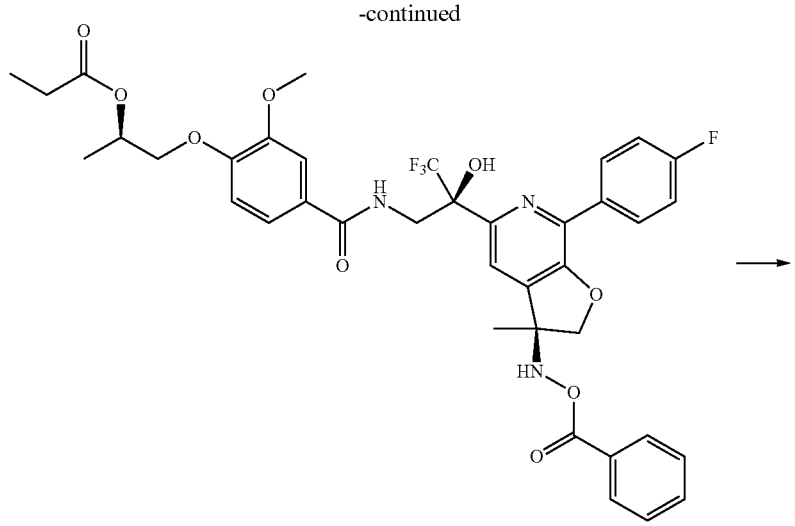
108-1

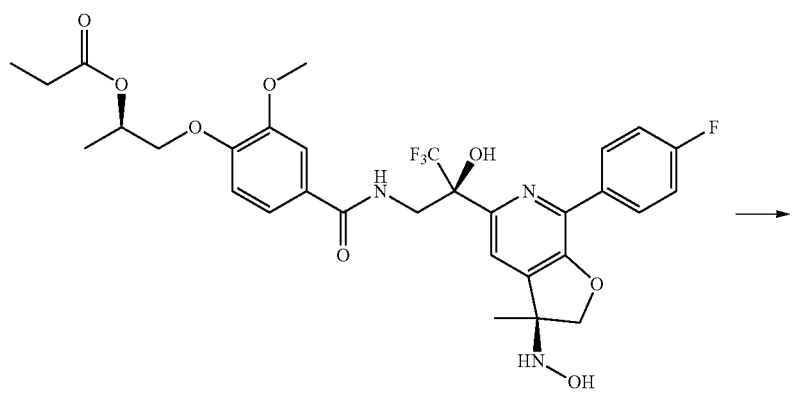
108-2

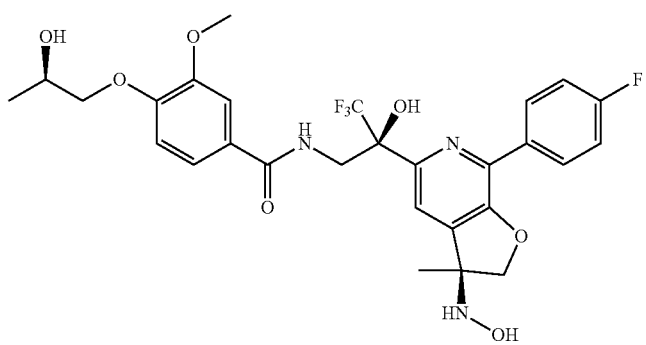
123

Benzoyl peroxide (0.25 g, 1.0 mmol) was added to a solution of 8 (131 mg, 0.21 mmol) and K$_2$HPO$_4$ (0.25 g, 1.4 mmol) in DMF (1 mL). The reaction was stirred at RT overnight. The reaction was diluted with ethyl acetate, washed with water and brine, dried and concentrated. 123-1 (0.15 g, 90%) was purified by flash chromatography (hexane:EA). LC/MS: m/z 756.25 [M+H]$^+$.

Hydrazine hydrate (0.5 mL) was added to a solution of 123-1 (250 mg, 0.32 mmol) in THF (0.5 mL), and the mixture was stirred overnight at RT. The reaction was diluted with ethyl acetate, washed with brine, dried and concentrated. 123-2 was used without purification. LC/MS: m/z 652.25 [M+H]$^+$.

2N HCl (0.1 mL) and conc. HCl (3 drops) were added to a solution of 123-2 (57 mg, 0.088 mmol) in THF (1 mL). The reaction was heated at 50° C. for 20 mins. The reaction was diluted with ethyl acetate, washed with brine, dried and concentrated. The final product was purified by HPLC to provide 123 (7 mg, 16%). LC/MS: m/z 596.25 [M+H]$^+$.

Example 110

Preparation of Compound 124

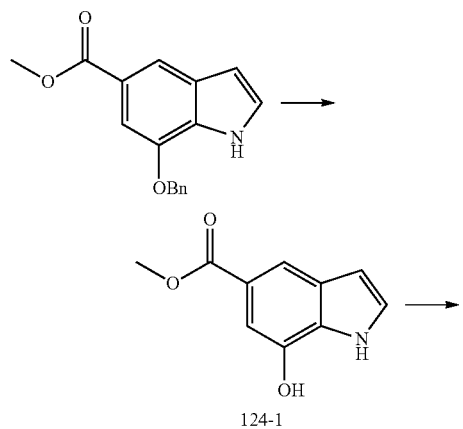

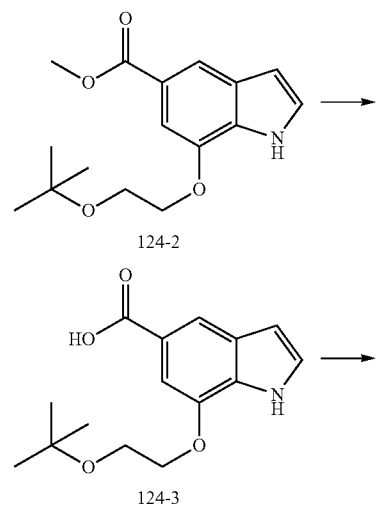

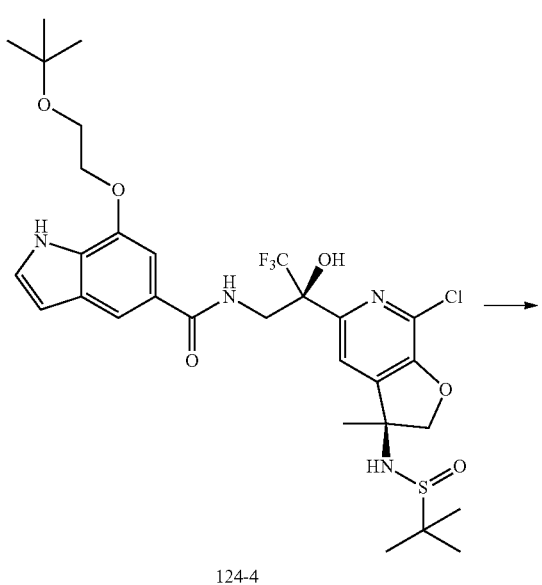

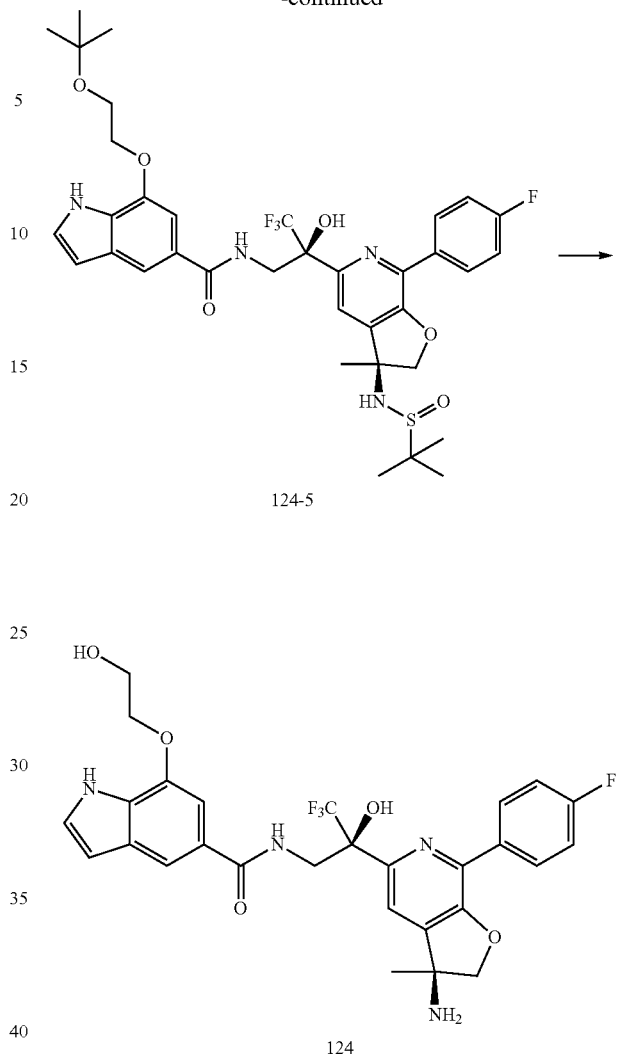

Methyl 7-(benzyloxy)-1H-indole-5-carboxylate (0.22 g) was hydrogenated over 10% Pd/C (30 mg) in EtOH for 2 h. The catalyst was removed by filtration, and the mixture was concentrated to yield 124-1 (0.13 g 92%), which was used without further purification. $^1$H NMR (400 MHz, CDCl$_3$): δ 8.54 (br. s, 1H), 8.03 (d, J=0.8, 1H), 7.37 (d, J=0.8, 1H), 7.25-7.27 (m, 1H), 6.61-6.62 (m, 1H), 3.92 (s, 3H).

Diisopropylazodicarboxylate (53 µL, 0.27 mmol) was added drop wise to a solution of 109-1 (47 mg, 0.25 mmol), 2-(tert-butoxy)ethanol (44 mg, 0.27 mmol) and triphenylphosphine (71 mg, 0.27 mmol). The reaction was stirred at RT for 2 h. The reaction was concentrated and the product 124-2 (50 mg, 68%) purified by flash chromatography (hexane/ethyl acetate). $^1$H NMR (400 MHz, CDCl$_3$): δ 9.31 (br. s, 1H), 8.08 (s, 1H), 7.37 (s, 1H), 7.19-7.20 (m, 1H), 6.58-6.59 (m, 1H), 5.28 (t, J=5.2, 2H), 3.89 (s, 3H), 3.77 (t, J=5.2, 2H), 1.26 (s, 9H).

Compound 124-3 was prepared in a similar manner to 19-2. Compound 124-4 was prepared in a similar manner to 18-7. LC/MS: m/z 675.20 [M+H]$^+$. Compound 124-5 was prepared in a similar manner to 18-5. LC/MS: m/z 735.30 [M+H]$^+$.

Compound 124 was prepared in a similar manner to 16. LC/MS: m/z 575.00 [M+H]$^+$.

Example 111
Preparation of Compound 125
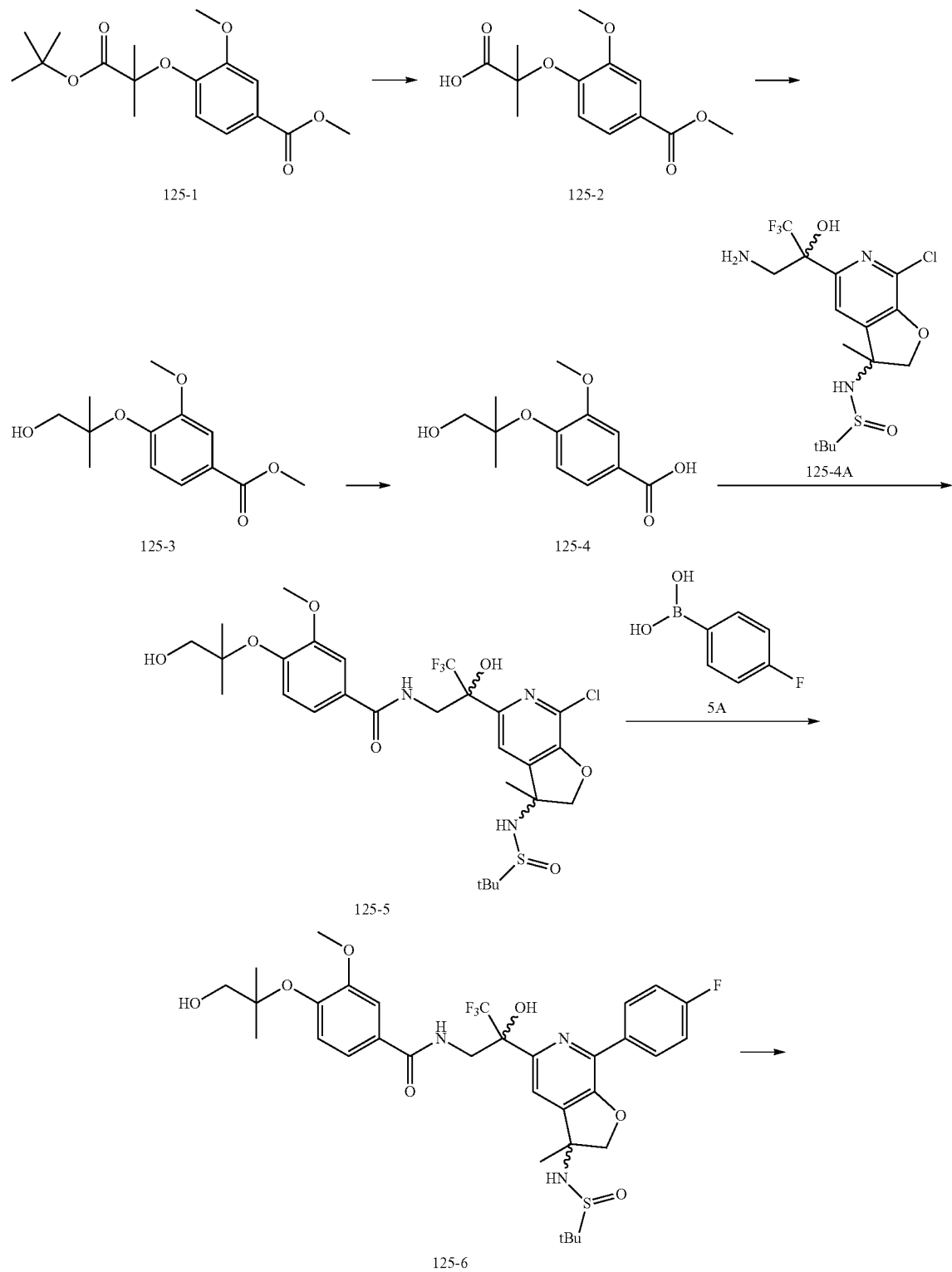

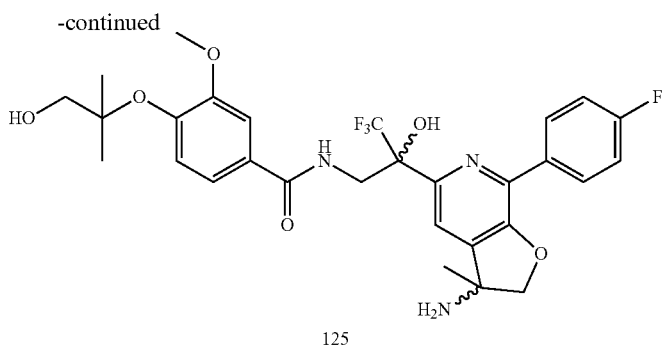

125

Compound 125-1 was prepared using methods similar to those provided in WO 2010/71813 A1, and Compound 125-4A was prepared using methods similar to those provided in WO 2015/26792 A1.

Compound 125 (5 mg, a white solid) was prepared using methods similar to those for preparing 21 using 125-1. MS: m/z 594.0 [M+M]⁺.

Example 112

Preparation of Compound 126

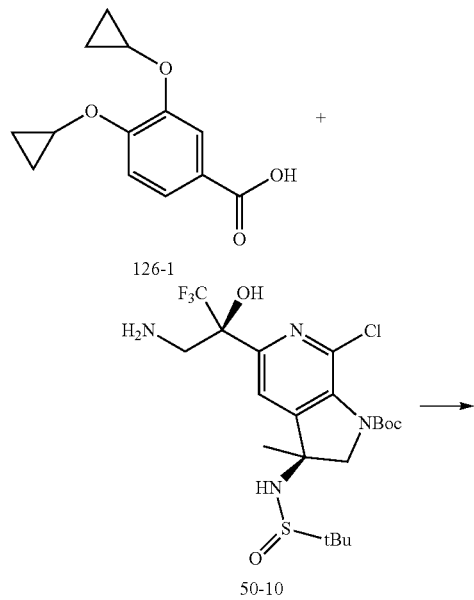

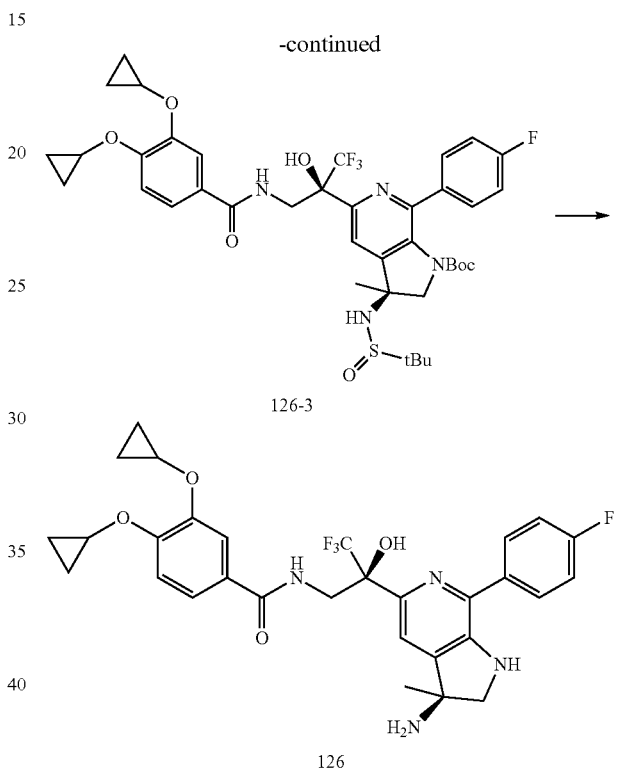

Compound 126-1 was prepared using as described in the preparation of 25.

Compound 126 (11 mg, a pale yellow solid) was prepared using methods similar to those for preparing 21 using 126-1 and 50-10. MS: m/z 609.1 [M+Na]⁺.

Example 113

Preparation of Compound 127

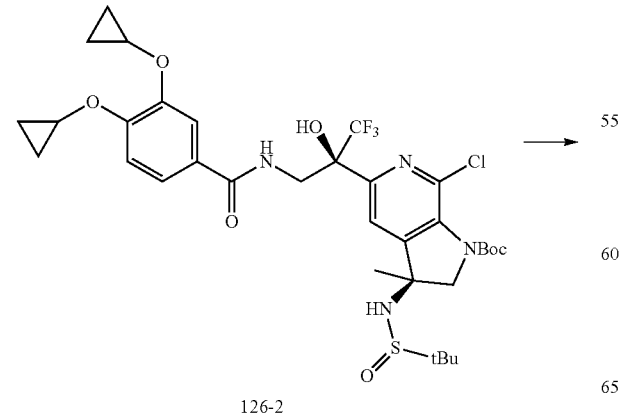

333
-continued
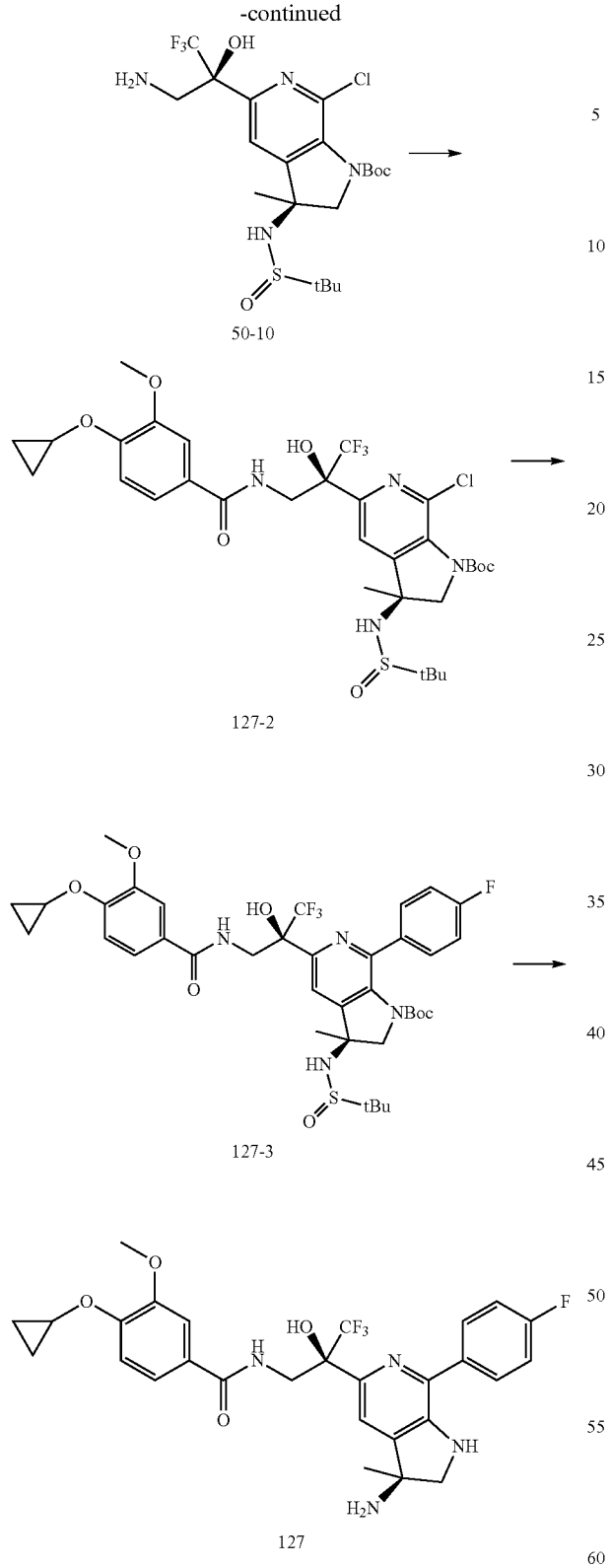
Compound 127-1 was prepared using methods similar to those provided in WO 2015/26792 A1.
Compound 127 (46 mg, a yellow solid) was prepared using methods similar to those for preparing 21 using 127-1 and 50-10. MS: m/z 561.1 [M+H]$^+$.
334
Example 114
Preparation of Compound 128
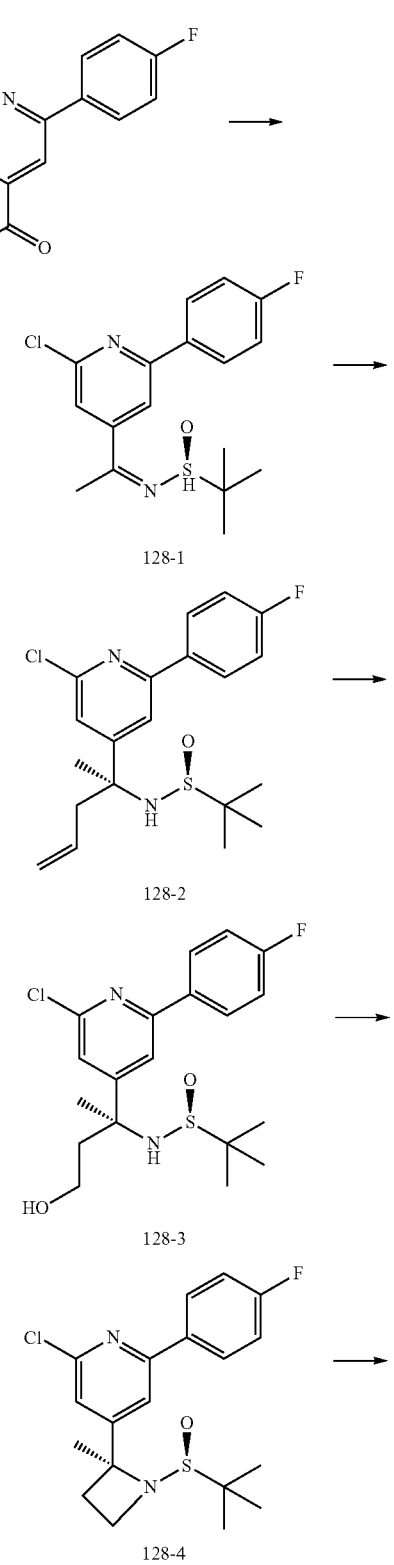

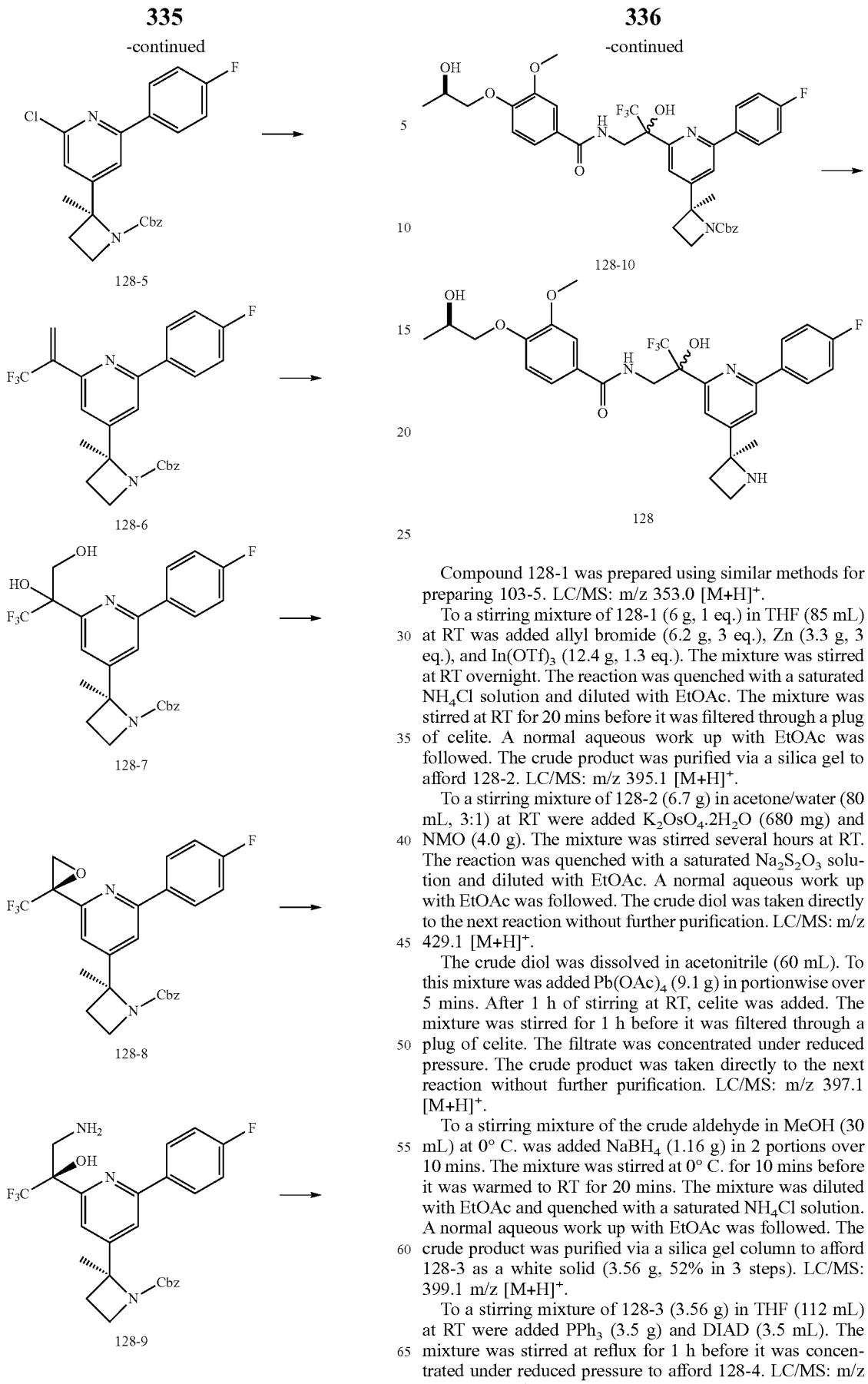

Compound 128-1 was prepared using similar methods for preparing 103-5. LC/MS: m/z 353.0 [M+H]$^+$.

To a stirring mixture of 128-1 (6 g, 1 eq.) in THF (85 mL) at RT was added allyl bromide (6.2 g, 3 eq.), Zn (3.3 g, 3 eq.), and In(OTf)$_3$ (12.4 g, 1.3 eq.). The mixture was stirred at RT overnight. The reaction was quenched with a saturated NH$_4$Cl solution and diluted with EtOAc. The mixture was stirred at RT for 20 mins before it was filtered through a plug of celite. A normal aqueous work up with EtOAc was followed. The crude product was purified via a silica gel to afford 128-2. LC/MS: m/z 395.1 [M+H]$^+$.

To a stirring mixture of 128-2 (6.7 g) in acetone/water (80 mL, 3:1) at RT were added K$_2$OsO$_4$·2H$_2$O (680 mg) and NMO (4.0 g). The mixture was stirred several hours at RT. The reaction was quenched with a saturated Na$_2$S$_2$O$_3$ solution and diluted with EtOAc. A normal aqueous work up with EtOAc was followed. The crude diol was taken directly to the next reaction without further purification. LC/MS: m/z 429.1 [M+H]$^+$.

The crude diol was dissolved in acetonitrile (60 mL). To this mixture was added Pb(OAc)$_4$ (9.1 g) in portionwise over 5 mins. After 1 h of stirring at RT, celite was added. The mixture was stirred for 1 h before it was filtered through a plug of celite. The filtrate was concentrated under reduced pressure. The crude product was taken directly to the next reaction without further purification. LC/MS: m/z 397.1 [M+H]$^+$.

To a stirring mixture of the crude aldehyde in MeOH (30 mL) at 0° C. was added NaBH$_4$ (1.16 g) in 2 portions over 10 mins. The mixture was stirred at 0° C. for 10 mins before it was warmed to RT for 20 mins. The mixture was diluted with EtOAc and quenched with a saturated NH$_4$Cl solution. A normal aqueous work up with EtOAc was followed. The crude product was purified via a silica gel column to afford 128-3 as a white solid (3.56 g, 52% in 3 steps). LC/MS: 399.1 m/z [M+H]$^+$.

To a stirring mixture of 128-3 (3.56 g) in THF (112 mL) at RT were added PPh$_3$ (3.5 g) and DIAD (3.5 mL). The mixture was stirred at reflux for 1 h before it was concentrated under reduced pressure to afford 128-4. LC/MS: m/z 381.1 [M+H]$^+$.

To a stirring mixture of 128-4 in MeOH (25 mL) at RT was added a solution of HCl in dioxane (5 mL). The mixture was stirred at RT for 10 mins before it was concentrated under reduced pressure and purified via a silica gel column.

To a stirring mixture of the HCl salt in DCM (30 mL) at 0° C. were added DIPEA (3.2 mL) and CbzCl (2.67 mL). The mixture was stirred at 0° C. for 10 mins and slowly warmed to RT for 30 mins. The reaction was quenched with a cold saturated NaHCO₃ solution and diluted with EtOAc. A normal aqueous work up with EtOAc was followed. The crude product was purified via a silica gel column to afford the N-Cbz protected amine (2.5 g). LC/MS: m/z 411.1 [M+H]⁺.

Compound 128-6 was prepared using similar methods for preparing 103-12. LC/MS: m/z 471.1 [M+H]⁺.

To a stirring mixture of 128-6 (680 mg) in tBuOH/water (2.4 mL each) at 0° C. were added NH₂SO₂Me (146 mg) and AD-mix β (4.2 g). The mixture was stirred at 0° C. for 5 h and slowly warmed to RT over the weekend. The crude product was diluted with EtOAc and quenched with a 10% aqueous solution of Na₂S₂O₃. A normal aqueous work up with EtOAc was followed. The crude product was purified via a silica gel column to afford the desired product as a colorless oil. LC/MS: m/z 505.2 [M+H]⁺.

Compound 128-8 was prepared using similar methods for preparing 103-14. LC/MS: m/z 487.1 [M+H]⁺. Compound 128-9 was prepared using similar methods for preparing 103-15. LC/MS: m/z 504.1 [M+H]⁺. Compound 128-10 was prepared using similar methods for preparing 103-16. LC/MS: m/z 712.3 [M+H]⁺.

To a stirring mixture of 128-10 (30 mg) in MeOH (0.7 mL) at RT were added Pd/C (7 mg) and Et₃SiH (51 mg total in 3 portions over 10 mins). The mixture was stirred at RT for 20 mins before it was filtered through a plug of celite. The filtrate was concentrated under reduced pressure and further purified via HPLC to afford 128 as a white solid. LCMS: m/z 578.2 [M+H]⁺.

Example 115

Preparation of Compound 14

The racemic mixture of 128 (120 mg) was separated by SFC using method showed below: "Column: Chiralpak AD-H 250×4.6 mm I.D., 5 μm Mobile phase: A: CO₂, B: ethanol (0.05% DEA) Gradient: from 5% to 40% of B in 4.2 mins and hold 40% for 3 mins, then 5% of B for 2.8 mins Flow rate: 2.5 mL/mins". After separation, the solution was concentrated, and re-purified by prep-HPLC (HCl condition) to give 14 (14 mg, 11.7%) as a light yellow solid. LCMS: m/z 578.0 [M+H]⁺.

Example 116

Preparation of Compound 13

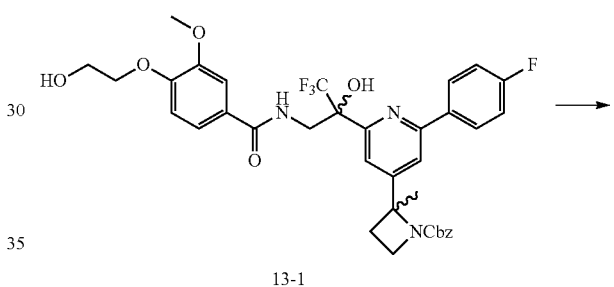

13-1

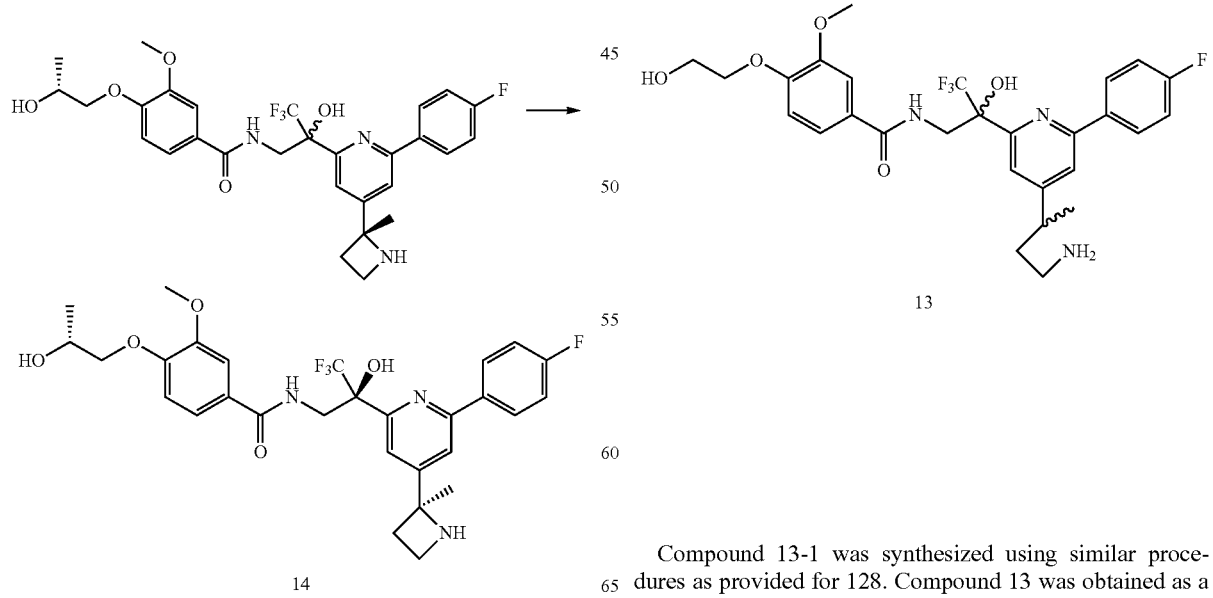

Compound 13-1 was synthesized using similar procedures as provided for 128. Compound 13 was obtained as a byproduct during the removal the N-Cbz protected amine using Et₃SiH, Pd/C in MeOH. LCMS: m/z 566.2 [M+H]⁺.

Example 117

Preparation of Compound 129

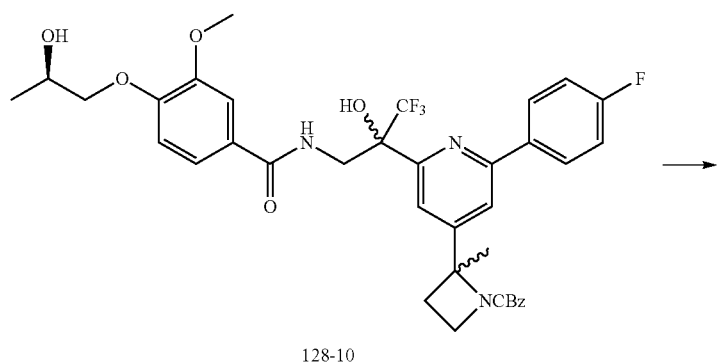

128-10

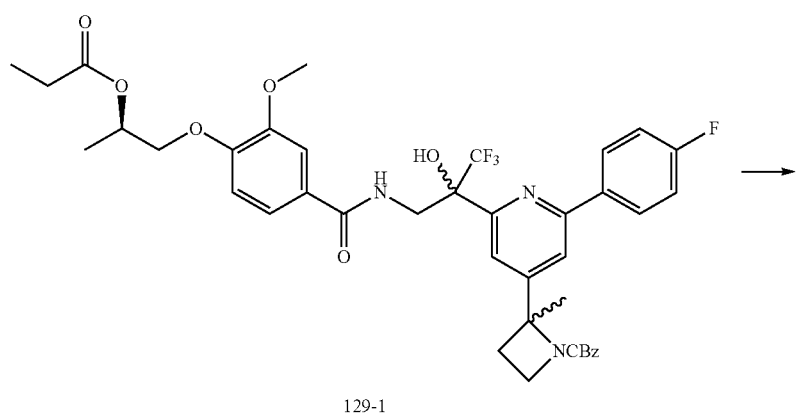

129-1

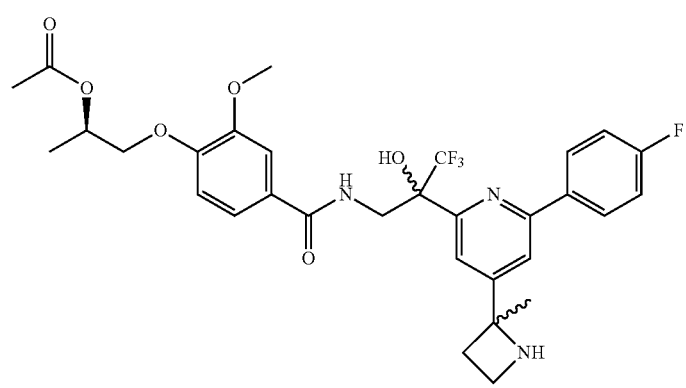

129

To stirring mixture of 128-10 (30 mg) and propionic acid (9.3 mg) in THF (1 mL) at RT were added a solution of DCC (60% in xylenes, 48 μL, 3 eq.) and DMAP (1 mg). The mixture was stirred at RT for 2 h before it was filtered. The filtrate was concentrated under reduced pressure. The crude product was purified via HPLC to afford 129-1 (28 mg, 88%). LC/MS: m/z 768.3 [M+H]$^+$.

To a stirring mixture of 129-1 (28 mg, 1 eq.) and Pd/C (6.3 mg) in MeOH (280 μL) was added Et$_3$SiH (13 mg) dropwise over 10 mins. The mixture was stirred for 15 mins before it was filtered and concentrated under reduced pressure. The crude product was purified via HPLC to afford 129 as a white solid. LC/MS: m/z 634.3 [M+H]$^+$.

Example 118
Preparation of Compound 130
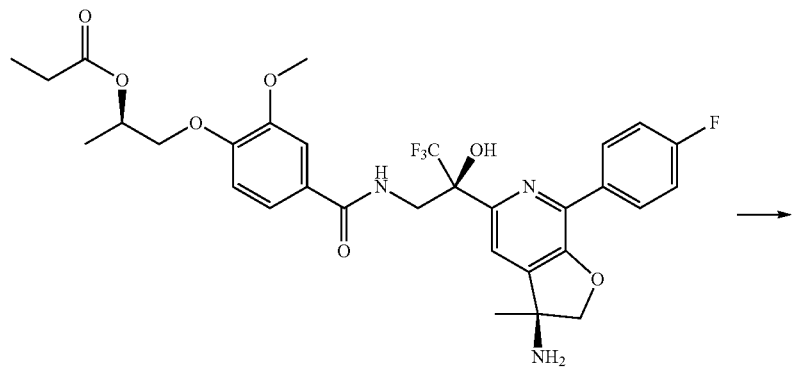
Trimethylaluminum (2M in hexane, 1.6 mL, 5.8 mmol) was added to a solution of 21 (0.403 g, 0.63 mmol) in acetonitrile (12 mL), and the solution was heating at 90° C. in a sealed tube for 1 h. The mixture was cooled to 0° C., quenched with MeOH, and concentrated. Crude 130-1 (50 mg, 13%) was purified by HPLC. LC/MS: m/z 677.10 [M+H]+.

HCl (2N, 0.1 mL) was added to a solution of 130-1 (50 mg, 0.074 mmol) in THF (3 mL). The solution was heated at 60° C. for 3 h. The reaction was concentrated and 130 (11.0 mg, 23%) was purified by HPLC. LC/MS: m/z 621.15 [M+H]+.

Example 119

Preparation of Compound 131

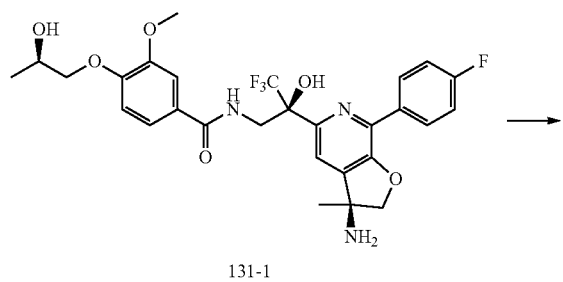

131-1

-continued

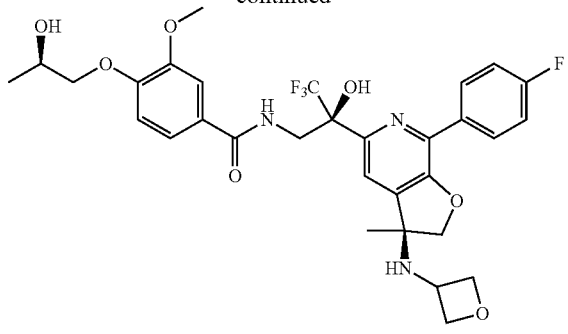

131

Sodium triacetoxyborohydride (93 mg, 0.24 mmol) was added to a solution of 131-1 (126 mg, 0.22 mmol), acetic acid (13 μL, 0.22 mmol) and 3-oxetanone (13 μL, 0.22 mmol) in dichloroethane (2 mL). The reaction was stirred at RT for 1 h, at which point additional reagents were added. The reaction was stirred at RT overnight. The reaction was diluted with EA, washed with 1N HCl and brine, dried and concentrated. Compound 131 (11 mg, 8%) was purified by HPLC. LC/MS: m/z 621.15 [M+H]+.

Example 120

Preparation of Compound 132

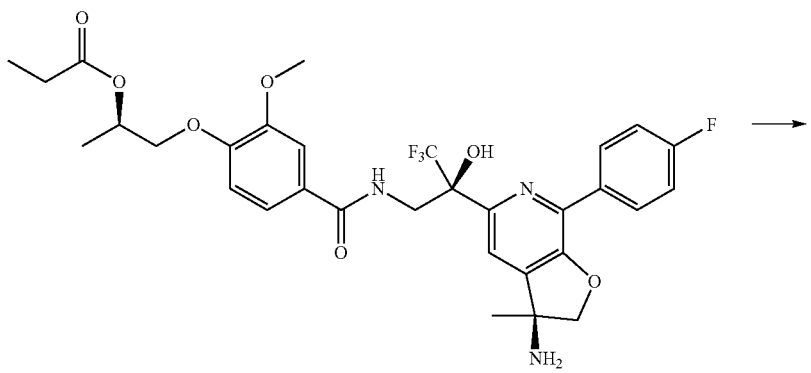

21

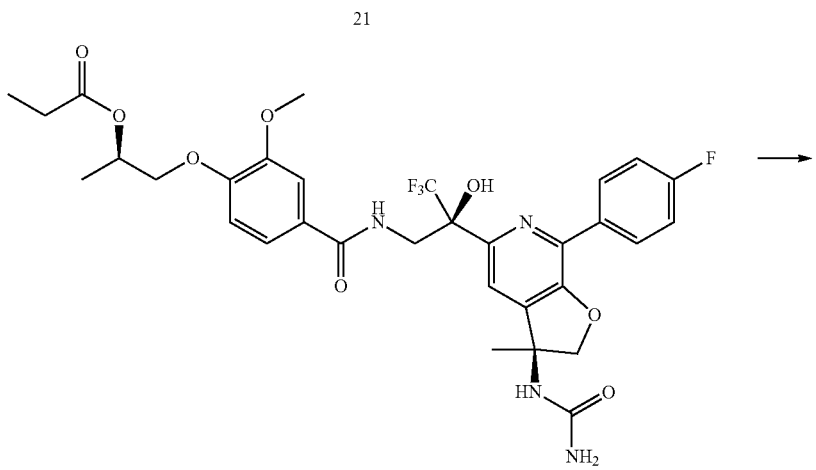

132-1

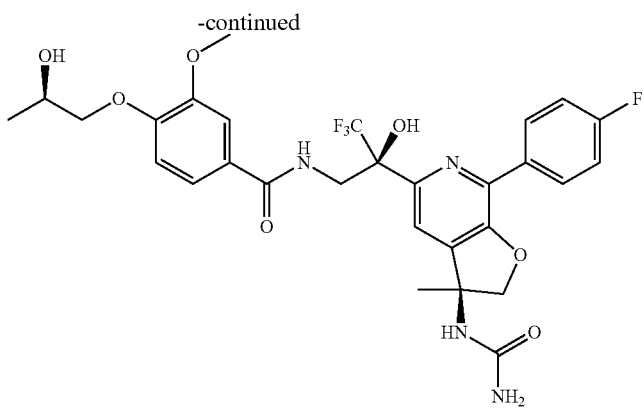
132
Ethyl-2-thiopseudourea hydrobromide (0.32 g, 1.7 mmol) was added to a solution of 21 (109 mg, 0.17 mmol) in EtOH (5 mL). The solution was heated at reflux for 2 days. The reaction was concentrated, and 132-1 (28 mg, 24%) was purified by HPLC. LC/MS: m/z 679.10 [M+H]⁺.
Compound 132 was prepared using methods similar to those for preparing 123 using 132-1. MS: m/z 623.05 [M+H]⁺.
Example 121
Preparation of Compounds 133, 134, 135 and 136
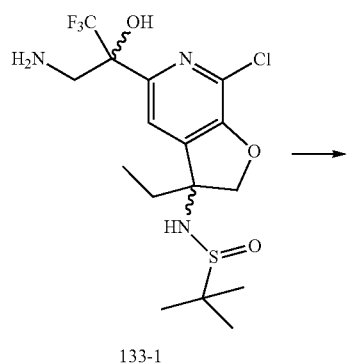
133-1
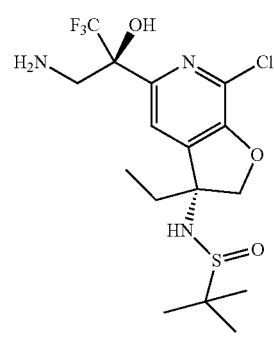
133-P1
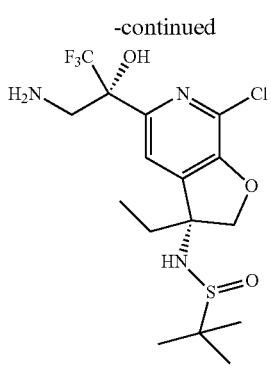
133-P2
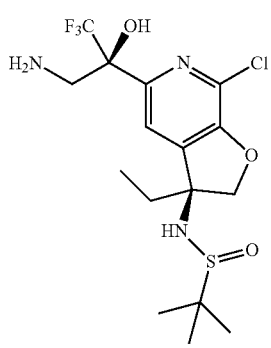
133-P3
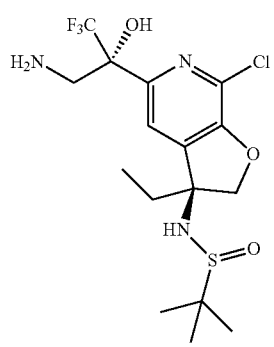
133-P4
133-P1 ⟶

133(2)-P1

133(3)-P1

133

133-P2 →

133(2)-P2

133(3)-P2

134

133-P3 →

133(2)-P3

133(3)-P3

-continued

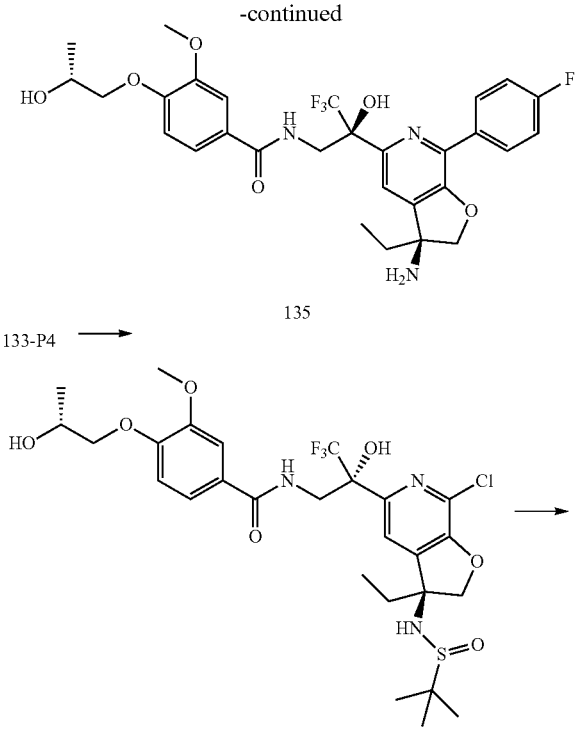

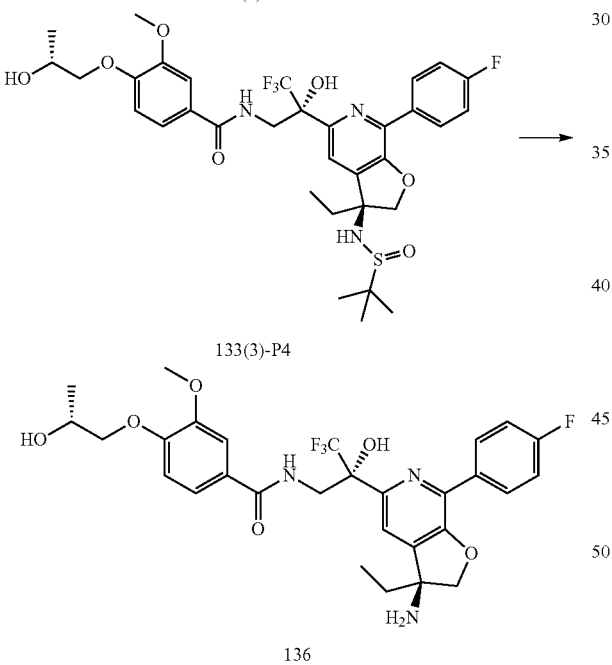

Compound 133-1 was prepared using methods similar to those provided in WO 2015/26792 A1.

Compound 133-1 (500 mg) was separated by prep-HPLC (FA condition). The separated solution was concentrated to give four desired isomers: 133-P1 (15.8 mg), 133-P2 (45 mg), 133-P3 (40 mg) and 133-P4 (68 mg) were obtained as a colorless oil. MS: m/z 429.9 [M+H]$^+$.

To a mixture of (R)-4-(2-hydroxypropoxy)-3-methoxybenzic acid (15.8 mg, 0.07 mmol, WO 2015/26792 A1) and DIPEA (14 mg, 0.1 mmol) in DMF (1 mL) was added HATU (13.3 mg, 0.035 mmol). The mixture was stirred at 25° C. for 5 mins and 133-P1 (15 mg, 0.035 mmol) was added. After stirring at 25° C. for 30 mins, the reaction was quenched with H$_2$O (5 mL) and extracted with EA (10 mL). The organic layer was concentrated to give crude 133(2)-P1 (12 mg) as a colorless oil. MS: m/z 638.0 [M+H]$^+$.

A mixture of 133(2)-P1 (12 mg, crude), 4-Fluorophenylboronic acid (10 mg, 0.07 mmol), Cs$_2$CO$_3$ (46.8 mg, 0.14 mmol) and Pd(dppf)Cl$_2$ (5 mg) in dioxane (2 mL):H$_2$O (0.2 mL) was heated at 120° C. for 30 mins under microwave. The mixture was concentrated, and the residue was purified by prep-TLC (EA) to give 133(3)-P1 (9.5 mg) as a colorless oil. MS: m/z 698.2 [M+H]$^+$.

To a solution of 133(3)-P1 (10 mg) in MeOH (0.5 mL) was added HCl/MeOH (4M, 0.5 mL). The mixture was stirred at 25° C. for 15 mins and concentrated. The residue was purified by prep-HPLC (HCl condition) to give 133 (2.5 mg) as a white solid. MS: m/z 594.1 [M+H]$^+$.

Compound 134 (9.3 mg, a white solid) 135 (32.1 mg, a white solid) and 136 (14.2 mg, a white solid) were prepared in a similar manner as preparing 133 using 133-P2, 133-P3 and 133-P4, respectively. 134: MS: m/z 594.2 [M+H]$^+$. 135: MS: m/z 594.1 [M+H]$^+$. 136: MS: m/z 594.1 [M+H]$^+$.

Example 121

Preparation of Compound 137

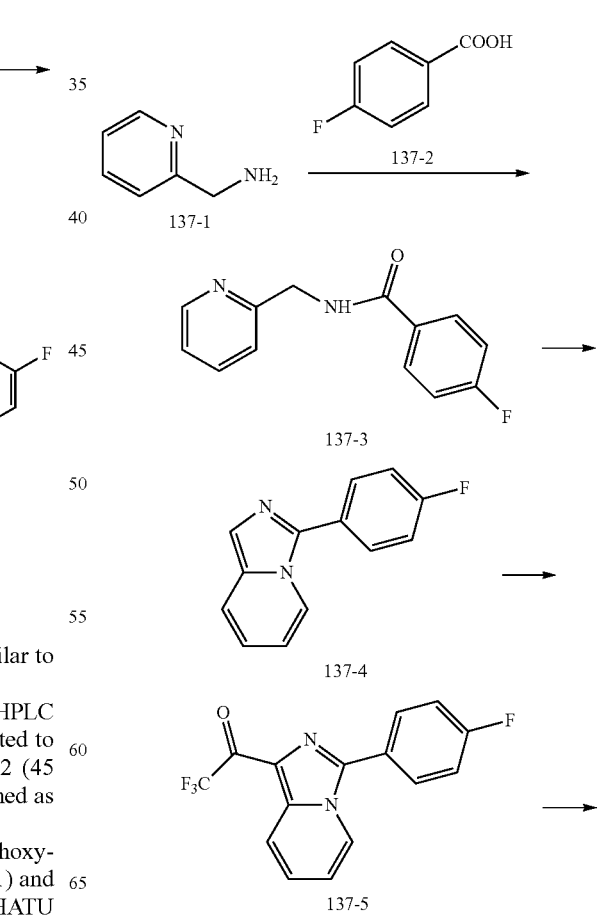

-continued

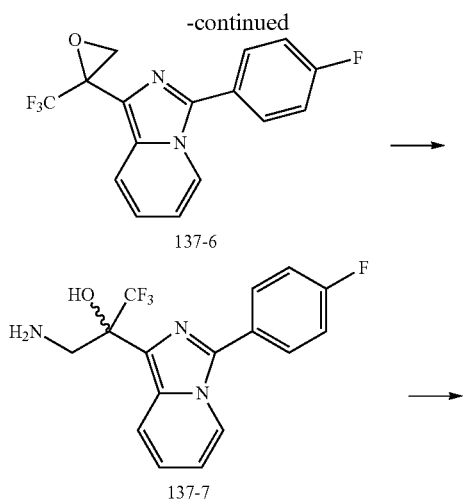

137-6

137-7

137

To a solution of 137-2 (2.6 g, 18.5 mmol) and DIPEA (4.8 g, 37.2 mmol) in DMF (20 mL) was added HATU (7.03 g, 18.5 mmol) in 1 portion. After stirring for 5 mins, 137-1 (2.0 g, 18.5 mmol) was added. The mixture was stirred at 25° C. for 30 mins. The mixture was poured into water (40 mL) and extracted with EA (2×20 mL). The combined organic layers were washed with brine (20 mL), dried over Na$_2$SO$_4$, filtered and concentrated. The residue was purified by column chromatography using 15~25% EA in PE as the eluent to give 137-3 (3.0 g, 70.5%) as light yellow oil. MS: m/z 230.9 [M+H]$^+$.

A mixture of 137-3 (2.8 g, 12.2 mmol) in TFAA (50 mL) was stirred at 50° C. for 3 h. 2 The reaction was quenched by saturated NaHCO$_3$ and extracted with EA (2×50 mL). The combined organic layers were dried, washed with brine (20 mL), dried over Na$_2$SO$_4$ and concentrated. The residue was purified by column chromatography using 5~15% EA in PE to give 137-4 (1.2 g, 46.6%) as a light yellow solid. MS: m/z 212.8 [M+H]$^+$.

To a solution of 137-4 (1.0 g, 4.7 mmol) in DMF (25.00 mL) was added TFAA (1.48 g, 7.1 mmol) dropwise. The mixture was stirred at 25° C. for 15 h. The reaction was quenched with saturated NaHCO$_3$ and extracted with EA (2×30 mL). The combined organic layers were washed with brine (20 mL), dried over Na$_2$SO$_4$, filtered and concentrated to give 137-5 (1.25 g, 86.1%) as a light yellow solid. MS: m/z 308.9 [M+H]$^+$.

To a mixture of t-BuOK (87 mg, 0.78 mmol) in CH$_3$CN (8 mL) was added Me$_3$SOI (143 mg, 0.65 mmol) in 1 portion. The mixture was degassed and stirred at 25° C. for 0.5 h. The clear solution was poured to a solution of 137-5 (200 mg, 0.65 mmol) in CH$_3$CN (8 mL), and the mixture was stirred at 25° C. for 1 h. The solution was used for the next step directly. MS: m/z 322.8 [M+H]$^+$.

A mixture of 137-6 (crude solution in CH$_3$CN) in NH$_3$-EtOH (10 mL, 7M) was stirred at RT for 1.5 h. The mixture was poured into water (40 mL) and extracted with EA (2×30 mL). The combined organic layers were washed with brine (20 mL), dried over Na$_2$SO$_4$, filtered and concentrated. The residue was purified by prep-TLC (DCM:MeOH=20:1) to give 137-7 (75 mg, 34% over 2 steps) as a light yellow gum.

To a solution of 4-(2-hydroxyethoxyl)-3-methoxybenzoic acid (41 mg, 0.19 mmol), DIEA (50 mg, 0.38 mmol) and 137-7 (65 mg, 0.19 mmol) in DMF (10 mL) was added HATU (73 mg, 0.19 mmol). The mixture was stirred at 25° C. for 2 h, poured into water (15 mL) and extracted with EA (2×15 mL). The combined organic layers were washed with brine (10 mL), dried over Na$_2$SO$_4$ and concentrated. The residue was purified by prep-HPLC (HCl condition) to give 137 (47 mg) as a white solid. MS: m/z 534.1 [M+H]$^+$.

Example 122

Preparation of Compound 138

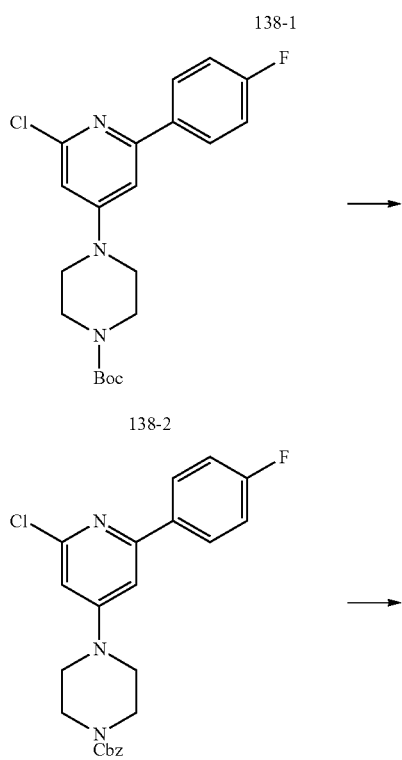

138-1

138-2

138-3

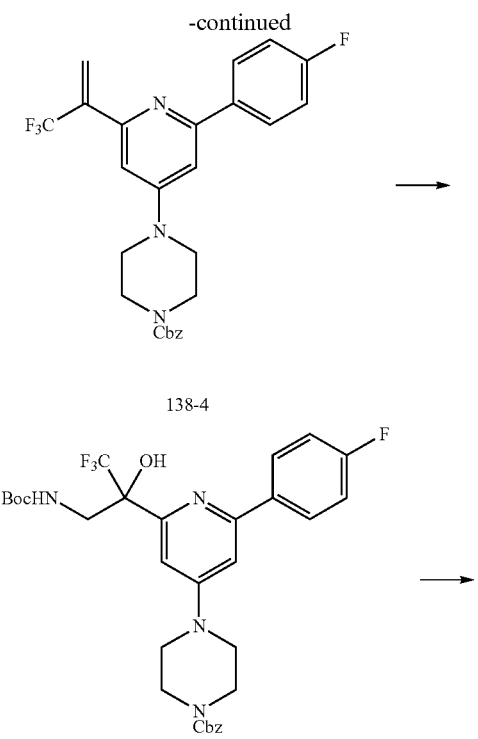

138-4

138-5

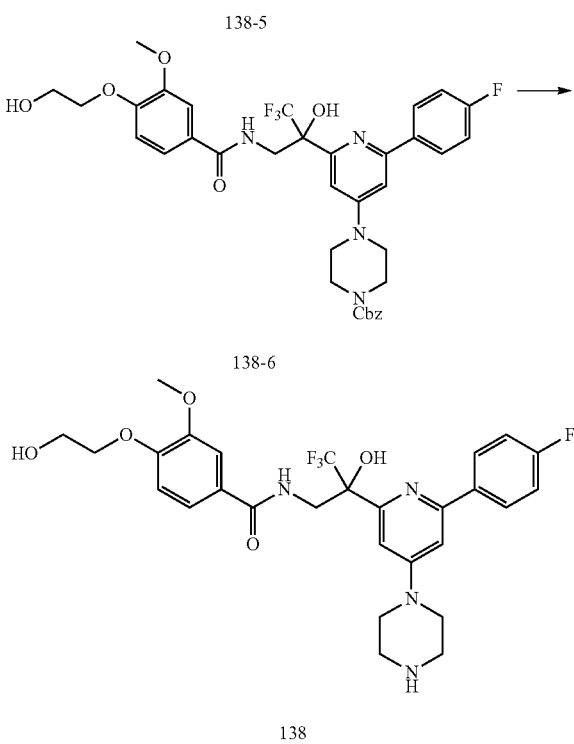

138-6

138

To a stirring mixture of 2,6-dichloro-4-nitropyridine (940 mg, 1 eq.) in THF:DMF (7.8 mL:2.3 mL) at RT were added Et$_3$N (670 µL) and 2,6-dichloro-4-nitropyridine (908 mg, 1 eq.). The mixture was stirred at RT for 2 h before it was concentrated under reduced pressure. The crude product mixture was purified via a silica gel column to afford the desired product as a yellow solid (560 mg, 37%). LC/MS: m/z 332.1 [M+H]$^+$.

To a stirring mixture of tert-butyl 4-(2,6-dichloropyridin-4-yl)piperazine-1-carboxylate (560 mg, 1 eq.) in a solution of TBAF in THF (5.1 mL, 3 eq.) at RT were added PdCl$_2$(dppf) (124 mg, 0.1 eq.) and (4-fluorophenyl)boronic acid (235 mg, 1 eq.). The mixture was carried under the microwave condition at 90° C. for 1 h. The mixture was concentrated under reduced pressure and purified via a silica gel column to afford the desired product as a white solid. LC/MS: m/z 392.2 [M+H]$^+$.

2N HCl in dioxane (3 mL) was added to 138-2 (0.11 g, 0.28 mmol), and the solution was stirred at RT for 1 h. The reaction was concentrated and then redissolved in dichloromethane (3 mL). DIEA (0.15 mL, 0.85 mmol) and benzyl chloroformate (52 µL, 0.37 mmol) were added, and the reaction was stirred at RT for 2 h. The reaction was concentrated, and 138-3 (0.116 g, 96%) was purified by flash chromatography (hexane:EA). LC/MS: [M+H] 426.05 [M+H]$^+$.

Compound 138-4 was prepared using methods similar to preparing 18-4. LC/MS: m/z 486.15 [M+H]$^+$. Compound 138-5 was prepared using methods similar to preparing 18-6. LC/MS: m/z 619.25 [M+H]$^+$. Compound 138-6 was prepared using methods similar to preparing 18-7. LC/MS: m/z 713.25 [M+H]$^+$.

Compound 138 was prepared by deprotecting 138-6 using methods similar to those for preparing 18. LC/MS: m/z 579.25 [M+H]$^+$.

Example A

RSV Antiviral Assay

CPE reduction assays are performed as described by Sidwell and Huffman et al., Appl. Microbiol. (1971) 22(5): 797-801 with slight modifications. HEp-2 cells (ATCC#, CCL-23) are seeded at a density of 1,500 cells/30 µL/well into the 384-well cell plate(s) (Corning#3701) one day prior to the assay. Compounds are added into 384-well cell plates by Labcyte POD 810 Plate Assembler system. Each of the test compounds is provided to duplicate wells of a 384-well cell plate at final concentrations starting from 100 µM or 1 µM using 1/3 stepwise dilutions for 9 points. Quick-thaw Respiratory Syncytial Virus (RSV) long strain (ATCC#VR-26) stock in a 37° C. water bath. Place on ice until ready to use. Viruses are diluted to the concentration of 100 TCID$_{50}$/30 µL with medium and 30 µl diluted RSV are added into related wells of 384-well cell plates. For each plate, sixteen wells are set aside as uninfected, untreated cell controls (CC), and nine wells per test plate receive virus only as a control for virus replication (VC). The final DMSO concentration of all wells is 1%. Place the plates at 37° C., 5% CO$_2$ for 5 days.

After 5 days incubation, observe the CPE of cells in all wells. Cell controls should be natural and have no cell fusion; Cells in the virus control wells should exhibit signs of virus cytopathology (giant cell formation, syncytia). Six µl of cell counting kit-8 reagent (CCK-8, Dojindo Molecular Technologies Inc., CK04-20) are added to each well, which allows colorimetric assays to determine the number of viable cells through the dehydrogenase activity detection. After 3-4 hour incubation, the absorbance of each well is measured with a spectrophotometric plate reader at 450 nm wavelength, using a 630 nm filter as background according to manufacturer's instruction. The 50% effective concentration (EC$_{50}$) is calculated by using regression analysis, based on the mean O.D. at each concentration of compound.

Compounds of Formula (I) are active in the assay against the RSV virus as demonstrated in Tables A and B. Table A includes compounds with an $EC_{50}$ value that is less than 1 µM. Table B includes compounds with an $EC_{50}$ value that is equal to or higher than 1 µM and less than 50 µM. Other tested compounds disclosed herein had an $EC_{50}$ value of 50 µM or greater.

TABLE A

| Compound |
| --- |
| 1 |
| 2 |
| 3 |
| 4 |
| 5 |
| 6 |
| 7 |
| 8 |
| 12 |

TABLE B

| Compound |
| --- |
| 10 |

Example B

Cytotoxicity Determination

In order to determine the compound cytotoxicity, in parallel, each of the compounds is applied to duplicate wells in a 384-well cell plate at serial final concentrations starting from 100 µM using ½ stepwise dilutions for 7 points without addition of virus. Incubate the cells at 37° C., 5% $CO_2$ for 5 days. Add 6 µL CCK-8 into each well and incubate in a $CO_2$ incubator at 37° C. for 3-4 h. Read the plates to obtain the optical densities which are used to calculate 50% cytotoxicity concentration ($CC_{50}$).

Compounds of Formula (I) are not cytotoxic as shown in Tables C and D. Table C includes compounds with a $CC_{50}$ value that is greater than 100 µM. Table D includes compounds with a $CC_{50}$ value that is equal to or less than 100 µM and greater than 10 µM. Other tested compounds disclosed herein had a $CC_{50}$ value of less than 10 µM.

TABLE C

| Compound |
| --- |
| 3 |
| 6 |
| 7 |
| 8 |
| 12 |
| 26 |
| 37 |
| 40 |
| 46 |
| 51 |
| 67 |
| 71 |
| 72 |
| 82 |
| 87 |
| 119 |
| 130 |

TABLE D

| Compound |
| --- |
| 1 |
| 2 |
| 5 |
| 10 |
| 11 |
| 13 |
| 14 |
| 15 |
| 16 |
| 18 |
| 19 |
| 20 |
| 21 |
| 22 |
| 23 |
| 24 |
| 25 |
| 27 |
| 30 |
| 31 |
| 34 |
| 35 |
| 36 |
| 38 |
| 39 |
| 41 |
| 43 |
| 44 |
| 47 |
| 48 |
| 49 |
| 55 |
| 57 |
| 59 |
| 60 |
| 61 |
| 62 |
| 65 |
| 68 |
| 69 |
| 70 |
| 73 |
| 74 |
| 75 |
| 76 |
| 79 |
| 80 |
| 81 |
| 83 |
| 84 |
| 85 |
| 86 |
| 88 |
| 90 |
| 91 |
| 92 |
| 93 |
| 94 |
| 95 |
| 98 |
| 101 |
| 102 |
| 103 |
| 106 |
| 107 |
| 108 |
| 109 |
| 110 |
| 111 |
| 112 |
| 113 |
| 114 |
| 115 |
| 116 |
| 117 |
| 118 |
| 120 |
| 121 |

TABLE D-continued

| Compound |
|---|
| 122 |
| 123 |
| 124 |
| 125 |
| 126 |
| 127 |
| 129 |
| 131 |
| 132 |
| 138 |

Example C

RSV Polymerase Inhibition Assay

Standard RSV polymerase assays were conducted in the presence of 10 nM recombinant RSV complex in a reaction buffer containing Tris-HCl pH7.5, 6 mM $MgCl_2$, and other additives and substrates including RNA oligonucleotides and radionucleotides. Standard reactions were incubated in 96-well plate format for 2 h at 30° C., in the presence of increasing concentration of inhibitor. The reaction was stopped with 90 µL of 0.1M EDTA, and the reaction product was transferred to a "reading" 96-well plate. After washing of the plate, radiolabeled RNA products were detected according to standard procedures with a Trilux Topcount scintillation counter. The compound concentration at which the enzyme-catalyzed rate was reduced by 50% ($IC_{50}$) was calculated by fitting the data to a non-linear regression (sigmoidal). The $IC_{50}$ values were derived from the mean of several independent experiments and are shown in Tables E and F.

Table E includes compounds with an $IC_{50}$ of <1 µM. Table F includes compounds with an $IC_{50}$<50 µM.

TABLE E

| Compound |
|---|
| 1 |
| 2 |
| 3 |
| 9 |
| 11 |
| 12 |
| 13 |
| 14 |
| 15 |
| 16 |
| 17 |
| 18 |
| 19 |
| 20 |
| 21 |
| 22 |
| 23 |
| 24 |
| 25 |
| 27 |
| 28 |
| 30 |
| 31 |
| 32 |
| 33 |
| 34 |
| 35 |
| 36 |
| 37 |
| 38 |
| 39 |

TABLE E-continued

| Compound |
|---|
| 40 |
| 41 |
| 42 |
| 43 |
| 44 |
| 47 |
| 49 |
| 51 |
| 53 |
| 55 |
| 56 |
| 57 |
| 58 |
| 59 |
| 60 |
| 61 |
| 65 |
| 68 |
| 69 |
| 70 |
| 71 |
| 72 |
| 73 |
| 74 |
| 75 |
| 76 |
| 77 |
| 79 |
| 80 |
| 81 |
| 82 |
| 83 |
| 84 |
| 85 |
| 86 |
| 87 |
| 88 |
| 89 |
| 90 |
| 91 |
| 92 |
| 94 |
| 95 |
| 96 |
| 97 |
| 98 |
| 99 |
| 101 |
| 102 |
| 103 |
| 106 |
| 108 |
| 109 |
| 110 |
| 111 |
| 112 |
| 113 |
| 114 |
| 115 |
| 116 |
| 118 |
| 119 |
| 120 |
| 121 |
| 122 |
| 123 |
| 124 |
| 125 |
| 126 |
| 127 |
| 130 |
| 131 |
| 132 |
| 133 |
| 137 |
| 138 |

TABLE F

| Compound |
|---|
| 10 |
| 26 |
| 48 |
| 54 |
| 62 |
| 67 |
| 78 |
| 93 |
| 100 |
| 107 |
| 117 |

Example D

RSV Assay

The RSV subgenomic replicon 395 HeLa and APC126 were licensed from Apath (Brooklyn, N.Y.) and were originally developed by Dr. Mark Meeples of Center for Vaccines & Immunity, the Research Institute at Nationwide Children's Hospital in Columbus, Ohio. To generate subgenomic RSV replicon, three glycoprotein genes, those for SH, G, and F, from a full-length recombinant GFP-expressing (rg) RSV antigenomic cDNA were deleted. In their place, a blasticidin S deaminase (bsd) gene was inserted. Through multiple steps, the RSV replicon was established in HeLa cells (395 Hela) or BHK cells (APC126). Both 395 HeLa and APC126 cells were cultured in Dulbecco's Modified Eagle Medium (DMEM) containing 4500 mg/L D-glucose, L-glutamine, and 110 mg/L sodium pyruvate (Invitrogen, Cat. #11995-040). The medium was further supplemented with 10% (v/v) fetal bovine serum (FBS) (Mediatech, Cat. #35-010-CV), 1% (v/v) penicillin/streptomycin (Mediatech, Cat. #30-002-CI), and 10 µg/mL of Blasticidin (BSD) (Invivogen, Cat. code ant-bl-1). Cells were maintained at 37° C. in a humidified 5% $CO_2$ atmosphere.

Determination of 50% inhibitory concentration ($EC_{50}$), 90% inhibitory concentration ($EC_{90}$) and 50% cytotoxic concentration ($CC_{50}$) in RSV replicon cells were performed by the following procedure. On the first day, 5000 RSV replicon cells per well were plated in a 96-well plate. On the following day, compounds to be tested were solubilized in 100% DMSO to 100X the desired final testing concentration. Each compound was serially diluted (1:3) up to 9 distinct concentrations. Compounds in 100% DMSO were reduced to 10% (v/v) DMSO by diluting 1:10 in cell culture media. A 10 µL sample of the compounds diluted to 10% (v/v) DMSO with cell culture media was used to treat the RSV replicon cells in 96-well format. The final DMSO concentration was 1% (v/v). Cells were incubated with compounds for 7 days (for 395Hela) or 3 days (for APC126) at 37° C. in a 5% $CO_2$ atmosphere. In each assay, positive control that was previously characterized in the RSV replicon assay was included.

The Renilla Luciferase Assay System (Promega, Cat. #E2820) was used to measure anti-RSV replicon activity. Assay plates were set up as stated above. Luminescence was recorded using a Perkin Elmer multilabel counter Victor3V. $EC_{50}$, the concentration of the drug required for reducing RSV replicon RNA by 50% in relation to the untreated cell control value, was calculated from the plot of percentage reductions of the optical density (OD) value against the drug concentrations using the Microsoft Excel forecast function.

395 HeLa or APC126 cell proliferation assay (Promega; CellTiter-Glo Luminescent Cell Viability Assay, Cat. #G7572) was used to measure cell viability. The CellTiter-Glo® Luminescent Cell Viability Assay is a homogeneous method to determine the number of viable cells in culture based on quantitation of the ATP present, which signals the presence of metabolically active cells. Assay plates were set up in the same format as noted above for the replicon assay. CellTiter-Glo reagent (100 µL) was added to each well and incubated at room temperature for 8 minutes. Luminescence was recorded using a Perkin Elmer multilabel counter Victor3V. The $CC_{50}$, the concentration of the drug required for reducing viable cells by 50% in relation to the untreated cell control value, was calculated from the plot of percentage reductions of the luminescence value against the drug concentrations using the Microsoft Excel forecast function.

Table G includes compounds with an $EC_{50}$ value that is less than 1 µM. Table H includes compounds with an $EC_{50}$ value that is equal to or higher than 1 µM and less than 50 µM. Other tested compounds disclosed herein had an $EC_{50}$ value of 50 µM or greater.

TABLE G

| Compound |
|---|
| 1 |
| 2 |
| 3 |
| 5 |
| 6 |
| 7 |
| 8 |
| 11 |
| 12 |
| 13 |
| 14 |
| 15 |
| 16 |
| 18 |
| 19 |
| 20 |
| 21 |
| 22 |
| 23 |
| 24 |
| 28 |
| 30 |
| 31 |
| 33 |
| 34 |
| 35 |
| 36 |
| 37 |
| 38 |
| 39 |
| 40 |
| 41 |
| 44 |
| 47 |
| 49 |
| 51 |
| 55 |
| 57 |
| 59 |
| 60 |
| 61 |
| 62 |
| 65 |
| 67 |
| 68 |
| 69 |
| 70 |
| 71 |
| 72 |
| 73 |

TABLE G-continued

| Compound |
|---|
| 74 |
| 75 |
| 76 |
| 79 |
| 80 |
| 81 |
| 82 |
| 83 |
| 84 |
| 85 |
| 87 |
| 88 |
| 90 |
| 91 |
| 92 |
| 94 |
| 95 |
| 96 |
| 97 |
| 98 |
| 101 |
| 103 |
| 106 |
| 112 |
| 113 |
| 114 |
| 115 |
| 118 |
| 119 |
| 120 |
| 121 |
| 122 |
| 123 |
| 124 |
| 125 |
| 126 |
| 127 |
| 129 |
| 130 |
| 131 |
| 132 |

TABLE H

| Compound |
|---|
| 10 |
| 26 |
| 43 |
| 86 |
| 93 |
| 102 |
| 107 |
| 108 |
| 117 |
| 138 |

Example E

Combination Studies

RSV with Renilla Reporter

RSV expressing Renilla luciferase (A2-RL-line19F) are generated by Dr. Martin Moore of Emory University, Atlanta, Ga., USA. The in vitro viral kinetics of A2-RL-line19F is similar to that of wild type RSV (See Hotard, A. L., Virology (2012) 434(1):129-136).

Host cell HEp-2 are purchased from ATCC (Cat. #CCL-23) and cells are cultured in DMEM/Ham's F-12 50/50 1× containing L-glutamine and 15 mM HEPES (Mediatech, Cat. #10-092-CM). The medium is further supplemented with 5% (v/v) FBS (Mediatech, Cat. #35-010-CV) and 1% (v/v) penicillin/streptomycin (Mediatech, Cat. #30-002-0). HEp-2 cells are maintained at 37° C. in a humidified 5% $CO_2$ atmosphere.

Drug Treatment and Viral Dosing

To determine the effect of a combination of compounds, the following procedure is followed. On the first day, 20,000 HEp-2 cells are plated per well in a 96-well plate. On the following day, test articles are solubilized in 100% DMSO (for chemicals) or 1×PBS (for biologics) to 200× the desired final testing concentration. Subsequently, Compound (A), or a pharmaceutically acceptable salt thereof, is serially diluted (1:3) to 9 distinct concentrations "horizontally" in a 96-well plate, and Compound (B), or a pharmaceutically acceptable salt thereof, is serially diluted (1:3) to 7 distinct concentrations "vertically" in 96-well plate. The serially diluted 200× test articles are then diluted 1:10 into cell culture media to generate 20× test articles. A 5 µL aliquot of the 20× test articles is added in a checkerboard fashion to the cells with 90 µL existing media. Space is also allotted for titrations of each of the compounds alone to be used as reference controls. After 12 hour pre-incubation of test articles, A2-RL-line19F at an MOI of 0.5 is added to the plate and is further incubated for 2 days at 37° C. in a 5% $CO_2$.

Determination of Anti-RSV Activity

The Renilla Luciferase Assay System (Promega, Cat. # E2820) is used to measure anti-RSV replicon activity. Assay plates are set up as stated above. Luminescence is recorded using a Perkin Elmer multilabel counter Victor3V.

Cell Viability Assay

Promega CellTiter-Glo Luminescent Cell Viability Assay, Cat. #G7572) is used to measure cell viability. The CellTiter-Glo® Luminescent Cell Viability Assay is a homogeneous method to determine the number of viable cells in culture based on quantitation of the adenosine triphosphate (ATP) present, which signals the presence of metabolically active cells. Assay plates are set up in the same format the anti-RSV assay, except that no virus is added to the cell viability assay. A 100-µL aliquot of CellTiter-Glo reagent is added to each well and incubated at room temperature for 8 minutes. Luminescence is recorded using a Perkin Elmer multilabel counter Victor3V.

Data Analysis

Each experiment is performed at N=5 for both anti-RSV activity and cell viability. Mean percent inhibition of the replicon values from the 5 experiments is generated and for anti-RSV activity, it is analyzed using two drug interaction analysis models, Isobologram Analysis and/or Prichard's Model.

Isobologram Analysis

The effects of drug-drug combinations are evaluated by the Loewe additivity model in which the experimental data are analyzed using CalcuSyn (Biosoft, Ferguson, Mo.), a computer program based on the method of Chou and Talalay. The combination index (CI) value and the isobologram for each experimental combination are calculated. CI values of <1, 1, and >1 indicate synergy, additive effect, and antagonism, respectively. Under the synergy category, CI<0.1 is considered very strong synergism; CI 0.1-0.3 strong synergism; CI 0.3-0.7 synergism and CI 0.7-0.85 moderate synergism. The isobologram analysis, which graphically represents additive, synergistic, and antagonistic drug effects, is also used to model the interaction of antiviral activities. In this representation, an effective concentration (EC) value of one drug is plotted on one axis and corresponding EC value of a second drug is plotted on the second axis; the line connecting these two points represents the amount of each drug in a combination that would be required to reach the equivalent EC value, given that their effects are additive.

Prichard's Model (MacSynergy II)

MacSynergy II software is kindly provided by Dr. M. Prichard (University of Michigan). This program allows the three-dimensional examination of drug interactions of all data points generated from the checkerboard combination of two inhibitors with Bliss-Independence model. Confidence bounds are determined from replicate data. If the 95% confidence limits (CL) do not overlap the theoretic additive surface, then the interaction between the two drugs differs significantly from additive. The volumes of synergy or antagonism can be determined and graphically depicted in three dimensions and represent the relative quantity of synergism or antagonism per change in the two drug concentrations. Synergy and antagonism volumes are based on the Bliss independence model, which assumes that both compounds act independently on different targets. A set of predicted fractional responses faAB under the Bliss independence model is calculated as faAB=faA+faB−faA·faB with faA and faB representing the fraction of possible responses, e.g. % inhibition, of compounds A and B at amounts dA and dB, respectively, and describes the % inhibition of a combination of compounds A and B at amount (dA+dB). If faAB>faA+faB−faA·faB then we have Bliss synergy; if faAB<faA+faB−faA·faB then we have Bliss antagonism. The 95% synergy/antagonism volumes are the summation of the differences between the observed inhibition and the 95% confidence limit on the prediction of faAB under the Bliss independence model. MacSynergy II is used for data analysis.

MacSynergy II Volume Descriptions: <25 $\mu M^2\%$=Additive; 25-50 $\mu M^2\%$=Minor synergism; 50-100 $\mu M^2\%$=Significant synergism; and >100 $\mu M^2\%$=Strong synergism.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, having the structure:

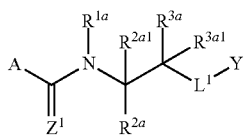

(I)

wherein:

$L^1$ is selected from the group consisting of

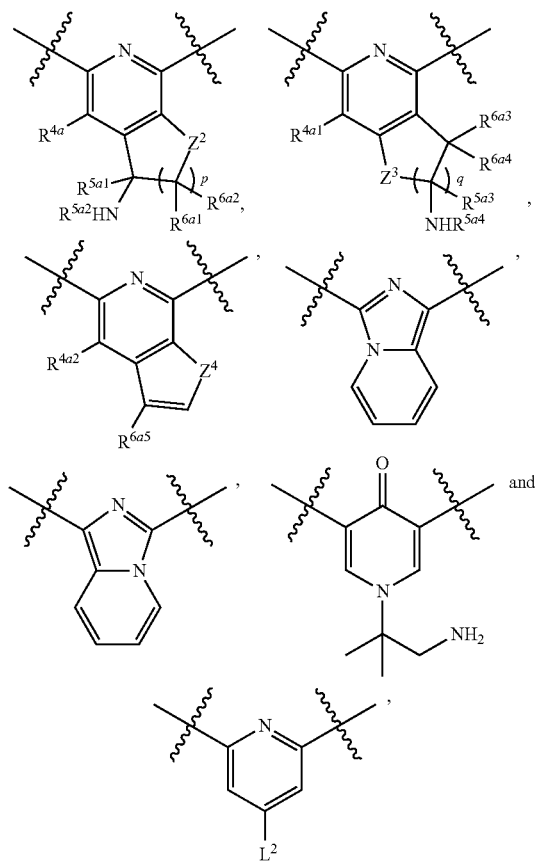

$L^2$ is selected from the group consisting of

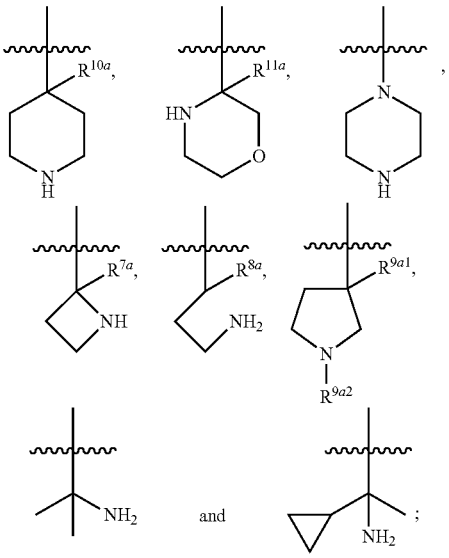

A is selected from the group consisting of an optionally substituted cycloalkyl, an optionally substituted cycloalkenyl, an optionally substituted aryl, an optionally substituted heteroaryl and an optionally substituted heterocyclyl;

Y is selected from the group consisting of an optionally substituted aryl, an optionally substituted heteroaryl and an optionally substituted heterocyclyl;

$R^{1a}$ is hydrogen or an unsubstituted $C_{1-4}$ alkyl;

$R^{2a}$ and $R^{2a1}$ are each independently hydrogen or an unsubstituted $C_{1-4}$ alkyl;

$R^{3a}$ and $R^{3a1}$ are each independently hydroxy, $CHF_2$, $CF_3$ or $NH_2$;

$R^{4a}$, $R^{4a1}$ and $R^{4a2}$ are each independently selected from the group consisting of hydrogen, halogen, hydroxy, an optionally substituted $C_{1-8}$ alkyl, an optionally substituted $C_{1-8}$ alkoxy and haloalkyl;

$R^{5a1}$ and $R^{5a3}$ are each independently an unsubstituted $C_{1-6}$ alkyl, an unsubstituted $C_{3-6}$ cycloalkyl, or —$(CH_2)_{1-4}OH$;

$R^{5a2}$ and $R^{5a4}$ are each independently hydrogen, hydroxy, an unsubstituted $C_{1-6}$ alkyl, an optionally substituted monocyclic heterocyclyl, —C(=O)$R^{5a5}$, an unsubstituted —C-amido, —C(=NH)-an unsubstituted $C_{1-6}$ alkyl; or $R^{5a1}$ and $R^{5a2}$ are taken together with the atoms to which they are attached to form an optionally substituted 4 to 6 membered ring; or R⁵ᵃ³ and R⁵ᵃ⁴ are taken together with the atoms to which they are attached to form an optionally substituted 4 to 6 membered ring;

R⁵ᵃ⁵ is an unsubstituted C₁₋₄ alkyl;

each R⁶ᵃ¹, each R⁶ᵃ², each R⁶ᵃ³ and each R⁶ᵃ⁴ are independently selected from the group consisting of hydrogen, halogen, an unsubstituted C₁₋₆ alkyl and hydroxy;

R⁶ᵃ⁵ is selected from the group consisting of halogen, an unsubstituted C₁₋₆ alkyl and hydroxy;

R⁷ᵃ and R⁸ᵃ are each independently an unsubstituted C₁₋₆ alkyl;

R⁹ᵃ¹, R⁹ᵃ², R¹⁰ᵃ and R¹¹ᵃ are each independently hydrogen or an unsubstituted C₁₋₆ alkyl;

Z¹ is O or S;
Z² is O, NR^Z or CR^{Z1}R^{Z2};
Z³ is O, NR^{Z3} or CR^{Z4}R^{Z5};
Z⁴ is O, NR^{Z6} or CR^{Z7}R^{Z8};
R^Z, R^{Z1}, R^{Z2}, R^{Z3}, R^{Z4}, R^{Z5}, R^{Z6}, R^{Z7} and R^{Z8} are each independently hydrogen or an unsubstituted C₁₋₄ alkyl;
p and q are each independently 1 or 2; and
provided that when L¹ is

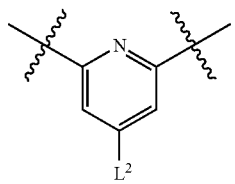

and L² is

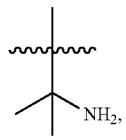

then one of R³ᵃ and R³ᵃ¹ is NH₂, and the other of R³ᵃ and R³ᵃ¹ is OH;

provided that when L¹ is

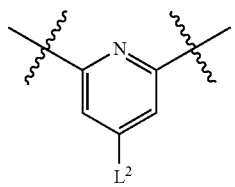

L² is

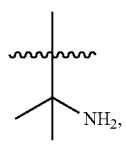

one of R³ᵃ and R³ᵃ¹ is CF₃, and other of R³ᵃ and R³ᵃ¹ is OH, then Y is

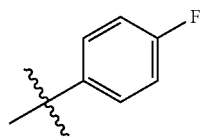 [SMILES: *c1ccc(F)cc1]

and A is a disubstituted phenyl wherein one substituent is

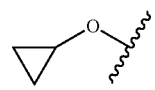 [SMILES: *OC1CC1]

and the other substituent is —O—(CH₂)₂₋₄OH or

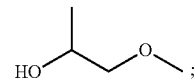

and provided that the compound of Formula (I) is not any one of the group consisting of:

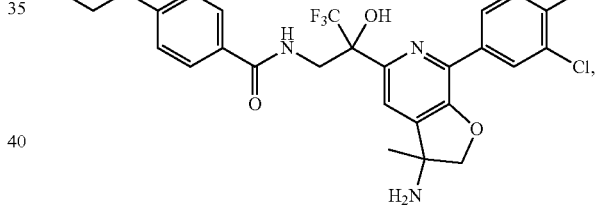

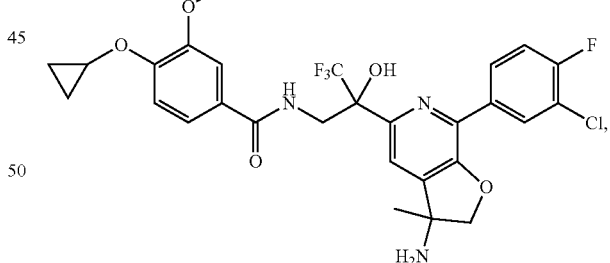

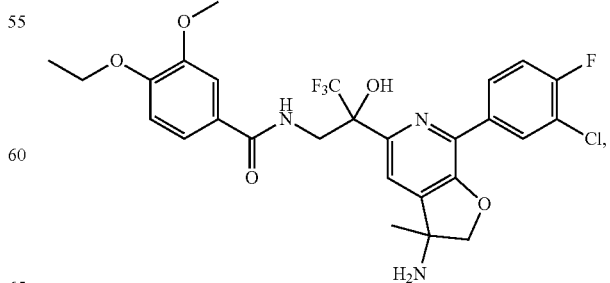

369
-continued
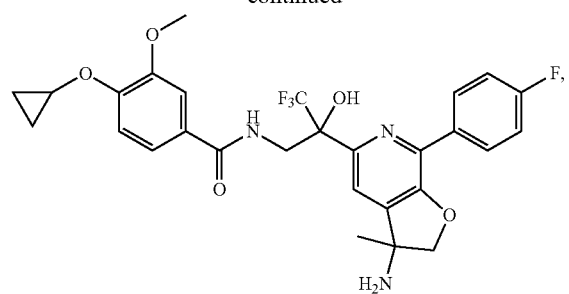
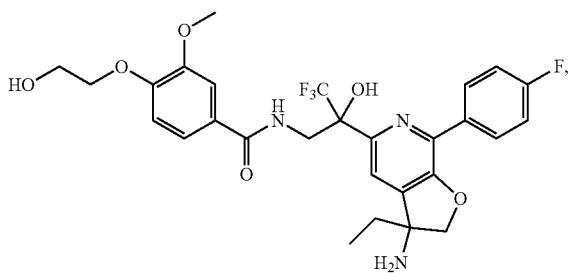
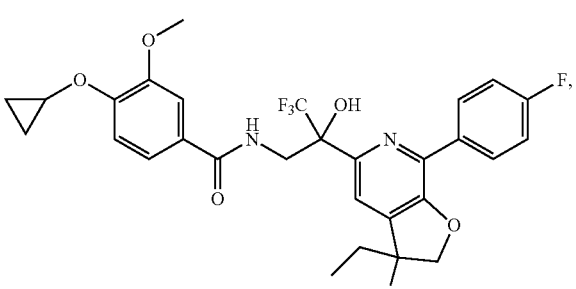
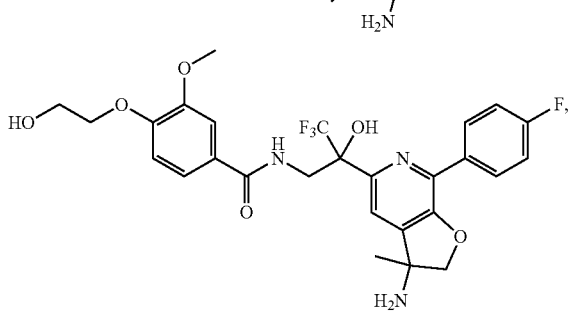
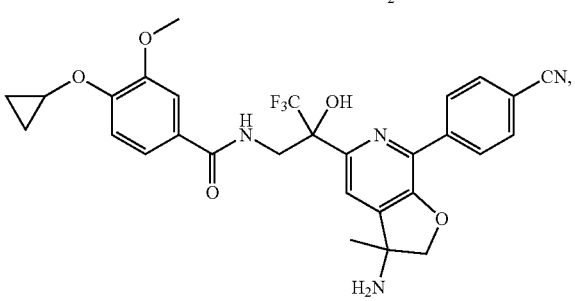
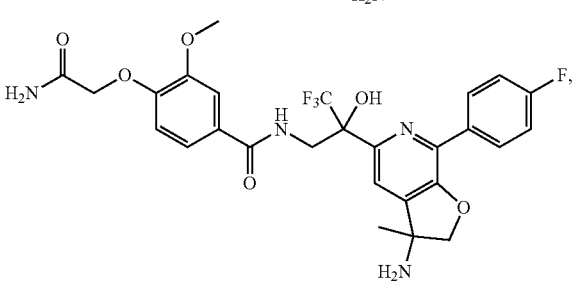
370
-continued
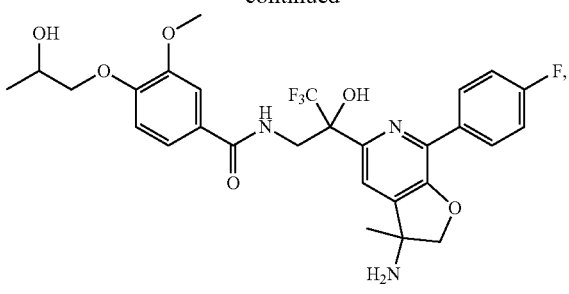
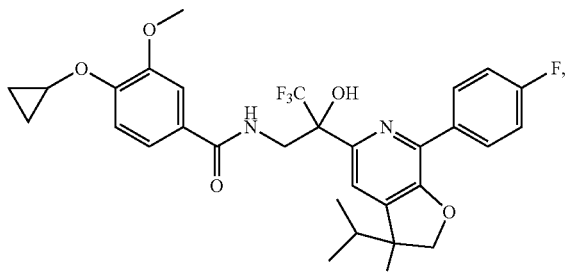
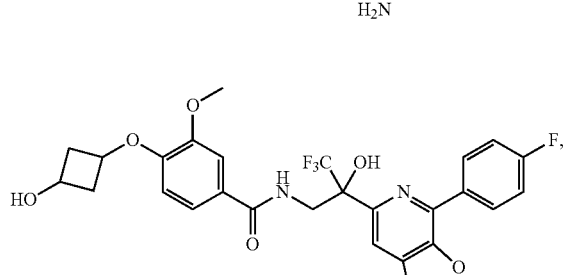
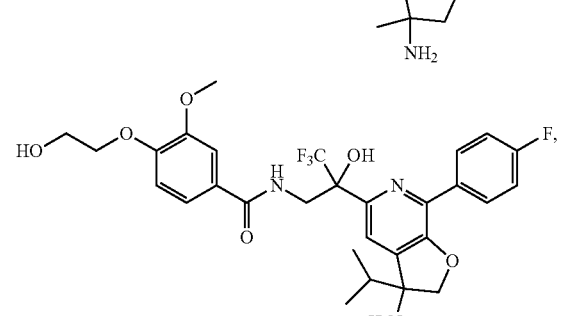
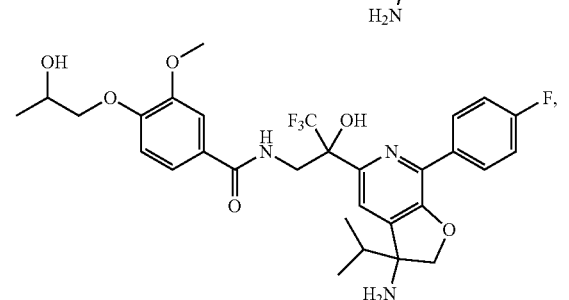
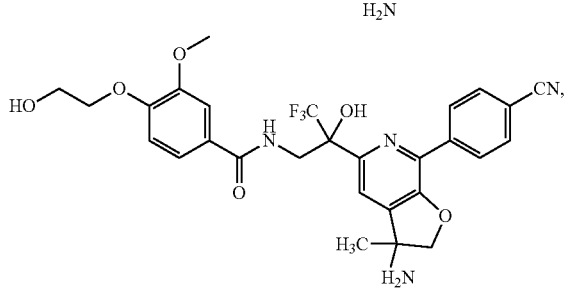

371
-continued
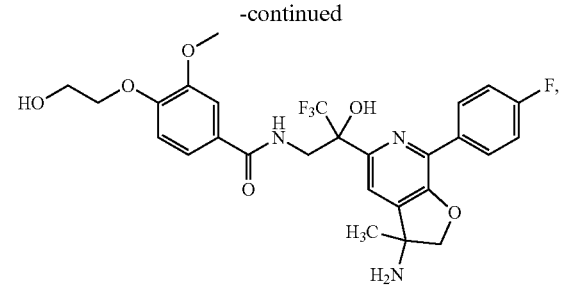
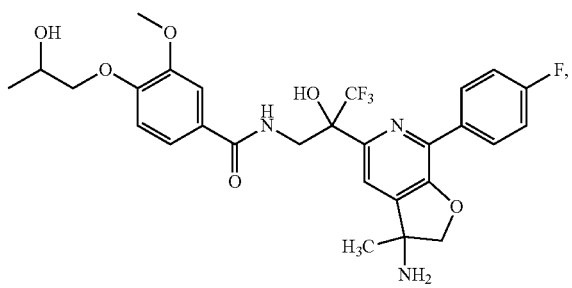
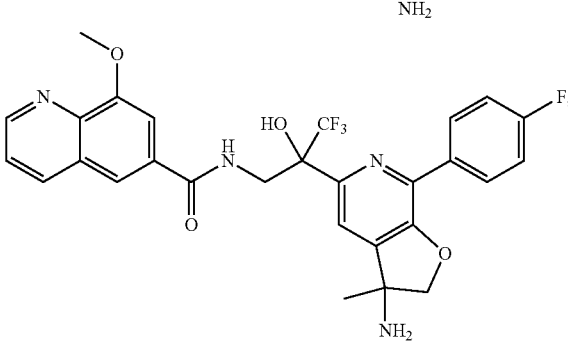
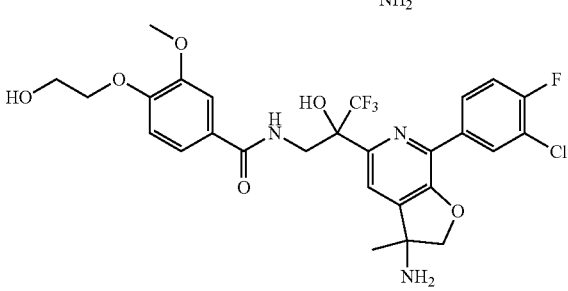
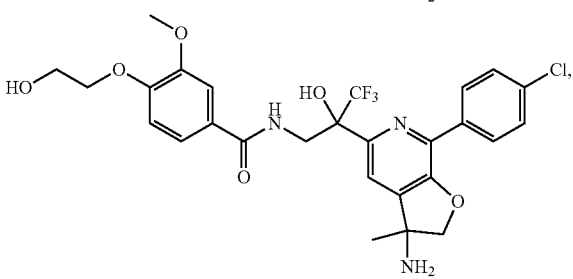
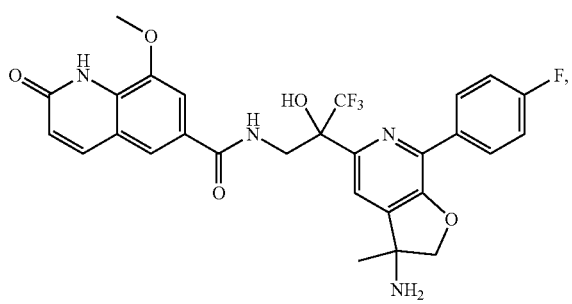
372
-continued
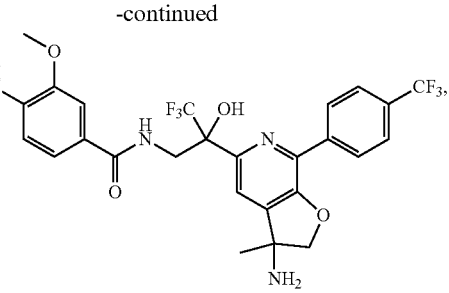
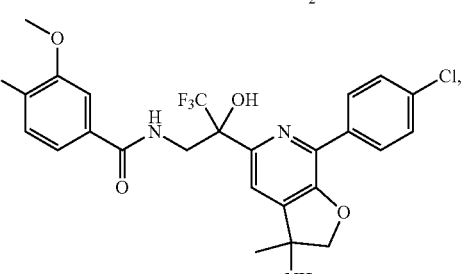
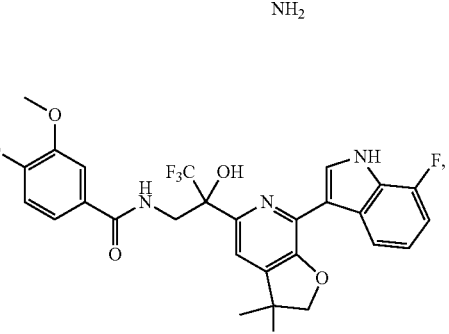
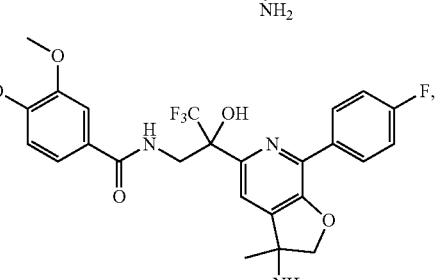
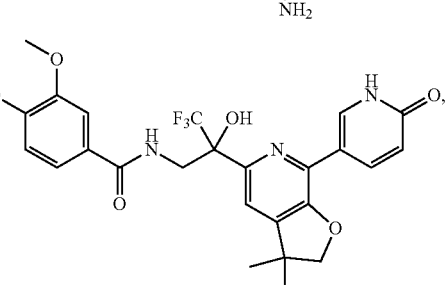
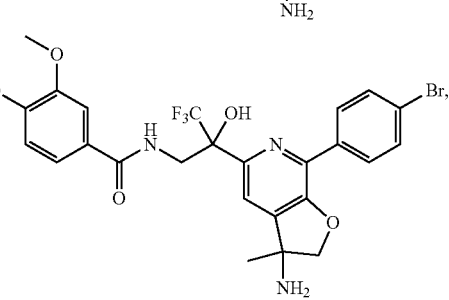

-continued
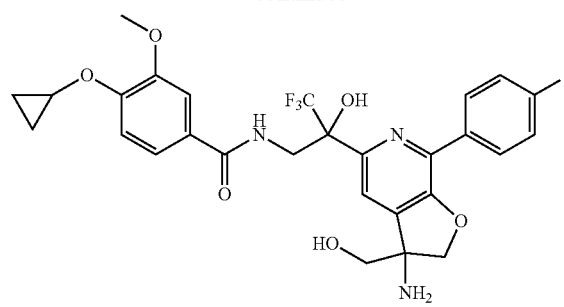
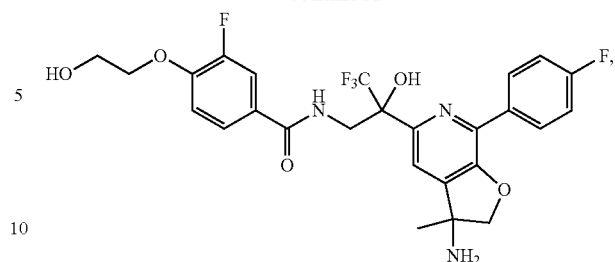
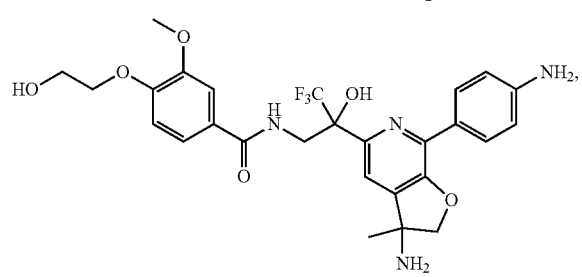
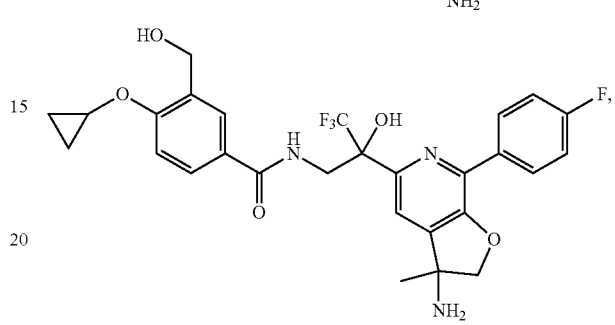
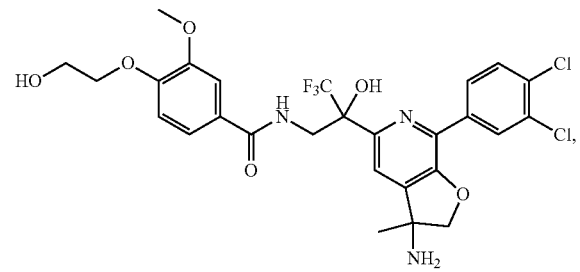
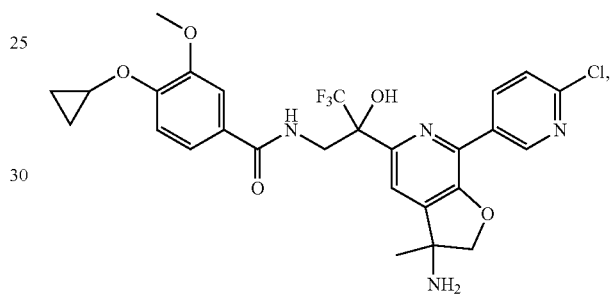
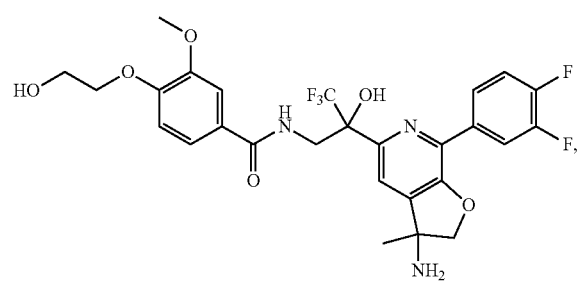
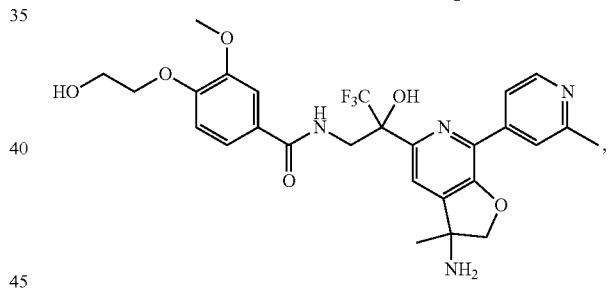
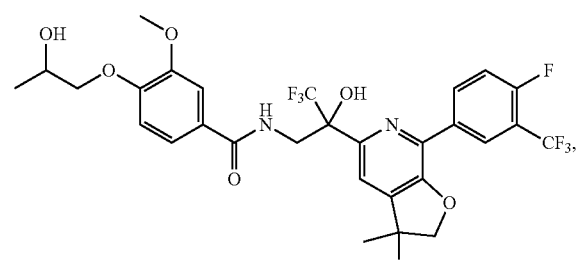
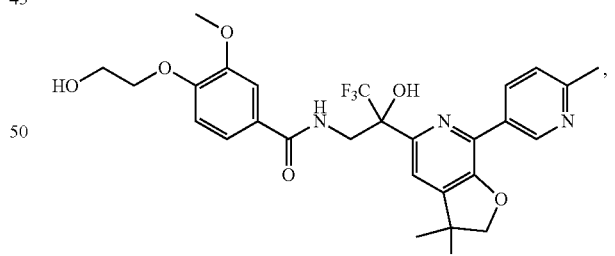
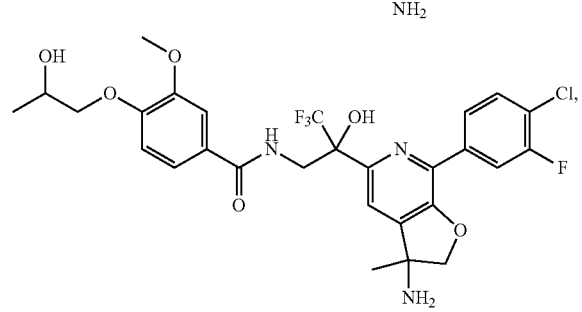
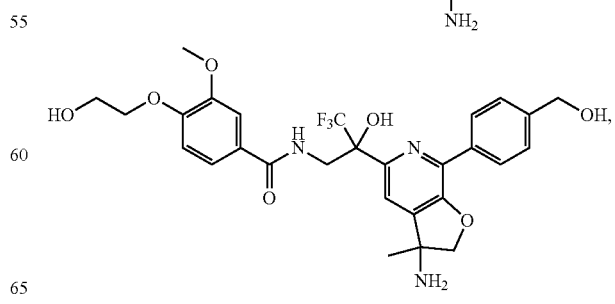

375
-continued
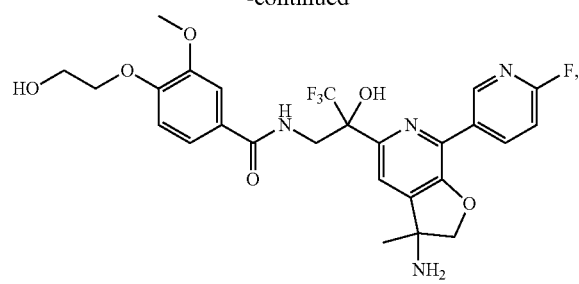
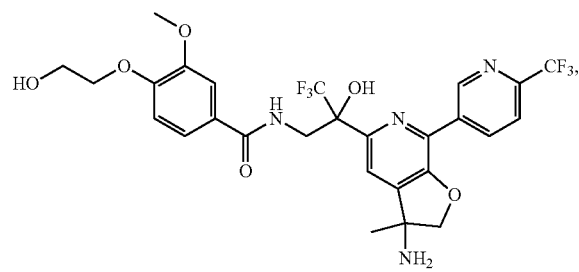
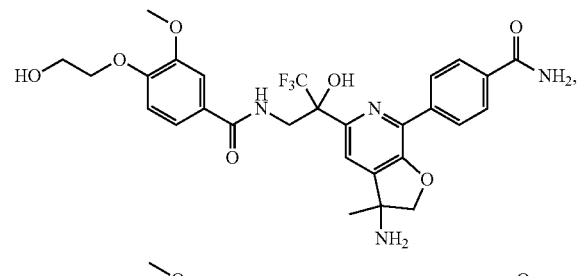
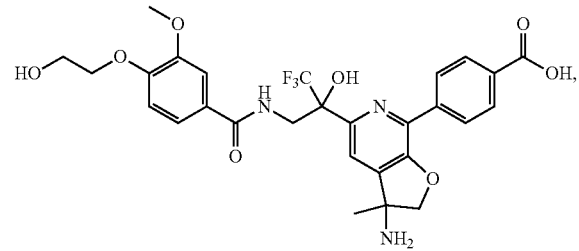
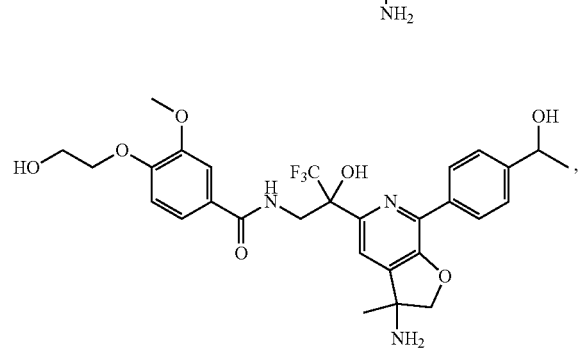
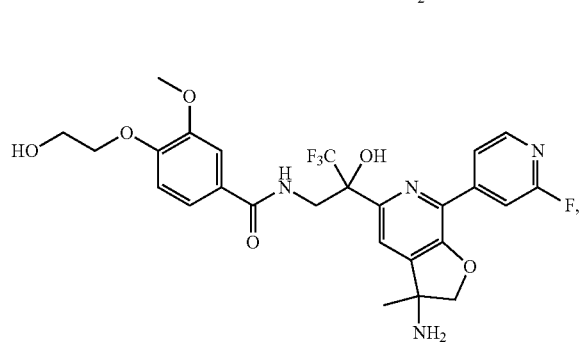
376
-continued
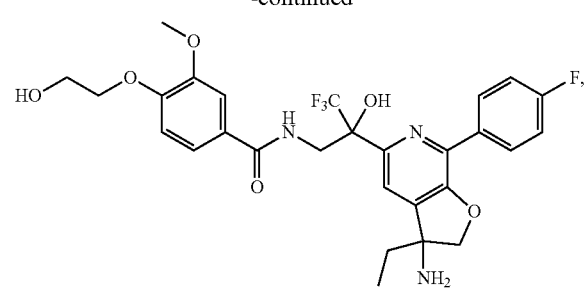
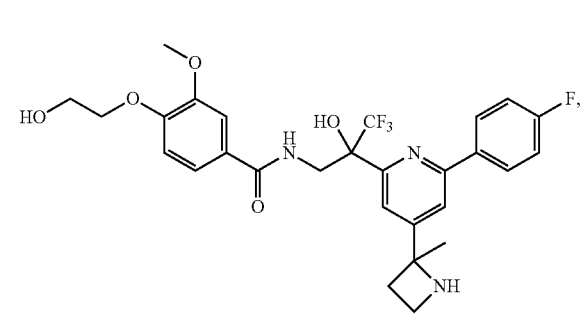

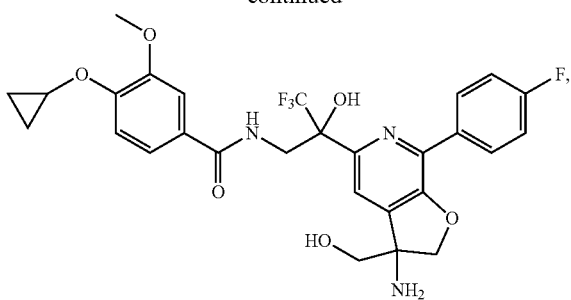
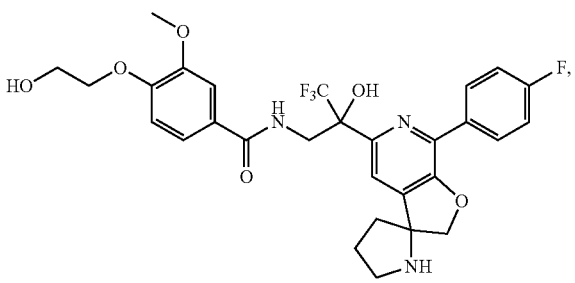
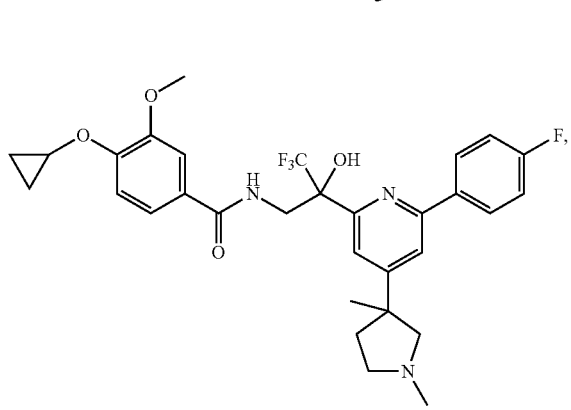
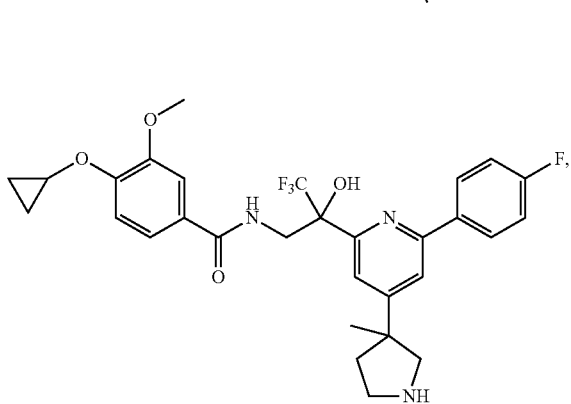
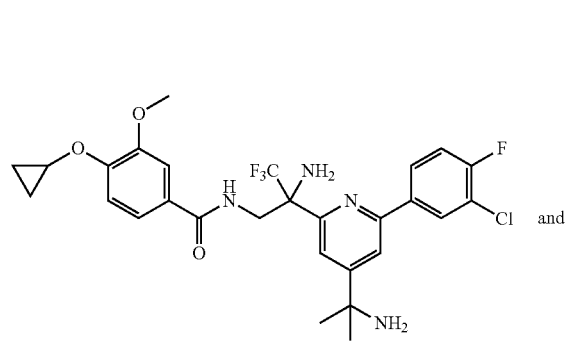

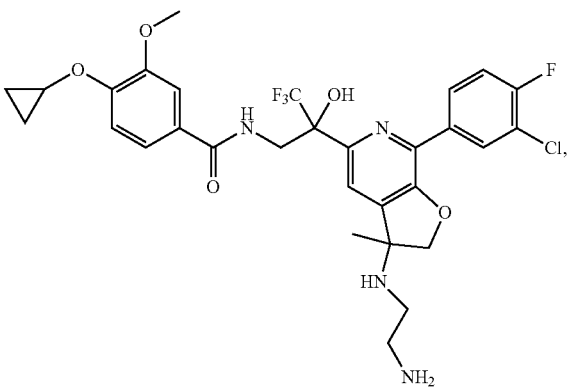 [SMILES: COc1cc(C(=O)NCC(O)(c2cc3c(c(-c4ccc(F)c(Cl)c4)n2)OCC3(C)NCCN)C(F)(F)F)ccc1OC1CC1]

or a pharmaceutically acceptable salt of any of the foregoing.

2. The compound of claim 1, or a pharmaceutically acceptable salt thereof, wherein $R^{1a}$ can be hydrogen.

3. The compound of any one of claim 1, or a pharmaceutically acceptable salt thereof, wherein $R^{2a}$ and $R^{2a1}$ are both hydrogen.

4. The compound of any one of claim 1, or a pharmaceutically acceptable salt thereof, wherein $R^{3a}$ is hydroxy, and $R^{3a1}$ is $CF_3$.

5. The compound of any one of claim 1, or a pharmaceutically acceptable salt thereof, wherein $R^{3a}$ is $CF_3$, and $R^{3a1}$ is $NH_2$.

6. The compound of any one of claim 1, or a pharmaceutically acceptable salt thereof, wherein $L^1$ is

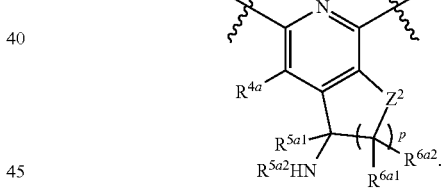

7. The compound of claim 6, or a pharmaceutically acceptable salt thereof, wherein $R^{5a1}$ is an unsubstituted $C_{1-6}$ alkyl.

8. The compound of any one of claim 6, or a pharmaceutically acceptable salt thereof, wherein $R^{5a2}$ is hydrogen.

9. The compound of any one of claim 6, or a pharmaceutically acceptable salt thereof, wherein p is 1.

10. The compound of any one of claim 6, or a pharmaceutically acceptable salt thereof, wherein p is 2.

11. The compound of any one of claim 6, or a pharmaceutically acceptable salt thereof, wherein $Z^2$ is O.

12. The compound of any one of claim 6, or a pharmaceutically acceptable salt thereof, wherein $Z^2$ is $NR^Z$.

13. The compound of any one of claim 6, or a pharmaceutically acceptable salt thereof, wherein $Z^2$ is $CR^{Z1}R^{Z2}$.

14. The compound of any one of claim 1, or a pharmaceutically acceptable salt thereof, wherein $L^1$ is

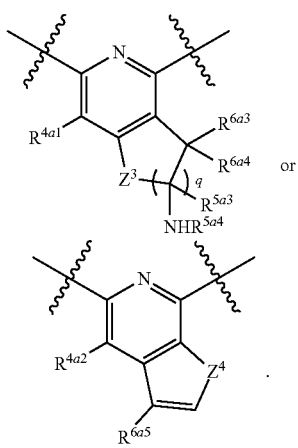

15. The compound of any one of claim 14, or pharmaceutically acceptable salt thereof, wherein $Z^3$ is O or $NR^{Z3}$.

16. The compound of any one of claim 1, or a pharmaceutically acceptable salt thereof, wherein $L^1$ is

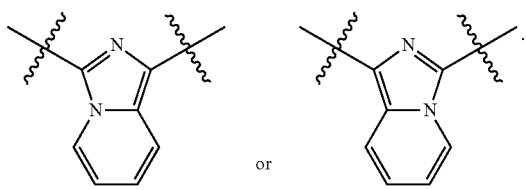 [SMILES: *c1nc(*)n2ccccc12 ; *c1nc(*)n2ccccc12]

17. The compound of any one of claim 1, or pharmaceutically acceptable salt thereof, wherein $L^1$ is

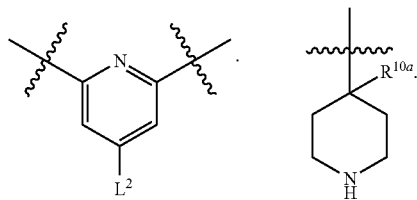

18. The compound of claim 17, or a pharmaceutically acceptable salt thereof, wherein $L^2$ is

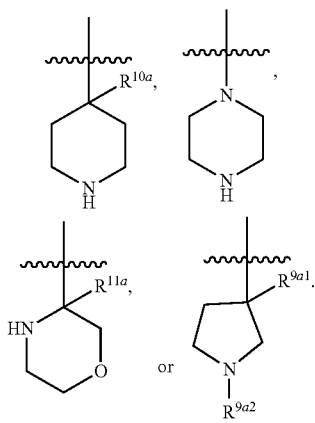

19. The compound of claim 17, or a pharmaceutically acceptable salt thereof, wherein $L^2$ is

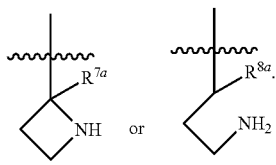

20. The compound of claim 17, or a pharmaceutically acceptable salt thereof, wherein $L^2$ is

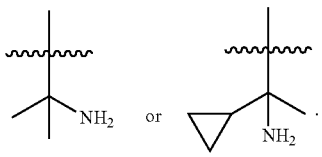

21. The compound of any one of claim 1, or a pharmaceutically acceptable salt thereof, wherein $L^1$ is

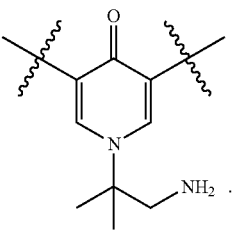 [SMILES: *c1cn(C(C)(C)CN)cc(*)c1=O]

22. The compound of any one of claim 1, or a pharmaceutically acceptable salt thereof, wherein A is an optionally substituted phenyl.

23. The compound of claim 22, or a pharmaceutically acceptable salt thereof, wherein A is a phenyl substituted with one or more substituents selected from the group consisting of: an unsubstituted $C_{1-4}$ alkyl, an optionally substituted $C_{1-4}$ alkyl, cycloalkyl, hydroxy, an optionally substituted $C_{1-4}$ alkoxy, $C_{1-4}$ alkoxy, halogen, haloalkyl, an optionally substituted haloalkoxy, nitro, amino, mono-substituted amino, di-substituted amine, —O-amido, sulfenyl, alkyoxyalkyl, an optionally substituted aryl, an optionally substituted mono-cyclic heteroaryl, an optionally substituted mono-cyclic heterocyclyl, an optionally substituted aryl($C_{1-4}$ alkyl), an optionally substituted monocyclic heteroaryl ($C_{1-4}$ alkyl), an optionally substituted monocyclic heterocyclyl($C_{1-4}$ alkyl), hydroxyalkyl and aminoalkyl.

24. The compound of claim 22, or a pharmaceutically acceptable salt thereof, wherein A is a phenyl substituted with one or more substituents selected from the group consisting of: methyl, ethyl, propyl, butyl, hydroxy, methoxy, ethoxy, n-propoxy, iso-propoxy, n-butoxy, iso-butoxy, t-butoxy, phenoxy, bromo, chloro, fluoro, trifluoromethyl, difluoromethoxy, trifluoromethoxy, cyano, N,N-di-methyl-amine, N,N-di-ethyl-amine, N-methyl-N-ethyl-amine, N-methyl-amino, N-ethyl-amino, amino, N-amido, N-sulfonamido, alkylthio, an optionally substituted phenyl, an optionally substituted imidazole, an optionally substituted morpholinyl, an optionally substituted pyrazole, an optionally substituted pyrrolidinyl, an optionally substituted pyridinyl, an optionally substituted piperidinyl, an optionally substituted piperidinone, an optionally substituted pyrrolidinone, an optionally substituted pyrimidine, an optionally substituted pyrazine, an optionally substituted 1,2,4-oxadiazole, —(CH$_2$)$_{1-4}$—OH, —(CH$_2$)$_{1-2}$—NH(CH$_3$), an optionally substituted —(CH$_2$)$_{1-2}$-imidazole, an optionally substituted —(CH$_2$)$_{1-2}$-pyrrolidinone, an optionally substituted —(CH$_2$)$_{1-2}$-imidazolidinone, —O(CH$_2$)$_2$—NH$_2$, —O(CH$_2$)$_2$—NH(CH$_3$), —O(CH$_2$)$_2$—N(CH$_3$)$_2$, —O—(CH$_2$)$_{2-4}$OH, —O(CH$_2$)$_2$OCH$_3$, an optionally substituted —O(CH$_2$)$_{0-2}$-cyclopentanone, an optionally substituted —O(CH$_2$)$_{0-2}$-pyrrolidinone, an optionally substituted —O(CH$_2$)$_{0-2}$-morpholinyl, an optionally substituted —O(CH$_2$)$_{0-2}$-triazole, an optionally substituted —O(CH$_2$)$_{0-2}$-imidazole, an optionally substituted —O(CH$_2$)$_{0-2}$-pyrazole, an optionally substituted —O(CH$_2$)$_{0-2}$-tetrahydrofuran, an optionally substituted —O(CH$_2$)$_{0-2}$-pyrrolidinone, an optionally substituted —O(CH$_2$)$_{0-2}$-tetrazole, an optionally substituted —O(CH$_2$)$_{0-2}$-tetrazolone, —NH(CH$_2$)$_{1-2}$OH,

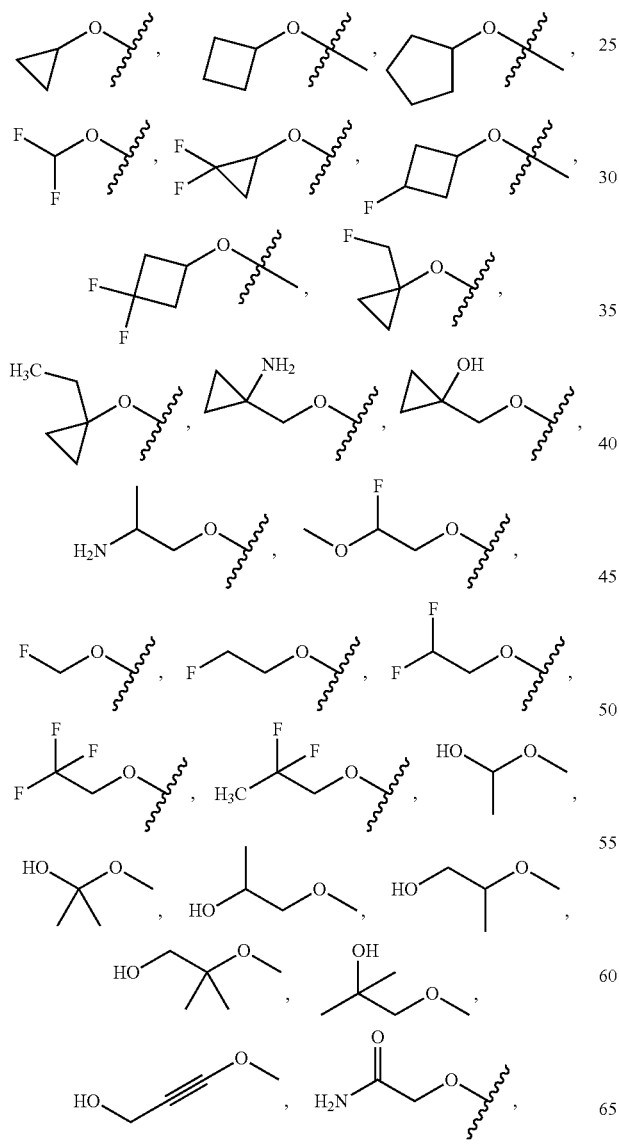

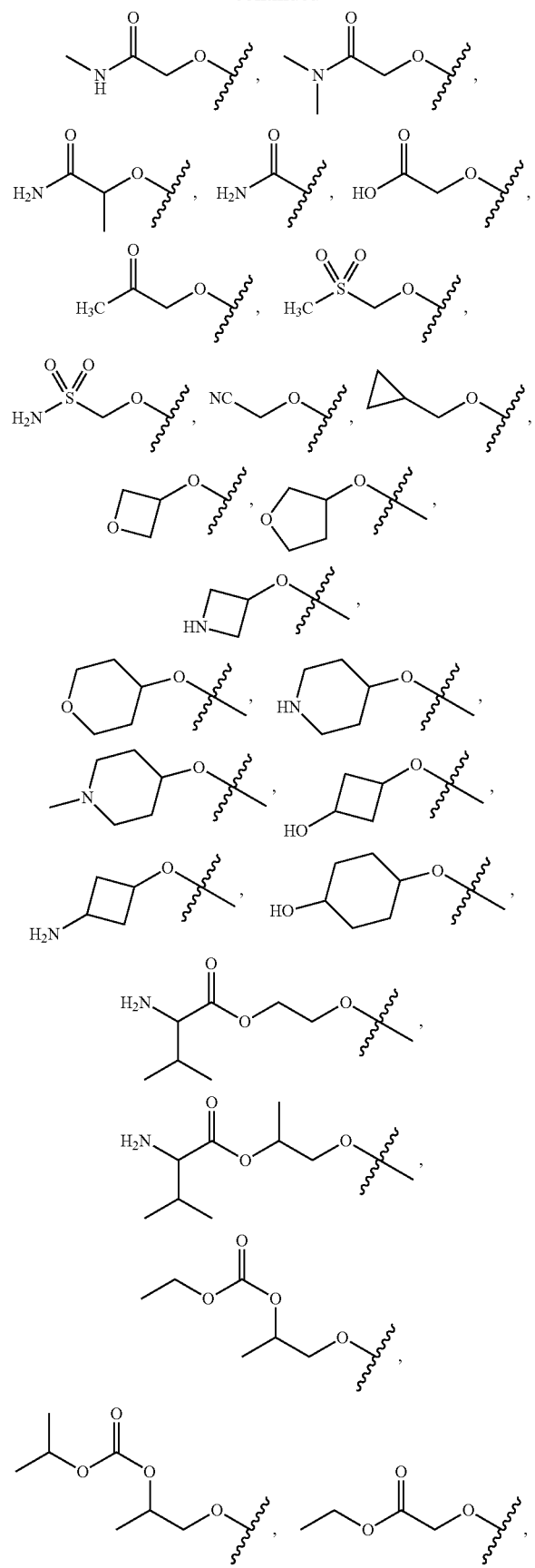

-continued

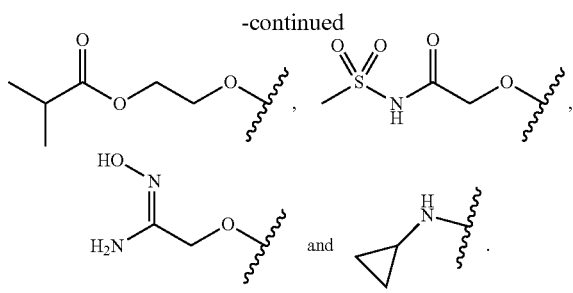

and

25. The compound of any one of claim 22, or a pharmaceutically acceptable salt thereof, wherein A is a di-substituted phenyl.

26. The compound of any one of claim 1, or a pharmaceutically acceptable salt thereof, wherein A is an optionally substituted heteroaryl or an optionally substituted heterocyclyl.

27. The compound of any one of claim 1, or a pharmaceutically acceptable salt thereof, wherein Y is an optionally substituted aryl.

28. The compound of any one of claim 27, or a pharmaceutically acceptable salt thereof, wherein Y is substituted with one or more $R^B$, wherein each $R^B$ is independently selected from the group consisting of: cyano, halogen, an optionally substituted $C_{1-4}$ alkyl, an unsubstituted $C_{2-4}$ alkenyl, an unsubstituted $C_{2-4}$ alkynyl, an optionally substituted aryl, an optionally substituted 5 or 6 membered heteroaryl, an optionally substituted 5 or 6 membered heterocyclyl, hydroxy, $C_{1-4}$ alkoxy, alkoxyalkyl, $C_{1-4}$ haloalkyl, haloalkoxy, an unsubstituted acyl, an optionally substituted —C-carboxy, an optionally substituted —C-amido, sulfonyl, carbonyl, amino, mono-substituted amine, di-substituted amine and

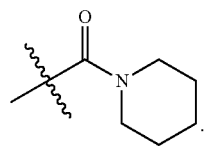 [SMILES: *C(=O)N1CCCCC1]

29. The compound of any one of claim 1, or a pharmaceutically acceptable salt thereof, wherein Y is an optionally substituted heteroaryl or an optionally substituted heterocyclyl.

30. The compound of claim 1, wherein the compound of Formula (I) is selected from the group consisting of:

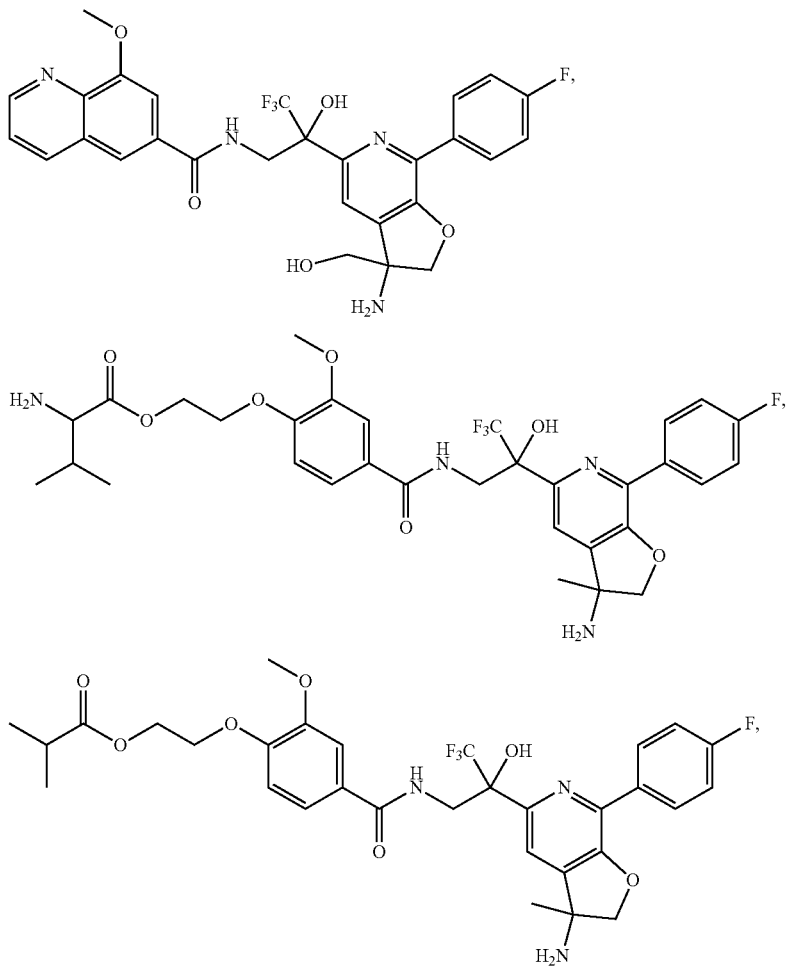

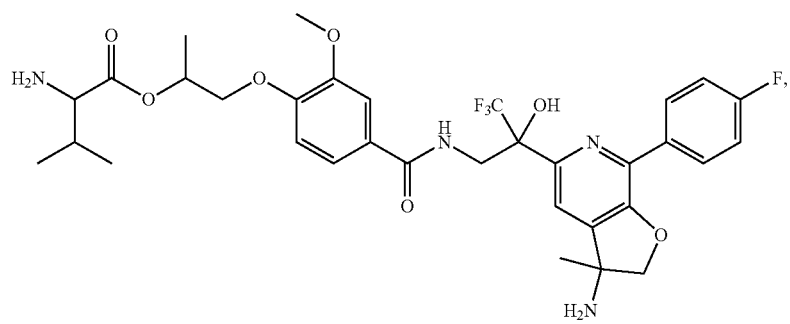
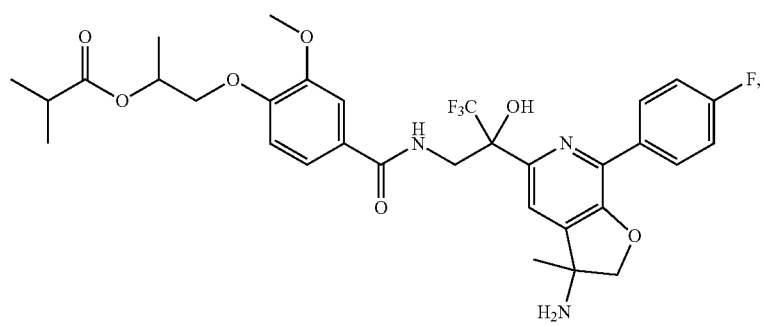
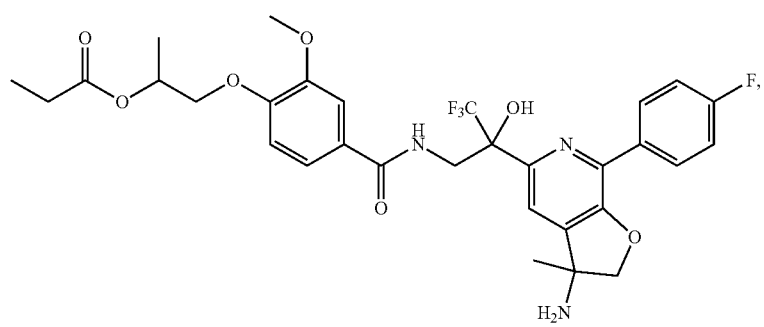
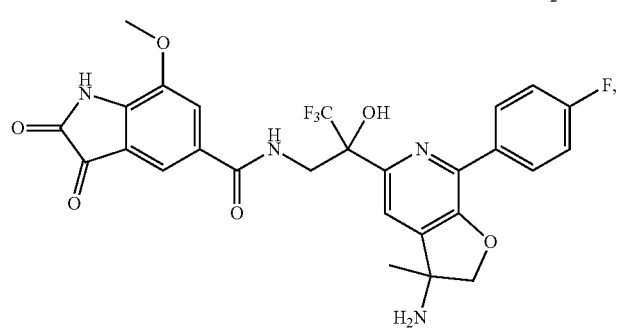
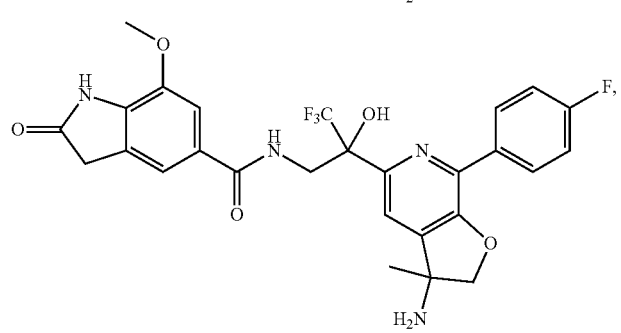

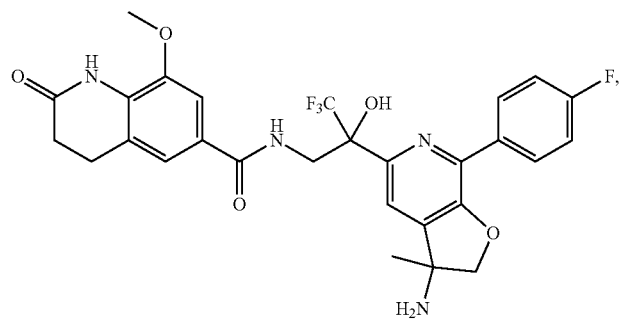
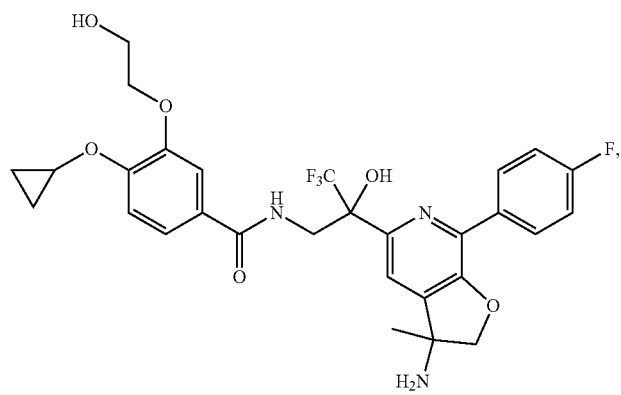
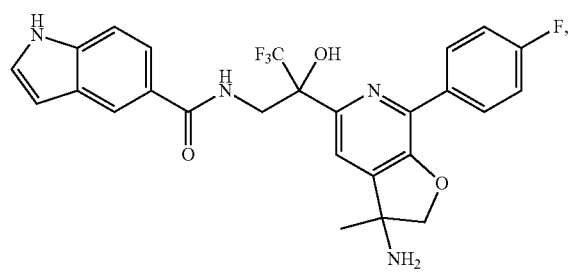
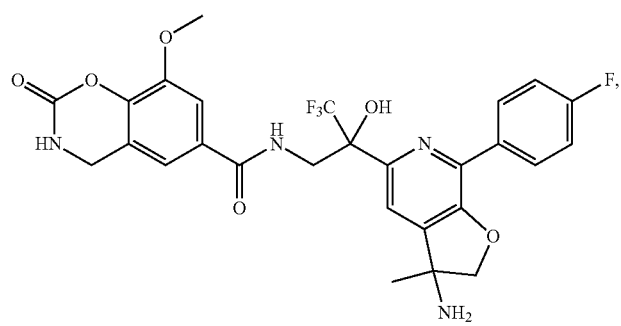
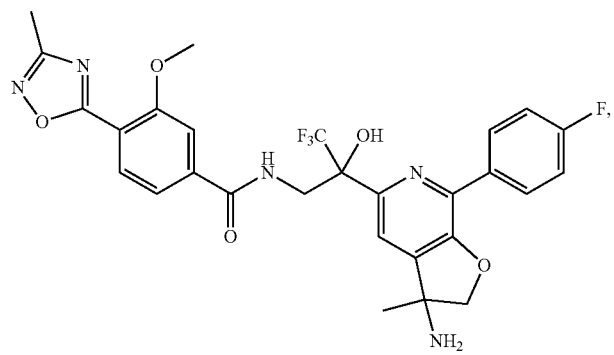

389
390
-continued
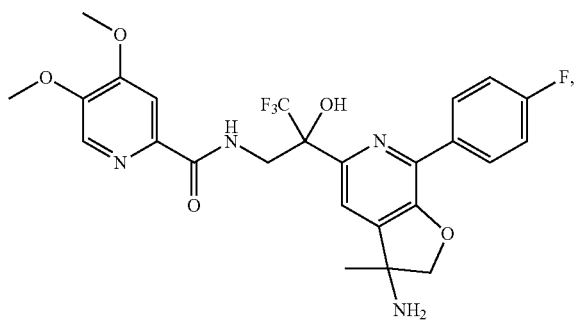
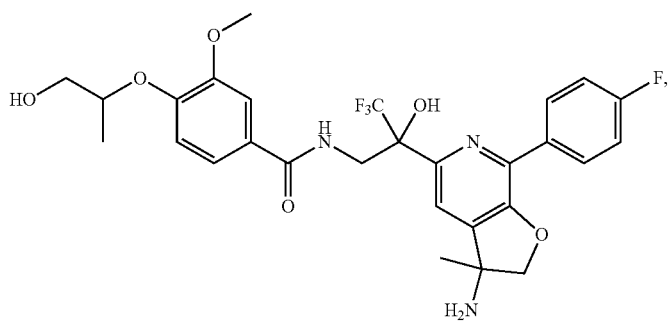
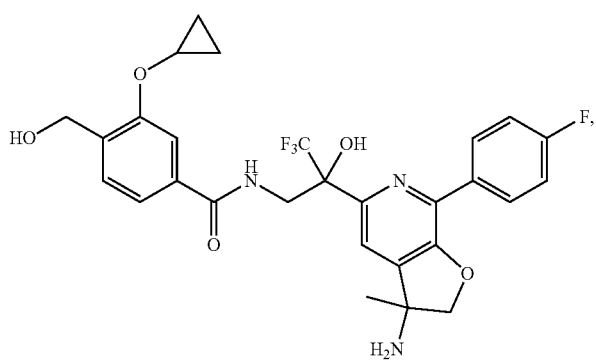
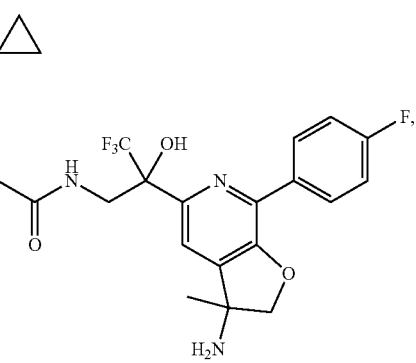
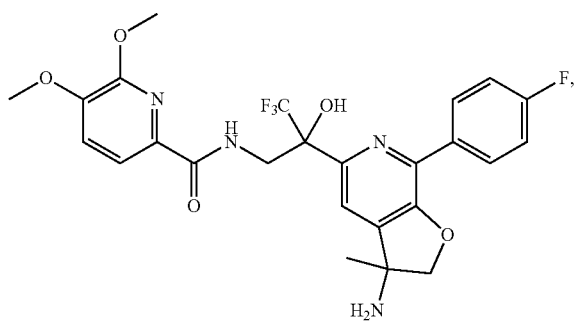
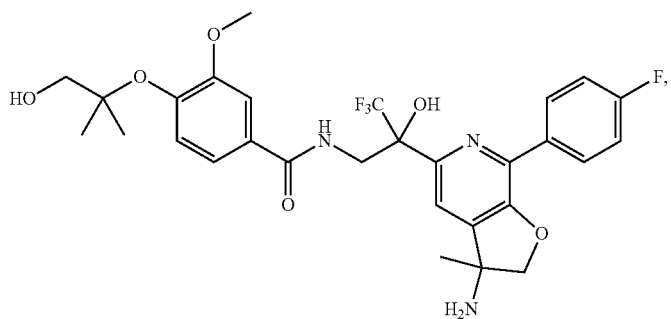

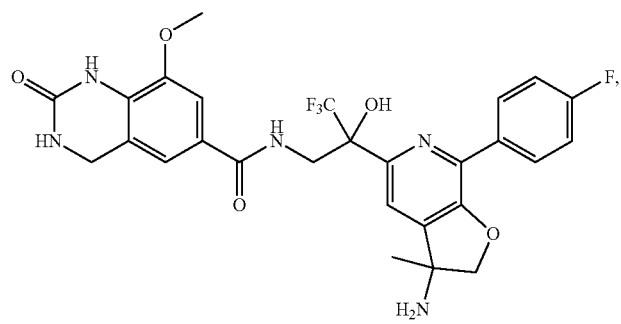
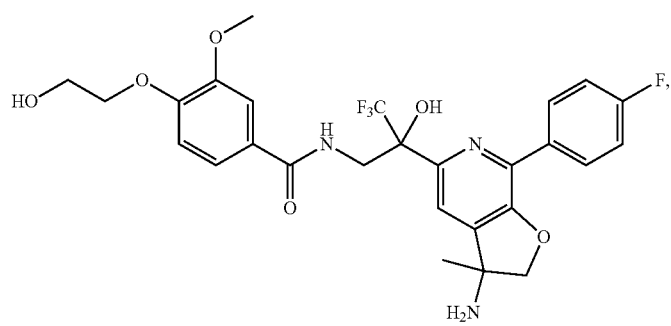
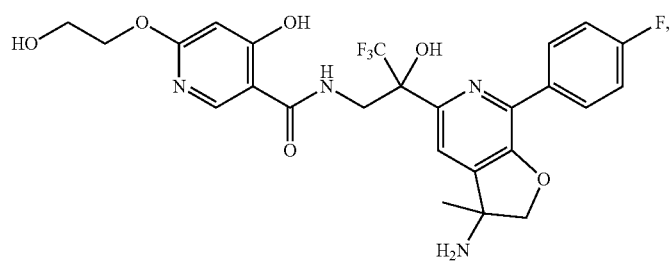
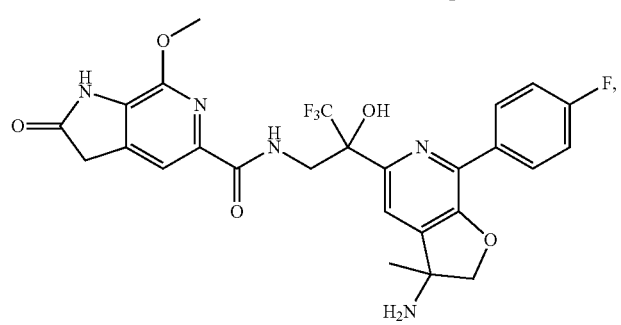
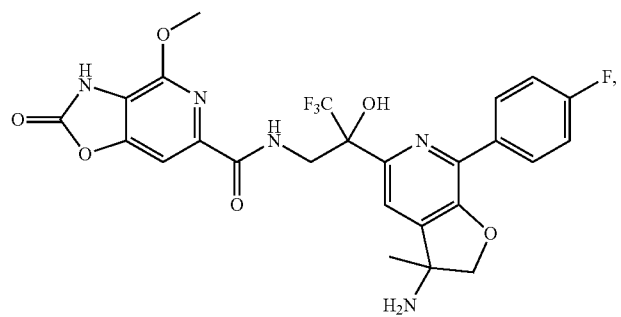

-continued
393
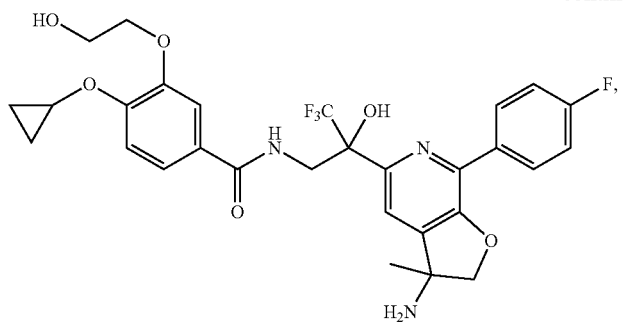
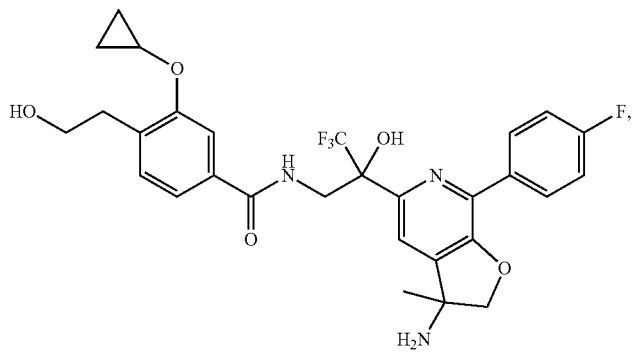
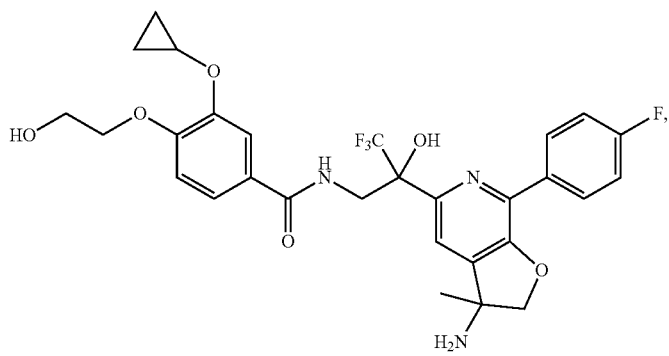
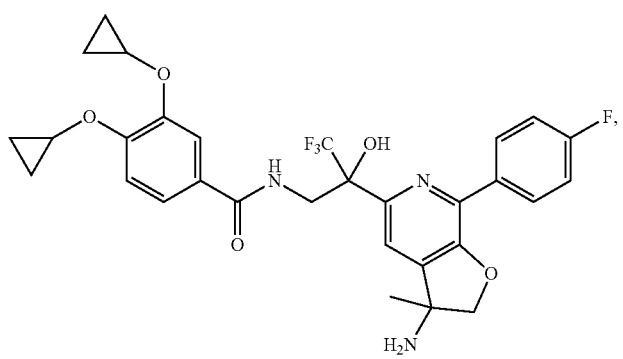
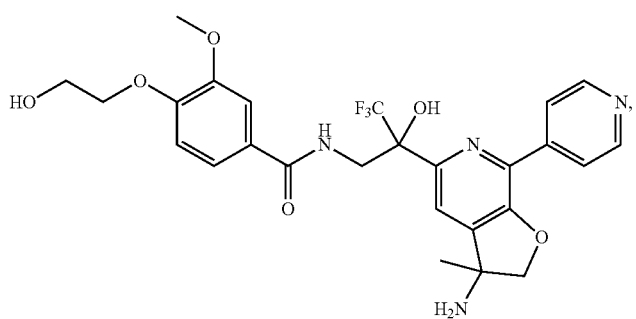
394
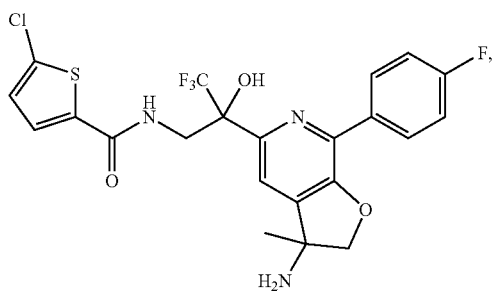
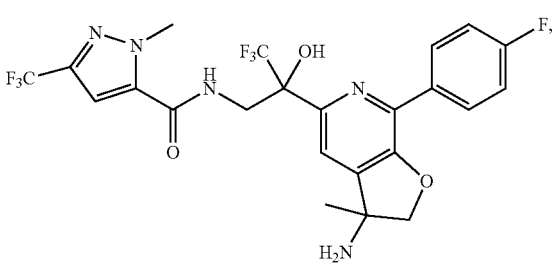

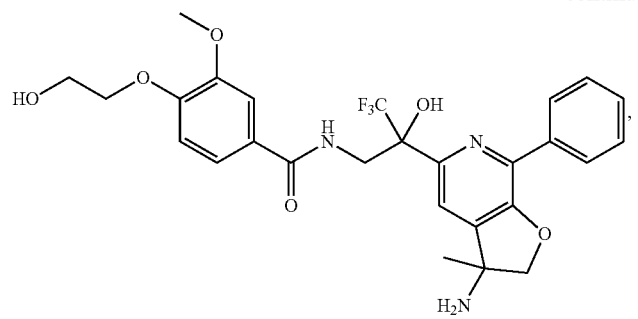
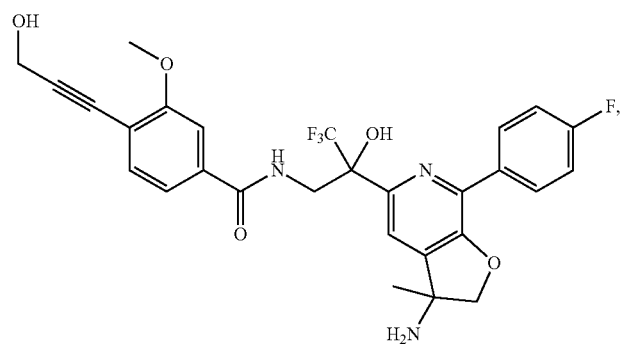
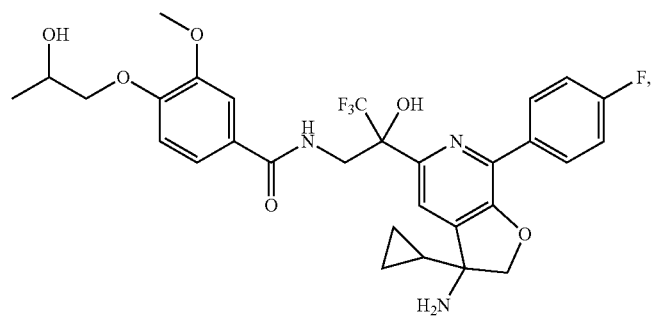
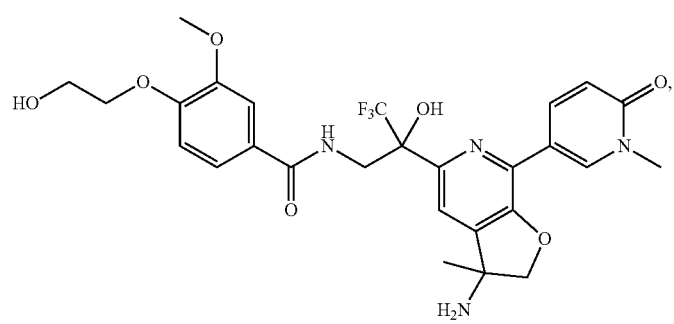
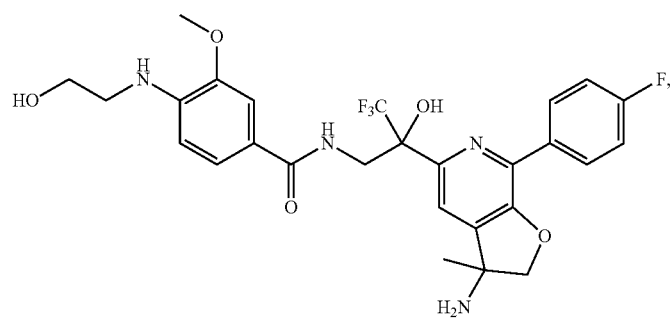

-continued
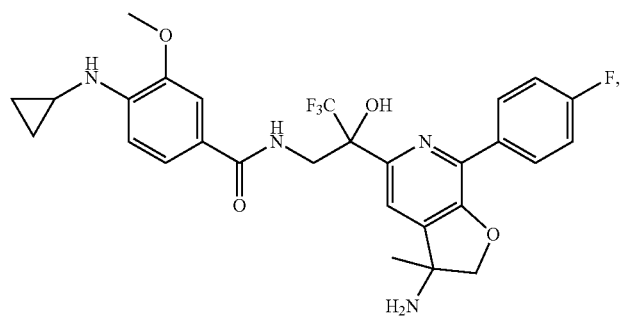
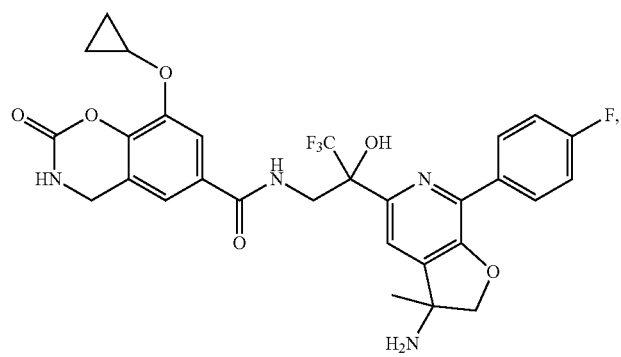
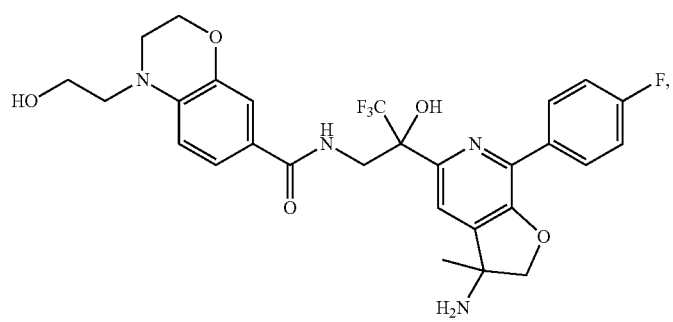
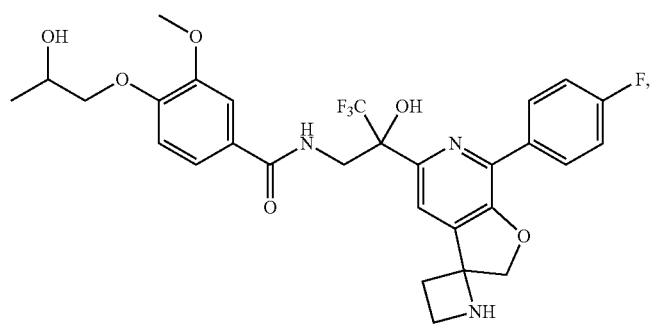
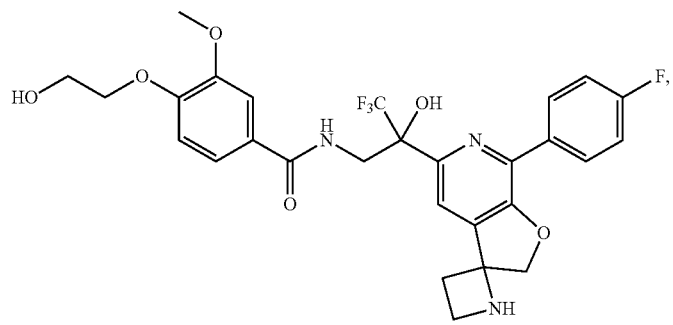

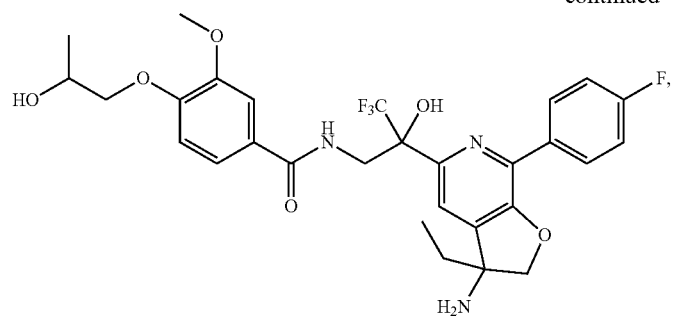
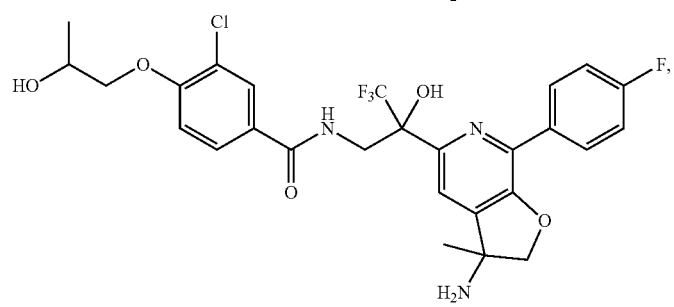
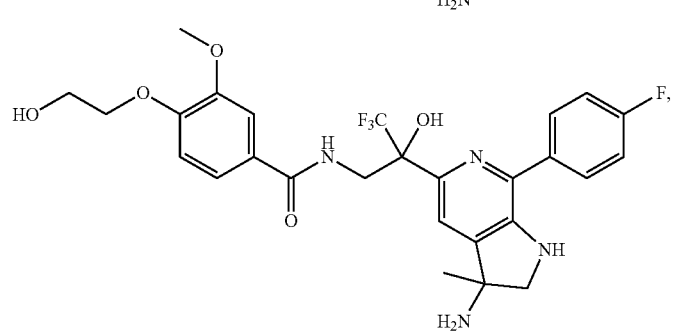
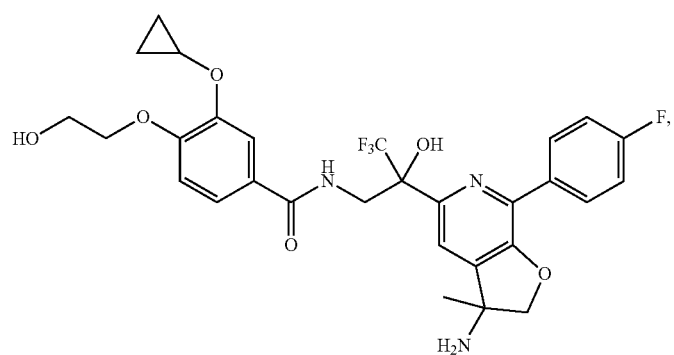
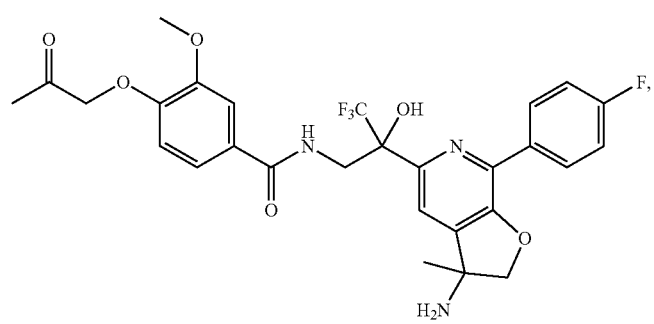

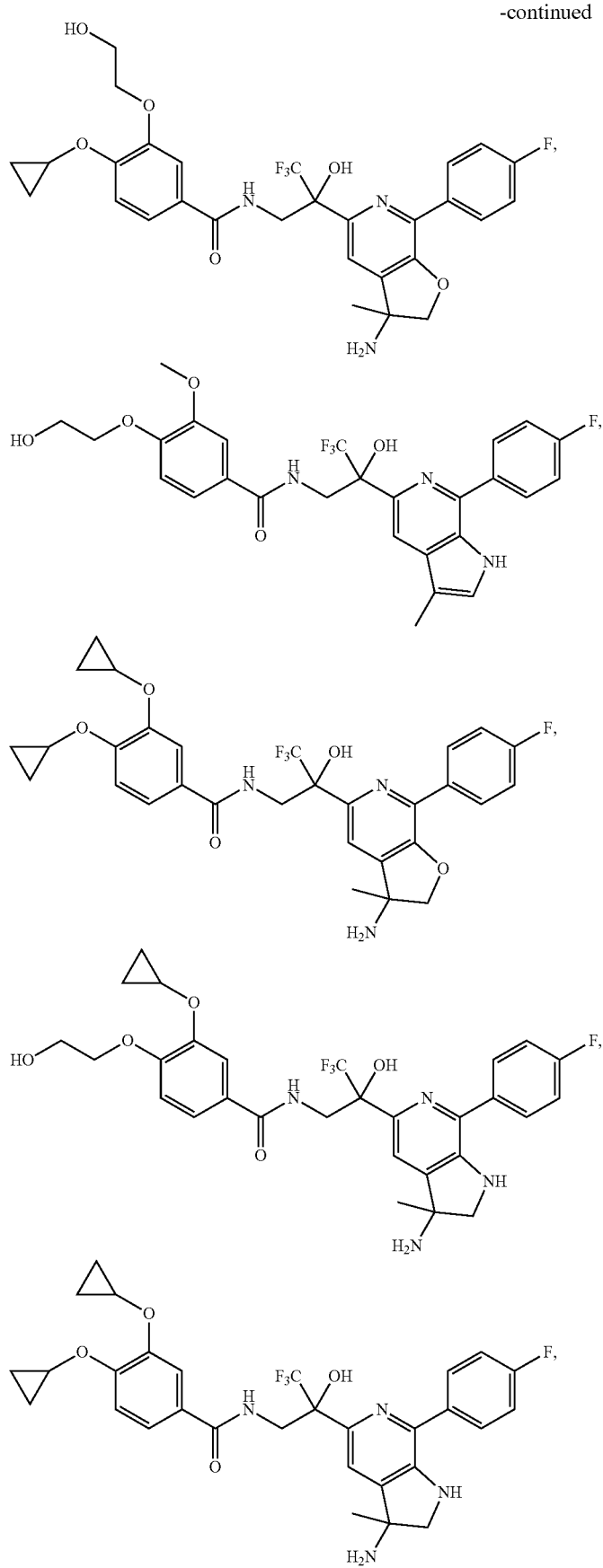

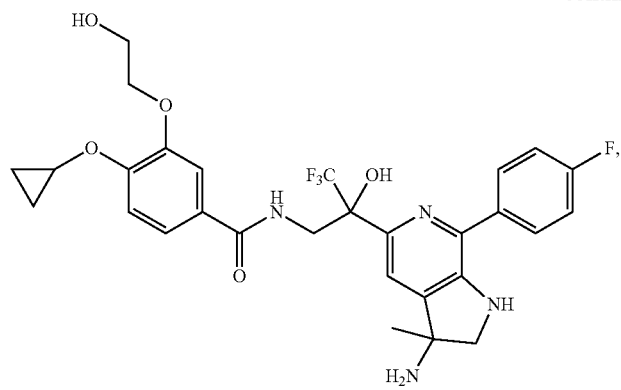
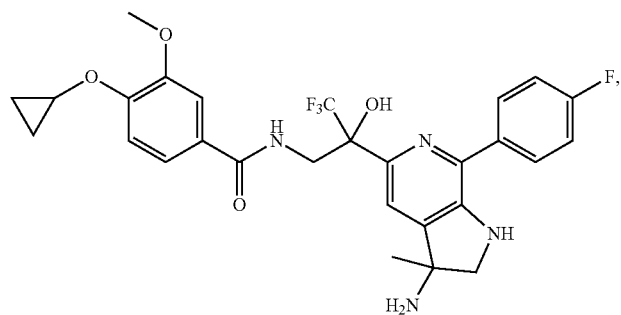
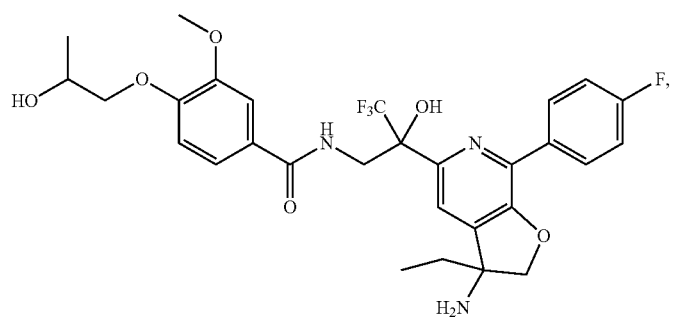
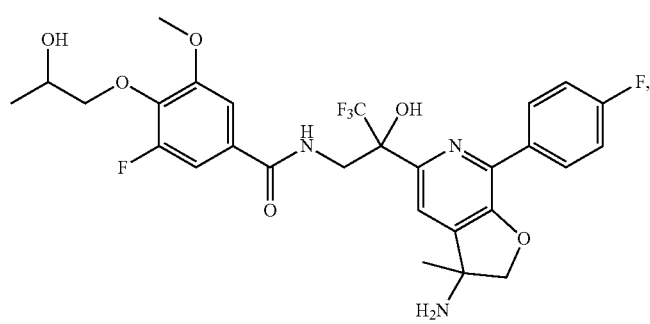
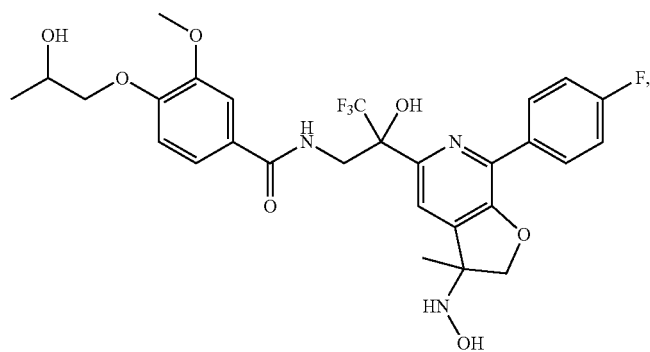

405
-continued
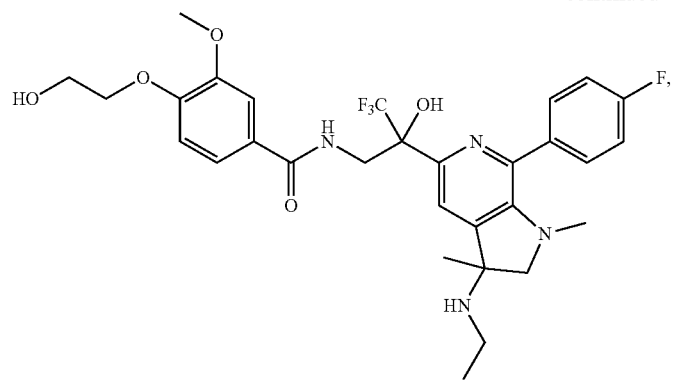
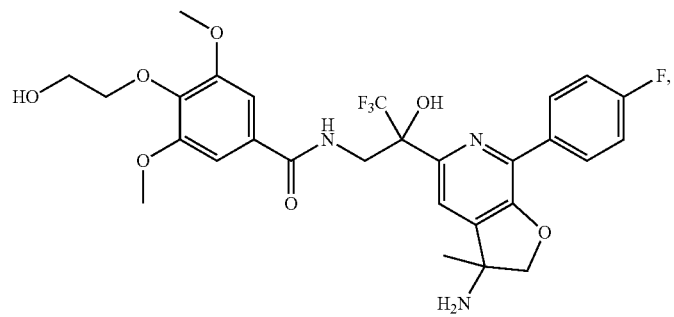
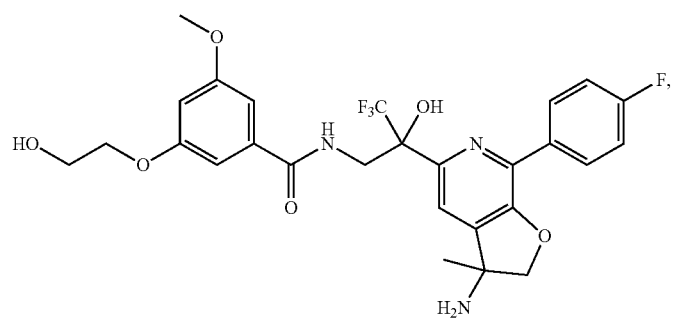
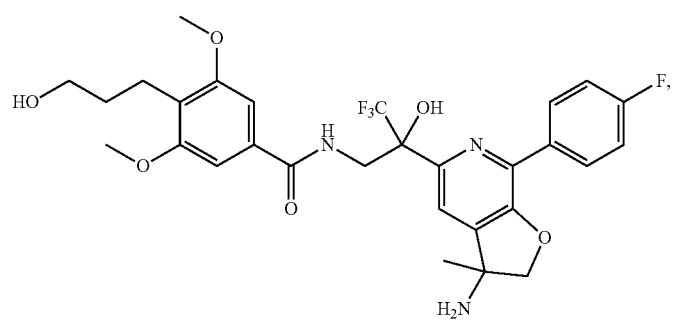
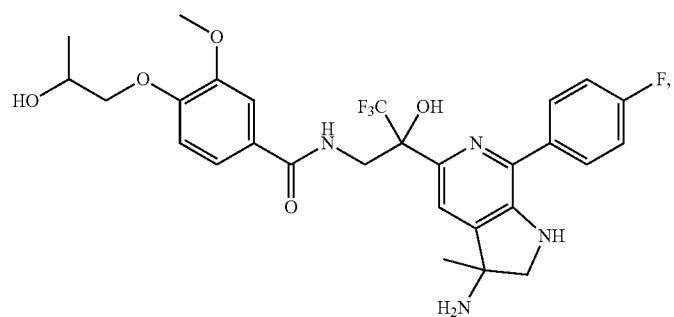
406

-continued
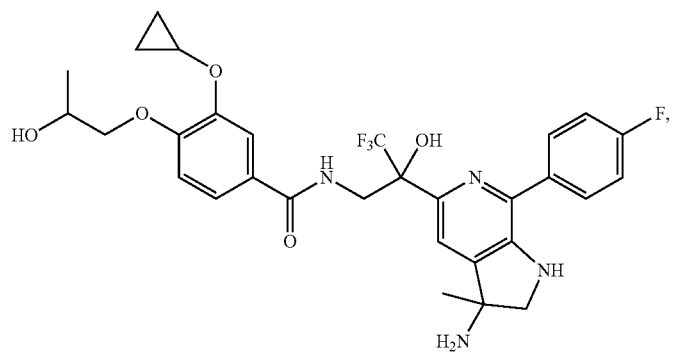
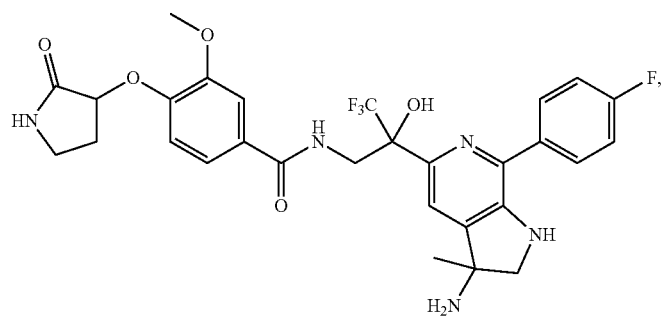
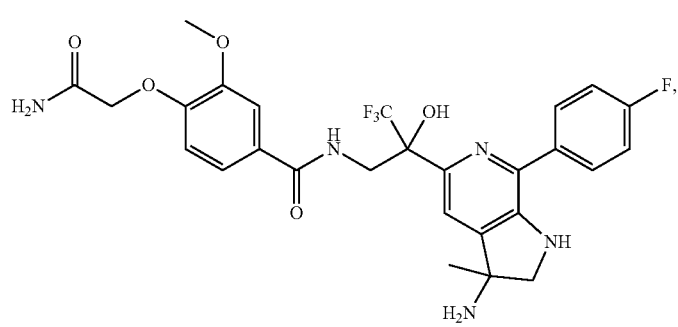
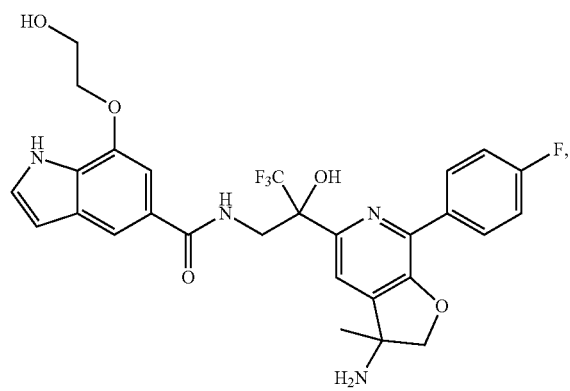
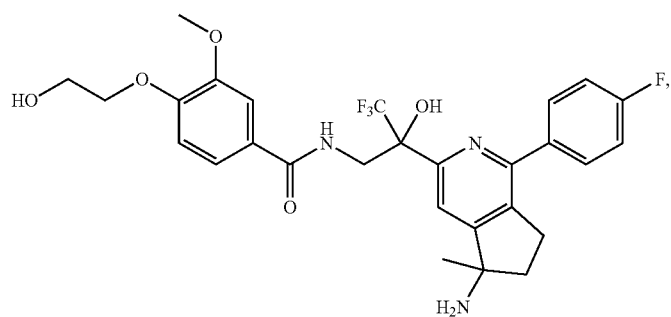

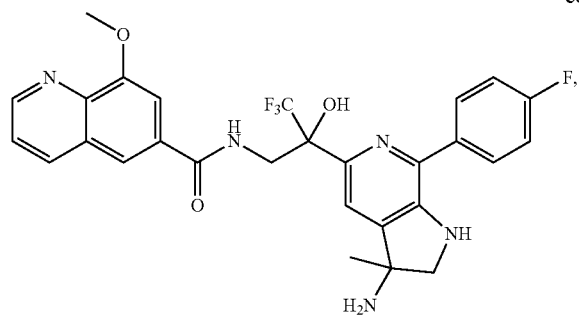
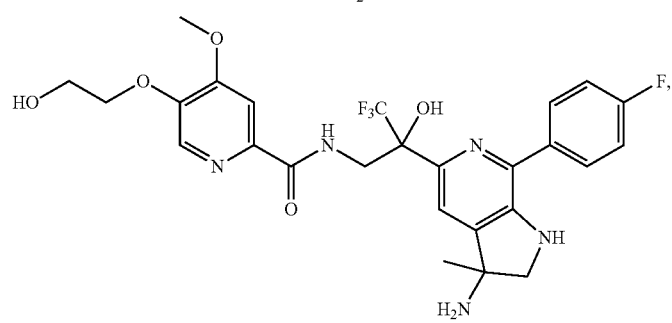
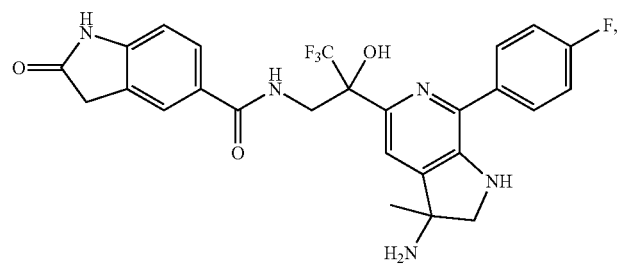
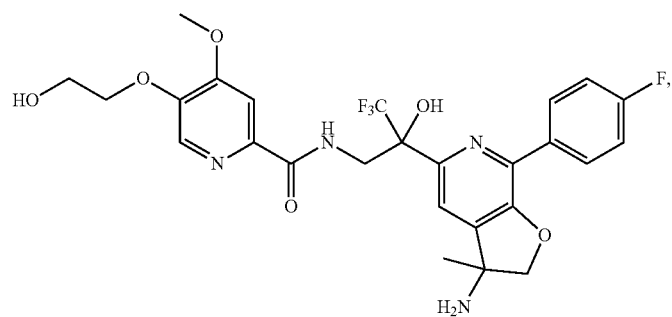
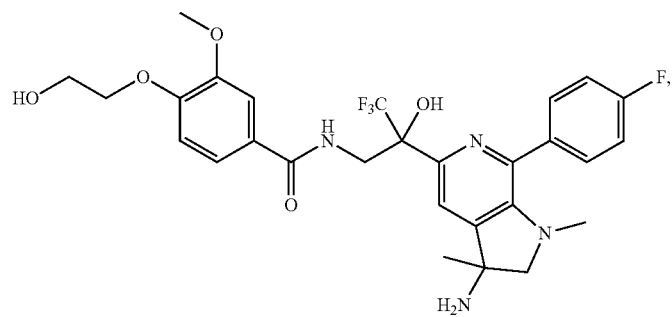

411 412
-continued
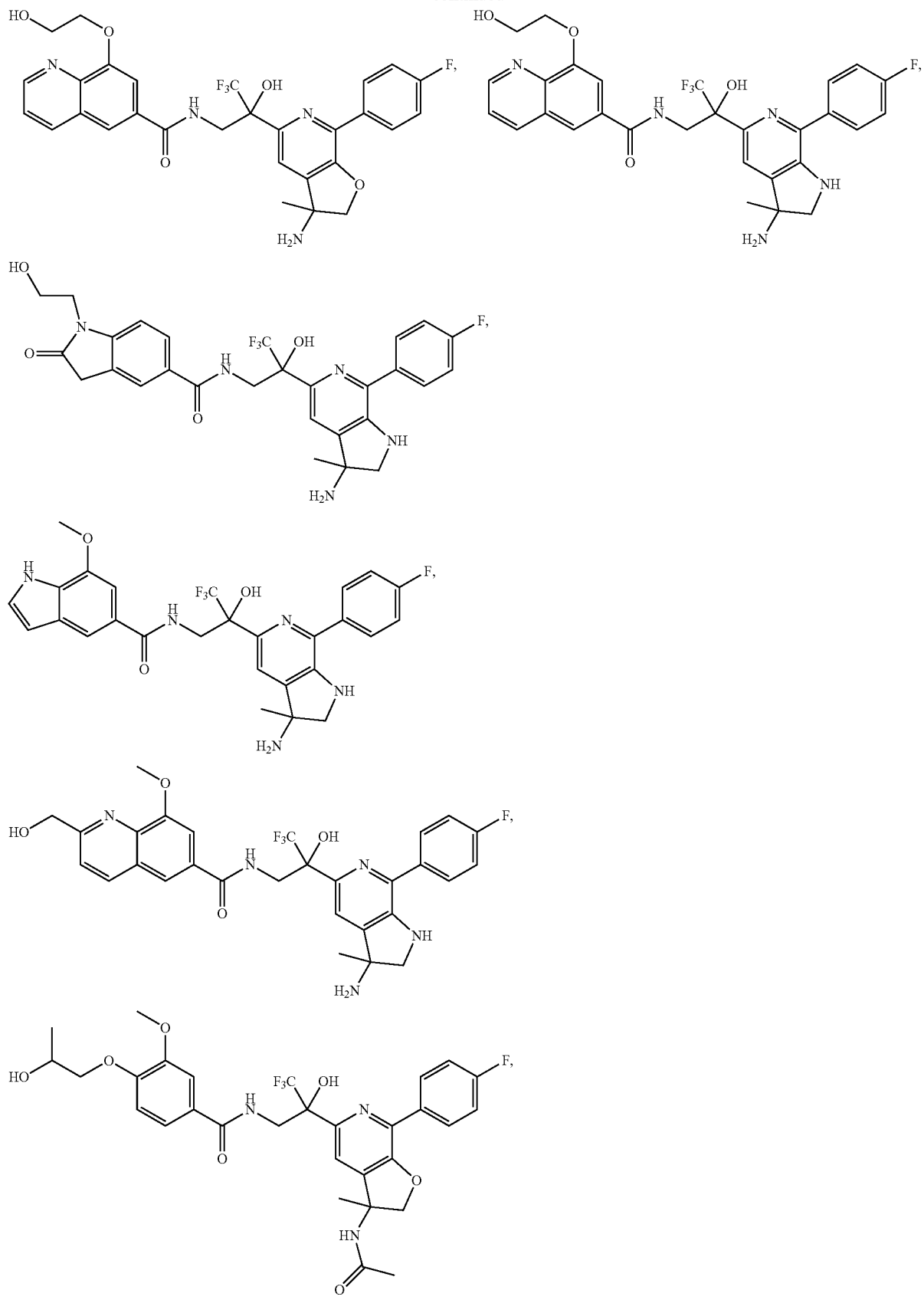

413
414
-continued
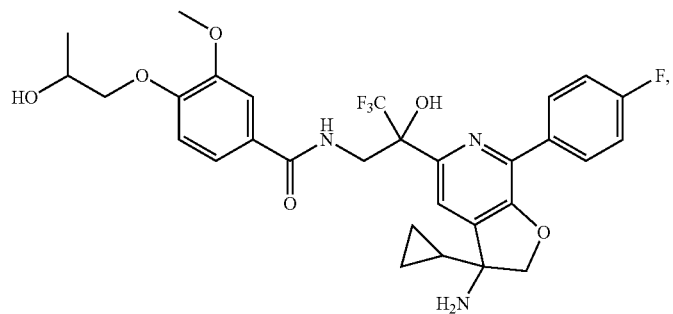
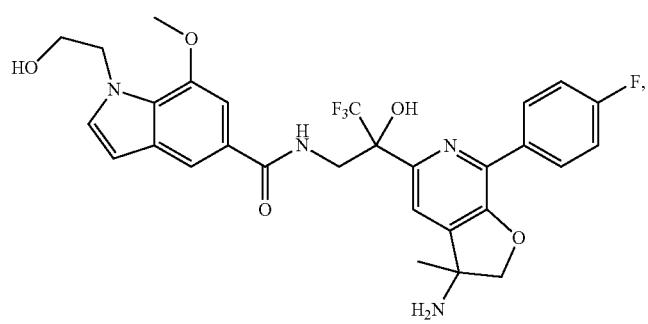
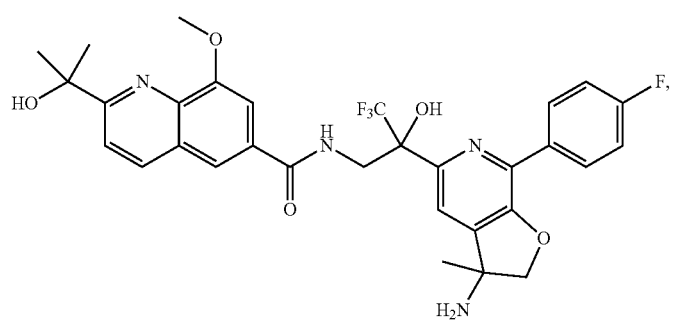
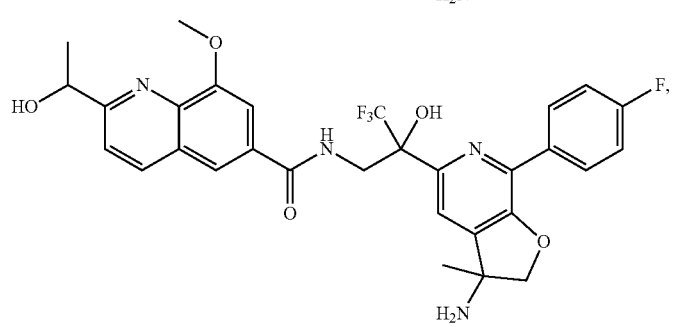
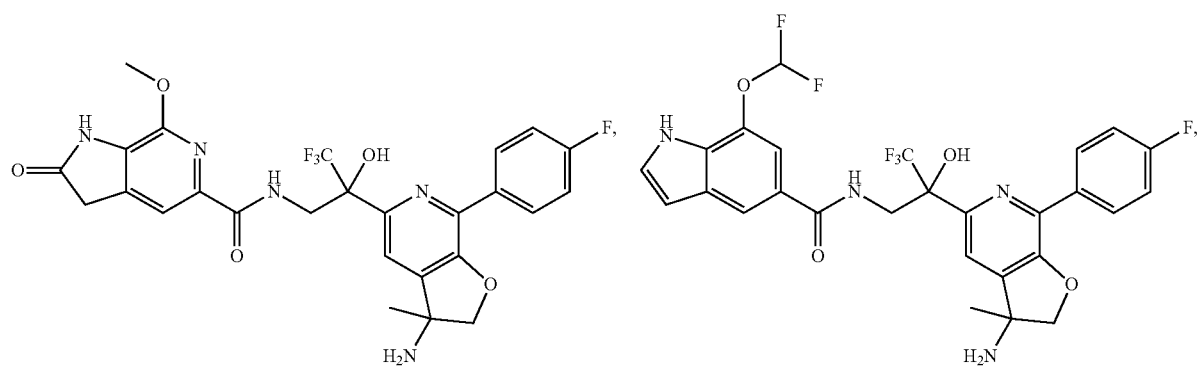

415 416
-continued
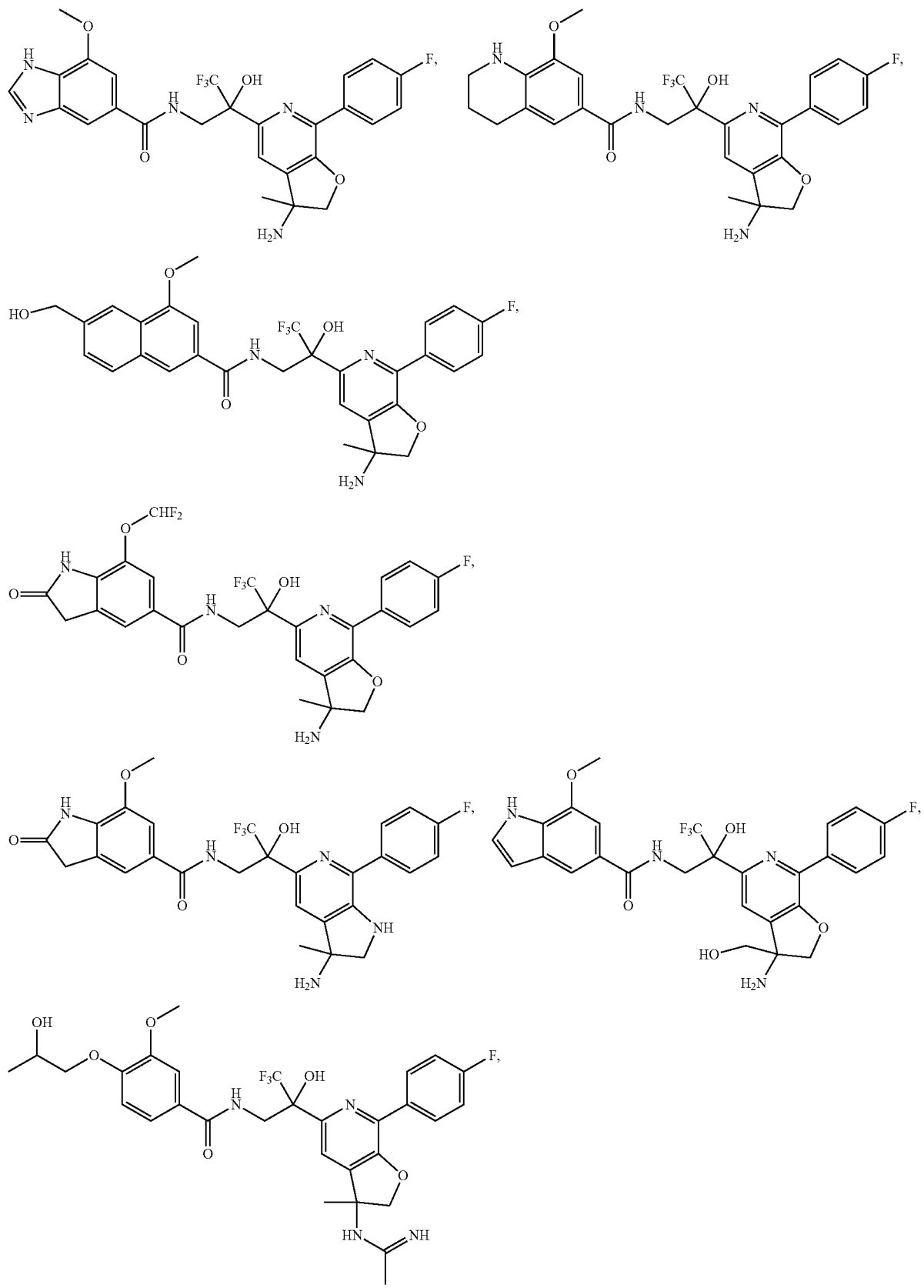

-continued
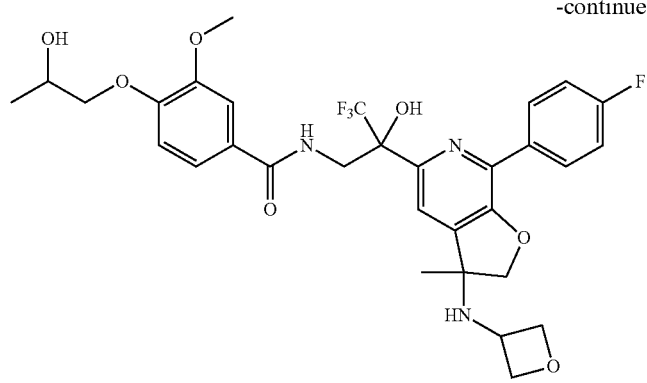
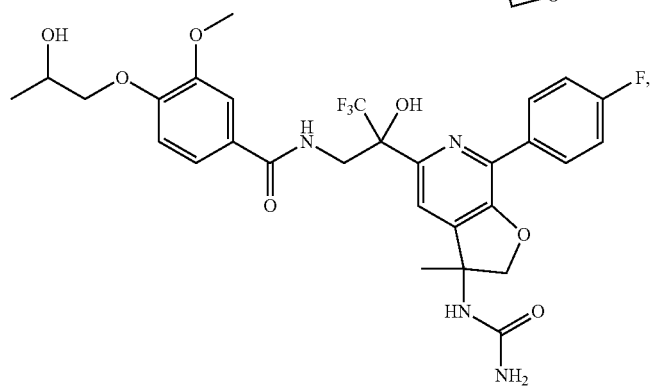
or a pharmaceutically acceptable salt of any of the foregoing.
31. The compound of claim 1, wherein the compound of Formula (I) is selected from the group consisting of:
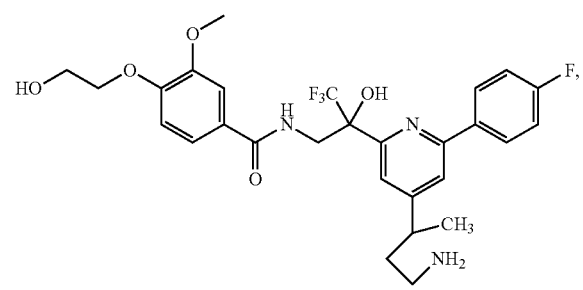
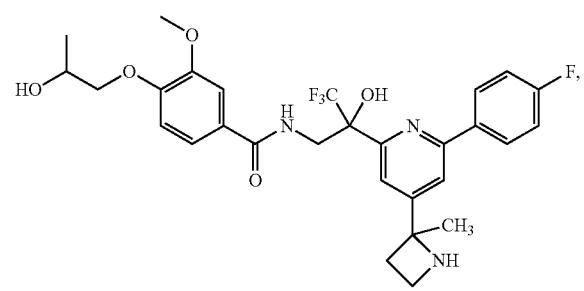
-continued
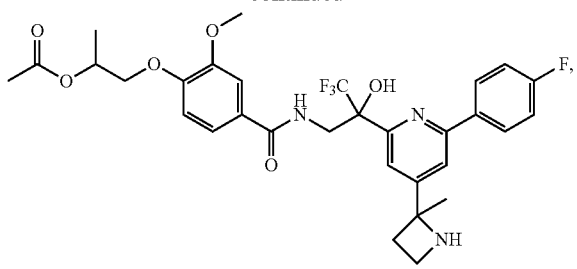
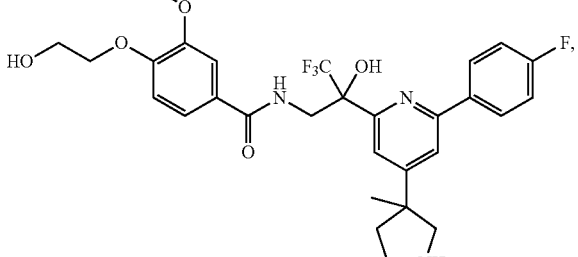
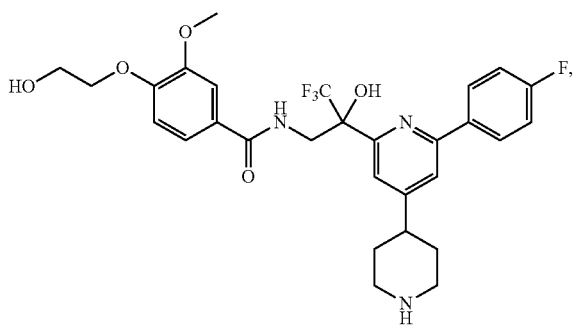

-continued
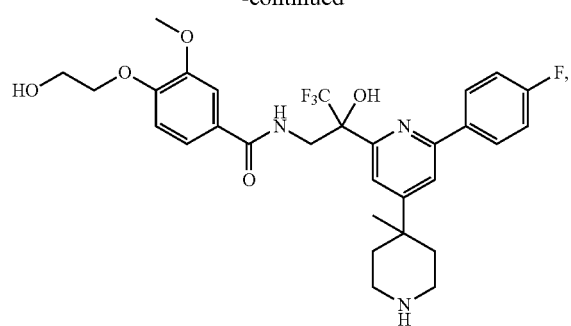
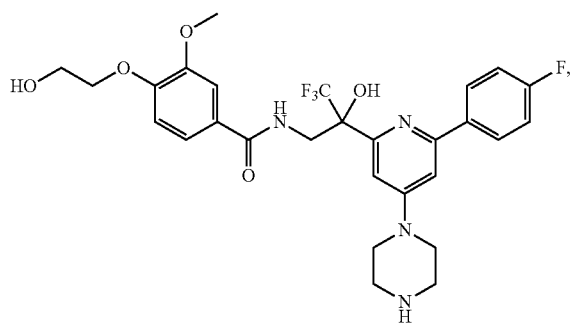
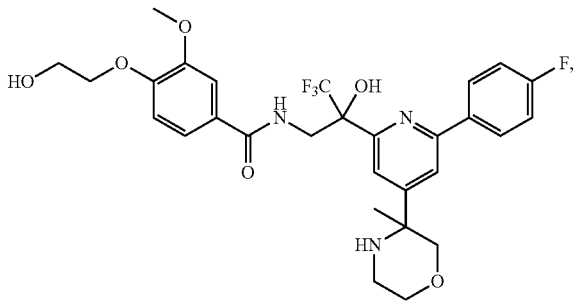
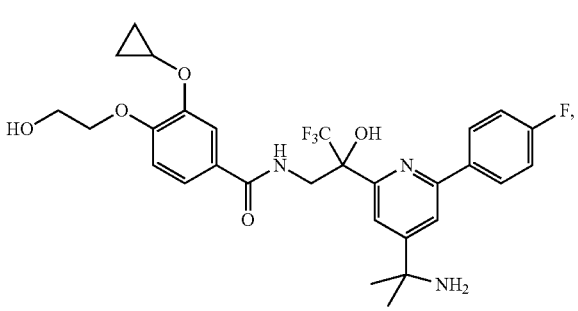
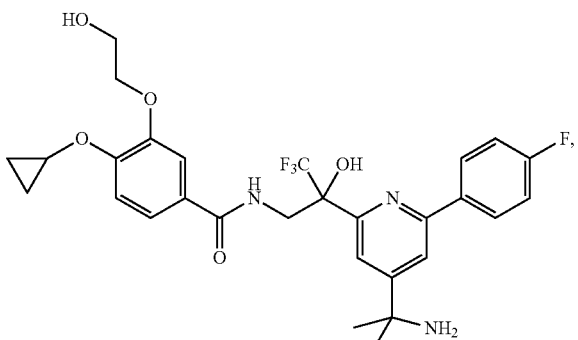
-continued
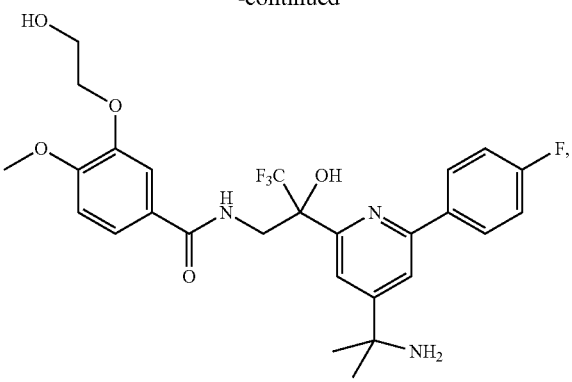
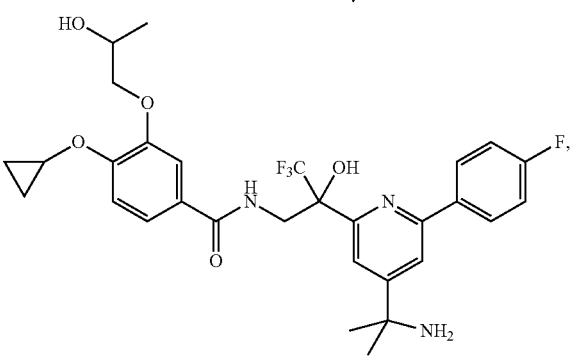
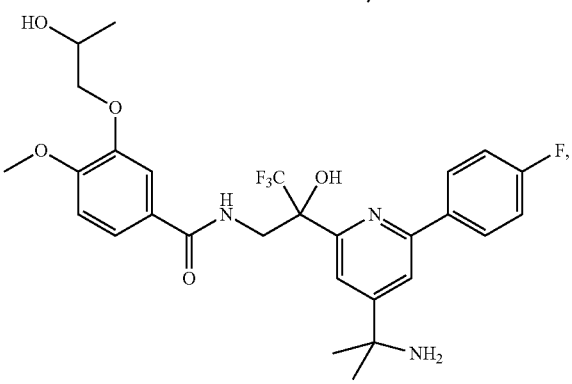
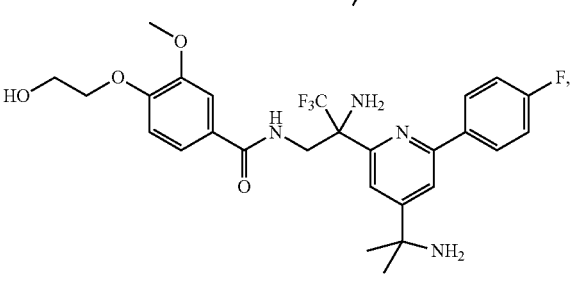
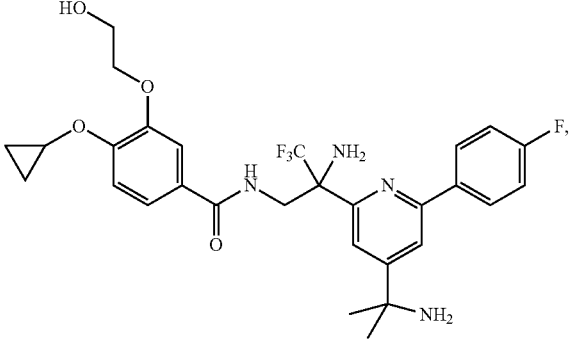

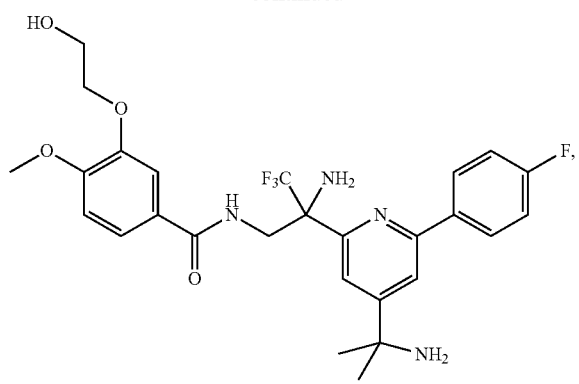

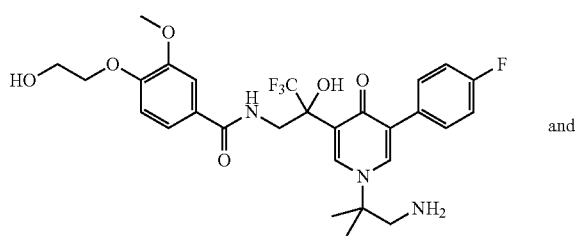

and

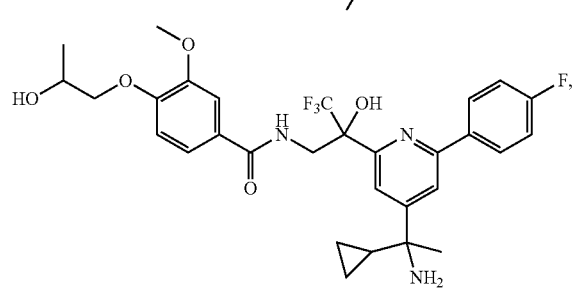

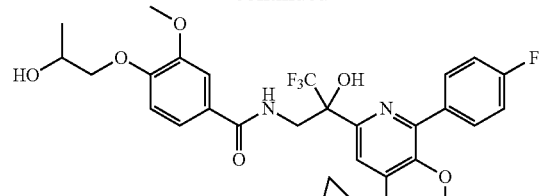

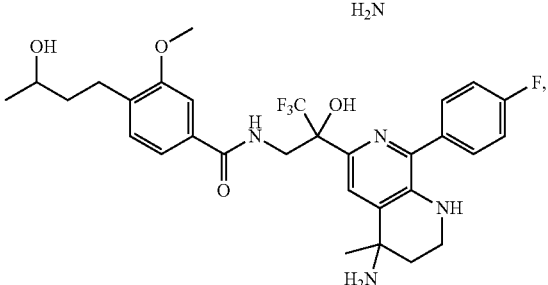

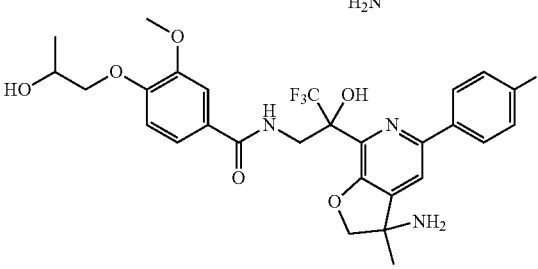

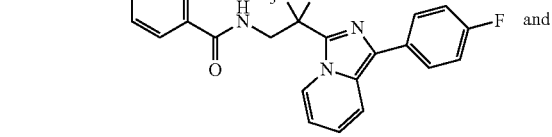

and

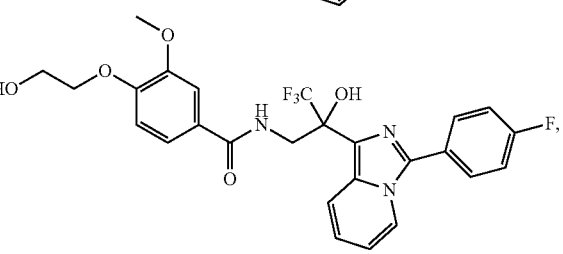

or a pharmaceutically acceptable salt of any of the foregoing.

32. The compound of claim 1, wherein the compound of Formula (I) is selected from the group consisting of:

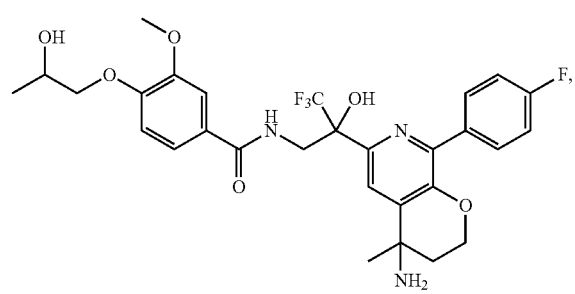

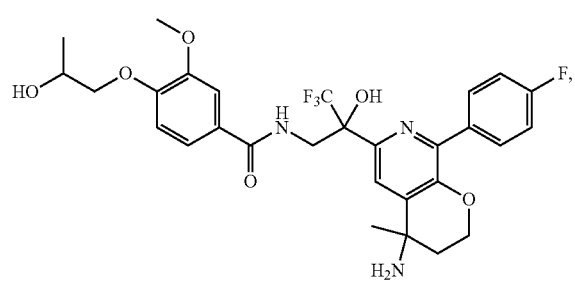

or a pharmaceutically acceptable salt of any of the foregoing.

33. A pharmaceutical composition comprising an effective amount of a compound of any one of claim 1, or a pharmaceutically acceptable salt thereof, and a pharmaceutically acceptable carrier, diluent, excipient, or combination thereof.

34. A method for ameliorating or treating a paramyxovirus infection comprising administering to a subject identified as suffering from the paramyxovirus infection an effective amount of a compound of claim 1, or a pharmaceutically acceptable salt thereof.

35. The use of claim 34, wherein the paramyxovirus infection is a human respiratory syncytial virus infection, further comprising administering one or more additional anti-viral agents, wherein the one or more additional anti-viral agents is an anti-RSV agent selected from the group consisting of an anti-RSV antibody, a fusion protein inhibitor, an N-protein inhibitor, a RSV polymerase inhibitor, an IMPDH inhibitor, an interferon and another compound that inhibits the RSV virus, or a pharmaceutically acceptable salt of any of the foregoing.

36. The use of claim 35, wherein the one or more additional anti-viral agents is selected from the group consisting of RSV-IGIV, palivizumab, motavizumab, 1-cyclopropyl-3-[[1-(4-hydroxybutyl)benzimidazol-2-yl]methyl] imidazo[4,5-c]pyridin-2-one (BMS-433771), 4,4''-bis-{4,6-bis-[3-(bis-carbamoylmethyl-sulfamoyl)-phenylamino]-(1, 3,5)triazin-2-ylamino}-biphenyl-2,2''-disulfonic-acid (RFI-641), 4,4'-Bis[4,6-di[3-aminophenyl-N,N-bis(2-carbamoylethyl)-sulfonilimino]-1,3,5-triazine-2-ylamino]-biphenyl-2,2'-disulfonic acid, disodium salt (CL387626), 2-[[2-[[1-(2-aminoethyl)-4-piperidinyl]amino]-4-methyl-1H-benzimidazol-1-yl]-6-methyl-3-pyridinol (JNJ-2408068), 2-[[6-[[[2-(3-Hydroxypropyl)-5-methylphenyl] amino]methyl]-2-[[3-(morpholin-4-yl)propyl]amino] benzimidazol-1-yl]methyl]-6-methylpyridin-3-ol (TMC-353121), 5,5'-bis[1-(((5-amino-1H-tetrazolyl)imino) methyl)]2,2',4''-methylidynetrisphenol (VP-14637, MDT-637), N-(2-hydroxyethyl)-4-methoxy-N-methyl-3-(6-methyl-[1,2,4]triazolo[3,4-a]phthalazin-3-yl) benzenesulfonamide (P13), 2-((2-((1-(2-aminoethyl) piperidin-4-yl)amino)-4-methyl-1H-benzo[d]imidazol-1-yl) methyl)-6-methylpyridin-3-ol (R170591), 1,4-bis(3-methylpyridin-4-yl)-1,4-diazepane (C15), (R)-9b-(4-chlorophenyl)-1-(4-fluorobenzoyl)-2,3-dihydro-1H-imidazo[1',2':1,2]pyrrolo[3,4-c]pyridin-5(9bH)-one (BTA9981), [2,2-bis(docosyloxy-oxymethyl)propyl-5-acetaoamido-3,5-dideoxy-4,7,8,9-tetra-O-(sodium-oxysulfonyl)-D-glycero-D-galacto-2-nonulopyranosid]onate (MBX-300), BTA-C286, N-(2-((S)-2-(5-((S)-3-aminopyrrolidin-1-yl)-6-methylpyrazolo[1,5-a]pyrimidin-2-yl)piperidine-1-carbonyl)-4-chlorophenyl)methanesulfonamide (GS-5806), an anti-RSV nanobody, a peptide fusion inhibitor (such as a peptide having the sequence DEFDASISQVNEKINQSLA-FIRKSDELL (T-67), a peptide having the sequence FDA-SISQVNEKINQSLAFIRKSDELLHNVNAGKST (T-118), (S)-1-(2-fluorophenyl)-3-(2-oxo-5-phenyl-2,3-dihydro-1H-benzo[e][1,4]diazepin-3-yl)urea (RSV-604), STP-92, iKT-041, 6-{4-[(biphenyl-2-ylcarbonyl) amino]benzoyl}-N-cyclopropyl-5,6-dihydro-4H-thieno[3,2-d][1]benzazepine-2-carboxamide (YM-53403). N-cyclopropyl-5-(4-(2-(pyrrolidin-1-yl)benzamido)benzoyl)-5,6,7,10-tetrahydrobenzo[b]cyclopenta[d]azepine-9-carboxamide, 6-(4-(2-(2-oxa-7-azaspiro[3.5]nonan-7-yl)nicotinamido) benzoyl)-N-cyclopropyl-5,6-dihydro-4H-benzo[b]thieno[2, 3-d]azepine-2-carboxamide, 4-amino-8-(3-{[2-(3,4-dimethoxyphenyl)ethyl]amino}propyl)-6,6-dimethyl-2-(4-methyl-3-nitrophenyl)-1H-imidazo[4,5-h]-isoquinoline-7,9 (6H,8H)-dione, AZ27, ribavirin, 5-ethynyl-1-beta-D-ribofuranosylimidazole-4-carboxamide (EICAR), 4-hydroxy-3-beta-D-ribofuranosylpyrazole-5-carboxamide (pyrazofurin), 1-((2R,3R,4S,5R)-3,4-dihydroxy-5-hydroxymethyl)tetrahydrofuran-2-yl)-1H-1,2,4-triazole-3-carboximidamide (Taribavirin, viramidine), (2R,3R,4R,5R)-5-(4-amino-2-oxopyrimidin-1(2H)-yl)-2-(chloromethyl)-4-fluoro-2-((isobutyryloxy)methyl)tetrahydrofuran-3-yl isobutyrate, (2R,3R,4R,5R)-5-(4-amino-2-oxopyrimidin-1 (2H)-yl)-2-(chloromethyl)-4-fluoro-2-(hydroxymethyl)tetrahydrofuran-3-yl isobutyrate, ((2R,3R,4R,5R)-5-(4-amino-2-oxopyrimidin-1(2H)-yl)-2-(chloromethyl)-4-fluoro-3-hydroxytetrahydrofuran-2-yl)methyl triphosphate, 4-amino-1-((2R,3R,4R,5R)-5-(chloromethyl)-3-fluoro-4-hydroxy-5-(hydroxymethyl)tetrahydrofuran-2-yl)pyrimidin-2(1H)-one, 1,3,4-thiadiazol-2-ylcyanamide (LY253963), tetrahydrofuran-3-yl-3-(3-(3-methoxy-4-(oxazol-5-yl)phenyl)ureido) benzylcarbamate (VX-497), (4E)-6-(4-Hydroxy-6-methoxy-7-methyl-3-oxo-1,3-dihydro-2-benzofuran-5-yl)-4-methylhex-4-enoic acid (Mycophenolic acid), 2-morpholin-4-ylethyl-(E)-6-(4-hydroxy-6-methoxy-7-methyl-3-oxo-1H-2-benzofuran-5-yl)-4-methylhex-4-enoate (Mycophenolate Mofetil), a Type 1 interferon, a Type 2 interferon, a Type 3 interferon, a double stranded RNA oligonucleotide, 5-methyl-N-[4-(trifluoromethyl) phenyl]-isoxazole-4-carboxamide (leflumomide), N-(2-chloro-4-methylphenyl)-2-((1-(4-methoxyphenyl)-1H-benzo[d]imidazol-2-yl)thio)propanamide (JMN3-003), an intratracheal formulation of recombinant human CC10 (CG-100), high titer, human immunoglobulin (RI-001), a non-neutralizing mAb against the G protein (mAb 131-2G), ALN-RSV01, ALN-RSV02, Medi-559, Medi-534 and Medi-557, or a pharmaceutically acceptable salt of any of the foregoing.

37. A method for inhibiting replication of a paramyxovirus comprising contacting a cell infected with the paramyxovirus with an effective amount of a compound of claim 1, or a pharmaceutically acceptable salt thereof.

38. The use of any one of claim 37, wherein the paramyxovirus infection is a human respiratory syncytial virus infection.

39. A compound, or a pharmaceutically acceptable salt thereof, wherein the compound has the structure of:

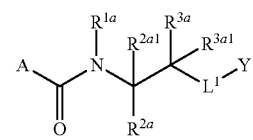

wherein:
$L^1$ is

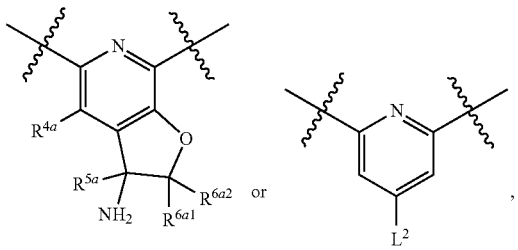

$L^2$ is selected from the group consisting of

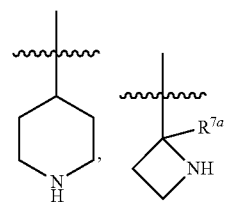

and

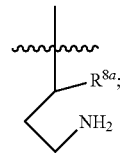

A is selected from the group consisting of an optionally substituted cycloalkyl, an optionally substituted cycloalkenyl, an optionally substituted aryl, an optionally substituted heteroaryl and an optionally substituted heterocyclyl;

Y is selected from the group consisting of an optionally substituted aryl, an optionally substituted heteroaryl and an optionally substituted heterocyclyl;

$R^{1a}$ is hydrogen or an unsubstituted $C_{1-4}$ alkyl;

$R^{2a}$ and $R^{2a1}$ are each independently hydrogen or an unsubstituted $C_{1-4}$ alkyl;

$R^{3a}$ and $R^{3a1}$ are each independently hydroxy, $CHF_2$ or $CF_3$;

$R^{4a}$ is selected from the group consisting of hydrogen, halogen, hydroxy, an optionally substituted $C_{1-8}$ alkyl, an optionally substituted $C_{1-8}$ alkoxy and haloalkyl;

$R^{5a}$ is an unsubstituted $C_{1-6}$ alkyl or $—(CH_2)_{1-4}OH$;

$R^{6a1}$ and $R^{6a2}$ are each independently selected from the group consisting of hydrogen, halogen, an unsubstituted $C_{1-6}$ alkyl and hydroxy; and $R^{7a}$ and $R^{8a}$ are each independently an unsubstituted $C_{1-6}$ alkyl; provided that the compound is not any one of the group consisting of:

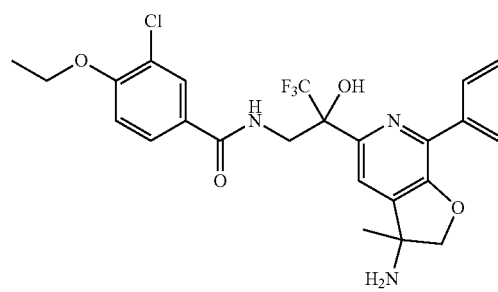

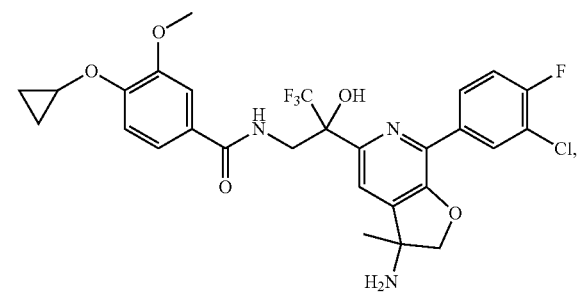

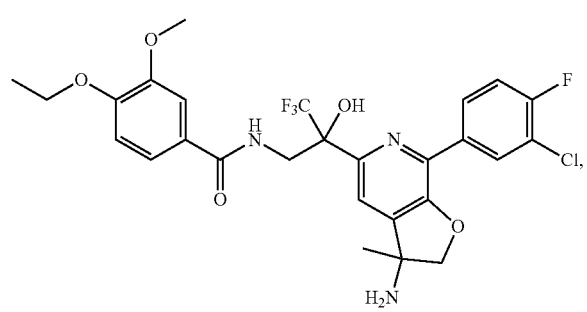

-continued

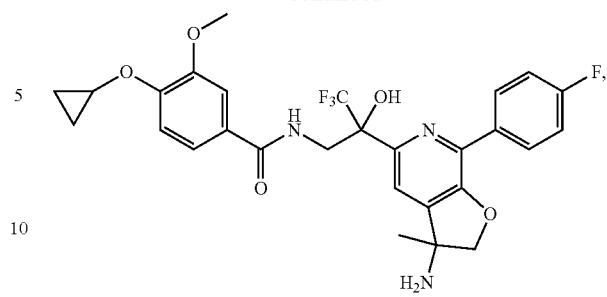

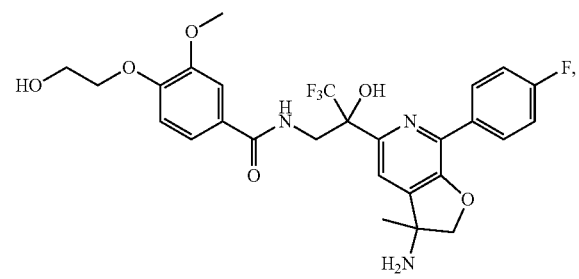

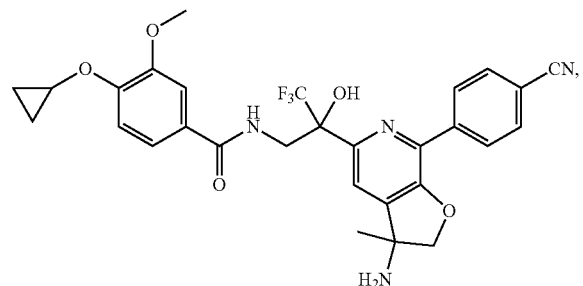

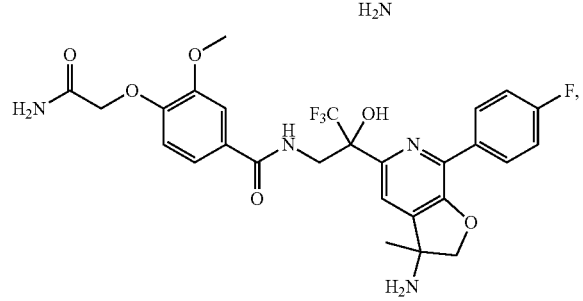

427
-continued
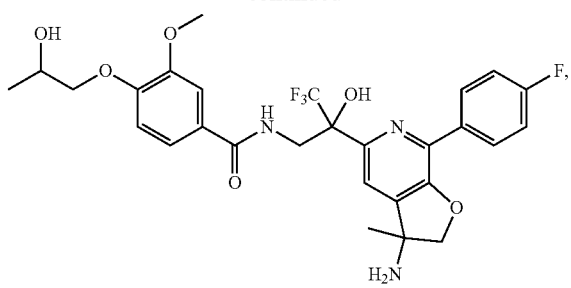
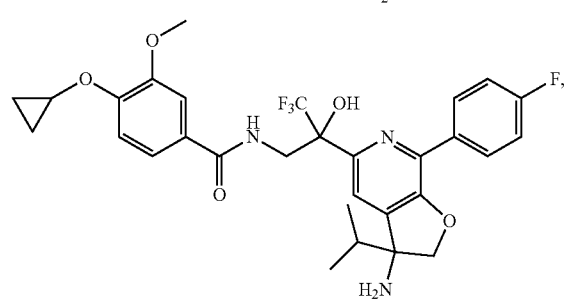
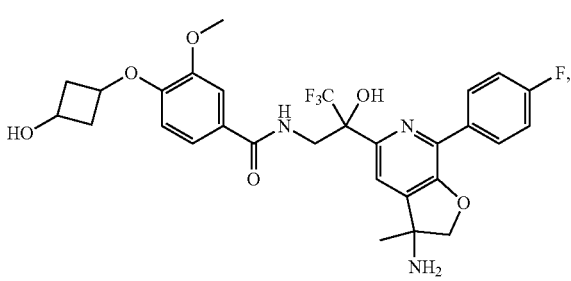
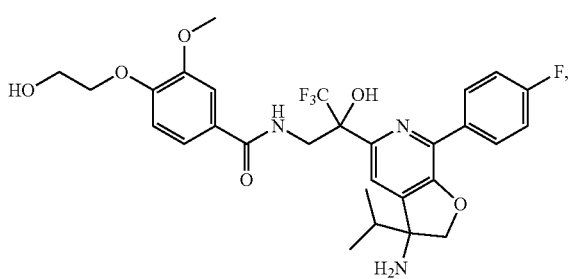
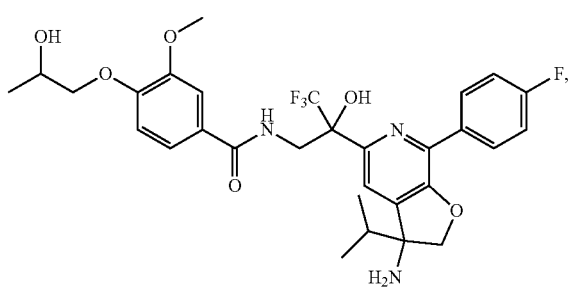
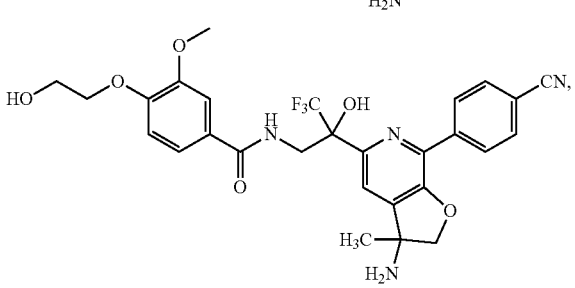
428
-continued
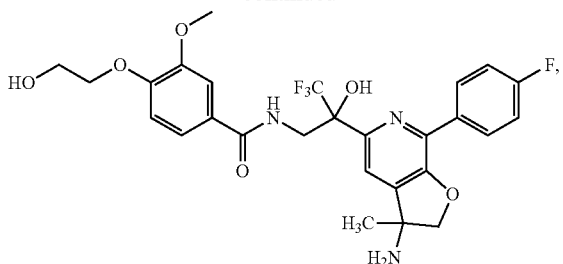
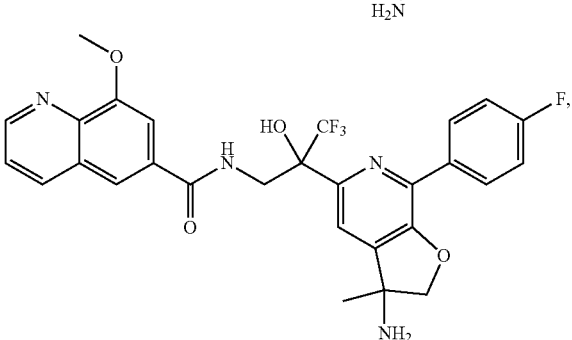
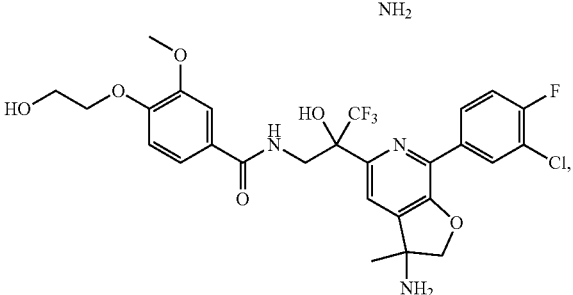
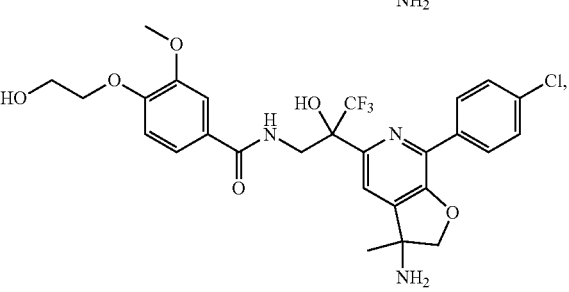
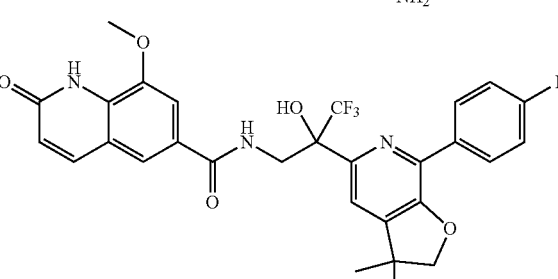
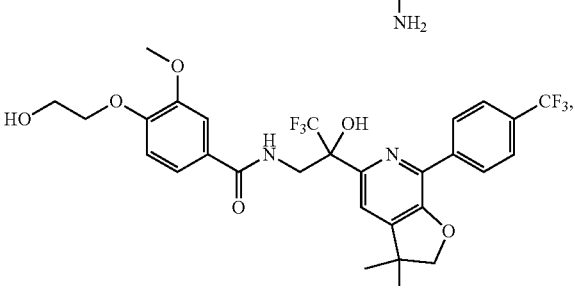

-continued
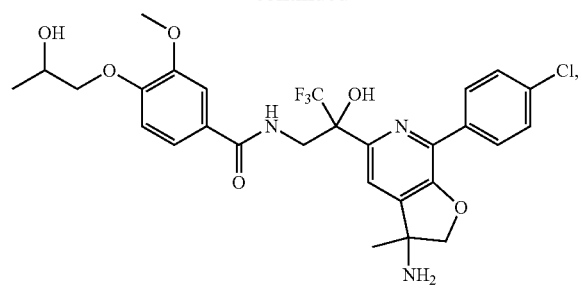
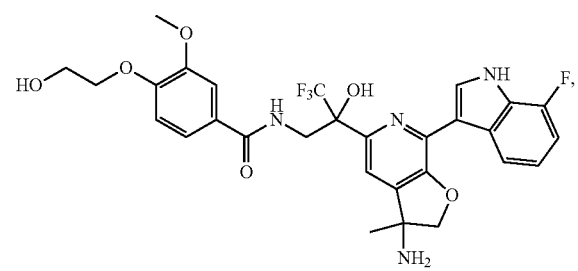
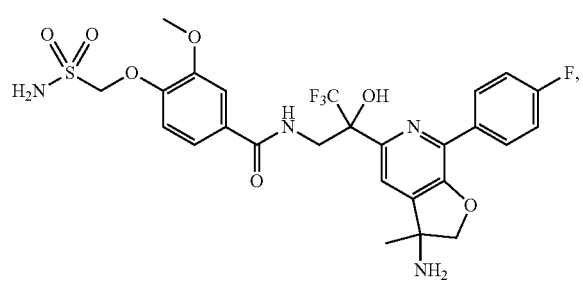
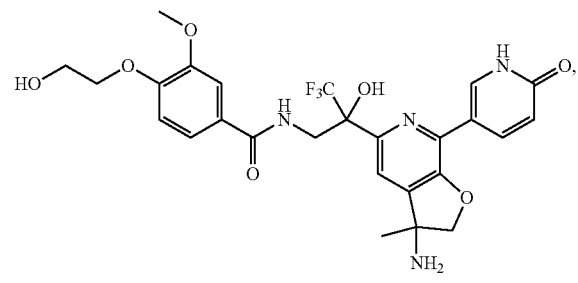
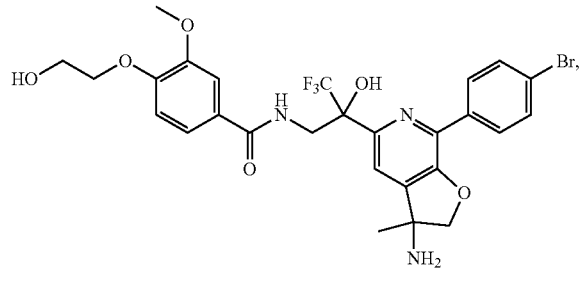
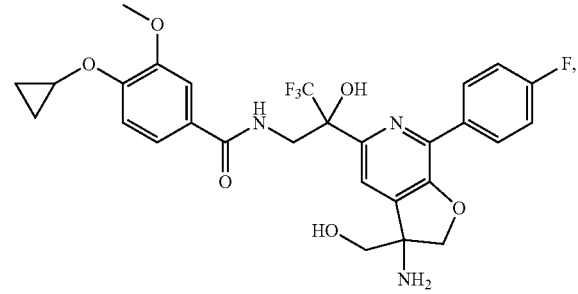
-continued
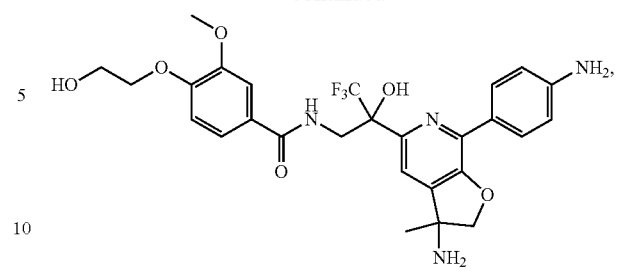
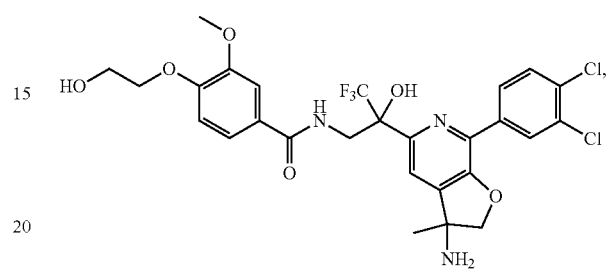
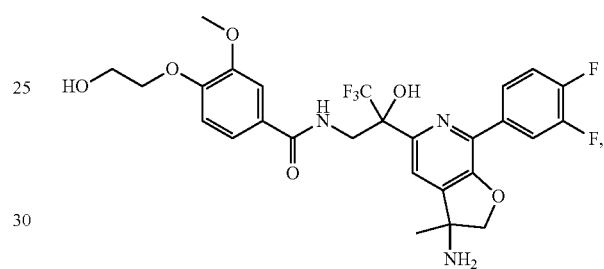
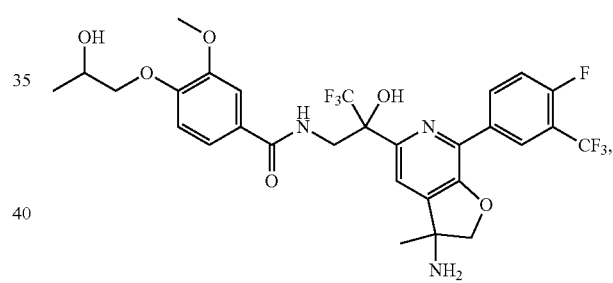
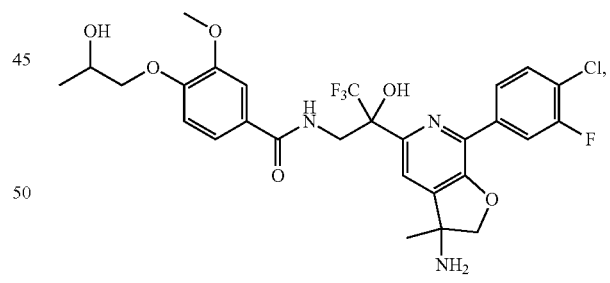
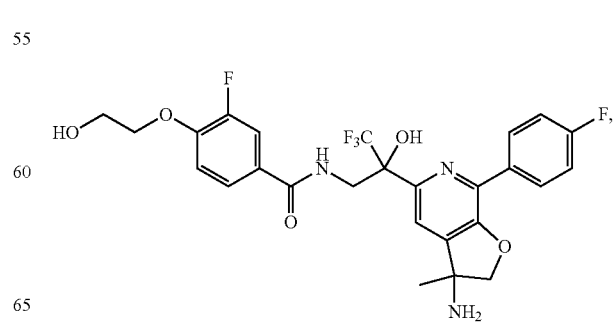

431
-continued
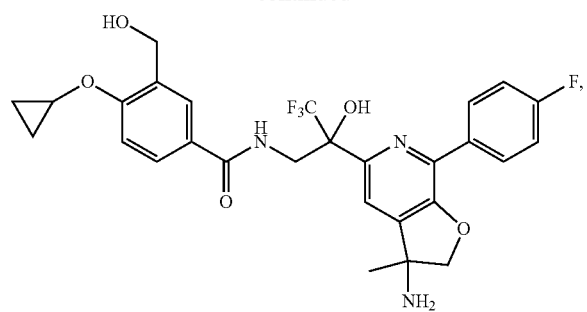
432
-continued
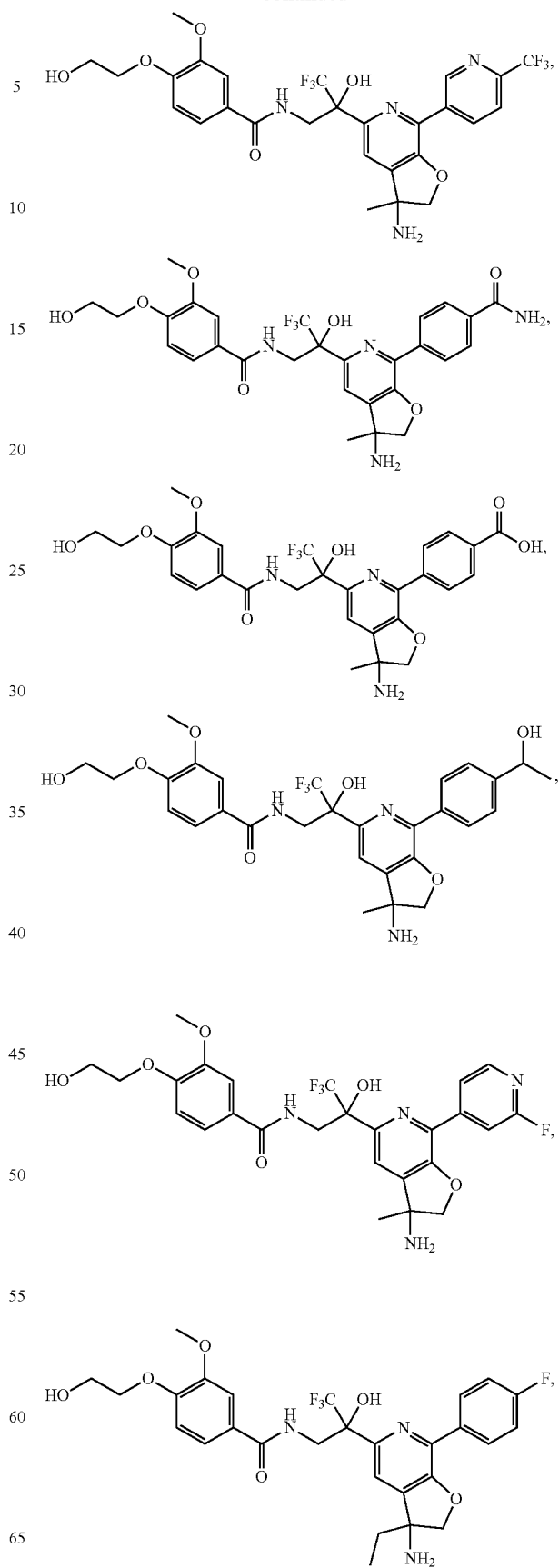

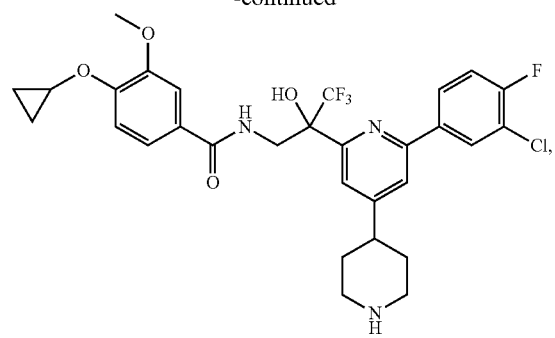

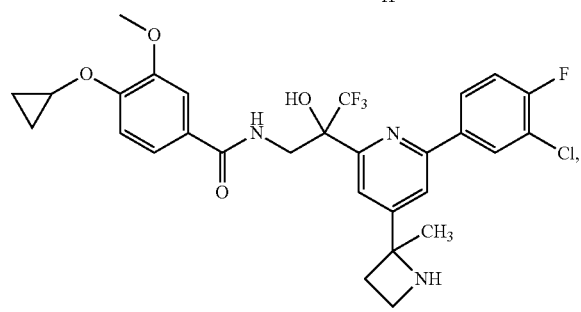

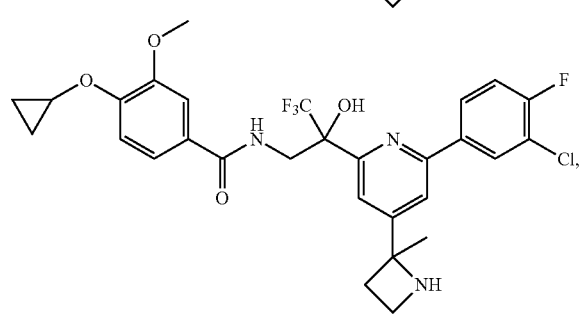

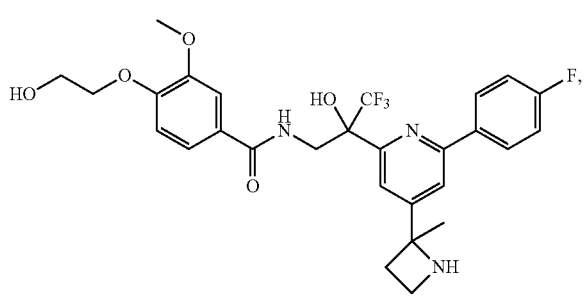

and or a pharmaceutically acceptable salt of any of the foregoing.

40. The compound of claim 39, or a pharmaceutically acceptable salt thereof, wherein $R^{1a}$ is hydrogen.

41. The compound of claim 39, or a pharmaceutically acceptable salt thereof, wherein $R^{2a}$ and $R^{2a1}$ are both hydrogen.

42. The compound of claim 39, or a pharmaceutically acceptable salt thereof, wherein $R^{3a}$ is hydroxy; and $R^{3a1}$ is $CF_3$.

43. The compound of claim 39, or a pharmaceutically acceptable salt thereof, wherein $L^1$ is

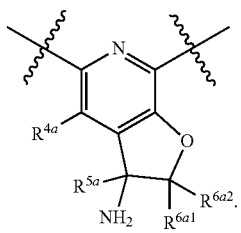

44. The compound of claim 39, or a pharmaceutically acceptable salt thereof, wherein $R^{5a}$ is an unsubstituted $C_{1-6}$ alkyl.

45. The compound of claim 39, or a pharmaceutically acceptable salt thereof, wherein $R^{5a}$ is —$(CH_2)_{1-4}OH$.

46. The compound of claim 39, or a pharmaceutically acceptable salt thereof, wherein $R^{6a1}$ and $R^{6a2}$ are each hydrogen.

47. The compound of claim 39, or a pharmaceutically acceptable salt thereof, wherein $R^{4a}$ is hydrogen.

48. The compound of claim 39, or a pharmaceutically acceptable salt thereof, wherein $L^1$ is

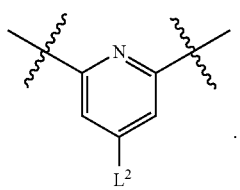

49. The compound of claim 48, or a pharmaceutically acceptable salt thereof, wherein $L^2$ is selected from the group consisting of

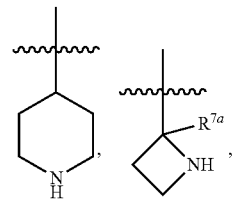

and

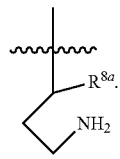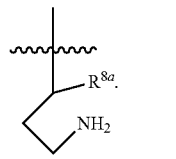

50. The compound of claim 39, or a pharmaceutically acceptable salt thereof, wherein A is a di-substituted phenyl; or wherein A is a phenyl substituted with one or more substituents selected from the group consisting of: an unsubstituted $C_{1-4}$ alkyl, a substituted $C_{1-4}$ alkyl, cycloalkyl, hydroxy, a substituted $C_{1-4}$ alkoxy, an unsubstituted $C_{1-4}$ alkoxy, halogen, haloalkyl, an optionally substituted haloalkoxy, nitro, amino, mono-substituted amine, di-substituted amine, -O-amido, sulfenyl, alkyoxyalkyl, an optionally substituted aryl, an optionally substituted mono-cyclic heteroaryl, an optionally substituted mono-cyclic heterocyclyl, an optionally substituted aryl($C_{1-4}$ alkyl), an optionally substituted monocyclic heteroaryl($C_{1-4}$ alkyl), an optionally substituted monocyclic heterocyclyl($C_{1-4}$ alkyl), hydroxyalkyl and aminoalkyl.

51. The compound of claim 39, or a pharmaceutically acceptable salt thereof, wherein A is a phenyl substituted with one or more substituents selected from the group consisting of: methyl, ethyl, propyl, butyl, hydroxy, methoxy, ethoxy, n-propoxy, iso-propoxy, n-butoxy, iso-butoxy, t-butoxy, bromo, chloro, fluoro, trifluoromethyl, difluoromethoxy, trifluoromethoxy, N,N-di-methyl-amine, N,N-di-ethyl-amine, N-methyl-N-ethyl-amine, N-methyl-amine, N-ethyl-amine, amino, an optionally substituted phenyl, an optionally substituted imidazole, an optionally substituted morpholinyl, an optionally substituted pyrazole, an optionally substituted pyrrolidinyl, an optionally substituted pyridinyl, an optionally substituted piperidinyl, an optionally substituted piperidinone, an optionally substituted pyrrolidinone, an optionally substituted pyrimidine, an optionally substituted pyrazine, an optionally substituted 1,2,4-oxadiazole, —$(CH_2)_{1-4}$—OH, —$(CH_2)_{1-2}$—NH($CH_3$), an optionally substituted —$(CH_2)_{1-2}$-imidazole, an optionally substituted —$(CH_2)_{1-2}$-pyrrolidinone, an optionally substituted —$(CH_2)_{1-2}$-imidazolidinone, —O$(CH_2)_2$—$NH_2$, —O$(CH_2)_2$—NH($CH_3$), —O$(CH_2)_2$—N($CH_3)_2$, —O—$(CH_2)_{2-4}$OH, —O$(CH_2)_2$O$CH_3$, —NH$(CH_2)_{1-2}$OH,

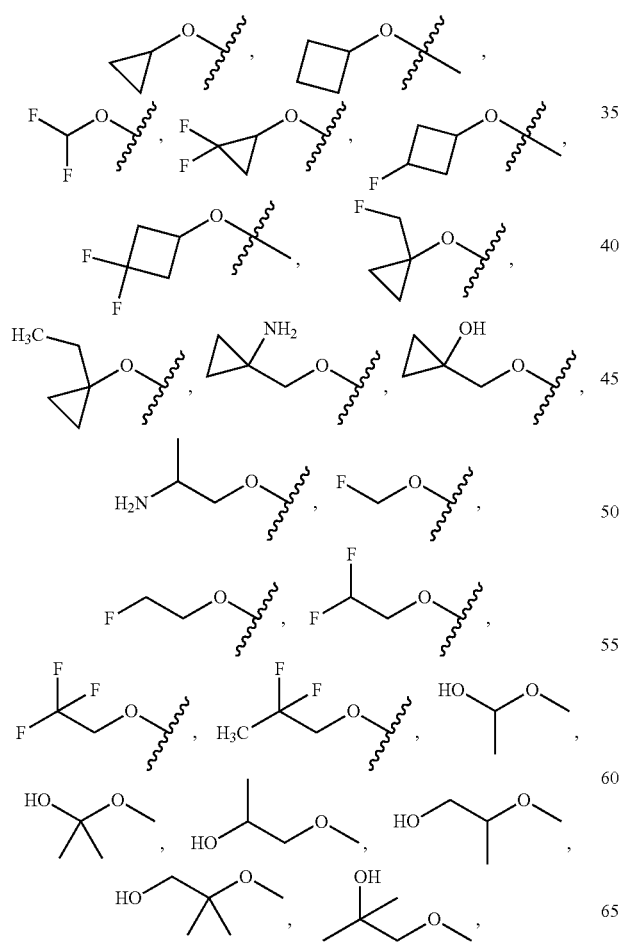

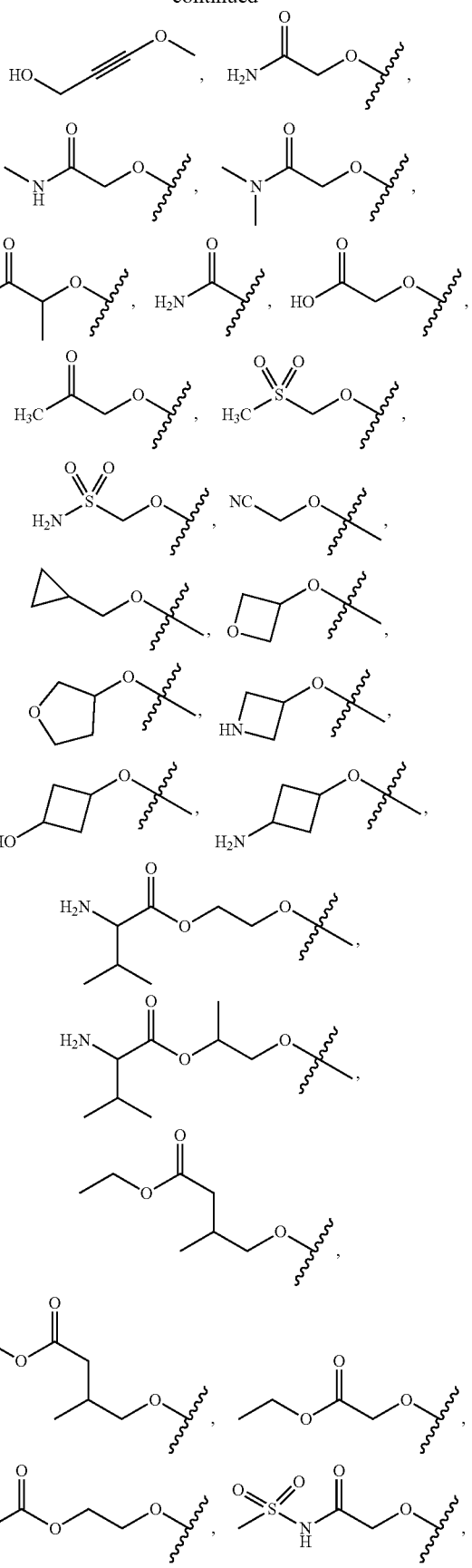

-continued

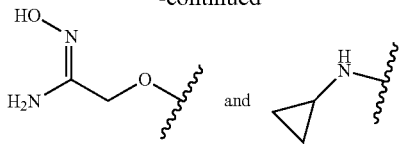

and

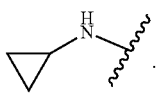

52. The compound of claim 39, or a pharmaceutically acceptable salt thereof, wherein A is an optionally substituted heteroaryl; or wherein A is a heteroaryl selected from the group consisting of: an optionally substituted imidazole, an optionally substituted indole, an optionally substituted thiazole, an optionally substituted furan, an optionally substituted thiophene, an optionally substituted pyrrole, an optionally substituted pyridine, an optionally substituted pyrimidine, an optionally substituted pyrazine, an optionally substituted pyrazole, an optionally substituted quinolone, an optionally substituted imidazole, an optionally substituted oxazole, an optionally substituted isoxazole, an optionally substituted benzoimidazole, an optionally substituted benzooxazole, an optionally substituted benzothiazole and an optionally substituted imidazo[1,2-a]pyrimidine.

53. The compound of claim 39, or a pharmaceutically acceptable salt thereof, wherein A is an optionally substituted heterocyclyl; or wherein A is an optionally substituted heterocyclyl selected from the group consisting of: an optionally substituted

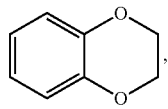

an optionally substituted

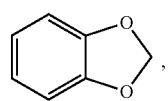

an optionally substituted

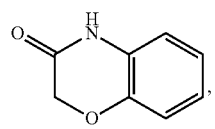 [SMILES: O=C1COc2ccccc2N1]

an optionally substituted an optionally substituted

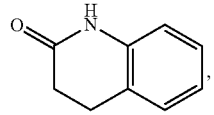 [SMILES: O=C1CCc2ccccc2N1]

an optionally substituted

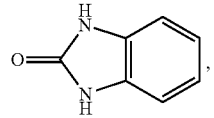

an optionally substituted

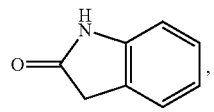

an optionally substituted

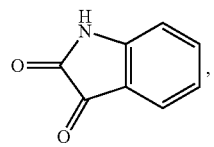 [SMILES: O=C1Nc2ccccc2C1=O]

an optionally substituted

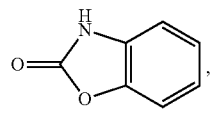

an optionally substituted

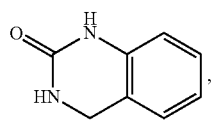 [SMILES: O=C1NCc2ccccc2N1]

an optionally substituted

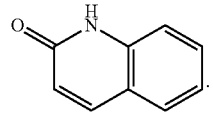

54. The compound of claim 39, or a pharmaceutically acceptable salt thereof, wherein Y is an optionally substituted aryl; or wherein Y is a mono-substituted phenyl.

55. The compound of claim 39, or a pharmaceutically acceptable salt thereof, wherein Y is an optionally substituted heteroaryl or heterocyclyl.

56. The compound of claim 39, or a pharmaceutically acceptable salt thereof, wherein the compound is selected from the group consisting of:
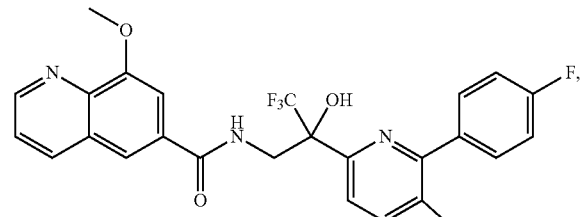
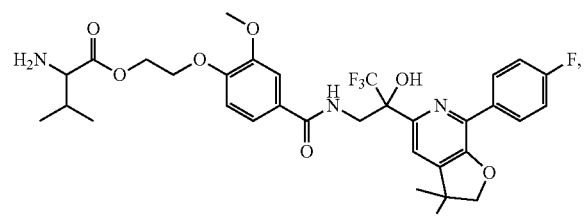
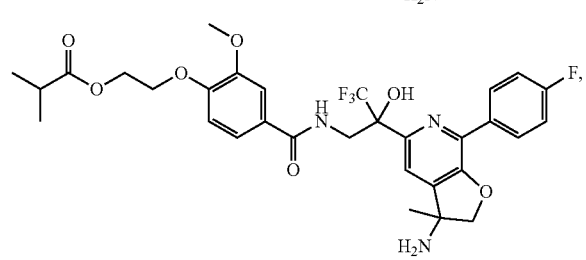
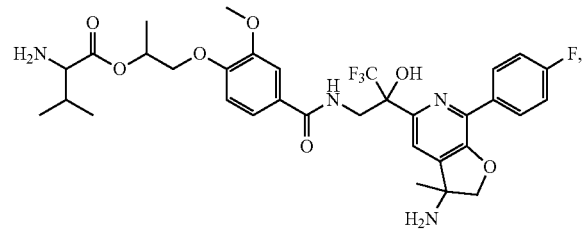
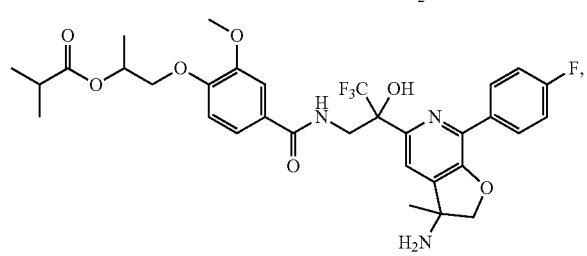
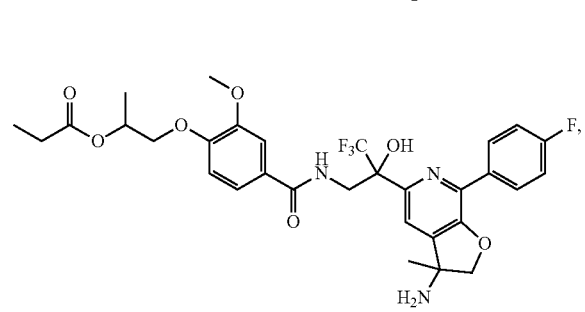
-continued
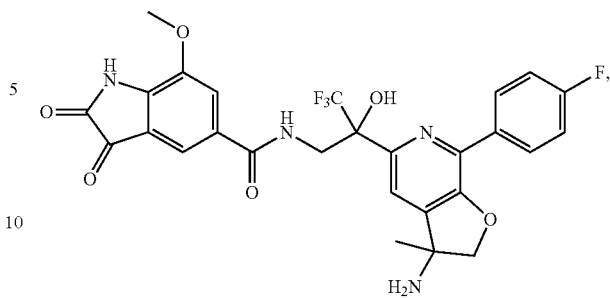
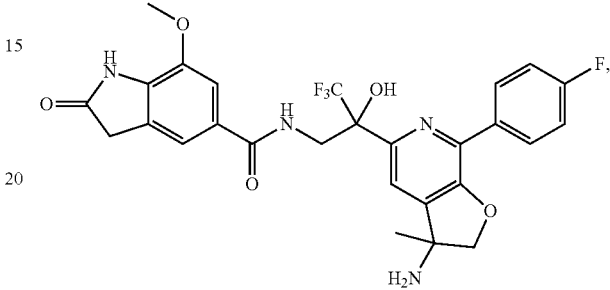
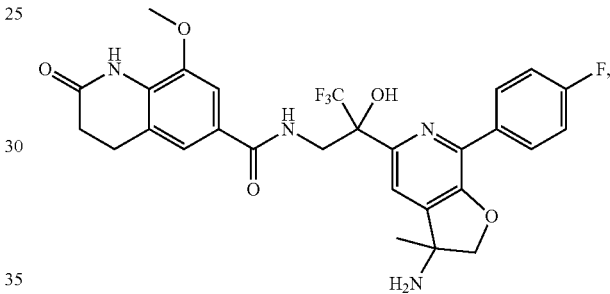
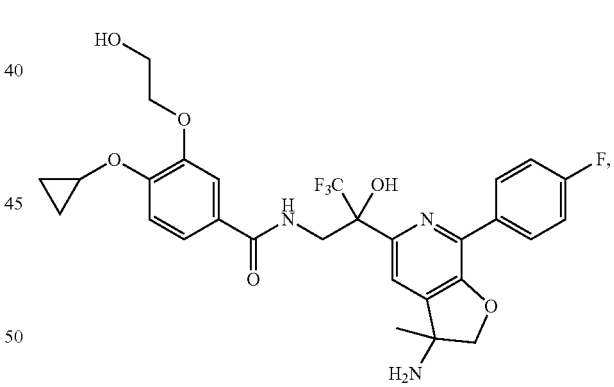
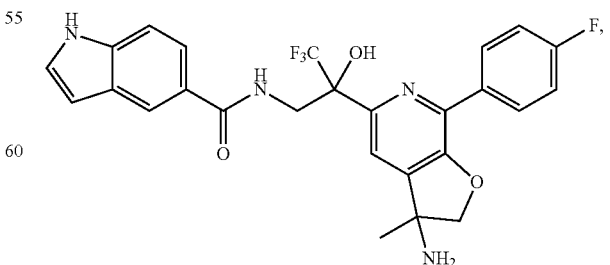

441

-continued

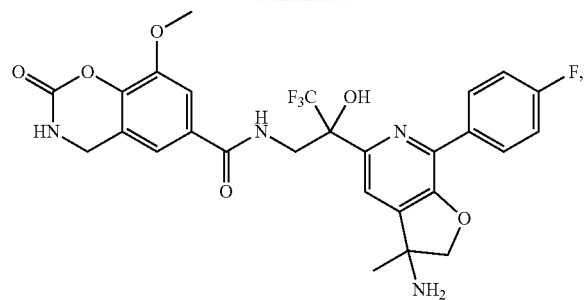

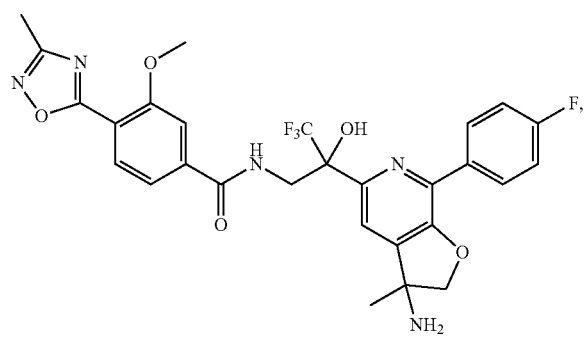

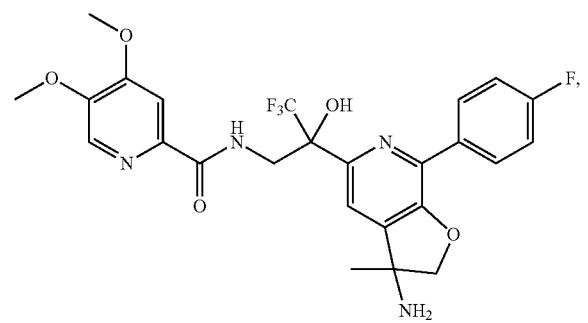

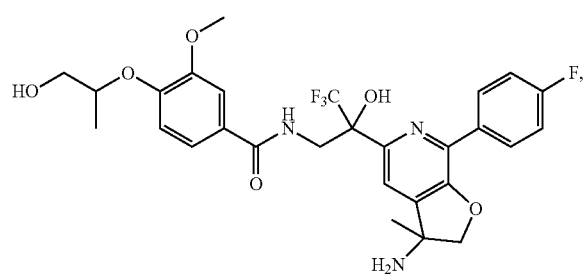

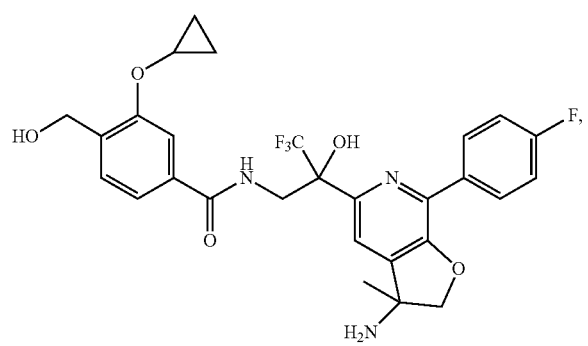

442 and

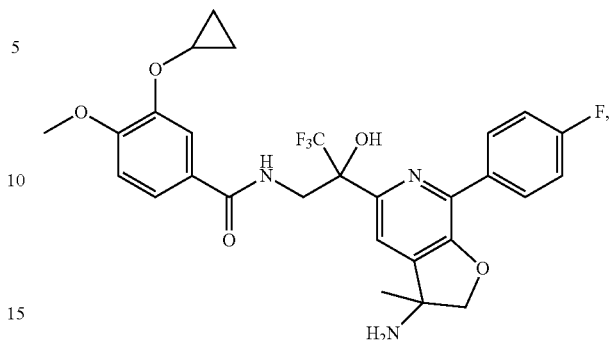

or a pharmaceutically acceptable salt of any of the foregoing.

57. The compound of claim 39, or a pharmaceutically acceptable salt thereof, wherein the compound is selected from the group consisting of:

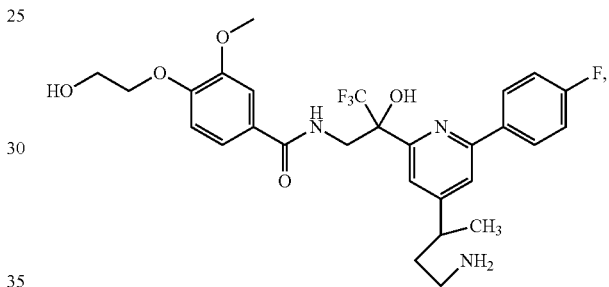

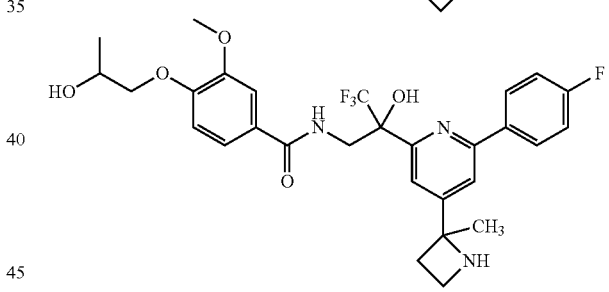

and

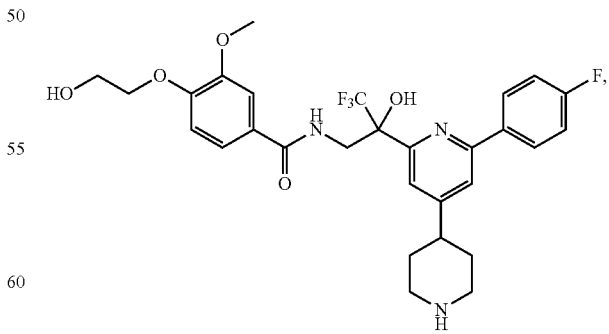

or a pharmaceutically acceptable salt of any of the foregoing.

58. A pharmaceutical composition comprising an effective amount of a compound of claim 39, or a pharmaceutically acceptable salt thereof, and a pharmaceutically acceptable carrier, diluent, excipient, or combination thereof.

59. A method for ameliorating or treating a paramyxovirus infection comprising administering to a subject identified as suffering from the paramyxovirus infection an effective amount of a compound of claim 39, or a pharmaceutically acceptable salt thereof.

60. A method for inhibiting replication of a paramyxovirus comprising contacting a cell infected with the paramyxovirus with an effective amount of a compound of claim 39, or a pharmaceutically acceptable salt thereof.

61. The method of claim 60, wherein the paramyxovirus infection is a human respiratory syncytial virus infection.

62. The method of claim 59, wherein the paramyxovirus infection is a human respiratory syncytial virus infection, further comprising administering one or more additional anti-viral agents, wherein the one or more additional anti-viral agents is an anti-RSV agent selected from the group consisting of an anti-RSV antibody, a fusion protein inhibitor, an N-protein inhibitor, a RSV polymerase inhibitor, an IMPDH inhibitor, an interferon and another compound that inhibits the RSV virus, or a pharmaceutically acceptable salt of any of the foregoing.

63. The method of Claim 62, wherein the one or more additional anti-viral agents is selected from the group consisting of RSV-IGIV, palivizumab, motavizumab, 1-cyclopropyl-3-[[1-(4-hydroxybutyl)benzimidazol-2-yl]methyl] imidazo[4,5-c]pyridin-2-one (BMS-433771), 4,4''-bis-{4,6-bis-[3-(bis-carbamoylmethyl-sulfamoyl)-phenylamino]-(1,3,5)triazin-2-ylamino}-biphenyl-2,2'-disulfonic-acid (RFI-641), 4,4'-Bis[4,6-di[3-aminophenyl -N,N-bis(2-carbamoylethyl)-sulfonilimino]-1,3,5-triazine-2-ylamino]-biphenyl-2,2'-disulfonic acid, disodium salt (CL387626), 2-[[2-[[1-(2-aminoethyl)-4-piperidinyl]amino]-4-methyl-1H-benzimidazol-1-yl]]-6-methyl-3-pyridinol (JNJ-2408068), 2-[[6-[[[2-(3-Hydroxypropyl)-5-methylphenyl] amino]methyl]-2-[[3-(morpholin-4-yl)propyl]amino] benzimidazol-1-yl]methyl]-6-methylpyridin-3-ol (TMC-353121), 5,5'-bis[1-(((5-amino-1H-tetrazolyl)imino) methyl)]2,2',4''-methylidynetrisphenol (VP-14637, MDT-637), N-(2-hydroxyethyl)-4-methoxy-N-methyl-3-(6-methyl-[1,2,4]triazolo[3,4-a]phthalazin-3-yl) benzenesulfonamide (P13), 2-((2-((1-(2-aminoethyl) piperidin-4-yl)amino)-4-methyl-1H -benzo[d]imidazol-1-yl)methyl)-6-methylpyridin-3-ol (R170591), 1,4-bis(3-methylpyridin-4-yl)-1,4-diazepane (C15), (R)-9b-(4-chlorophenyl)-1-(4-fluorobenzoyl)-2,3-dihydro-1H -imidazo[1',2':1,2]pyrrolo[3,4-c]pyridin-5(9bH)-one (BTA9981), [2,2-bis(docosyloxy -oxymethyl)propyl-5-acetaoamido-3,5-dideoxy-4,7,8,9-tetra-O-(sodium-oxysulfonyl)-D-glycero-D-galacto-2-nonulopyranosid]onate (MBX-300), BTA-C286, N-(2-((S)-2-(5-((S)-3-aminopyrrolidin-1-yl)-6-methylpyrazolo[1,5-a]pyrimidin-2-yl)piperidine-1-carbonyl)-4-chlorophenyl)methanesulfonamide (GS-5806), an anti-RSV nanobody, a peptide fusion inhibitor (such as a peptide having the sequence DEFDASISQVNEKINQSLA-FIRKSDELL (T-67), a peptide having the sequence FDA-SISQVNEKINQSLAFIRKSDELLHNVNAGKST (T-118), (S)-1-(2-fluorophenyl)-3-(2-oxo-5-phenyl-2,3-dihydro-1H-benzo[e][1,4]diazepin-3-yl)urea (RSV-604), STP-92, iKT-041, 6-{4-[(biphenyl-2-ylcarbonyl) amino]benzoyl }-N-cyclopropyl-5,6-dihydro-4H-thieno[3,2-d][1]benzazepine-2-carboxamide (YM-53403). N-cyclopropyl-5-(4-(2-(pyrrolidin-1-yl)benzamido)benzoyl)-5,6,7,10-tetrahydrobenzo[b]cyclopenta[d]azepine-9-carboxamide, 6-(4-(2-(2-oxa-7-azaspiro[3,5]nonan-7-yl)nicotinamido) benzoyl)-N-cyclopropyl-5,6-dihydro-4H-benzo[b]thieno[2, 3-d]azepine-2-carboxamide, 4-amino-8-(3-{[2-(3,4-dimethoxyphenyl)ethyl]amino}propyl)-6,6-dimethyl-2-(4-methyl-3-nitrophenyl)-1H-imidazo[4,5-h]-isoquinoline-7,9 (6H,8H)-dione, AZ27, ribavirin, 5-ethynyl-1-beta-D -ribofuranosylimidazole-4-carboxamide (EICAR), 4-hydroxy-3-beta-D-ribofuranosylpyrazole-5-carboxamide (pyrazofurin), 1-((2R,3R,4S,5R)-3,4-dihydroxy-5-(hydroxymethyl)tetrahydrofuran -2-yl)-1H-1,2,4-triazole-3-carboximidamide (taribavirin, viramidine), (2R,3R,4R,5R)-5-(4-amino-2-oxopyrimidin -1(2H)-yl)-2-(chloromethyl)-4-fluoro-2-((isobutyryloxy)methyl)tetrahydrofuran-3-yl isobutyrate, (2R,3R,4R,5R)-5-(4-amino-2-oxopyrimidin -1(2H)-yl)-2-(chloromethyl)-4-fluoro-2-(hydroxymethyl) tetrahydrofuran-3-yl isobutyrate, ((2R,3R,4R,5R)-5-(4-amino-2-oxopyrimidin-1(2H)-yl)-2-(chloromethyl)-4-fluoro-3-hydroxytetrahydrofuran-2-yl)methyl triphosphate, 4-amino-1-((2R,3R,4R,5R)-5-(chloromethyl)-3-fluoro-4-hydroxy-5-(hydroxymethyl)tetrahydrofuran-2-yl)pyrimidin-2(1H)-one, 1,3,4-thiadiazol-2-ylcyanamide (LY253963), tetrahydrofuran-3-yl-3-(3-(3-methoxy-4-(oxazol-5-yl)phenyl)ureido)benzylcarbamate (VX-497), (4E)-6-(4-Hydroxy-6-methoxy-7-methyl-3-oxo-1,3-dihydro-2-benzofuran-5-yl)-4-methylhex-4-enoic acid (Mycophenolic acid), 2-morpholin-4-ylethyl -(E)-6-(4-hydroxy-6-methoxy-7-methyl-3-oxo-1H-2-benzofuran-5-yl)-4-methylhex-4-enoate (Mycophenolate Mofetil), a Type 1 interferon, a Type 2 interferon, a Type 3 interferon, a double stranded RNA oligonucleotide, 5-methyl-N-[4-(trifluoromethyl) phenyl]-isoxazole-4-carboxamide (leflumomide), N-(2-chloro-4-methylphenyl)-2-((1-(4-methoxyphenyl)-1H -benzo[d]imidazol-2-yl)thio)propanamide (JMN3-003), an intratracheal formulation of recombinant human CC00 (CG-100), high titer, human immunoglobulin (RI-001), a non-neutralizing mAb against the G protein (mAb 131-2G), ALN-RSV01, ALN-RSV02, Medi-559, Medi-534 and Medi-557, or a pharmaceutically acceptable salt of any of the foregoing.

* * * * *

UNITED STATES PATENT AND TRADEMARK OFFICE
CERTIFICATE OF CORRECTION

PATENT NO. : 10,358,453 B2  
APPLICATION NO. : 15/052631  
DATED : July 23, 2019  
INVENTOR(S) : Guangyi Wang et al.

Page 1 of 6

It is certified that error appears in the above-identified patent and that said Letters Patent is hereby corrected as shown below:

On the Title Page

In item (60), in Column 1, in "Related U.S. Patent Documents", Line 1, delete "62/126,671," and insert -- 62/120,671, --, therefor.

In the Claims

In Column 367, Line 50, in Claim 1, after " 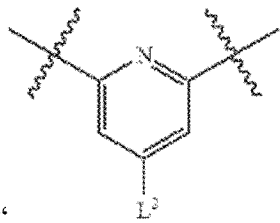 " insert -- , --.

In Column 378, Line 22, in Claim 2, delete "can be" and insert -- is --, therefor.

In Column 378, Line 23, in Claim 3, after "of" delete "any one of".

In Column 378, Line 27, in Claim 4, after "of" delete "any one of".

In Column 378, Line 30, in Claim 5, after "of" delete "any one of".

In Column 378, Line 34, in Claim 6, after "of" delete "any one of".

In Column 378, Line 52, in Claim 8, after "of" delete "any one of".

In Column 378, Line 54, in Claim 9, after "of" delete "any one of".

Signed and Sealed this  
Twenty-fifth Day of October, 2022

Katherine Kelly Vidal  
*Director of the United States Patent and Trademark Office*

In Column 378, Line 56, in Claim 10, after "of" delete "any one of".

In Column 378, Line 59, in Claim 11, after "of" delete "any one of".

In Column 378, Line 61, in Claim 12, after "of" delete "any one of".

In Column 378, Line 64, in Claim 13, after "of" delete "any one of".

In Column 378, Line 66, in Claim 14, after "of" delete "any one of".

In Column 379, Line 20, in Claim 15, after "of" delete "any one of".

In Column 379, Line 20, in Claim 15, after "or" insert -- a --.

In Column 379, Line 22, in Claim 16, after "of" delete "any one of".

In Column 379, Line 34, in Claim 17, after "of" delete "any one of".

In Column 379, Line 34, in Claim 17, after "or" insert -- a --.

In Column 379, Lines 36-45, in Claim 17, after " 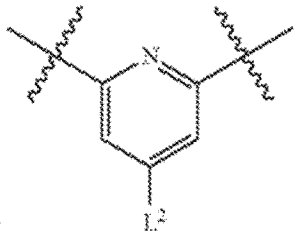 " delete " 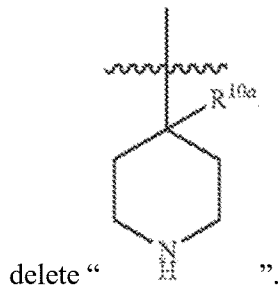 ".

In Column 380, Line 24, in Claim 21, after "of" delete "any one of".

In Column 380, Line 38, in Claim 22, after "of" delete "any one of".

In Column 380, Line 46, in Claim 23, after "substituted $C_{1-4}$ alkoxy" delete "$C_{1-4}$ alkoxy,".

In Column 380, Line 49, in Claim 23, delete "alkyoxyalkyl," and insert -- alkoxyalkyl, --, therefor.

In Column 383, Line 13, in Claim 25, after "of" delete "any one of".

CERTIFICATE OF CORRECTION (continued)
U.S. Pat. No. 10,358,453 B2

In Column 383, Line 16, in Claim 26, after "of" delete "any one of".

In Column 383, Line 20, in Claim 27, after "of" delete "any one of".

In Column 383, Line 23, in Claim 28, after "of" delete "any one of".

In Column 384, Line 20, in Claim 29, after "of" delete "any one of".

In Column 411, Lines 50-55, in Claim 30, delete " 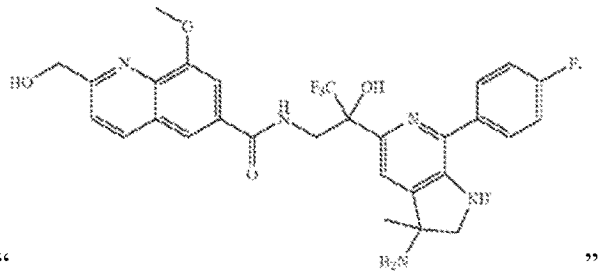 "

and insert -- 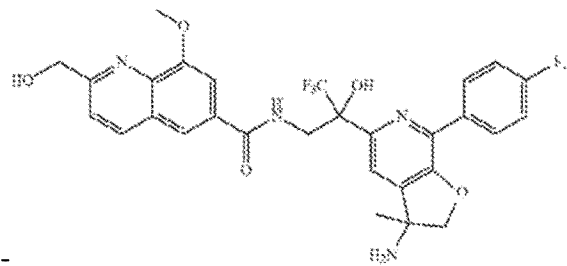 --, therefor.

In Column 422, Line 53, in Claim 33, after "of" delete "any one of".

In Column 422, Line 62, in Claim 35, delete "use" and insert -- method --, therefor.

In Column 423, Line 5, in Claim 36, delete "use" and insert -- method --, therefor.

In Column 423, Line 42, in Claim 36, delete "(YM-53403)." and insert -- (YM-53403), --, therefor.

In Column 423, Line 52, in Claim 36, delete "-5-" and insert -- -5-( --, therefor.

In Column 424, Line 6, in Claim 36, delete "(leflumomide)," and insert -- (leflunomide), --, therefor.

In Column 424, Line 18, in Claim 38, delete "use" and insert -- method --, therefor.

In Column 424, Line 18, in Claim 38, after "of" delete "any one of".

In Column 431, Lines 46-55, in Claim 39, delete " 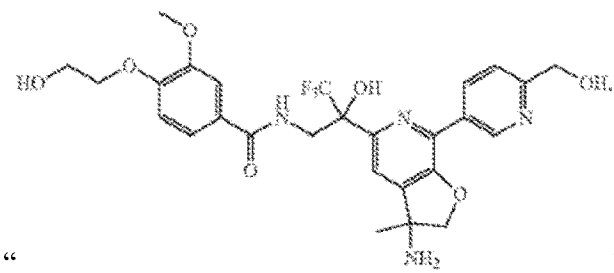 "
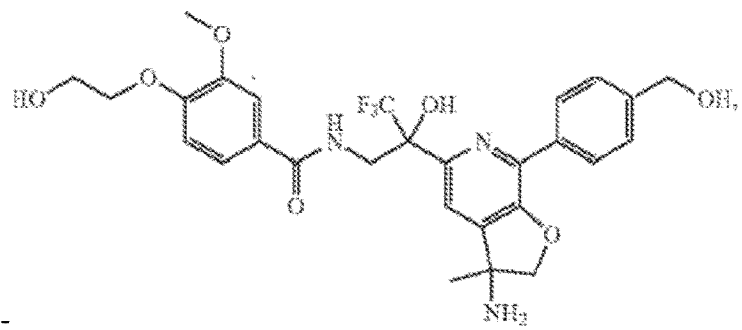
and insert -- -- , therefor.
In Column 434, Line 67, in Claim 50, delete "alkyoxyalkyl," and insert -- alkoxyalkyl, --, therefor.
In Column 436, Lines 47-54, in Claim 51, delete " 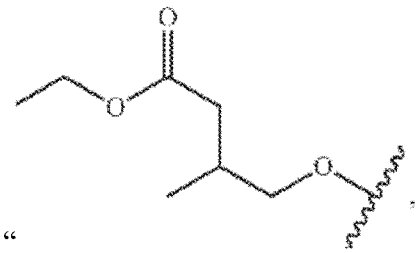 " and
insert -- 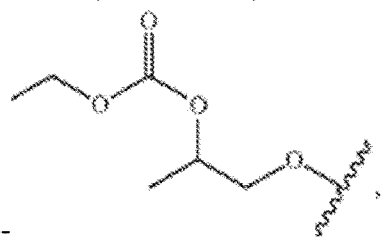 --, therefor.
In Column 436, Lines 55-61, in Claim 51, delete " 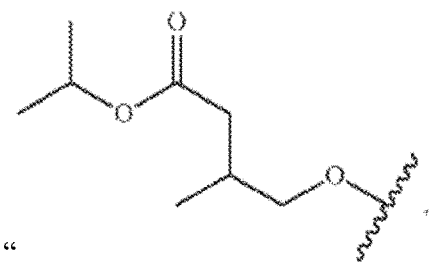 " and insert -- 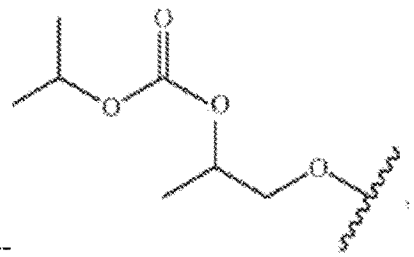 --, therefor.

In Column 437, Lines 7-13, in Claim 51, after " 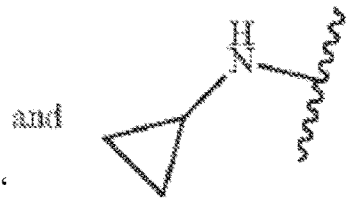 " delete

"  ".

In Column 438, Line 54, in Claim 53, before "an" insert -- and --.

In Column 443, Line 30, in Claim 63, delete "-2,2'-" and insert -- -2,2"- --, therefor.

In Column 443, Line 31, in Claim 63, delete "aminophenyl -N," and insert -- aminophenyl-N, --, therefor.

In Column 443, Line 42, in Claim 63, delete "-3 -yl)" and insert -- -3-yl) --, therefor.

In Column 443, Line 44, in Claim 63, delete "-1H -" and insert -- -1H- --, therefor.

In Column 443, Line 49, in Claim 63, delete "(docosyloxy -" and insert -- (docosyloxy- --, therefor.

In Column 444, Line 7, in Claim 63, delete "fluoropheny1)" and insert -- fluorophenyl) --, therefor.

In Column 444, Line 9, in Claim 63, delete "benzoyl }" and insert -- benzoyl} --, therefor.

In Column 444, Line 11, in Claim 63, delete "(YM-53403)." and insert -- (YM-53403), --, therefor.

In Column 444, Line 14, in Claim 63, delete "[3,5]" and insert -- [3.5] --, therefor.

In Column 444, Line 23, in Claim 63, delete ")tetrahydrofuran -" and insert -- )tetrahydrofuran- --, therefor.

In Column 444, Line 24, in Claim 63, delete "(taribavirin," and insert -- (Taribavirin, --, therefor.

In Column 444, Line 25, in Claim 63, delete "-oxopyrimidin -" and insert -- -oxopyrimidin- --, therefor.

In Column 444, Line 44, in Claim 63, delete "(leflumomide)," and insert -- (leflunomide), --, therefor.

In Column 444, Line 45, in Claim 63, delete "-1H -" and insert -- -1H- --, therefor.

In Column 444, Line 47, in Claim 63, delete "CC0O" and insert -- CC10 --, therefor.

SEQUENCE LISTING

```
<160> NUMBER OF SEQ ID NOS: 4

<210> SEQ ID NO 1
<211> LENGTH: 28
<212> TYPE: PRT
<213> ORGANISM: Artificial Sequence
<220> FEATURE:
<223> OTHER INFORMATION: Core polypeptide

<400> SEQUENCE: 1

Asp Glu Phe Asp Ala Ser Ile Ser Gln Val Asn Glu Lys Ile Asn Gln
1               5                   10                  15

Ser Leu Ala Phe Ile Arg Lys Ser Asp Glu Leu Leu
            20                  25

<210> SEQ ID NO 2
<211> LENGTH: 35
<212> TYPE: PRT
<213> ORGANISM: Artificial Sequence
<220> FEATURE:
<223> OTHER INFORMATION: Core polypeptide

<400> SEQUENCE: 2

Phe Asp Ala Ser Ile Ser Gln Val Asn Glu Lys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 3
<211> LENGTH: 21
<212> TYPE: DNA
<213> ORGANISM: Artificial Sequence
<220> FEATURE:
<223> OTHER INFORMATION: Combined DNA/RNA Molecule: Synthetic
      oligonucleotide

<400> SEQUENCE: 3
ggcucuuagc aaagucaagt t                                              21
```

```
<210> SEQ ID NO 4
<211> LENGTH: 21
<212> TYPE: DNA
<213> ORGANISM: Artificial Sequence
<220> FEATURE:
<223> OTHER INFORMATION: Combined DNA/RNA Molecule: Synthetic
      oligonucleotide

<400> SEQUENCE: 4
cuugacuuug cuaagagcct t                                            21
```